US009469645B2

(12) United States Patent
Chatterjee et al.

(10) Patent No.: US 9,469,645 B2
(45) Date of Patent: Oct. 18, 2016

(54) COMPOUNDS AND COMPOSITIONS FOR THE TREATMENT OF PARASITIC DISEASES

(71) Applicants: Arnab K. Chatterjee, San Diego, CA (US); Advait S. Nagle, San Diego, CA (US); Tao Wu, San Diego, CA (US); David C. Tully, Emeryville, CA (US); Kelli L. Kuhen, Solana Beach, CA (US)

(72) Inventors: Arnab K. Chatterjee, San Diego, CA (US); Advait S. Nagle, San Diego, CA (US); Tao Wu, San Diego, CA (US); David C. Tully, Emeryville, CA (US); Kelli L. Kuhen, Solana Beach, CA (US)

(73) Assignee: Novartis AG, Basel (CH)

(*) Notice: Subject to any disclaimer, the term of this patent is extended or adjusted under 35 U.S.C. 154(b) by 141 days.

(21) Appl. No.: 13/912,898

(22) Filed: Jun. 7, 2013

(65) Prior Publication Data

US 2013/0281403 A1    Oct. 24, 2013

Related U.S. Application Data

(62) Division of application No. 12/833,909, filed on Jul. 9, 2010, now Pat. No. 8,557,801.

(60) Provisional application No. 61/224,433, filed on Jul. 9, 2009.

(51) Int. Cl.
| | |
|---|---|
| *A61K 31/397* | (2006.01) |
| *C07D 487/04* | (2006.01) |
| *C07D 487/14* | (2006.01) |
| *C07D 519/00* | (2006.01) |
| *A61K 31/4985* | (2006.01) |
| *A61K 31/506* | (2006.01) |
| *A61K 31/513* | (2006.01) |
| *A61K 31/5377* | (2006.01) |
| *A61K 31/541* | (2006.01) |
| *A61K 31/69* | (2006.01) |
| *A61K 45/06* | (2006.01) |
| *C07D 495/04* | (2006.01) |
| *C07F 5/02* | (2006.01) |

(52) U.S. Cl.
CPC ......... *C07D 487/04* (2013.01); *A61K 31/4985* (2013.01); *A61K 31/506* (2013.01); *A61K 31/513* (2013.01); *A61K 31/5377* (2013.01); *A61K 31/541* (2013.01); *A61K 31/69* (2013.01); *A61K 45/06* (2013.01); *C07D 487/14* (2013.01); *C07D 495/04* (2013.01); *C07D 519/00* (2013.01); *C07F 5/022* (2013.01)

(58) Field of Classification Search
None
See application file for complete search history.

(56) References Cited

U.S. PATENT DOCUMENTS

| 4,870,073 A | 9/1989 | Watjen |
| 2004/0186148 A1 | 9/2004 | Shankar et al. |
| 2008/0242862 A1 | 10/2008 | Calderwood et al. |

FOREIGN PATENT DOCUMENTS

| CN | 101357922 | 4/2009 |
|---|---|---|
| EP | 1382607 | 1/2004 |
| FR | 2856688 | 12/2004 |
| WO | WO9730053 | 8/1997 |
| WO | WO9964401 | 12/1999 |
| WO | WO0002881 | 1/2000 |
| WO | WO0039130 | 7/2000 |
| WO | WO01/34203 | 5/2001 |
| WO | WO01/49322 | 7/2001 |
| WO | WO0210140 | 2/2002 |
| WO | WO02053558 | 7/2002 |
| WO | WO02096348 | 12/2002 |
| WO | WO03004498 | 1/2003 |
| WO | WO03082817 | 10/2003 |
| WO | WO2004028541 | 4/2004 |
| WO | WO2004058266 | 7/2004 |
| WO | WO2004058762 | 7/2004 |
| WO | WO2004103276 | 12/2004 |
| WO | WO2007017423 | 2/2007 |
| WO | WO2007117180 | 10/2007 |
| WO | WO2007124423 | 11/2007 |
| WO | WO2008006085 | 1/2008 |
| WO | WO2008094737 | 8/2008 |
| WO | WO2009005675 | 1/2009 |
| WO | WO2009095253 | 8/2009 |
| WO | WO2009095254 | 8/2009 |
| WO | WO2009155388 | 12/2009 |

OTHER PUBLICATIONS

Ayoub, et al., "Inhibition of Heterotrimeric G Protein Signaling by a Small Molecule Acting on G alpha Subunit", The Journal of Biological Chemistry, Oct. 16, 2009, pp. 29136-29145, vol. 284, No. 42, The American Society for Biochemistry and Molecular Biology, Inc., USA.

Doerig, et al., "Stopping malaria parasites dead in their tracks", Nature Chemical Biology, Jun. 2008, pp. 334-335, vol. 4, No. 6, Nature Publishing Group, USA.

Kercher, et al., "Diversification of the Three-Component Coupling of 2-Aminoheterocycles, Aldehydes, and Isonitriles: Efficient Parallel Synthesis of a Diverse and Druglike Library of Imidazo- and Tetrahydroimidazo[1,2-alpha] Heterocycles", J. Comb. Chem., 2007, pp. 1177-1187, vol. 9, American Chemical Society, USA.

(Continued)

*Primary Examiner* — Craig Ricci
(74) *Attorney, Agent, or Firm* — Chihang Amy Smith; Genomics Institute of the Novartis Research Foundation

(57) ABSTRACT

The invention provides a class of compounds, pharmaceutical compositions comprising such compounds and methods of using such compounds to treat or prevent malaria.

13 Claims, No Drawings

(56) References Cited

OTHER PUBLICATIONS

Lewandowicz, et al., "Energetic Mapping of Transition State Analogue Interactins with Human and Plasmodium falciparum Purine Nucleoside Phosphorylases", The Journal of Biological Chemistry, Aug. 26, 2005, pp. 30320-30328, vol. 280, No. 34, The American Society for Biochemistry and Molecular Biology, Inc., USA.

Lyon, et al., "Glyoxylic Acid and MP-Glyoxylate; Efficient Formaldehyde Equivalents in the 3-CC of 2-Aminoazines, Aldehydes, and Isonitriles", Organic Letters, 2004, pp. 4989-4992, vol. 6, No. 26, American Chemical Society, USA.

Scarpelli, et al., "Studies of the metabolic stability in cells of 5-(trifluoroacetyl)thiophene-2-carboxamides and identification of more stable class I histone deacetylase (HDCC) inhibitors", Bioorganic & Medicinal Chemistry Letters, 2008, pp. 6078-6082, vol. 18, Elsevier Ltd.

Varma, et al., "Microwave-accelerated three-component condensation reaction on clay: solvent-free synthesis of imidazo[1,2-a] annulated pyridines, pyrazines and pyrimidines", Tetrahedron Letters, 1999, pp. 7665-7669, vol. 40, Elsevier Science Ltd.

Bouzid, et al., "A New Heterocyclic Multicomponent Reaction for the Combinatorial Synthesis of Fused 3-Aminoimidazoles", Angew. Cjhem. Int. Ed., 1998, pp. 2234-2237, vol. 37. No. 16, Wiley-VCH Verlag GmbH, DE.

Groebke, et al., "Synthesis of Imidazo[1,2-a] annulated Pyridines, Pyrazines and Pyrimidines by a Novel Three-Component Condensation", Synlett, Jun. 1998, pp. 661-663.

COMPOUNDS AND COMPOSITIONS FOR THE TREATMENT OF PARASITIC DISEASES

CROSS-REFERENCE TO RELATED APPLICATIONS

This application claims the benefit of priority to U.S. application Ser. No. 12/833,909, filed 9 Jul. 2010, which claims the benefit of U.S. Provisional Patent Application No. 61/224,433, filed 9 Jul. 2009. The full disclosures of these applications are incorporated herein by reference in their entirety and for all purposes.

BACKGROUND OF THE INVENTION

1. Field of the Invention

The invention provides a class of compounds, pharmaceutical compositions comprising such compounds and methods of using such compounds to treat or prevent malaria.

2. Background

Malaria is an infectious disease caused by four protozoan parasites: *Plasmodium falciparum*; *Plasmodium vivax*; *Plasmodium ovale*; and *Plasmodium malaria*. These four parasites are typically transmitted by the bite of an infected female *Anopheles* mosquito. Malaria is a problem in many parts of the world and over the last few decades the malaria burden has steadily increased. An estimated 1-3 million people die every year from malaria—mostly children under the age of 5. This increase in malaria mortality is due in part to the fact that *Plasmodium falciparum*, the deadliest malaria parasite, has acquired resistance against nearly all available antimalarial drugs, with the exception of the artemisinin derivatives.

Leishmaniasis is caused by one or more than 20 varieties of parasitic protozoa that belong to the genus *Leishmania*, and is transmitted by the bite of female sand flies. Leishmaniasis is endemic in about 88 countries, including many tropical and sub-tropical areas.

There are four main forms of Leishmaniasis. Visceral leishmaniasis, also called kala-azar, is the most serious form and is caused by the parasite *Leishmania donovani*. Patients who develop visceral leishmaniasis can die within months unless they receive treatment. The two main therapies for visceral leishmaniasis are the antimony derivatives sodium stibogluconate (Pentostam®) and meglumine antimoniate (Glucantim®). Sodium stibogluconate has been used for about 70 years and resistance to this drug is a growing problem. In addition, the treatment is relatively long and painful, and can cause undesirable side effects.

Human African Trypanosomiasis, also known as sleeping sickness, is a vector-borne parasitic disease. The parasites concerned are protozoa belonging to the *Trypanosoma* Genus. They are transmitted to humans by tsetse fly (*Glossina* Genus) bites which have acquired their infection from human beings or from animals harboring the human pathogenic parasites.

Chagas disease (also called American Trypanosomiasis) is another human parasitic disease that is endemic amongst poor populations on the American continent. The disease is caused by the protozoan parasite *Trypanosoma cruzi*, which is transmitted to humans by blood-sucking insects. The human disease occurs in two stages: the acute stage, which occurs shortly after infection and the chronic stage, which can develop over many years. Chronic infections result in various neurological disorders, including dementia, damage to the heart muscle and sometimes dilation of the digestive tract, as well as weight loss. Untreated, the chronic disease is often fatal.

The drugs currently available for treating Chagas disease are Nifurtimox and benznidazole. However, problems with these current therapies include their diverse side effects, the length of treatment, and the requirement for medical supervision during treatment. Furthermore, treatment is really only effective when given during the acute stage of the disease. Resistance to the two frontline drugs has already occurred. The antifungal agent Amphotericin b has been proposed as a second-line drug, but this drug is costly and relatively toxic.

In view of the foregoing, it is desirable to develop novel compounds as antiparasitic agents.

SUMMARY OF THE INVENTION

In one aspect, the present invention provides a compound selected from Formula Ia, Ib and Ic:

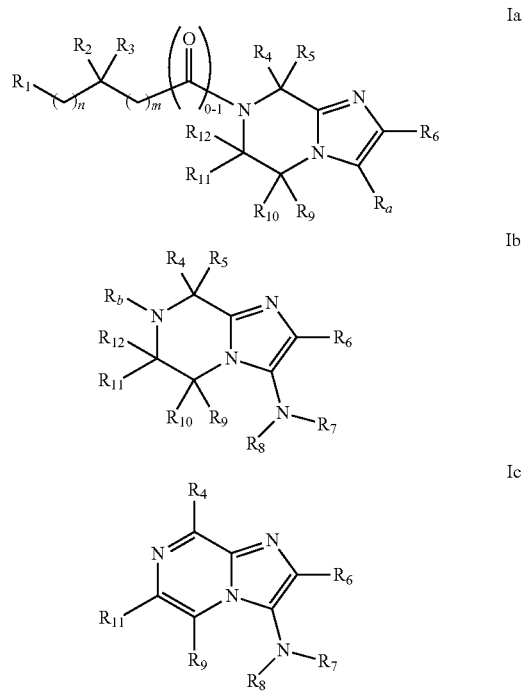

in which:

n is selected from 0, 1, 2, 3 and 4;

m is selected from 0, 1, 2, 3 and 4;

$R_a$ is selected from hydrogen, halo, —$X_3NR_7R_8$, —$X_3OR_8$, —$X_3S(O)_{0-2}R_8$, —$X_3C(O)NR_7R_8$, —$X_3R_8$, benzyl and $C_{6-10}$aryl optionally substituted with 1 to 3 radicals independently selected from halo, $C_{1-4}$alkyl, halo-substituted-$C_{1-4}$alkyl, $C_{1-4}$alkoxy and halo-substituted-$C_{1-4}$alkoxy; wherein $X_3$ is selected from a bond and $C_{1-4}$alkylene;

$R_b$ is selected from hydrogen and $C_{1-4}$alkyl;

$R_1$ is selected from halo, —$OR_{13}$, —$C(O)OR_{13}$, —$NR_{13}R_{14}$, $C_{6-10}$aryl and a saturated, unsaturated or partially unsaturated 4-9 member heterocyclic ring containing up to three nitrogens; wherein $R_{13}$ is selected from hydrogen, $C_{1-6}$alkyl, halo-substituted-$C_{1-6}$alkyl, hydroxy-substituted-$C_{1-6}$alkyl, $C_{6-10}$aryl-$C_{0-4}$alkyl, $C_{3-8}$cycloalkyl- $C_{0-4}$alkyl, —$X_1$NHC(O)$R_{15}$, —$X_1$C(NH)NH$R_{15}$, —$X_1$C(O)NH$R_{15}$, —$X_1$NH$R_{15}$, —$X_1$O$R_{15}$, —C(O)$R_{15}$ and —C(O)O$R_{15}$; wherein $X_1$ is selected from a bond and $C_{1-4}$alkylene; $R_{15}$ is selected from hydrogen, $C_{1-6}$alkyl, halo-substituted-$C_{1-6}$alkyl and benzyl; and $R_{14}$ is selected from hydrogen, $C_{1-6}$alkyl and hydroxy-substituted-$C_{1-6}$alkyl; wherein any aryl or heterocyclic of $R_1$ is optionally substituted with 1-3 radicals independently selected from halo, $C_{1-6}$alkyl, halo-substituted-$C_{1-6}$alkyl, $C_{1-6}$alkoxy and halo-substituted-$C_{1-6}$alkoxy;

or $R_{13}$ and $R_{14}$ together with the nitrogen to which $R_{13}$ and $R_{14}$ are attached form a saturated, unsaturated or partially unsaturated 5-9 member heterocyclic ring containing up to three heteroatoms selected from N, $NR_{30}$, $S(O)_{0-2}$ and O; wherein $R_{30}$ is selected from hydrogen and $C_{1-6}$alkyl; wherein said heterocyclic ring formed by the combination of $R_{13}$ and $R_{14}$ is optionally substituted with 1 to 3 radicals independently selected from halo, hydroxy, $C_{1-6}$alkyl, amino-substituted-$C_{1-6}$alkyl and halo-substituted-$C_{1-6}$alkyl;

$R_2$ is selected from hydrogen, $C_{1-6}$alkyl, amino, $C_{3-8}$cycloalkyl-$C_{0-4}$alkyl, $C_{6-10}$aryl-$C_{0-4}$alkyl, halo-substituted-$C_{1-6}$alky, hydroxy-substituted-$C_{1-6}$alkyl and heterocyclyl-$C_{0-4}$alkyl; wherein said heterocyclyl is a saturated, unsaturated or partially unsaturated 5-9 member heterocyclic ring containing up to three heteroatoms selected from N, $NR_{30}$, $S(O)_{0-2}$ and O; wherein $R_{30}$ is selected from hydrogen and $C_{1-6}$alkyl; wherein said $C_{6-10}$aryl or heterocyclic of $R_2$ is optionally substituted with 1 to 3 radicals independently selected from halo, hydroxy, cyano, nitro, —NH$R_{17}$, —$(CH_2)_{0-2}$NHC(O)$R_{17}$, $C_{1-6}$alkyl, halo-substituted-$C_{1-6}$alkyl, amino-substituted-$C_{1-6}$alkyl and $C_{1-6}$alkoxy; wherein $R_{17}$ is selected from hydrogen and $C_{1-6}$alkyl;

$R_3$ is selected from hydrogen, $C_{1-6}$alkyl, $C_{6-10}$aryl-$C_{0-4}$alkyl, —$X_2$C(O)O$R_{16}$, —$X_2$S(O)$_{0-2}R_{16}$, —$X_2$O$R_{16}$, —$X_2$C(O)NH$R_{16}$ and —$X_2$NHC(O)$R_{16}$; wherein $X_2$ is selected from a bond and $C_{1-4}$alkylene; and $R_{16}$ is selected from hydrogen, $C_{1-6}$alkyl and $C_{6-10}$aryl-$C_{0-4}$alkyl; wherein said aryl of $R_{16}$ is optionally substituted with 1 to 3 radicals independently selected from halo, $C_{1-6}$alkyl, halo-substituted-$C_{1-6}$alkyl, $C_{1-6}$alkoxy and halo-substituted-$C_{1-6}$alkoxy;

or $R_2$ and $R_3$ together with the carbon atom to which $R_2$ and $R_3$ are attached forms $C_{3-8}$cycloalkyl;

or $R_2$ and $R_{13}$ together with the atoms to which $R_2$ and $R_{13}$ are attached form a ring selected from $C_{3-8}$cycloalkyl and a saturated, unsaturated or partially unsaturated 5-9 member mono or fused heterocyclic ring containing up to three heteroatoms or groups selected from N, C(O), $NR_{30}$, $S(O)_{0-2}$ and O; wherein $R_{30}$ is selected from hydrogen and $C_{1-6}$alkyl; wherein said heterocyclic form the combination of $R_2$ and $R_{13}$ is optionally substituted with 1 to 3 radicals independently selected from halo, hydroxy, $C_{1-6}$alkyl and halo-substituted-$C_{1-6}$alkyl;

$R_4$ is selected from hydrogen and $C_{1-6}$alkyl;

$R_5$ is selected from hydrogen and $C_{1-6}$alkyl; or $R_4$ and $R_5$ together with the carbon atom to which $R_4$ and $R_5$ are attached forms $C_{3-8}$cycloalkyl;

$R_6$ is selected from $C_{6-10}$aryl, $C_{3-8}$cycloalkyl and a saturated, unsaturated or partially unsaturated 5-9 member mono or fused heterocyclic ring containing up to three heteroatoms or groups selected from N, C(O), $NR_{30}$, $S(O)_{0-2}$ and O; wherein $R_{30}$ is selected from hydrogen and $C_{1-6}$alkyl; wherein said aryl or heterocyclic of $R_6$ is optionally substituted by 1 to 3 radicals independently selected from halo, hydroxy, $C_{1-6}$alkyl and $C_{1-6}$alkoxy;

$R_7$ is selected from hydrogen and $C_{1-3}$alkyl;

$R_8$ is selected from $C_{1-10}$alkyl (straight or branched), $C_{6-10}$aryl-$C_{0-4}$alkyl, $C_{3-8}$cycloalkyl and a saturated, unsaturated or partially unsaturated 5-9 member mono or fused heterocyclic ring containing up to three heteroatoms or groups selected from N, C(O), $NR_{30}$, $S(O)_{0-2}$ and O; wherein $R_{30}$ is selected from hydrogen and $C_{1-6}$alkyl; wherein said aryl or heterocyclic of $R_8$ is optionally substituted by 1 to 3 radicals independently selected from halo, cyano, hydroxy, $C_{1-6}$alkyl, halo-substituted-$C_{1-6}$alkyl, halo-substituted-$C_{1-6}$alkoxy, $C_{1-6}$alkoxy, —C(O)O$R_{18}$, —$S(O)_{0-2}R_{18}$, —C(O)NH$R_{18}$, —NHS(O)$_{0-2}R_{18}$, phenyl and a saturated, unsaturated or partially unsaturated 5-6 member heterocyclic ring containing up to three heteroatoms or groups selected from N, C(O), $NR_{30}$, $S(O)_{0-2}$ and O; wherein $R_{30}$ is selected from hydrogen and $C_{1-6}$alkyl; wherein said aryl or heterocyclic substituent of $R_8$ is optionally substituted by 1 to 3 radicals independently selected from halo, cyano, hydroxy, $C_{1-6}$alkyl, halo-substituted-$C_{1-6}$alkyl and halo-substituted-$C_{1-6}$alkoxy; wherein $R_{18}$ is selected from hydrogen and $C_{1-6}$alkyl;

$R_9$ is selected from hydrogen and $C_{1-6}$alkyl;

$R_{10}$ is selected from hydrogen and $C_{1-6}$alkyl;

$R_{11}$ is selected from hydrogen and $C_{1-6}$alkyl;

$R_{12}$ is selected from hydrogen and $C_{1-6}$alkyl; or $R_{11}$ and $R_{12}$ combine to form C(O); and the N-oxide derivatives, prodrug derivatives, protected derivatives, individual isomers and mixture of isomers thereof; and the pharmaceutically acceptable salts and solvates (e.g. hydrates) of such compounds; with the proviso that the following compounds are excluded from the invention: 2-amino-1-(3-(benzo[d][1,3]dioxol-5-ylamino)-2-phenyl-5,6-dihydroimidazo[1,2-a]pyrazin-7(8H)-yl)ethanone; 2-(2-methoxyphenyl)-N-(2,4,4-trimethylpentan-2-yl)imidazo[1,2-a]pyridin-3-amine; 2-phenyl-N-(2,4,4-trimethylpentan-2-yl)imidazo[1,2-a]pyridin-3-amine; 2-(pyridin-3-yl)-N-(2,4,4-trimethylpentan-2-yl)imidazo[1,2-a]pyridin-3-amine; and 2-(4-fluorophenyl)-N-(2,4,4-trimethylpentan-2-yl)imidazo[1,2-a]pyridin-3-amine.

In a second aspect, the present invention provides a pharmaceutical composition which contains a compound selected from Formula Ia, Ib and Ic or a N-oxide derivative, individual isomers and mixture of isomers thereof; or a pharmaceutically acceptable salt thereof, in admixture with one or more suitable excipients.

In a third aspect, the present invention provides a method of treating a disease in an animal in which a compound of the invention can prevent, inhibit or ameliorate the pathology and/or symptomology of disease caused by a parasite (such as, for example, *Plasmodium falciparum, Plasmodium vivax, Plasmodium ovale, Plasmodium malaria, Trypanosoma cruzi* or a parasite of the *Leishmania* genus such as, for example, *Leishmania donovani*) which method comprises administering to the animal a therapeutically effective amount of a compound selected from Formula Ia, Ib and Ic or a N-oxide derivative, individual isomers and mixture of isomers thereof, or a pharmaceutically acceptable salt thereof.

In a fourth aspect, the present invention provides the use of a compound selected from Formula Ia, Ib and Ic in the manufacture of a medicament for treating a disease caused by a parasite in an animal. The disease may be malaria, leishmaniasis and/or Chagas disease.

In a fifth aspect, the present invention provides a process for preparing compounds selected from Formula Ia, Ib and Ic and the N-oxide derivatives, prodrug derivatives, individual isomers and mixture of isomers thereof, and the pharmaceutically acceptable salts thereof.

DETAILED DESCRIPTION OF THE INVENTION

Definitions

"Alkyl" as a group and as a structural element of other groups, for example halo-substituted-alkyl and alkoxy, can be either straight-chained or branched. $C_{1-4}$-alkoxy includes, methoxy, ethoxy, and the like. Halo-substituted alkyl includes trifluoromethyl, pentafluoroethyl, and the like.

"Aryl" means a monocyclic or fused bicyclic aromatic ring assembly containing six to ten ring carbon atoms. For example, aryl may be phenyl or naphthyl, preferably phenyl. "Arylene" means a divalent radical derived from an aryl group.

"Heteroaryl" is as defined for aryl where one or more of the ring members are a heteroatom selected from N, O, C(O) and $S(O)_{0-2}$. For example 5-10 member heteroaryl includes pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc.

"Cycloalkyl" means a saturated or partially unsaturated, monocyclic, fused bicyclic or bridged polycyclic ring assembly containing the number of ring atoms indicated. For example, $C_{3-10}$cycloalkyl includes cyclopropyl, cyclobutyl, cyclopentyl, cyclohexyl, etc.

"Heterocyclic" means cycloalkyl, as defined in this application, provided that one or more of the ring carbons indicated, are replaced by a moiety selected from —O—, —N═, —NR—, —C(O)—, —S—, —S(O)— or —S(O)$_2$—, wherein R is hydrogen, $C_{1-4}$alkyl or a nitrogen protecting group. For example, 3-8 member heterocycloalkyl as used in this application to describe compounds of the invention includes morpholino, pyrrolidinyl, piperazinyl, piperidinyl, piperidinylone, 1,4-dioxa-8-aza-spiro[4.5]dec-8-yl, etc.

"Halogen" (or halo) represents chloro, fluoro, bromo or iodo.

"Treat", "treating" and "treatment" refer to a method of alleviating or abating a disease and/or its attendant symptoms. In the present description, the term "treatment" includes both prophylactic or preventative treatment as well as curative or disease suppressive treatment, including treatment of patients at risk of contracting the disease or suspected to have contracted the disease as well as ill patients. This term further includes the treatment for the delay of progression of the disease.

DESCRIPTION OF THE PREFERRED EMBODIMENTS

The invention provides a novel class of compounds, pharmaceutical compositions comprising such compounds and methods of using such compounds to treat or prevent diseases or disorders associated with a parasite. In particular, the compounds can be used to treat malaria, leishmaniasis and/or Chagas disease.

In one embodiment, with reference to compounds of Formula Ia, Ib and Ic: $R_1$ is selected from —$OR_{13}$, —C(O)$OR_{13}$, —$NR_{13}R_{14}$, phenyl, pyridinyl, indolyl, azetidinyl, 1H-indazolyl, piperidinyl and pyrimidinyl; wherein $R_{13}$ is selected from hydrogen, methyl, ethyl, propyl, butyl, pentyl, cyclopropyl, phenyl, benzyl, amino-butyl, hydroxy-ethyl, methoxy-ethyl, butoxy-ethyl, methoxy-propyl, —C(O)$R_{15}$, —C(O)$OR_{15}$, —$X_1OR_{15}$, —$X_1C(NH)NHR_{15}$, —$X_1NHC(O)R_{15}$ and $X_1C(O)NHR_{15}$; wherein $X_1$ is selected from a bond and $C_{1-4}$alkylene; and $R_{15}$ is selected from hydrogen, methyl, ethyl, propyl, butyl, t-butyl, trifluoromethyl and trifluoromethyl-carbonyl; $R_{14}$ is selected from hydrogen, methyl, ethyl, propyl, butyl, pentyl, isobutyl, hydroxy-ethyl, difluoroethyl and isobutyl; wherein any phenyl, benzyl or heterocyclic of $R_1$ is optionally substituted with 1-3 radicals independently selected from halo, methyl, ethyl, trifluoromethoxy and trifluoromethyl; or $R_{13}$ and $R_{14}$ together with the nitrogen to which $R_{13}$ and $R_{14}$ are attached form pyrrolidinyl, morpholino, thiomorpholino and piperidinyl; wherein said heterocyclic form the combination of $R_{13}$ and $R_{14}$ is optionally substituted with 1 to 3 radicals independently selected from halo, trifluoromethyl, hydroxy and amino-ethyl.

In another embodiment, $R_2$ is selected from hydrogen, methyl, ethyl, isopropyl, propyl, isobutyl, butyl, t-butyl, trifluoromethyl, trifluoro-ethyl, phenyl, benzyl, phenethyl, cyclobutyl-methyl, cyclopentyl, cyclohexyl, cyclohexyl-methyl, hydroxy-methyl and 1-hydroxy-ethyl; wherein said phenyl, benzyl or phenethyl of $R_2$ is optionally substituted with 1 to 3 radicals independently selected from halo, methoxy, trifluoromethyl, hydroxy, amino, nitro, cyano, amino-methyl, methyl-sulfonyl-ethyl, methyl-carbonyl-amino, —$NHR_{17}$, —$CH_2NHC(O)R_{17}$ and —$NHC(O)R_{17}$; wherein $R_{17}$ is selected from hydrogen, ethyl, propyl, butyl and pentyl.

In another embodiment, $R_3$ is selected from hydrogen, methyl, methyl-carbonyl-amino-butyl, propyl-amino-carbonyl-methyl, carboxy-methyl, propyl-amino-carbonyl-methyl, butyl-amino-carbonyl-methyl, pentyl-amino-carbonyl-methyl, propyl-amino-carbonyl-ethyl, trifluoromethyl-carbonyl-amino-butyl, phenyl, benzyl-sulfanyl-methyl, benzoxy-carbonyl-methyl, methyl-sulfonyl-methyl, 1-(benzyloxy)ethyl, benzoxy-carbonyl-ethyl and benzoxy-carbonyl-amino.

In another embodiment, $R_2$ and $R_3$ together with the carbon atom to which $R_2$ and $R_3$ are attached form cyclopropyl, cyclobutyl, cyclopentyl or cyclohexyl.

In another embodiment, $R_2$ and $R_{13}$ together with the atoms to which $R_2$ and $R_{13}$ are attached form piperidinyl, cyclobutyl, pyrrolidinyl, morpholino, piperidinyl, tetrahydrofuranyl, tetrahydro-2H-pyran-4-yl, 4-oxoazetidin-2-yl, indolyl, 2,6-dioxo-1,2,3,6-tetrahydropyrimidin-4-yl, 1,2,3,4-tetrahydroisoquinolin-3-yl, oxopiperidin-3-yl or 4,5,6,7-tetrahydro-3H-imidazo[4,5-c]pyridin-6-yl.

In a further embodiment, $R_4$, $R_5$, $R_9$ and $R_{10}$ are independently selected from hydrogen and methyl; $R_{11}$ and $R_{12}$ are both hydrogen; or $R_{11}$ and $R_{12}$ combine to form C(O).

In a further embodiment, $R_6$ is selected from phenyl, cyclohexyl and pyridinyl; wherein said phenyl or pyridinyl of $R_6$ is optionally substituted by 1 to 3 radicals independently selected from halo, pentyl, hydroxy, methyl and methoxy.

In a further embodiment, $R_7$ is selected from hydrogen, methyl, ethyl and isopropyl; and $R_8$ is selected from phenyl, benzyl, benzo[d][1,3]dioxol-5-yl, cyclobutyl, cyclopentyl, cycloheptyl, cyclohexyl, bicyclo[2.2.1]heptyl, tetrahydro-2H-pyranyl, pyridinyl, piperidinyl, piperazinyl, quinolinyl, pyrrolidinyl and pyrazolyl; wherein said phenyl, benzyl, benzo[d][1,3]dioxol-5-yl, cyclobutyl, cyclopentyl, cycloheptyl, cyclohexyl, bicyclo[2.2.1]heptyl, tetrahydro-2H-pyranyl, pyridinyl, piperidinyl, piperazinyl, quinolinyl, pyrrolidinyl or pyrazolyl of $R_8$ is optionally substituted by 1 to 3 radicals independently selected from halo, cyano, methyl, ethyl, t-butyl, trifluoromethyl, trifluoromethoxy, dimethylamino, difluoromethoxy, carboxy, methoxy-carbonyl, methyl-sulfonyl-amino, methyl-sulfonyl, methyl-amino-carbonyl, phenyl, piperidinyl, piperidinyl-methyl, piperazinyl and piperazinyl-methyl.

In another embodiment is a compound of Formula Id:

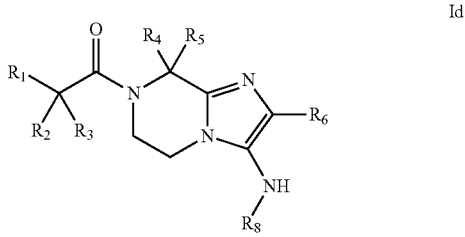

Id in which: R$_1$ is —NH$_2$; R$_2$ and R$_3$ are independently selected from hydrogen and methyl; R$_4$ and R$_5$ are independently selected from hydrogen and methyl; R$_6$ is phenyl substituted with a fluoro; and R$_8$ is a phenyl substituted with 1 to 2 radicals independently selected from chloro and fluoro.

In a further embodiment are compounds selected from: 2-amino-1-(2-(4-fluorophenyl)-3-(4-fluorophenylamino)-8,8-dimethyl-5,6-dihydroimidazo[1,2-a]pyrazin-7(8H)-yl) ethanone; 2-amino-1-(3-(3,4-difluorophenylamino)-2-(4-fluorophenyl)-5,6-dihydroimidazo[1,2-a]pyrazin-7(8H)-yl)-2-methylpropan-1-one; and 2-amino-1-(3-(4-chlorophenylamino)-2-(4-fluorophenyl)-8,8-dimethyl-5,6-dihydroimidazo[1,2-a]pyrazin-7(8H)-yl)ethanone.

In a further embodiment are compounds selected from: 2-amino-1-{3-[(3,5-dimethylphenyl)amino]-2-phenyl-5H,6H,7H,8H-imidazo[1,2-a]pyrazin-7-yl}ethan-1-one; 2-amino-1-[2-(4-fluorophenyl)-3-[(4-fluorophenyl)amino]-5H,6H,7H,8H-imidazo[1,2-a]pyrazin-7-yl]-2-methylpropan-1-one; 2-amino-1-[2-(4-fluorophenyl)-3-[(4-fluorophenyl)amino]-5H,6H,7H,8H-imidazo[1,2-a]pyrazin-7-yl]ethan-1-one; 2-amino-1-[3-(2H-1,3-benzodioxol-5-ylamino)-2-(4-fluorophenyl)-5H,6H,7H,8H-imidazo[1,2-a]pyrazin-7-yl]-2-methylpropan-1-one; 2-amino-1-[3-(cyclopentylamino)-2-(4-fluorophenyl)-5H,6H,7H,8H-imidazo[1,2-a]pyrazin-7-yl]ethan-1-one; 2-amino-1-[3-(cyclopentylamino)-2-phenyl-5H,6H,7H,8H-imidazo[1,2-a]pyrazin-7-yl]ethan-1-one; 2-amino-2-methyl-1-[2-phenyl-3-(phenylamino)-5H,6H,7H,8H-imidazo[1,2-a]pyrazin-7-yl]propan-1-one; methyl 4-{[7-(2-amino-2-methylpropanoyl)-2-phenyl-5H,6H,7H,8H-imidazo[1,2-a]pyrazin-3-yl]amino}benzoate; 2-amino-1-[2-(2-fluorophenyl)-3-[(4-fluorophenyl)amino]-5H,6H,7H,8H-imidazo[1,2-a]pyrazin-7-yl]-2-methylpropan-1-one; 2-amino-1-{3-[(4-fluorophenyl)amino]-2-phenyl-5H,6H,7H,8H-imidazo[1,2-a]pyrazin-7-yl}-2-methylpropan-1-one; 2-amino-1-{3-[(4-fluorophenyl)amino]-2-(2,4,6-trifluorophenyl)-5H,6H,7H,8H-imidazo[1,2-a]pyrazin-7-yl}-2-methylpropan-1-one; 2-amino-1-[2-(3,5-difluorophenyl)-3-[(4-fluorophenyl)amino]-5H,6H,7H,8H-imidazo[1,2-a]pyrazin-7-yl]-2-methylpropan-1-one; 2-amino-1-{3-[(4-fluorophenyl)amino]-2-(4-pentylphenyl)-5H,6H,7H,8H-imidazo[1,2-a]pyrazin-7-yl}-2-methylpropan-1-one; 2-amino-1-{2-cyclohexyl-3-[(4-fluorophenyl)amino]-5H,6H,7H,8H-imidazo[1,2-a]pyrazin-7-yl}-2-methylpropan-1-one; 2-amino-1-[2-(4-fluorophenyl)-3-(pyridin-3-ylamino)-5H,6H,7H,8H-imidazo[1,2-a]pyrazin-7-yl]-2-methylpropan-1-one; (2S)-2-amino-1-[2-(4-fluorophenyl)-3-[(4-fluorophenyl)amino]-5H,6H,7H,8H-imidazo[1,2-a]pyrazin-7-yl]propan-1-one; 4-amino-1-[2-(4-fluorophenyl)-3-[(4-fluorophenyl)amino]-5H,6H,7H,8H-imidazo[1,2-a]pyrazin-7-yl]butan-1-one; (2S)-2-amino-1-[2-(4-fluorophenyl)-3-[(4-fluorophenyl)amino]-5H,6H,7H,8H-imidazo[1,2-a]pyrazin-7-yl]-3-phenylpropan-1-one; (2R)-2-amino-1-[2-(4-fluorophenyl)-3-[(4-fluorophenyl)amino]-5H,6H,7H,8H-imidazo[1,2-a]pyrazin-7-yl]-3-phenylpropan-1-one; 2-amino-1-{3-[(4-bromophenyl)amino]-2-(4-fluorophenyl)-5H,6H,7H,8H-imidazo[1,2-a]pyrazin-7-yl}-2-methylpropan-1-one; 2-(dimethylamino)-1-[2-(4-fluorophenyl)-3-[(4-fluorophenyl)amino]-5H,6H,7H,8H-imidazo[1,2-a]pyrazin-7-yl]ethan-1-one; 2-amino-1-[3-(benzylamino)-2-(4-fluorophenyl)-5H,6H,7H,8H-imidazo[1,2-a]pyrazin-7-yl]-2-methylpropan-1-one; 2-(4-chlorophenyl)-3-(4-methylphenyl)imidazo[1,2-a]pyrazine; N-{2-[2-(4-fluorophenyl)-3-[(4-fluorophenyl)amino]-5H,6H,7H,8H-imidazo[1,2-a]pyrazin-7-yl]-2-oxoethyl}acetamide; N,2-bis(4-fluorophenyl)imidazo[1,2-a]pyrazin-3-amine; 2-amino-1-[3-(cyclohexylamino)-2-(4-fluorophenyl)-5H,6H,7H,8H-imidazo[1,2-a]pyrazin-7-yl]-2-methylpropan-1-one; N,2-bis(4-fluorophenyl)-5H,6H,7H,8H-imidazo[1,2-a]pyrazin-3-amine; 2-amino-1-{3-[(3,4-difluorophenyl)amino]-2-(4-fluorophenyl)-5H,6H,7H,8H-imidazo[1,2-a]pyrazin-7-yl}-2-methylpropan-1-one; 2-amino-1-{3-[(3,4-difluorophenyl)amino]-2-(4-fluorophenyl)-5H,6H,7H,8H-imidazo[1,2-a]pyrazin-7-yl}ethan-1-one; 2-amino-1-[2,3-bis(4-fluorophenyl)-5H,6H,7H,8H-imidazo[1,2-a]pyrazin-7-yl]-2-methylpropan-1-one; 1-[2-(4-fluorophenyl)-3-[(4-fluorophenyl)amino]-5H,6H,7H,8H-imidazo[1,2-a]pyrazin-7-yl]-2-(methylamino)ethan-1-one; 1-[2-(4-fluorophenyl)-3-[(4-fluorophenyl)amino]-5H,6H,7H,8H-imidazo[1,2-a]pyrazin-7-yl]-2-(pyrrolidin-1-yl)ethan-1-one; 3-amino-1-[2-(4-fluorophenyl)-3-[(4-fluorophenyl)amino]-5H,6H,7H,8H-imidazo[1,2-a]pyrazin-7-yl]propan-1-one; 2-amino-1-[2-(4-fluorophenyl)-3-[(3-fluorophenyl)amino]-5H,6H,7H,8H-imidazo[1,2-a]pyrazin-7-yl]-2-methylpropan-1-one; 2-amino-1-[2-(4-fluorophenyl)-3-[(3-fluorophenyl)amino]-5H,6H,7H,8H-imidazo[1,2-a]pyrazin-7-yl]ethan-1-one; 2-amino-1-[2-(4-fluorophenyl)-3-[(4-methylphenyl)amino]-5H,6H,7H,8H-imidazo[1,2-a]pyrazin-7-yl]-2-methylpropan-1-one; 2-amino-1-[2-(4-fluorophenyl)-3-[(4-methylphenyl)amino]-5H,6H,7H,8H-imidazo[1,2-a]pyrazin-7-yl]ethan-1-one; 2-amino-1-{3-[(4-chlorophenyl)amino]-2-(4-fluorophenyl)-5H,6H,7H,8H-imidazo[1,2-a]pyrazin-7-yl}-2-methylpropan-1-one; 2-amino-1-{3-[(4-chlorophenyl)amino]-2-(4-fluorophenyl)-5H,6H,7H,8H-imidazo[1,2-a]pyrazin-7-yl}ethan-1-one; 1-[2-(4-fluorophenyl)-3-[(4-fluorophenyl)amino]-5H,6H,7H,8H-imidazo[1,2-a]pyrazin-7-yl]-2-(morpholin-4-yl)ethan-1-one; 4-{2-[2-(4-fluorophenyl)-3-[(4-fluorophenyl)amino]-5H,6H,7H,8H-imidazo[1,2-a]pyrazin-7-yl]-2-oxoethyl}-1$1^{6}$,4-thiomorpholine-1,1-dione; 2-(3,3-difluoropiperidin-1-yl)-1-[2-(4-fluorophenyl)-3-[(4-fluorophenyl)amino]-5H,6H,7H,8H-imidazo[1,2-a]pyrazin-7-yl]ethan-1-one; 1-[2-(4-fluorophenyl)-3-[(4-fluorophenyl)amino]-5H,6H,7H,8H-imidazo[1,2-a]pyrazin-7-yl]-2-hydroxyethan-1-one; 7-[(1-aminocyclopropyl)carbonyl]-N,2-bis(4-fluorophenyl)-5H,6H,7H,8H-imidazo[1,2-a]pyrazin-3-amine; N-{1-[2-(4-fluorophenyl)-3-[(4-fluorophenyl)amino]-5H,6H,7H,8H-imidazo[1,2-a]pyrazin-7-yl]-2-methyl-1-oxopropan-2-yl}acetamide; 2-amino-1-[2-(4-chlorophenyl)-3-(4-methylphenyl)-5H,6H,7H,8H-imidazo[1,2-a]pyrazin-7-yl]-2-methylpropan-1-one; 7-benzyl-N,2-bis(4-fluorophenyl)-5H,6H,7H,8H-imidazo[1,2-a]pyrazin-3-amine; benzyl N-{2-[2-(4-fluorophenyl)-3-[(4-fluorophenyl)amino]-5H,6H,7H,8H-imidazo[1,2-a]pyrazin-7-yl]-2-oxoethyl}carbamate; 2-amino-3,3,3-trifluoro-1-[2-(4-fluorophenyl)-3-[(4-fluorophenyl)amino]-

5H,6H,7H, 8H-imidazo[1,2-a]pyrazin-7-yl]propan-1-one; 2-amino-1-[2-(4-fluoro-2-hydroxyphenyl)-3-[(4-fluorophenyl)amino]-5H,6H,7H,8H-imidazo[1,2-a]pyrazin-7-yl] ethan-1-one; 2-amino-1-{3-[(4-fluorophenyl)amino]-2-(4-methylphenyl)-5H,6H,7H,8H-imidazo[1,2-a]pyrazin-7-yl}ethan-1-one; 2-amino-1-{3-[(4-fluorophenyl)amino]-2-(4-methoxyphenyl)-5H,6H,7H,8H-imidazo[1,2-a]pyrazin-7-yl}ethan-1-one; 2-amino-1-[2-(4-bromophenyl)-3-[(4-fluorophenyl)amino]-5H,6H,7H,8H-imidazo[1,2-a]pyrazin-7-yl]ethan-1-one; 2-amino-1-[2-(4-chlorophenyl)-3-[(4-fluorophenyl)amino]-5H,6H,7H,8H-imidazo[1,2-a]pyrazin-7-yl]ethan-1-one; 2-amino-1-[2-(3-fluorophenyl)-3-[(4-fluorophenyl)amino]-5H,6H,7H, 8H-imidazo[1,2-a]pyrazin-7-yl]ethan-1-one; 2-(3,3-difluoropyrrolidin-1-yl)-1-[2-(4-fluorophenyl)-3-[(4-fluorophenyl)amino]-5H,6H,7H, 8H-imidazo[1,2-a]pyrazin-7-yl]ethan-1-one; 1-[2-(4-fluorophenyl)-3-[(4-fluorophenyl)amino]-5H,6H,7H,8H-imidazo[1,2-a]pyrazin-7-yl]-2-[(3R)-3-fluoropyrrolidin-1-yl]ethan-1-one; 1-[2-(4-fluorophenyl)-3-[(4-fluorophenyl)amino]-5H,6H,7H,8H-imidazo[1,2-a]pyrazin-7-yl]-2-[(3S)-3-fluoropyrrolidin-1-yl]ethan-1-one; 1-[2-(4-fluorophenyl)-3-[(4-fluorophenyl)amino]-5H,6H,7H, 8H-imidazo[1,2-a]pyrazin-7-yl]-2-(4-fluoropiperidin-1-yl)ethan-1-one; 1-[2-(4-fluorophenyl)-3-[(4-fluorophenyl)amino]-5H,6H,7H,8H-imidazo[1,2-a]pyrazin-7-yl]-2-[4-(trifluoromethyl) piperidin-1-yl]ethan-1-one; 2-(4,4-difluoropiperidin-1-yl)-1-[2-(4-fluorophenyl)-3-[(4-fluorophenyl)amino]-5H,6H, 7H,8H-imidazo[1,2-a]pyrazin-7-yl]ethan-1-one; 1-[2-(4-fluorophenyl)-3-[(4-fluorophenyl)amino]-5H,6H,7H,8H-imidazo[1,2-a]pyrazin-7-yl]-2-[3-(trifluoromethyl) piperidin-1-yl]ethan-1-one; 1-[2-(4-fluorophenyl)-3-[(4-fluorophenyl)amino]-5H,6H,7H,8H-imidazo[1,2-a]pyrazin-7-yl]-2-(3-hydroxypiperidin-1-yl)ethan-1-one; 2-[(2,2-difluoroethyl)amino]-1-[2-(4-fluorophenyl)-3-[(4-fluorophenyl)amino]-5H,6H,7H,8H-imidazo[1,2-a]pyrazin-7-yl]ethan-1-one; 2-amino-1-{3-[(3,5-difluorophenyl)amino]-2-(4-fluorophenyl)-5H,6H,7H,8H-imidazo[1,2-a]pyrazin-7-yl}-2-methylpropan-1-one; 2-amino-1-{3-[(3,5-difluorophenyl)amino]-2-(4-fluorophenyl)-5H,6H,7H,8H-imidazo[1,2-a]pyrazin-7-yl}ethan-1-one; 2-cyclopropylamino)-1-[2-(4-fluorophenyl)-3-[(4-fluorophenyl)amino]-5H,6H,7H,8H-imidazo[1,2-a]pyrazin-7-yl] ethan-1-one; 1-[2-(4-fluorophenyl)-3-[(4-fluorophenyl)amino]-5H,6H,7H,8H-imidazo[1,2-a]pyrazin-7-yl]-2-[(2-methylpropyl)amino]ethan-1-one; 2-amino-1-[2-(3-fluorophenyl)-3-[(4-fluorophenyl)amino]-5H,6H,7H,8H-imidazo[1,2-a]pyrazin-7-yl]-2-methylpropan-1-one; 2-amino-1-{3-[(4-chloro-3-fluorophenyl)amino]-2-(4-fluorophenyl)-5H,6H,7H,8H-imidazo[1,2-a]pyrazin-7-yl}ethan-1-one; 2-amino-1-[2-(4-fluorophenyl)-3-{[4-(trifluoromethyl)phenyl]amino}-5H,6H,7H,8H-imidazo[1,2-a] pyrazin-7-yl]-2-methylpropan-1-one; 2-amino-1-[2-(4-fluorophenyl)-3-{[4-(trifluoromethyl)phenyl]amino}-5H, 6H,7H,8H-imidazo[1,2-a]pyrazin-7-yl]ethan-1-one; 2-(3,3-difluoropiperidin-1-yl)-1-[2-(4-fluorophenyl)-3-[(4-methylphenyl)amino]-5H,6H,7H,8H-imidazo[1,2-a] pyrazin-7-yl]ethan-1-one; 1-[2-(4-fluorophenyl)-3-[(4-methylphenyl)amino]-5H,6H,7H,8H-imidazo[1,2-a] pyrazin-7-yl]-2-(methylamino)ethan-1-one; 1-{3-[(4-chlorophenyl)amino]-2-(4-fluorophenyl)-5H,6H,7H,8H-imidazo[1,2-a]pyrazin-7-yl}-2-(3,3-difluoropiperidin-1-yl) ethan-1-one; 1-{3-[(4-chlorophenyl)amino]-2-(4-fluorophenyl)-5H,6H,7H,8H-imidazo[1,2-a]pyrazin-7-yl}-2-(methylamino)ethan-1-one; 2-amino-1-{3-[(3-chloro-4-fluorophenyl)amino]-2-(4-fluorophenyl)-5H,6H,7H,8H-imidazo[1,2-a]pyrazin-7-yl}ethan-1-one; 2-amino-1-{3-[(2,4-difluorophenyl)amino]-2-(4-fluorophenyl)-5H,6H,7H, 8H-imidazo[1,2-a]pyrazin-7-yl}-2-methylpropan-1-one; 2-amino-1-{3-[(2,4-difluorophenyl)amino]-2-(4-fluorophenyl)-5H,6H,7H,8H-imidazo[1,2-a]pyrazin-7-yl}ethan-1-one; (2S)-1-[2-(4-fluorophenyl)-3-[(4-methylphenyl) amino]-5H,6H,7H,8H-imidazo[1,2-a]pyrazin-7-yl]-2-hydroxypropan-1-one; 1-[2-(4-fluorophenyl)-3-[(4-methylphenyl)amino]-5H,6H,7H,8H-imidazo[1,2-a] pyrazin-7-yl]-2-hydroxy-2-phenylethan-1-one; (2S)-2-amino-1-[2-(4-fluorophenyl)-3-[(4-methylphenyl)amino]-5H,6H,7H,8H-imidazo[1,2-a]pyrazin-7-yl]propan-1-one; (2R)-2-amino-1-[2-(4-fluorophenyl)-3-[(4-methylphenyl)amino]-5H,6H,7H,8H-imidazo[1,2-a]pyrazin-7-yl]propan-1-one; (2S)-2-amino-1-[2-(4-fluorophenyl)-3-[(4-methylphenyl)amino]-5H,6H,7H,8H-imidazo[1,2-a]pyrazin-7-yl] butan-1-one; 2-(4-fluorophenyl)-N-(4-methylphenyl)-7-{[(3R)-piperidin-3-yl]carbonyl}-5H,6H,7H,8H-imidazo[1,2-a]pyrazin-3-amine; 2-(4-fluorophenyl)-N-(4-methylphenyl)-7-{[(3S)-piperidin-3-yl]carbonyl}-5H,6H,7H,8H-imidazo[1,2-a]pyrazin-3-amine; 7-[2-(diethylamino)ethyl]-2-(4-fluorophenyl)-N-(4-methylphenyl)-5H,6H,7H,8H-imidazo[1,2-a]pyrazin-3-amine; 7-{[(2S)-azetidin-2-yl] carbonyl}-2-(4-fluorophenyl)-N-(4-methylphenyl)-5H,6H, 7H,8H-imidazo[1,2-a]pyrazin-3-amine; 2-(4-fluorophenyl)-N-(4-methylphenyl)-7-{[(2R)-pyrrolidin-2-yl]carbonyl}-5H,6H,7H,8H-imidazo[1,2-a]pyrazin-3-amine; 2-(4-fluorophenyl)-N-(4-methylphenyl)-7-{[(2S)-pyrrolidin-2-yl]carbonyl}-5H,6H,7H,8H-imidazo[1,2-a]pyrazin-3-amine; 2-(4-fluorophenyl)-N-(4-methylphenyl)-7-{[(2S)-piperidin-2-yl]carbonyl}-5H,6H,7H,8H-imidazo[1,2-a] pyrazin-3-amine; 2-(4-fluorophenyl)-N-(4-methylphenyl)-7-{[(2R)-piperidin-2-yl]carbonyl}-5H,6H,7H,8H-imidazo [1,2-a]pyrazin-3-amine; 2-amino-1-{3-[(4-chloro-3-fluorophenyl)amino]-2-(4-fluorophenyl)-5H,6H,7H,8H-imidazo[1,2-a]pyrazin-7-yl}-2-methylpropan-1-one; 2-(4-fluorophenyl)-N-(4-methylphenyl)-7-{[(3R)-pyrrolidin-3-yl]carbonyl}-5H,6H,7H,8H-imidazo[1,2-a]pyrazin-3-amine; 2-(4-fluorophenyl)-N-(4-methylphenyl)-7-{[(3S)-pyrrolidin-3-yl]carbonyl}-5H,6H,7H,8H-imidazo[1,2-a] pyrazin-3-amine; (2R)-2-amino-1-[2-(4-fluorophenyl)-3-[(4-methylphenyl)amino]-5H,6H,7H,8H-imidazo[1,2-a] pyrazin-7-yl]-2-phenylethan-1-one; (2S)-2-amino-1-[2-(4-fluorophenyl)-3-[(4-methylphenyl)amino]-5H,6H,7H,8H-imidazo[1,2-a]pyrazin-7-yl]-2-phenylethan-1-one; 1-{[2-(4-fluorophenyl)-3-[(4-methylphenyl)amino]-5H,6H,7H, 8H-imidazo[1,2-a]pyrazin-7-yl]carbonyl}cyclopropan-1-ol; 1-[2-(4-fluorophenyl)-3-[(4-methylphenyl)amino]-5H,6H, 7H,8H-imidazo[1,2-a]pyrazin-7-yl]-3-hydroxy-3-methylbutan-1-one; N-[(5S)-5-amino-6-[2-(4-fluorophenyl)-3-[(4-methylphenyl)amino]-5H,6H,7H,8H-imidazo[1,2-a] pyrazin-7-yl]-6-oxohexyl]acetamide; N-[(5S)-5-amino-6-[2-(4-fluorophenyl)-3-[(4-methylphenyl)amino]-5H,6H,7H, 8H-imidazo[1,2-a]pyrazin-7-yl]-6-oxohexyl]-2,2,2-trifluoroacetamide; 1-[2-(4-fluorophenyl)-3-[(4-methylphenyl)amino]-5H,6H,7H,8H-imidazo[1,2-a] pyrazin-7-yl]-3-hydroxypropan-1-one; 1-[2-(4-fluorophenyl)-3-[(4-methylphenyl)amino]-5H,6H,7H,8H-imidazo[1,2-a]pyrazin-7-yl]-2-hydroxy-3-methylbutan-1-one; (1S,2S)-2-{[2-(4-fluorophenyl)-3-[(4-methylphenyl) amino]-5H,6H,7H, 8H-imidazo[1,2-a]pyrazin-7-yl] carbonyl}cyclopentan-1-ol; (2S)-1-[2-(4-fluorophenyl)-3-[(4-methylphenyl)amino]-5H,6H,7H,8H-imidazo[1,2-a] pyrazin-7-yl]-2-hydroxy-3-phenylpropan-1-one; 2-(4-fluorophenyl)-1-[2-(4-fluorophenyl)-3-[(4-methylphenyl) amino]-5H,6H,7H, 8H-imidazo[1,2-a]pyrazin-7-yl]-2-hydroxyethan-1-one; 1-[2-(4-fluorophenyl)-3-[(4-methylphenyl)amino]-5H,6H,7H,8H-imidazo[1,2-a] pyrazin-7-yl]-3-hydroxybutan-1-one; (2R)-1-[2-(4- fluorophenyl)-3-[(4-methylphenyl)amino]-5H,6H,7H,8H-imidazo[1,2-a]pyrazin-7-yl]-2-hydroxy-3-phenylpropan-1-one; (2S)-1-[2-(4-fluorophenyl)-3-[(4-methylphenyl)amino]-5H,6H,7H,8H-imidazo[1,2-a]pyrazin-7-yl]-2-hydroxy-3,3-dimethylbutan-1-one; 1-[2-(4-fluorophenyl)-3-[(4-methylphenyl)amino]-5H,6H,7H, 8H-imidazo[1,2-a]pyrazin-7-yl]-2-hydroxy-2-phenylpropan-1-one; 1-[2-(4-fluorophenyl)-3-[(4-methylphenyl)amino]-5H,6H,7H,8H-imidazo[1,2-a]pyrazin-7-yl]-2-hydroxy-2,2-diphenylethan-1-one; 2-(4-fluorophenyl)-N-(4-methylphenyl)-5H,6H,7H, 8H-imidazo[1,2-a]pyrazin-3-amine; 1-[2-(4-fluorophenyl)-3-[(4-methylphenyl)amino]-5H,6H,7H,8H-imidazo[1,2-a]pyrazin-7-yl]-2-hydroxy-2-(trifluoromethyl)butan-1-one; 1-[2-(4-fluorophenyl)-3-[(4-methylphenyl)amino]-5H,6H,7H,8H-imidazo[1,2-a]pyrazin-7-yl]-2-hydroxy-2-methylpropan-1-one; 1-{[2-(4-fluorophenyl)-3-[(4-methylphenyl)amino]-5H,6H,7H,8H-imidazo[1,2-a]pyrazin-7-yl]carbonyl}cyclopentan-1-ol; 1-{[2-(4-fluorophenyl)-3-[(4-methylphenyl)amino]-5H,6H,7H,8H-imidazo[1,2-a]pyrazin-7-yl]carbonyl}cyclohexan-1-ol; (2R)-1-[2-(4-fluorophenyl)-3-[(4-methylphenyl)amino]-5H,6H,7H,8H-imidazo[1,2-a]pyrazin-7-yl]-2-hydroxy-4-phenylbutan-1-one; 1-[2-(4-fluorophenyl)-3-[(4-methylphenyl)amino]-5H, 6H,7H,8H-imidazo[1,2-a]pyrazin-7-yl]-3-hydroxy-2,2-dimethyl-3-(4-methylphenyl)propan-1-one; 4,4,4-trifluoro-1-[2-(4-fluorophenyl)-3-[(4-methylphenyl)amino]-5H,6H, 7H,8H-imidazo[1,2-a]pyrazin-7-yl]-3-hydroxy-3-methylbutan-1-one; (2S)-2-cyclohexyl-1-[2-(4-fluorophenyl)-3-[(4-methylphenyl)amino]-5H,6H,7H,8H-imidazo[1,2-a]pyrazin-7-yl]-2-hydroxyethan-1-one; 1-[2-(4-fluorophenyl)-3-[(4-methylphenyl)amino]-5H,6H,7H, 8H-imidazo[1,2-a]pyrazin-7-yl]-2-hydroxy-2-(4-methoxyphenyl)ethan-1-one; 2-(3,5-difluorophenyl)-1-[2-(4-fluorophenyl)-3-[(4-methylphenyl)amino]-5H,6H,7H, 8H-imidazo[1,2-a]pyrazin-7-yl]-2-hydroxyethan-1-one; 1-[2-(4-fluorophenyl)-3-[(4-methylphenyl)amino]-5H,6H, 7H,8H-imidazo[1,2-a]pyrazin-7-yl]-2-hydroxy-2-[3-(trifluoromethyl)phenyl]ethan-1-one; 1-[2-(4-fluorophenyl)-3-[(4-methylphenyl)amino]-5H,6H,7H,8H-imidazo[1,2-a]pyrazin-7-yl]-2-methoxy-2-phenylethan-1-one; 2-(4-bromophenyl)-1-[2-(4-fluorophenyl)-3-[(4-methylphenyl)amino]-5H,6H,7H,8H-imidazo[1,2-a]pyrazin-7-yl]-2-hydroxyethan-1-one; 1-[2-(4-fluorophenyl)-3-[(4-methylphenyl)amino]-5H,6H,7H,8H-imidazo[1,2-a]pyrazin-7-yl]-2-hydroxy-2-[4-(trifluoromethyl)phenyl]ethan-1-one; 3,3,3-trifluoro-1-[2-(4-fluorophenyl)-3-[(4-methylphenyl)amino]-5H,6H,7H,8H-imidazo[1,2-a]pyrazin-7-yl]-2-methoxy-2-phenylpropan-1-one; 1-[2-(4-fluorophenyl)-3-[(4-methylphenyl)amino]-5H,6H,7H,8H-imidazo[1,2-a]pyrazin-7-yl]-2-hydroxy-2-(3-hydroxyphenyl)ethan-1-one; 1-[2-(4-fluorophenyl)-3-[(4-methylphenyl)amino]-5H,6H,7H,8H-imidazo[1,2-a]pyrazin-7-yl]-2-hydroxy-2-(4-hydroxyphenyl)ethan-1-one; 2-(2-chlorophenyl)-1-[2-(4-fluorophenyl)-3-[(4-methylphenyl)amino]-5H,6H,7H,8H-imidazo[1,2-a]pyrazin-7-yl]-2-hydroxyethan-1-one; 2-(4-bromo-2-fluorophenyl)-1-[2-(4-fluorophenyl)-3-[(4-methylphenyl)amino]-5H,6H,7H,8H-imidazo[1,2-a]pyrazin-7-yl]-2-hydroxyethan-1-one; 2-(4-chlorophenyl)-1-[2-(4-fluorophenyl)-3-[(4-methylphenyl)amino]-5H,6H,7H,8H-imidazo[1,2-a]pyrazin-7-yl]-2-hydroxyethan-1-one; (2S)-1-[2-(4-fluorophenyl)-3-[(4-methylphenyl)amino]-5H,6H,7H,8H-imidazo[1,2-a]pyrazin-7-yl]-2-hydroxy-4-methylpentan-1-one; (3S)-1-[2-(4-fluorophenyl)-3-[(4-methylphenyl)amino]-5H,6H,7H,8H-imidazo[1,2-a]pyrazin-7-yl]-3-hydroxy-3-phenylpropan-1-one; 2-(4-fluorophenyl)-N-(4-methylphenyl)imidazo[1,2-a]pyrazin-3-amine; (2R)-1-[2-(4-fluorophenyl)-3-[(4-methylphenyl)amino]-5H,6H,7H, 8H-imidazo[1,2-a]pyrazin-7-yl]-2-hydroxy-2-phenylethan-1-one; (2S)-1-[2-(4-fluorophenyl)-3-[(4-methylphenyl)amino]-5H,6H,7H,8H-imidazo[1,2-a]pyrazin-7-yl]-2-hydroxy-2-phenylethan-1-one; 7-[(1-aminocyclobutyl)carbonyl]-2-(4-fluorophenyl)-N-(4-methylphenyl)-5H,6H,7H,8H-imidazo[1,2-a]pyrazin-3-amine; 7-[(1-aminocyclopentyl)carbonyl]-2-(4-fluorophenyl)-N-(4-methylphenyl)-5H,6H,7H,8H-imidazo[1,2-a]pyrazin-3-amine; 7-[(1-aminocyclohexyl)carbonyl]-2-(4-fluorophenyl)-N-(4-methylphenyl)-5H,6H,7H,8H-imidazo[1,2-a]pyrazin-3-amine; 2-amino-4,4,4-trifluoro-1-[2-(4-fluorophenyl)-3-[(4-methylphenyl)amino]-5H,6H,7H,8H-imidazo[1,2-a]pyrazin-7-yl]butan-1-one; 1-[2-(4-fluorophenyl)-3-[(4-methylphenyl)amino]-5H,6H,7H,8H-imidazo[1,2-a]pyrazin-7-yl]-3-hydroxy-3-methylpentan-1-one; 2-amino-3,3,3-trifluoro-1-[2-(4-fluorophenyl)-3-[(4-methylphenyl)amino]-5H,6H,7H,8H-imidazo[1,2-a]pyrazin-7-yl]propan-1-one; (2S)-3-cyclohexyl-1-[2-(4-fluorophenyl)-3-[(4-methylphenyl)amino]-5H,6H,7H,8H-imidazo[1,2-a]pyrazin-7-yl]-2-hydroxypropan-1-one; 2-(benzylamino)-1-[2-(4-fluorophenyl)-3-[(4-methylphenyl)amino]-5H,6H,7H,8H-imidazo[1,2-a]pyrazin-7-yl]ethan-1-one; 2-(dipropylamino)-1-[2-(4-fluorophenyl)-3-[(4-methylphenyl)amino]-5H,6H,7H,8H-imidazo[1,2-a]pyrazin-7-yl]ethan-1-one; (2S)-2-(dipropylamino)-1-[2-(4-fluorophenyl)-3-[(4-methylphenyl)amino]-5H,6H,7H,8H-imidazo[1,2-a]pyrazin-7-yl]propan-1-one; (2S)-1-[2-(4-fluorophenyl)-3-[(4-methylphenyl)amino]-5H,6H,7H,8H-imidazo[1,2-a]pyrazin-7-yl]-2-(methylamino)-3-phenylpropan-1-one; benzyl(4S)-4-{[(tert-butoxy)carbonyl]amino}-5-[2-(4-fluorophenyl)-3-[(4-methylphenyl)amino]-5H,6H,7H,8H-imidazo[1,2-a]pyrazin-7-yl]-5-oxopentanoate; benzyl(3S)-3-{[(tert-butoxy)carbonyl]amino}-4-[2-(4-fluorophenyl)-3-[(4-methylphenyl)amino]-5H,6H,7H,8H-imidazo[1,2-a]pyrazin-7-yl]-4-oxobutanoate; tert-butyl N-[(5S)-5-{[(benzyloxy)carbonyl]amino}-6-[2-(4-fluorophenyl)-3-[(4-methylphenyl)amino]-5H,6H,7H,8H-imidazo[1,2-a]pyrazin-7-yl]-6-oxohexyl]carbamate; 2-(cyclopropylamino)-1-[2-(4-fluorophenyl)-3-[(4-methylphenyl)amino]-5H,6H,7H,8H-imidazo[1,2-a]pyrazin-7-yl]ethan-1-one; N-[4-({2-[2-(4-fluorophenyl)-3-[(4-methylphenyl)amino]-5H,6H,7H,8H-imidazo[1,2-a]pyrazin-7-yl]-2-oxoethyl}amino)butyl]acetamide; 2-(4-fluorophenyl)-7-{2-[2-(4-fluorophenyl)-3-[(4-methylphenyl)amino]-5H,6H,7H,8H-imidazo[1,2-a]pyrazin-7-yl]ethyl}-N-(4-methylphenyl)-5H,6H,7H,8H-imidazo[1,2-a]pyrazin-3-amine; (2S)-2,6-diamino-1-[2-(4-fluorophenyl)-3-[(4-methylphenyl)amino]-5H,6H,7H,8H-imidazo[1,2-a]pyrazin-7-yl]hexan-1-one; (2S)-2-amino-3-(4-aminophenyl)-1-[2-(4-fluorophenyl)-3-[(4-methylphenyl)amino]-5H,6H,7H,8H-imidazo[1,2-a]pyrazin-7-yl]propan-1-one; N-[(5S)-5-amino-6-[2-(4-fluorophenyl)-3-[(4-methylphenyl)amino]-5H,6H,7H,8H-imidazo[1,2-a]pyrazin-7-yl]-6-oxohexyl]butanamide; N-[(5S)-5-amino-6-[2-(4-fluorophenyl)-3-[(4-methylphenyl)amino]-5H,6H,7H,8H-imidazo[1,2-a]pyrazin-7-yl]-6-oxohexyl]-1-(5-{2-oxo-hexahydro-1H-thieno[3,4-d]imidazolidin-4-yl}pentanamido)-3,6,9,12-tetraoxapentadecan-15-amide; N-{4-[(2S)-2-amino-3-[2-(4-fluorophenyl)-3-[(4-methylphenyl)amino]-5H,6H,7H,8H-imidazo[1,2-a]pyrazin-7-yl]-3-oxopropyl]phenyl}acetamide; 2-[bis(2-hydroxyethyl)amino]-1-[2-(4-fluorophenyl)-3-[(4-methylphenyl)amino]-5H,6H,7H,8H-imidazo[1,2-a]pyrazin-7-yl]ethan-1-one; (4S)-4-{[2-(4-fluorophenyl)-3-[(4-methylphenyl)amino]-5H,6H,7H,8H-imidazo[1,2-a]pyrazin-7-yl]carbonyl}azetidin-2-one; (2S)-2-amino-1-[2-(4-fluorophenyl)-3-[(4-methylphenyl)amino]-5H,6H,7H,8H-imidazo[1,2-a]pyrazin-7-yl]-3-hydroxypropan-1-one; 2,2,2-trifluoro-N-[(2S)-1-[2-(4-fluorophenyl)-3-[(4-methylphenyl)amino]-5H,6H,7H,8H-imidazo[1,2-a]pyrazin-7-yl]-3-hydroxy-1-oxopropan-2-yl]acetamide; 6-{[2-(4-fluorophenyl)-3-[(4-methylphenyl)amino]-5H,6H,7H,8H-imidazo[1,2-a]pyrazin-7-yl]carbonyl}-1,2,3,4-tetrahydropyrimidine-2,4-dione; {2-[2-(4-fluorophenyl)-3-[(4-methylphenyl)amino]-5H,6H,7H,8H-imidazo[1,2-a]pyrazin-7-yl]-2-oxoethyl}urea; 1-{2-[2-(4-fluorophenyl)-3-[(4-methylphenyl)amino]-5H,6H,7H,8H-imidazo[1,2-a]pyrazin-7-yl]-2-oxoethyl}guanidine; 1-[2-(4-fluorophenyl)-3-[(4-methylphenyl)amino]-5H,6H,7H,8H-imidazo[1,2-a]pyrazin-7-yl]-2-(phenylamino)ethan-1-one; (2S)-2-amino-1-[2-(4-fluorophenyl)-3-[(4-methylphenyl)amino]-5H,6H,7H,8H-imidazo[1,2-a]pyrazin-7-yl]-3-methylbutan-1-one; (2S)-2-amino-1-[2-(4-fluorophenyl)-3-[(4-methylphenyl)amino]-5H,6H,7H,8H-imidazo[1,2-a]pyrazin-7-yl]-3,3-dimethylbutan-1-one; (3S)-3-amino-4-(4-bromophenyl)-1-[2-(4-fluorophenyl)-3-[(4-methylphenyl)amino]-5H,6H,7H,8H-imidazo[1,2-a]pyrazin-7-yl]butan-1-one; (3S)-3-amino-1-[2-(4-fluorophenyl)-3-[(4-methylphenyl)amino]-5H,6H,7H,8H-imidazo[1,2-a]pyrazin-7-yl]-4-(2,4,5-trifluorophenyl)butan-1-one; 2-(4-chlorophenyl)-1-[2-(4-fluorophenyl)-3-[(4-methylphenyl)amino]-5H,6H,7H,8H-imidazo[1,2-a]pyrazin-7-yl]propan-1-one; 2-(4-chlorophenyl)-1-[2-(4-fluorophenyl)-3-[(4-methylphenyl)amino]-5H,6H,7H,8H-imidazo[1,2-a]pyrazin-7-yl]-2-methylpropan-1-one; (2S)-1-[2-(4-fluorophenyl)-3-[(4-methylphenyl)amino]-5H,6H,7H,8H-imidazo[1,2-a]pyrazin-7-yl]-2-phenylpropan-1-one; 2-(4-fluorophenyl)-7-{[(6S)-1H,4H,5H,6H,7H-imidazo[4,5-c]pyridin-6-yl]carbonyl}-N-(4-methylphenyl)-5H,6H,7H,8H-imidazo[1,2-a]pyrazin-3-amine; (2S)-2-(dimethylamino)-1-[2-(4-fluorophenyl)-3-[(4-methylphenyl)amino]-5H,6H,7H,8H-imidazo[1,2-a]pyrazin-7-yl]-3-phenylpropan-1-one; 2-[4-(2-aminoethyl)piperidin-1-yl]-1-[2-(4-fluorophenyl)-3-[(4-methylphenyl)amino]-5H,6H,7H,8H-imidazo[1,2-a]pyrazin-7-yl]ethan-1-one; 2-(4-fluorophenyl)-7-[(4-methanesulfonylphenyl)methyl]-N-(4-methylphenyl)-5H,6H,7H,8H-imidazo[1,2-a]pyrazin-3-amine; 2-(4-fluorophenyl)-N-(4-methylphenyl)-7-{[4-(morpholin-4-yl)phenyl]methyl}-5H,6H,7H,8H-imidazo[1,2-a]pyrazin-3-amine; 2-(4-fluorophenyl)-N-(4-methylphenyl)-7-{[4-(4-methylpiperazin-1-yl)phenyl]methyl}-5H,6H,7H,8H-imidazo[1,2-a]pyrazin-3-amine; 7-{[4-(diethylamino)phenyl]methyl}-2-(4-fluorophenyl)-N-(4-methylphenyl)-5H,6H,7H,8H-imidazo[1,2-a]pyrazin-3-amine; 7-({4-[3-(dimethylamino)propoxy]phenyl}methyl)-2-(4-fluorophenyl)-N-(4-methylphenyl)-5H,6H,7H,8H-imidazo[1,2-a]pyrazin-3-amine; 2-(4-fluorophenyl)-N-(4-methylphenyl)-7-{[4-(pyridin-4-yl)phenyl]methyl}-5H,6H,7H,8H-imidazo[1,2-a]pyrazin-3-amine; tert-butyl N-[(2S)-1-[2-(4-fluorophenyl)-3-[(4-methylphenyl)amino]-5H,6H,7H,8H-imidazo[1,2-a]pyrazin-7-yl]-1-oxo-3-(4-propanamidophenyl)propan-2-yl]carbamate; tert-butyl N-[(2S)-1-[2-(4-fluorophenyl)-3-[(4-methylphenyl)amino]-5H,6H,7H,8H-imidazo[1,2-a]pyrazin-7-yl]-1-oxo-3-(propylcarbamoyl)propan-2-yl]carbamate; N-{4-[(2S)-2-amino-3-[2-(4-fluorophenyl)-3-[(4-methylphenyl)amino]-5H,6H,7H,8H-imidazo[1,2-a]pyrazin-7-yl]-3-oxopropyl]phenyl}propanamide; (4S)-4-amino-5-[2-(4-fluorophenyl)-3-[(4-methylphenyl)amino]-5H,6H,7H,8H-imidazo[1,2-a]pyrazin-7-yl]-5-oxo-N-propylpentanamide; (3S)-3-amino-4-[2-(4-fluorophenyl)-3-[(4-methylphenyl)amino]-5H,6H,7H,8H-imidazo[1,2-a]pyrazin-7-yl]-4-oxo-N-propylbutanamide; 3-amino-4,4,4-trifluoro-1-[2-(4-fluorophenyl)-3-[(4-methylphenyl)amino]-5H,6H,7H,8H-imidazo[1,2-a]pyrazin-7-yl]butan-1-one; 2-(3-fluorophenyl)-N-(4-fluorophenyl)-5H,6H,7H,8H-imidazo[1,2-a]pyrazin-3-amine; N-(4-chloro-3-fluorophenyl)-2-(4-fluorophenyl)-5H,6H,7H,8H-imidazo[1,2-a]pyrazin-3-amine; 7-{[(1S,2R)-2-aminocyclopentyl]carbonyl}-2-(4-fluorophenyl)-N-(4-methylphenyl)-5H,6H,7H,8H-imidazo[1,2-a]pyrazin-3-amine; 2-amino-1-{3-[(4-chloro-3-fluorophenyl)amino]-2-(4-fluorophenyl)-5H,6H,7H,8H-imidazo[1,2-a]pyrazin-7-yl}-3,3,3-trifluoropropan-1-one; (2R)-2-amino-3,3,3-trifluoro-1-[2-(4-fluorophenyl)-3-[(4-fluorophenyl)amino]-5H,6H,7H,8H-imidazo[1,2-a]pyrazin-7-yl]propan-1-one; (2S)-2-amino-3,3,3-trifluoro-1-[2-(4-fluorophenyl)-3-[(4-fluorophenyl)amino]-5H,6H,7H,8H-imidazo[1,2-a]pyrazin-7-yl]propan-1-one; N-{4-[(2S)-2-amino-3-[2-(4-fluorophenyl)-3-[(4-methylphenyl)amino]-5H,6H,7H,8H-imidazo[1,2-a]pyrazin-7-yl]-3-oxopropyl]phenyl}butanamide; (2S)-1-[2-(4-fluorophenyl)-3-[(4-methylphenyl)amino]-5H,6H,7H,8H-imidazo[1,2-a]pyrazin-7-yl]-2-methoxypropan-1-one; 2-(4-fluorophenyl)-N-(4-methylphenyl)-7-{[(2R)-oxolan-2-yl]carbonyl}-5H,6H,7H,8H-imidazo[1,2-a]pyrazin-3-amine; 2-(4-fluorophenyl)-N-(4-methylphenyl)-7-{[(2S)-oxolan-2-yl]carbonyl}-5H,6H,7H,8H-imidazo[1,2-a]pyrazin-3-amine; 1-[2-(4-fluorophenyl)-3-[(4-methylphenyl)amino]-5H,6H,7H,8H-imidazo[1,2-a]pyrazin-7-yl]-2-phenoxybutan-1-one; 1-[2-(4-fluorophenyl)-3-[(4-methylphenyl)amino]-5H,6H,7H,8H-imidazo[1,2-a]pyrazin-7-yl]-2-phenoxypropan-1-one; 2-(3-chlorophenoxy)-1-[2-(4-fluorophenyl)-3-[(4-methylphenyl)amino]-5H,6H,7H,8H-imidazo[1,2-a]pyrazin-7-yl]propan-1-one; (2S)-1-[2-(4-fluorophenyl)-3-[(4-methylphenyl)amino]-5H,6H,7H,8H-imidazo[1,2-a]pyrazin-7-yl]-2-hydroxy-3-methylbutan-1-one; (2R)-1-[2-(4-fluorophenyl)-3-[(4-methylphenyl)amino]-5H,6H,7H,8H-imidazo[1,2-a]pyrazin-7-yl]-2-hydroxy-3-methylbutan-1-one; 1-[2-(4-fluorophenyl)-3-[(4-methylphenyl)amino]-5H,6H,7H,8H-imidazo[1,2-a]pyrazin-7-yl]-2-(pyrimidin-4-yl)ethan-1-one; N-(4-chloro-3-fluorophenyl)-2-(3-fluorophenyl)imidazo[1,2-a]pyrazin-3-amine; 1-[2-(4-fluorophenyl)-3-[(4-methylphenyl)amino]-5H,6H,7H,8H-imidazo[1,2-a]pyrazin-7-yl]-3-methyl-2-(2-methylphenoxy)butan-1-one; 2-(4-fluorophenyl)-N-(4-methylphenyl)-7-[(oxan-4-yl)carbonyl]-5H,6H,7H,8H-imidazo[1,2-a]pyrazin-3-amine; (2S)-2-ethoxy-1-[2-(4-fluorophenyl)-3-[(4-methylphenyl)amino]-5H,6H,7H,8H-imidazo[1,2-a]pyrazin-7-yl]-3-(4-hydroxyphenyl)propan-1-one; 1-[2-(4-fluorophenyl)-3-[(4-methylphenyl)amino]-5H,6H,7H,8H-imidazo[1,2-a]pyrazin-7-yl]-2-(oxolan-2-yl)ethan-1-one; 2-(4-fluorophenyl)-N-(4-methylphenyl)-7-[(oxolan-3-yl)carbonyl]-5H,6H,7H,8H-imidazo[1,2-a]pyrazin-3-amine; (2S)-2-amino-3-[4-(aminomethyl)phenyl]-1-[2-(4-fluorophenyl)-3-[(4-methylphenyl)amino]-5H,6H,7H,8H-imidazo[1,2-a]pyrazin-7-yl]propan-1-one; 2-(1-ethylpiperidin-4-yl)-1-[2-(4-fluorophenyl)-3-[(4-methylphenyl)amino]-5H,6H,7H,8H-imidazo[1,2-a]pyrazin-7-yl]ethan-1-one; 1-[2-(4-fluorophenyl)-3-[(4-methylphenyl)amino]-5H,6H,7H,8H-imidazo[1,2-a]pyrazin-7-yl]-2-(oxolan-3-yl)ethan-1-one; 1-[2-(4-fluorophenyl)-3-[(4-methylphenyl)amino]-5H,6H,7H,8H-imidazo[1,2-a]pyrazin-7-yl]-2-(oxan-2-yl)ethan-1-one; N-(4-chloro-3-fluorophenyl)-2-(3-fluorophenyl)-5H,6H,7H,8H-imidazo[1,2-a]pyrazin-3-amine; N-({4-[(2S)-2-amino-3-[2-(4-fluorophenyl)-3-[(4-methylphenyl)amino]-5H,6H,7H,8H-imidazo[1,2-a]pyrazin-7-yl]-3-oxopropyl]phenyl}methyl)butanamide; N-({4-[(2S)-2-amino-3-[2-(4-fluorophenyl)-3-[(4-methylphenyl)amino]-5H,6H,7H,8H-imidazo[1,2-a]pyrazin-7-yl]-3-oxopropyl]phenyl}methyl)propanamide; 1-[2-(4-fluorophenyl)-3-[(4-methylphenyl)amino]-5H,6H, 7H,8H-imidazo[1,2-a]pyrazin-7-yl]-2-(piperidin-4-yl) ethan-1-one; 2-amino-1-{3-[(4-chloro-3-fluorophenyl) amino]-2-(3-fluorophenyl)-5H,6H,7H,8H-imidazo[1,2-a] pyrazin-7-yl}-3,3,3-trifluoropropan-1-one; (2R)-1-{3-[(4-chloro-3-fluorophenyl)amino]-2-(3-fluorophenyl)-5H,6H, 7H,8H-imidazo[1,2-a]pyrazin-7-yl}-2-phenylpropan-1-one; (2S)-1-{3-[(4-chloro-3-fluorophenyl)amino]-2-(3-fluorophenyl)-5H,6H,7H,8H-imidazo[1,2-a]pyrazin-7-yl}-2-phenylpropan-1-one; (2R)-1-[2-(4-fluorophenyl)-3-[(4-methylphenyl)amino]-5H,6H,7H,8H-imidazo[1,2-a]pyrazin-7-yl]-2-phenylbutan-1-one; (2S)-1-[2-(4-fluorophenyl)-3-[(4-methylphenyl)amino]-5H,6H,7H,8H-imidazo[1,2-a] pyrazin-7-yl]-2-phenylbutan-1-one; 2-cyclopentyl-1-[2-(4-fluorophenyl)-3-[(4-methylphenyl)amino]-5H,6H,7H,8H-imidazo[1,2-a]pyrazin-7-yl]-2-phenylethan-1-one; 1-[2-(4-fluorophenyl)-3-[(4-methylphenyl)amino]-5H,6H,7H,8H-imidazo[1,2-a]pyrazin-7-yl]-2-(pyridin-4-yl)ethan-1-one; 2-amino-1-{3-[(4-chloro-3-fluorophenyl)amino]-2-(3-fluorophenyl)-5H,6H,7H,8H-imidazo[1,2-a]pyrazin-7-yl}ethan-1-one; 2-amino-1-{3-[(4-chloro-3-fluorophenyl) amino]-2-(3-fluorophenyl)-5H,6H,7H,8H-imidazo[1,2-a] pyrazin-7-yl}-2-methylpropan-1-one; 2-(3,5-dichlorophenyl)-1-[2-(4-fluorophenyl)-3-[(4-methylphenyl) amino]-5H,6H,7H,8H-imidazo[1,2-a]pyrazin-7-yl]ethan-1-one; 1-[2-(4-fluorophenyl)-3-[(4-methylphenyl)amino]-5H, 6H,7H, 8H-imidazo[1,2-a]pyrazin-7-yl]-3-methyl-2-phenylbutan-1-one; 1-[2-(4-fluorophenyl)-3-[(4-methylphenyl)amino]-5H,6H,7H,8H-imidazo[1,2-a] pyrazin-7-yl]-2-(4-methylphenyl)ethan-1-one; 2-(4-fluorophenyl)-1-[2-(4-fluorophenyl)-3-[(4-methylphenyl) amino]-5H,6H,7H,8H-imidazo[1,2-a]pyrazin-7-yl]ethan-1-one; 1-{3-[(4-chloro-3-fluorophenyl)amino]-2-(3-fluorophenyl)-5H,6H,7H,8H-imidazo[1,2-a]pyrazin-7-yl}-3-hydroxy-3-methylbutan-1-one; 1-[2-(3-fluorophenyl)-3-[(4-fluorophenyl)amino]-5H,6H,7H,8H-imidazo[1,2-a] pyrazin-7-yl]-3-hydroxy-3-methylbutan-1-one; benzyl(3S)-3-{[(tert-butoxy)carbonyl]amino}-4-{3-[(4-chloro-3-fluorophenyl)amino]-2-(3-fluorophenyl)-5H,6H,7H,8H-imidazo[1,2-a]pyrazin-7-yl}-4-oxobutanoate; benzyl(3S)-3-{[(tert-butoxy)carbonyl]amino}-4-[2-(3-fluorophenyl)-3-[(4-fluorophenyl)amino]-5H,6H,7H,8H-imidazo[1,2-a] pyrazin-7-yl]-4-oxobutanoate; tert-butyl N-[(2S)-1-{3-[(4-chloro-3-fluorophenyl)amino]-2-(3-fluorophenyl)-5H,6H, 7H, 8H-imidazo[1,2-a]pyrazin-7-yl}-3-(4-nitrophenyl)-1-oxopropan-2-yl]carbamate; tert-butyl N-[(2S)-1-[2-(3-fluorophenyl)-3-[(4-fluorophenyl)amino]-5H,6H,7H,8H-imidazo[1,2-a]pyrazin-7-yl]-3-(4-nitrophenyl)-1-oxopropan-2-yl]carbamate; (3S)-3-{[(tert-butoxy)carbonyl] amino}-4-{3-[(4-chloro-3-fluorophenyl)amino]-2-(3-fluorophenyl)-5H,6H,7H,8H-imidazo[1,2-a]pyrazin-7-yl}-4-oxobutanoic acid; (3S)-3-{[(tert-butoxy)carbonyl] amino}-4-[2-(3-fluorophenyl)-3-[(4-fluorophenyl)amino]-5H,6H,7H,8H-imidazo[1,2-a]pyrazin-7-yl]-4-oxobutanoic acid; tert-butyl N-[(2S)-3-(4-aminophenyl)-1-{3-[(4-chloro-3-fluorophenyl)amino]-2-(3-fluorophenyl)-5H,6H,7H,8H-imidazo[1,2-a]pyrazin-7-yl}-1-oxopropan-2-yl]carbamate; tert-butyl N-[(2S)-3-(4-aminophenyl)-1-[2-(3-fluorophenyl)-3-[(4-fluorophenyl)amino]-5H,6H,7H,8H-imidazo[1, 2-a]pyrazin-7-yl]-1-oxopropan-2-yl]carbamate; 1-[2-(4-fluorophenyl)-3-[(4-methylphenyl)amino]-5H,6H,7H,8H-imidazo[1,2-a]pyrazin-7-yl]-3-hydroxy-2,2-dimethylpropan-1-one; 1-[2-(4-fluorophenyl)-3-[(4-methylphenyl)amino]-5H,6H,7H,8H-imidazo[1,2-a] pyrazin-7-yl]-3-hydroxy-2-(hydroxymethyl)-2-methylpropan-1-one; tert-butyl N-[(2S)-3-(3-aminophenyl)-1-[2-(4-fluorophenyl)-3-[(4-methylphenyl)amino]-5H,6H, 7H,8H-imidazo[1,2-a]pyrazin-7-yl]-1-oxopropan-2-yl] carbamate; tert-butyl N-[(2S)-1-{3-[(4-chloro-3-fluorophenyl)amino]-2-(3-fluorophenyl)-5H,6H,7H,8H-imidazo[1,2-a]pyrazin-7-yl}-1-oxo-3-(propylcarbamoyl) propan-2-yl]carbamate; tert-butyl N-[(2S)-1-[2-(3-fluorophenyl)-3-[(4-fluorophenyl)amino]-5H,6H,7H,8H-imidazo[1,2-a]pyrazin-7-yl]-1-oxo-3-(propylcarbamoyl) propan-2-yl]carbamate; 4-{[2-(4-fluorophenyl)-5H,6H,7H, 8H-imidazo[1,2-a]pyrazin-3-yl]amino}benzonitrile; tert-butyl N-[(2S)-1-[2-(3-fluorophenyl)-3-[(4-fluorophenyl) amino]-5H,6H,7H,8H-imidazo[1,2-a]pyrazin-7-yl]-1-oxo-3-(pentylcarbamoyl)propan-2-yl]carbamate; 1-{[2-(4-fluorophenyl)-3-[(4-methylphenyl)amino]-5H,6H,7H,8H-imidazo[1,2-a]pyrazin-7-yl]carbonyl}-N,N-dimethylpyrrolidin-3-amine; tert-butyl N-[(2S)-1-{3-[(4-chloro-3-fluorophenyl)amino]-2-(3-fluorophenyl)-5H,6H, 7H,8H-imidazo[1,2-a]pyrazin-7-yl}-1-oxo-3-(4-pentanamidophenyl)propan-2-yl]carbamate; tert-butyl N-[(2S)-1-{3-[(4-chloro-3-fluorophenyl)amino]-2-(3-fluorophenyl)-5H,6H,7H,8H-imidazo[1,2-a]pyrazin-7-yl]-1-oxo-3-(4-propanamidophenyl)propan-2-yl]carbamate; tert-butyl N-[(2S)-1-[2-(3-fluorophenyl)-3-[(4-fluorophenyl) amino]-5H,6H,7H,8H-imidazo[1,2-a]pyrazin-7-yl]-1-oxo-3-(4-pentanamidophenyl)propan-2-yl]carbamate; (3S)-3-amino-4-{3-[(4-chloro-3-fluorophenyl)amino]-2-(3-fluorophenyl)-5H,6H,7H,8H-imidazo[1,2-a]pyrazin-7-yl}-4-oxo-N-propylbutanamide; (3S)-3-amino-4-[2-(3-fluorophenyl)-3-[(4-fluorophenyl)amino]-5H,6H,7H,8H-imidazo[1,2-a]pyrazin-7-yl]-4-oxo-N-propylbutanamide; (3S)-3-amino-4-[2-(3-fluorophenyl)-3-[(4-fluorophenyl) amino]-5H,6H,7H,8H-imidazo[1,2-a]pyrazin-7-yl]-4-oxo-N-pentylbutanamide; N-{4-[(2S)-2-amino-3-{3-[(4-chloro-3-fluorophenyl)amino]-2-(3-fluorophenyl)-5H,6H,7H,8H-imidazo[1,2-a]pyrazin-7-yl}-3-oxopropyl] phenyl}pentanamide; N-{4-[(2S)-2-amino-3-{3-[(4-chloro-3-fluorophenyl)amino]-2-(3-fluorophenyl)-5H,6H,7H,8H-imidazo[1,2-a]pyrazin-7-yl}-3-oxopropyl] phenyl}propanamide; N-{4-[(2S)-2-amino-3-[2-(3-fluorophenyl)-3-[(4-fluorophenyl)amino]-5H,6H,7H, 8H-imidazo[1,2-a]pyrazin-7-yl]-3-oxopropyl] phenyl}pentanamide; N-{4-[(2S)-2-amino-3-[2-(3-fluorophenyl)-3-[(4-fluorophenyl)amino]-5H,6H,7H,8H-imidazo [1,2-a]pyrazin-7-yl]-3-oxopropyl]phenyl}propanamide; N-(4-chlorophenyl)-2-(4-fluorophenyl)-5H,6H,7H, 8H-imidazo[1,2-a]pyrazin-3-amine; 4-{[7-(2-amino-2-methylpropanoyl)-2-(4-fluorophenyl)-5H,6H,7H,8H-imidazo[1,2-a] pyrazin-3-yl]amino}benzonitrile; 4-{[7-(2-aminoacetyl)-2-(4-fluorophenyl)-5H,6H,7H,8H-imidazo[1,2-a]pyrazin-3-yl]amino}benzonitrile; 4-{[2-(4-fluorophenyl)-7-(3-hydroxy-3-methylbutanoyl)-5H,6H,7H,8H-imidazo[1,2-a] pyrazin-3-yl]amino}benzonitrile; 2-(3-methylphenyl)-N-(4-methylphenyl)-5H,6H,7H,8H-imidazo[1,2-a]pyrazin-3-amine; tert-butyl N-[(2S)-1-[2-(4-fluorophenyl)-3-[(4-methylphenyl)amino]-5H,6H,7H,8H-imidazo[1,2-a] pyrazin-7-yl]-1-oxo-3-[4-(pentylamino)phenyl]propan-2-yl]carbamate; 2-[2-(4-fluorophenyl)-3-[(4-methylphenyl) amino]-5H,6H,7H,8H-imidazo[1,2-a]pyrazin-7-yl]-2-oxo-1-phenylethyl propanoate; 2-[2-(4-fluorophenyl)-3-[(4-methylphenyl)amino]-5H,6H,7H,8H-imidazo[1,2-a] pyrazin-7-yl]-2-oxo-1-phenylethyl butanoate; 2-[2-(4-fluorophenyl)-3-[(4-methylphenyl)amino]-5H,6H,7H,8H-imidazo[1,2-a]pyrazin-7-yl]-2-oxo-1-phenylethyl pentanoate; 2-{3-[(4-chlorophenyl)amino]-2-(4-fluorophenyl)-5H,6H,7H,8H-imidazo[1,2-a]pyrazin-7-yl}-1-(4-fluorophenyl)ethan-1-one; (2S)-2-amino-1-[2-(4-fluorophenyl)-3-[(4-methylphenyl)amino]-5H,6H,7H,8H-imidazo[1,2-a] pyrazin-7-yl]-3-[4-(pentylamino)phenyl]propan-1-one; 2-(4-fluorophenyl)-N-(4-methylphenyl)-7-{[4-(3-methylpiperidin-1-yl)piperidin-1-yl]carbonyl}-5H,6H,7H, 8H-imidazo[1,2-a]pyrazin-3-amine; 2-(4-fluorophenyl)-N-(4-methylphenyl)-7-{[4-(piperidin-1-yl)piperidin-1-yl]carbonyl}-5H,6H,7H,8H-imidazo[1,2-a]pyrazin-3-amine; 2-(4-fluorophenyl)-7-{[4-(4-fluorophenyl)piperidin-1-yl]carbonyl}-N-(4-methylphenyl)-5H,6H,7H,8H-imidazo[1,2-a]pyrazin-3-amine; ethyl 1-{[2-(4-fluorophenyl)-3-[(4-methylphenyl)amino]-5H,6H,7H,8H-imidazo[1,2-a]pyrazin-7-yl]carbonyl}piperidine-3-carboxylate; N-[2-(diethylamino)ethyl]-2-(4-fluorophenyl)-3-[(4-methylphenyl)amino]-5H,6H,7H,8H-imidazo[1,2-a]pyrazine-7-carboxamide; 2-(3,4-difluorophenyl)-N-(4-methylphenyl)-5H,6H,7H,8H-imidazo[1,2-a]pyrazin-3-amine; 2-(3-chlorophenyl)-N-(4-methylphenyl)-5H,6H,7H,8H-imidazo[1,2-a]pyrazin-3-amine; 2-(2,4-difluorophenyl)-N-(4-methylphenyl)-5H,6H,7H,8H-imidazo[1,2-a]pyrazin-3-amine; (2S)-1-{3-[(4-chloro-3-fluorophenyl)amino]-2-(4-fluorophenyl)-5H,6H,7H,8H-imidazo[1,2-a]pyrazin-7-yl}-2-[(2-hydroxypropyl)amino]-3-phenylpropan-1-one; (2S)-1-{3-[(4-chloro-3-fluorophenyl)amino]-2-(4-fluorophenyl)-5H,6H,7H,8H-imidazo[1,2-a]pyrazin-7-yl}-2-[(2-methoxyethyl)amino]-3-phenylpropan-1-one; 3-{[(5R,8S)-2,8-dibenzyl-3-methyl-5-(2-phenylethyl)-5H,6H,7H,8H-imidazo[1,2-a]pyrazin-7-yl]carbonyl}pyridine; (2R)-2-amino-1-[2-(4-fluorophenyl)-3-[(4-methylphenyl)amino]-5H,6H,7H,8H-imidazo[1,2-a]pyrazin-7-yl]-3-hydroxypropan-1-one; (2R,3S)-2-amino-1-[2-(4-fluorophenyl)-3-[(4-methylphenyl)amino]-5H,6H,7H,8H-imidazo[1,2-a]pyrazin-7-yl]-3-hydroxybutan-1-one; (2S)-2-amino-1-[2-(4-fluorophenyl)-3-[(4-methylphenyl)amino]-5H,6H,7H,8H-imidazo[1,2-a]pyrazin-7-yl]-4-methanesulfonylbutan-1-one; (3R)-3-amino-4-[2-(4-fluorophenyl)-3-[(4-methylphenyl)amino]-5H,6H,7H,8H-imidazo[1,2-a]pyrazin-7-yl]-4-oxobutanoic acid; (2R)-2-amino-1-[2-(4-fluorophenyl)-3-[(4-methylphenyl)amino]-5H,6H,7H,8H-imidazo[1,2-a]pyrazin-7-yl]-3-methanesulfonylpropan-1-one; (5R,8R)-2,8-dibenzyl-3-methyl-5-(2-phenylethyl)-5H,6H,7H,8H-imidazo[1,2-a]pyrazin-6-one; N-[(1S)-2-[2-(4-fluorophenyl)-3-[(4-methylphenyl)amino]-5H,6H,7H,8H-imidazo[1,2-a]pyrazin-7-yl]-2-oxo-1-phenylethyl]propanamide; N-[(1S)-2-[2-(4-fluorophenyl)-3-[(4-methylphenyl)amino]-5H,6H,7H,8H-imidazo[1,2-a]pyrazin-7-yl]-2-oxo-1-phenylethyl]butanamide; N-(4-chloro-3-fluorophenyl)-2-(4-fluorophenyl)-N-methyl-5H,6H,7H,8H-imidazo[1,2-a]pyrazin-3-amine; 2-amino-1-{3-[(4-chloro-3-fluorophenyl)(methyl)amino]-2-(4-fluorophenyl)-5H,6H,7H, 8H-imidazo[1,2-a]pyrazin-7-yl}ethan-1-one; 2-amino-1-{3-[(4-chloro-3-fluorophenyl)(methyl)amino]-2-(4-fluorophenyl)-5H,6H,7H,8H-imidazo[1,2-a]pyrazin-7-yl}-2-methylpropan-1-one; (2S)-2-(butylamino)-1-[2-(4-fluorophenyl)-3-[(4-methylphenyl)amino]-5H,6H,7H,8H-imidazo[1,2-a]pyrazin-7-yl]-2-phenylethan-1-one; (2S)-1-[2-(4-fluorophenyl)-3-[(4-methylphenyl)amino]-5H,6H,7H,8H-imidazo[1,2-a]pyrazin-7-yl]-2-(pentylamino)-2-phenylethan-1-one; N-tert-butyl-2-(4-fluorophenyl)-5H,6H,7H, 8H-imidazo[1,2-a]pyrazin-3-amine; N-[(1S)-2-[2-(4-fluorophenyl)-3-[(4-methylphenyl)amino]-5H,6H,7H,8H-imidazo[1,2-a]pyrazin-7-yl]-2-oxo-1-phenylethyl]-1-(5-{2-oxohexahydro-1H-thieno[3,4-d]imidazolidin-4-yl}pentanamido)-3,6,9,12-tetraoxapentadecan-15-amide; 3-amino-2-(4-fluorophenyl)-7-(4-methylphenyl)-5H,6H,7H,8H-imidazo[1,2-a]pyrazin-6-one; 2-(4-fluorophenyl)-3-[(4-methylphenyl)amino]-5H,6H,7H, 8H-imidazo[1,2-a]pyrazin-6-one; (2S)-2-amino-1-{3-[(4-chloro-3-fluorophenyl)amino]-2-(4-fluorophenyl)-5H,6H,7H, 8H-imidazo[1,2-a]pyrazin-7-yl}-3-methoxypropan-1-one; 1-{3-[(4-chloro-3-fluorophenyl)amino]-2-(4-fluorophenyl)-5H,6H,7H, 8H-imidazo[1,2-a]pyrazin-7-yl}-2-(pyridin-4-yl)ethan-1-one; 1-{3-[(4-chloro-3-fluorophenyl)amino]-2-(4-fluorophenyl)-5H,6H,7H,8H-imidazo[1,2-a]pyrazin-7-yl}-2-(1H-indol-1-yl)ethan-1-one; 1-{3-[(4-chloro-3-fluorophenyl)amino]-2-(4-fluorophenyl)-5H,6H,7H, 8H-imidazo[1,2-a]pyrazin-7-yl}-2-(1-ethylpiperidin-4-yl)ethan-1-one; 1-{3-[(4-chloro-3-fluorophenyl)amino]-2-(4-fluorophenyl)-5H,6H,7H,8H-imidazo[1,2-a]pyrazin-7-yl}-2-(phenylamino)ethan-1-one; 1-{3-[(4-chloro-3-fluorophenyl)amino]-2-(4-fluorophenyl)-5H,6H,7H,8H-imidazo[1,2-a]pyrazin-7-yl}-2-(1H-indazol-3-yl)ethan-1-one; 1-[2-(4-fluorophenyl)-3-[(4-methylphenyl)amino]-5H,6H,7H,8H-imidazo[1,2-a]pyrazin-7-yl]-2-(propylamino)ethan-1-one; 1-[2-(4-fluorophenyl)-3-[(4-methylphenyl)amino]-5H,6H,7H,8H-imidazo[1,2-a]pyrazin-7-yl]-2-(pentylamino)ethan-1-one; 1-[2-(4-fluorophenyl)-3-[(4-methylphenyl)amino]-5H,6H,7H,8H-imidazo[1,2-a]pyrazin-7-yl]-2-[(2-methoxyethyl)amino]ethan-1-one; 1-[2-(4-fluorophenyl)-3-[(4-methylphenyl)amino]-5H,6H,7H, 8H-imidazo[1,2-a]pyrazin-7-yl]-2-[(3-methoxypropyl)amino]ethan-1-one; (2R)-2-amino-1-{3-[(4-chloro-3-fluorophenyl)amino]-2-(4-fluorophenyl)-5H,6H,7H,8H-imidazo[1,2-a]pyrazin-7-yl}-3-phenylpropan-1-one; (2S,3S)-2-amino-3-(benzyloxy)-1-{3-[(4-chloro-3-fluorophenyl)amino]-2-(4-fluorophenyl)-5H,6H,7H,8H-imidazo[1,2-a]pyrazin-7-yl}butan-1-one; (2S)-2-amino-1-{3-[(4-chloro-3-fluorophenyl)amino]-2-(4-fluorophenyl)-5H,6H,7H,8H-imidazo[1,2-a]pyrazin-7-yl}-3-methylbutan-1-one; (2S)-2-amino-1-{3-[(4-chloro-3-fluorophenyl)amino]-2-(4-fluorophenyl)-5H,6H,7H,8H-imidazo[1,2-a]pyrazin-7-yl}propan-1-one; (2S)-2-amino-1-{3-[(4-chloro-3-fluorophenyl)amino]-2-(4-fluorophenyl)-5H,6H,7H,8H-imidazo[1,2-a]pyrazin-7-yl}-3-(1,3-thiazol-4-yl)propan-1-one; (2S)-2-amino-1-{3-[(4-chloro-3-fluorophenyl)amino]-2-(4-fluorophenyl)-5H,6H,7H,8H-imidazo[1,2-a]pyrazin-7-yl}-3-(4-fluorophenyl)propan-1-one; (2S,3S)-2-amino-1-{3-[(4-chloro-3-fluorophenyl)amino]-2-(4-fluorophenyl)-5H,6H,7H,8H-imidazo[1,2-a]pyrazin-7-yl}-3-methylpentan-1-one; (2R)-2-amino-1-{3-[(4-chloro-3-fluorophenyl)amino]-2-(4-fluorophenyl)-5H,6H,7H,8H-imidazo[1,2-a]pyrazin-7-yl}-3-methylbutan-1-one; (2S)-2-amino-1-{3-[(4-chloro-3-fluorophenyl)amino]-2-(4-fluorophenyl)-5H,6H,7H,8H-imidazo[1,2-a]pyrazin-7-yl}-3-(3,4-difluorophenyl)propan-1-one; 1-{3-[(4-chloro-3-fluorophenyl)amino]-2-(4-fluorophenyl)-5H,6H,7H,8H-imidazo[1,2-a]pyrazin-7-yl}-2-methyl-2-(methylamino)propan-1-one; 7-{[(2S)-azetidin-2-yl]carbonyl}-N-(4-chloro-3-fluorophenyl)-2-(4-fluorophenyl)-5H,6H,7H,8H-imidazo[1,2-a]pyrazin-3-amine; (2S)-2-amino-1-{3-[(4-chloro-3-fluorophenyl)amino]-2-(4-fluorophenyl)-5H,6H,7H,8H-imidazo[1,2-a]pyrazin-7-yl}-4-methylpentan-1-one; N-(4-chloro-3-fluorophenyl)-2-(4-fluorophenyl)-7-[(morpholin-3-yl)carbonyl]-5H,6H,7H,8H-imidazo[1,2-a]pyrazin-3-amine; (2S)-2-amino-1-{3-[(4-chloro-3-fluorophenyl)amino]-2-(4-fluorophenyl)-5H,6H,7H,8H-imidazo[1,2-a]pyrazin-7-yl}-3-phenylpropan-1-one; (2S)-2-amino-1-{3-[(4-chloro-3-fluorophenyl)amino]-2-(4-fluorophenyl)-5H,6H,7H, 8H-imidazo[1,2-a]pyrazin-7-yl}-3-cyclobutylpropan-1-one; (2S)-2-amino-1-{3-[(4-chloro-3-fluorophenyl)amino]-2-(4-fluorophenyl)-5H,6H,7H,8H-imidazo[1,2-a]pyrazin-7-yl}-3,3-dimethylbutan-1-one; (2R)-2-amino-1-{3-[(4-chloro-3-fluorophenyl)amino]-2-(4-fluorophenyl)-5H,6H,7H, 8H-imidazo[1,2-a]pyrazin-7-yl}propan-1-one; 4-[(2S)-2-amino-3-{3-[(4-chloro-3-fluorophenyl)amino]-2-(4-fluorophenyl)-5H,6H,7H,8H-imidazo[1,2-a]pyrazin-7-yl}-3-oxopropyl]benzonitrile;

2-(4-fluorophenyl)-6-methyl-N-(4-methylphenyl)-5H,6H, 7H,8H-imidazo[1,2-a]pyrazin-3-amine; 2-(2,5-difluorophenyl)-N-(4-methylphenyl)-5H,6H,7H,8H-imidazo[1,2-a]pyrazin-3-amine; N-(3,4-difluorophenyl)-2-(4-fluorophenyl)-5H,6H,7H,8H-imidazo[1,2-a]pyrazin-3-amine; 1-{3-[(4-chloro-3-fluorophenyl)amino]-2-(4-fluorophenyl)-5H,6H,7H,8H-imidazo[1,2-a]pyrazin-7-yl}-2-phenyl-2-(phenylamino)ethan-1-one; 1-{3-[(4-chloro-3-fluorophenyl)amino]-2-(4-fluorophenyl)-5H,6H,7H, 8H-imidazo[1,2-a]pyrazin-7-yl}-2-[2-(trifluoromethoxy)phenyl]ethan-1-one; (2S)-1-{3-[(4-chloro-3-fluorophenyl)amino]-2-(4-fluorophenyl)-5H,6H,7H,8H-imidazo[1,2-a]pyrazin-7-yl}-2-hydroxy-3-phenylpropan-1-one; 1-{3-[(4-chloro-3-fluorophenyl)amino]-2-(4-fluorophenyl)-5H,6H, 7H,8H-imidazo[1,2-a]pyrazin-7-yl}-2-[4-fluoro-3-(trifluoromethyl)phenyl]ethan-1-one; 1-{3-[(4-chloro-3-fluorophenyl)amino]-2-(4-fluorophenyl)-5H,6H,7H, 8H-imidazo[1,2-a]pyrazin-7-yl}-2-phenoxyethan-1-one; 5-({3-[(4-chloro-3-fluorophenyl)amino]-2-(4-fluorophenyl)-5H,6H,7H,8H-imidazo[1,2-a]pyrazin-7-yl}carbonyl)piperidin-2-one; N-(4-chloro-3-fluorophenyl)-2-(4-fluorophenyl)-7-{[(2S)-pyrrolidin-2-yl]carbonyl}-5H,6H,7H,8H-imidazo[1,2-a]pyrazin-3-amine; 3-amino-1-{3-[(4-chloro-3-fluorophenyl)amino]-2-(4-fluorophenyl)-5H,6H,7H, 8H-imidazo[1,2-a]pyrazin-7-yl}-4,4,4-trifluorobutan-1-one; N-(4-chloro-3-fluorophenyl)-2-(4-fluorophenyl)-7-{[(3S)-pyrrolidin-3-yl]carbonyl}-5H,6H,7H,8H-imidazo[1,2-a]pyrazin-3-amine; (2S)-2-amino-1-{3-[(4-chloro-3-fluorophenyl)amino]-2-(4-fluorophenyl)-5H,6H,7H,8H-imidazo[1,2-a]pyrazin-7-yl}-3-(4-methylphenyl)propan-1-one; N-(4-chloro-3-fluorophenyl)-7-[(2,3-dihydro-1H-isoindol-1-yl)carbonyl]-2-(4-fluorophenyl)-5H,6H,7H,8H-imidazo[1,2-a]pyrazin-3-amine; N-(4-chloro-3-fluorophenyl)-7-{[(2S)-2,3-dihydro-1H-indol-2-yl]carbonyl}-2-(4-fluorophenyl)-5H,6H,7H,8H-imidazo[1,2-a]pyrazin-3-amine; (3S)-3-amino-4-(4-bromophenyl)-1-{3-[(4-chloro-3-fluorophenyl)amino]-2-(4-fluorophenyl)-5H,6H,7H, 8H-imidazo[1,2-a]pyrazin-7-yl}butan-1-one; (2R)-2-amino-3-(4-bromophenyl)-1-{3-[(4-chloro-3-fluorophenyl)amino]-2-(4-fluorophenyl)-5H,6H,7H,8H-imidazo[1,2-a]pyrazin-7-yl}propan-1-one; (2S)-2-amino-1-{3-[(4-chloro-3-fluorophenyl)amino]-2-(4-fluorophenyl)-5H,6H,7H,8H-imidazo[1,2-a]pyrazin-7-yl}-3-{[(4-methoxyphenyl)methyl]sulfanyl}propan-1-one; N-(4-chloro-3-fluorophenyl)-2-(4-fluorophenyl)-7-{[(3R)-1,2,3,4-tetrahydroisoquinolin-3-yl]carbonyl}-5H,6H,7H, 8H-imidazo[1,2-a]pyrazin-3-amine; 2-amino-1-{3-[(4-chloro-3-fluorophenyl)amino]-2-(4-fluorophenyl)-5H,6H, 7H,8H-imidazo[1,2-a]pyrazin-7-yl}-4,4,4-trifluorobutan-1-one; 2-(2-butoxyethoxy)-1-[2-(4-fluorophenyl)-3-[(4-methylphenyl)amino]-5H,6H,7H,8H-imidazo[1,2-a]pyrazin-7-yl]ethan-1-one; 2-ethoxy-1-[2-(4-fluorophenyl)-3-[(4-methylphenyl)amino]-5H,6H,7H,8H-imidazo[1,2-a]pyrazin-7-yl]ethan-1-one; 1-[2-(4-fluorophenyl)-3-[(4-methylphenyl)amino]-5H,6H,7H,8H-imidazo[1,2-a]pyrazin-7-yl]-2-(2-methoxyethoxy)ethan-1-one; 2-amino-1-[2-(4-fluorophenyl)-6-methyl-3-[(4-methylphenyl)amino]-5H,6H,7H,8H-imidazo[1,2-a]pyrazin-7-yl]ethan-1-one; 5-{[7-(2-amino-2-methylpropanoyl)-2-(3-fluorophenyl)-5H, 6H,7H,8H-imidazo[1,2-a]pyrazin-3-yl]amino}-2-fluorobenzonitrile; N-(4-methylphenyl)-2-(pyridin-4-yl)-5H, 6H,7H,8H-imidazo[1,2-a]pyrazin-3-amine; 2-{[2-chloro-4-(trifluoromethyl)phenyl]amino}-1-[2-(4-fluorophenyl)-3-[(4-methylphenyl)amino]-5H,6H,7H,8H-imidazo[1,2-a]pyrazin-7-yl]-3-methylbutan-1-one; N-(4-chloro-3-fluorophenyl)-2-(4-fluorophenyl)-7-{[(2R)-oxolan-2-yl]carbonyl}-5H,6H,7H, 8H-imidazo[1,2-a]pyrazin-3-amine; 1-{3-[(4-chloro-3-fluorophenyl)amino]-2-(4-fluorophenyl)-5H,6H,7H,8H-imidazo[1,2-a]pyrazin-7-yl}-2-(1-methyl-1H-indol-3-yl)ethan-1-one; (2S)-1-{3-[(4-chloro-3-fluorophenyl)amino]-2-(4-fluorophenyl)-5H,6H,7H,8H-imidazo[1,2-a]pyrazin-7-yl}-2-hydroxy-4-methylpentan-1-one; 1-{3-[(4-chloro-3-fluorophenyl)amino]-2-(4-fluorophenyl)-5H,6H,7H, 8H-imidazo[1,2-a]pyrazin-7-yl}-3-(2-fluorophenyl)propan-1-one; (2R)-1-{3-[(4-chloro-3-fluorophenyl)amino]-2-(4-fluorophenyl)-5H,6H,7H, 8H-imidazo[1,2-a]pyrazin-7-yl}-2-hydroxy-3-methylbutan-1-one; 2-[(3-chlorophenyl)amino]-1-[2-(4-fluorophenyl)-3-[(4-methylphenyl)amino]-5H,6H,7H,8H-imidazo[1,2-a]pyrazin-7-yl]ethan-1-one; 1-[2-(4-fluorophenyl)-3-[(4-methylphenyl)amino]-5H,6H,7H, 8H-imidazo[1,2-a]pyrazin-7-yl]-2-[(4-methylphenyl)amino]ethan-1-one; 2-(4-chloro-3-fluorophenyl)-1-{3-[(4-chloro-3-fluorophenyl)amino]-2-(4-fluorophenyl)-5H,6H,7H,8H-imidazo[1,2-a]pyrazin-7-yl}ethan-1-one; 1-[2-(4-fluorophenyl)-3-[(4-methylphenyl)amino]-5H,6H,7H,8H-imidazo[1,2-a]pyrazin-7-yl]-2-[(4-methoxyphenyl)amino]-2-methylpropan-1-one; 2-amino-1-{3-[(4-chloro-3-fluorophenyl)amino]-2-(4-fluorophenyl)-5H,6H,7H,8H-imidazo[1,2-a]pyrazin-7-yl}-2-(3,4-dichlorophenyl)ethan-1-one; 2-amino-3,3,3-trifluoro-1-[2-(4-fluorophenyl)-3-[(4-methylphenyl)amino]-5H,6H,7H,8H-imidazo[1,2-a]pyrazin-7-yl]-2-methylpropan-1-one; N-(4-chloro-3-fluorophenyl)-2-(4-fluorophenyl)-7-[(morpholin-2-yl)carbonyl]-5H,6H,7H,8H-imidazo[1,2-a]pyrazin-3-amine; 2-amino-1-{3-[(4-chloro-3-fluorophenyl)amino]-2-(4-fluorophenyl)-5H,6H,7H,8H-imidazo[1,2-a]pyrazin-7-yl}-2-[4-(trifluoromethyl)phenyl]ethan-1-one; 2-amino-1-{3-[(4-chloro-3-fluorophenyl)amino]-2-(4-fluorophenyl)-5H,6H, 7H,8H-imidazo[1,2-a]pyrazin-7-yl}-2-(4-chlorophenyl)ethan-1-one; N-(4-chloro-3-fluorophenyl)-2-(4-fluorophenyl)-7-[(quinolin-6-yl)carbonyl]-5H,6H,7H,8H-imidazo[1,2-a]pyrazin-3-amine; 1-[2-(4-fluorophenyl)-3-[(4-methylphenyl)amino]-5H,6H,7H,8H-imidazo[1,2-a]pyrazin-7-yl]-2-[(4-methylphenyl)amino]-2-phenylethan-1-one; N-(4-chloro-3-fluorophenyl)-2-(4-fluorophenyl)-7-[(4-methylmorpholin-2-yl)carbonyl]-5H,6H,7H,8H-imidazo[1, 2-a]pyrazin-3-amine; 1-[2-(4-fluorophenyl)-3-[(4-methylphenyl)amino]-5H,6H,7H,8H-imidazo[1,2-a]pyrazin-7-yl]-2-[(2-fluorophenyl)amino]ethan-1-one; 1-[2-(4-fluorophenyl)-3-[(4-methylphenyl)amino]-5H,6H,7H, 8H-imidazo[1,2-a]pyrazin-7-yl]-2-methyl-2-(phenylamino)propan-1-one; 2-amino-1-(3-{[4-fluoro-2-(trifluoromethyl)phenyl]amino}-2-(3-fluorophenyl)-5H,6H,7H,8H-imidazo[1,2-a]pyrazin-7-yl)-2-methylpropan-1-one; (2S)-1-[2-(4-fluorophenyl)-3-[(4-methylphenyl)amino]-5H,6H,7H,8H-imidazo[1,2-a]pyrazin-7-yl]-3-methyl-2-(methylamino)butan-1-one; (2R)-1-[2-(4-fluorophenyl)-3-[(4-methylphenyl)amino]-5H,6H,7H,8H-imidazo[1,2-a]pyrazin-7-yl]-4-methyl-2-(methylamino)pentan-1-one; (2S)-1-[2-(4-fluorophenyl)-3-[(4-methylphenyl)amino]-5H, 6H,7H,8H-imidazo[1,2-a]pyrazin-7-yl]-4-methyl-2-(methylamino)pentan-1-one; 2-amino-1-[2-(3,4-difluorophenyl)-3-[(4-methylphenyl)amino]-5H,6H,7H,8H-imidazo[1,2-a]pyrazin-7-yl]-2-methylpropan-1-one; 2-[(2,6-dimethylphenyl)amino]-1-[2-(4-fluorophenyl)-3-[(4-methylphenyl)amino]-5H,6H,7H,8H-imidazo[1,2-a]pyrazin-7-yl]propan-1-one; 2-amino-1-[2-(2-methoxyphenyl)-3-[(4-methylphenyl)amino]-5H,6H,7H, 8H-imidazo[1,2-a]pyrazin-7-yl]ethan-1-one; 2-amino-1-{3-[(4-methylphenyl)amino]-2-(pyridin-4-yl)-5H,6H,7H,8H-imidazo[1,2-a]pyrazin-7-yl}ethan-1-one; 2-amino-1-[2-(3-chlorophenyl)-3-[(4-methylphenyl)amino]-5H,6H,7H, 8H-imidazo[1,2-a]pyrazin-7-yl]ethan-1-one; 2-[(2,4-dimethylphenyl)amino]-1-[2-(4-fluorophenyl)-3-[(4-methylphenyl)amino]-5H,6H,7H,8H-imidazo[1,2-a]pyrazin-7-yl]ethan-1-one; 2-amino-1-[2-(3,4-difluorophenyl)-3-[(4-methylphenyl)amino]-5H,6H,7H,8H-imidazo[1,2-a]pyrazin-7-yl]ethan-1-one; 1-[2-(4-fluorophenyl)-3-[(4-methylphenyl)amino]-5H,6H,7H,8H-imidazo[1,2-a]pyrazin-7-yl]-2-methyl-2-[(4-methylphenyl)amino]propan-1-one; 2-amino-1-[2-(2,4-difluorophenyl)-3-[(4-methylphenyl)amino]-5H,6H,7H,8H-imidazo[1,2-a]pyrazin-7-yl]ethan-1-one; (2S)-2-[benzyl(methyl)amino]-1-[2-(4-fluorophenyl)-3-[(4-methylphenyl)amino]-5H,6H,7H,8H-imidazo[1,2-a]pyrazin-7-yl]propan-1-one; (2S)-1-[2-(4-fluorophenyl)-3-[(4-methylphenyl)amino]-5H,6H,7H,8H-imidazo[1,2-a]pyrazin-7-yl]-2-(methylamino)hexan-1-one; 1-[2-(3,4-difluorophenyl)-3-[(4-methylphenyl)amino]-5H,6H,7H,8H-imidazo[1,2-a]pyrazin-7-yl]-2-(4-methylphenyl)ethan-1-one; (2R)-1-[2-(3,4-difluorophenyl)-3-[(4-methylphenyl)amino]-5H,6H,7H,8H-imidazo[1,2-a]pyrazin-7-yl]-2-hydroxy-3-methylbutan-1-one; (2S)-1-[2-(4-fluorophenyl)-3-[(4-methylphenyl)amino]-5H,6H,7H,8H-imidazo[1,2-a]pyrazin-7-yl]-2-(methylamino)pentan-1-one; (2S)-2-amino-1-{3-[(4-chloro-3-fluorophenyl)amino]-2-(4-fluorophenyl)-5H,6H,7H,8H-imidazo[1,2-a]pyrazin-7-yl}butan-1-one; (2R)-2-amino-1-{3-[(4-chloro-3-fluorophenyl)amino]-2-(4-fluorophenyl)-5H,6H,7H,8H-imidazo[1,2-a]pyrazin-7-yl}-4-methylpentan-1-one; 2-amino-1-[2-(2,4-difluorophenyl)-3-[(4-methylphenyl)amino]-5H,6H,7H,8H-imidazo[1,2-a]pyrazin-7-yl]-2-methylpropan-1-one; (2S)-2-amino-1-[2-(3,4-difluorophenyl)-3-[(4-methylphenyl)amino]-5H,6H,7H,8H-imidazo[1,2-a]pyrazin-7-yl]-3-methylbutan-1-one; 2-amino-1-[2-(3-chlorophenyl)-3-[(4-methylphenyl)amino]-5H,6H,7H,8H-imidazo[1,2-a]pyrazin-7-yl]-2-methylpropan-1-one; 2-amino-2-methyl-1-{3-[(4-methylphenyl)amino]-2-(pyridin-4-yl)-5H,6H,7H,8H-imidazo[1,2-a]pyrazin-7-yl}propan-1-one; 2-(tert-butylamino)-1-[2-(4-fluorophenyl)-3-[(4-methylphenyl)amino]-5H,6H,7H,8H-imidazo[1,2-a]pyrazin-7-yl]ethan-1-one; (2S)-3-(4-chlorophenyl)-1-[2-(4-fluorophenyl)-3-[(4-methylphenyl)amino]-5H,6H,7H,8H-imidazo[1,2-a]pyrazin-7-yl]-2-(methylamino)propan-1-one; (2S)-2-amino-3-cyclopropyl-1-[2-(4-fluorophenyl)-3-[(4-methylphenyl)amino]-5H,6H,7H,8H-imidazo[1,2-a]pyrazin-7-yl]propan-1-one; (2R)-2-(benzylamino)-1-[2-(4-fluorophenyl)-3-[(4-methylphenyl)amino]-5H,6H,7H,8H-imidazo[1,2-a]pyrazin-7-yl]propan-1-one; (2S)-2-(benzylamino)-1-[2-(4-fluorophenyl)-3-[(4-methylphenyl)amino]-5H,6H,7H,8H-imidazo[1,2-a]pyrazin-7-yl]propan-1-one; (2S)-2-amino-2-cyclopropyl-1-[2-(4-fluorophenyl)-3-[(4-methylphenyl)amino]-5H,6H,7H,8H-imidazo[1,2-a]pyrazin-7-yl]ethan-1-one; (2S)-2-amino-3-(3,4-difluorophenyl)-1-[2-(3,4-difluorophenyl)-3-[(4-methylphenyl)amino]-5H,6H,7H,8H-imidazo[1,2-a]pyrazin-7-yl]propan-1-one; (2S)-2-amino-1-[2-(3,4-difluorophenyl)-3-[(4-methylphenyl)amino]-5H,6H,7H,8H-imidazo[1,2-a]pyrazin-7-yl]propan-1-one; 1-[2-(4-fluorophenyl)-3-[(4-methylphenyl)amino]-5H,6H,7H,8H-imidazo[1,2-a]pyrazin-7-yl]-2-[(4-methylphenyl)amino]propan-1-one; 2-amino-1-[2-(2,5-difluorophenyl)-3-[(4-methylphenyl)amino]-5H,6H,7H,8H-imidazo[1,2-a]pyrazin-7-yl]-2-methylpropan-1-one; 2-amino-1-[2-(4-fluorophenyl)-8,8-dimethyl-3-[(4-methylphenyl)amino]-5H,6H,7H,8H-imidazo[1,2-a]pyrazin-7-yl]ethan-1-one; 2-amino-1-{3-[(3,4-dichlorophenyl)amino]-2-(4-fluorophenyl)-5H,6H,7H,8H-imidazo[1,2-a]pyrazin-7-yl}-2-methylpropan-1-one; N-(3,4-dichlorophenyl)-2-(4-fluorophenyl)-5H,6H,7H,8H-imidazo[1,2-a]pyrazin-3-amine; 2-amino-1-[2-(4-fluorophenyl)-3-[(4-methylphenyl)amino]-8,8-dimethyl-5H,6H,7H,8H-imidazo[1,2-a]pyrazin-7-yl]ethan-1-one; N-(4-chloro-3-fluorophenyl)-N-ethyl-2-(4-fluorophenyl)-5H,6H,7H,8H-imidazo[1,2-a]pyrazin-3-amine; (2R)-1-[2-(4-fluorophenyl)-3-[(4-methylphenyl)amino]-5H,6H,7H,8H-imidazo[1,2-a]pyrazin-7-yl]-3-methyl-2-(methylamino)butan-1-one; 2-(4-fluorophenyl)-8,8-dimethyl-N-(4-methylphenyl)-5H,6H,7H,8H-imidazo[1,2-a]pyrazin-3-amine; N-(4-chlorophenyl)-2-(4-fluorophenyl)-8,8-dimethyl-5H,6H,7H,8H-imidazo[1,2-a]pyrazin-3-amine; 2-amino-1-{3-[(4-chlorophenyl)amino]-2-(4-fluorophenyl)-8,8-dimethyl-5H,6H,7H,8H-imidazo[1,2-a]pyrazin-7-yl}ethan-1-one; 2-amino-1-[2-(2,5-difluorophenyl)-3-[(4-methylphenyl)amino]-5H,6H,7H,8H-imidazo[1,2-a]pyrazin-7-yl]ethan-1-one; 2-amino-1-{3-[(4-chloro-3-fluorophenyl)amino]-2-(4-fluorophenyl)-8,8-dimethyl-5H,6H,7H,8H-imidazo[1,2-a]pyrazin-7-yl}ethan-1-one; N-(4-chloro-3-fluorophenyl)-2-(4-fluorophenyl)-8,8-dimethyl-5H,6H,7H,8H-imidazo[1,2-a]pyrazin-3-amine; 2-amino-1-{3-[(3,4-difluorophenyl)amino]-2-(4-fluorophenyl)-8,8-dimethyl-5H,6H,7H,8H-imidazo[1,2-a]pyrazin-7-yl}ethan-1-one; N-(3,4-difluorophenyl)-2-(4-fluorophenyl)-8,8-dimethyl-5H,6H,7H,8H-imidazo[1,2-a]pyrazin-3-amine; 2-amino-1-{3-[(3-chloro-4-fluorophenyl)amino]-2-(4-fluorophenyl)-8,8-dimethyl-5H,6H,7H,8H-imidazo[1,2-a]pyrazin-7-yl}ethan-1-one; N-(3-chloro-4-fluorophenyl)-2-(4-fluorophenyl)-8,8-dimethyl-5H,6H,7H, 8H-imidazo[1,2-a]pyrazin-3-amine; 4-{[7-(2-aminoacetyl)-2-(4-fluorophenyl)-8,8-dimethyl-5H,6H,7H, 8H-imidazo[1,2-a]pyrazin-3-yl]amino}benzonitrile; 4-{[2-(4-fluorophenyl)-8,8-dimethyl-5H,6H,7H,8H-imidazo[1,2-a]pyrazin-3-yl]amino}benzonitrile; 2-amino-1-{3-[(3,4-difluoro-5-methoxyphenyl)amino]-2-(4-fluorophenyl)-5H,6H,7H,8H-imidazo[1,2-a]pyrazin-7-yl}-2-methylpropan-1-one; 2-amino-1-{3-[(4-fluoro-3,5-dimethylphenyl)amino]-2-(4-fluorophenyl)-5H,6H,7H,8H-imidazo[1,2-a]pyrazin-7-yl}-2-methylpropan-1-one; (2S)-2-amino-3-cyclobutyl-1-{3-[(3,4-difluorophenyl)amino]-2-(4-fluorophenyl)-5H,6H,7H,8H-imidazo[1,2-a]pyrazin-7-yl}propan-1-one; (2R)-1-{3-[(3,4-difluorophenyl)amino]-2-(4-fluorophenyl)-5H,6H,7H,8H-imidazo[1,2-a]pyrazin-7-yl}-2-hydroxy-3-methylbutan-1-one; (2S)-2-amino-1-{3-[(3,4-difluorophenyl)amino]-2-(4-fluorophenyl)-5H,6H,7H,8H-imidazo[1,2-a]pyrazin-7-yl}-3-(1,3-thiazol-4-yl)propan-1-one; (2S)-2-amino-1-{3-[(3,4-difluorophenyl)amino]-2-(4-fluorophenyl)-5H,6H,7H,8H-imidazo[1,2-a]pyrazin-7-yl}-3-(4-methylphenyl)propan-1-one; (2S)-2-amino-3-(3,4-difluorophenyl)-1-{3-[(3,4-difluorophenyl)amino]-2-(4-fluorophenyl)-5H,6H,7H,8H-imidazo[1,2-a]pyrazin-7-yl}propan-1-one; (2S)-2-amino-1-{3-[(3,4-difluorophenyl)amino]-2-(4-fluorophenyl)-5H,6H,7H,8H-imidazo[1,2-a]pyrazin-7-yl}-3-methylbutan-1-one; (2S)-2-amino-1-{3-[(3,4-difluorophenyl)amino]-2-(4-fluorophenyl)-5H,6H,7H,8H-imidazo[1,2-a]pyrazin-7-yl}propan-1-one; (2S)-2-amino-1-{3-[(3,4-difluorophenyl)amino]-2-(4-fluorophenyl)-5H,6H,7H,8H-imidazo[1,2-a]pyrazin-7-yl}-2-(4-fluorophenyl)ethan-1-one; (2S)-2-amino-2-cyclopropyl-1-{3-[(3,4-difluorophenyl)amino]-2-(4-fluorophenyl)-5H,6H,7H,8H-imidazo[1,2-a]pyrazin-7-yl}ethan-1-one; (2S)-2-amino-3-cyclopropyl-1-{3-[(3,4-difluorophenyl)amino]-2-(4-fluorophenyl)-5H,6H,7H,8H-imidazo[1,2-a]pyrazin-7-yl}propan-1-one; (2S)-2-amino-1-{3-[(3,4-difluorophenyl)amino]-2-(4-fluorophenyl)-5H,6H,7H,8H-imidazo[1,2-a]pyrazin-7-yl}-4-methylpentan-1-one; (2S)-1-{3-[(3,4-difluorophenyl)amino]-2-(4-fluorophenyl)-5H,6H,7H,8H-imidazo[1,2-a]pyrazin-7-yl}-2-hydroxy-3-methylbutan-1-one; 7-{[(2S)-azetidin-2-yl]carbonyl}-N-(3,4-difluorophenyl)-2-(4-fluorophenyl)-5H,6H,7H,8H-imidazo[1,2-a]pyrazin-3-amine; (2S,3S)-2-amino-1-{3-[(3,4- difluorophenyl)amino]-2-(4-fluorophenyl)-5H,6H,7H,8H-imidazo[1,2-a]pyrazin-7-yl}-3-methylpentan-1-one; (2S)-2-amino-1-{3-[(3,4-difluorophenyl)amino]-2-(4-fluorophenyl)-5H,6H,7H,8H-imidazo[1,2-a]pyrazin-7-yl}-3-(4-fluorophenyl)propan-1-one; N-(4-chloro-3-fluorophenyl)-2-(4-fluorophenyl)-N-(propan-2-yl)-5H,6H,7H,8H-imidazo[1,2-a]pyrazin-3-amine; N-(3-fluorophenyl)-2-(4-fluorophenyl)-N-(propan-2-yl)-5H,6H,7H,8H-imidazo[1,2-a]pyrazin-3-amine; N-ethyl-N-(3-fluorophenyl)-2-(4-fluorophenyl)-5H,6H,7H,8H-imidazo[1,2-a]pyrazin-3-amine; N-(3-chloro-4-fluorophenyl)-2-(4-fluorophenyl)-5H,6H,7H,8H-imidazo[1,2-a]pyrazin-3-amine; (2S)-2-amino-1-{3-[(4-chlorophenyl)amino]-2-(4-fluorophenyl)-5H,6H,7H,8H-imidazo[1,2-a]pyrazin-7-yl}propan-1-one; (2S)-2-amino-1-{3-[(4-chlorophenyl)amino]-2-(4-fluorophenyl)-5H,6H,7H,8H-imidazo[1,2-a]pyrazin-7-yl}-3-methylbutan-1-one; (2S)-2-amino-1-{3-[(4-chlorophenyl)amino]-2-(4-fluorophenyl)-5H,6H,7H,8H-imidazo[1,2-a]pyrazin-7-yl}-2-cyclopropylethan-1-one; (2S)-2-amino-1-{3-[(4-chlorophenyl)amino]-2-(4-fluorophenyl)-5H,6H,7H,8H-imidazo[1,2-a]pyrazin-7-yl}-3-cyclopropylpropan-1-one; (2S)-2-amino-1-{3-[(4-chlorophenyl)amino]-2-(4-fluorophenyl)-5H,6H,7H,8H-imidazo[1,2-a]pyrazin-7-yl}-3-cyclobutylpropan-1-one; (2S)-2-amino-1-{3-[(4-chlorophenyl)amino]-2-(4-fluorophenyl)-5H,6H,7H,8H-imidazo[1,2-a]pyrazin-7-yl}-4-methylpentan-1-one; (2S,3S)-2-amino-1-{3-[(4-chlorophenyl)amino]-2-(4-fluorophenyl)-5H,6H,7H,8H-imidazo[1,2-a]pyrazin-7-yl}-3-methylpentan-1-one; (2S)-1-{3-[(4-chlorophenyl)amino]-2-(4-fluorophenyl)-5H,6H,7H,8H-imidazo[1,2-a]pyrazin-7-yl}-2-hydroxy-3-methylbutan-1-one; (2R)-1-{3-[(4-chlorophenyl)amino]-2-(4-fluorophenyl)-5H,6H,7H,8H-imidazo[1,2-a]pyrazin-7-yl}-2-hydroxy-3-methylbutan-1-one; (2S)-2-amino-1-{3-[(4-chlorophenyl)amino]-2-(4-fluorophenyl)-5H,6H,7H,8H-imidazo[1,2-a]pyrazin-7-yl}-2-(4-fluorophenyl)ethan-1-one; (2S)-2-amino-1-{3-[(4-chlorophenyl)amino]-2-(4-fluorophenyl)-5H,6H,7H,8H-imidazo[1,2-a]pyrazin-7-yl}-3-(4-fluorophenyl)propan-1-one; (2S)-2-amino-1-{3-[(4-chlorophenyl)amino]-2-(4-fluorophenyl)-5H,6H,7H,8H-imidazo[1,2-a]pyrazin-7-yl}-3-(4-methylphenyl)propan-1-one; (2S)-2-amino-1-{3-[(4-chlorophenyl)amino]-2-(4-fluorophenyl)-5H,6H,7H,8H-imidazo[1,2-a]pyrazin-7-yl}-3-(3,4-difluorophenyl)propan-1-one; (2S)-2-amino-1-{3-[(4-chlorophenyl)amino]-2-(4-fluorophenyl)-5H,6H,7H,8H-imidazo[1,2-a]pyrazin-7-yl}-3-(1,3-thiazol-4-yl)propan-1-one; 7-{[(2S)-azetidin-2-yl]carbonyl}-N-(4-chlorophenyl)-2-(4-fluorophenyl)-5H,6H,7H,8H-imidazo[1,2-a]pyrazin-3-amine; (2S)-2-amino-1-{3-[(4-chlorophenyl)amino]-2-(4-fluorophenyl)-5H,6H,7H,8H-imidazo[1,2-a]pyrazin-7-yl}-3,3-dimethylbutan-1-one; (2S)-2-amino-1-[2-(4-fluorophenyl)-3-[(4-fluorophenyl)amino]-5H,6H,7H,8H-imidazo[1,2-a]pyrazin-7-yl]-3-methylbutan-1-one; (2S)-2-amino-2-cyclopropyl-1-[2-(4-fluorophenyl)-3-[(4-fluorophenyl)amino]-5H,6H,7H,8H-imidazo[1,2-a]pyrazin-7-yl]ethan-1-one; (2S)-2-amino-3-cyclopropyl-1-[2-(4-fluorophenyl)-3-[(4-fluorophenyl)amino]-5H,6H,7H,8H-imidazo[1,2-a]pyrazin-7-yl]propan-1-one; (2S)-2-amino-3-cyclobutyl-1-[2-(4-fluorophenyl)-3-[(4-fluorophenyl)amino]-5H,6H,7H,8H-imidazo[1,2-a]pyrazin-7-yl]propan-1-one; (2S)-2-amino-1-[2-(4-fluorophenyl)-3-[(4-fluorophenyl)amino]-5H,6H,7H,8H-imidazo[1,2-a]pyrazin-7-yl]-4-methylpentan-1-one; (2S,3S)-2-amino-1-[2-(4-fluorophenyl)-3-[(4-fluorophenyl)amino]-5H,6H,7H,8H-imidazo[1,2-a]pyrazin-7-yl]-3-methylpentan-1-one; (2S)-1-[2-(4-fluorophenyl)-3-[(4-fluorophenyl)amino]-5H,6H,7H,8H-imidazo[1,2-a]pyrazin-7-yl]-2-hydroxy-3-methylbutan-1-one; (2R)-1-[2-(4-fluorophenyl)-3-[(4-fluorophenyl)amino]-5H,6H,7H,8H-imidazo[1,2-a]pyrazin-7-yl]-2-hydroxy-3-methylbutan-1-one; (2S)-2-amino-2-(4-fluorophenyl)-1-[2-(4-fluorophenyl)-3-[(4-fluorophenyl)amino]-5H,6H,7H,8H-imidazo[1,2-a]pyrazin-7-yl]ethan-1-one; (2S)-2-amino-3-(4-fluorophenyl)-1-[2-(4-fluorophenyl)-3-[(4-fluorophenyl)amino]-5H,6H,7H,8H-imidazo[1,2-a]pyrazin-7-yl]propan-1-one; (2S)-2-amino-1-[2-(4-fluorophenyl)-3-[(4-fluorophenyl)amino]-5H,6H,7H,8H-imidazo[1,2-a]pyrazin-7-yl]-3-(4-methylphenyl)propan-1-one; (2S)-2-amino-3-(3,4-difluorophenyl)-1-[2-(4-fluorophenyl)-3-[(4-fluorophenyl)amino]-5H,6H,7H,8H-imidazo[1,2-a]pyrazin-7-yl]propan-1-one; (2S)-2-amino-1-[2-(4-fluorophenyl)-3-[(4-fluorophenyl)amino]-5H,6H,7H,8H-imidazo[1,2-a]pyrazin-7-yl]-3-(1,3-thiazol-4-yl)propan-1-one; 7-{[(2S)-azetidin-2-yl]carbonyl}-N,2-bis(4-fluorophenyl)-5H,6H,7H,8H-imidazo[1,2-a]pyrazin-3-amine; (2S)-2-amino-1-[2-(4-fluorophenyl)-3-[(4-fluorophenyl)amino]-5H,6H,7H,8H-imidazo[1,2-a]pyrazin-7-yl]-3,3-dimethylbutan-1-one; (2S)-2-amino-3-cyclobutyl-1-[2-(4-fluorophenyl)-3-[(4-methylphenyl)amino]-5H,6H,7H,8H-imidazo[1,2-a]pyrazin-7-yl]propan-1-one; (2S)-2-amino-1-[2-(4-fluorophenyl)-3-[(4-methylphenyl)amino]-5H,6H,7H,8H-imidazo[1,2-a]pyrazin-7-yl]-4-methylpentan-1-one; (2S,3S)-2-amino-1-[2-(4-fluorophenyl)-3-[(4-methylphenyl)amino]-5H,6H,7H,8H-imidazo[1,2-a]pyrazin-7-yl]-3-methylpentan-1-one; (2S)-2-amino-2-(4-fluorophenyl)-1-[2-(4-fluorophenyl)-3-[(4-methylphenyl)amino]-5H,6H,7H,8H-imidazo[1,2-a]pyrazin-7-yl]ethan-1-one; (2S)-2-amino-1-[2-(4-fluorophenyl)-3-[(4-methylphenyl)amino]-5H,6H,7H,8H-imidazo[1,2-a]pyrazin-7-yl]-3-(4-methylphenyl)propan-1-one; (2S)-2-amino-3-(4-fluorophenyl)-1-[2-(4-fluorophenyl)-3-[(4-methylphenyl)amino]-5H,6H,7H,8H-imidazo[1,2-a]pyrazin-7-yl]propan-1-one; (2S)-2-amino-3-(3,4-difluorophenyl)-1-[2-(4-fluorophenyl)-3-[(4-methylphenyl)amino]-5H,6H,7H,8H-imidazo[1,2-a]pyrazin-7-yl]propan-1-one; (2S)-2-amino-1-[2-(4-fluorophenyl)-3-[(4-methylphenyl)amino]-5H,6H,7H,8H-imidazo[1,2-a]pyrazin-7-yl]-3-(1,3-thiazol-4-yl)propan-1-one; (2S)-2-amino-1-{3-[(4-chloro-3-fluorophenyl)amino]-2-(4-fluorophenyl)-5H,6H,7H,8H-imidazo[1,2-a]pyrazin-7-yl}-2-cyclopropylethan-1-one; (2S)-2-amino-1-{3-[(4-chloro-3-fluorophenyl)amino]-2-(4-fluorophenyl)-5H,6H,7H,8H-imidazo[1,2-a]pyrazin-7-yl}-3-cyclopropylpropan-1-one; (2S)-1-{3-[(4-chloro-3-fluorophenyl)amino]-2-(4-fluorophenyl)-5H,6H,7H,8H-imidazo[1,2-a]pyrazin-7-yl}-2-hydroxy-3-methylbutan-1-one; (2S)-2-amino-1-{3-[(4-chloro-3-fluorophenyl)amino]-2-(4-fluorophenyl)-5H,6H,7H,8H-imidazo[1,2-a]pyrazin-7-yl}-2-(4-fluorophenyl)ethan-1-one; (2S)-2-amino-1-{3-[(3,4-difluorophenyl)amino]-2-(4-fluorophenyl)-5H,6H,7H,8H-imidazo[1,2-a]pyrazin-7-yl}-3,3-dimethylbutan-1-one; 2-amino-1-{3-[(3-chloro-4-fluorophenyl)amino]-2-(4-fluorophenyl)-5H,6H,7H,8H-imidazo[1,2-a]pyrazin-7-yl}-2-methylpropan-1-one; N,2-bis(4-fluorophenyl)-8,8-dimethyl-5H,6H,7H,8H-imidazo[1,2-a]pyrazin-3-amine; 2-(4-fluoro-3-methylphenyl)-N-(4-methylphenyl)-5H,6H,7H,8H-imidazo[1,2-a]pyrazin-3-amine; 2-amino-1-{3-[(4-fluoro-3-methylphenyl)amino]-2-(4-fluorophenyl)-8,8-dimethyl-5H,6H,7H,8H-imidazo[1,2-a]pyrazin-7-yl}ethan-1-one; 2-amino-1-{3-[(4-chloro-3-methylphenyl)amino]-2-(4-fluorophenyl)-8,8-dimethyl-5H,6H,7H,8H-imidazo[1,2-a]pyrazin-7-yl}ethan-1-one; 2-(3-chloro-4-fluorophenyl)-N-(4-methylphenyl)-5H,6H,7H,8H-imidazo[1,2-a]pyrazin-3-amine; 2-(4-chloro-3-fluorophenyl)-N-(4-methylphenyl)-5H,6H,7H,8H-imidazo[1,2-a]pyrazin-3-amine; 2-amino-1-[2-(4-fluorophenyl)-8,8-dimethyl-3-[(3-methylphenyl)

amino]-5H,6H,7H,8H-imidazo[1,2-a]pyrazin-7-yl]ethan-1-one; 2-(4-fluorophenyl)-8,8-dimethyl-3-{[3-(trifluoromethyl)phenyl]amino}-5H,6H,7H,8H-imidazo[1,2-a]pyrazin-6-one; 2-(4-fluorophenyl)-3-[(3-fluorophenyl)amino]-8,8-dimethyl-5H,6H,7H,8H-imidazo[1,2-a]pyrazin-6-one; (2S)-2-amino-3-(4-fluorophenyl)-1-[2-(4-fluorophenyl)-3-[(4-methylphenyl)amino]-5H,6H,7H,8H-imidazo[1,2-a]pyrazin-7-yl]-2-methylpropan-1-one; 2-amino-1-[2-(4-fluorophenyl)-3-[(4-methylphenyl)amino]-5H,6H,7H,8H-imidazo[1,2-a]pyrazin-7-yl]-2,4-dimethylpentan-1-one; (2S)-2-amino-1-[2-(4-fluorophenyl)-3-[(4-methylphenyl)amino]-5H,6H,7H,8H-imidazo[1,2-a]pyrazin-7-yl]-3-hydroxy-2-methylpropan-1-one; (2R)-2-amino-1-[2-(4-fluorophenyl)-3-[(4-methylphenyl)amino]-5H,6H,7H,8H-imidazo[1,2-a]pyrazin-7-yl]-3-hydroxy-2-methylpropan-1-one; 3-[(3,4-dichlorophenyl)amino]-2-(4-fluorophenyl)-8,8-dimethyl-5H,6H,7H,8H-imidazo[1,2-a]pyrazin-6-one; 2-(4-fluorophenyl)-8,8-dimethyl-3-[(4-methylphenyl)amino]-5H,6H,7H,8H-imidazo[1,2-a]pyrazin-6-one; 3-[(4-chlorophenyl)amino]-2-(4-fluorophenyl)-8,8-dimethyl-5H,6H,7H,8H-imidazo[1,2-a]pyrazin-6-one; 3-[(3,4-difluorophenyl)amino]-2-(4-fluorophenyl)-8,8-dimethyl-5H,6H,7H,8H-imidazo[1,2-a]pyrazin-6-one; 4-{[2-(4-fluorophenyl)-8,8-dimethyl-6-oxo-5H,6H,7H,8H-imidazo[1,2-a]pyrazin-3-yl]amino}benzonitrile; 3-[(4-chloro-3-fluorophenyl)amino]-2-(4-fluorophenyl)-8,8-dimethyl-5H,6H,7H,8H-imidazo[1,2-a]pyrazin-6-one; 2-(4-fluorophenyl)-3-[(4-fluorophenyl)amino]-8,8-dimethyl-5H,6H,7H,8H-imidazo[1,2-a]pyrazin-6-one; 3-[(3-chloro-4-fluorophenyl)amino]-2-(4-fluorophenyl)-8,8-dimethyl-5H,6H,7H,8H-imidazo[1,2-a]pyrazin-6-one; N-(3-fluorophenyl)-2-(4-fluorophenyl)-8,8-dimethyl-5H,6H,7H,8H-imidazo[1,2-a]pyrazin-3-amine; 2-(4-fluorophenyl)-8,8-dimethyl-N-[3-(trifluoromethyl)phenyl]-5H,6H,7H,8H-imidazo[1,2-a]pyrazin-3-amine; 2,2,2-trifluoro-1-[2-(4-fluorophenyl)-3-[(3-fluorophenyl)amino]-8,8-dimethyl-5H,6H,7H,8H-imidazo[1,2-a]pyrazin-7-yl]ethan-1-one; 2-amino-1-[2-(4-fluoro-3-methylphenyl)-3-[(4-methylphenyl)amino]-5H,6H,7H,8H-imidazo[1,2-a]pyrazin-7-yl]ethan-1-one; 2-amino-1-[2-(4-fluoro-3-methylphenyl)-3-[(4-methylphenyl)amino]-5H,6H,7H,8H-imidazo[1,2-a]pyrazin-7-yl]-2-methylpropan-1-one; 2-amino-1-[2-(3-chloro-4-fluorophenyl)-3-[(4-methylphenyl)amino]-5H,6H,7H,8H-imidazo[1,2-a]pyrazin-7-yl]ethan-1-one; 2-amino-1-[2-(4-chloro-3-fluorophenyl)-3-[(4-methylphenyl)amino]-5H,6H,7H,8H-imidazo[1,2-a]pyrazin-7-yl]ethan-1-one; 2-amino-1-[2-(4-chloro-3-fluorophenyl)-3-[(4-methylphenyl)amino]-5H,6H,7H,8H-imidazo[1,2-a]pyrazin-7-yl]-2-methylpropan-1-one; 5-{[7-(2-aminoacetyl)-2-(4-fluorophenyl)-8,8-dimethyl-5H,6H,7H,8H-imidazo[1,2-a]pyrazin-3-yl]amino}-2-fluorobenzonitrile; 2-fluoro-5-{[2-(4-fluorophenyl)-8,8-dimethyl-5H,6H,7H,8H-imidazo[1,2-a]pyrazin-3-yl]amino}benzoic acid; 2-fluoro-5-{[2-(4-fluorophenyl)-8,8-dimethyl-5H,6H,7H,8H-imidazo[1,2-a]pyrazin-3-yl]amino}benzonitrile; 5-{[7-(2-aminoacetyl)-2-(4-fluorophenyl)-8,8-dimethyl-5H,6H,7H,8H-imidazo[1,2-a]pyrazin-3-yl]amino}-2-methylbenzonitrile; 5-{[2-(4-fluorophenyl)-8,8-dimethyl-5H,6H,7H,8H-imidazo[1,2-a]pyrazin-3-yl]amino}-2-methylbenzoic acid; 5-{[2-(4-fluorophenyl)-8,8-dimethyl-5H,6H,7H,8H-imidazo[1,2-a]pyrazin-3-yl]amino}-2-methylbenzonitrile; 2,2,2-trifluoro-1-[2-(4-fluorophenyl)-8,8-dimethyl-3-{[3-(trifluoromethyl)phenyl]amino}-5H,6H,7H,8H-imidazo[1,2-a]pyrazin-7-yl]ethan-1-one; 2-amino-1-[2-(4-fluorophenyl)-8,8-dimethyl-3-[(4-methylphenyl)amino]-5H,6H,7H,8H-imidazo[1,2-a]pyrazin-7-yl]-2-methylpropan-1-one; tert-butyl N-{1-[3-bromo-2-(4-fluorophenyl)-5H,6H,7H,8H-imidazo[1,2-a]pyrazin-7-yl]-2-methyl-1-oxopropan-2-yl}carbamate; 2-amino-1-[3-(cyclohexylamino)-2-(4-fluorophenyl)-8,8-dimethyl-5H,6H,7H,8H-imidazo[1,2-a]pyrazin-7-yl]ethan-1-one; 2-amino-1-{3-[(3-chloro-4-methylphenyl)amino]-2-(4-fluorophenyl)-8,8-dimethyl-5H,6H,7H,8H-imidazo[1,2-a]pyrazin-7-yl}ethan-1-one; 2-amino-1-{3-[(3-fluoro-4-methylphenyl)amino]-2-(4-fluorophenyl)-8,8-dimethyl-5H,6H,7H,8H-imidazo[1,2-a]pyrazin-7-yl}ethan-1-one; 4-{[7-(2-aminoacetyl)-2-(4-fluorophenyl)-8,8-dimethyl-5H,6H,7H,8H-imidazo[1,2-a]pyrazin-3-yl]amino}-2-chlorobenzonitrile; 5-{[2-(4-fluorophenyl)-8,8-dimethyl-6-oxo-5H,6H,7H,8H-imidazo[1,2-a]pyrazin-3-yl]amino}-2-methylbenzonitrile; N,2-bis(4-fluorophenyl)-5,5,7,8,8-pentamethyl-5H,6H,7H,8H-imidazo[1,2-a]pyrazin-3-amine; 2-fluoro-5-{[2-(4-fluorophenyl)-8,8-dimethyl-6-oxo-5H,6H,7H,8H-imidazo[1,2-a]pyrazin-3-yl]amino}benzonitrile; 2-(4-fluorophenyl)-5,5,7,8,8-pentamethyl-3-[(4-methylphenyl)amino]-5H,6H,7H,8H-imidazo[1,2-a]pyrazin-6-one; 2-(4-fluorophenyl)-5,5,7,8,8-pentamethyl-N-(4-methylphenyl)-5H,6H,7H,8H-imidazo[1,2-a]pyrazin-3-amine; tert-butyl N-{2-[2-(4-fluorophenyl)-5H,6H,7H,8H-imidazo[1,2-a]pyrazin-7-yl]-2-oxoethyl}carbamate; N-(3-fluoro-4-methylphenyl)-2-(4-fluorophenyl)-8,8-dimethyl-5H,6H,7H,8H-imidazo[1,2-a]pyrazin-3-amine; N-(3-chloro-4-methylphenyl)-2-(4-fluorophenyl)-8,8-dimethyl-5H,6H,7H,8H-imidazo[1,2-a]pyrazin-3-amine; 2-(4-fluorophenyl)-8,8-dimethyl-3-[(3,4,5-trifluorophenyl)amino]-5H,6H,7H,8H-imidazo[1,2-a]pyrazin-6-one; 3-[(4-fluoro-3-methylphenyl)amino]-2-(4-fluorophenyl)-8,8-dimethyl-5H,6H,7H,8H-imidazo[1,2-a]pyrazin-6-one; 2-(4-fluorophenyl)-3-[(6-methoxypyridin-3-yl)amino]-8,8-dimethyl-5H,6H,7H,8H-imidazo[1,2-a]pyrazin-6-one; 3-[(3-chloro-4-methylphenyl)amino]-2-(4-fluorophenyl)-8,8-dimethyl-5H,6H,7H,8H-imidazo[1,2-a]pyrazin-6-one; 2-(4-fluorophenyl)-8,8-dimethyl-3-[(4-methylpyridin-2-yl)amino]-5H,6H,7H,8H-imidazo[1,2-a]pyrazin-6-one; 2-chloro-4-{[2-(4-fluorophenyl)-8,8-dimethyl-6-oxo-5H,6H,7H,8H-imidazo[1,2-a]pyrazin-3-yl]amino}benzonitrile; (8R)-3-[(4-chlorophenyl)amino]-2-(4-fluorophenyl)-8-(propan-2-yl)-5H,6H,7H,8H-imidazo[1,2-a]pyrazin-6-one; (8R)-3-[(4-chloro-3-fluorophenyl)amino]-2-(4-fluorophenyl)-8-(propan-2-yl)-5H,6H,7H,8H-imidazo[1,2-a]pyrazin-6-one; 3-[(4-chloro-3-fluorophenyl)amino]-2-(3,4-difluorophenyl)-8,8-dimethyl-5H,6H,7H,8H-imidazo[1,2-a]pyrazin-6-one; N-(3-{[7-(2-aminoacetyl)-2-(4-fluorophenyl)-8,8-dimethyl-5H,6H,7H,8H-imidazo[1,2-a]pyrazin-3-yl]amino}phenyl)methanesulfonamide; 3-{[7-(2-aminoacetyl)-2-(4-fluorophenyl)-8,8-dimethyl-5H,6H,7H,8H-imidazo[1,2-a]pyrazin-3-yl]amino}-N-methylbenzamide; 2-amino-1-[2-(4-fluorophenyl)-8,8-dimethyl-3-[(3,4,5-trifluorophenyl)amino]-5H,6H,7H,8H-imidazo[1,2-a]pyrazin-7-yl]ethan-1-one; 2-(4-fluorophenyl)-8,8-dimethyl-N-(3,4,5-trifluorophenyl)-5H,6H,7H,8H-imidazo[1,2-a]pyrazin-3-amine; N-(4-chlorophenyl)-2-(4-fluorophenyl)-6,6,7-trimethyl-5H,6H,7H,8H-imidazo[1,2-a]pyrazin-3-amine; 2-amino-1-{3-[(4-chlorophenyl)amino]-2-(4-fluorophenyl)-6,6-dimethyl-5H,6H,7H,8H-imidazo[1,2-a]pyrazin-7-yl}ethan-1-one; N-(4-chlorophenyl)-2-(4-fluorophenyl)-6,6-dimethyl-5H,6H,7H,8H-imidazo[1,2-a]pyrazin-3-amine; (8S)-3-[(4-chloro-3-fluorophenyl)amino]-2-(4-fluorophenyl)-8-methyl-5H,6H,7H,8H-imidazo[1,2-a]pyrazin-6-one; 3-[(1,5-dimethyl-1H-pyrazol-3-yl)amino]-2-(4-fluorophenyl)-8,8-dimethyl-5H,6H,7H,8H-imidazo[1,2-a]pyrazin-6-one; 3-({[(2S)-1-ethylpyrrolidin-2-yl]methyl}amino)-2-(4-fluorophenyl)-8,8-dimethyl-5H,6H,7H,8H-imidazo[1,2-a]pyrazin-6-one;

(8S)-3-[(4-chloro-3-fluorophenyl)amino]-2-(4-fluorophenyl)-8-(propan-2-yl)-5H,6H,7H,8H-imidazo[1,2-a]pyrazin-6-one; (8S)-3-[(4-chlorophenyl)amino]-2-(4-fluorophenyl)-8-methyl-5H,6H,7H,8H-imidazo[1,2-a]pyrazin-6-one; (8R)-3-[(4-chloro-3-fluorophenyl)amino]-2-(4-fluorophenyl)-8-methyl-5H,6H,7H,8H-imidazo[1,2-a]pyrazin-6-one; (8R)-3-[(4-chlorophenyl)amino]-2-(4-fluorophenyl)-8-methyl-5H,6H,7H,8H-imidazo[1,2-a]pyrazin-6-one; 2-(4-fluorophenyl)-8,8-dimethyl-3-(quinolin-3-ylamino)-5H,6H,7H,8H-imidazo[1,2-a]pyrazin-6-one; 2-(4-fluorophenyl)-3-[(4-methanesulfonylphenyl)amino]-8,8-dimethyl-5H,6H,7H,8H-imidazo[1,2-a]pyrazin-6-one; 2-(4-fluorophenyl)-8,8-dimethyl-3-{[4-(4-methylpiperazin-1-yl)phenyl]amino}-5H,6H,7H,8H-imidazo[1,2-a]pyrazin-6-one; 2-(4-fluorophenyl)-8,8-dimethyl-3-({3-[(4-methylpiperazin-1-yl)methyl]phenyl}amino)-5H,6H,7H,8H-imidazo[1,2-a]pyrazin-6-one; 2-amino-1-[2-(4-fluorophenyl)-3-[(4-methanesulfonylphenyl)amino]-8,8-dimethyl-5H,6H,7H,8H-imidazo[1,2-a]pyrazin-7-yl]ethan-1-one; 2-amino-1-[2-(4-fluorophenyl)-8,8-dimethyl-3-{[4-(4-methylpiperazin-1-yl)phenyl]amino}-5H,6H,7H,8H-imidazo[1,2-a]pyrazin-7-yl]ethan-1-one; 2-(4-fluorophenyl)-8,8-dimethyl-N-[4-(4-methylpiperazin-1-yl)phenyl]-5H,6H,7H,8H-imidazo[1,2-a]pyrazin-3-amine; 2-amino-1-[2-(4-fluorophenyl)-6,6-dimethyl-3-[(4-methylphenyl)amino]-5H,6H,7H,8H-imidazo[1,2-a]pyrazin-7-yl]ethan-1-one; 2-amino-1-[2-(4-fluorophenyl)-3-[(4-fluorophenyl)amino]-6,6-dimethyl-5H,6H,7H,8H-imidazo[1,2-a]pyrazin-7-yl]ethan-1-one; 2-amino-1-{3-[(3,4-difluorophenyl)amino]-2-(4-fluorophenyl)-6,6-dimethyl-5H,6H,7H,8H-imidazo[1,2-a]pyrazin-7-yl}ethan-1-one; 2-amino-1-{3-[(3-chloro-4-fluorophenyl)amino]-2-(4-fluorophenyl)-6,6-dimethyl-5H,6H,7H,8H-imidazo[1,2-a]pyrazin-7-yl}ethan-1-one; 5-{[7-(2-aminoacetyl)-2-(4-fluorophenyl)-6,6-dimethyl-5H,6H,7H,8H-imidazo[1,2-a]pyrazin-3-yl]amino}-2-fluorobenzonitrile; 2-(4-fluorophenyl)-6,6-dimethyl-N-(4-methylphenyl)-5H,6H,7H,8H-imidazo[1,2-a]pyrazin-3-amine; N,2-bis(4-fluorophenyl)-6,6-dimethyl-5H,6H,7H,8H-imidazo[1,2-a]pyrazin-3-amine; N-(3,4-difluorophenyl)-2-(4-fluorophenyl)-6,6-dimethyl-5H,6H,7H,8H-imidazo[1,2-a]pyrazin-3-amine; 2-fluoro-5-{[2-(4-fluorophenyl)-6,6-dimethyl-5H,6H,7H,8H-imidazo[1,2-a]pyrazin-3-yl]amino}benzonitrile; 2-(3-fluorophenyl)-7-[(4-methoxyphenyl)methyl]-5,5-dimethyl-N-(4-methylphenyl)-5H,6H,7H,8H-imidazo[1,2-a]pyrazin-3-amine; 2-amino-1-[2-(4-fluorophenyl)-3-[(4-fluorophenyl)amino]-8,8-dimethyl-5H,6H,7H,8H-imidazo[1,2-a]pyrazin-7-yl]-2-methylpropan-1-one; 2-amino-1-{3-[(4-chlorophenyl)amino]-2-(4-fluorophenyl)-8,8-dimethyl-5H,6H,7H,8H-imidazo[1,2-a]pyrazin-7-yl}-2-methylpropan-1-one; 2-amino-1-{3-[(3,4-difluorophenyl)amino]-2-(4-fluorophenyl)-8,8-dimethyl-5H,6H,7H,8H-imidazo[1,2-a]pyrazin-7-yl}-2-methylpropan-1-one; 2-amino-1-{3-[(3-chloro-4-fluorophenyl)amino]-2-(4-fluorophenyl)-8,8-dimethyl-5H,6H,7H,8H-imidazo[1,2-a]pyrazin-7-yl}-2-methylpropan-1-one; 2-amino-1-{3-[(3,4-dichlorophenyl)amino]-2-(4-fluorophenyl)-8,8-dimethyl-5H,6H,7H,8H-imidazo[1,2-a]pyrazin-7-yl}-2-methylpropan-1-one; 2-amino-1-{3-[(4-fluoro-3-methylphenyl)amino]-2-(4-fluorophenyl)-8,8-dimethyl-5H,6H,7H,8H-imidazo[1,2-a]pyrazin-7-yl}-2-methylpropan-1-one; 2-amino-1-{3-[(4-chloro-3-methylphenyl)amino]-2-(4-fluorophenyl)-8,8-dimethyl-5H,6H,7H,8H-imidazo[1,2-a]pyrazin-7-yl}-2-methylpropan-1-one; 5-{[7-(2-amino-2-methylpropanoyl)-2-(4-fluorophenyl)-8,8-dimethyl-5H,6H,7H,8H-imidazo[1,2-a]pyrazin-3-yl]amino}-2-methylbenzonitrile; 4-{[7-(2-amino-2-methylpropanoyl)-2-(4-fluorophenyl)-8,8-dimethyl-5H,6H,7H, 8H-imidazo[1,2-a]pyrazin-3-yl]amino}-2-chlorobenzonitrile; (2S)-1-[2-(3-fluorophenyl)-5,5-dimethyl-3-[(4-methylphenyl)amino]-5H,6H,7H,8H-imidazo[1,2-a]pyrazin-7-yl]-2-hydroxy-3-methylbutan-1-one; 2-amino-1-[2-(3-fluorophenyl)-5,5-dimethyl-3-[(4-methylphenyl)amino]-5H,6H,7H,8H-imidazo[1,2-a]pyrazin-7-yl]-2-methylpropan-1-one; 2-amino-1-[2-(3-fluorophenyl)-5,5-dimethyl-3-[(4-methylphenyl)amino]-5H,6H,7H,8H-imidazo[1,2-a]pyrazin-7-yl]ethan-1-one; 2-amino-1-[(8S)-3-[(4-chloro-3-fluorophenyl)amino]-2-(4-fluorophenyl)-8-(propan-2-yl)-5H,6H,7H, 8H-imidazo[1,2-a]pyrazin-7-yl]ethan-1-one; 2-amino-1-[(8R)-3-[(4-chloro-3-fluorophenyl)amino]-2-(4-fluorophenyl)-8-methyl-5H,6H,7H,8H-imidazo[1,2-a]pyrazin-7-yl]ethan-1-one; 2-amino-1-[(8S)-3-[(4-chloro-3-fluorophenyl)amino]-2-(4-fluorophenyl)-8-methyl-5H,6H,7H,8H-imidazo[1,2-a]pyrazin-7-yl]ethan-1-one; 3-[(3-fluoro-4-methylphenyl)amino]-2-(4-fluorophenyl)-8,8-dimethyl-5H,6H,7H,8H-imidazo[1,2-a]pyrazin-6-one; (2S)-1-[2-(3-fluorophenyl)-5,5-dimethyl-3-[(4-methylphenyl)amino]-5H,6H,7H,8H-imidazo[1,2-a]pyrazin-7-yl]-2-hydroxy-3-phenylpropan-1-one; 2-amino-1-{3-[(1,5-dimethyl-1H-pyrazol-3-yl)amino]-2-(4-fluorophenyl)-8,8-dimethyl-5H,6H,7H,8H-imidazo[1,2-a]pyrazin-7-yl}ethan-1-one; 2-amino-1-{3-[(1-ethyl-1H-pyrazol-5-yl)amino]-2-(4-fluorophenyl)-8,8-dimethyl-5H,6H,7H,8H-imidazo[1,2-a]pyrazin-7-yl}ethan-1-one; 2-amino-1-[(8R)-3-[(4-chloro-3-fluorophenyl)amino]-2-(4-fluorophenyl)-8-(propan-2-yl)-5H,6H,7H,8H-imidazo[1,2-a]pyrazin-7-yl]ethan-1-one; 3-[(3-fluoro-4-methylphenyl)amino]-2-(3-fluorophenyl)-8,8-dimethyl-5H,6H,7H,8H-imidazo[1,2-a]pyrazin-6-one; 3-[(3-chloro-4-methylphenyl)amino]-2-(3-fluorophenyl)-8,8-dimethyl-5H,6H,7H,8H-imidazo[1,2-a]pyrazin-6-one; 3-[(4-chloro-3-fluorophenyl)amino]-2-(3-fluorophenyl)-8,8-dimethyl-5H,6H,7H,8H-imidazo[1,2-a]pyrazin-6-one; N,2-bis(4-fluorophenyl)-7,8,8-trimethyl-5H,6H,7H,8H-imidazo[1,2-a]pyrazin-3-amine; N-(4-chlorophenyl)-2-(4-fluorophenyl)-7,8,8-trimethyl-5H,6H,7H,8H-imidazo[1,2-a]pyrazin-3-amine; N-(4-chlorophenyl)-2-(4-fluorophenyl)-5,5,7-trimethyl-5H,6H,7H,8H-imidazo[1,2-a]pyrazin-3-amine; N-(4-chloro-3-fluorophenyl)-2-(4-fluorophenyl)-5,5,7-trimethyl-5H,6H,7H,8H-imidazo[1,2-a]pyrazin-3-amine; N-(4-chloro-3-methylphenyl)-2-(4-fluorophenyl)-5,5,7-trimethyl-5H,6H,7H,8H-imidazo[1,2-a]pyrazin-3-amine; N-(3,4-difluorophenyl)-2-(4-fluorophenyl)-5,5,7-trimethyl-5H,6H,7H,8H-imidazo[1,2-a]pyrazin-3-amine; 5-{[2-(4-fluorophenyl)-5,5,7-trimethyl-5H,6H,7H,8H-imidazo[1,2-a]pyrazin-3-yl]amino}-2-methylbenzonitrile; 3-[(4-chloro-3-fluorophenyl)amino]-2-(4-fluorophenyl)-7-[(4-methoxyphenyl)methyl]-5,5-dimethyl-5H,6H,7H, 8H-imidazo[1,2-a]pyrazin-6-one; 3-[(4-chloro-3-methylphenyl)amino]-2-(4-fluorophenyl)-7-[(4-methoxyphenyl)methyl]-5,5-dimethyl-5H,6H,7H,8H-imidazo[1,2-a]pyrazin-6-one; 3-[(4-chloro-3-fluorophenyl)amino]-2-(4-fluorophenyl)-5,5,7-trimethyl-5H,6H,7H,8H-imidazo[1,2-a]pyrazin-6-one; 3-[(4-chloro-3-methylphenyl)amino]-2-(4-fluorophenyl)-5,5,7-trimethyl-5H,6H,7H,8H-imidazo[1,2-a]pyrazin-6-one; 3-[(4-fluoro-3-methylphenyl)amino]-2-(4-fluorophenyl)-5,5,7-trimethyl-5H,6H,7H,8H-imidazo[1,2-a]pyrazin-6-one; 3-[(4-chloro-3-fluorophenyl)amino]-2-(4-fluorophenyl)-5,5-dimethyl-5H,6H,7H,8H-imidazo[1,2-a]pyrazin-6-one; 3-[(4-chloro-3-methylphenyl)amino]-2-(4-fluorophenyl)-5,5-dimethyl-5H,6H,7H,8H-imidazo[1,2-a]pyrazin-6-one; 2-amino-1-{3-[(4-chlorophenyl)amino]-2-(3-fluorophenyl)-5,5-dimethyl-5H,6H,7H,8H-imidazo[1,2-a]pyrazin-7-yl}ethan-1-one; 2-amino-1-[2-(3-fluorophenyl)-3-[(4-fluorophenyl)amino]-5,5-dimethyl-5H,6H,7H,8H-imidazo[1,2-a]pyrazin-7-yl]

ethan-1-one; 2-amino-1-{3-[(3,4-difluorophenyl)amino]-2-(3-fluorophenyl)-5,5-dimethyl-5H,6H,7H,8H-imidazo[1,2-a]pyrazin-7-yl}ethan-1-one; 2-amino-1-{3-[(4-chloro-3-fluorophenyl)amino]-2-(3-fluorophenyl)-5,5-dimethyl-5H,6H,7H,8H-imidazo[1,2-a]pyrazin-7-yl}ethan-1-one; 2-amino-1-{3-[(3-chloro-4-fluorophenyl)amino]-2-(3-fluorophenyl)-5,5-dimethyl-5H,6H,7H,8H-imidazo[1,2-a]pyrazin-7-yl}ethan-1-one; 2-amino-1-{3-[(4-fluoro-3-methylphenyl)amino]-2-(3-fluorophenyl)-5,5-dimethyl-5H,6H,7H,8H-imidazo[1,2-a]pyrazin-7-yl}ethan-1-one; 2-amino-1-{3-[(4-chloro-3-methylphenyl)amino]-2-(3-fluorophenyl)-5,5-dimethyl-5H,6H,7H,8H-imidazo[1,2-a]pyrazin-7-yl}ethan-1-one; N-(3-chloro-4-fluorophenyl)-2-(4-fluorophenyl)-7,8,8-trimethyl-5H,6H,7H,8H-imidazo[1,2-a]pyrazin-3-amine; 2-amino-1-{3-[(4-fluoro-3-methylphenyl)amino]-2-(4-fluorophenyl)-5H,6H,7H,8H-imidazo[1,2-a]pyrazin-7-yl}-2-methylpropan-1-one; 2-amino-1-{3-[(4-chloro-3-methylphenyl)amino]-2-(4-fluorophenyl)-5H,6H,7H,8H-imidazo[1,2-a]pyrazin-7-yl}-2-methylpropan-1-one; 5-{[7-(2-amino-2-methylpropanoyl)-2-(4-fluorophenyl)-5H,6H,7H,8H-imidazo[1,2-a]pyrazin-3-yl]amino}-2-methylbenzonitrile; 2-amino-1-{3-[(3-fluoro-4-methylphenyl)amino]-2-(4-fluorophenyl)-5H,6H,7H,8H-imidazo[1,2-a]pyrazin-7-yl}-2-methylpropan-1-one; 2-amino-1-{3-[(3-chloro-4-methylphenyl)amino]-2-(4-fluorophenyl)-5H,6H,7H,8H-imidazo[1,2-a]pyrazin-7-yl}-2-methylpropan-1-one; 2-amino-1-(3-{[3-chloro-4-(trifluoromethyl)phenyl]amino}-2-(4-fluorophenyl)-5H,6H,7H,8H-imidazo[1,2-a]pyrazin-7-yl)-2-methylpropan-1-one; 2-amino-1-(3-{[4-fluoro-3-(trifluoromethyl)phenyl]amino}-2-(4-fluorophenyl)-5H,6H,7H,8H-imidazo[1,2-a]pyrazin-7-yl)-2-methylpropan-1-one; 4-{[7-(2-amino-2-methylpropanoyl)-2-(4-fluorophenyl)-5H,6H,7H,8H-imidazo[1,2-a]pyrazin-3-yl]amino}-2-(trifluoromethyl)benzonitrile; 5-{[7-(2-amino-2-methylpropanoyl)-2-(4-fluorophenyl)-5H,6H,7H,8H-imidazo[1,2-a]pyrazin-3-yl]amino}-2-fluorobenzonitrile; 2-amino-1-{3-[(3,4-dimethylphenyl)amino]-2-(4-fluorophenyl)-5H,6H,7H,8H-imidazo[1,2-a]pyrazin-7-yl}-2-methylpropan-1-one; 2-amino-1-[2-(4-fluorophenyl)-3-[(3-methylphenyl)amino]-5H,6H,7H,8H-imidazo[1,2-a]pyrazin-7-yl]-2-methylpropan-1-one; 2-amino-1-{3-[(3-chlorophenyl)amino]-2-(4-fluorophenyl)-5H,6H,7H,8H-imidazo[1,2-a]pyrazin-7-yl}-2-methylpropan-1-one; 2-amino-1-[2-(4-fluorophenyl)-3-{[3-(trifluoromethoxy)phenyl]amino}-5H,6H,7H,8H-imidazo[1,2-a]pyrazin-7-yl]-2-methylpropan-1-one; 2-amino-1-{3-[(4-ethylphenyl)amino]-2-(4-fluorophenyl)-5H,6H,7H,8H-imidazo[1,2-a]pyrazin-7-yl}-2-methylpropan-1-one; 2-amino-1-(3-{[4-(difluoromethoxy)phenyl]amino}-2-(4-fluorophenyl)-5H,6H,7H,8H-imidazo[1,2-a]pyrazin-7-yl)-2-methylpropan-1-one; 2-amino-1-[2-(4-fluorophenyl)-3-{[4-(trifluoromethoxy)phenyl]amino}-5H,6H,7H,8H-imidazo[1,2-a]pyrazin-7-yl]-2-methylpropan-1-one; 2-amino-1-{3-[(3,5-dichlorophenyl)amino]-2-(4-fluorophenyl)-5H,6H,7H,8H-imidazo[1,2-a]pyrazin-7-yl}-2-methylpropan-1-one; 10-[(3,4-difluorophenyl)amino]-11-(4-fluorophenyl)-4,4-dimethyl-3,6,9,12-tetraazatricyclo[7.3.0.0 {2,6}]dodeca-1(12),2,10-trien-5-one; 10-[(3,4-difluorophenyl)amino]-11-(4-fluorophenyl)-4,4-dimethyl-3,6,9,12-tetraazatricyclo[7.3.0.0 {2,6}]dodeca-1(12),10-dien-5-one; 2-amino-1-[2-(4-fluorophenyl)-8,8-dimethyl-3-[(4-phenylphenyl)amino]-5H,6H,7H,8H-imidazo[1,2-a]pyrazin-7-yl]ethan-1-one; 2-amino-1-{3-[(4-ethylphenyl)amino]-2-(4-fluorophenyl)-8,8-dimethyl-5H,6H,7H,8H-imidazo[1,2-a]pyrazin-7-yl}ethan-1-one; 2-amino-1-[2-(4-fluorophenyl)-8,8-dimethyl-3-{[4-(trifluoromethoxy)phenyl]amino}-5H,6H,7H,8H-imidazo[1,2-a]pyrazin-7-yl]ethan-1-one; 2-amino-1-[2-(4-fluorophenyl)-8,8-dimethyl-3-{[3-(trifluoromethoxy)phenyl]amino}-5H,6H,7H,8H-imidazo[1,2-a]pyrazin-7-yl]ethan-1-one; 2-amino-1-{3-[(3-chlorophenyl)amino]-2-(4-fluorophenyl)-8,8-dimethyl-5H,6H,7H,8H-imidazo[1,2-a]pyrazin-7-yl}ethan-1-one; 2-amino-1-[2-(4-fluorophenyl)-8,8-dimethyl-3-{[3-(trifluoromethyl)phenyl]amino}-5H,6H,7H,8H-imidazo[1,2-a]pyrazin-7-yl]ethan-1-one; 3-{[7-(2-aminoacetyl)-2-(4-fluorophenyl)-8,8-dimethyl-5H,6H,7H,8H-imidazo[1,2-a]pyrazin-3-yl]amino}benzonitrile; 2-amino-1-{3-[(3,4-dimethylphenyl)amino]-2-(4-fluorophenyl)-8,8-dimethyl-5H,6H,7H,8H-imidazo[1,2-a]pyrazin-7-yl}ethan-1-one; 4-{[7-(2-aminoacetyl)-2-(4-fluorophenyl)-8,8-dimethyl-5H,6H,7H,8H-imidazo[1,2-a]pyrazin-3-yl]amino}-2-(trifluoromethyl)benzonitrile; 2-amino-1-{3-[(3,5-dimethylphenyl)amino]-2-(4-fluorophenyl)-8,8-dimethyl-5H,6H,7H,8H-imidazo[1,2-a]pyrazin-7-yl}ethan-1-one; 2-amino-1-(3-{[4-fluoro-3-(trifluoromethyl)phenyl]amino}-2-(4-fluorophenyl)-8,8-dimethyl-5H,6H,7H,8H-imidazo[1,2-a]pyrazin-7-yl)ethan-1-one; 2-amino-1-(3-{[3-chloro-4-(trifluoromethyl)phenyl]amino}-2-(4-fluorophenyl)-8,8-dimethyl-5H,6H,7H,8H-imidazo[1,2-a]pyrazin-7-yl)ethan-1-one; 2-amino-1-{3-[(4-chloro-3-methylphenyl)amino]-2-(4-fluorophenyl)-5,5-dimethyl-5H,6H,7H,8H-imidazo[1,2-a]pyrazin-7-yl}ethan-1-one; 2-amino-1-{3-[(4,4-difluorocyclohexyl)amino]-2-(4-fluorophenyl)-8,8-dimethyl-5H,6H,7H,8H-imidazo[1,2-a]pyrazin-7-yl}ethan-1-one; 2-amino-1-[2-(4-fluorophenyl)-8,8-dimethyl-3-[(4-phenylcyclohexyl)amino]-5H,6H,7H,8H-imidazo[1,2-a]pyrazin-7-yl]ethan-1-one; 2-amino-1-[2-(4-fluorophenyl)-8,8-dimethyl-3-{[4-(trifluoromethyl)cyclohexyl]amino}-5H,6H,7H,8H-imidazo[1,2-a]pyrazin-7-yl]ethan-1-one; 2-amino-1-{3-[(4-tert-butylcyclohexyl)amino]-2-(4-fluorophenyl)-8,8-dimethyl-5H,6H,7H,8H-imidazo[1,2-a]pyrazin-7-yl}ethan-1-one; 2-amino-1-[2-(4-fluorophenyl)-8,8-dimethyl-3-[(2-methylcyclohexyl)amino]-5H,6H,7H,8H-imidazo[1,2-a]pyrazin-7-yl]ethan-1-one; 2-amino-1-[3-(cycloheptylamino)-2-(4-fluorophenyl)-8,8-dimethyl-5H,6H,7H,8H-imidazo[1,2-a]pyrazin-7-yl]ethan-1-one; 2-amino-1-[2-(4-fluorophenyl)-8,8-dimethyl-3-[(3,3,5-trimethylcyclohexyl)amino]-5H,6H,7H,8H-imidazo[1,2-a]pyrazin-7-yl]ethan-1-one; 2-amino-1-{3-[(1R,2R,4S)-bicyclo[2.2.1]heptan-2-ylamino]-2-(4-fluorophenyl)-8,8-dimethyl-5H,6H,7H,8H-imidazo[1,2-a]pyrazin-7-yl}ethan-1-one; 2-amino-1-{3-[3-(dimethylamino)pyrrolidin-1-yl]-2-(4-fluorophenyl)-8,8-dimethyl-5H,6H,7H,8H-imidazo[1,2-a]pyrazin-7-yl}ethan-1-one; 2-amino-1-[2-(4-fluorophenyl)-8,8-dimethyl-3-[4-(piperidin-1-yl)piperidin-1-yl]-5H,6H,7H,8H-imidazo[1,2-a]pyrazin-7-yl]ethan-1-one; 2-amino-1-[3-(cyclopentylamino)-2-(4-fluorophenyl)-8,8-dimethyl-5H,6H,7H,8H-imidazo[1,2-a]pyrazin-7-yl]ethan-1-one; 2-amino-1-[3-(cyclobutylamino)-2-(4-fluorophenyl)-8,8-dimethyl-5H,6H,7H,8H-imidazo[1,2-a]pyrazin-7-yl]ethan-1-one; 2-amino-1-[2-(4-fluorophenyl)-8,8-dimethyl-3-(oxan-4-ylamino)-5H,6H,7H,8H-imidazo[1,2-a]pyrazin-7-yl]ethan-1-one; 2-amino-1-[2-(4-fluorophenyl)-8,8-dimethyl-3-[4-(1-methylpiperidin-4-yl)piperazin-1-yl]-5H,6H,7H,8H-imidazo[1,2-a]pyrazin-7-yl]ethan-1-one; 2-amino-1-[2-(4-fluorophenyl)-8,8-dimethyl-3-[(2-methylbutyl)amino]-5H,6H,7H,8H-imidazo[1,2-a]pyrazin-7-yl]ethan-1-one; 2-amino-1-{3-[(4-chloro-3-fluorophenyl)amino]-2-(4-fluorophenyl)-5,5-dimethyl-5H,6H,7H,8H-imidazo[1,2-a]pyrazin-7-yl}ethan-1-one; 2-amino-1-[2-(4-fluorophenyl)-3-[(4-fluorophenyl)amino]-5,5-dimethyl-5H,6H,7H,8H-imidazo[1,2-a]pyrazin-7-yl]ethan-1-one; 2-amino-1-[2-(4-fluorophenyl)-5,5-dimethyl-3-[(4-methylphenyl)amino]-

5H,6H,7H,8H-imidazo[1,2-a]pyrazin-7-yl]ethan-1-one; 2-amino-1-{3-[(4-chlorophenyl)amino]-2-(4-fluorophenyl)-5,5-dimethyl-5H,6H,7H,8H-imidazo[1,2-a]pyrazin-7-yl}ethan-1-one; 2-amino-1-{3-[(4-chlorophenyl)(methyl)amino]-2-(4-fluorophenyl)-8,8-dimethyl-5H,6H,7H,8H-imidazo[1,2-a]pyrazin-7-yl}ethan-1-one; 7-[2-(dimethylamino)ethyl]-2-(4-fluorophenyl)-8,8-dimethyl-3-[(4-methylphenyl)amino]-5H,6H,7H,8H-imidazo[1,2-a]pyrazin-6-one; 7-[2-(dimethylamino)ethyl]-3-[(3-fluoro-4-methylphenyl)amino]-2-(4-fluorophenyl)-8,8-dimethyl-5H,6H,7H,8H-imidazo[1,2-a]pyrazin-6-one; 3-[(3-chloro-4-methylphenyl)amino]-7-[2-(dimethylamino)ethyl]-2-(4-fluorophenyl)-8,8-dimethyl-5H,6H,7H, 8H-imidazo[1,2-a]pyrazin-6-one; 7-[2-(dimethylamino)ethyl]-3-[(4-fluoro-3-methylphenyl)amino]-2-(4-fluorophenyl)-8,8-dimethyl-5H,6H,7H,8H-imidazo[1,2-a]pyrazin-6-one; 3-[(4-chloro-3-methylphenyl)amino]-7-[2-(dimethylamino)ethyl]-2-(4-fluorophenyl)-8,8-dimethyl-5H,6H,7H, 8H-imidazo[1,2-a]pyrazin-6-one; 3-[(4-chloro-3-fluorophenyl)amino]-7-[2-(dimethylamino)ethyl]-2-(4-fluorophenyl)-8,8-dimethyl-5H,6H,7H,8H-imidazo[1,2-a]pyrazin-6-one; 7-(azetidin-3-ylmethyl)-3-[(4-fluoro-3-methylphenyl)amino]-2-(3-fluorophenyl)-8,8-dimethyl-5H,6H,7H,8H-imidazo[1,2-a]pyrazin-6-one; 7-(2-aminoethyl)-2-(4-fluorophenyl)-3-[(4-fluorophenyl)amino]-8,8-dimethyl-5H,6H,7H,8H-imidazo[1,2-a]pyrazin-6-one; 2-(4-fluorophenyl)-3-[(4-fluorophenyl)amino]-7-(2-hydroxyethyl)-8,8-dimethyl-5H,6H,7H, 8H-imidazo[1,2-a]pyrazin-6-one; 7-(3-aminopropyl)-3-[(4-fluoro-3-methylphenyl)amino]-2-(3-fluorophenyl)-8,8-dimethyl-5H,6H,7H,8H-imidazo[1,2-a]pyrazin-6-one; 3-[(4-fluoro-3-methylphenyl)amino]-2-(3-fluorophenyl)-7-(3-hydroxypropyl)-8,8-dimethyl-5H,6H, 7H,8H-imidazo[1,2-a]pyrazin-6-one; 3-[(4-fluoro-3-methylphenyl)amino]-2-(3-fluorophenyl)-7-(3-methoxypropyl)-8,8-dimethyl-5H,6H,7H,8H-imidazo[1,2-a]pyrazin-6-one; 4-{3-[(4-fluoro-3-methylphenyl)amino]-2-(3-fluorophenyl)-8,8-dimethyl-6-oxo-5H,6H,7H,8H-imidazo[1,2-a]pyrazin-7-yl}butanoic acid; 2-amino-1-[2-(4-fluorophenyl)-3-[(4-fluorophenyl)methyl]-8,8-dimethyl-5H,6H,7H, 8H-imidazo[1,2-a]pyrazin-7-yl]ethan-1-one; 2-amino-1-[2-(4-fluorophenyl)-8,8-dimethyl-3-[(4-methylphenyl)methyl]-5H,6H,7H,8H-imidazo[1,2-a]pyrazin-7-yl]ethan-1-one; 2-amino-1-[2-(4-fluorophenyl)-3-[(4-methoxyphenyl)methyl]-8,8-dimethyl-5H,6H,7H,8H-imidazo[1,2-a]pyrazin-7-yl]ethan-1-one; 2-amino-1-{3-[(3,4-difluorophenyl)methyl]-2-(4-fluorophenyl)-8,8-dimethyl-5H,6H,7H, 8H-imidazo[1,2-a]pyrazin-7-yl}ethan-1-one; 2-amino-1-[2-(4-fluorophenyl)-3-[(4-fluorophenyl)methyl]-5H,6H,7H,8H-imidazo[1,2-a]pyrazin-7-yl]-2-methylpropan-1-one; 2-amino-1-[2-(4-fluorophenyl)-8,8-dimethyl-3-[(4-methylpiperazin-1-yl)methyl]-5H,6H,7H, 8H-imidazo[1,2-a]pyrazin-7-yl]ethan-1-one; 2-amino-1-[3-(cyclohexylmethyl)-2-(4-fluorophenyl)-8,8-dimethyl-5H,6H,7H,8H-imidazo[1,2-a]pyrazin-7-yl]ethan-1-one; 2-amino-1-[2-(4-fluorophenyl)-8,8-dimethyl-5H,6H,7H, 8H-imidazo[1,2-a]pyrazin-7-yl]-3-(4-methylphenyl)propan-1-one; 2-amino-4-(3-fluorophenyl)-1-[2-(4-fluorophenyl)-8,8-dimethyl-5H,6H,7H,8H-imidazo[1,2-a]pyrazin-7-yl]butan-1-one; 2-amino-4-(4-chlorophenyl)-1-[2-(4-fluorophenyl)-8,8-dimethyl-5H,6H,7H,8H-imidazo[1,2-a]pyrazin-7-yl]butan-1-one; 2-amino-3-cyclohexyl-1-[2-(4-fluorophenyl)-8,8-dimethyl-5H,6H,7H,8H-imidazo[1,2-a]pyrazin-7-yl]propan-1-one; 2-amino-1-[2-(4-fluorophenyl)-8,8-dimethyl-3-(4-methylphenyl)-5H,6H,7H, 8H-imidazo[1,2-a]pyrazin-7-yl]ethan-1-one; 2-amino-1-[2,3-bis(4-fluorophenyl)-8,8-dimethyl-5H,6H,7H, 8H-imidazo[1,2-a]pyrazin-7-yl]ethan-1-one; 2-amino-1-[3-(3-chloro-4-fluorophenyl)-2-(4-fluorophenyl)-8,8-dimethyl-5H,6H,7H, 8H-imidazo[1,2-a]pyrazin-7-yl]ethan-1-one; N,2-bis(4-fluorophenyl)-8,8-dimethyl-5H,6H,7H,8H-imidazo[1,2-a]pyrazine-3-carboxamide; 7-(2-aminoacetyl)-N,2-bis(4-fluorophenyl)-8,8-dimethyl-5H,6H,7H,8H-imidazo[1,2-a]pyrazine-3-carboxamide; 2-amino-1-[3-(4-fluorophenoxy)-2-(4-fluorophenyl)-8,8-dimethyl-5H,6H,7H,8H-imidazo[1,2-a]pyrazin-7-yl]ethan-1-one; 2-amino-1-[3-(4-chlorophenoxy)-2-(4-fluorophenyl)-8,8-dimethyl-5H,6H, 7H,8H-imidazo[1,2-a]pyrazin-7-yl]ethan-1-one; 2-amino-1-[3-(3,4-difluorophenoxy)-2-(4-fluorophenyl)-8,8-dimethyl-5H,6H,7H, 8H-imidazo[1,2-a]pyrazin-7-yl]ethan-1-one; 2-amino-1-[3-(4-fluoro-3-methylphenoxy)-2-(4-fluorophenyl)-8,8-dimethyl-5H,6H,7H,8H-imidazo[1,2-a]pyrazin-7-yl]ethan-1-one; 2-amino-1-[2-(4-fluorophenyl)-8,8-dimethyl-3-[(4-methylphenyl)sulfanyl]-5H,6H,7H,8H-imidazo[1,2-a]pyrazin-7-yl]ethan-1-one; 2-amino-1-[2-(4-fluorophenyl)-3-[(3-fluorophenyl)sulfanyl]-8,8-dimethyl-5H,6H,7H,8H-imidazo[1,2-a]pyrazin-7-yl]ethan-1-one; 2-amino-1-[2-(4-fluorophenyl)-3-[(4-fluorophenyl)sulfanyl]-8,8-dimethyl-5H,6H,7H,8H-imidazo[1,2-a]pyrazin-7-yl]ethan-1-one; 2-amino-1-{3-[(4-chlorophenyl)sulfanyl]-2-(4-fluorophenyl)-8,8-dimethyl-5H,6H,7H, 8H-imidazo[1,2-a]pyrazin-7-yl}ethan-1-one; 2-amino-1-{3-[(3,5-dimethylphenyl)sulfanyl]-2-(4-fluorophenyl)-8,8-dimethyl-5H,6H,7H, 8H-imidazo[1,2-a]pyrazin-7-yl}ethan-1-one; 2-amino-1-{3-[(3,4-difluorophenyl)sulfanyl]-2-(4-fluorophenyl)-8,8-dimethyl-5H,6H,7H,8H-imidazo[1,2-a]pyrazin-7-yl}ethan-1-one; 2-amino-1-{3-[(3-fluorobenzene)sulfinyl]-2-(4-fluorophenyl)-8,8-dimethyl-5H,6H,7H, 8H-imidazo[1,2-a]pyrazin-7-yl}ethan-1-one; 2-amino-1-{3-[(4-fluorobenzene)sulfinyl]-2-(4-fluorophenyl)-8,8-dimethyl-5H,6H,7H, 8H-imidazo[1,2-a]pyrazin-7-yl}ethan-1-one; 2-amino-1-[2-(4-fluorophenyl)-8,8-dimethyl-3-[(4-methylbenzene)sulfinyl]-5H,6H,7H,8H-imidazo[1,2-a]pyrazin-7-yl]ethan-1-one; 2-amino-1-{3-[(3,5-dimethylbenzene)sulfinyl]-2-(4-fluorophenyl)-8,8-dimethyl-5H,6H,7H,8H-imidazo[1,2-a]pyrazin-7-yl}ethan-1-one; 2-amino-1-{3-[(3,4-difluorobenzene)sulfinyl]-2-(4-fluorophenyl)-8,8-dimethyl-5H,6H,7H,8H-imidazo[1,2-a]pyrazin-7-yl}ethan-1-one; 2-amino-1-{3-[(4-chlorobenzene)sulfinyl]-2-(4-fluorophenyl)-8,8-dimethyl-5H,6H,7H,8H-imidazo[1,2-a]pyrazin-7-yl}ethan-1-one; and 2-amino-1-[2-(4-fluorophenyl)-8,8-dimethyl-3-[(4-methylbenzene)sulfonyl]-5H,6H,7H,8H-imidazo[1,2-a]pyrazin-7-yl]ethan-1-one.

In an embodiment of the invention are compounds selected from: N-{2-[2-(4-fluorophenyl)-3-[(4-fluorophenyl)amino]-8,8-dimethyl-5H,6H,7H,8H-imidazo[1,2-a]pyrazin-7-yl]-2-oxoethyl}-3-phenylpropanamide; N-{2-[2-(4-fluorophenyl)-3-[(4-fluorophenyl)amino]-8,8-dimethyl-5H,6H,7H,8H-imidazo[1,2-a]pyrazin-7-yl]-2-oxoethyl}-3-{8-oxatricyclo[7.4.0.0 {2,7}]trideca-1(9),2,4,6,10,12-hexaen-4-yl}propanamide; N-{2-[2-(4-fluorophenyl)-3-[(4-fluorophenyl)amino]-8,8-dimethyl-5H,6H,7H,8H-imidazo[1,2-a]pyrazin-7-yl]-2-oxoethyl}-3-(3-phenylpropanamido)propanamide; N-{2-[2-(4-fluorophenyl)-3-[(4-fluorophenyl)amino]-8,8-dimethyl-5H,6H,7H,8H-imidazo[1,2-a]pyrazin-7-yl]-2-oxoethyl}-3-(3-{8-oxatricyclo[7.4.0.0 {2,7}]trideca-1(9),2,4,6,10,12-hexaen-4-yl}propanamido)propanamide; N-[3-({2-[2-(4-fluorophenyl)-3-[(4-fluorophenyl)amino]-8,8-dimethyl-5H, 6H,7H,8H-imidazo[1,2-a]pyrazin-7-yl]-2-oxoethyl}amino)propyl]-3-phenylpropanamide; 5,5-difluoro-3-(3-(2-(2-(4-fluorophenyl)-3-(4-fluorophenylamino)-8,8-dimethyl-5,6-dihydroimidazo[1,2-a]pyrazin-7(8H)-yl)-2-oxoethylamino)-3-oxopropyl)-7-phenyl-5H-dipyrrolo[1,2- c:1',2'-f][1,3,2]diazaborinin-4-ium-5-uide; and 5,5-difluoro-2-(3-(6-(2-(2-(4-fluorophenyl)-3-(4-fluorophenylamino)-8,8-dimethyl-5,6-dihydroimidazo[1,2-a]pyrazin-7(8H)-yl)-2-oxoethylamino)-6-oxohexylamino)-3-oxopropyl)-7-(4-methoxyphenyl)-1,3-dimethyl-5H-dipyrrolo[1,2-c:1',2'-f][1,3,2]diazaborinin-4-ium-5-uide.

In an embodiment of the invention are compounds selected from: N-(4-methylphenyl)-2-(pyridin-3-yl)-5H,6H,7H,8H-imidazo[1,2-a]pyridin-3-amine; 2-cyclohexyl-N-(2,4,4-trimethylpentan-2-yl)imidazo[1,2-a]pyridin-3-amine; 2-(diphenylmethyl)-N-(2,4,4-trimethylpentan-2-yl)imidazo[1,2-a]pyridin-3-amine; 2-(2-nitrophenyl)-N-(2,4,4-trimethylpentan-2-yl)imidazo[1,2-a]pyridin-3-amine; 2-[2-(thiophen-2-yl)phenyl]-N-(2,4,4-trimethylpentan-2-yl)imidazo[1,2-a]pyridin-3-amine; 2-[2-(difluoromethoxy)phenyl]-N-(2,4,4-trimethylpentan-2-yl)imidazo[1,2-a]pyridin-3-amine; 2-(2-bromophenyl)-N-(2,4,4-trimethylpentan-2-yl)imidazo[1,2-a]pyridin-3-amine; 2-{2-[2-(diethylamino)ethoxy]phenyl}-N-(2,4,4-trimethylpentan-2-yl)imidazo[1,2-a]pyridin-3-amine; 2-[2-(trifluoromethyl)phenyl]-N-(2,4,4-trimethylpentan-2-yl)imidazo[1,2-a]pyridin-3-amine; 2-(2-{3-[(2,4,4-trimethylpentan-2-yl)amino]imidazo[1,2-a]pyridin-2-yl}phenoxy)ethan-1-ol; 2-[2-(furan-2-yl)phenyl]-N-(2,4,4-trimethylpentan-2-yl)imidazo[1,2-a]pyridin-3-amine; 2-(4-fluorophenyl)-6-methyl-N-(4-methylphenyl)imidazo[1,2-a]pyridin-3-amine; N-(4-chloro-3-fluorophenyl)-2-(4-fluorophenyl)-5H,6H,7H,8H-imidazo[1,2-a]pyridin-3-amine; 2-(4-fluorophenyl)-N-(4-methylphenyl)-5H,6H,7H,8H-imidazo[1,2-a]pyridin-3-amine; 2-(4-fluorophenyl)-N-(4-methylphenyl)imidazo[1,2-a]pyridin-3-amine; N-(4-chloro-3-fluorophenyl)-2-(4-fluorophenyl)-6-methylimidazo[1,2-a]pyridin-3-amine; 2-(4-fluorophenyl)-6-methyl-N-(4-methylphenyl)-5H,6H,7H,8H-imidazo[1,2-a]pyridin-3-amine; N-(4-chloro-3-fluorophenyl)-2-(4-fluorophenyl)-6-methyl-5H,6H,7H,8H-imidazo[1,2-a]pyridin-3-amine; 8-(3,4-difluorophenylamino)-9-(4-fluorophenyl)-2,2-dimethyl-5,6-dihydrodiimidazo[1,2-a:2',1'-c]pyrazin-3(2H)-one; and 8-(3,4-difluorophenylamino)-9-(4-fluorophenyl)-2,2-dimethyl-1,2,5,6-tetrahydrodiimidazo[1,2-a:2',1'-c]pyrazin-3(10bH)-one.

In a further embodiment of the invention is a method for treating a *Plasmodium* related disease in a subject to prevent, inhibit or ameliorate the pathology and/or symptamology of the *Plasmodium* related disease, comprising administering to a subject, in vivo or in vitro, a therapeutically effective amount of a compound of the invention alone or in combination with a second agent.

In a further embodiment is a method for treating a *Plasmodium* related disease in a subject to prevent, inhibit or ameliorate the pathology and/or symptamology of the *Plasmodium* related disease, comprising administering to a subject, in vivo or in vitro, a therapeutically effective amount of a compound alone or in combination with a second agent, wherein the compound is selected from: 2-amino-1-(3-(benzo[d][1,3]dioxol-5-ylamino)-2-phenyl-5,6-dihydroimidazo[1,2-a]pyrazin-7(8H)-yl)ethanone; 2-(2-methoxyphenyl)-N-(2,4,4-trimethylpentan-2-yl)imidazo[1,2-a]pyridin-3-amine; 2-phenyl-N-(2,4,4-trimethylpentan-2-yl)imidazo[1,2-a]pyridin-3-amine; 2-(pyridin-3-yl)-N-(2,4,4-trimethylpentan-2-yl)imidazo[1,2-a]pyridin-3-amine; and 2-(4-fluorophenyl)-N-(2,4,4-trimethylpentan-2-yl)imidazo[1,2-a]pyridin-3-amine.

In a further embodiment, the *Plasmodium* related disease is malaria.

In a further embodiment, the second agent is selected from a kinase inhibitor, an anti-malarial drug and an anti-inflammatory agent. The anti-malarial drug is selected from proguanil, chlorproguanil, trimethoprim, chloroquine, mefloquine, lumefantrine, atovaquone, pyrimethamine-sulfadoxine, pyrimethamine-dapsone, halofantrine, quinine, quinidine, amodiaquine, amopyroquine, sulphonamides, artemisinin, arteflene, artemether, artesunate, primaquine, and pyronaridine.

In a further embodiment, the compounds of the invention can be administered prior to, simultaneously with, or after the second agent.

In a further embodiment, the subject is a human.

Pharmacology and Utility

Compounds of the invention are useful in the treatment and/or prevention of infections such as those caused by *Plasmodium falciparum; Plasmodium vivax; Plasmodium ovale*; and *Plasmodium malaria, trypanosoma cruzi* and parasites of the *Leishmania* genus, such as, for example, *Leishmania donovani*.

Malaria is an infectious disease caused by four protozoan parasites: *Plasmodium falciparum; Plasmodium vivax; Plasmodium ovale*; and *Plasmodium malaria*. These four parasites are typically transmitted by the bite of an infected female *Anopheles* mosquito. Malaria is a problem in many parts of the world and over the last few decades the malaria burden has steadily increased. An estimated 1-3 million people die every year from malaria—mostly children under the age of 5. This increase in malaria mortality is due in part to the fact that *Plasmodium falciparum*, the deadliest malaria parasite, has acquired resistance against nearly all available antimalarial drugs, with the exception of the artemisinin derivatives.

Leishmaniasis is caused by one or more than 20 varieties of parasitic protozoa that belong to the genus *Leishmania*, and is transmitted by the bite of female sand flies. Leishmaniasis is endemic in about 88 countries, including many tropical and sub-tropical areas.

There are four main forms of Leishmaniasis. Visceral leishmaniasis, also called kala-azar, is the most serious form and is caused by the parasite *Leishmania donovani*. Patients who develop visceral leishmaniasis can die within months unless they receive treatment. The two main therapies for visceral leishmaniasis are the antimony derivatives sodium stibogluconate (Pentostam®) and meglumine antimoniate (Glucantim®). Sodium stibogluconate has been used for about 70 years and resistance to this drug is a growing problem. In addition, the treatment is relatively long and painful, and can cause undesirable side effects.

Human African Trypanosomiasis, also known as sleeping sickness, is a vector-borne parasitic disease. The parasites concerned are protozoa belonging to the *Trypanosoma* Genus. They are transmitted to humans by tsetse fly (*Glossina* Genus) bites which have acquired their infection from human beings or from animals harboring the human pathogenic parasites.

Chagas disease (also called American Trypanosomiasis) is another human parasitic disease that is endemic amongst poor populations on the American continent. The disease is caused by the protozoan parasite *Trypanosoma cruzi*, which is transmitted to humans by blood-sucking insects. The human disease occurs in two stages: the acute stage, which occurs shortly after infection and the chronic stage, which can develop over many years. Chronic infections result in various neurological disorders, including dementia, damage to the heart muscle and sometimes dilation of the digestive tract, as well as weight loss. Untreated, the chronic disease is often fatal.

The drugs currently available for treating Chagas disease are Nifurtimox and benznidazole. However, problems with these current therapies include their diverse side effects, the length of treatment, and the requirement for medical supervision during treatment. Furthermore, treatment is really only effective when given during the acute stage of the disease. Resistance to the two frontline drugs has already occurred. The antifungal agent Amphotericin b has been proposed as a second-line drug, but this drug is costly and relatively toxic.

The phylum, Apicomplexa, contains many members that are human or animal pathogens including, but not limited to, *Plasmodium* spp. (Malaria), *Toxoplasma gondii* (congenital neurological defects in humans), *Eimeria* spp. (poultry and cattle pathogens), *Cryptosporidia* (opportunistic human and animal pathogens), *Babesia* (cattle parasites) and *Theileria* (cattle parasites). The pathogenesis associated with these parasitic diseases is due to repeated cycles of host-cell invasion, intracellular replication and host-cell lysis. Therefore, understanding parasite proliferation is essential for development of novel drugs and vaccines, for example, to treat malaria.

In vertebrate hosts, the parasite undergoes two main phases of development, the hepathocytic and erythrocytic phases, but it is the erythrocytic phase of its life cycle that causes severe pathology. During the erythrocytic phase, the parasite goes through a complex but well synchronized series of stages, suggesting the existence of tightly regulated signaling pathways.

Calcium serves as an intracellular messenger to control synchronization and development in the erythrocytic life phase. The *Plasmodium* spp. genomes reveal many sequence identities with calcium binding/sensing protein motifs that include Pf39, calmodulin, and calcium dependent protein kinases (CDPKs). *Plasmodium* CDPKs, *Plasmodium* CDPK3 and 4, have been shown to be involved in mosquito infection. CDPK4 has been demonstrated to be essential for the sexual reproduction in the midgut of mosquito by translating the calcium signal into a cellular response and regulating cell cycle progression in the male gametocyte. CDPK3 regulates ookinete gliding motility and penetration of the layer covering the midgut epithelium. *P. falciparum* CDPK1 (PfCDPK1) is expressed during late schizogony of blood stage and in the infectious sporozoite stage and is secreted to the parasitophorous vacuole by an acylation-dependent mechanism. It can be myristoylated and is abundantly found in detergent-resistant membrane fractions isolated from schizogony-phase parasites. Ontology based pattern identification analysis reveals that PfCDPK1 is clustered with genes associated with either parasite egress or erythrocyte invasion. Direct inhibition of PfCDPK1 can arrest the parasite erythrocytic life cycle progression in the late schizogony phase.

Therefore, kinase activity is distributed in all the stages of *P. falciparum* parasite maturation and kinase inhibitors of the present invention can be used for treating *Plasmodium* related diseases. In particular, kinase inhibitors of the present invention can be a route for treating malaria by inhibiting the kinase PfCDPK1. The in vitro cellular assay, infra, can be used to assess the activity of compounds of the invention against a variety of malarial parasite strains.

Compounds of the invention are inactive against mitogen-activated protein kinase-activated protein kinase 2 (Map-Kap2 or MK-2). For example, 2-amino-1-(2-(4-fluorophenyl)-3-(4-fluorophenylamino)-8,8-dimethyl-5,6-dihydroimidazo[1,2-a]pyrazin-7(8H)-yl)ethanone (example 412) and 2-amino-1-(3-(3,4-difluorophenylamino)-2-(4-fluorophenyl)-5,6-dihydroimidazo[1,2-a]pyrazin-7(8H)-yl)-2-methylpropan-1-one (Example 29) exhibit only 7% and 15% inhibition, respectively, in a single point concentration on this enzyme.

Compounds of the invention are relatively inactive against cannabinoid receptor 1 (CB1). For example, 2-amino-1-(2-(4-fluorophenyl)-3-(4-fluorophenylamino)-8,8-dimethyl-5,6-dihydroimidazo[1,2-a]pyrazin-7(8H)-yl) ethanone (example 412) and 2-amino-1-(3-(3,4-difluorophenylamino)-2-(4-fluorophenyl)-5,6-dihydroimidazo[1,2-a] pyrazin-7(8H)-yl)-2-methylpropan-1-one (Example 29) have an $IC_{50}$ of 24 µM and greater than 30 µM, respectively.

In accordance with the foregoing, the present invention further provides a method for preventing or treating malaria in a subject in need of such treatment, which method comprises administering to said subject a therapeutically effective amount of a compound selected from Formula Ia, Ib, Ic or a pharmaceutically acceptable salt thereof. The required dosage will vary depending on the mode of administration, the particular condition to be treated and the effect desired.

Administration and Pharmaceutical Compositions

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Compounds of the invention can be administered in therapeutically effective amounts in combination with one or more therapeutic agents (pharmaceutical combinations). Non-limiting examples of compounds which can be used in combination with compounds of the invention are known anti-malarial drugs, for example, proguanil, chlorproguanil, trimethoprim, chloroquine, mefloquine, lumefantrine, atovaquone, pyrimethamine-sulfadoxine, pyrimethamine-dapsone, halofantrine, quinine, quinidine, amodiaquine, amopyroquine, sulphonamides, artemisinin, arteflene, artemether, artesunate, primaquine, pyronaridine, etc.

Where the compounds of the invention are administered in conjunction with other therapies, dosages of the co-administered compounds will of course vary depending on the type of co-drug employed, on the specific drug employed, on the condition being treated and so forth.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Compounds of Formula I can be prepared by proceeding as in the Reaction Schemes 1-5; $R_2$, $R_3$, $R_4$, $R_5$, $R_6$, $R_8$, $R_9$, $R_{10}$, $R_{11}$ and $R_{12}$ are as defiled in the Summary of the Invention. The following reaction schemes are given to be illustrative, not limiting, descriptions of the synthesis of compounds of the invention:

Reaction Scheme 1: General Synthetic Route by Three Component Ugi Reaction

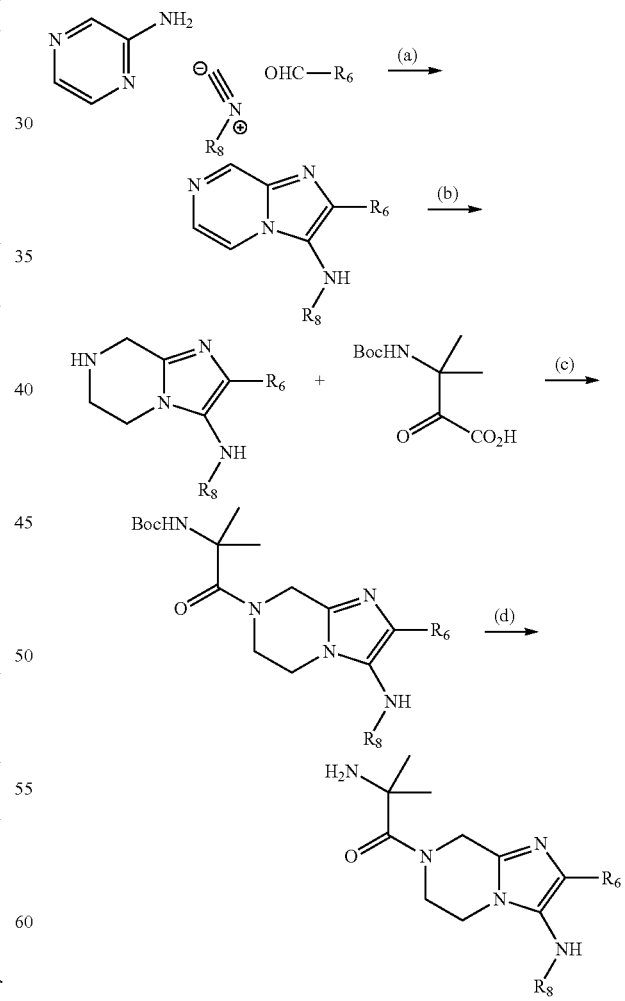

Reagents and Conditions:
(a) $HClO_4$, MeOH, rt; (b) Pd/C (or $PtO_2$), $H_2$, MeOH, rt; (c) HATU, DIEA, DMF, rt; (d) TFA, DCM, rt

Reaction Scheme 2:
Alternative Synthetic Route by Amination to Achieve Core

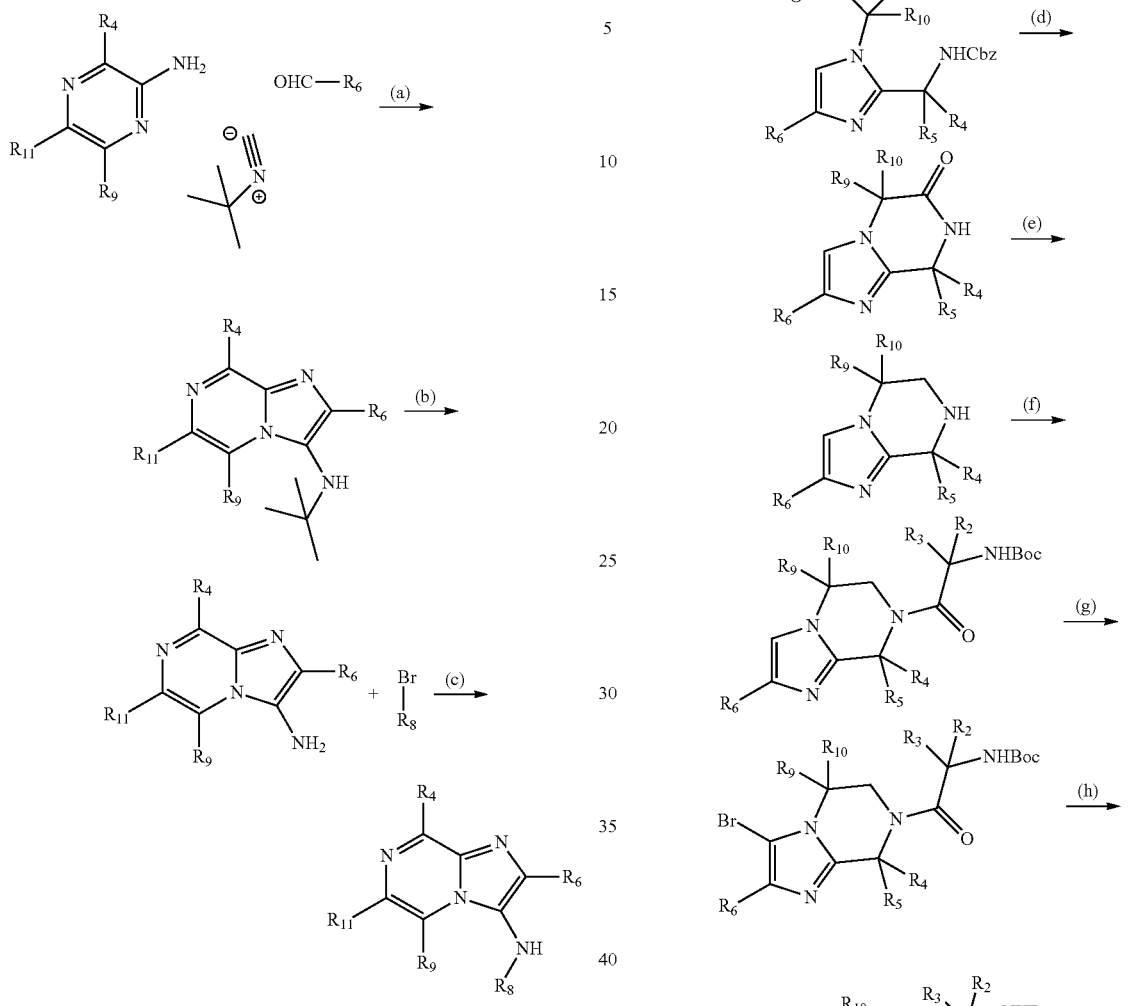

Reagents and Conditions:

(a) HClO$_4$, MeOH, rt; (b) TFA, DCM, rt; (c) Pd$_2$(dba)$_3$, XantPhos, Cs$_2$CO$_3$, Dioxane, 140° C.

Reaction Scheme 3: General Synthetic Route by Imidazole Formation-8,8 Dimethyl Modification

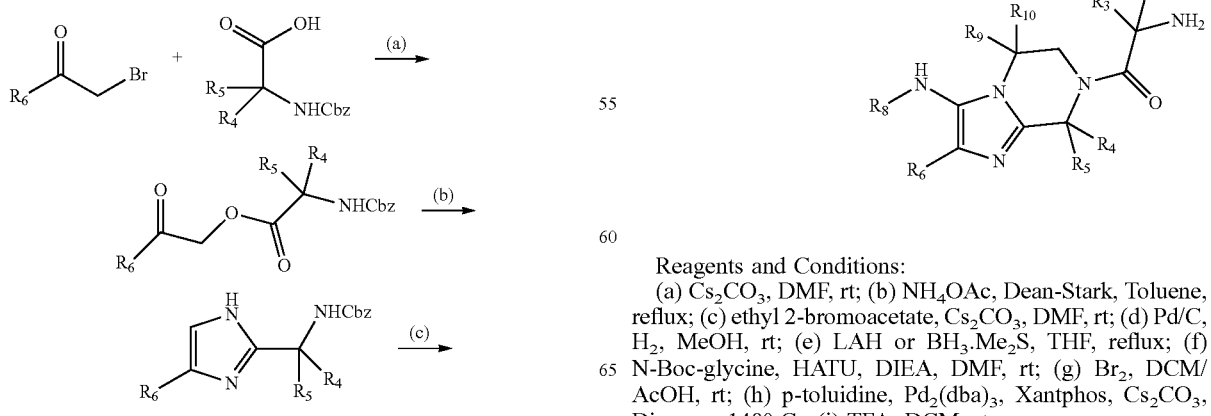

Reagents and Conditions:

(a) Cs$_2$CO$_3$, DMF, rt; (b) NH$_4$OAc, Dean-Stark, Toluene, reflux; (c) ethyl 2-bromoacetate, Cs$_2$CO$_3$, DMF, rt; (d) Pd/C, H$_2$, MeOH, rt; (e) LAH or BH$_3$.Me$_2$S, THF, reflux; (f) N-Boc-glycine, HATU, DIEA, DMF, rt; (g) Br$_2$, DCM/AcOH, rt; (h) p-toluidine, Pd$_2$(dba)$_3$, Xantphos, Cs$_2$CO$_3$, Dioxane, 140° C.; (i) TFA, DCM, rt.

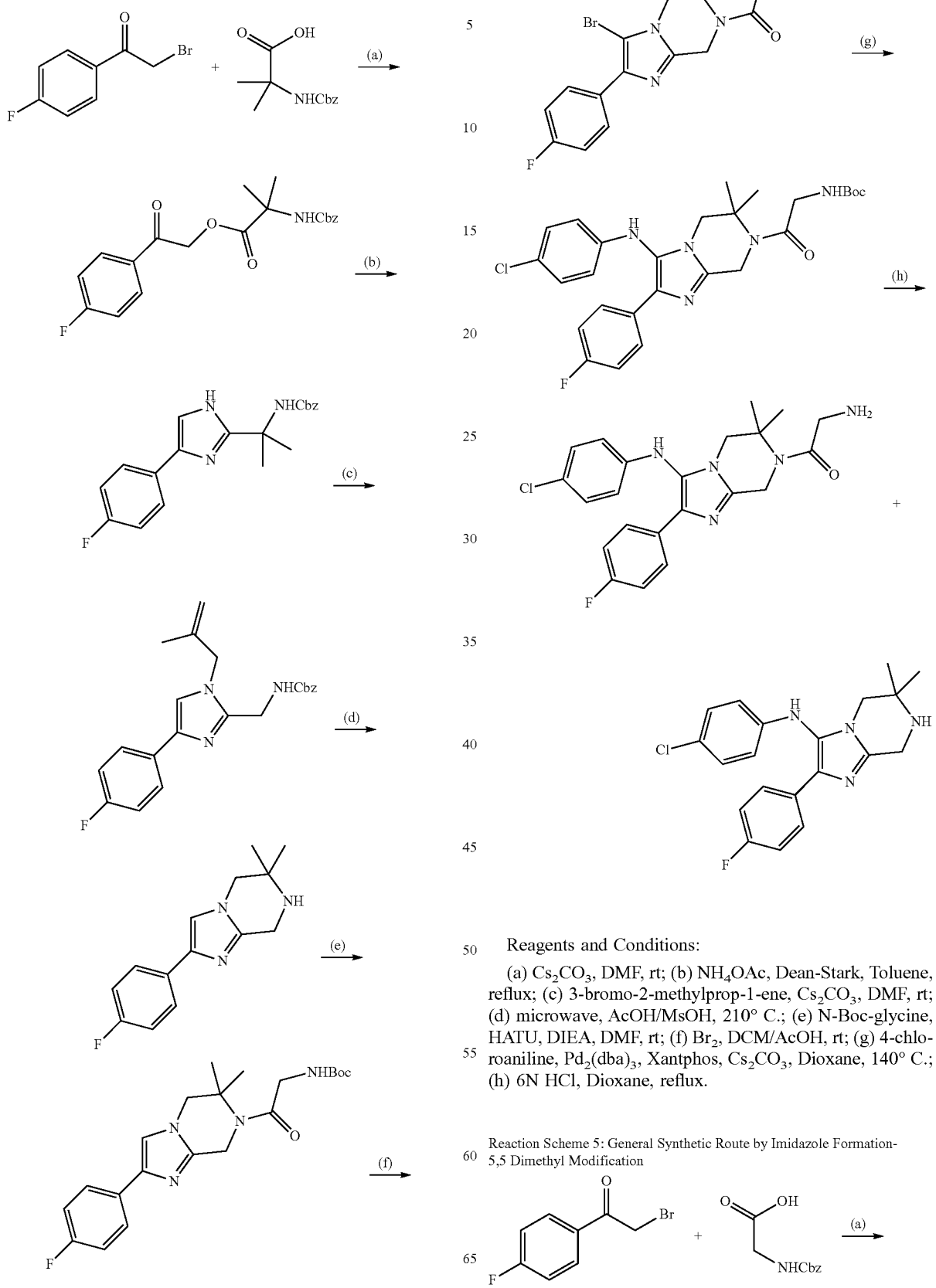

Reaction Scheme 4: General Synthetic Route by Imidazole Formation-6,6 Dimethyl Modification Reagents and Conditions:
(a) $Cs_2CO_3$, DMF, rt; (b) $NH_4OAc$, Dean-Stark, Toluene, reflux; (c) 3-bromo-2-methylprop-1-ene, $Cs_2CO_3$, DMF, rt; (d) microwave, AcOH/MsOH, 210° C.; (e) N-Boc-glycine, HATU, DIEA, DMF, rt; (f) $Br_2$, DCM/AcOH, rt; (g) 4-chloroaniline, $Pd_2(dba)_3$, Xantphos, $Cs_2CO_3$, Dioxane, 140° C.; (h) 6N HCl, Dioxane, reflux.

Reaction Scheme 5: General Synthetic Route by Imidazole Formation-5,5 Dimethyl Modification

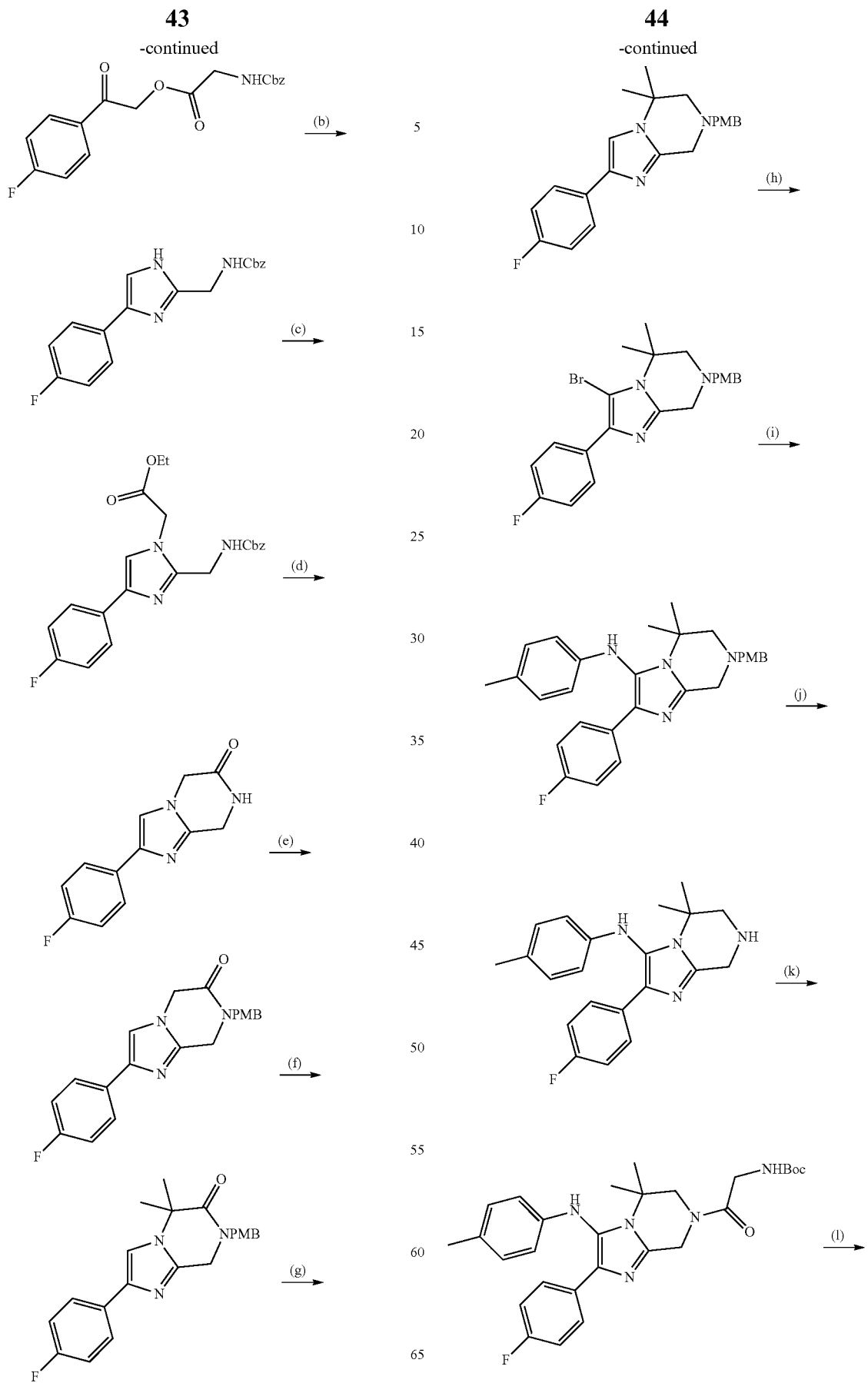

-continued

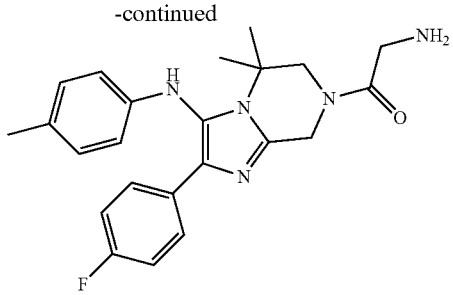

Reagents and Conditions:

(a) Cs$_2$CO$_3$, DMF, rt; (b) NH$_4$OAc, Dean-Stark, Toluene, reflux; (c) ethyl 2-bromoacetate, Cs$_2$CO$_3$, DMF, rt; (d) Pd/C, H$_2$, MeOH, rt; (e) PMBCl, KOH, THF, rt; (f) MeI, NaH, DMF, rt; (g) BH$_3$.Me$_2$S, THF, reflux; (h) Br$_2$, DCM/AcOH, rt; (i) p-toluidine, Pd$_2$(dba)$_3$, Xantphos, Cs$_2$CO$_3$, Dioxane, 150° C.; (j) TFA, 70° C.; (k) N-Boc-glycine, HATU, DIEA, DMF, rt; (l) TFA, DCM, rt.

Detailed descriptions of the synthesis of compounds of the Invention are given in the Examples, infra.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base. Alternatively, the salt forms of the compounds of the invention, for example, fumarate salts, can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3$^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:

(a) that of reaction scheme 1, 2, 3, 4 and/or 5; and (b) optionally converting a compound of the invention into a pharmaceutically acceptable salt;

(c) optionally converting a salt form of a compound of the invention to a non-salt form;

(d) optionally converting an unoxidized form of a compound of the invention into a pharmaceutically acceptable N-oxide;

(e) optionally converting an N-oxide form of a compound of the invention to its unoxidized form;

(f) optionally resolving an individual isomer of a compound of the invention from a mixture of isomers;

(g) optionally converting a non-derivatized compound of the invention into a pharmaceutically acceptable prodrug derivative; and (h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The present invention is further exemplified, but not limited, by the following Examples (Table 2) and intermediates (Reference compounds Table 1) that illustrate the preparation of compounds of the invention.

TABLE 1

| Compound | Structure | Physical Data MS (m/z) and/or ¹H NMR |
|---|---|---|
| Ref. comp. 1 | 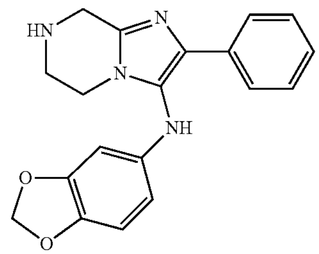 [SMILES: c1ccc(-c2nc3n(c2Nc2ccc4c(c2)OCO4)CCNC3)cc1] | [M + H] = 335.2<br>¹H NMR (CDCl₃, 400 MHz) δ 7.64 (d, J = 7.2 Hz, 2H), 7.91-7.94 (m, 3H), 7.21-7.27 (m, 3H), 6.59 (d, J = 8.4 Hz, 1H), 6.26 (d, J = 2.0 Hz, 1H), 5.99 (dd, J = 2.0, 9.2 Hz, 1H), 5.83 (s, 2H), 4.48 (s, 2H), 3.89 (s, 2H), 3.38 (s, 2H). |
| Ref. comp. 2 | 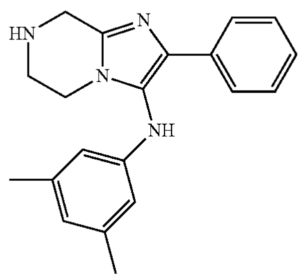 [SMILES: Cc1cc(C)cc(Nc2c(-c3ccccc3)nc3n2CCNC3)c1] | [M + H] = 319.2<br>¹H NMR (CDCl₃, 400 MHz) δ 7.34 (s, 2H), 7.10 (s, 2H), 6.79-6.81 (m, 2H), 6.70-6.74 (m, 1H), 6.40 (br., 1H), 5.19 (s, 2H), 4.22 (s, 2H), 1.98 (s, 6H). |
| Ref. comp. 3 | 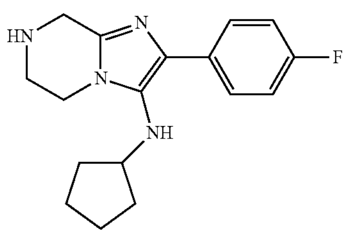 [SMILES: Fc1ccc(-c2nc3n(c2NC2CCCC2)CCNC3)cc1] | [M + H] = 301.2 |
| Ref. comp. 4 | 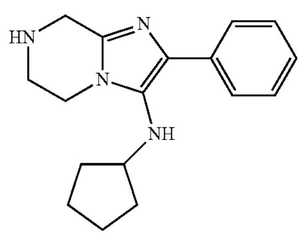 [SMILES: c1ccc(-c2nc3n(c2NC2CCCC2)CCNC3)cc1] | [M + H] = 283.2 |
| Ref. comp. 5 | 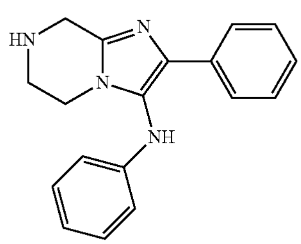 [SMILES: c1ccc(Nc2c(-c3ccccc3)nc3n2CCNC3)cc1] | [M + H] = 291.2 |

TABLE 1-continued

| Compound | Structure | Physical Data MS (m/z) and/or $^1$H NMR |
|---|---|---|
| Ref. comp. 6 | 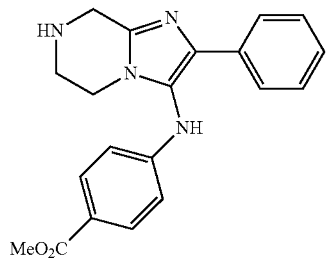 [SMILES: COC(=O)c1ccc(Nc2c(-c3ccccc3)nc3n2CCNC3)cc1] | [M + H] = 349.2 |
| Ref. comp. 7 | 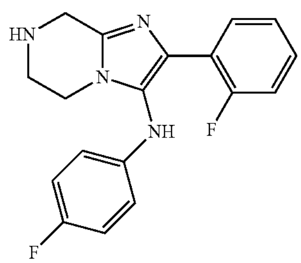 [SMILES: Fc1ccc(Nc2c(-c3ccccc3F)nc3n2CCNC3)cc1] | [M + H] = 327.2 |
| Ref. comp. 8 | 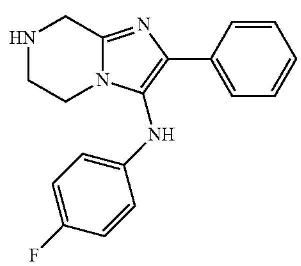 [SMILES: Fc1ccc(Nc2c(-c3ccccc3)nc3n2CCNC3)cc1] | [M + H] = 309.2 |
| Ref. comp. 9 | 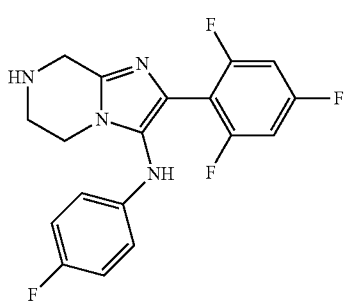 [SMILES: Fc1ccc(Nc2c(-c3c(F)cc(F)cc3F)nc3n2CCNC3)cc1] | [M + H] = 363.1 |
| Ref. comp. 10 | 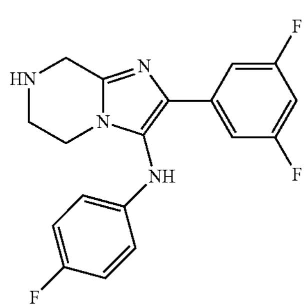 [SMILES: Fc1ccc(Nc2c(-c3cc(F)cc(F)c3)nc3n2CCNC3)cc1] | [M + H] = 345.1 |

TABLE 1-continued

| Compound | Structure | Physical Data MS (m/z) and/or $^1$H NMR |
|---|---|---|
| Ref. comp. 11 | 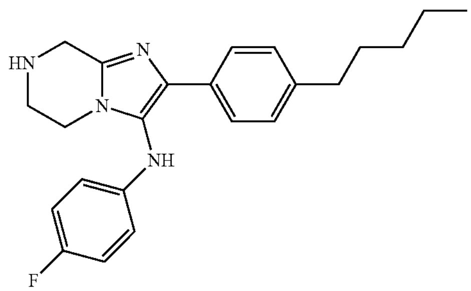 [SMILES: CCCCCc1ccc(-c2nc3n(c2Nc2ccc(F)cc2)CCNC3)cc1] | [M + H] = 379.2 |
| Ref. comp. 12 | 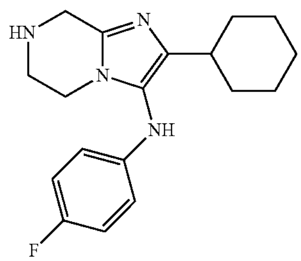 [SMILES: Fc1ccc(Nc2c(C3CCCCC3)nc3n2CCNC3)cc1] | [M + H] = 315.2 |
| Ref. comp. 13 | 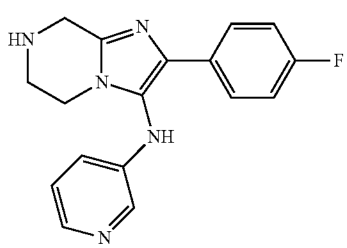 [SMILES: Fc1ccc(-c2nc3n(c2Nc2cccnc2)CCNC3)cc1] | [M + H] = 310.2 |
| Ref. comp. 14 | 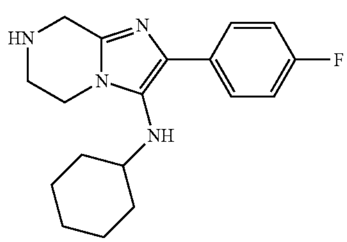 [SMILES: Fc1ccc(-c2nc3n(c2NC2CCCCC2)CCNC3)cc1] | [M + H] = 315.0 |
| Ref. comp. 15 | 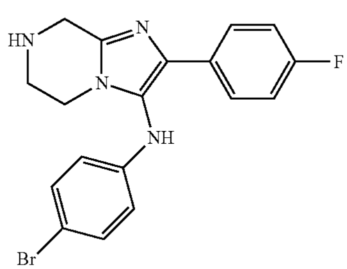 | [M + H] = 387.1 |

TABLE 1-continued
| Compound | Structure | Physical Data MS (m/z) and/or ¹H NMR |
|---|---|---|
| Ref. comp. 16 | 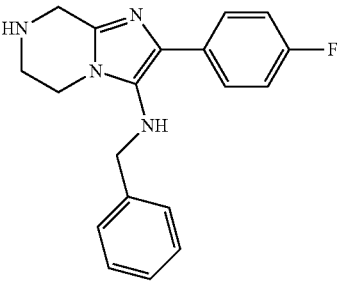 [SMILES: Fc1ccc(-c2nc3n(c2NCc2ccccc2)CCNC3)cc1] | [M + H] = 323.2 |
| Ref. comp. 17 | 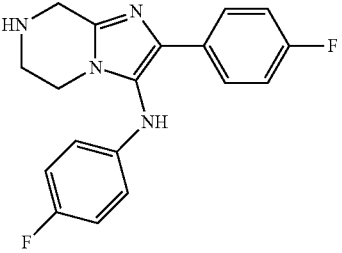 [SMILES: Fc1ccc(Nc2c(-c3ccc(F)cc3)nc3n2CCNC3)cc1] | [M + H] = 327<br>¹H NMR: (300 MHz, DMSO-d₆): δ 7.81-7.72 (m, 2H), 7.11 (m, 2H), 6.97 (m, 2H,), 6.56-6.52 (m, 2H), 3.86 (s, 2H), 3.55 (m, 2H), 3.02 (m, 2H) |
| Ref. comp. 18 | 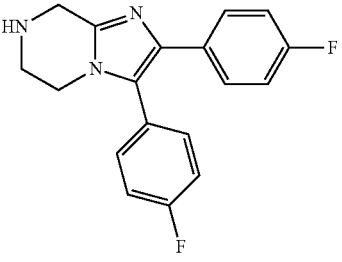 [SMILES: Fc1ccc(-c2nc3n(c2-c2ccc(F)cc2)CCNC3)cc1] | [M + H] = 311.9 |
| Ref. comp. 19 | 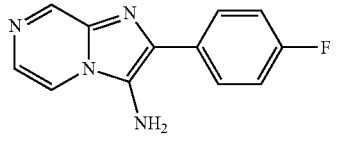 [SMILES: Nc1c(-c2ccc(F)cc2)nc2cnccn12] | [M + H] = 229<br>¹H NMR (300 MHz, CDCl₃): δ 8.82 (s, 1H), 8.28 (d, J = 4.8 Hz, 1H) 8.05-8.09 (m, 2H) 7.76 (d, J = 4.5 Hz, 1H) 7.27-7.33 (m, 2H) 5.79 (s, 2H) |
| Ref. comp. 20 | 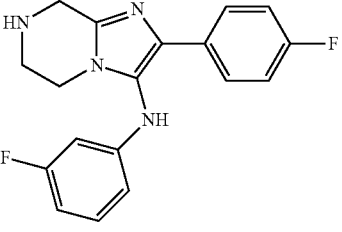 [SMILES: Fc1ccc(-c2nc3n(c2Nc2cccc(F)c2)CCNC3)cc1] | [M + H] = 327.2 |
| Ref. comp. 21 | 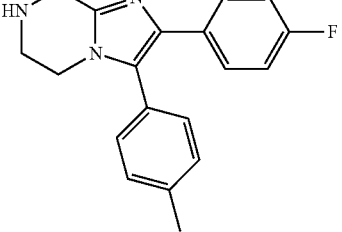 | [M + H] = 324.3 |

TABLE 1-continued

| Compound | Structure | Physical Data MS (m/z) and/or $^1$H NMR |
|---|---|---|
| Ref. comp. 22 | 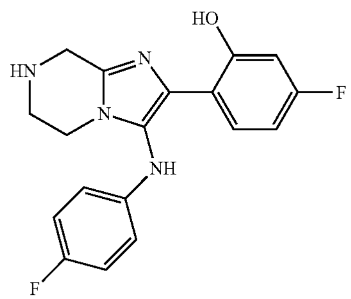 [SMILES: Oc1cc(F)ccc1-c1nc2n(c1Nc1ccc(F)cc1)CCNC2] | [M + H] = 343.2 |
| Ref. comp. 23 | 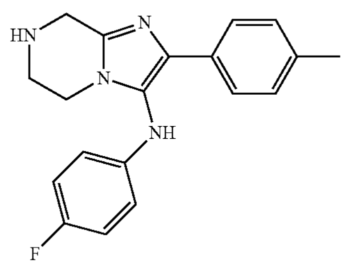 [SMILES: Cc1ccc(-c2nc3n(c2Nc2ccc(F)cc2)CCNC3)cc1] | [M + H] = 323.2 |
| Ref. comp. 24 | 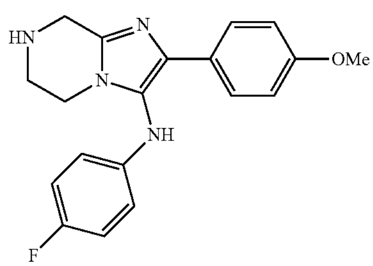 [SMILES: COc1ccc(-c2nc3n(c2Nc2ccc(F)cc2)CCNC3)cc1] | [M + H] = 339.1 |
| Ref. comp. 25 | 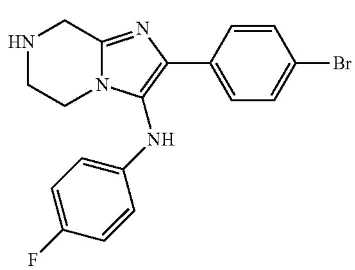 [SMILES: Fc1ccc(Nc2c(-c3ccc(Br)cc3)nc3n2CCNC3)cc1] | [M + H] = 387.1 |
| Ref. comp. 26 | 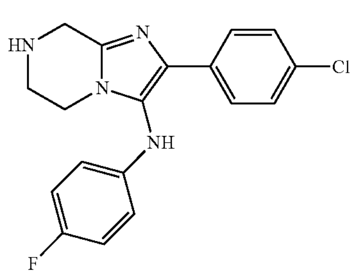 [SMILES: Fc1ccc(Nc2c(-c3ccc(Cl)cc3)nc3n2CCNC3)cc1] | [M + H] = 343.2 |

TABLE 1-continued

| Compound | Structure | Physical Data MS (m/z) and/or $^1$H NMR |
|---|---|---|
| Ref. comp. 27 | 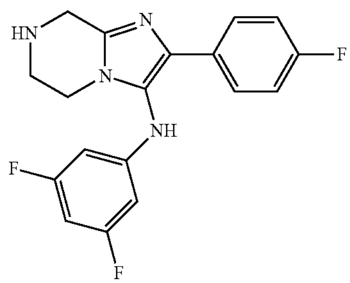 [SMILES: Fc1ccc(-c2nc3n(c2Nc2cc(F)cc(F)c2)CCNC3)cc1] | [M + H] = 345.1 |
| Ref. comp. 28 | 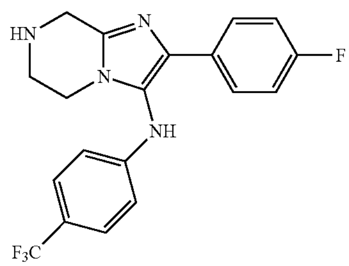 [SMILES: Fc1ccc(-c2nc3n(c2Nc2ccc(C(F)(F)F)cc2)CCNC3)cc1] | [M + H] = 377.1 |
| Ref. comp. 29 | 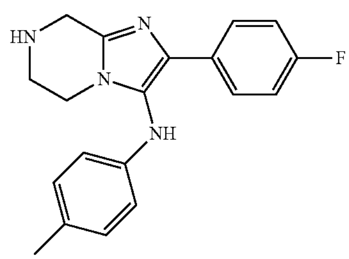 [SMILES: Cc1ccc(Nc2c(-c3ccc(F)cc3)nc3n2CCNC3)cc1] | [M + H] = 323<br>$^1$H NMR (400 MHz, CD$_3$OD) δ 7.73 (d, J = 6.8 Hz, 2H), 7.00-6.99 (m, 4H), 6.49 (d, J = 8.0 Hz, 2H), 4.01 (s, 2H), 3.72 (s, 2H), 3.15 (s, 2H), 2.19 (s, 3H). |
| Ref. comp. 30 | 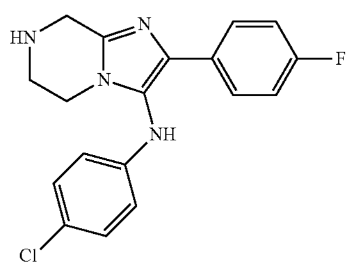 [SMILES: Fc1ccc(-c2nc3n(c2Nc2ccc(Cl)cc2)CCNC3)cc1] | [M + H] = 343<br>$^1$H NMR-: (300 MHz, DMSO-d$_6$): δ 7.94 (s, 1H), 7.80-7.74 (m, 2H), 7.18-7.09 (m, 4H), 6.56 (d, J = 8.7 Hz, 2H), 3.87 (s, 2H), 3.55 (s, 2H), 3.02 (t, J = 5.4 Hz, 2H). |
| Ref. comp. 31 | 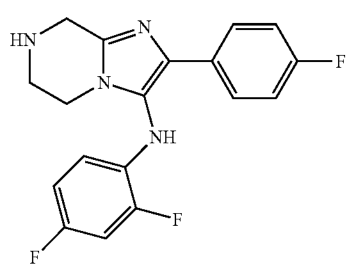 [SMILES: Fc1ccc(-c2nc3n(c2Nc2ccc(F)cc2F)CCNC3)cc1] | [M + H] = 341<br>$^1$H NMR (300 MHz, CDCl$_3$) δ 7.70-7.62 (m, 1H), 7.01 (d, J = 8.1 Hz, 2H), 6.92-6.76 (m, 2H), 6.52 (d, J = 8.1 Hz, 2H), 5.33 (s, 1H), 4.23 (s, 2H), 3.77 (m, 2H), 3.26 (m, 2H), 2.25 (s, 3H). |

TABLE 1-continued

| Compound | Structure | Physical Data MS (m/z) and/or ¹H NMR |
|---|---|---|
| Ref. comp. 32 | (structure) | [M + H] = 229<br>¹H NMR (300 MHz, DMSO-$d_6$) δ 8.83 (s, 1H), 8.30-8.28 (m, 1H), 7.89-7.76 (m, 3H), 7.54-7.47 (m, 1H), 7.12-7.17 (m, 1H), 5.94 (s, 2H). |
| Ref. comp. 33 | (structure) | [M + H] = 243.1 |
| Ref. comp. 34 | (structure) | [M + H] = 452.2 |
| Ref. comp. 35 | (structure) | [M + H] = 482<br>¹H-NMR: (400 MHz, CD$_3$OD) δ 7.84-7.81 (m, 2H), 7.14 (t, J = 8.8 Hz, 2H), 4.09-4.01 (m, 4H), 3.81 (t, J = 4.8 Hz, 2H), 1.89 (s, 6H), 1.46 (s, 9H). |
| Ref. comp. 36 | (structure) | [M + H] = 515.0 |
| Ref. comp. 37 | (structure) | [M + H] = 452.2 |
| Ref. comp. 38 | (structure) | [M + H] = 243<br>¹H NMR: (300 MHz, DMSO-$d_6$) δ 8.79 (d, J = 0.9 Hz, 1H), 8.26-8.24 (m, 1H), 7.93-7.86 (m, 1H), 7.85-7.83 (m, 1H), 7.74 (d, J = 4.8 Hz, 1H), 7.21 (t, J = 9.3 Hz, 1H), 5.80 (s, 2H), 2.29 (d, J = 13.5 Hz, 3H |

TABLE 1-continued

| Compound | Structure | Physical Data MS (m/z) and/or ¹H NMR |
|---|---|---|
| Ref. comp. 39 | 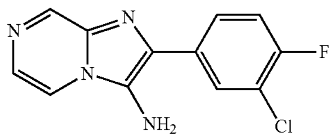 [SMILES: Nc1c(-c2ccc(F)c(Cl)c2)nc2cnccn12] | [M + H] = 263<br>¹H NMR (300 MHz, DMSO-d₆): δ 8.83 (d, J = 1.2 Hz, 1H), 8.30-8.28 (m, 1H), 8.18-8.15 (m, 1H), 8.06-8.00 (m, 1H), 7.78 (d, J = 4.5 Hz, 1H), 7.51 (d, J = 9 Hz, 1H), 5.91 (s, 2H) |
| Ref. comp. 40 | 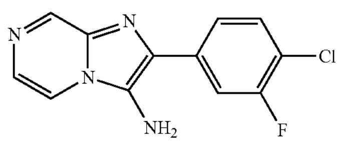 [SMILES: Nc1c(-c2ccc(Cl)c(F)c2)nc2cnccn12] | [M + H] = 263<br>¹H NMR-: (300 MHz, DMSO-d₆): δ 8.84 (1H, d, J = 1.2 Hz), 8.30-8.28 (1H, m), 7.99-7.88 (2H, m), 7.77 (1H, d, J = 4.8 Hz), 7.66 (1H, t, J = 8.1 Hz), 6.01 (2H, s) |
| Ref. comp. 41 | 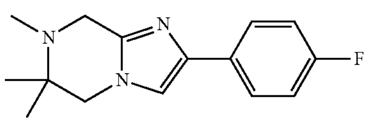 [SMILES: CN1Cc2nc(-c3ccc(F)cc3)cn2CC1(C)C] | [M + H] = 260<br>¹H NMR: (300 MHz, CDCl₃) δ 7.75-7.70 (m, 2H), 7.10-7.03 (m, 3H), 3.89 (s, 2H), 3.78 (s, 2H), 2.43 (s, 3H), 1.19 (s, 6H) |
| Ref. comp. 42 | 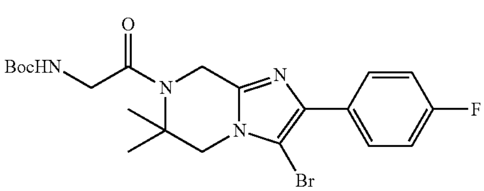 [SMILES: CC(C)(C)OC(=O)NCC(=O)N1Cc2nc(-c3ccc(F)cc3)c(Br)n2CC1(C)C] | [M + H] = 481.0 |
| Ref. comp. 43 | 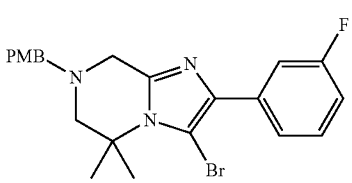 | [M + H] = 445.0 |
| Ref. comp. 44 | 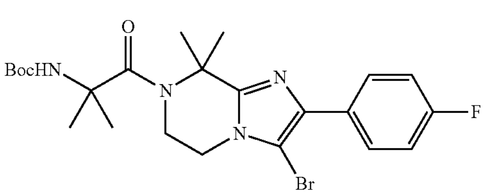 [SMILES: CC(C)(C)OC(=O)NC(C)(C)C(=O)N1CCn2c(nc(-c3ccc(F)cc3)c2Br)C1(C)C] | ¹H NMR: (400 MHz, CDCl₃) δ 7.88-7.92 (m, 2H), 7.07-7.11 (m, 2H), 4.88 (s, 1H), 4.87 (s, 2H), 3.84 (s, 1H), 1.55 (s, 6H), 1.51 (s, 6H), 1.37 (s, 9H) |

TABLE 1-continued

| Compound | Structure | Physical Data MS (m/z) and/or ¹H NMR |
|---|---|---|
| Ref. comp. 45 | 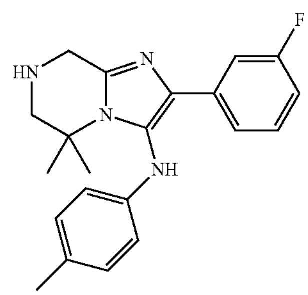 [SMILES: Cc1ccc(Nc2c(-c3cccc(F)c3)nc3n2C(C)(C)CNC3)cc1] | [M + H] = 351.2 |
| Ref. comp. 46 | 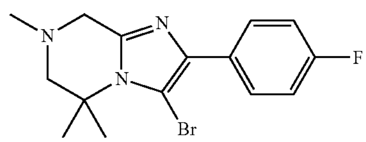 [SMILES: CN1Cc2nc(-c3ccc(F)cc3)c(Br)n2C(C)(C)C1] | [M + H] = 338.0 |
| Ref. comp. 47 | 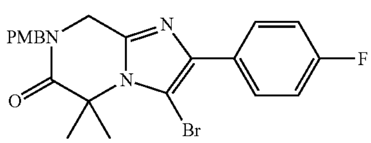 | [M + H] = 458.0 |
| Ref. comp. 48 | 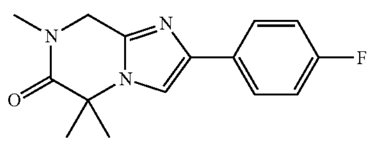 [SMILES: CN1Cc2nc(-c3ccc(F)cc3)cn2C(C)(C)C1=O] | ¹H NMR: (400 MHz, CDCl$_3$) δ 7.65-7.69 (m, 2H), 7.14 (s, 1H) 7.03 (t, J = 8.8 Hz, 2H), 4.62 (s, 2H), 3.11 (s, 3H), 1.70 (m, 6H) |
| Ref. comp. 49 | 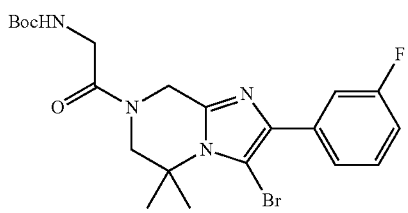 [SMILES: CC(C)(C)OC(=O)NCC(=O)N1Cc2nc(-c3cccc(F)c3)c(Br)n2C(C)(C)C1] | [M + H] = 481.1 |
| Ref. comp. 50 | 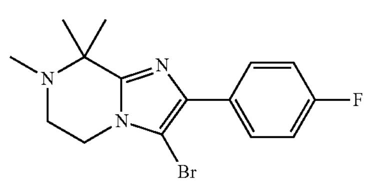 [SMILES: CN1CCn2c(nc(-c3ccc(F)cc3)c2Br)C1(C)C] | ¹H NMR: (400 MHz, CDCl$_3$ 7.87-7.90 (m, 2H), 7.07 (t, J = 8.8 Hz, 2H), 3.86 (t, J = 5.6 Hz, 2H), 3.03 (t, J = 5.6 Hz, 2H), 2.44 (s, 3H), 1.50 (s, 6H) |
| Ref. comp. 51 | 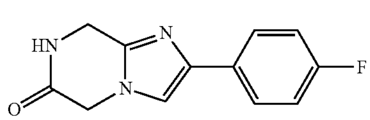 [SMILES: O=C1Cn2cc(-c3ccc(F)cc3)nc2CN1] | [M + H] = 232 ¹H NMR (300 MHz, DMSO-d$_6$) δ 4.47 (s, 2H), 4.65 (s, 2H), 7.15-7.21 (m, 2H), 7.55 (s, 1H), 7.74-7.79 (m, 2H), 8.48 (s, 1H) |

TABLE 1-continued

| Compound | Structure | Physical Data MS (m/z) and/or $^1$H NMR |
|---|---|---|
| Ref. comp. 52 | 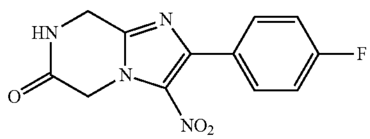 [SMILES: O=C1Cn2c(nc(-c3ccc(F)cc3)c2[N+](=O)[O-])CN1] | [M + H] = 277.0<br>$^1$H NMR:<br>(400 MHz, CD$_3$OD) δ 7.12-7.07 (m, 2H), 4.95 (t, J = 2.0 Hz, 2H), 4.57 (t, J = 2.00 Hz, 2H). |
| Ref. comp. 53 | 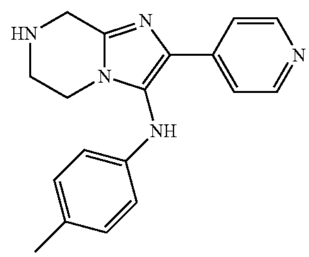 [SMILES: Cc1ccc(Nc2c(-c3ccncc3)nc3n2CCNC3)cc1] | [M + H] = 306<br>$^1$H NMR:<br>(300 MHz, CDCl$_3$): δ 8.44-8.46 (m, 2H), 7.79 (m, 2H), 7.06-7.09 (d, J = 8.1 Hz, 2H), 6.60-6.63 (d, J = 8.4 Hz, 2H), 5.57 9s, 1H), 3.90 9s, 2H), 3.81 (m, 2H), 3.43 9s, 1H), 3.03 (m, 2H), 2.29 (s, 3H) |
| Ref. comp. 54 | 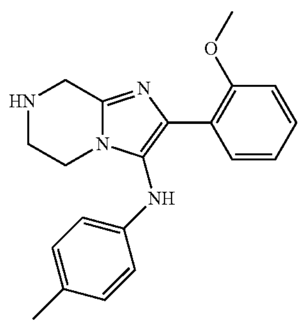 [SMILES: COc1ccccc1-c1nc2n(c1Nc1ccc(C)cc1)CCNC2] | [M + H] = 335<br>$^1$H NMR:<br>(300 MHz, CDCl$_3$): δ 7.67 (d, J = 6 Hz, 1H), 7.25 (d, J = 6.6 Hz, 1H), 7.01 (t, J = 4.2 Hz, 2H), 6.94 (t, J = 8.1 Hz, 2H), 6.52 (d, J = 8.1 Hz, 2H), 5.87 (s, 1H), 4.20 (s, 2H), 3.83 (s, 3H), 3.75 (m, 2H), 3.49 (s, 1H), 3.22 (m, 2H), 2.24 (s, 3H) |
| Ref. comp. 55 | 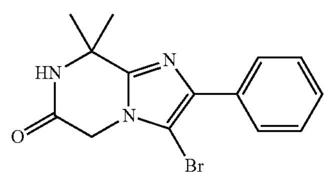 | [M + H] = 338<br>$^1$H NMR: (300 MHz, DMSO-d$_6$) δ 8.76 (s, 1H), 7.94-7.89 (m, 2H), 7.31-7.25 (m, 2H), 4.57 (s, 2H), 1.56 (s, 6H). |
| Ref. comp. 56 | 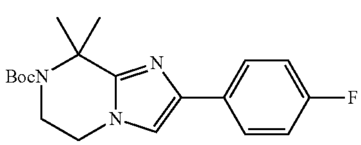 [SMILES: CC(C)(C)OC(=O)N1CCn2cc(-c3ccc(F)cc3)nc2C1(C)C] | $^1$H NMR:<br>(400 MHz, CD$_3$OD) δ 7.61-7.57 (m, 2H), 7.16 (s, 1H); 7.00-6.96 (m, 2H), 3.96 (t, J = 5.2 Hz, 2H), 3.77 (t, J = 5.2 Hz, 2H), 1.76 (s, 6H), 1.42 (s, 9H) |
| Ref. comp. 57 | 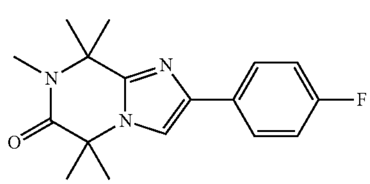 [SMILES: CN1C(=O)C(C)(C)n2cc(-c3ccc(F)cc3)nc2C1(C)C] | [M + H] = 302.2 |

TABLE 1-continued

| Compound | Structure | Physical Data MS (m/z) and/or ¹H NMR |
|---|---|---|
| Ref. comp. 58 | 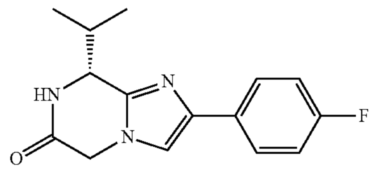 [SMILES: CC(C)[C@H]1NC(=O)Cn2cc(-c3ccc(F)cc3)nc21] | [M + H] = 274<br>¹H NMR:<br>(300 MHz, CDCl₃): δ 7.73-7.78 (m, 2H), 7.06-7.13 (m, 3H), 6.73 (s, 1H), 4.77 (s, 2H), 4.72 (s, 1H), 2.51-2.58 (m, 1H), 1.09-1.12 (d, J = 6.9 Hz, 3H), 0.87-0.91 (d, J = 6.9 Hz, 3H) |
| Ref. comp. 59 | 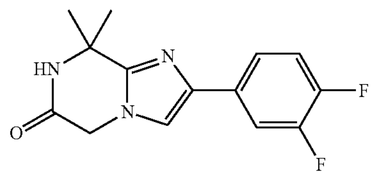 [SMILES: CC1(C)NC(=O)Cn2cc(-c3ccc(F)c(F)c3)nc21] | [M + H] = 278<br>¹H NMR:<br>(300 MHz, CDCl₃): δ 7.60-7.64 (m, 1H), 7.42-7.60 (m, 1H), 7.12-7.22 (m, 1H), 7.08 (s, 1H), 6.94 (s, 1H), 4.72 (s, 2H) |
| Ref. comp. 60 | 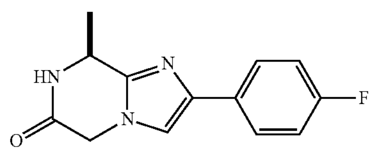 [SMILES: C[C@@H]1NC(=O)Cn2cc(-c3ccc(F)cc3)nc21] | ¹H NMR: (300 MHz, DMSO-d₆) δ 8.60 (s, 1H), 7.75-7.79 (m, 2H), 7.54 (s, 1H), 7.16-7.22 (m, 2H), 4.62-4.73 (m, 3H), 1.51 (d, J = 6.3 Hz, 3H) |
| Ref. comp. 61 | 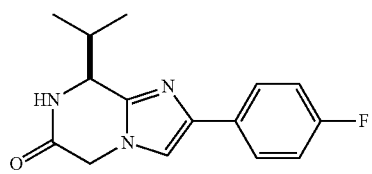 [SMILES: CC(C)[C@@H]1NC(=O)Cn2cc(-c3ccc(F)cc3)nc21] | [M + H] = 274<br>¹H NMR<br>(300 MHz, CDCl₃): δ 7.76-7.71 (m, 2H), 7.12 (m, 3H), 6.61 (s, 1H), 4.71 (s, 3H), 2.53-2.48 (m, 1H), 1.11-1.08 (m, 3H), 0.91-0.88 (m, 3H). |
| Ref. comp. 62 | 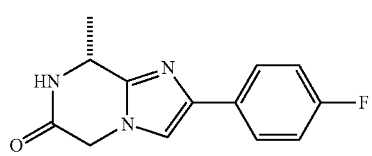 [SMILES: C[C@H]1NC(=O)Cn2cc(-c3ccc(F)cc3)nc21] | [M + H] = 246<br>¹H NMR (300 MHz, DMSO-d₆): δ 8.60 (s, 1H), 7.80-7.74 (m, 2H), 7.54 (s, 1H), 7.23-7.15 (m, 2H), 4.73-4.61 (m, 3H), 1.51 (d, J = 6.3 Hz, 3H,) |
| Ref. comp. 63 | 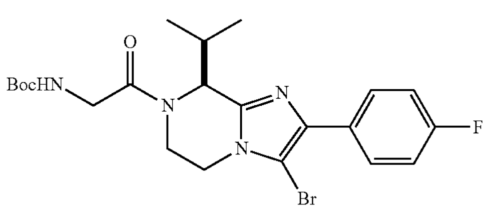 [SMILES: CC(C)[C@H]1c2nc(-c3ccc(F)cc3)c(Br)n2CCN1C(=O)CNC(=O)OC(C)(C)C] | [M + H] = 496<br>¹H NMR<br>(300 MHz, CDCl₃) 5.62-5.65 (m, 1H), 5.39 (s, 1H), 5.02-5.07 (m, 1H), 4.62 (m, 1H), 3.77-4.11 (m, 6H), 3.35-3.39 (m, 1H), 2.31 (s, 1H), 1.47 (s, 9H), 1.26-1.34 (m, 3H), δ 0.88-1.13 (m, 3H), |

TABLE 1-continued
| Compound | Structure | Physical Data MS (m/z) and/or ¹H NMR |
|---|---|---|
| Ref. comp. 64 | 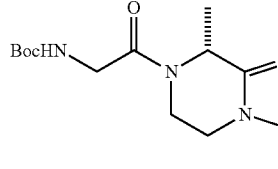 | [M + H] = 467<br>¹H NMR: (300 MHz, CDCl₃) δ 7.88-7.92 (t, J = 6.6 Hz, 2H), 7.10-7.15 (m, 2H), 5.41-5.51 (m, 1H), 5.02-5.19 (m, 2H), 4.05-4.11 (m, 4H), 3.70-3.88 (m, 2H), 3.30 (m, 1H), 1.71-1.74 (m, 2H), 1.61-1.63 (m, 1H), 1.47 (s, 9H) |
| Ref. comp. 65 | 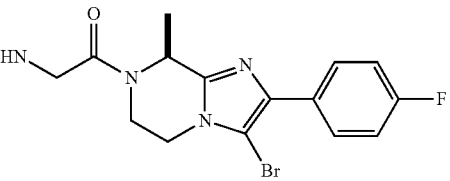 | [M + H] = 467 |
| Ref. comp. 66 | 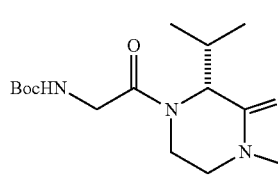 | [M + H] = 496<br>¹H NMR: (300 MHz, DMSO-d₆): δ 7.93-7.86 (m, 2H), 7.31-7.25 (m, 2H), 6.89 (s, 1H), 5.30-5.16 (m, 1H), 4.75-4.65 (m, 1H), 4.35-4.26 (m, 1H), 3.99-3.66 (m, 4H), 2.28-2.15 (m, 1H), 1.62-1.39 (m, 10 H), 1.01-0.88 (m, 3H). |
| Ref. comp. 67 | 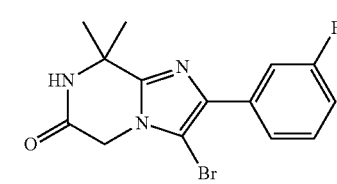 | [M + H] = 338<br>¹H NMR (300 MHz, DMSO-d₆) δ 8.76 (s, 1H), 7.78 (m, 1H), 7.65 (m, 1H), 7.53-7.45 (m, 1H), 7.18-7.12 (m, 1H), 4.58 (s, 1H), 1.58 (s, 6H) |
| Ref. comp. 68 | 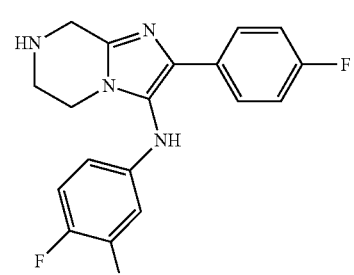 | [M + H] = 345<br>¹H NMR: (300 MHz, CDCl₃) δ 7.76-7.72 (m, 2H) 7.08-6.99 (m, 3H) 6.50-6.43 (m, H) 6.38-6.35 (m, 1H) 5.26 (s, H), 4.17 (s, 2H) 3.73-3.69 (m, 2H) 3.27-3.23 (m, 2H) 2.05 (s, 2H) |

TABLE 1-continued

| Compound | Structure | Physical Data MS (m/z) and/or ¹H NMR |
|---|---|---|
| Ref. comp. 69 | (structure) | [M + H] = 361<br>¹H NMR (300 MHz, DMSO-d$_6$) δ 8.27 (s, 1H), 7.58 (d, J = 7.8 Hz, 1H), 7.48 (d, J = 7.2 Hz, 1H), 7.28-7.38 (m, 2H), 6.94-7.00 (m, 1H), 6.42-6.52 (m, 2H), 3.88 (s, 2H), 3.57 (s, 2H), 3.04 (t, J = 5.1 Hz, 2H) |
| Ref. comp. 70 | (structure) | [M + H] = 361<br>¹H NMR (400 MHz, CDCl$_3$) δ 7.75-7.70 (m, 2H) 7.25-7.19 (m, H), 7.05-7.02 (m, 2H), 6.48-6.41 (m, 2H), 4.16 (s, 2H), 3.70 (m, 2H), 3.24 (m, 2H). |

Reference Compound 1

N-(benzo[d][1,3]dioxol-5-yl)-2-phenyl-5,6,7,8-tetrahydroimidazo[1,2-a]pyrazin-3-amine

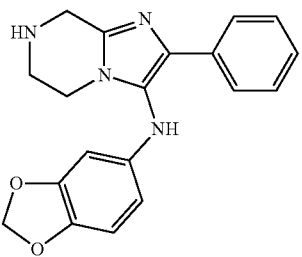 [SMILES: c1ccc(-c2nc3n(c2Nc2ccc4c(c2)OCO4)CCNC3)cc1]

Reference Compound 1 was prepared in the following way:

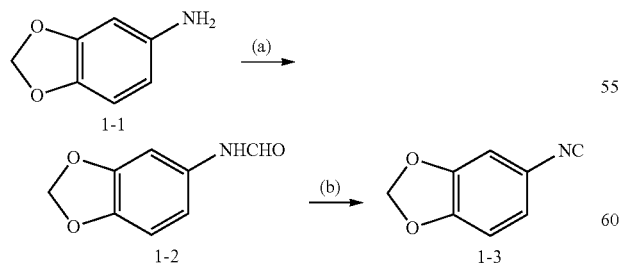

A stirred solution of Compound 1-1 (685 mg, 10 mmol) in 10 mL of ethyl formate was heated to 120° C. for 2 hours in a microwave oven. Solvent was removed and the residue was subjected to MS-triggered HPLC purification to give 728 mg of Compound 1-2 as brown oil after neutralization. To a solution of Compound 1-2 (728 mg, 4.4 mmol) in 20 mL of DCM were added DIEA (2.30 mL, 13.2 mmol) and POCl$_3$ (0.45 mL, 4.84 mmol) at 0° C. The reaction mixture was stirred at the same temperature for 2 hours and at room temperature for 2 additional hours. Solvent was removed and the residue was subjected to MS-triggered HPLC purification to give 281 mg of Compound 1-3 as yellow solid after neutralization: ¹H NMR (CDCl$_3$, 400 MHz) δ 6.88 (dd, J=2.0, 8.4 Hz, 1H), 6.79 (d, J=1.6 Hz, 1H), 6.74 (d, J=8.4 Hz, 1H), 6.01 (s, 2H).

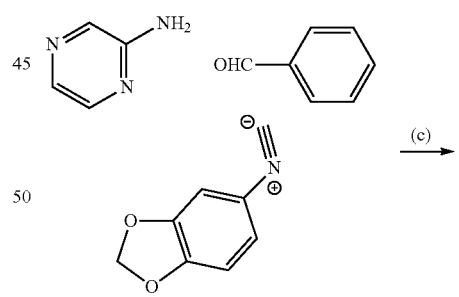

To a stirred solution of compound Compound 1-3 (158 mg, 1.66 mmol) in 10 mL of MeOH were added benzaldehyde (0.25 mL, 2.49 mmol), 2-aminopyrazine (281 mg, 1.91 mmol), and followed by 1.0 N HClO$_4$ in MeOH (0.17 mL, 0.17 mmol). The reaction mixture was stirred at room temperature for 3 hours. The reaction mixture was directly taken to mass-triggered HPLC purification. The collected MeCN/water solution was concentrated and dried on a lyophilizer to give 296 mg of Compound 1-4 as powdery product: $^1$H NMR (CDCl$_3$, 400 MHz) δ 9.23 (d, J=1.2 Hz, 1H), 8.03 (d, J=4.8 Hz, 1H), 7.91-7.94 (m, 3H), 7.26-7.44 (m, 3H), 6.68 (d, J=8.4 Hz, 1H), 6.32 (br, 1H), 6.25 (d, J=2.4 Hz, 1H), 6.00 (dd, J=2.4, 8.4 Hz, 1H), 5.93 (s, 2H).

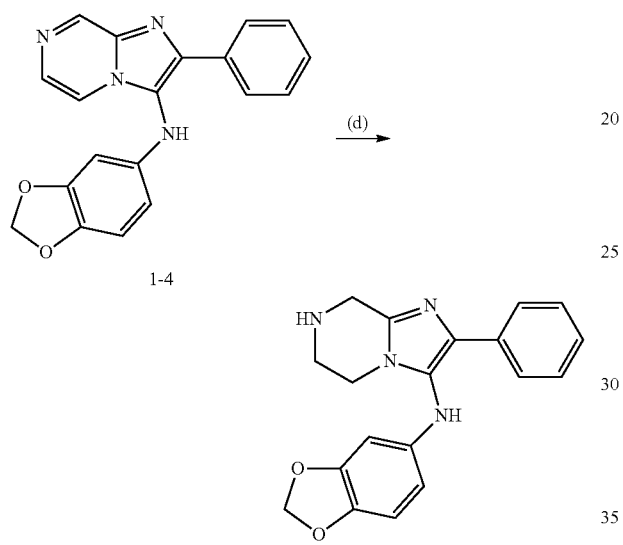

To a stirred solution of Compound 1-4 (181 mg, 0.54 mmol) in 10 mL of MeOH was added Pd/C (58 mg, 0.054 mmol). The reaction mixture was evacuated and back filled with H$_2$. The reaction mixture was stirred at room temperature overnight. The solid was filtered off and solvent was removed. 400 MHz proton NMR of the crude product proved it to be the title compound: $^1$H NMR (CDCl$_3$, 400 MHz) δ 7.64 (d, J=7.2 Hz, 2H), 7.91-7.94 (m, 3H), 7.21-7.27 (m, 3H), 6.59 (d, J=8.4 Hz, 1H), 6.26 (d, J=2.0 Hz, 1H), 5.99 (dd, J=2.0, 9.2 Hz, 1H), 5.83 (s, 2H), 4.48 (s, 2H), 3.89 (s, 2H), 3.38 (s, 2H).

The following reference compounds were prepared by the same three component Ugi reaction used to prepare Reference Compound 1, using appropriate starting materials, followed by a Pd/C mediated hydrogenation: Reference Compound 2 was prepared from 2-aminopyridine, benzaldehyde and 1-isocyano-3,5-dimethylbenzene; Reference Compound 3 was prepared from 2-aminopyrazine, 4-fluorobenzaldehyde and isocyanocyclopentane; Reference Compound 4 was prepared from 2-aminopyrazine, benzaldehyde and isocyanocyclopentane; Reference Compound 5 was prepared from 2-aminopyrazine, benzaldehyde and isocyanobenzene; Reference Compound 6 was prepared from 2-aminopyrazine, benzaldehyde and methyl 4-isocyanobenzoate; Reference Compound 7 was prepared from 2-aminopyrazine, 2-fluorobenzaldehyde and 1-fluoro-4-isocyanobenzene; Reference Compound 8 was prepared from 2-aminopyrazine, benzaldehyde and 1-fluoro-4-isocyanobenzene; Reference Compound 9 was prepared from 2-aminopyrazine, 2,4,6-trifluorobenzaldehyde and 1-fluoro-4-isocyanobenzene; Reference Compound 10 was prepared from 2-aminopyrazine, 3,5-difluorobenzaldehyde and 1-fluoro-4-isocyanobenzene; Reference Compound 11 was prepared from 2-aminopyrazine, 4-pentylbenzaldehyde and 1-fluoro-4-isocyanobenzene; Reference Compound 12 was prepared from 2-aminopyrazine, cyclohexanecarbaldehyde and 1-fluoro-4-isocyanobenzene; Reference Compound 13 was prepared from 2-aminopyrazine, 4-fluorobenzaldehyde and 3-isocyanopyridine; Reference Compound 14 was prepared from 2-aminopyrazine, 4-fluorobenzaldehyde and isocyanocyclohexane; Reference Compound 15 was prepared from 2-aminopyrazine, 4-fluorobenzaldehyde and 1-bromo-4-isocyanobenzene; Reference Compound 16 was prepared from 2-aminopyrazine, 4-fluorobenzaldehyde and (isocyanomethyl)benzene; Reference Compound 17 was prepared from 2-aminopyrazine, 4-fluorobenzaldehyde and isocyanofluoro)benzene; Reference Compound 22 was prepared from 2-aminopyrazine, 4-fluoro-2-hydroxy benzaldehyde and 1-fluoro-4-isocyanobenzene; Reference Compound 23 was prepared from 2-aminopyrazine, 4-methylbenzaldehyde and 1-fluoro-4-isocyanobenzene; Reference Compound 24 was prepared from 2-aminopyrazine, 4-methoxybenzaldehyde and 1-fluoro-4-isocyanobenzene; Reference Compound 25 was prepared from 2-aminopyrazine, 4-bromobenzaldehyde and 1-fluoro-4-isocyanobenzene; Reference Compound 26 was prepared from 2-aminopyrazine, 4-chlorobenzaldehyde and 1-fluoro-4-isocyanobenzene; and Reference Compound 29 was prepared from 2-aminopyrazine, 4-fluorobenzaldehyde and 1-methyl-4-isocyanobenzene.

Reference Compound 18

2,3-bis(4-fluorophenyl)-5,6,7,8-tetrahydroimidazo[1,2-a]pyrazine

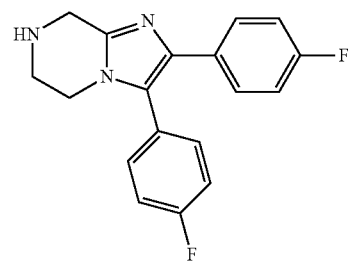

Reference Compound 18 was prepared by the following way:

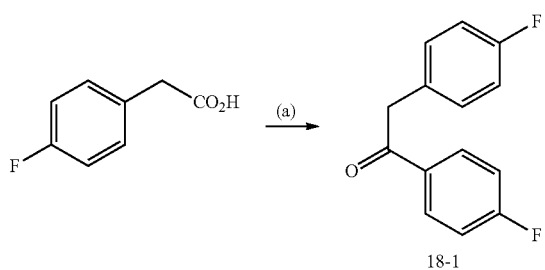 [SMILES: O=C(O)Cc1ccc(F)cc1 ; O=C(Cc1ccc(F)cc1)c1ccc(F)cc1]

To a solution of 2-(4-fluorophenyl)acetic acid (1.54 g, 10 mmol) in 30 mL dry DCM was added slowly SOCl$_2$ (2.18 mL, 30 mmol), 2 drops of DMF was added. The reaction mixture was stirred at reflux for 1 hour before the solvent was removed. The residue was dissolved in 30 mL of DCM and AlCl₃ (2.67 g, 22 mmol) was added at 0° C. The reaction mixture was stirred at room temperature for 10 mins. Fluorobenzene (0.94 mL, 10 mmol) in 2 mL of DCM was added dropwise at 0° C. The reaction mixture was allowed to stir at the same temperature for 2 hours. The reaction mixture was poured into a mixture of 30 mL of 0.1M HCl and 50 g crushed ice. The resulting mixture was separated and the aqueous layer was washed with DCM. The combined DCM solution was dried and concentrated. The residue was subjected to flash chromatography purification to give 983 mg of Compound 18-1 as light yellow solid: ¹H NMR (CDCl₃, 400 MHz) δ 8.04-8.08 (m, 2H), 7.23-7.26 (m, 2H), 7.15 (t, J=8.8 Hz, 2H), 7.04 (t, J=8.8 Hz, 2H), 4.26 (s, 2H).

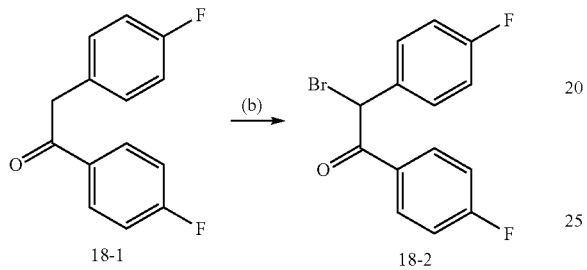

To a solution of Compound 18-1 (232 mg, 1.0 mmol) in 6 mL of DCM was added Br₂ (61 μL, 1.2 mmol) in 12 mL of acetic acid. The reaction mixture was stirred at room temperature overnight. The reaction mixture was concentrated and the residue was directly subjected to mass-triggered HPLC purification to give 181 mg yellow solid. The mass of the desired product on preparative HPLC was not right and did not show the characteristic peak pattern of bromides. The peak was collected by that mass and the compound was verified to be the right mass on the analytical HPLC, and also by 400 MHz proton NMR: ¹H NMR (CDCl₃, 400 MHz) δ 8.02-8.05 (m, 2H), 7.51-7.54 (m, 2H), 7.10-7.15 (m, 2H), 7.04-7.08 (m, 2H), 6.31 (s, 1H).

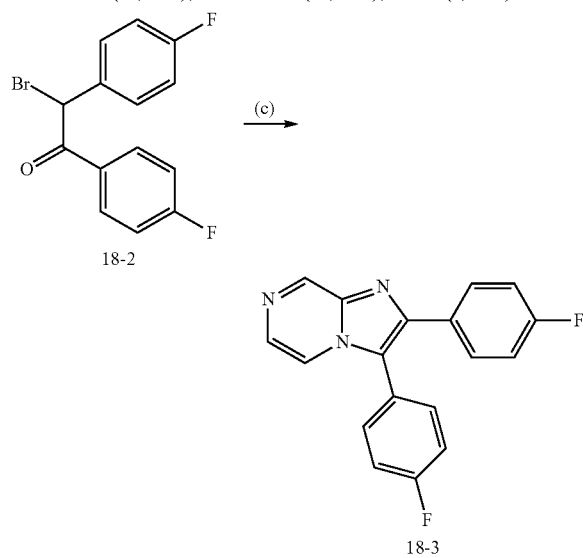

A solution of 2-aminopyrazine (57 mg, 0.60 mmol), Compound 18-2 (156 mg, 0.50 mmol) and K₂CO₃ (83 mg, 0.60 mmol) in 5 mL of EtOH was stirred at 120° C. for 3 hours. Solvent was removed and the residue was subjected to MS-triggered HPLC purification. The collected MeCN/water solution was neutralized. The organic solution was dried and concentrated to give Compound 18-3 as yellow oil: ¹H NMR (CDCl₃, 400 MHz) δ 9.14 (d, J=1.2 Hz, 1H), 7.86 (d, J=1.6 Hz, 2H), 7.62-7.65 (m, 2H), 7.42-7.45 (m, 2H), 7.28 (t, J=8.4 Hz, 2H), 7.02 (t, J=8.8 Hz, 2H), 6.31 (s, 1H).

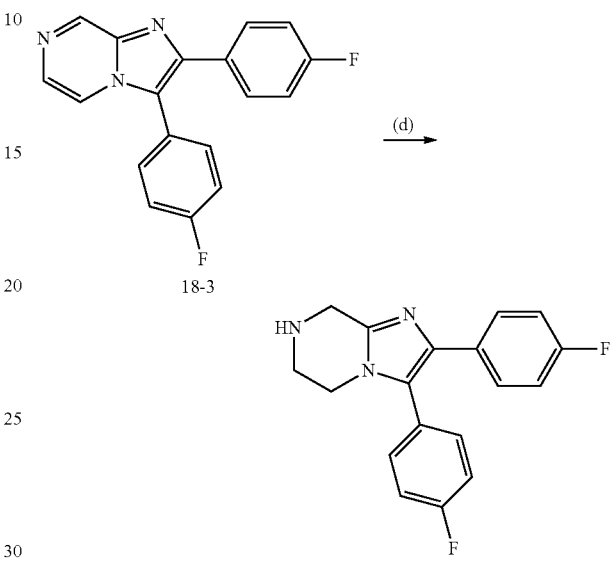

To a stirred solution of Compound 18-3 (10 mg, 0.033 mmol) in 6 mL of MeOH was added Pd/C (4 mg, 0.0033 mmol). The reaction mixture was evacuated and back filled with H₂. The reaction mixture was stirred at room temperature overnight. The solid was filtered off and solvent was removed. The product was subjected to mass-triggered HPLC purification to give the title compound as yellow oil after neutralization.

Reference Compound 19

2-(4-fluorophenyl)imidazo[1,2-a]pyrazin-3-amine

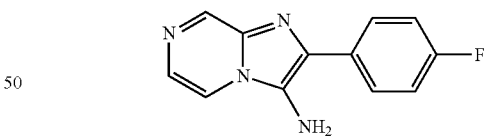

Reference Compound 19 was prepared by the following way:

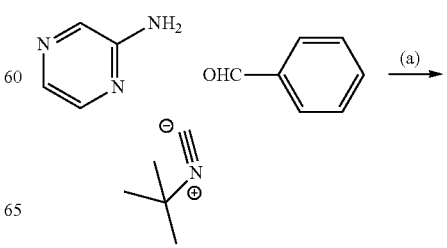

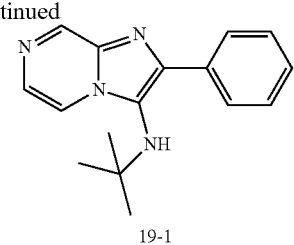

19-1

To a stirred solution of 2-aminopyrazine (571 mg, 6.0 mmol) in 10 mL of MeOH were added 4-fluorobenzaldehyde (0.97 mL, 9.0 mmol), 2-isocyano-2-methylpropane (0.78 mL, 6.9 mmol), and followed by 1.0 N $HClO_4$ in MeOH (0.60 mL, 0.60 mmol). The reaction mixture was stirred at room temperature for 3 hours. Solvent was removed and the residue was subjected to flash chromatography purification to give Compound 19-1 as white solid: $^1$H NMR (CDCl$_3$, 400 MHz) δ 8.97 (d, J=1.6 Hz, 1H), 8.10 (dd, J=1.6, 4.4 Hz, 1H), 7.90-7.94 (m, 2H), 7.13 (t, J=8.8 Hz, 2H), 1.04 (s, 9H).

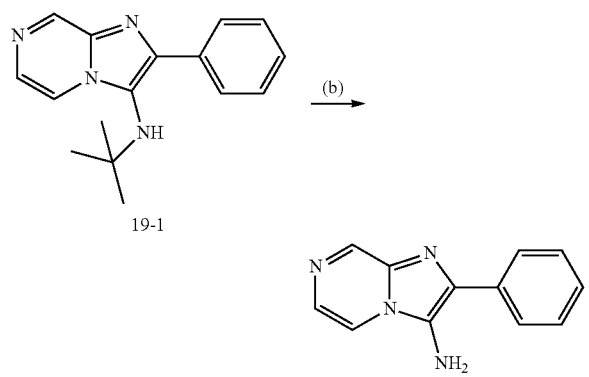

19-1

A solution of Compound 19-1 (284 mg, 1.0 mmol) in 10 mL of 4:1 DCM and TFA was stirred at room temperature for 2 hours. Solvent was removed and the product was directly used in the next step after neutralization.

Reference Compound 20

N-(3-fluorophenyl)-2-(4-fluorophenyl)-5,6,7,8-tetrahydroimidazo[1,2-a]pyrazin-3-amine

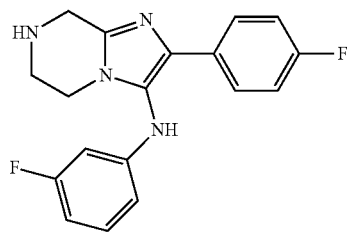 [SMILES: Fc1ccc(-c2nc3n(c2Nc2cccc(F)c2)CCNC3)cc1]

Reference Compound 20 was prepared by the following way: to a solution of Reference Compound 19 (69 mg, 0.30 mmol) in 6 mL of dioxane were added 1-bromo-3-fluorobenzene (66 μL, 0.60 mmol), Pd$_2$(dba)$_3$ (8 mg, 0.009 mmol), Xantphos (11 mg, 0.018 mmol) and Cs$_2$CO$_3$ (196 mg, 0.60 mmol) at room temperature. The reaction mixture was degassed and stirred at 120° C. under N$_2$ for 5 hours. The reaction mixture was cooled to room temperature and solid was filtered off. The resulting filtrate was concentrated. The residue was subjected to mass-triggered HPLC purification to give a yellow oil after neutralization. To a stirred solution of the obtained adduct (64 mg, 0.20 mmol) in 5 mL of MeOH was added Pd/C (21 mg, 0.02 mmol). The reaction mixture was evacuated and back filled with H$_2$. The reaction mixture was stirred at room temperature overnight. The solid was filtered off and solvent was removed. The residue was subjected to mass-triggered HPLC purification to give a yellow solid.

Reference Compound 27 was prepared from Reference Compound 19 by an amination reaction with 1-bromo-3,5-difluorobenzene followed by a Pd/C mediated hydrogenation; Reference Compound 28 was prepared from Reference Compound 19 by an amination reaction with 1-bromo-4-(trifluoromethyl)benzene followed by a Pd/C mediated hydrogenation; Reference Compound 30 was prepared from Reference Compound 19 by an amination reaction with 1-bromo-4-(trifluoromethyl)benzene followed by a Pd/C mediated hydrogenation; Reference Compound 31 was prepared from Reference Compound 11 by an amination reaction with 1-bromo-2,4-difluorobenzene followed by a Pd/C mediated hydrogenation; Reference Compound 32 was prepared by the same way that Reference Compound 19 was prepared: a three component Ugi reaction among 2-aminopyrazine, 3-fluorobenzaldehyde and 2-isocyano-2-methylpropane followed by a TFA mediated deprotection; Reference Compound 34 was prepared by a three component Ugi reaction among 2-aminopyrazine, 3-fluorobenzaldehyde, and 2-isocyano-2-methylpropane followed by a HATU mediated amidation reaction with 2-(benzyloxycarbonylamino)-2-methylpropanoic acid and HCl mediated deprotection.

Reference Compound 33

2-(4-fluorophenyl)-6-methylimidazo[1,2-a]pyrazin-3-amine

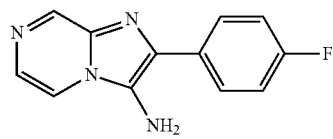

Reference Compound 33 was prepared by the same way that Reference Compound 1 was prepared:

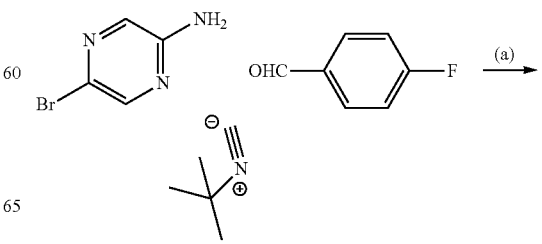

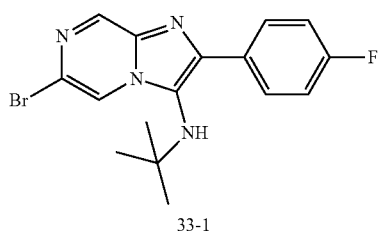

33-1

To a stirred solution of 5-bromopyrazin-2-amine (313 mg, 1.8 mmol) in 20 mL of MeOH were added 4-fluorobenzaldehyde (191 µL, 1.8 mmol), and followed by 1.0 N HClO$_4$ in MeOH (0.15 mL, 0.15 mmol). The reaction mixture was stirred at room temperature for 0.5 hour which was followed by addition of 2-isocyano-2-methylpropane (170 µL, 1.5 mmol). The stirring was continued at room temperature overnight. The reaction mixture was subjected to direct mass-triggered HPLC purification to give 299 mg of Compound 33-1 as a yellow solid.

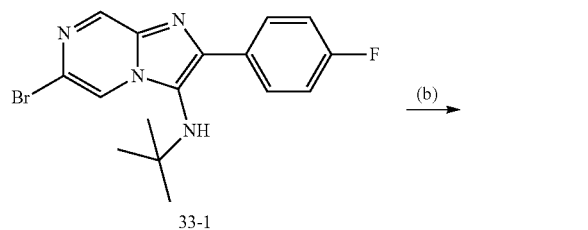

To a stirred solution of Compound 33-1 (131 mg, 0.36 mmol) in 10 mL of dioxane were added 2.0 M Me$_2$Zn in toluene (0.75 mL, 1.5 mmol) and Ni(DPPP)$_2$Cl$_2$ (98 mg, 0.18 mmol). The reaction mixture was evacuated and back filled with N$_2$. The reaction mixture was stirred at reflux overnight. Reaction mixture was quenched with methanol. Solid was filtered off and solvent was removed. The residue was subjected to mass-triggered HPLC purification to give Compound 33-2 as yellow oil.

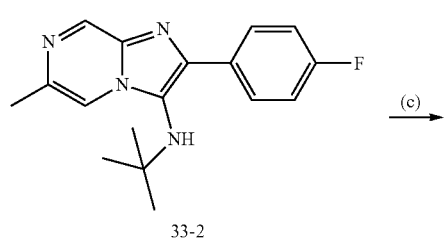

33-2

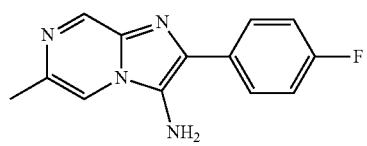

To a solution of Compound 33-2 (9 mg, 0.03 mmol) in 2 mL of DCM was added 4 mL of TFA. The reaction mixture was stirred at room temperature overnight. The reaction mixture was concentrated and the residue was subjected to mass-triggered HPLC purification to give the titled compound in quantitative yield after neutralization.

Reference Compound 35

2-(4-fluorophenyl)-6-methylimidazo[1,2-a]pyrazin-3-amine

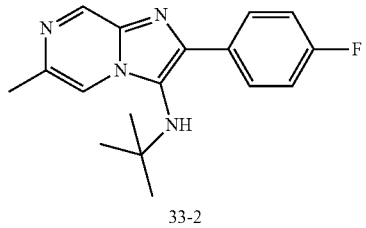

Reference Compound 35 was prepared by the following way:

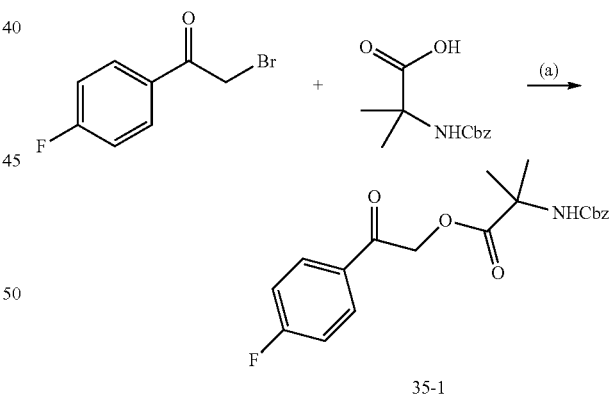

35-1

To a solution of 2-bromo-1-(4-fluorophenyl)ethanone (46.5 g, 214.29 mmol) in DMF (400 mL), were added 2-(benzyloxycarbonyl)-2-methylpropanoic acid (55.8 g, 236.4 mmol) and potassium carbonate (35.4 g, 256.5 mmol). The resulting solution was stirred for 4 h at room temperature. The resulting solution was diluted with 1000 mL of water. The resulting solution was extracted with ethyl acetate (2×800 mL) and the combined organic layer was washed with water (2×800 mL), brine (1×800 mL). The resulting mixture was concentrated under vacuum. This resulted in 67 g (84%) of Compound 35-1 as a white solid.

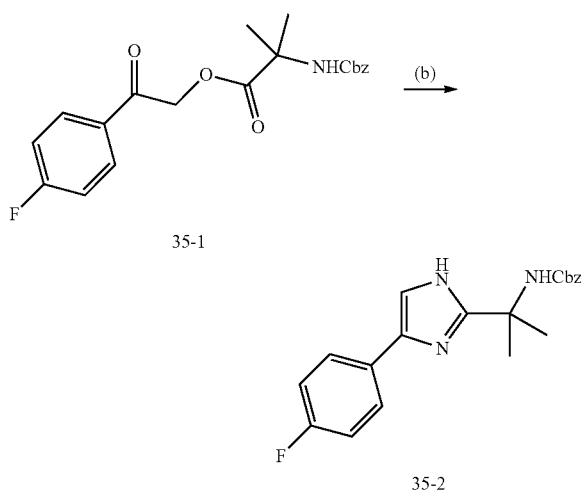

35-1

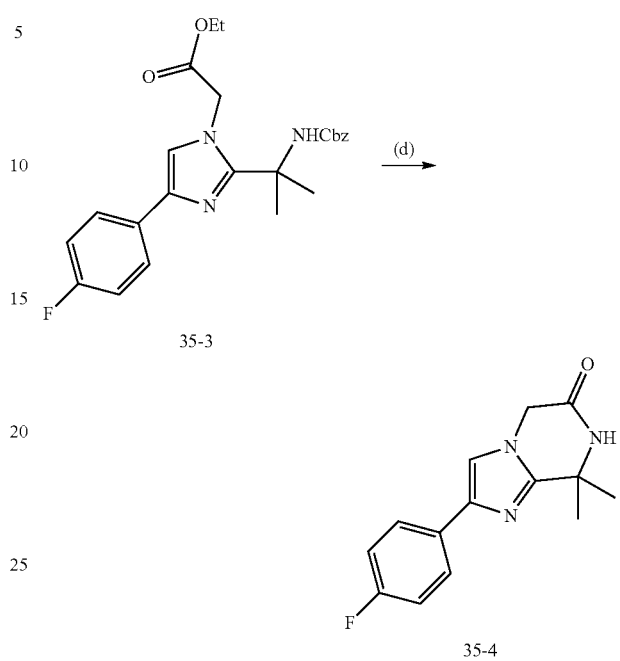

35-3

To a solution of Compound 35-1 (70 g, 187.7 mmol) in toluene (700 mL), was added NH₄OAc (144.5 g, 1.88 mol). The resulting solution was heated to reflux for 3 h in an oil bath. The resulting mixture was concentrated under vacuum. The residue was dissolved in 800 mL of water. The resulting solution was extracted with ethyl acetate (2×500 mL) and the combined organic layer was washed with water (2×800 mL) and brine (1×800 mL). The resulting mixture was concentrated under vacuum. This resulted in 58 g (88%) of Compound 35-2 as a white solid.

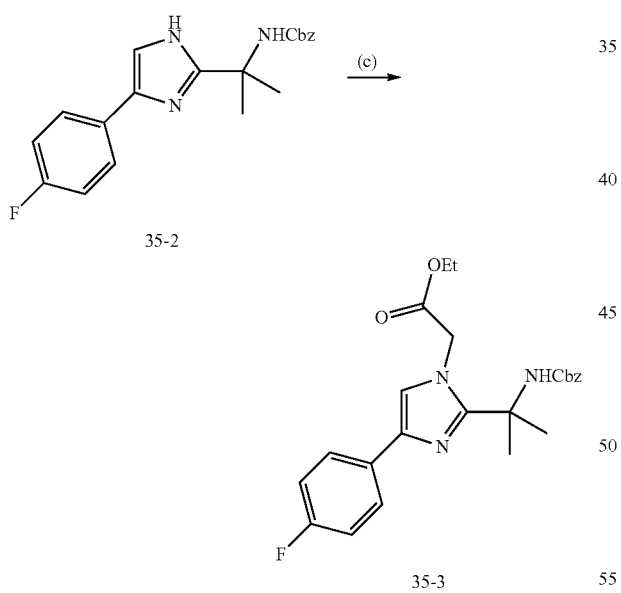

35-2

35-3

To a solution of Compound 35-2 (58 g, 164.3 mmol) in DMF (400 mL), were added cesium carbonate (134 g, 411.0 mmol). This was followed by the addition of ethyl 2-bromoacetate (33 g, 197.6 mmol) dropwise with stirring at room temperature in 30 min. The resulting solution was stirred for 2 h at room temperature. The resulting solution was diluted with 1000 mL of water/ice. The resulting solution was extracted with ethyl acetate (2×700 mL) and the combined organic layer was washed with water (2×800 mL) and brine (1×800 mL). The resulting mixture was concentrated under vacuum. This resulted in 60 g (83%) of Compound 35-3 as a yellow solid.

To a solution of Compound 35-3 (70 g, 159.4 mmol) in methanol (800 mL), was added 10% Pd/C (10 g). The resulting solution was degassed and back filled with hydrogen. The solution was stirred for 3 days at 35° C. The solids were filtered out. The filtrate was concentrated under reduced pressure. This resulted in Compound 35-4 as a white solid: ¹H NMR: (DMSO, 300 MHz): δ 7.79-7.74 (m, 2H), 7.13-7.07 (m, 3H), 6.35 (s, 2H), 4.73 (s, 2H), 1.79 (s, 6H)

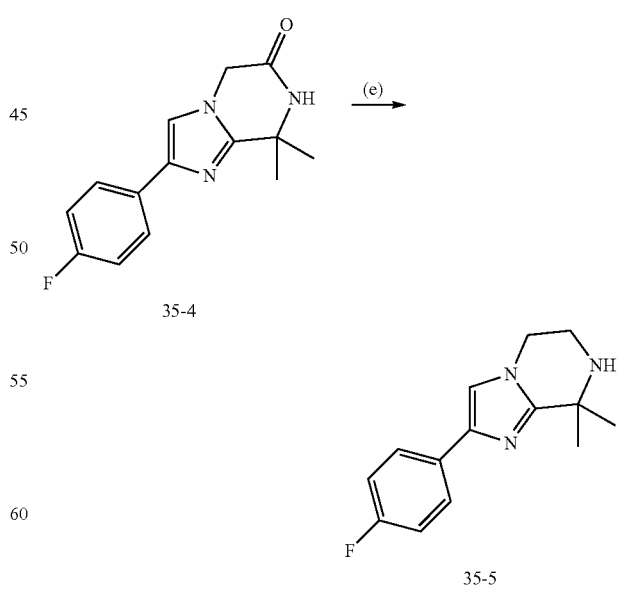

35-4

35-5

To a stirred solution of Compound 40-4 (15 g, 57.9 mmol) in THF (300 mL) was added of BH₃ Me₂S complex (144.2 mL, 2M) dropwise at room temperature in 30 min. The resulting solution was reflux for 4 h. After cooling to room temperature, the resulting solution was diluted with 100 mL of methanol. The pH was adjusted to 1-2 with hydrochloric acid (12N). The mixture was reflux for 1 h. The resulting mixture was concentrated under vacuum. The residue was dissolved in 100 mL of water. pH was adjusted to 9-10 with aqueous potassium carbonate (40%). The resulting solution was extracted with 3×200 mL of DCM and the organic layers were combined, dried over anhydrous sodium sulfate and concentrated under vacuum. This resulted in Compound 35-5 as a white solid.

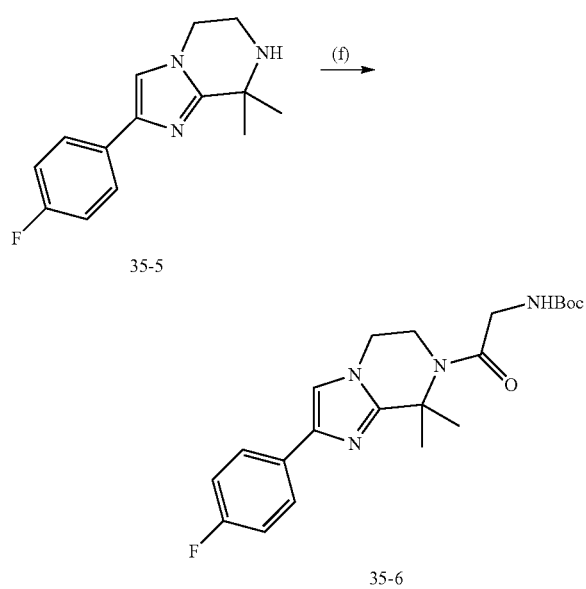

To a stirred solution of Compound 35-5 (7.3 g, 29.8 mmol) in DMF (150 mL) was added N-Boc-glycine (17 g, 89.4 mmol), followed by HATU (37.2 g, 122 mmol) & DIEA (25.3 g, 178 mmol). The resulting solution was stirred for 3 h at room temperature. The resulting mixture diluted with 600 mL of ethyl acetate, washed with saturated aqueous NaHCO$_3$ (30 mL×6), brine (30 mL×3), dried over anhydrous Na$_2$SO$_4$ and concentrated in vacuo. This resulted in crude product, which was triturated and sonicated with ether (20 mL×3) to give Compound 35-6: $^1$H NMR (300 MHz, DMSO-d$_6$,) δ7.77-7.72 (m, 2H), 7.54 (s, 1H), 7.20-7.14 (m, 2H), 6.84-6.80 (m, 1H), 4.07 (s, 2H), 3.90 (d, J=3 Hz, 2H), 3.70 (s, 2H), 1.80 (s, 6H), 1.40 (s, 9H).

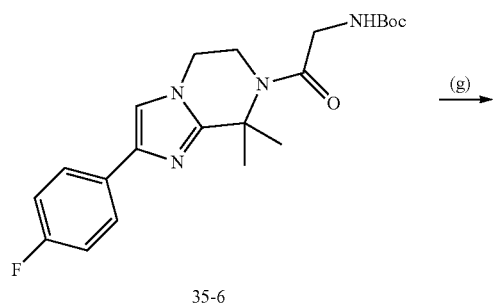

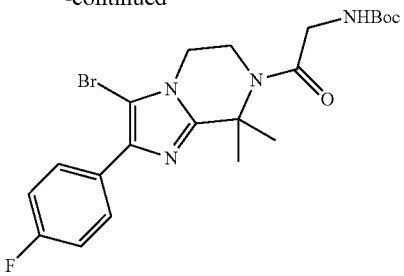

To a stirred solution of Compound 35-6 (3.02 g, 7.51 mmol) in 30 mL of DCM was added Br$_2$ (0.43 mL, 8.26 mmol) in 3 mL of acetic acid. The reaction mixture was stirred at room temperature for 30 mins. HPLC/MS test showed that desired product (II) was the only peak. Solvent was removed via rotavap at a temperature no higher than 20° C. After neutralization, 3.76 g white solid was obtained. The product was confirmed by 400 MHz proton NMR to be the title compound. The product was used in the next step without further purifications.

Reference Compound 36 was prepared by a similar way that Reference Compound 35 was made except that N-Cbz-glycine was used in step (f). Reference Compound 37 was prepared by a three component Ugi reaction among 2-aminopyrazine, 4-fluorobenzaldehyde, and 2-isocyano-2-methylpropane followed by a HATU mediated amidation reaction with 2-(benzyloxycarbonylamino)-2-methylpropanoic acid and a HCl mediated deprotection. Reference Compound 38 was prepared in the same way that Reference Compound 19, by a three component Ugi reaction among 2-aminopyrazine, 4-fluoro-3-methylbenzaldehyde, and 2-isocyano-2-methylpropane followed by a TFA mediated deprotection. Similarly, Reference Compound 39 was prepared from Reference Compound 19 by a three component Ugi reaction among 2-aminopyrazine, 3-chloro-4-fluorobenzaldehyde, and 2-isocyano-2-methylpropane followed by a TFA mediated deprotection. Reference Compound 40 was prepared by the same way that Reference Compound 19 was prepared: a three component Ugi reaction among 2-aminopyrazine, 4-chloro-3-fluorobenzaldehyde, and 2-isocyano-2-methylpropane followed by a TFA mediated deprotection.

Reference Compound 41

2-(4-fluorophenyl)-6,6,7-trimethyl-5,6,7,8-tetrahydro imidazo[1,2-a]pyrazine

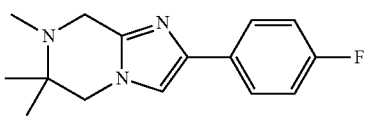 [SMILES: CN1Cc2nc(-c3ccc(F)cc3)cn2CC1(C)C]

Reference Compound 41 was prepared from Compound 42-2 by the following way:

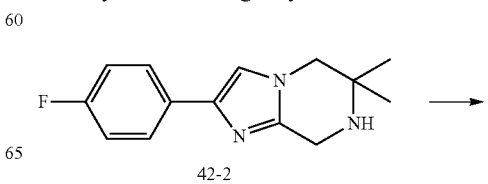

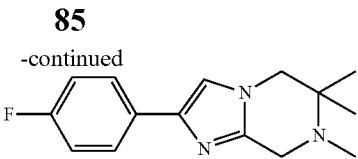

To a stirred solution of Compound 42-2 (500 mg, 2.04 mmol, 1.00 equiv) in CH₃CN (10 mL) was added formalin (5 mL). The reaction mixture was stirred at RT for 20 min, which were followed by addition of NaBH₃CN (400 mg, 6.35 mmol, 3.00 equiv) and acetic acid (1 mL, 1.00 equiv). The reaction mixture was allowed to stir for an additional 1 h at room temperature. Sodium hydroxide ON aqueous) was added to neutralize the mixture. The solution was extracted with ethyl acetate (3×10 ml) and the combined organic layer was washed with brine (3×10 mL), dried over anhydrous sodium sulfate. The mixture was concentrated under vacuum. The residue was applied onto a silica gel column with dichloromethane/methanol (40:1). This resulted in the title compound as a light-yellow solid.

Reference Compound 42 tert-butyl 2-(3-bromo-2-(4-fluorophenyl)-6,6-dimethyl-5,6-dihydroimidazo[1,2-a]pyrazin-7(8H)-yl)-2-oxoethylcarbamate

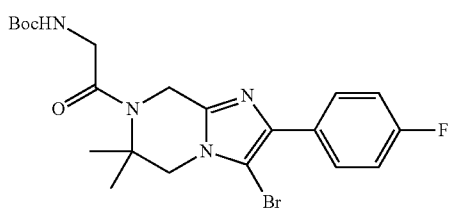 [SMILES: CC(C)(C)OC(=O)NCC(=O)N1Cc2nc(-c3ccc(F)cc3)c(Br)n2CC1(C)C]

Reference Compound 42 was prepared from Compound 51-2 by the following way:

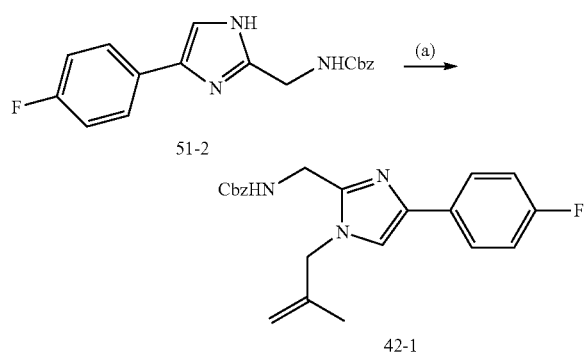

To a stirred solution of Compound 51-2 (1.1 g, 3.38 mmol, 1.00 equiv) in DMF (30 mL) was added 3-chloro-2-methylprop-1-ene (500 mg, 5.49 mmol, 1.50 equiv), potassium carbonate (560 mg, 4.06 mmol, 1.10 equiv) and KI (1.12 g, 6.75 mmol, 2.00 equiv) at room temperature. The reaction mixture was stirred for 48 h at 40° C. The reaction mixture was diluted with 100 ml of ethyl acetate. The mixture was washed with brine (3×10 mL), dried over sodium sulfate, concentrated under vacuum. The residue was applied onto a silica gel column with Petroleum Ether/EtOAc (5:1) to give Compound 42-1 as a light yellow solid.

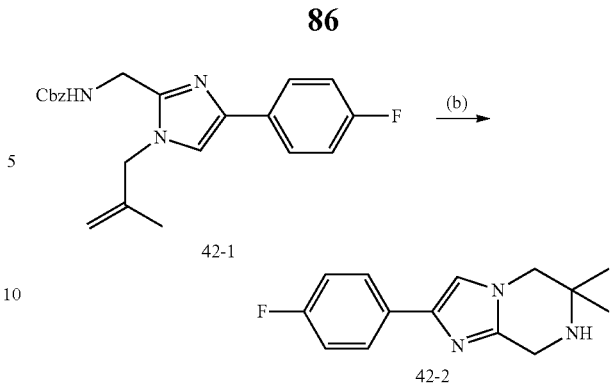

Into a 30-mL sealed tube, was placed Compound 42-1 (2.0 g, 5.28 mmol, 1.00 equiv), AcOH (12 mL), MsOH (2 mL). The reaction mixture was stirred for 12 h at 260° C. (the temperature of the sand bath). The reaction mixture was cooled to room temperature. The mixture was poured into 20 ml of water. The aqueous layer was washed with ethyl acetate (3×10 mL). Aqueous sodium hydroxide (1N) was added to adjust pH to 8. The aqueous layer was extracted with ethyl acetate (3×10 mL). The combined organic layers were washed with brine (3×10 ml), dried over sodium sulfate, concentrated under vacuum. The solid was collected by filtration and washed with 5 mL of n-hexane to give Compound 42-2 as a white solid.

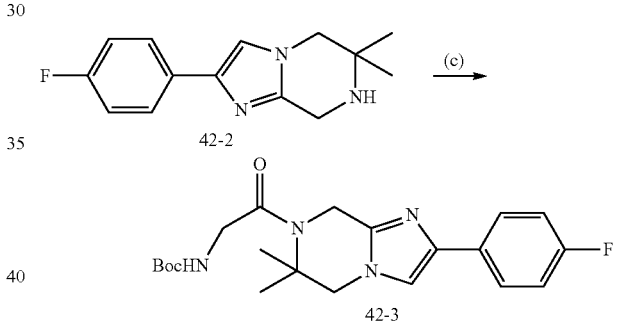

To a stirred solution of Compound 42-2 (280 mg, 1.14 mmol, 1.00 equiv) in DMF (10 mL) was added 2-(tert-butoxycarbonyl)acetic acid (600 mg, 3.43 mmol, 3.00 equiv), HATU (1.3 g, 3.42 mmol, 3.00 equiv) and DIEA (880 mg, 6.82 mmol, 6.00 equiv) at room temperature. The reaction mixture was stirred overnight at room temperature. The reaction mixture was diluted with 100 ml of ethyl acetate. The organic layer was washed with brine (3×10 mL), dried over sodium sulfate, concentrated under vacuum. The residue was applied onto a silica gel column with DCM/MeOH (10:1) to give Compound 42-3 as a brown solid: ¹H NMR: (300 MHz, CDCl₃) δ 7.72-7.68 (m, 2H), 7.23 (s, 1H), 7.13-7.07 (m, 2H), 5.46 (s, 1H), 4.65 (s, 2H), 4.05-4.04 (m, 2H), 3.97 (s, 2H), 1.55-1.39 (m, 15H).

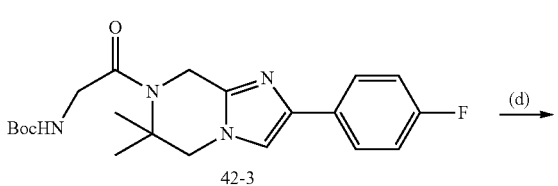

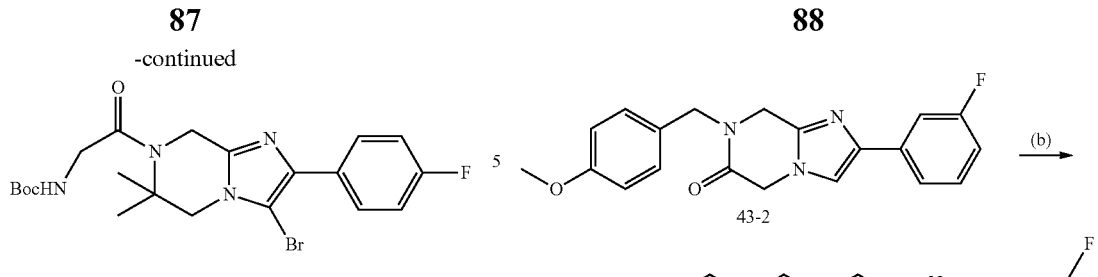

To a stirred solution of Compound 42-3 (386 g, 0.96 mmol) in 6 mL of DCM was added $Br_2$ (55 μL, 1.06 mmol) in 2 mL of acetic acid. The reaction mixture was stirred at room temperature for 30 mins. Solvent was removed via rotavap at a temperature no higher than 20° C. After neutralization, the residue was subjected to flash chromatography (40 g, 0-100% ethyl acetate in hexane, 50 mins, dry loading) purification to give the title compound as a colorless oil.

Reference Compound 43

3-bromo-2-(3-fluorophenyl)-7-(4-methoxybenzyl)-5,5-dimethyl-5,6,7,8-tetra hydroimidazo[1,2-a]pyrazine

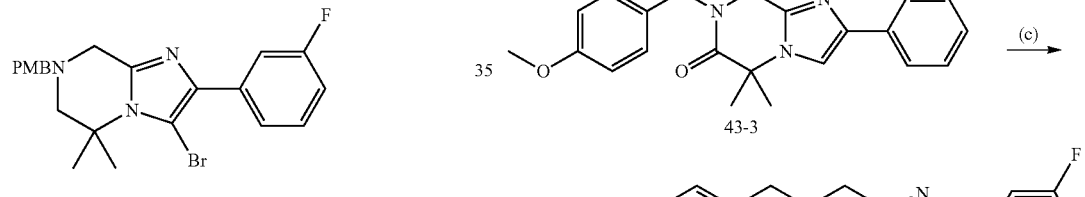

Reference Compound 43 was prepared from Compound 51-2 by the following way:

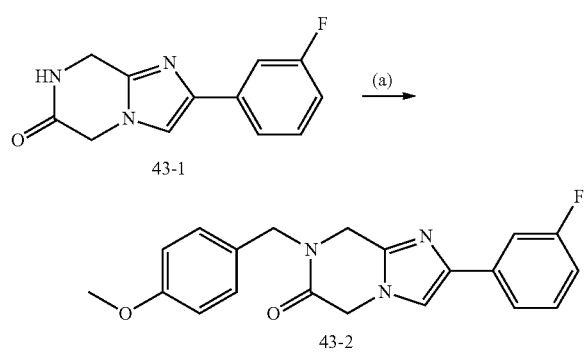

To a solution of Compound 43-1 (231 mg, 1.0 mmol) in 10 mL of DMF were added KOH (168 mg, 3.0 mmol), and PMBCl (405 μL, 3.0 mmol) at 0° C. The reaction mixture was stirred at the same temperature for 2 hours and at room temperature for 2 additional hours. The reaction mixture was directly taken to LC/MS purification to give Compound 43-2 as white solid after neutralization.

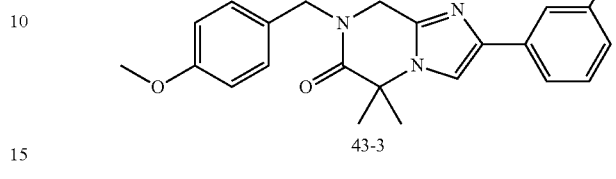

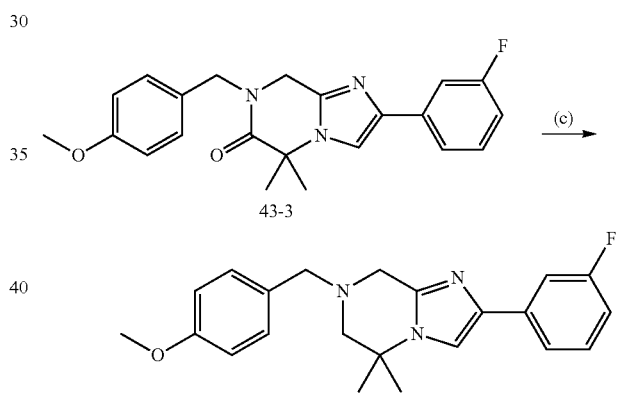

To a solution of Compound 43-2 (253 mg, 0.72 mmol) in 15 mL of DMF were added 60% NaH (87 mg, 0.085 mmol), and MeI (0.45 mL, 7.2 mmol) at room temperature. The reaction mixture was stirred at room temperature for 2 hours. The reaction mixture was quenched with methanol and directly subjected to mass-triggered HPLC purification to give mg of Compound 43-3 as a white solid after neutralization: $^1$H-NMR: (400 MHz, $CDCl_3$) δ 7.47-7.49 (m, 1H), 7.41-7.45 (m, 1H), 7.28-7.32 (m, 1H), 7.22 (d, J=8.8 Hz, 2H), 6.88-6.93 (m, 1H), 6.86 (d, J=8.8 Hz, 2H), 4.67 (s, 2H), 4.51 (s, 2H), 3.77 (s, 3H), 1.75 (s, 6H).

To a solution of Compound 43-3 (170 mg, 0.45 mmol) in 9 mL of THF was added 1.0 N $BH_3$.THF (2.70 mL, 2.70 mmol) at room temperature. The reaction mixture was stirred at reflux for 2 hours. Pd/C was added (gas generated). The reaction mixture was stirred for 1 hour. Solid was filtered off and solvent was removed. The crude Compound 43-4 was directly tested with 400 MHz proton NMR to prove that the product was the right one. The product was assumed to be of 100% yield and used in the next step without further purifications.

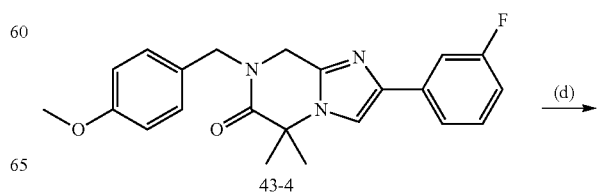

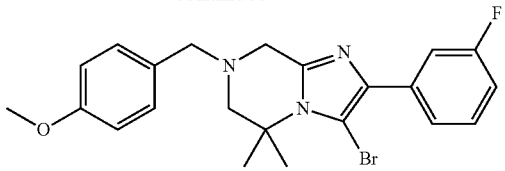

To a stirred solution of Compound 43-4 (164 g, 0.45 mmol) in 6 mL of DCM was added Br$_2$ (26 µL, 0.50 mmol) in 2 mL of acetic acid. The reaction mixture was stirred at room temperature for 30 mins. Solvent was removed via rotavap at a temperature no higher than 20° C. After neutralization, the residue was subjected to ISCO (24 g, 0-100% ethyl acetate in hexane, 25 mins, dry loading) purification to give the title compound as white solid.

Reference Compound 44 tert-butyl 1-(3-bromo-2-(4-fluorophenyl)-8,8-dimethyl-5,6-dihydro imidazo[1,2-a]pyrazin-7(8H)-yl)-2-methyl-1-oxopropan-2-ylcarbamate

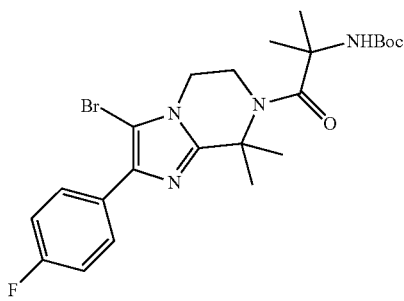 [SMILES: CC(C)(C)OC(=O)NC(C)(C)C(=O)N1CCn2c(nc(-c3ccc(F)cc3)c2Br)C1(C)C]

Reference Compound 44 was prepared from Compound 40-5 by the following way:

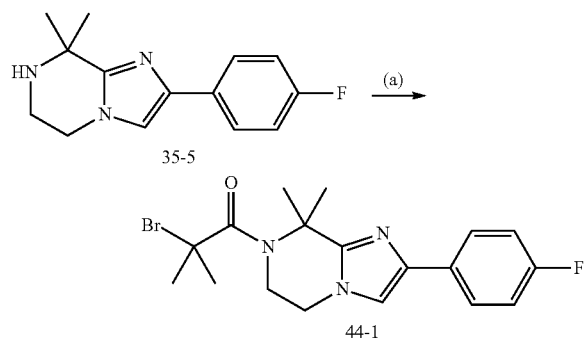

To a stirred solution of Compound 35-5 (1.48 g, 6.04 mmol) and NEt$_3$ (6.0 g, 59.4 mmol,) in DCM (20 mL) was added 2-bromo-2-methylpropanoyl bromide (14 g, 60.9 mmol) dropwise at room temperature. After being stirred for 3 h at room temperature, the reaction was then quenched by the addition of 30 mL of water. The resulting solution was extracted with 3×30 mL of ethyl acetate. The combined organic layers were washed with brine, dried over anhydrous sodium sulfate and concentrated under vacuum. This resulted in crude product as a dark solid, which was washed with EtOAc: Petroleum Ether (1:10) to remove the impurities to produce Compound 44-1 as a gray solid.

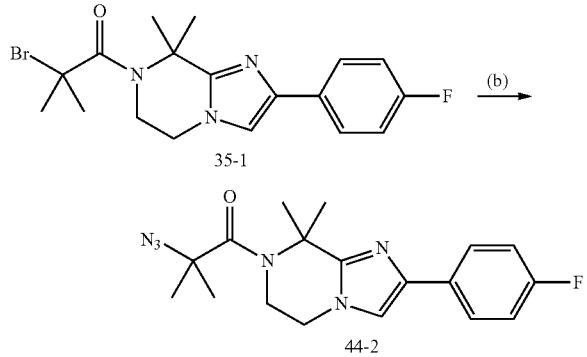

To a solution of Compound 44-1 (2.0 g, 5.08 mmol, 1.00 equiv) in DMF (10 mL) was NaN$_3$ (1.0 g, 15.38 mmol, 3.00 equiv) at r.t. The reaction mixture was stirred overnight at room temperature. The resulting solution was diluted with 300 mL of ethyl acetate. The resulting mixture was washed with 3×20 mL of brine, dried over anhydrous sodium sulfate and concentrated under vacuum. The residue was applied onto a silica gel column with Petroleum Ether/EtOAc (5:1) to give Compound 44-2 as a white solid.

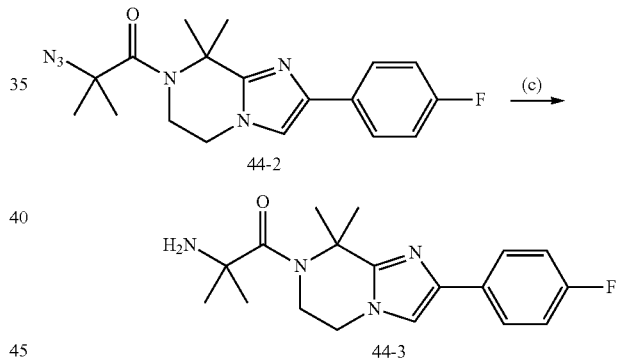

To a stirred solution of Compound 44-2 (1.2 g, 3.37 mmol, 1.00 equiv) in methanol (20 mL) was added Pd/C (80 mg, 0.75 mmol, 0.20 equiv) at room temperature. The reaction mixture was evacuated and back filled with H$_2$. The reaction mixture was stirred overnight at room temperature. The solids were filtered out. The resulting mixture was concentrated under vacuum. The solid was washed with Petroleum Ether. This resulted in Compound 44-3 as a white solid.

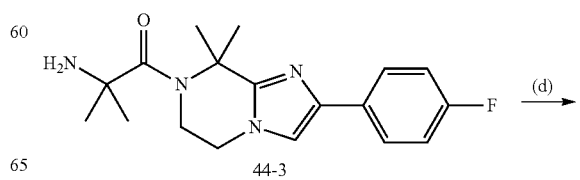

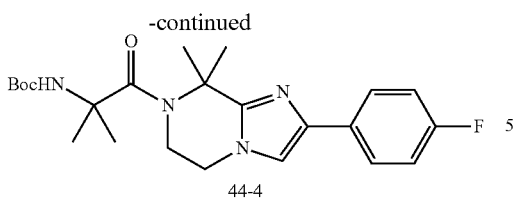

44-4

To a stirred solution of Compound 44-3 (910 mg, 2.76 mmol, 1.00 equiv) in THF (50 mL) was added BOC anhydride (3.2 g, 14.68 mmol, 5.00 equiv), followed by aqueous NaOH (1N, 6 ml, 2.00 equiv) at rt. The resulting solution was stirred for 24 h at 40° C. The resulting solution was concentrated under vacuum. The mixture was diluted with 60 ml of EtOAc. The organic layer was washed with 3×10 ml of brine, dried over $Na_2SO_4$, concentrated under vacuum. The solid was collected by filtration and washed with n-hexane (5 ml) to give Compound 44-4 as a white solid: $^1$H-NMR: (300 MHz, $CDCl_3$) δ 7.75-7.71 (m, 2H), 7.09-7.02 (m, 3H), 4.84 (s, 1H), 4.09-4.0 (m, 4H), 1.98 (s, 6H), 1.55 (s, 6H), 1.45 (s, 9H).

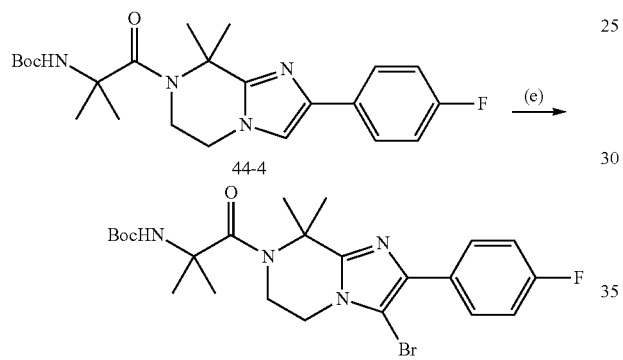

To a stirred solution of Compound 44-4 (32 mg, 0.074 mmol) in 3 mL of DCM was added $Br_2$ (4.2 µL, 0.082 mmol) in 1 mL of acetic acid. The reaction mixture was stirred at room temperature for 30 mins. Solvent was removed via rotavap at a temperature no higher than 20° C. After neutralization, the residue was subjected to flash chromatography (4 g, 0-60% ethyl acetate in hexane, 16 mins) purification to give the title compound as colorless oil.

Reference Compound 45

2-(3-fluorophenyl)-5,5-dimethyl-N-p-tolyl-5,6,7,8-tetrahydroimidazo[1,2-a]pyrazin-3-amine

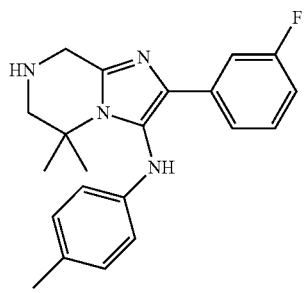

Reference Compound 45 was prepared from Reference Compound 43 in the following way: To a solution of Reference Compound 43 (116 mg, 0.26 mmol) in 8 mL of dioxane were added 4-methylaniline (84 mg, 0.78 mmol), $Pd_2(dba)_3$ (24 mg, 0.026 mmol), XantPhos (30 mg, 0.052 mmol) and $Cs_2CO_3$ (169 mg, 0.52 mmol) at room temperature. The reaction mixture was degassed and stirred at 150° C. under $N_2$ for 6 hours. Solid was filtered off and solvent was removed. The residue was subjected to mass-triggered HPLC purification to give 116 mg yellow solid as TFA salt. A solution of the adduct (108 mg, 0.23 mmol) in 2 mL of TFA was stirred at 70° C. for 90 mins in a microwave oven. HPLC test showed that the starting material was gone and the desired product was the major peak. TFA was removed and the residue was directly subjected to flash chromatography purification (12 g, 0-10% methanol in DCM with $NH_3$ modification, 30 mins) to give the title compound as clear oil.

Reference Compound 46 was prepared from Compound 43-4 by a TFA mediated deprotection followed by alkylation. Reference Compound 47 was prepared in the same way that Compound 48-3 was made followed by bromination (except that Reference Compound 51 was used in step (a)).

Reference Compound 48

2-(4-fluorophenyl)-5,5,7-trimethyl-7,8-dihydroimidazo[1,2-a]pyrazine-6(5H)-one

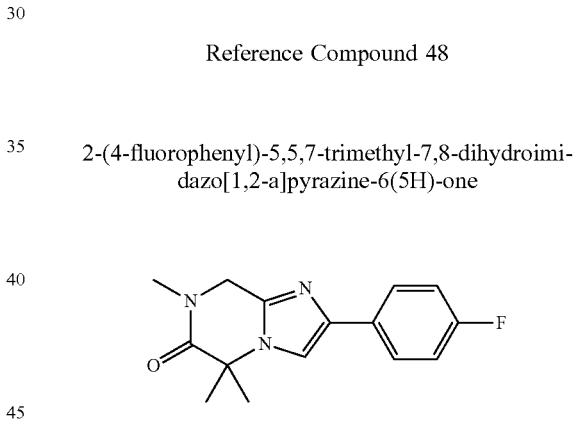

Reference Compound 48 was prepared from Reference Compound 51 by the following way: To a solution of Reference Compound 51 (694 mg, 3.0 mmol) in 20 mL of DMF were added 60% NaH (600 mg, 15 mmol), and MeI (1.87 mL, 30 mmol) at 0° C. The reaction mixture was stirred at the same temperature for 2 hours and at room temperature for 2 additional hours. The reaction mixture was diluted with ethyl acetate and washed with water. The organic solution was dried and concentrated to give the methylated product white solid after flash chromatography purification: $^1$H NMR: (400 MHz, $CDCl_3$) δ 7.65-7.69 (m, 2H), 7.14 (s, 1H) 7.03 (t, J=8.8 Hz, 2H), 4.62 (s, 2H), 3.11 (s, 3H), 1.70 (m, 6H).

To a stirred solution of (I) (216 mg, 0.79 mmol) in 6 mL of DCM was added $Br_2$ (45 µL, 0.87 mmol) in 2 mL of acetic acid. The reaction mixture was stirred at room temperature for 30 mins. Solvent was removed via rotavap at a temperature no higher than 20° C. After neutralization, the residue was used in the next step without further purifications.

Reference Compound 49 tert-butyl 2-(3-bromo-2-(3-fluorophenyl)-5,5-dimethyl-5,6-dihydro imidazo[1,2-a]pyrazin-7(8H)-yl)-2-oxoethylcarbamate

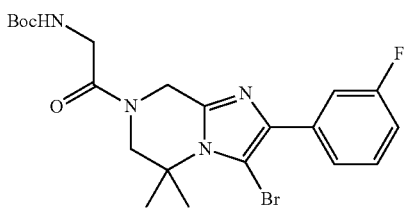

Reference Compound 49 was prepared from Compound 43-4 by the following way:

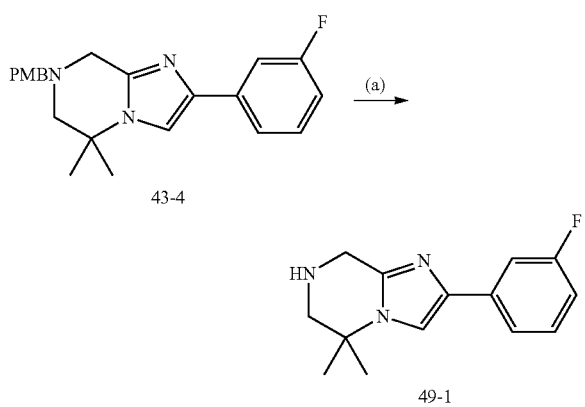

A solution of (I) (365 mg, 1.0 mmol) in 10 mL of TFA was stirred at 70° C. for 20 mins HPLC test showed that the starting material was remaining and small amount desired product was detected. The reaction mixture was stirred at 75° C. for 30 mins in a microwave oven. TFA was removed and the residue neutralized to give about 252 mg of Compound 49-1 (100%) as yellow oil.

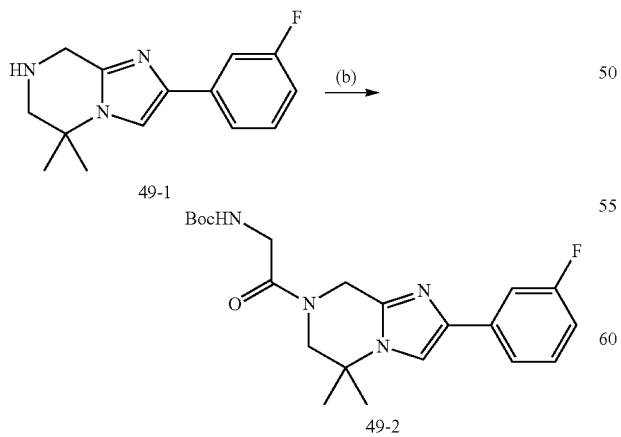

To a stirred solution of Compound 49-1 (245 mg, 1.0 mmol) and N-Boc-glycine (350 mg, 2.0 mmol) in 10 mL of DMF were added HATU (760 mg, 2.0 mmol) and DIEA (0.52 mL, 3.0 mmol). The reaction mixture was stirred at room temperature for 3 hours The reaction mixture diluted with ethyl acetate and washed with water. The organic solution was dried and concentrated. The residue was subjected to flash chromatography purification (24 g, 0-100% ethyl acetate in hexane, 36 mins) to give Compound 49-2 as clear oil.

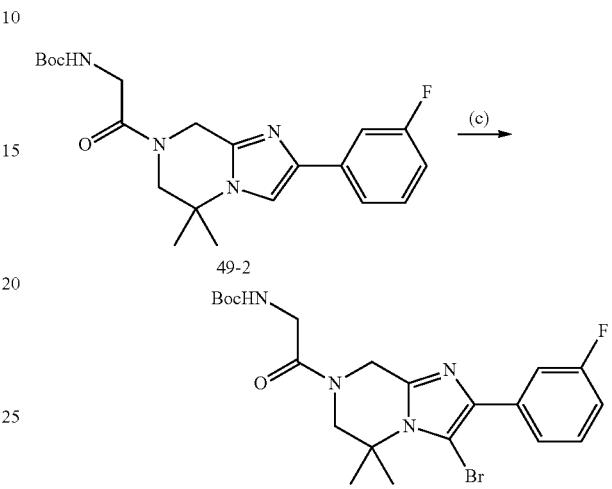

To a stirred solution of Compound 49-2 (312 mg, 0.78 mmol) in 6 mL of DCM was added $Br_2$ (57 μL, 1.1 mmol) in 2 mL of acetic acid. The reaction mixture was stirred at room temperature for 30 mins. Solvent was removed via rotavap at a temperature no higher than 20° C. After neutralization, the residue was subjected to flash chromatography (25 g, 0-100% ethyl acetate in hexane, 32 mins, dry loading) purification to give the title compound as colorless oil.

Reference Compound 50

3-bromo-2-(4-fluorophenyl)-7,8,8-trimethyl-5,6,7,8-tetrahydro imidazo[1,2-a]pyrazine

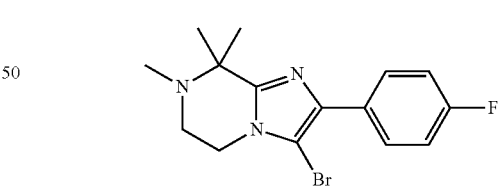

Reference Compound 50 was prepared from Compound 35-5 by the following way:

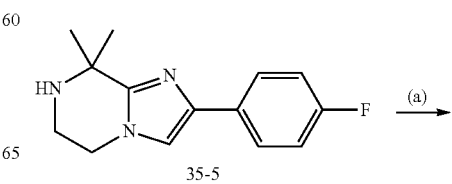

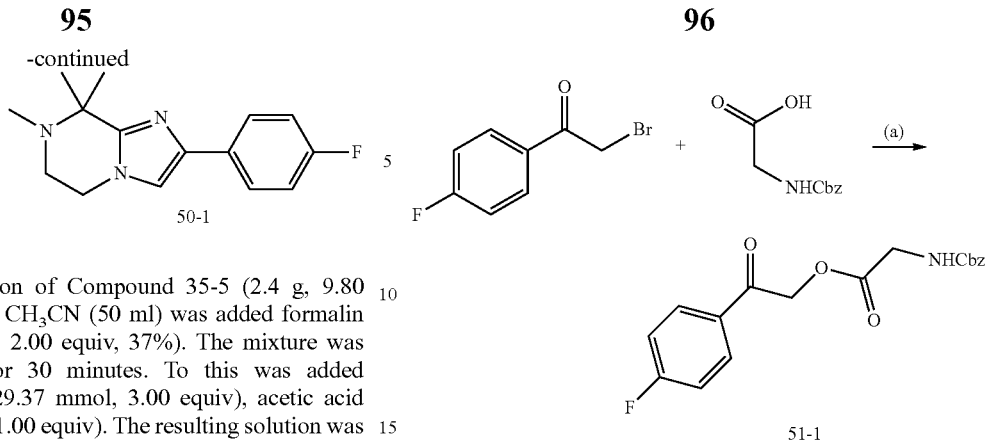

To a stirred solution of Compound 35-5 (2.4 g, 9.80 mmol, 1.00 equiv) in CH₃CN (50 ml) was added formalin (1.71 g, 21.09 mmol, 2.00 equiv, 37%). The mixture was stirred at 30° C. for 30 minutes. To this was added NaCNBH₃ (1.85 g, 29.37 mmol, 3.00 equiv), acetic acid (590 mg, 9.83 mmol, 1.00 equiv). The resulting solution was stirred for 2 h at room temperature. The resulting mixture was concentrated under vacuum. The resulting solution was diluted with 10 ml of water. The pH value of the solution was adjusted to 8-9 with sodium carbonate (saturated). The resulting solution was extracted with DCM (3×100 ml) and the combined organic layer was dried over anhydrous sodium sulfate, concentrated. The residue was applied onto a silica gel column with ethyl acetate/petroleum ether (1:7) to give Compound 50-1 as a white solid: $^1$H NMR: (300 MHz, CDCl₃) δ 7.69-7.75 (m, 2H), 7.02-7.09 (t, J=9 Hz, 2H), 6.97 (s, 1H), 4.01-4.06 (t, J=5.4 Hz, 2H), 3.02-3.07 (t, J=5.4 Hz, 2H), 2.49 (s, 3H), 1.52-1.57 (m, 6H).

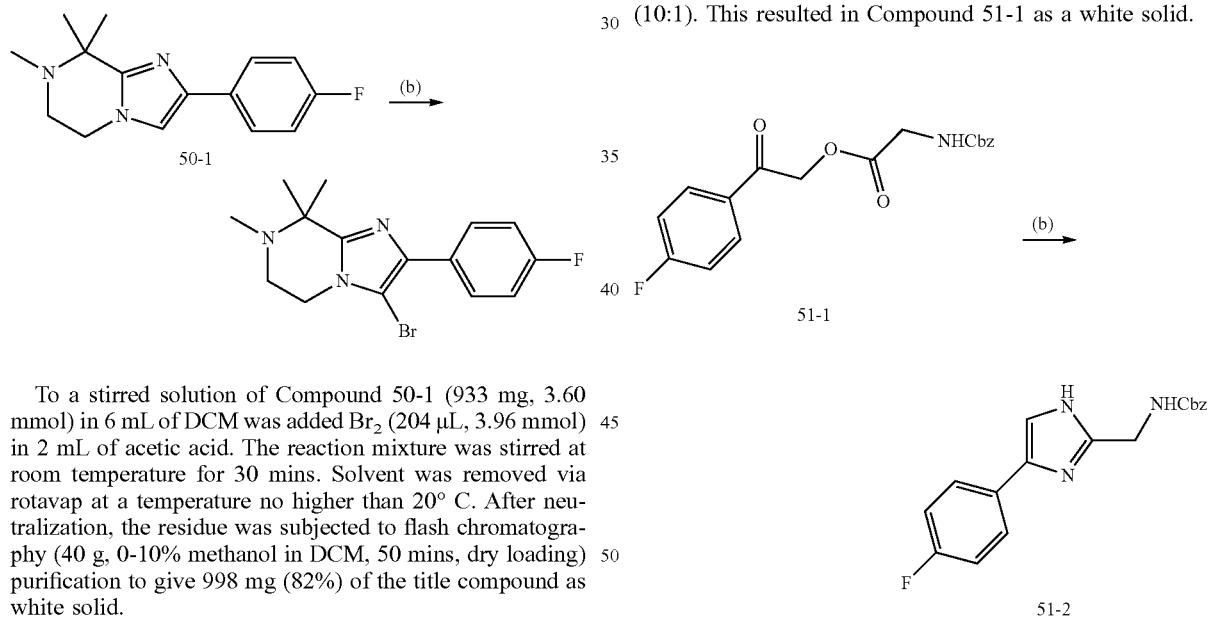

To a stirred solution of Compound 50-1 (933 mg, 3.60 mmol) in 6 mL of DCM was added Br₂ (204 μL, 3.96 mmol) in 2 mL of acetic acid. The reaction mixture was stirred at room temperature for 30 mins. Solvent was removed via rotavap at a temperature no higher than 20° C. After neutralization, the residue was subjected to flash chromatography (40 g, 0-10% methanol in DCM, 50 mins, dry loading) purification to give 998 mg (82%) of the title compound as white solid.

Reference Compound 51

2-(4-fluorophenyl)-7,8-dihydroimidazo[1,2-a]pyrazin-6(5H)-one

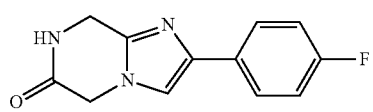 [SMILES: O=C1Cn2cc(-c3ccc(F)cc3)nc2CN1]

Reference Compound 51 was prepared by the following way:

To a stirred solution of 2-bromo-1-(4-fluorophenyl)ethanone (3.0 g, 13.82 mmol) in DMF (30 mL) was added 2-(tert-butoxycarbonyl)acetic acid (2.5 g, 14.29 mmol) and Cs₂CO₃ (5.0 g, 15.34 mmol). The resulting solution was allowed to stir overnight at 30° C. The resulting solution was poured into 40 ml of water. The aqueous layer was extracted with ethyl acetate (3×20 mL) and the combined organic layer was washed with brine (3×20 mL), dried over anhydrous sodium sulfate and concentrated under vacuum. The solid was washed with a mixture of n-hexane/ethyl acetate (10:1). This resulted in Compound 51-1 as a white solid.

To a stirred solution of Compound 51-1 (25.95 g, 75.14 mmol) in toluene (200 mL), was added NH₄OAc (110 g, 20.00 equiv). The resulting solution was heated to reflux for 4 h. The mixture was cooled to room temperature and concentrated under vacuum. The residue was diluted with 800 mL of ethyl acetate. The resulting mixture was washed with brine (3×30 mL), dried over anhydrous sodium sulfate and concentrated under vacuum. The residue was washed with 10 mL of Petroleum Ether/EtOAc (20:1) to give Compound 51-2 as a white solid.

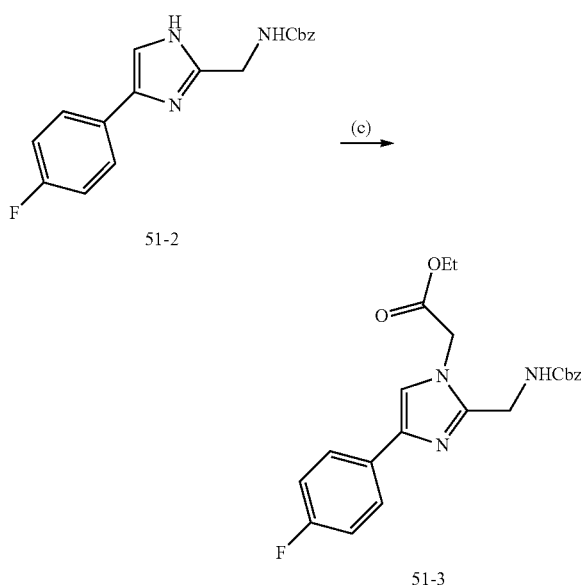

To a stirred solution of Compound 51-2 (2.58 g, 8.87 mmol) in DMF (30 mL) was added ethyl 2-bromoacetate (4.4 g, 26.35 mmol, 3.00 equiv) and Cs₂CO₃ (8.7 g, 26.69 mmol, 3.00 equiv). The resulting solution was stirred overnight at 30° C. The resulting solution was diluted with 30 mL of ethyl acetate and the combined organic layer was washed with brine (3×20 mL), dried over anhydrous sodium sulfate and concentrated under vacuum. The residue was applied onto a silica gel column with ethyl acetate/petroleum ether (1:10). This resulted in Compound 51-3 as a light white solid.

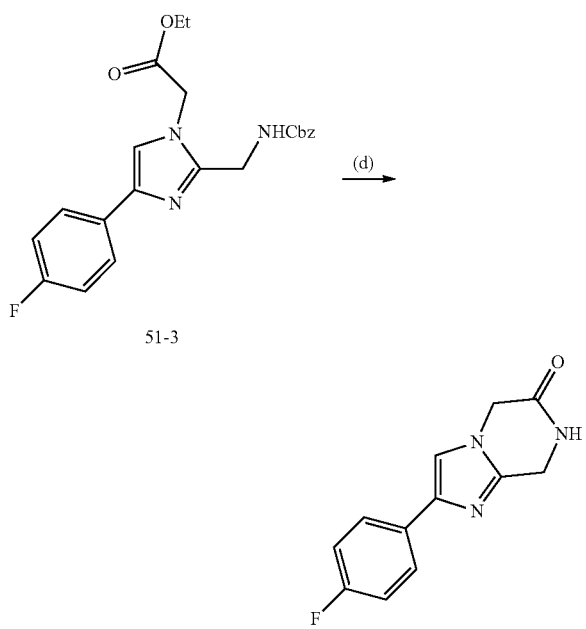

To a stirred solution of Compound 51-3 (8 g, 19.46 mmol) in methanol (200 mL), was added Pd/C (0.8 g). The resulting solution was degassed and back filled with hydrogen. The mixture was stirred overnight at room temperature. The solids were filtered out. The resulting mixture was concentrated under vacuum. The resulting crude solid was washed with 100 mL of Petroleum Ether/EtOAc (1:10). This resulted in the title compound as a white solid.

Reference Compound 52 was prepared from Reference Compound 51 by nitrating with fuming nitric acid in TFA. Reference Compound 53 was prepared in the same way that Reference Compound 19 was prepared: a three component Ugi reaction among 2-aminopyrazine, isonicotinaldehyde, and 2-isocyano-2-methylpropane followed by a TFA mediated deprotection. The free amine was subjected to Pd₂(dba)₃ mediated amination reaction with 1-bromo-4-methylbenzene followed by a PtO₂ mediated hydrogenation. Reference Compound 54 was prepared from 2-aminopyrazine, 2-methoxybenzaldehyde, 1-isocyano-4-methylbenzene by the same three component Ugi reaction to prepare Reference Compound 1, and then followed by a PtO₂ mediated hydrogenation.

Reference Compound 55

3-bromo-2-(4-fluorophenyl)-8,8-dimethyl-7,8-dihydroimidazo[1,2-a]pyrazin-6(5H)-one

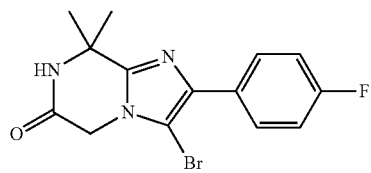 [SMILES: CC1(C)NC(=O)Cn2c1nc(-c1ccc(F)cc1)c2Br]

Reference Compound 55 was prepared from Compound 35-4 in the following way: To a stirred solution of Compound 35-4 (390 mg, 1.51 mmol, 1.00 equiv) in DCM (20 mL) was added NBS (0.28 g, 1.00 equiv). The resulting solution was stirred for 2 hours at room temperature. The solid was filtered out and the mixture was washed with a saturated solution of Na₂S₂O₃, dried over Na₂SO₄. The mixture was concentrated under vacuum. The solids was purified by silica gel chromatography (Petroleum Ether/EtOAc=1:2) to result in the title compound as a white solid. Reference Compound 56 was prepared from Compound 35-5 by reacting with Boc-OSu in THF at 50° C. Reference Compound 57 was prepared from Compound 35-4 by alkylation using NaH/MeI. Reference Compound 58 was prepared by the same way that Compound 35-4 except that (R)-2-(benzyloxycarbonyl)-3-methylbutanoic acid was used in step (a). Reference Compound 59 was prepared in the same way that compound 35-4 except that 2-bromo-1-(3,4-difluorophenyl)ethanone was used in step (a). Reference Compound 60 was prepared by the same way that Compound 35-4 was made except that (S)-2-(benzyloxycarbonyl)propanoic acid was used in step (a). Reference Compound 61 was prepared by the same way that Compound 35-4 was made except that (S)-2-(benzyloxycarbonyl)3-methylbutanoic acid was used in step (a). Reference Compound 62 was prepared by the same way that Compound 35-4 was made except that (R)-2-(benzyloxycarbonyl)propanoic acid was used in step (a). Reference Compound 63 was prepared from by the same method that Reference Compound 35 was prepared except that (S)-2-(benzyloxycarbonyl)-3-methylbutanoic acid was used in step (a). Reference Compound 64 was prepared from by the same method that Reference Compound 35 was prepared except that (R)-2-(benzyloxycarbonyl)-3-methylbutanoic acid was used in step (a). Reference Compound 65 was prepared from by the same method that Reference Compound 35 was prepared except that (S)-2-(benzyloxycarbonyl)-3-methylbutanoic acid was used in step (a). Reference Compound 66 was prepared from by the same method that Reference Compound 35 was prepared except that (R)-2-(benzyloxycarbonyl)-3-methylbutanoic acid was used in step (a). Reference Compound 67 was prepared in the same way that Reference Compound 55 was made except that 2-bromo-1-(3-fluorophenyl)ethanone was used in step (a). Reference Compound 68 was prepared from Reference Compound 19 by an amination reaction with 1-bromo-2,4-difluorobenzene followed by a Pd/C mediated hydrogenation. Reference Compound 69 was synthesized from Reference Compound 32 was prepared from an amination reaction with 1-bromo-3-fluoro-4-chlorobenzene followed by a PtO₂ mediated hydrogenation. Reference Compound 70 was synthesized from Reference Compound 11 was prepared from an amination reaction with 1-bromo-3-fluoro-4-chlorobenzene followed by a PtO₂ mediated hydrogenation. Reference Compound 71 was synthesized from Reference Compound 51 in a similar way as Reference Compound 49 was prepared.

Reference Compound 72

3-bromo-7-(2-(dimethylamino)ethyl)-2-(4-fluorophenyl)-8,8-dimethyl-7,8-dihydroimidazo[1,2-a]pyrazin-6(5H)-one

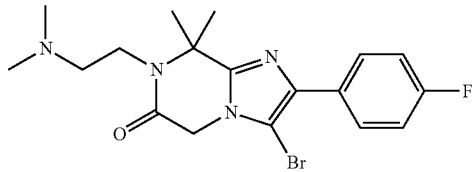 [SMILES: CN(C)CCN1C(=O)Cn2c(nc(-c3ccc(F)cc3)c2Br)C1(C)C]

Reference Compound 72 was prepared from Compound 35-4 by the following reaction:

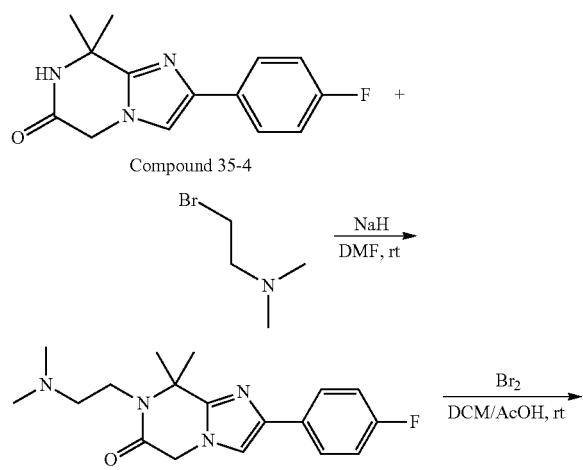

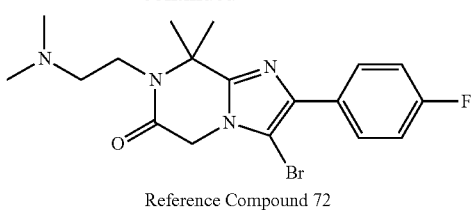

Reference Compound 72

To a solution of Compound 35-4 (259 mg, 1.0 mmol) in 5 mL of DMF were added 60% NaH (60 mg, 1.5 mmol, and 2-bromo-N,N-dimethylethanamine (228 mg, 1.5 mmol) at room temperature. The reaction mixture was stirred at room temperature for 6 hours. LC/MS test showed that Compound 35-4 was gone and the desired product ([M+1]=331 was one the major peaks.

The reaction mixture was diluted with ethyl acetate and washed with water twice. The organic solution was dried and concentrated. The obtained crude product was used in the next step without further purifications.

To a stirred solution of crude product obtained from the previous step (198 mg, 0.60 mmol) in 3 mL of DCM was added Br₂ (34 μL, 0.66 mmol) in 1 mL of acetic acid. The reaction mixture was stirred at room temperature for 30 minutes. HPLC/MS test showed that starting material gone and Reference Compound 72 was the major product.

Solvent was removed via rotavap at a temperature no higher than 20° C. The residue was subjected to a mass-triggered HPLC purification to give 110 mg of Reference Compound 72.

Reference Compound 73: 3-(4-fluoro-3-methylphenylamino)-2-(3-fluorophenyl)-8,8-dimethyl-7,8-dihydroimidazo[1,2-a]pyrazin-6 (5H)-one was synthesized from Reference Compound 67 by a Pd₂(dba)₃ mediated amination reaction with 4-fluoro-3-methylaniline. Reference Compound 74: tert-butyl 3-bromo-2-(4-fluorophenyl)-8,8-dimethyl-5,6-dihydro imidazo[1,2-a]pyrazine-7(8H)-carboxylate was prepared from Reference Compound 56 by a bromination reaction with Br₂. Reference Compound 75: 2-bromo-1-(2-(4-fluorophenyl)-3-(4-fluorophenylamino)-8,8-dimethyl-5,6-dihydroimidazo[1,2-a]pyrazin-7(8H)-yl) ethanone was prepared from Example 493 by an amidate reaction with 2-bromoacetyl bromide.

Reference Compound 76

2-(4-fluorophenyl)-6-methylimidazo[1,2-a]pyridin-3-amine

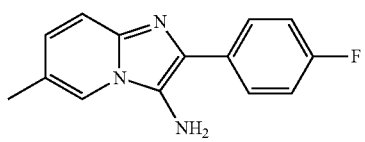

Reference Compound 76 was prepared by the following steps:

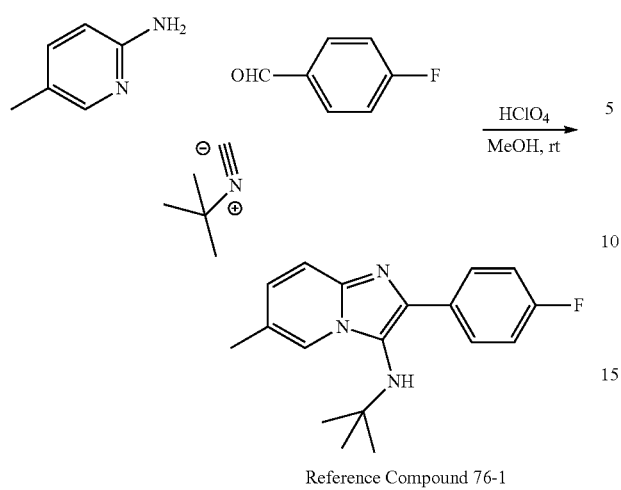

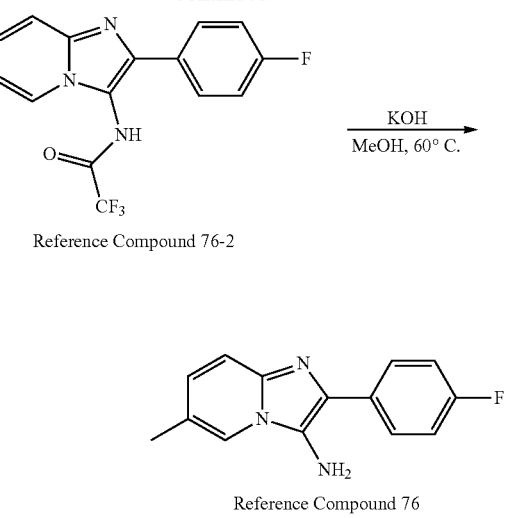

Reference Compound 76-2

Reference Compound 76

Reference Compound 76-1

To a stirred solution of 5-methylpyridin-2-amine (260 mg, 2.4 mmol) in 20 mL of MeOH was added 4-fluorobenzaldehyde (0.26 mL, 2.40 mmol), and followed by 1.0 N HClO₄ in MeOH (0.20 mL, 0.20 mmol). The reaction mixture was stirred at room temperature for 0.5 hour which was followed by addition of 2-isocyano-2-methylpropane (0.23 mL, 2.0 mmol). The stirring was continued at room temperature overnight. HPLC/MS test showed that the desired product Reference Compound 76-1 was a major peak.

The reaction mixture was subjected to direct mass-triggered HPLC purification. The obtained 62 mg of the Ugi adduct as yellow solid.

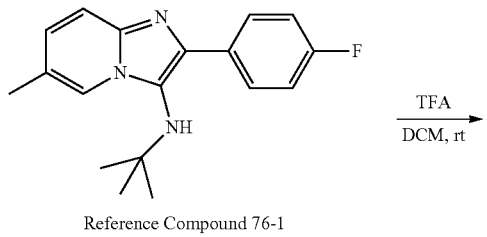

Reference Compound 76-1

To a solution of the Ugi adduct (366 mg, 1.23 mmol) in 5 mL of DCM was added 5 mL of TFA. The reaction mixture was stirred at room temperature. LC/MS test showed a major peak with [M+1]=338, which corresponded to Reference Compound 76-2. The reaction mixture was concentrated to give 431 mg yellow solid.

To a solution of Reference Compound 76-2 (101 mg, 0.30 mmol) in 3 mL of MeOH and 3 mL of water was added KOH (168 mg, 3.0 mmol). The reaction mixture was stirred at 60° C. for 3 hours. LC/MS test showed a major peak with [M+1]=242, which corresponded to the desired product of Reference Compound 76. The reaction mixture was concentrated and the residue was dissolved in DCM. The organic solution is washed with NaHCO₃, dried and concentrated. The product was used without further purifications.

Reference Compound 77: 2-(4-fluorophenyl)imidazo[1,2-a]pyridin-3-amine was prepared by the same steps as Reference Compound 76.

| Compound | Structure | Physical Data MS (m/z) and/or ¹H NMR |
|---|---|---|
| Ref. comp. 71 | 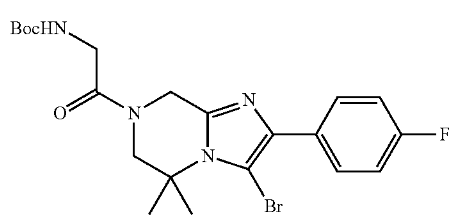 [SMILES: CC(C)(C)OC(=O)NCC(=O)N1Cc2nc(-c3ccc(F)cc3)c(Br)n2C(C)(C)C1] | [M + 1] = 481<br>¹H NMR (400 MHz, CDCl₃): δ 7.77 (d, J = 7.2 Hz, 2H), 7.05 (d, J = 8.8 Hz, 2H), 4.67-4.82 (m, 2H), 4.05 (s, 2H), 3.55-3.78 (m, 2H), 1.71 (s, 3H), 1.67 (s, 3H), 1.41 (s, 9H) |
| Ref. comp. 72 | 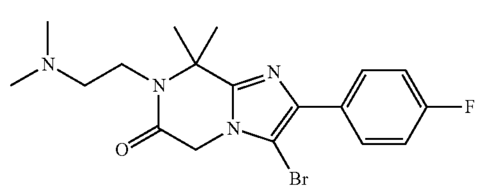 [SMILES: CN(C)CCN1C(=O)Cn2c(nc(-c3ccc(F)cc3)c2Br)C1(C)C] | [M + 1] = 409<br>¹H NMR (400 MHz, CD₃OD): δ 7.61-7.65 (m, 2H), 7.31 (d, J = 8.4 Hz, 2H), 7.23-7.26 (m, 2H), 7.08 (d, J = 8.4 Hz, 2H), 4.26 (s, 2H), 4.15 (s, 2H), 4.11 (s, 2H), 3.88 (s, 2H), 2.08 (s, 6H) |

-continued

| Compound | Structure | Physical Data MS (m/z) and/or ¹H NMR |
|---|---|---|
| Ref. comp. 73 | 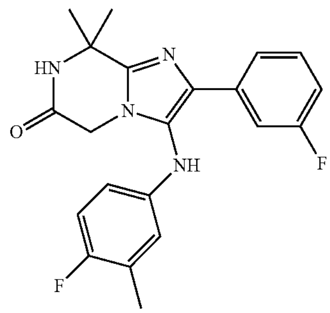 [SMILES: Cc1cc(Nc2c(-c3cccc(F)c3)nc3n2CC(=O)NC3(C)C)ccc1F] | [M + 1] = 383 |
| Ref. comp. 74 | 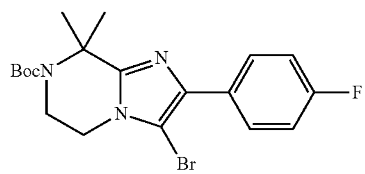 [SMILES: CC(C)(C)OC(=O)N1CCn2c(nc(-c3ccc(F)cc3)c2Br)C1(C)C] | [M + 1] = 424<br>¹H NMR (400 MHz, CDCl₃):<br>δ 7.87-7.90 (m, 2H), 7.08 (t,<br>J = 8.8 Hz, 2H), 3.88-3.94 (m,<br>4H), 1.85 (s, 6H), 1.53 (s, 9H) |
| Ref. comp. 75 | 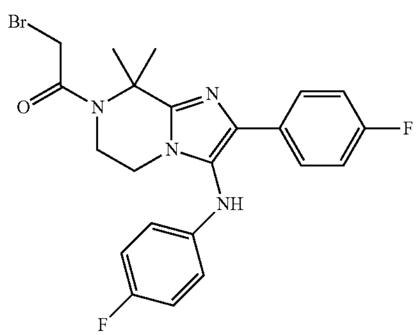 [SMILES: CC1(C)c2nc(-c3ccc(F)cc3)c(Nc3ccc(F)cc3)n2CCN1C(=O)CBr] | [M + 1] = 475 |
| Ref. comp. 76 | 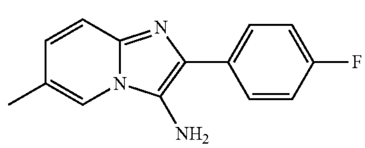 [SMILES: Cc1ccc2nc(-c3ccc(F)cc3)c(N)n2c1] | [M + 1] = 242 |
| Ref. comp. 77 | 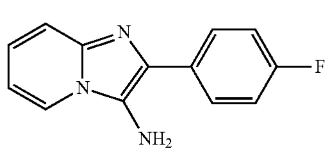 [SMILES: Nc1c(-c2ccc(F)cc2)nc2ccccn12] | [M + 1] = 228<br>¹H NMR (400 MHz, CDCl₃):<br>δ 7.94-7.80 (m, 3H), 7.52 (dt,<br>J = 1.2, 9.2 Hz, 1H), 7.10-7.15<br>(m, 3H), 6.81 (dt, J = 1.2, 6.8<br>Hz, 1H), 3.33 (br, 2H) |

Example 1

2-amino-1-(3-(benzo[d][1,3]dioxol-5-ylamino)-2-phenyl-5,6-dihydroimidazo[1,2-a]pyrazin-7(8H)-yl)ethanone

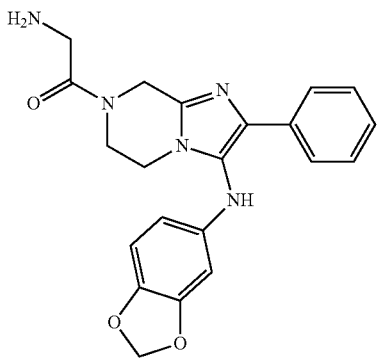 [SMILES: NCC(=O)N1CCn2c(nc(-c3ccccc3)c2Nc2ccc3c(c2)OCO3)C1]

Example 1 was prepared in the following way: to a stirred solution of N—BOC-glycine (142 mg, 0.81 mmol) in 2 mL of DMF were added HATU (308 mg, 0.81 mmol) and DIEA (0.28 mL, 1.62 mmol). After stirring for 10 minutes, Reference Compound 1 (180 mg, 0.54 mmol) was added. The reaction mixture was stirred at room temperature for 3 hours.

Solvent was removed and the crude product was subjected to MS-triggered HPLC purification. The collected MeCN/water solution was concentrated till no more MeCN was left. The remaining aqueous solution was neutralized with NaHCO$_3$ and extracted with DCM. The organic solution was dried and concentrated. The residue was dissolved in 1:1 MeCN/water solvent, dried on a lyophilizer to give 192 mg powdery product.

A solution of the above obtained amide (265 mg, 0.54 mmol) in 10 mL of 4:1 DCM and TFA was stirred at room temperature for 2 hours. Solvent was removed and the crude product was subjected to MS-triggered HPLC purification. The collected MeCN/water solution was concentrated till no more MeCN was left. The remaining aqueous solution was neutralized with NaHCO$_3$ and extracted with DCM. The organic solution was dried and concentrated. Then was dissolved in 1:1 MeCN/water solvent, dried on lyophilizer to give powdery product.

Example 26

N,2-bis(4-fluorophenyl)imidazo[1,2-a]pyrazin-3-amine

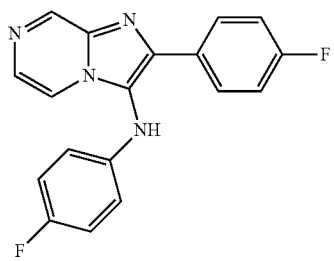 [SMILES: Fc1ccc(Nc2c(-c3ccc(F)cc3)nc3cnccn23)cc1]

Example 26 was synthesized by the following way: to a stirred solution of 2-aminopyrazine (683 mg, 7.18 mmol) in 50 mL of MeOH were added 4-fluorobenzaldehyde (1.16 mL, 10.8 mmol), 1-fluoro-4-isocyanobenzene (1.0 g, 8.25 mmol), and followed by 1.0 N HClO$_4$ in MeOH (0.72 mL, 0.72 mmol). The reaction mixture was stirred at room temperature overnight. The reaction mixture was concentrated and the residue was subjected to flash chromatography purification. The collected organic solution was concentrated to give the title compound as yellow oil.

Example 28

N,2-bis(4-fluorophenyl)-5,6,7,8-tetrahydroimidazo[1,2-a]pyrazin-3-amine

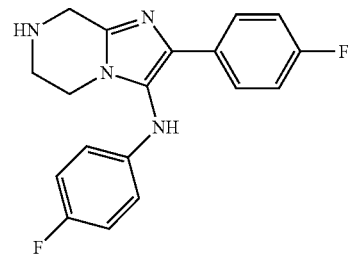

Example 28 was synthesized by the following way: to a stirred solution of Example 26 (761 mg, 2.36 mmol) in 10 mL of MeOH was added Pd/C (258 mg, 0.24 mmol). The reaction mixture was evacuated and back filled with H$_2$. The reaction mixture was stirred at room temperature overnight. The solid was filtered off and solvent was removed. The product was subjected to mass-triggered HPLC purification. The obtained MeCN/water solution was combined and concentrated to give the final product as yellow oil after neutralization.

Example 29

2-amino-1-(3-(3,4-difluorophenylamino)-2-(4-fluorophenyl)-5,6-dihydroimidazo[1,2-a]pyrazin-7(8H)-yl)-2-methylpropan-1-one

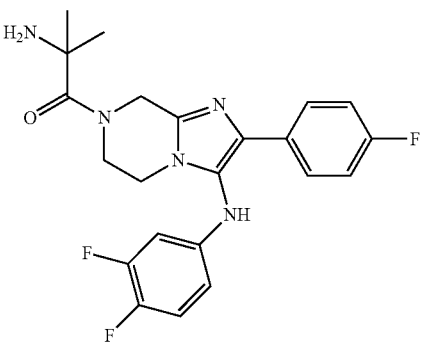 [SMILES: CC(C)(N)C(=O)N1CCn2c(nc(-c3ccc(F)cc3)c2Nc2ccc(F)c(F)c2)C1]

Example 29 was synthesized by the following way: To a stirred solution of 2-(tert-butoxycarbonylamino)-2-methylpropanoic acid (25 mg, 0.12 mmol) in 2 mL of DMF were added HATU (46 mg, 0.12 mmol) and DIEA (63 μL, 0.36 mmol). After stirring for 10 minutes, Example 331 (21 mg, 0.06 mmol) was added. The reaction mixture was stirred at room temperature for 3 hours. The reaction mixture was directly subjected to a mass-triggered HPLC purification. The collected MeCN/water solution was concentrated and neutralized. The obtained product (26 mg, 0.05 mmol) in 5 mL of 4:1 DCM and TFA was stirred at room temperature for 2 hours. The reaction mixture was concentrated and the residue was subjected to mass-trigger HPLC purification. The collected MeCN/water solution was combined and MeCN was removed.

Example 32

1-(2-(4-fluorophenyl)-3-(4-fluorophenylamino)-5,6-dihydroimidazo[1,2-a]pyrazin-7(8H)-yl)-2-(methylamino)ethanone

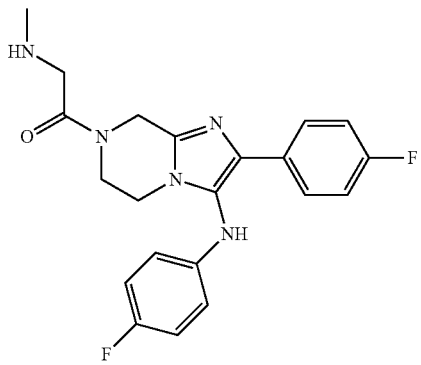 [SMILES: CNCC(=O)N1CCn2c(nc(-c3ccc(F)cc3)c2Nc2ccc(F)cc2)C1]

Example 32 was prepared from Example 28 by the following way:

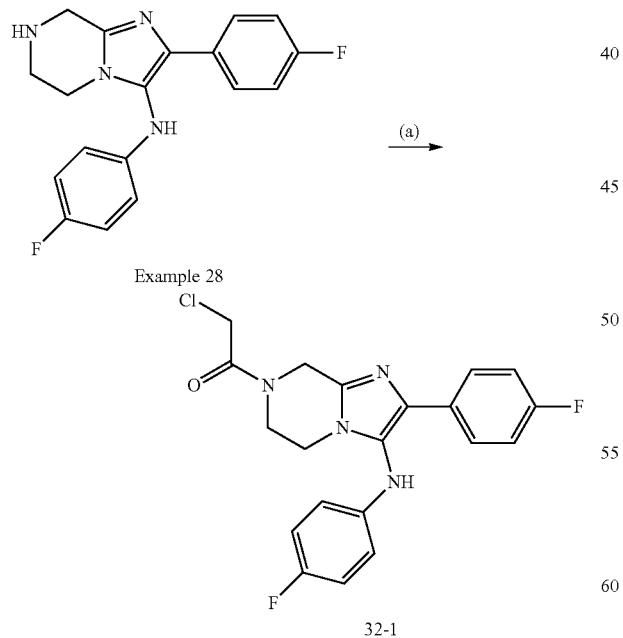

Example 28 (33 mg, 0.10 mmol) in 10 mL of DCM were added Et₃N (84 μL, 0.60 mmol) and 2-chloroacetyl chloride (24 μL, 0.30 mmol) at 0° C. The reaction mixture was stirred at the same temperature for 2 hours and at room temperature for 2 additional hours. Solvent was removed and the residue was subjected to MS-triggered HPLC purification to give 40 mg of Compound 32-1 as yellow solid (100%) after neutralization: $^1$H NMR (CDCl₃, 400 MHz) δ 7.63-7.66 (m, 2H), 6.99 (t, J=8.8 Hz, 2H), 6.90 (t, J=8.4 Hz, 2H), 6.60-6.63 (m, 2H), 4.97-5.14 (m, 2H), 4.13-4.21 (m, 2H), 4.03 (d, J=3.2 Hz, 2H), 3.91 (s, 2H).

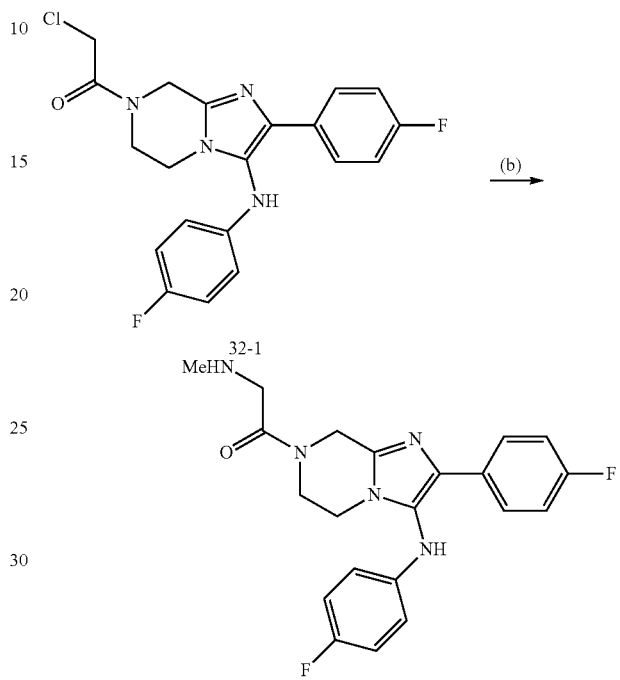

Compound 32-1 (20 mg, 0.05 mmol) in 5 mL of DMF were added K₂CO₃ (21 mg, 0.15 mmol) and 2.0 M MeNH₂ (0.30 mL, 0.60 mmol) at room temperature. The reaction mixture was stirred at the same temperature overnight. Solvent was removed and the residue was subjected to MS-triggered HPLC purification to give the title compound as yellow solid after neutralization.

Example 44

1-(2-(4-fluorophenyl)-3-(4-fluorophenylamino)-5,6-dihydroimidazo[1,2-a]pyrazin-7(8H)-yl)-2-hydroxy-ethanone

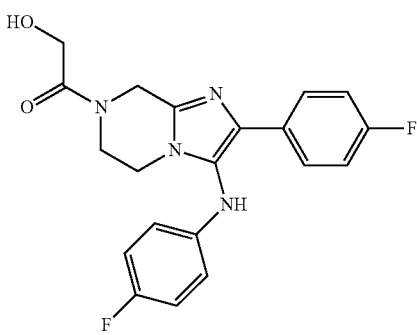 [SMILES: O=C(CO)N1CCn2c(nc(-c3ccc(F)cc3)c2Nc2ccc(F)cc2)C1]

Example 44 was synthesized by the following way: to a solution of Compound 32-1 (20 mg, 0.05 mmol) in 5 mL of DMF were added KI (8 mg, 0.05 mmol) and AcOK (15 mg, 0.15 mmol) at room temperature. The reaction mixture was stirred at the same temperature overnight. Solvent was removed and the residue was subjected to MS-triggered HPLC purification to give yellow solid. A solution of the solid (21 mg, 0.05 mmol) in 3 mL of methanol and 1 mL of water was added LiOH (6 mg, 0.25 mmol). The reaction mixture was stirred at 40° C. for 2 hours. The reaction mixture was cooled to room temperature and organic solvent was removed. The residue was taken to mass triggered HPLC separation. The collected MeCN/water solution was concentrated to give the title compound as yellowish oil.

Example 113

2-(4-fluorophenyl)-N-p-tolyl-5,6,7,8-tetrahydroimidazo[1,2-a]pyrazin-3-amine

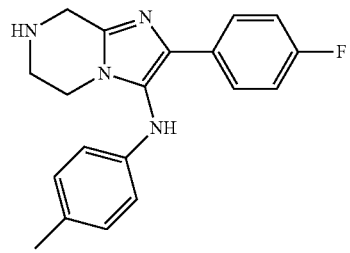 [SMILES: Cc1ccc(Nc2c(-c3ccc(F)cc3)nc3n2CCNC3)cc1]

Example 113 was prepared by the following way: to a stirred solution of the Example 136 (64 mg, 0.20 mmol) in 5 mL of MeOH was added Pd/C (21 mg, 0.02 mmol). The reaction mixture was evacuated and back filled with $H_2$. The reaction mixture was stirred at room temperature overnight. The solid was filtered off and solvent was removed. The residue was subjected to mass-triggered HPLC purification to give a yellow solid.

Example 136

2-(4-fluorophenyl)-N-p-tolylimidazo[1,2-a]pyrazin-3-amine

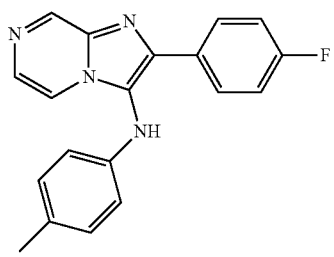 [SMILES: Cc1ccc(Nc2c(-c3ccc(F)cc3)nc3cnccn23)cc1]

Example 136 was prepared by the following way: to a solution of Reference Compound 19 (69 mg, 0.30 mmol) in 6 mL of dioxane were added 4-bromotoluene (74 µL, 0.60 mmol), $Pd_2(dba)_3$ (8 mg, 0.009 mmol), Xantphos (11 mg, 0.018 mmol) and $Cs_2CO_3$ (196 mg, 0.60 mmol) at room temperature. The reaction mixture was degassed and stirred at 120° C. under $N_2$ for 5 hours. The reaction mixture was cooled to room temperature and solid was filtered off. The resulting filtrate was concentrated. The residue was subjected to mass-triggered HPLC purification to give about 72 mg of the title compound as yellow oil (75%) after neutralization.

Example 251

(3-(dimethylamino)pyrrolidin-1-yl)(2-(4-fluorophenyl)-3-(p-tolylamino)-5,6-dihydroimidazo[1,2-a]pyrazin-7(8H)-yl)methanone

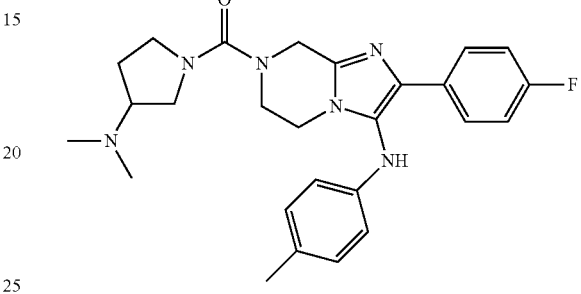

Example 251 was prepared from Example 113 by the following way:

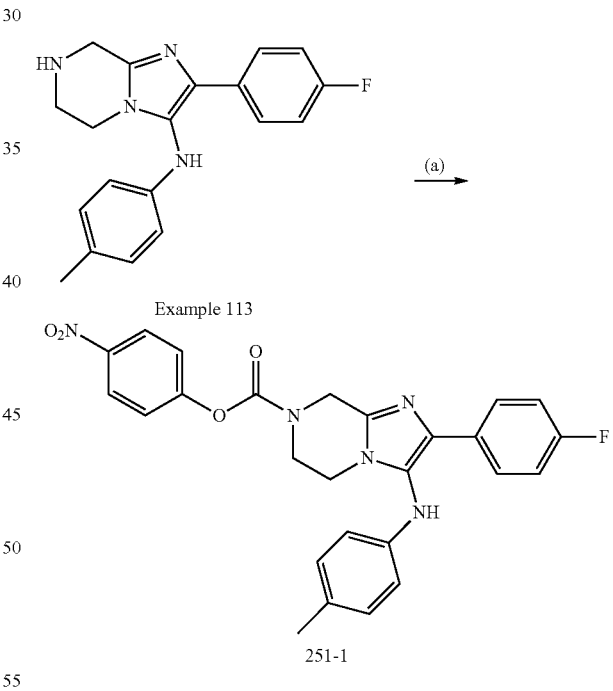

To a stirred solution of Example 113 (161 mg, 0.50 mmol) and $Et_3N$ (139 µL, 1.5 mmol) in 10 mL of DCM were added 4-nitrophenyl carbonochloridate (202 mg, 1.0 mmol). The reaction mixture was stirred at room temperature for 3 hours. The reaction mixture was subjected to MS-triggered HPLC separation. The collected MeCN/water solution was combined and concentrated to give Compound 251-1 as yellow oil: $^1$H NMR: (300 MHz, DMSO-$d_6$) δ8.34-8.31 (m, 3H) 7.80-7.75 (m, 2H) 7.54 (m, 2H) 7.35-7.29 (m, 1H) 7.20-7.14 (m, 2H) 6.60-6.50 (m, 2H) 4.93 (s, 1H) 4.74 (s, 1H) 4.07 (s, 1H) 3.92 (s, 1H) 3.81 (m, 2H).

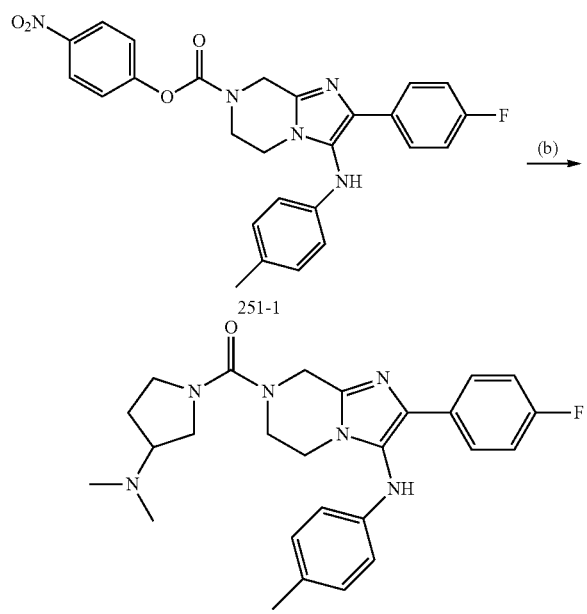

Compound 251-1 (20 mg, 0.041 mmol) and Et₃N (17 μL, 0.123 mmol) in 2 mL of NMP were added N,N-dimethyl-pyrrolidin-3-amine (15 μL, 0.123 mmol). The reaction mixture was stirred at room temperature for 3 hours. The reaction mixture was subjected to MS-triggered HPLC purification. The collected MeCN/water solution was combined and concentrated to give the title compound as yellow oil.

Example 262

N-(4-chlorophenyl)-2-(4-fluorophenyl)-5,6,7,8-tetra-hydroimidazo[1,2-a]pyrazin-3-mine

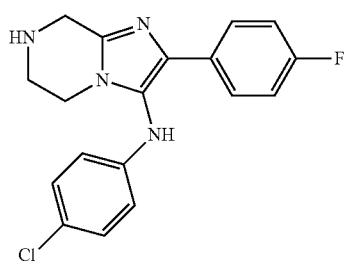

Example 262: was prepared by the following way: to a solution of Reference Compound 19 (69 mg, 0.30 mmol) in 6 mL of dioxane were added 1-bromo-4-chlorobenzene (115 mg, 0.60 mmol), Pd₂(dba)₃ (8 mg, 0.009 mmol), Xantphos (11 mg, 0.018 mmol) and Cs₂CO₃ (196 mg, 0.60 mmol) at room temperature. The reaction mixture was degassed and stirred at 120° C. under N₂ for 5 hours. The reaction mixture was cooled to room temperature and solid was filtered off. The resulting filtrate was concentrated. The residue was subjected to mass-triggered HPLC purification to give a yellow oil after neutralization. To a stirred solution of the obtained adduct (68 mg, 0.20 mmol) in 5 mL of MeOH was added Pd/C (21 mg, 0.02 mmol). The reaction mixture was evacuated and back filled with H₂. The reaction mixture was stirred at room temperature overnight. The solid was filtered off and solvent was removed. The residue was subjected to mass-triggered HPLC purification to give 39 mg (57%) of the title compound as yellow solid.

Example 266

2-m-tolyl-N-p-tolyl-5,6,7,8-tetrahydroimidazo[1,2-a]pyrazin-3-amine

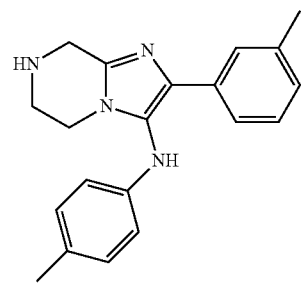 [SMILES: Cc1ccc(Nc2c(-c3cccc(C)c3)nc3n2CCNC3)cc1]

Example 266 was synthesized by the following way: to a 100-mL round-bottom flask, was placed a solution of pyrazin-2-amine (1.2 g, 12.6 mmol), 3-methylbenzaldehyde (1.44 g, 12.0 mmol) and HClO₄ (200 mg, 2.0 mmol) in methanol (10 mL). The reaction mixture was stirred at room temperature for 30 minutes, then to the mixture was added 1-isocyano-4-methylbenzene (1.2 g, 10.3 mmol). The resulting solution was allowed to stir for 12 hr at room temperature. After removing the solvent, the residue was applied onto a silica gel column with dichloromethane/methanol (10:1) to result 1.1 g the Ugi adduct. To a solution of the obtained Ugi adduct (1.0 g, 3.18 mmol) in methanol (50 mL) was added PtO₂ (72 mg, 0.32 mmol). Then the reaction mixture was evacuated and back filled with H₂. The reaction mixture was stirred at RT overnight. The solid was filtered out and the filtrate was concentrated under vacuum to result in the title compound as a white solid.

Example 267

(S)-tert-butyl 1-(2-(4-fluorophenyl)-3-(p-tolylamino)-5,6-dihydroimidazo[1,2-a]pyrazin-7(8H)-yl)-1-oxo-3-(4-(pentylamino)phenyl)propan-2-ylcarbamate

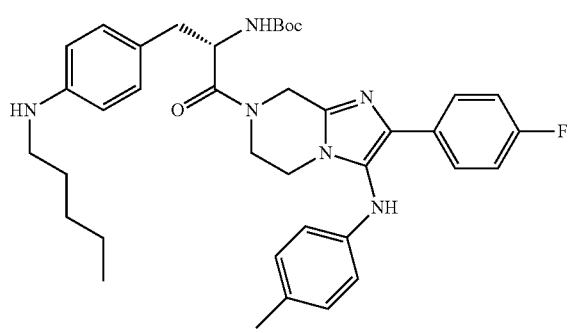 [SMILES: CCCCCNc1ccc(C[C@H](NC(=O)OC(C)(C)C)C(=O)N2CCn3c(nc(-c4ccc(F)cc4)c3Nc3ccc(C)cc3)C2)cc1]

Example 267 was synthesized from Example 113 by a HATU mediated coupling with (S)-2-(tert-butoxycarbonylamino)-3-(4-nitrophenyl)propanoic acid followed by Pd/C mediated hydrogenation for the aniline derivative. To a stirred solution of aniline derivative (33 mg, 0.056 mmol) in 5 mL of dry THF was added pentanal (18 μL, 0.168 mmol) under nitrogen at room temperature. NaBH₄ (6 mg, 0.168 mmol) was added after 30 mins. The reaction mixture was stirred at room temperature for 3 hours. Solvent was removed. The residue was dissolved in methanol and subjected to mass-triggered HPLC purification. The obtained MeCN/water solution was combined and concentrated to give yellow oil.

Example 289

(5R,8R)-2,8-dibenzyl-3-methyl-5-phenethyl-7,8-dihydroimidazo[1,2-a]pyrazin-6(5H)-one

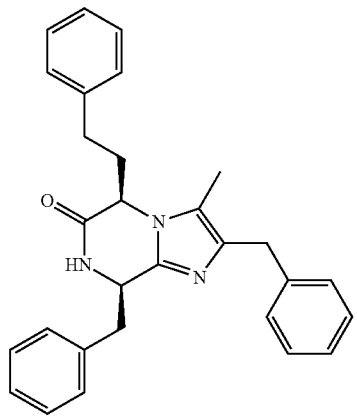 [SMILES: Cc1c(Cc2ccccc2)nc2n1[C@H](CCc1ccccc1)C(=O)N[C@@H]2Cc1ccccc1]

Example 289 was prepared in the following way:

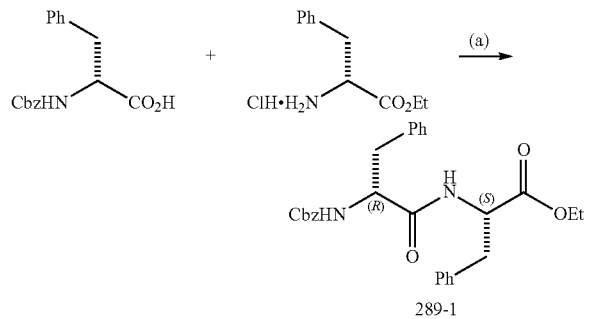

To a stirred solution of (R)-2-(benzyloxycarbonylamino)-3-phenylpropanoic acid (5 gm, 1.0 eq.) and (R)-ethyl 2-amino-3-phenylpropanoate hydrochloride (3.83 gm, 1.0 eq.) in 30 mL of DMF were added HATU (6.98 gm, 1.1 eq.) and DIEA (3.44 ml, 1.1 eq.). The reaction mixture was stirred at room temperature for 6 hours. HPLC/MS test showed that desired product Compound 289-1 was the only product, but was contaminated with other peak. The reaction was partitioned between EtOAc/water and then crude was purified with flash chromatography to give Compound 289-1.

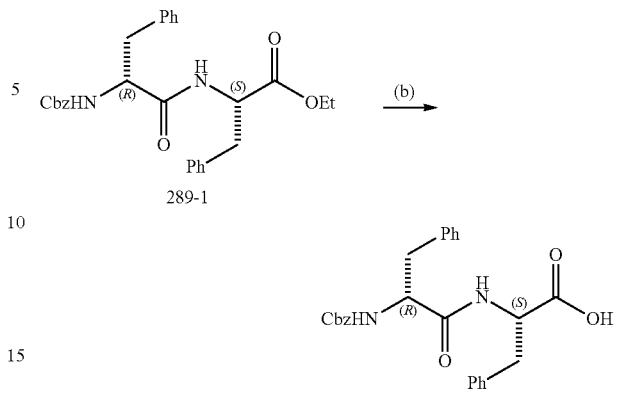

To a stirred solution of Compound 289-1 (3 gm, 1.0 eq.) and 9.5 ml of 2 N NaOH and 30 ml THF were mixed. The reaction mixture was stirred at room temperature for 6 hours. The reaction was acidified and then partitioned between EtOAc/water and then crude was as such in the next step.

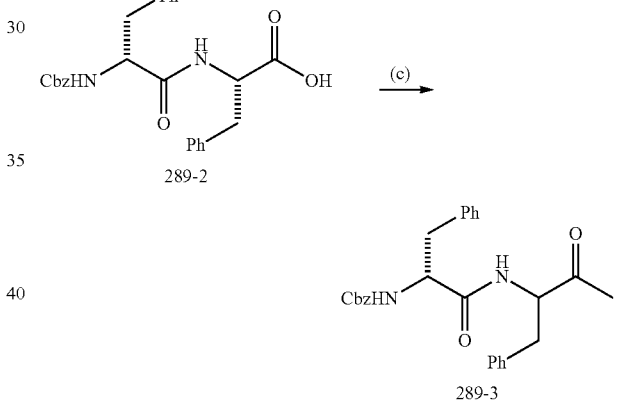

To a stirred solution of Compound 289-2 (1 gm, 1.0 eq.) and acetic anhydride (0.254 ml, 1.2 eq.) in dichloromethane (25 ml) were added DIEA (0.756 ml, 4.4 eq.)) and DMAP (13.4 mg, 5 m %). The reaction mixture was stirred at room temp. for 8 hrs. LCMS indicated that the desired product was formed. The organic layer was quenched with MeOH and concentrated. The organic layer was washed with water/EtOAc and used as crude in next step.

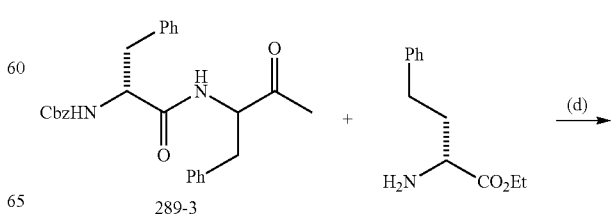

-continued

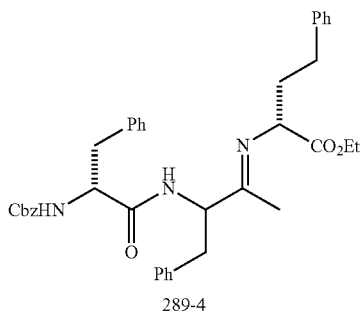
289-4

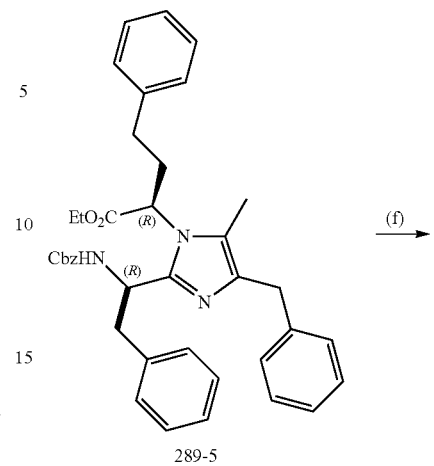
289-5

Compound 289-3 (0.8 gm, 1.0 eq.) and (R)-ethyl 2-amino-4-phenylbutanoate (0.596 gm, 1.6 eq.) were mixed along with PTSA (10 m %). The reaction was heated to 130° C. in a Dean-Stark apparatus. Slight vacuum was applied from the top to get vigorous reflux. The reaction was heated for 2 hrs. Toluene was removed from the side arm and the volume was replenished in the main vessel 3-4 times to drive the reaction to completion. LCMS indicated completion of reaction as indicated by formation of new peak. The new peak had no mass. The reaction was concentrated and crude was subjected to next step.

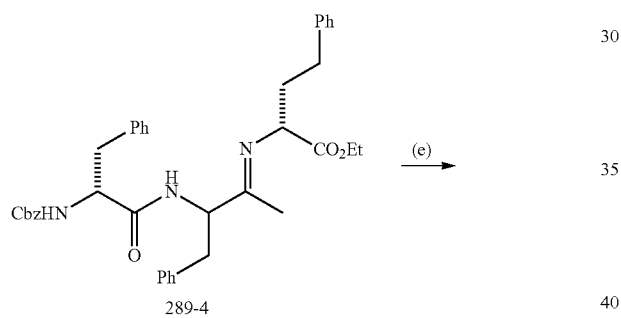
289-4

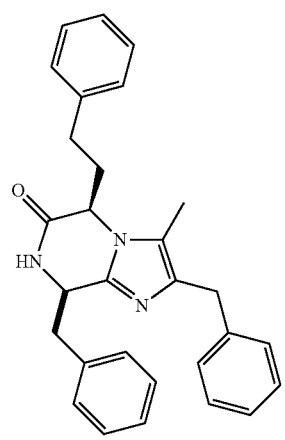

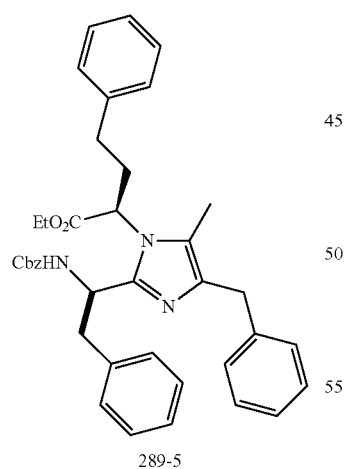
289-5

Compound 289-4 was dissolved in pyridine and POCl$_3$ was added the reaction was stirred for 48 hrs. LCMS indicated that desired product was formed. The reaction was concentrated. The oil was neutralized with sat. NaHCO$_3$. and extracted with dichloromethane. The organic layer was dried/concentrated and subjected to column chromatography.

To a stirred solution of Compound 289-5 (0.7 g, 1.0 eq.) in 30 mL of MeOH was added Pd/C (0.007 g). The reaction mixture was evacuated and back filled with H$_2$. The reaction mixture was stirred at room temperature overnight. HPLC test showed that the starting material is all gone and (II) was the major peak. Solid was filtered off and solvent was removed to give the title compound. LCMS indicated that the reaction had racemized (2 peaks).

Example 292

N-(4-chloro-3-fluorophenyl)-2-(4-fluorophenyl)-N-methyl-5,6,7,8-tetrahydro imidazo[1,2-a]pyrazin-3-amine

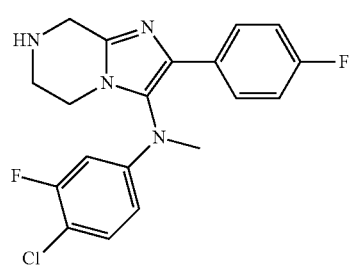 [SMILES: CN(c1ccc(Cl)c(F)c1)c1c(-c2ccc(F)cc2)nc2n1CCNC2]

117

Example 292 was prepared by the following way: to a stirred solution of pyrazin-2-amine (2.4 g, 25.26 mmol) in 20 ml of MeOH, were added 4-fluorobenzaldehyde (3.0 g, 24.19 mmol), and HClO$_4$ (70%, 0.4 g), then the mixture was stirred at room temperature for 30 min which was followed by addition of 1-chloro-2-fluoro-4-isocyanobenzene (3.2 g, 20.58 mmol). The stirring was continued at room temperature overnight, Then the solvent was removed in vacuo, and the crude product was purified by silica gel chromatography with dichloromethane/methanol to yield the Ugi adduct as a yellow solid.

To a solution of the obtained Ugi adduct (1.2 g, 3.36 mmol, 1.00 equiv) in DMF (10 mL) was added sodium hydride (1.0 g, 25.00 mmol, 1.20 equiv, 60%) at 0° C. The reaction mixture was stirred at this temperature for 30 mins, which was followed by addition of iodomethane (1.7 g, 11.97 mmol, 3.56 equiv). The resulting solution was allowed to react, with stirring, for 30 min at 0° C. The reaction mixture was poured into 20 ml of ice water. The solid was collected by filtration and washed with 10 ml of water to result in 1.1 g (88%) of the N-methyl product.

To a solution of the N-methyl product (1.0 g, 2.70 mmol, 1.00 equiv) in methanol (100 mL) was added PtO$_2$ (30 mg, 0.13 mmol, 0.10 equiv). The resulting solution was allowed to react, with stirring, for 8 hr at room temperature. The solids were filtrated out, and the resulting solution was concentrated under vacuum. The residue was applied onto silica gel chromatography with dichloromethane/methanol (20:1) to result in 500 mg (49%) of the title compound as a white solid.

Example 297

N-tert-butyl-2-(4-fluorophenyl)-5,6,7,8-tetrahydroimidazo[1,2-a]pyrazin-3-amine

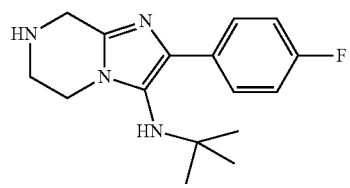 [SMILES: CC(C)(C)Nc1c(-c2ccc(F)cc2)nc2n1CCNC2]

Example 297 was synthesized from the precursor of Reference Compound 19-1 by the following way: to a solution of Reference Compound 19-1 (1.0 g, 3.52 mmol, 1.00 equiv) in methanol (20 mL), was added PtO$_2$ (80 mg, 0.35 mmol, 0.10 equiv). The resulting solution was evacuated and back filled with hydrogen, and the stirring was continued at room temperature overnight. The solid was filtered off and the solvent was evaporated under vacuum. The residue was applied to silica gel chromatography with dichloromethane/methanol (50:1) to give 837 mg (83.7%) of the title compound as a white solid.

118

Example 412

2-amino-1-(2-(4-fluorophenyl)-3-(4-fluorophenylamino)-8,8-dimethyl-5,6-dihydroimidazo[1,2-a]pyrazin-7(8H)-yl)ethanone

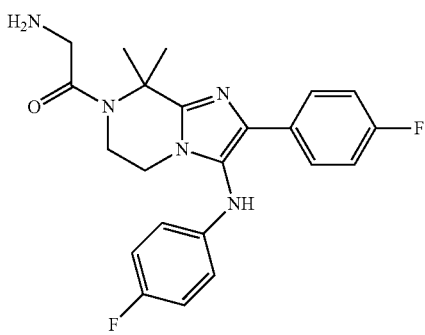 [SMILES: CC1(C)c2nc(-c3ccc(F)cc3)c(Nc3ccc(F)cc3)n2CCN1C(=O)CN]

Example 412 was prepared from Reference Compound 35 by a Pd$_2$(dba)$_3$ mediated amination reaction with p-toluidine followed by a TFA mediated deprotection.

Synthesis of Reference Compound 35-4:

To a stirred solution of Reference Compound 35-3 (70 g, 159.45 mmol, 1.00 equiv.) in methanol (800 mL) was added Palladium on carbon (10 g). The resulting solution was degassed and back filled with hydrogen. The solution was stirred for 3 days at 25° C. The solids were filtered out and washed with MeOH. The filtrate was concentrated under reduced pressure. This resulted in Reference Compound 35-4 (38 g, 145.56 mmol, 91%) of as a white solid. LC-MS: (ES, m/z): [M+H]$^+$ calculated for C$_{14}$H$_{14}$FN$_3$O 260, found 260. H-NMR: (DMSO, 300 Hz) δ 7.79-7.74 (2H, m), 7.13-7.07 (3H, m), 6.35 (H, s), 4.73 (2H, s), 1.79 (6H, s).

Synthesis of Reference Compound 35-5:

Reference Compound 35-4 (5 g, 19.2 mmol, 1 equiv.) was dissolved in 50 mL of THF, 1M Borane/THF complex (57 ml, 57 mmol, 3 equiv.) was added slowly and reaction was refluxed overnight. LCMS indicated that the reaction was complete. THF was removed under reduced pressure. The reaction was quenched with MeOH. The crude product of Reference Compound 35-5 (4.5 g, 18.3 mmol, 95%) was used in the next step. LC-MS: (ES, m/z): [M+H]$^+$ calcd for C$_{14}$H$_{17}$FN$_3$ 246, found 246. H-NMR: (DMSO, 300 Hz) δ 7.75-7.70 (2H, m), 7.4 (s, 1H), 7.14 (2H, J=9 Hz, t), 3.9 (2H, J=5.4 Hz, t), 2.51 (2H, J=5.4 Hz, t), 1.41 (6H, s).

Synthesis of Reference Compound 35-6:

To a stirred solution of Reference Compound 35-5 (2.9 g, 11.82 mmol, 1.1 equiv.) and 2-(tert-butoxycarbonylamino) acetic acid (2.27 g, 13 mmol, 1.1 equiv.) in 15 mL of dichloromethane were added DIEA (2.47 ml, 14.18 mmol, 1.2 equiv.), HATU (5.39 gm, 14.18 mmol, 1.2 equiv.). The reaction mixture was stirred at room temperature for 8 hours. HPLC/MS analysis showed that desired product Reference Compound 35-6 was the major product. The reaction was diluted 70 ml dichloromethane. The organic layer was washed with washed with water (1×30 ml), followed by saturate NaHCO$_3$ (1×30 ml) and finally with brine (1×30 ml). The organic layer was then dried over anhydrous Na$_2$SO$_4$, and concentrated in vacuo. The resulting oil was purified using column chromatography with hexanes/ethyl acetate (0-100% linear gradient) used as eluant. The desired product Reference Compound 35-6 was obtained as an oil (3.3 g, 8.27 mmol, 70%). $^1$H NMR: (300 Hz, DMSO-d$_6$,) δ7.77~7.72 (2H, m), 7.54 (1H, s), 7.20~7.14 (2H, m), 6.84~6.80 (1H, m), 4.07 (2H, s), 3.90 (2H, d, J=3 Hz), 3.70 (2H, s), 1.80 (6H, s), 1.40 (9H, s). LC-MS: (ES, m/z): [M+H]$^+$ calcd for $C_{21}H_{28}FN_4O_3$ 403 found 403.

Synthesis of Reference Compound 36:

To a solution of Reference Compound 35-6 (2.0 g, 4.97 mmol, 1.00 equiv.) in MeCN (20 mL) was added NBS (0.88 g, 1.00 equiv). The resulting solution was stirred for 15 minutes at room temperature. HPLC/MS indicated that the desired product Reference Compound 36 was formed exclusively. The reaction was evaporated under reduced pressure. The solids were dissolved in 50 ml dichloromethane. The organic layer was then dried over anhydrous $Na_2SO_4$, and concentrated in vacuo. The resulting solids were purified with column chromatography using hexanes/ethyl acetate (0-100%) as eluant. The desired compound Reference Compound 36 was obtained as an off white/glassy solid (1.9 g, 3.96 mmol, 80%). LC-MS: (ES, m/z): [M+H]$^+$ calcd for $C_{21}H_{27}BrFN_4O_3$ 482 found 482. H-NMR: (MeOH-d$_4$, 400 Hz) δ 7.84-7.81 (2H, m), 7.14 (2H, J=8.8 Hz, t), 4.09-4.01 (4H, m), 3.81 (2H, J=4.8 Hz, t), 1.89 (6H, s), 1.46 (9H, s).

Synthesis of Example 412

In a glass vial, $Cs_2CO_3$, 4F-aniline (0.462 g, 4.1 mmol, 2.0 equiv.), $Pd_2(dba)_3$ (0.095 g, 0.104 mmol, 0.05 equiv.), Xantphos (0.120 g, 0.208 mmol, 0.1 equiv.) and dioxane were stirred for 5 minutes at room temperature. Reference Compound 36 (1 g, 2.08 mmol, 1.0 equiv.) was added to the reaction mixture after which the reaction mixture was degassed for 15 mins and then stirred at 120° C. under $N_2$ for 8 hours. HPLC/MS test showed that the starting material Reference Compound 36 was consumed and desired product was formed predominantly along with some Reference Compound 35-6. The reaction was filtered to remove solids. The reaction mixture was concentrated and then purified by normal phase column chromatography (silicagel 80 gm) using a gradient of 100%-0 to 0-100% hexane:EtOAc. The desired product elutes at 60:40 EtOAc:hexanes. The organic layer was concentrated at reduced pressure to yield the Boc derivative (950 mg, 89.3%) yield. LC-MS: (ES, m/z): [M+H]$^+$ calcd for $C_{27}H_{32}F_2N_5O_3$ 512 found 512.

The Boc-compound was treated with 20% TFA in $CH_2Cl_2$ (50 ml) was the reaction was stirred for 4 hours) was added to the mixture. After the completion of this reaction (monitored by LCMS), the resulting mixture was concentrated under reduced pressure. The resulting residue was purified by reverse phase HPLC to yield product as a TFA salt. The ACN-water layer was concentrated to remove all the solvents. The residue was dissolved in dichloromethane and carefully neutralized by sat. $NaHCO_3$. The organic layer was successively washed with brine followed by water. The organic layer was concentrated to yield Example 412 (450 mg, 52% for 2 steps). LC-MS: (ES, m/z): [M+H]$^+$ calcd for $C_{22}H_{23}F_2N_5O$ 412 found 412. H-NMR: (MeOH-d$_4$, 400 Hz) δ 7.61-7.57 (2H, m), 6.94 (2H, J=8.8 Hz, t), 6.81 (2H, J=8.8 Hz, t), 6.47 (2H, m), 3.72 (2H, m), 3.58 (2H, m), 3.42 (2H, m), 1.85 (6H, s). Elemental Analysis: (Example 412 with 0.65 equiv. $H_2O$): C, 62.44; N, 16.55; H, 5.79, (calculated). C=62.54/62.44; N=16.35/16.29; H=5.52/5.61 (experimental).

Example 417

2-amino-1-(3-(4-chlorophenylamino)-2-(4-fluorophenyl)-8,8-dimethyl-5,6-dihydroimidazo[1,2-a]pyrazin-7(8H)-yl)ethanone

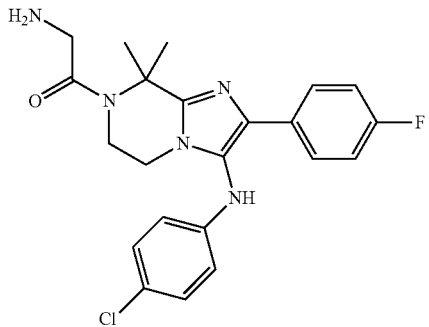 [SMILES: CC1(C)c2nc(-c3ccc(F)cc3)c(Nc3ccc(Cl)cc3)n2CCN1C(=O)CN]

Example 417 was prepared from Reference Compound 36 by a $Pd_2(dba)_3$ mediated amination reaction with 4-chloroaniline followed by a 6N HCl mediated deprotection.

Example 331

N-(3,4-difluorophenyl)-2-(4-fluorophenyl)-5,6,7,8-tetrahydroimidazo[1,2-a]pyrazin-3-amine

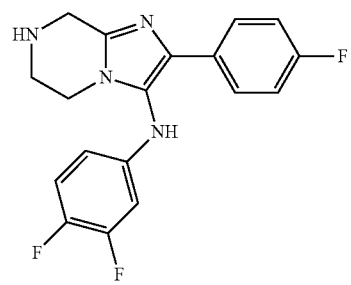 [SMILES: Fc1ccc(-c2nc3n(c2Nc2ccc(F)c(F)c2)CCNC3)cc1]

Example 331 was synthesized from Reference Compound 19 by the following way: to a 250-mL 3-necked round-bottom flask purged and maintained with an inert atmosphere of nitrogen, was placed a solution of Reference Compound 19 (1.5 g, 6.12 mmol) and 4-bromo-1,2-difluorobenzene (2.4 g, 12.44 mmol) in 1,4-dioxane (100 mL) were added $Pd_2(dba)_3$ (170 mg, 0.19 mmol), X-Phos (175 mg, 0.37 mmol) and $Cs_2CO_3$ (4 g, 12.28 mmol) under nitrogen. The resulting solution was heated to 120° C. and stirred overnight. The solids were filtrated out and the resulting mixture was concentrated under vacuum. The residue was applied onto a silica gel column with ethyl acetate/petroleum ether (1:2) to result in 1.9 g (87%) of diaryl amine as a brown solid.

To a solution of the obtained diaryl amine (1.9 g, 5.33 mmol) in methanol (50 mL) was added $PtO_2$ (130 mg, 0.57 mmol). The mixture was degassed and backed filled with hydrogen. The resulting solution was allowed to react, with stirring, overnight at room temperature. The solids were filtrated and the resulting mixture was concentrated under vacuum. The residue was applied onto a silica gel column with DCM/MeOH (50:1) to result in the title compound as a brown solid.

Example 529

2-amino-1-(2-(4-fluorophenyl)-8,8-dimethyl-3-(p-tolylamino)-5,6-dihydro imidazo[1,2-a]pyrazin-7(8H)-yl)-2-methylpropan-1-one

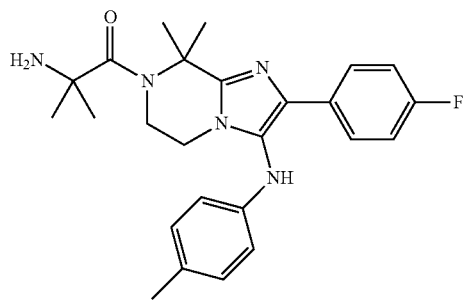 [SMILES: Cc1ccc(Nc2c(-c3ccc(F)cc3)nc3n2CCN(C(=O)C(C)(C)N)C3(C)C)cc1]

Example 529 was prepared from Example 415 by the following way:

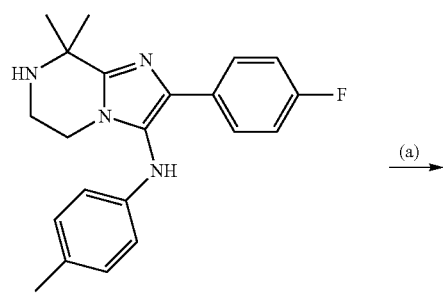

Example 415

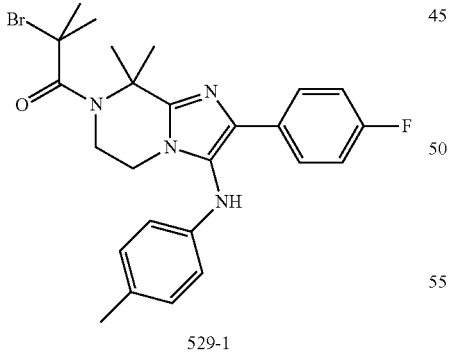

529-1

To a stirred solution of Example 415 (21 mg, 0.06 mmol) and Et₃N (83 µL, 0.60 mmol) in 6 mL of dry DCM was added 2-bromo-2-methylpropanoyl bromide (71 µL, 0.60 mmol). The reaction mixture was stirred at room temperature for 5 hour. The reaction mixture was concentrated and subjected to mass-triggered LC/MS purification directly. The obtained solutions were concentrated to give 22 mg (73%) of Compound 529-1 as yellow oil after neutralization.

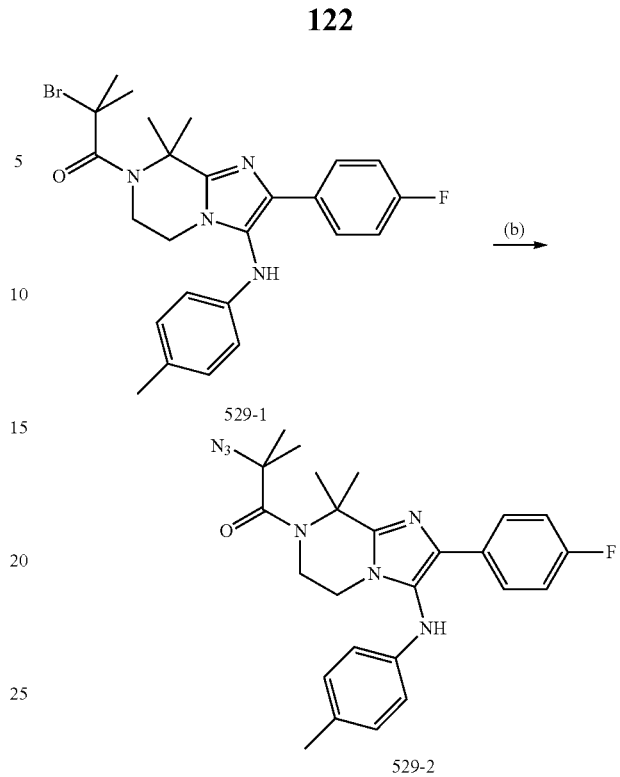

529-1

529-2

To a solution of Compound 529-1 (22 mg, 0.044 mmol) in 3 mL of DMF was added NaN₃ (8.6 mg, 0.132 mmol) at room temperature. The reaction mixture was stirred at room temperature for 2 hours. The reaction mixture was directly subjected to mass-triggered LC/MS purification directly. The obtained MeCN/aqueous solution was combined and concentrated to give 15 mg (75%) of Compound 529-2 as yellow oil after neutralization.

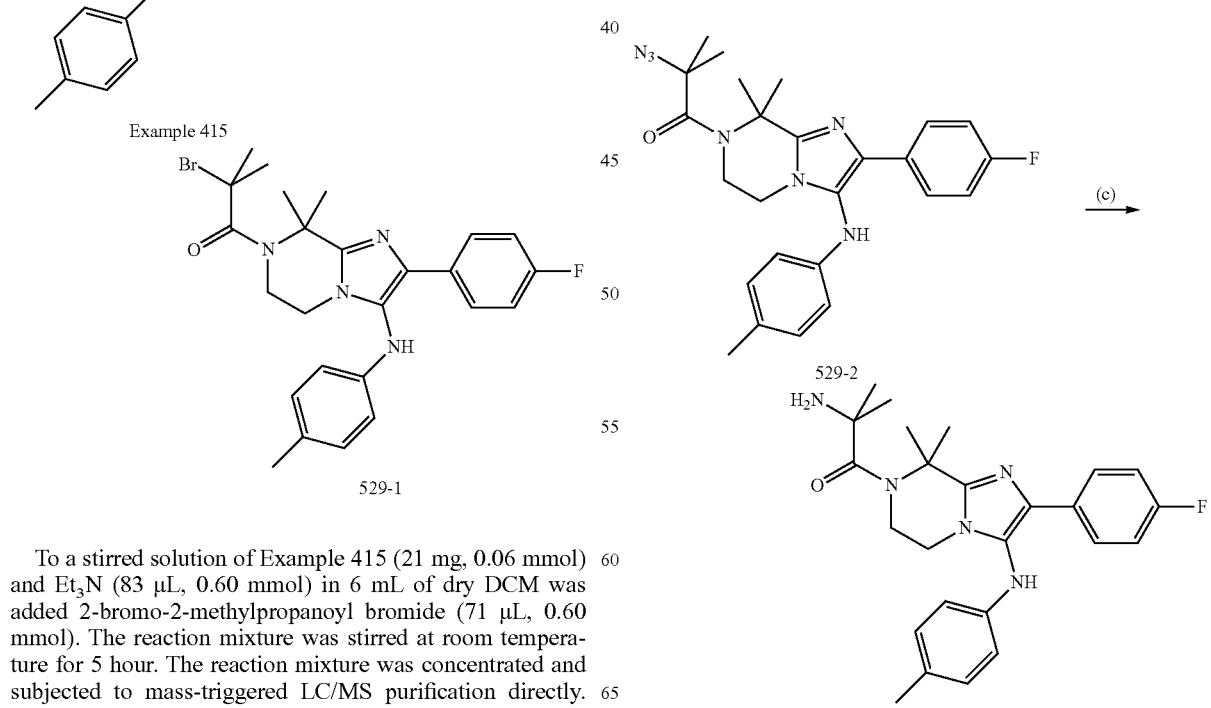

529-2

To a solution of Compound 529-2 (15 mg, 0.033 mmol) in 3 mL of MeOH was added 10% Pd/C (4 mg, 0.003 mmol) at room temperature. Air was removed and H₂ was filled. The reaction mixture was stirred at room temperature for 2 hours. Solid was filtered off and solvent was removed. The reaction mixture was directly subjected to mass-triggered HPLC purification to give 15 mg (100%) of the title compound yellow oil.

Example 530 tert-butyl 1-(2-(4-fluorophenyl)-5,6-dihydroimidazo[1,2-a]pyrazin-7(8H)-yl)-2-methyl-1-oxopropan-2-ylcarbamate

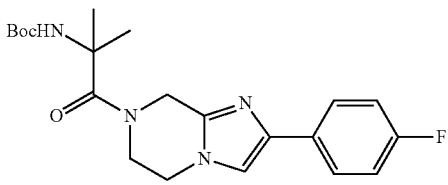 [SMILES: CC(C)(C)OC(=O)NC(C)(C)C(=O)N1CCn2cc(-c3ccc(F)cc3)nc2C1]

Example 530 was prepared from Compound 540-1 by the following way:

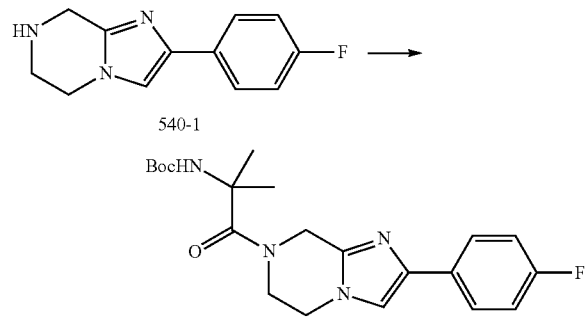 [SMILES: Fc1ccc(-c2cn3c(n2)CNCC3)cc1 ; CC(C)(C)OC(=O)NC(C)(C)C(=O)N1CCn2cc(-c3ccc(F)cc3)nc2C1]

To a stirred solution of Compound 540-1 (1.0 g, 4.61 mmol, 1.00 equiv) in DMF (20 mL) was added 2-(tert-butoxycarbonyl)-2-methylpropanoic acid (1.12 g, 5.52 mmol, 1.20 equiv), EDC (1.06 g, 5.52 mmol, 1.20 equiv), HOBT (1.8 g, 13.24 mmol, 2.87 equiv), DIEA (1.78 g, 13.80 mmol, 2.99 equiv). The resulting solution was stirred overnight at 60° C. The resulting mixture was concentrated under vacuum. The resulting solution was diluted with 100 mL of water. The resulting solution was extracted with ethyl acetate (2×150 mL) and the organic combined layer was concentrated. The residue was applied onto a silica gel column with ethyl acetate/petroleum ether (1:10~1:2~1). This resulted in the title compound as a yellow solid.

Example 540 tert-butyl 2-(2-(4-fluorophenyl)-5,6-dihydroimidazo[1,2-a]pyrazin-7(8H)-yl)-2-oxoethylcarbamate

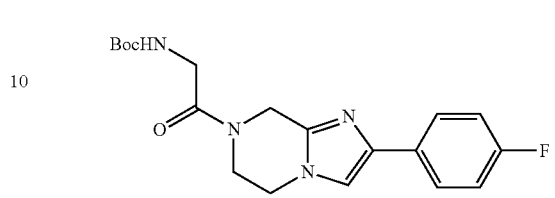

Example 540 was prepared from Reference Compound 51 by the following way:

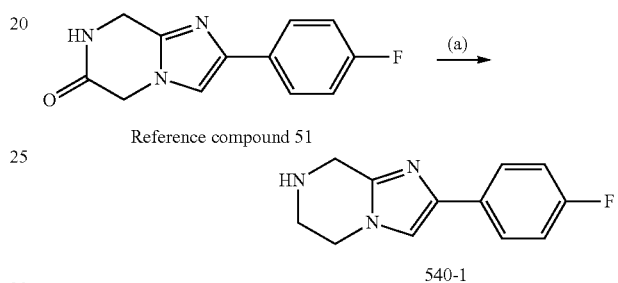

To a stirred solution of Reference Compound 51 (4.2 g, 18.18 mmol, 1.00 equiv) in THF (150 mL) was added BH₃.Me₂S (45 mL, 2M) dropwise at room temperature in 10 mins. The resulting solution was heated to reflux overnight. The resulting mixture was concentrated under vacuum. The resulting solution was diluted with 100 mL of methanol. The pH value of the solution was adjusted to 1 with conc. HCl, and the mixture was refluxed for 1 hr. The resulting mixture was concentrated under vacuum. The residue was dissolved in 100 mL of water. Potassium carbonate was employed to adjust the pH to 10. The resulting solution was extracted with THF (4×200 mL) and the combined organic layer was washed with brine (2×200 mL), dried over anhydrous sodium sulfate and concentrated under vacuum. This resulted in 3 g (76%) of Compound 540-1 as a white solid.

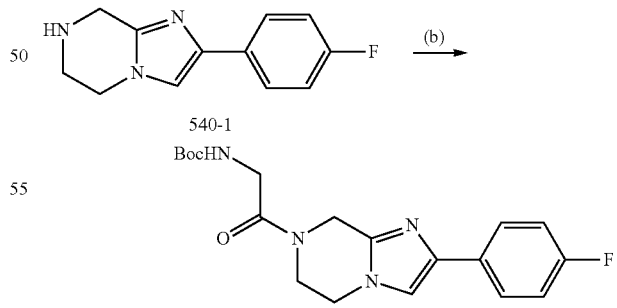

To a stirred solution of Compound 540-1 (1.0 g, 4.61 mmol, 1.00 equiv) in DMF (20 mL) was added 2-(tert-butoxycarbonyl)acetic acid (1.2 g, 6.86 mmol, 1.49 equiv) and HATU (5.2 g, 13.68 mmol, 2.97 equiv). The resulting solution was stirred for 4 h at room temperature. The resulting mixture was concentrated under vacuum. The residue was applied onto a silica gel column with ethyl acetate/petroleum ether (1:1). This resulted in 300 mg (17%) of the title compound as a white solid.

Example 556

N-(4-chlorophenyl)-2-(4-fluorophenyl)-6,6,7-trimethyl-5,6,7,8-tetrahydroimidazo[1,2-a]pyrazin-3-amine

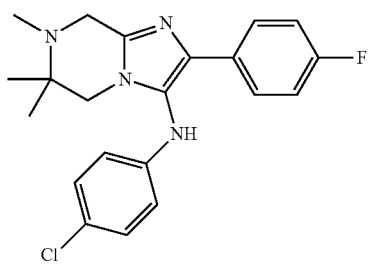 [SMILES: CN1Cc2nc(-c3ccc(F)cc3)c(Nc3ccc(Cl)cc3)n2CC1(C)C]

Example 556 was prepared from Reference Compound 41 bromination followed by a $Pd_2(dba)_3$ mediated amination reaction with 4-chloroaniline. The bromination procedure is shown below:

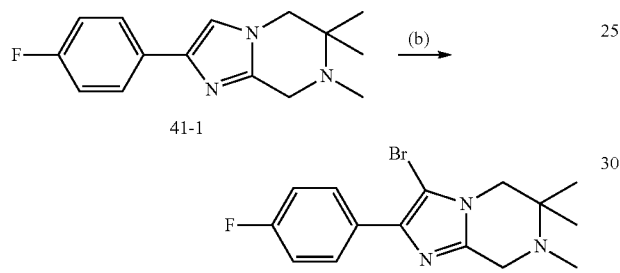

To a stirred solution of Compound 41-1 (52 mg, 0.20 mmol) in 6 mL of DCM was added $Br_2$ (11.3 μL, 0.22 mmol) in 2 mL of acetic acid. The reaction mixture was stirred at room temperature for 30 mins. Solvent was removed via rotavap at a temperature no higher than 20° C. After neutralization, the residue was subjected to flash chromatography (40 g, 0-10% methanol in DCM, 50 mins, dry loading) purification to give 59 mg (87%) of the title compound as white solid.

Example 645

8-(3,4-difluorophenylamino)-9-(4-fluorophenyl)-2,2-dimethyl-5,6-dihydrodiimidazo[1,2-a:2',1'-c]pyrazin-3 (2H)-one

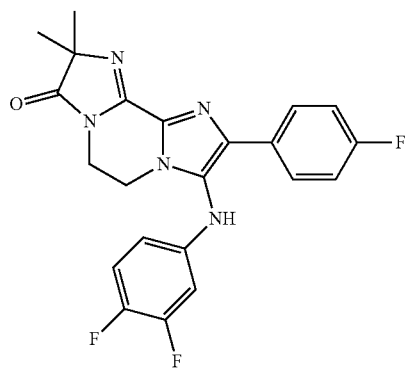 [SMILES: CC1(C)N=C2c3nc(-c4ccc(F)cc4)c(Nc4ccc(F)c(F)c4)n3CCN2C1=O]

Example 645 was prepared from Example 29 by the following method: to a stirred solution of Example 29 (12 mg, 0.03 mmol) was added $MnO_2$ (52 mg, 0.60 mmol). The reaction mixture was stirred at room temperature for 2 hours. LC/MS test showed that Example 29 was almost gone and the desired product ([M+1]=526) was detected as one of the major peaks. Solid was filtered off and solvent was removed. The residue was subjected to a mass-triggered HPLC purification to give Example 645.

Example 646

8-(3,4-difluorophenylamino)-9-(4-fluorophenyl)-2,2-dimethyl-1,2,5,6-tetrahydrodiimidazo[1,2-a:2',1'-c]pyrazin-3(10bH)-one

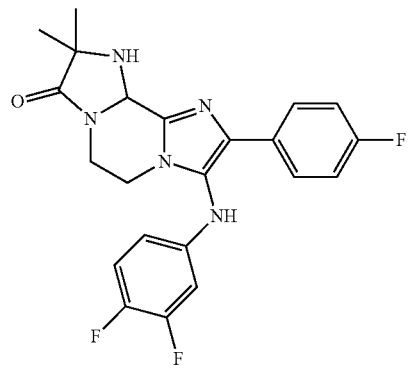 [SMILES: CC1(C)NC2c3nc(-c4ccc(F)cc4)c(Nc4ccc(F)c(F)c4)n3CCN2C1=O]

Example 646 was prepared from Example 29 by the following method: to a stirred solution of Example 29 (12 mg, 0.03 mmol) was added $MnO_2$ (52 mg, 0.60 mmol). The reaction mixture was stirred at room temperature for 2 hours. LC/MS test showed that Example 29 was almost gone and the desired product ([M+1]=528) was detected as one of the major peaks. Solid was filtered off and solvent was removed. The residue was subjected to a mass-triggered HPLC purification to give Example 646.

Example 687

7-(2-aminoethyl)-2-(4-fluorophenyl)-3-(4-fluorophenylamino)-8,8-dimethyl-7,8-dihydroimidazo[1,2-a]pyrazin-6(5H)-one

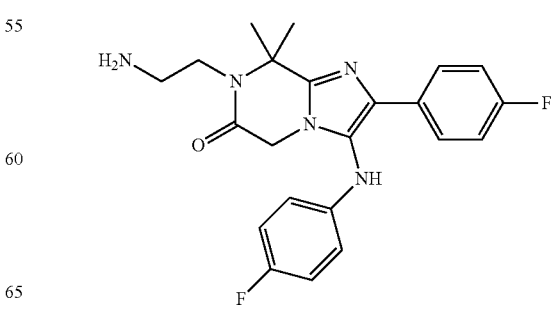

127

Example 687 was prepared from Example 688 by the following steps:

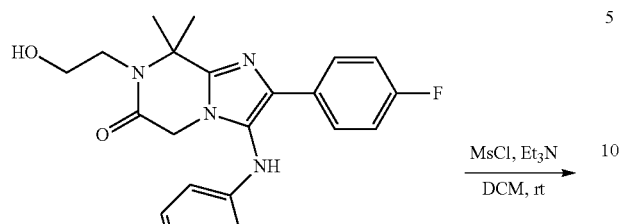

Example 688

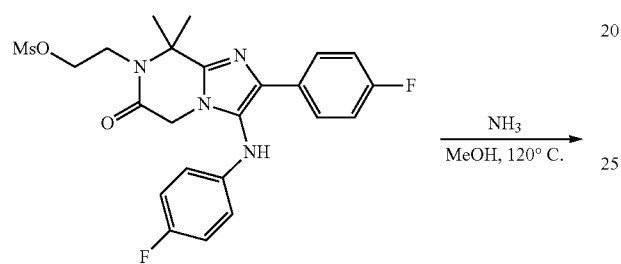

Example 687

To a stirred solution of Example 688 (22 mg, 0.05 mmol) and Et₃N (42 μL, 0.30 mmol) in 3 mL of DCM were added MsCl (12 μL, 0.15 mmol). The reaction mixture was stirred at room temperature for 3 hours. HPLC/MS test showed that Example 688 was all gone and the desired product ([M+1]=519) was formed as the only major peak. Solvent was removed and the residue was subjected to a mass-triggered HPLC purification to give 18 mg of mesylate. To a stirred solution of the mesylate (5 mg, 0.01 mmol) in 2 mL of MeOH was added 1 mL of 5 M in MeOH. The reaction mixture was stirred at 120° C. for 20 minutes in a microwave oven. HPLC/MS test showed that the mesylate was all gone and Example 687 ([M+1]=440) was formed as the one of the major peaks. Solvent was removed and the residue was subjected to a mass-triggered HPLC purification to give 3 mg of Example 687.

128

Example 692

4-(3-(4-fluoro-3-methylphenylamino)-2-(3-fluorophenyl)-8,8-dimethyl-6-oxo-5,6-dihydroimidazo[1,2-a]pyrazin-7(8H)-yl)butanoic acid

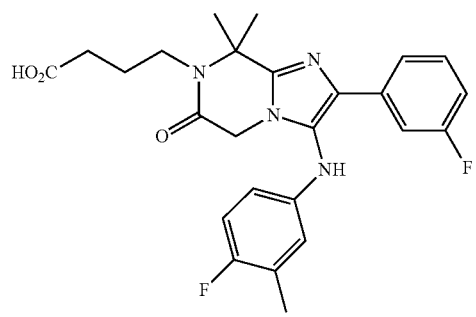

Example 692 was prepared from Reference Compound 73 by the following steps:

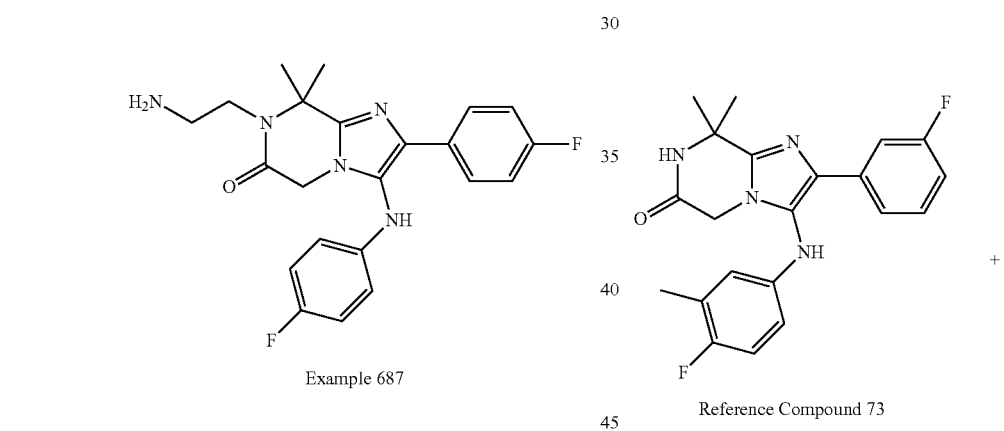

Reference Compound 73

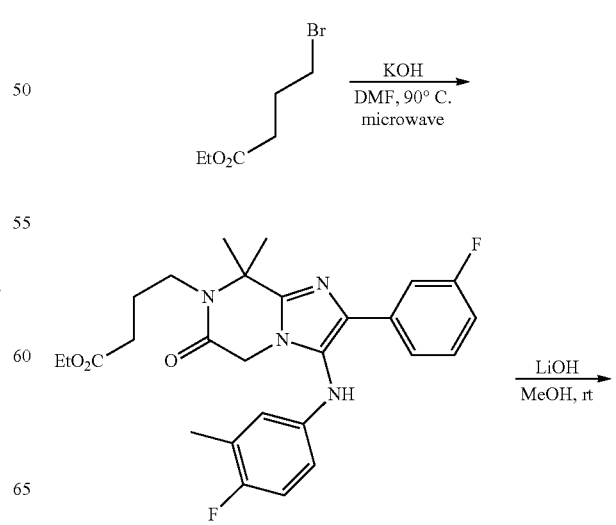

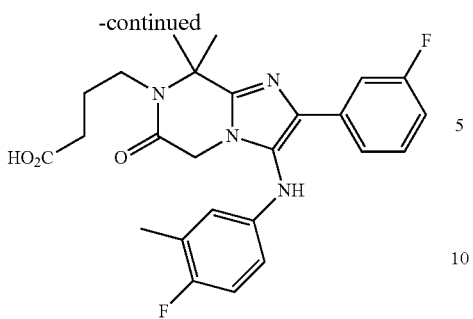

Example 692

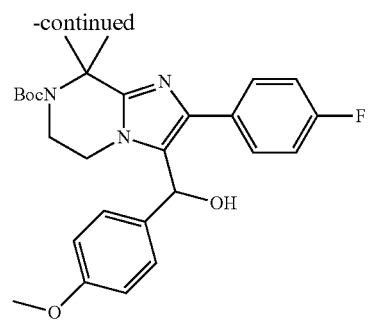

Example 695-1

To a solution of Reference Compound 73 (10 mg, 0.03 mmol) in 3 mL of DMF were added KOH (8 mg, 0.12 mmol), and ethyl 4-bromobutanoate (24 mg, 0.12 mmol) at room temperature. The reaction mixture was stirred in a microwave oven at 90° C. for 20 minutes. LC/MS test showed that 50% of starting material was remaining and the desired product ester ([M+1]=497) was the major product. The reaction mixture was filtered and subjected to mass-triggered HPLC purification to give the ester as colorless oil. The obtained ester was hydrolyzed by LiOH to give Example 692.

Example 695

2-amino-1-(2-(4-fluorophenyl)-3-(4-methoxybenzyl)-8,8-dimethyl-5,6-dihydroimidazol[1,2-a]pyrazin-7(8H)-yl)ethanone

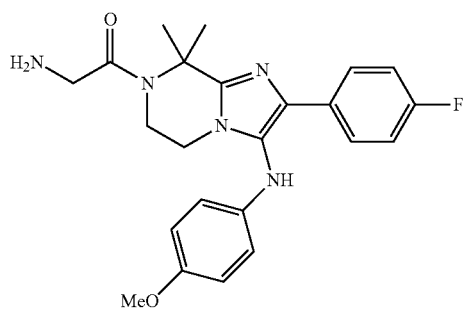

Example 695 was prepared from Reference Compound 74 by the following steps:

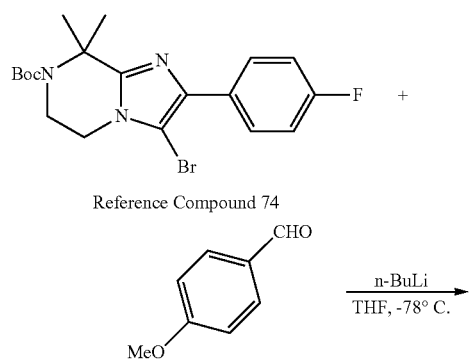

To a solution of Reference Compound 74 (21 mg, 0.05 mmol) in 3 mL of dry THF was added 2.5 N (0.025 mL, 0.06 mmol) at −78° C. The reaction mixture was stirred at the same temperature for 20 mins and (II) (41 mg, 0.30 mmol) in 1 mL of dry THF was added. The reaction mixture was stirred for another 5 hours while the temperature raised to room temperature. LC/MS test showed that starting material was all gone and the desired adduct Example 695-1 (20 mg, 84%) was isolated as the major product.

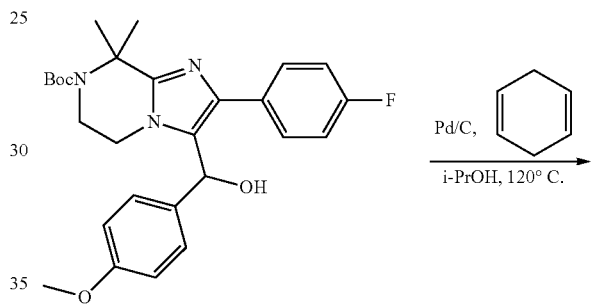

Example 695-1

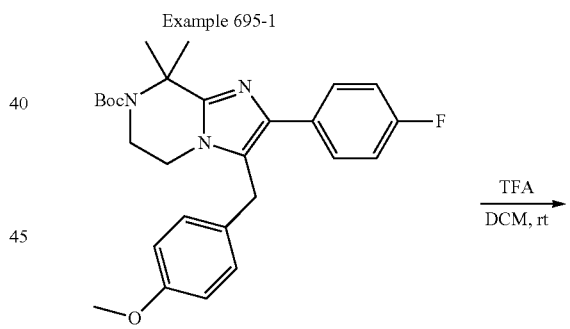

Example 695-2

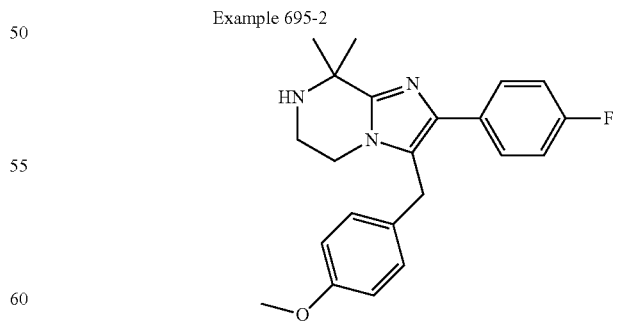

Example 695-3

To a solution of Example 695-1 (10 mg, 0.021 mmol) in 3 mL of i-PrOH were added 10% Pd/C (3 mg, 0.004 mmol) and 1,4-cyclohexadiene (20 μL, 0.21 mmol). The reaction mixture was stirred at 120° C. for 3 hours in a Q-tube.

LC/MS test showed that the starting material was gone and there was a major peak with [M+1]=466, which corresponded to the desired product. Solid was filtered off and solvent was removed. The residue was subjected to mass-triggered HPLC purification to give 16 mg of crude Example 695-2 as brown oil. Example 695-2 was subjected to a TFA mediated deprotection to get 3 mg of Example 695-3 ([M+1]=366).

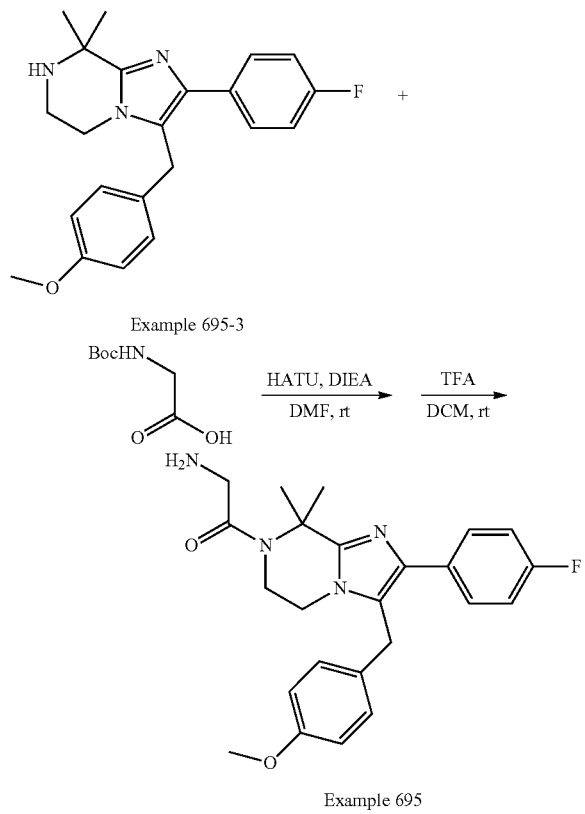

Example 695-3 / Example 695

To a stirred solution of Example 695-3 (4 mg, 0.01 mmol) and 2-(tert-butoxycarbonylamino)acetic acid (5.2 mg, 0.03 mmol) in 2 mL of DMF were added HATU (12 mg, 0.03 mmol) and DIEA (5.2 µL, 0.03 mmol). The reaction mixture was stirred at room temperature for 3 hours. LC/MS test showed that the starting material was almost gone and the desired adduct ([M+1]=523) was formed as the one of the major peaks. The reaction subjected to a mass-triggered HPLC purification to give the adduct, which was subjected to a TFA mediated deprotection to get 6 mg of Example 695 ([M+1]=422).

Example 700

2-amino-1-(2-(4-fluorophenyl)-8,8-dimethyl-5,6-dihydroimidazo[1,2-a]pyrazin-7(8H)-yl)-3-p-tolyl-propan-1-one

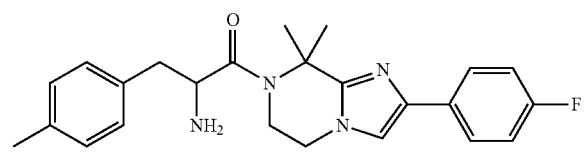 [SMILES: Cc1ccc(CC(N)C(=O)N2CCn3cc(-c4ccc(F)cc4)nc3C2(C)C)cc1]

Example 700 was prepared from Reference Compound 35 by the following steps:

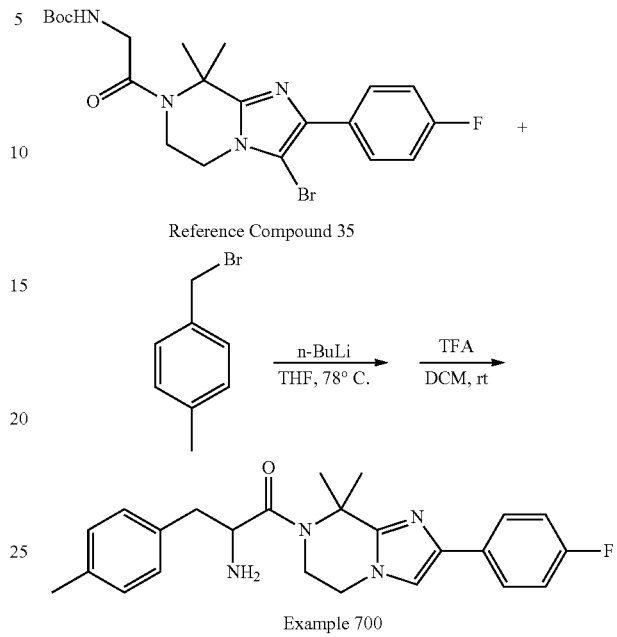

Reference Compound 35 / Example 700

To a solution of Reference Compound 35 (48 mg, 0.10 mmol) in 3 mL of dry THF was added 2.2 N n-BuLi (0.11 mL, 0.24 mmol) at −78° C. The reaction mixture was stirred at the same temperature for 20 minutes and 1-(bromomethyl)-4-methylbenzene (111 mg, 0.60 mmol) in 1 mL of dry THF was added. The reaction mixture was stirred for another 5 hours while the temperature raised to room temperature. LC/MS test showed that starting material was all gone and adduct. The reaction mixture was quenched with NH$_4$Cl aqueous solution and diluted with ethyl acetate. The organic solution was separated, dried and concentrated. The residue was subjected to a mass-triggered HPLC purification to give 28 mg of the adduct as clear oil. This was subjected to a TFA mediated deprotection to give Example 700.

Example 704

2-amino-1-(2-(4-fluorophenyl)-8,8-dimethyl-3-p-tolyl-5,6-dihydroimidazo-[1,2-a]pyrazin-7(8H)-yl)ethanone

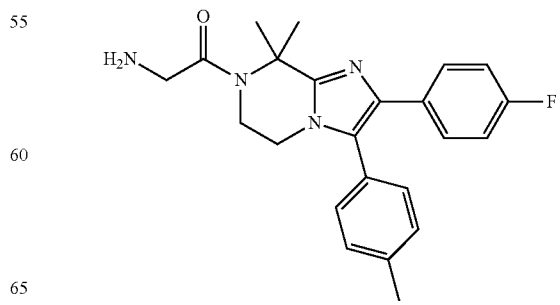

Example 704 was prepared from Reference Compound 35 in the following steps:

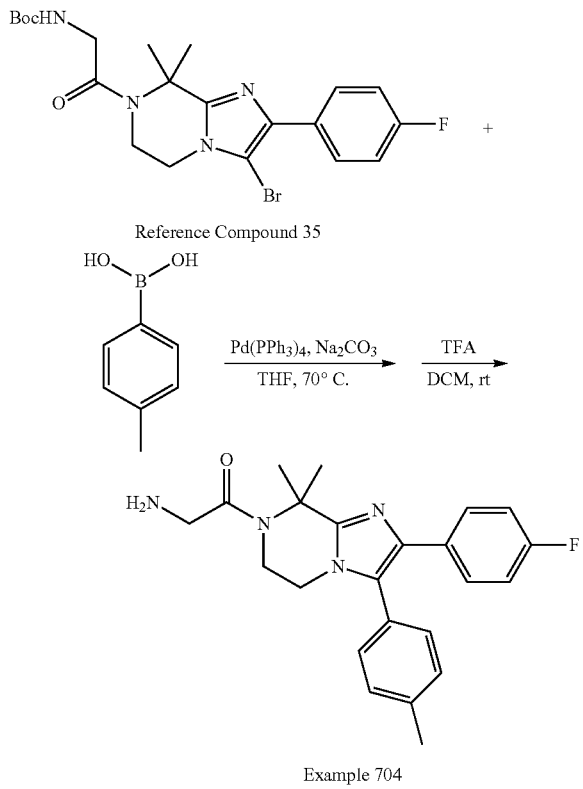

Reference Compound 35

Example 704

Reference Compound 35 (48 mg, 0.10 mmol), p-tolylboronic acid (27 mg, 0.20 mmol), Pd(PPh₃)₄ (12 mg, 0.01 mmol), and 1.0 N Na₂CO₃ (0.20 mL, 0.20 mmol) were combine in a 40 mL vial. 5 mL of THF was added. The reaction mixture was de-gassed by repeated evacuation and re-fill with nitrogen. And the reaction mixture was stirred at 70° C. for 2 hours. LC/MS test showed that Reference Compound 35 was almost gone and the desired adduct was detected as one of the major peaks. Solid was filtered and solvent was removed. The residue was subjected to a mass-triggered HPLC purification to give 22 mg of the desired adduct. This was subjected to a TFA mediated deprotection to give Example 704.

Example 707

N,2-bis(4-fluorophenyl)-8,8-dimethyl-5,6,7,8-tetrahydroimidazo[1,2-a]pyrazine-3-carboxamide

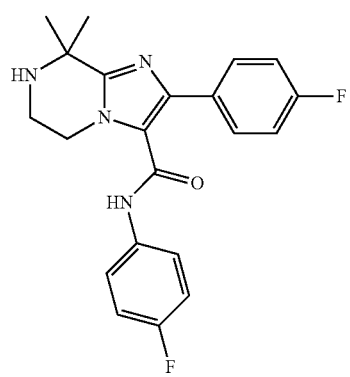 [SMILES: CC1(C)NCCn2c1nc(-c1ccc(F)cc1)c2C(=O)Nc1ccc(F)cc1]

Example 707 was prepared from Reference Compound 74 by the following steps:

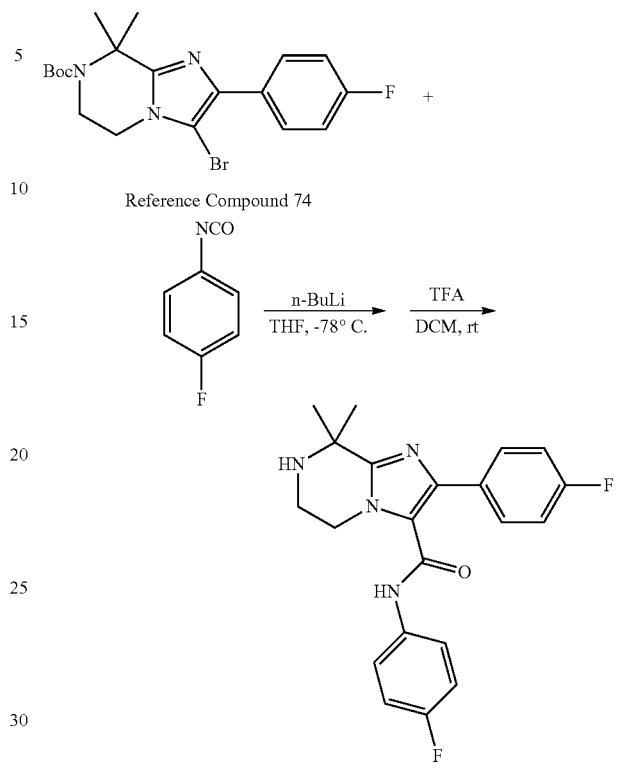

Reference Compound 74

Example 707

To a solution of Reference Compound 74 (21 mg, 0.05 mmol) in 3 mL of dry THF was added 2.5 N n-BuLi (0.04 mL, 0.10 mmol) at −78° C. The reaction mixture was stirred at the same temperature for 20 mins and 1-fluoro-4-isocyanatobenzene (33 μL, 0.30 mmol) in 1 mL of dry THF was added. The reaction mixture was stirred for another 5 hours while the temperature raised to room temperature. LC/MS test showed that starting material was all gone and the desired adduct was detected as a major peak. Solid was filtered and solvent was removed. The residue was subjected to mass-triggered HPLC purification to give 56 mg of the desired adduct as brown oil. The adduct was subjected to a TFA mediated deprotection to get 22 mg of Example 707 ([M+1]=393) as yellow solid.

Example 709

2-amino-1-(3-(4-fluorophenoxy)-2-(4-fluorophenyl)-8,8-dimethyl-5,6-dihydroimidazo[1,2-a]pyrazin-7(8H)-yl)ethanone

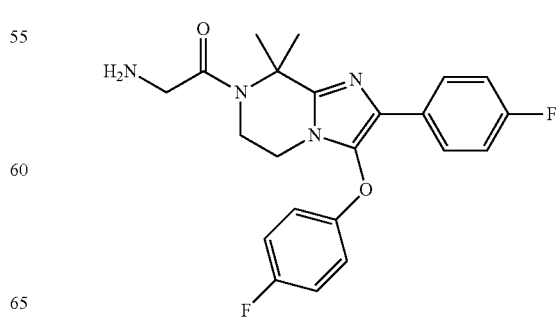

Example 709 was prepared from Reference Compound 35 in the following steps:

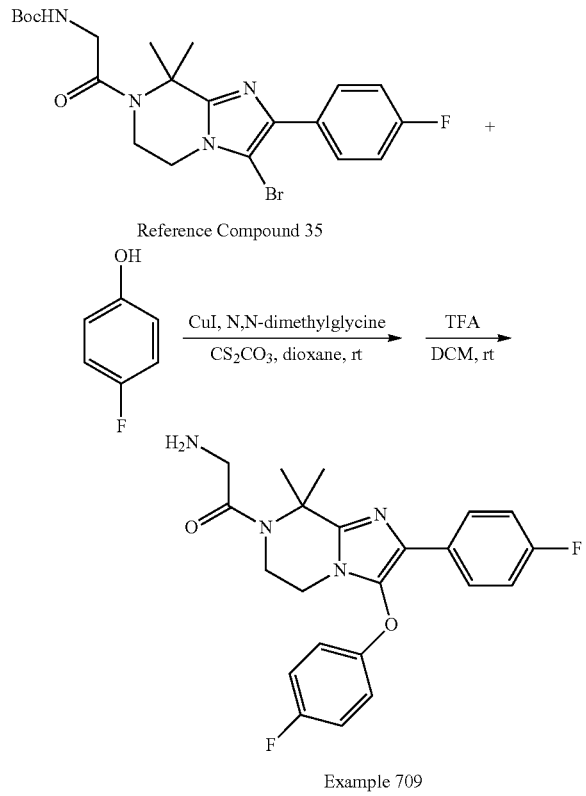

Example 709

To a solution of Reference Compound 35 (48 mg, 0.10 mmol) in 5 mL of dioxane were added 4-fluorophenol (34 mg, 0.30 mmol), CuI (3.8 mg, 0.02 mmol), N,N-dimethylglycine (4.1 mg, 0.04 mmol) and $Cs_2CO_3$ (98 mg, 0.30 mmol) at room temperature. The reaction mixture was degassed and stirred at 120° C. under $N_2$ overnight. LC/MS test showed that the starting material was all gone and the desired adduct ([M+1]=513) was detected as a major peak. Solid was filtered and solvent was removed. The residue was subjected to a mass-triggered HPLC purification to give 28 mg of the desired adduct. This was deprotected with TFA to give Example 709.

Example 713

2-amino-1-(2-(4-fluorophenyl)-8,8-dimethyl-3-(p-tolylthio)-5,6-dihydro imidazo[1,2-a]pyrazin-7(8H)-yl)ethanone

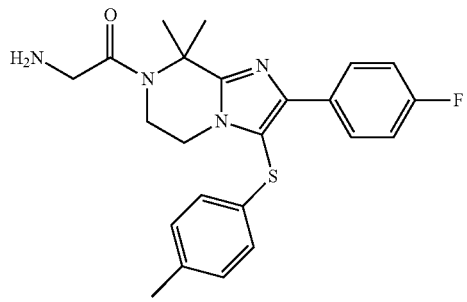

Example 713 was prepared from Reference Compound 35 in the following steps:

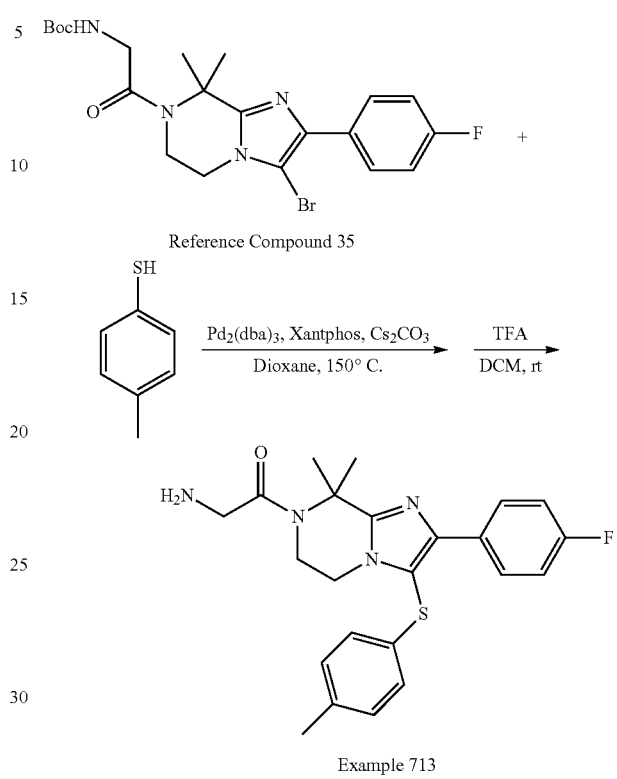

Example 713

To a solution of Reference Compound 35 (24 mg, 0.05 mmol) in 3 mL of dioxane were added 4-methylbenzenethiol (17 mg, 0.15 mmol), $Pd_2(dba)_3$ (9.2 mg, 0.01 mmol), XantPhos (12 mg, 0.02 mmol) and $Cs_2CO_3$ (33 mg, 0.10 mmol) at room temperature. The reaction mixture was degassed and stirred at 150° C. under $N_2$ overnight. LC/MS test showed that about 50% of the starting material was remaining and the desired adduct was one of the major peaks ([M+1]=525). Solid was filtered and solvent was removed. The residue was subjected to mass-triggered HPLC purification to give 32 mg of the adduct as brown oil. This was deprotected with TFA to give Example 713.

Example 721

2-amino-1-(2-(4-fluorophenyl)-8,8-dimethyl-3-(p-tolylsulfinyl)-5,6-dihydro imidazo[1,2-a]pyrazin-7(8H)-yl)ethanone

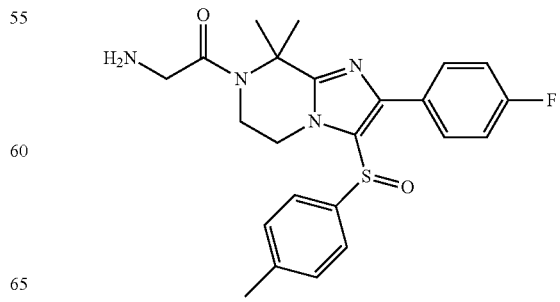

Example 721 was prepared from Reference Compound 35 in the following steps:\

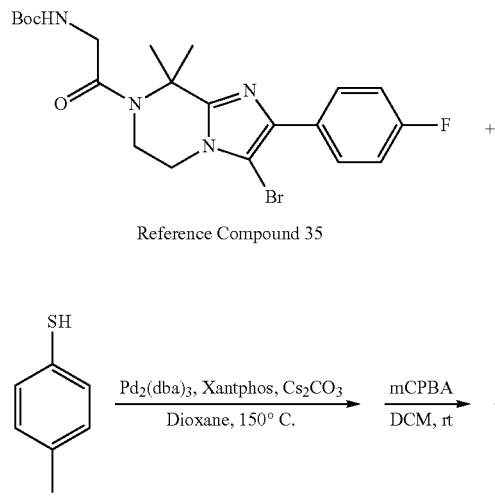

Reference Compound 35

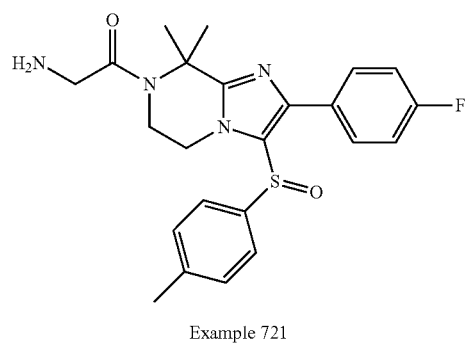

Example 721

To a solution of Reference Compound 35 (24 mg, 0.05 mmol) in 3 mL of dioxane were added 4-methylbenzenethiol (17 mg, 0.15 mmol), Pd$_2$(dba)$_3$ (9.2 mg, 0.01 mmol), XantPhos (12 mg, 0.02 mmol) and Cs$_2$CO$_3$ (33 mg, 0.10 mmol) at room temperature. The reaction mixture was degassed and stirred at 150° C. under N$_2$ overnight. LC/MS test showed that about 50% of the starting material was remaining and the desired adduct was one of the major peaks ([M+1]=525). Solid was filtered and solvent was removed. The residue was subjected to mass-triggered HPLC purification to give 32 mg of the adduct as brown oil. To a solution of the adduct (32 mg, 0.061 mmol) in 10 mL of DCM was added mCPBA (63 mg, 0.37 mmol) at 0° C. The reaction mixture was stirred at the same temperature for 20 mins allowed to warm to room temperature. LC/MS test showed that starting material was all gone and the desired sulfoxide ([M+1]=557) was the major peak. The reaction mixture was quenched with NH$_4$Cl aqueous solution and diluted with ethyl acetate. The organic solution was separated, dried and concentrated. The residue was subjected to a mass-triggered HPLC purification to give 27 mg of the desired sulfoxide as clear oil. This was deprotected with TFA to give Example 721.

Example 730

N-(3-(2-(2-(4-fluorophenyl)-3-(4-fluorophenylamino)-8,8-dimethyl-5,6-dihydroimidazo[1,2-a]pyrazin-7(8H)-yl)-2-oxoethylamino)propyl)-3-phenylpropanamide

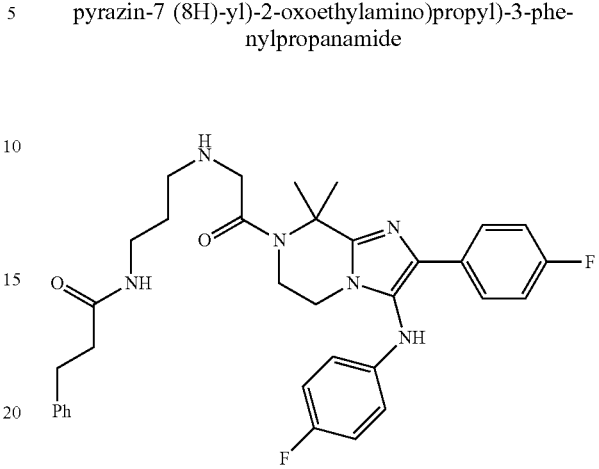

Example 730 was prepared from Reference Compound 75 by the following way:

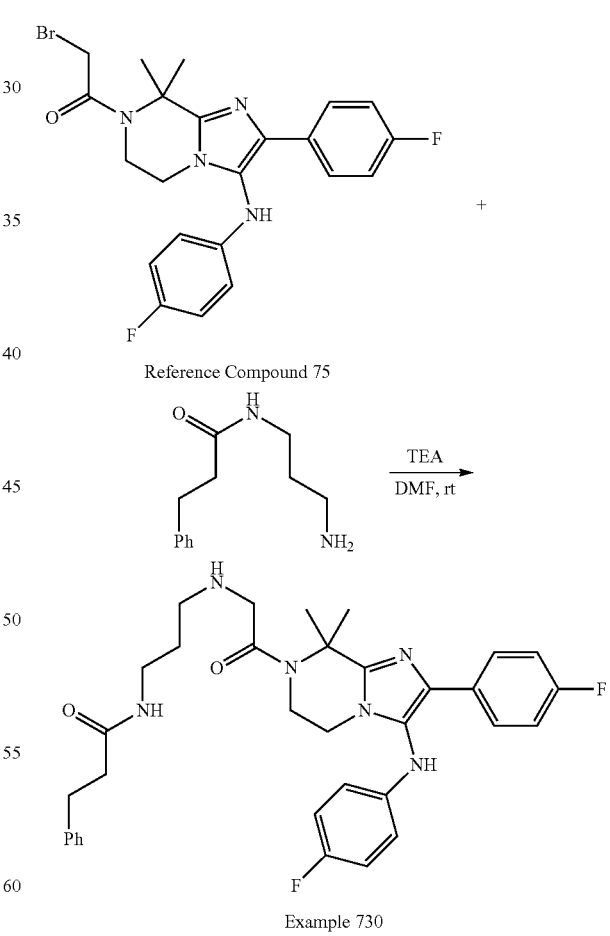

Example 730

To a solution of Reference Compound 75 (10 mg, 0.02 mmol) in 2 mL of DMF were added N-(3-aminopropyl)-3-phenylpropanamide (9 mg, 0.04 mmol) and Et$_3$N (21 µL, 0.15 mmol) at room temperature. The reaction mixture was stirred at room temperature for 3 hours. HPLC/MS test showed that the starting material was gone and the desired product ([M+1]=601) was detected as a major peak. Reaction mixture was subjected to mass-triggered HPLC purification to give 8 mg of Example 730.

By repeating the procedures described in the above examples, using appropriate starting materials, the following compounds of Formula Ia, Ib or Ic, as identified in Table 2, are obtained. Table 2 also documents the physical data obtained from the associated examples above.

TABLE 2

| Compound | Structure | Physical Data MS (m/z) and/or $^1$H NMR | EC$_{50}$ 3D7 strain (μM) | EC$_{50}$ W2 strain (μM) |
|---|---|---|---|---|
| 1 | 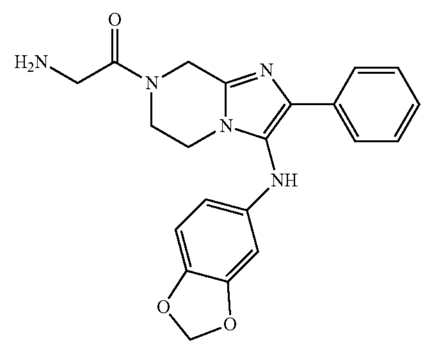 [SMILES: NCC(=O)N1CCn2c(nc(-c3ccccc3)c2Nc2ccc3c(c2)OCO3)C1] | 392.5 (M + 1) | 0.46 | 0.473 |
| 2 | 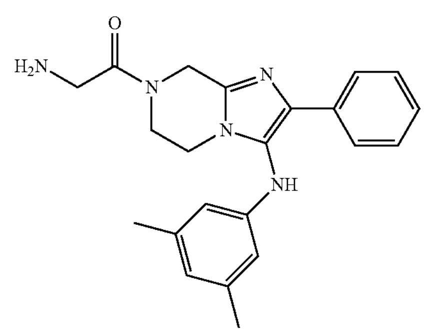 [SMILES: Cc1cc(C)cc(Nc2c(-c3ccccc3)nc3n2CCN(C(=O)CN)C3)c1] | 376.4 (M + 1)<br>$^1$H-NMR: (MeOH-d$_4$, 400 Hz) δ 7.93 (d, J = 7.6 Hz, 2H); 7.33 (t, J = 7.6 Hz, 2H); 6.97 (d, J = 7.6 Hz, 1H); 5.08 (m, 1H); 4.85-4.67 (m, 2H); 3.93-3.38 (m, 6H); 2.17-2.08 (ss, 6H) | 3.48 | 3.348 |
| 3 | 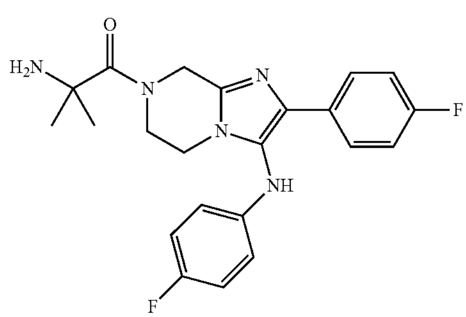 [SMILES: CC(C)(N)C(=O)N1CCn2c(nc(-c3ccc(F)cc3)c2Nc2ccc(F)cc2)C1] | 412.2 (M + 1)<br>$^1$H-NMR: (MeOH-d$_4$, 400 Hz) δ 7.70-7.67 (m, 2H); 7.22 (t, J = 8.8 Hz, 2H); 6.97 (t, J = 8.8 Hz, 2H), 6.8-6.77 (m, 2H); 5.16 (s, 2H); 4.24 (m, 2H), 4.07 (m, 2H); 1.76 (s, 6H).<br>Elemental Analysis: (compound + 2 HCl + 0.50 H$_2$O): Elemental Analysis: % C, 53.56; H, 5.31; N, 14.19 (calculated).<br>% C = 53.98/53.69; % N = 14.07/13.97; % H = 516/4.98 (experimental). | 0.02 | 0.025 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 4 | 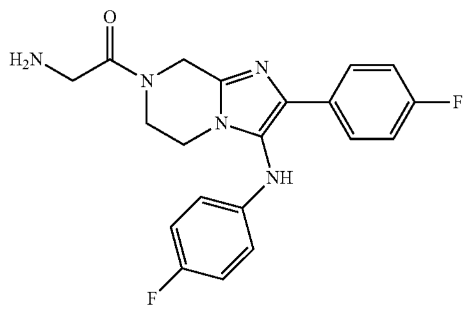 [SMILES: NCC(=O)N1CCn2c(nc(-c3ccc(F)cc3)c2Nc2ccc(F)cc2)C1] | 384.2 (M + 1) $^1$H-NMR (400 MHz, MeOH-d$_4$) δ 7.59-7.56 (m, 2H); 7.12 (t, J = 8.8 Hz, 2H); 6.86 (t, J = 8.8 Hz, 2H); 6.68-6.65 (m, 2H); 5.04-5.00 (m, 2H); 4.08-3.92 (m, 6H). | 0.02 | 0.023 |
| 5 | 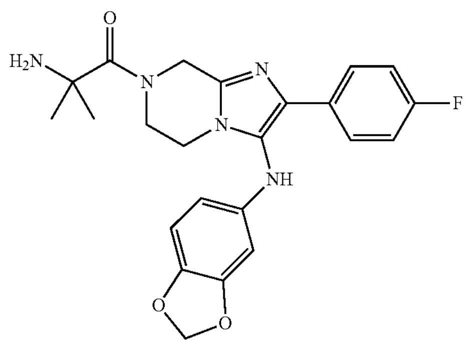 [SMILES: CC(C)(N)C(=O)N1CCn2c(nc(-c3ccc(F)cc3)c2Nc2ccc3c(c2)OCO3)C1] | 438.2 (M + 1) | 4.33 | >8.9 |
| 6 | 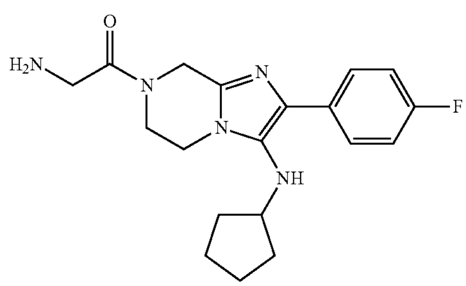 [SMILES: NCC(=O)N1CCn2c(nc(-c3ccc(F)cc3)c2NC2CCCC2)C1] | 358.4 (M + 1) | 4.38 | 4.643 |
| 7 | 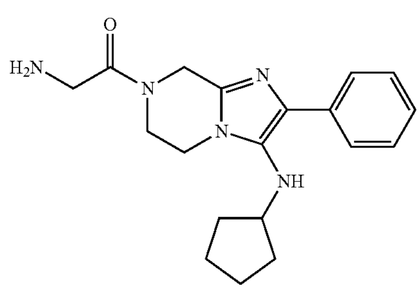 [SMILES: NCC(=O)N1CCn2c(nc(-c3ccccc3)c2NC2CCCC2)C1] | 340.4 (M + 1) | 15.82 | 7.78 |
| 8 | 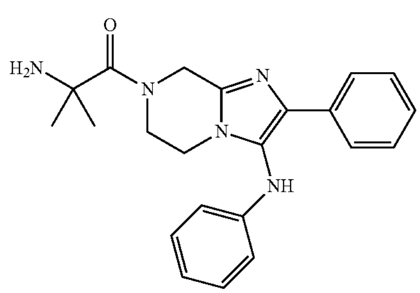 [SMILES: CC(C)(N)C(=O)N1CCn2c(nc(-c3ccccc3)c2Nc2ccccc2)C1] | 376.4 (M + 1) | 0.62 | 0.501 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 9 | 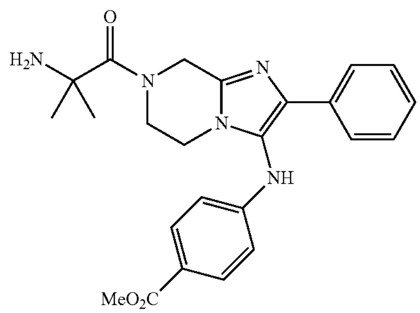 [SMILES: COC(=O)c1ccc(Nc2c(-c3ccccc3)nc3n2CCN(C(=O)C(C)(C)N)C3)cc1] | 434.4 (M + 1) | 13.84 | 3.988 |
| 10 | 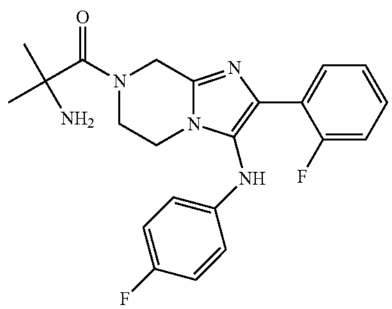 [SMILES: CC(C)(N)C(=O)N1CCn2c(nc(-c3ccccc3F)c2Nc2ccc(F)cc2)C1] | 412.4 (M + 1) | 1.39 | 1.284 |
| 11 | 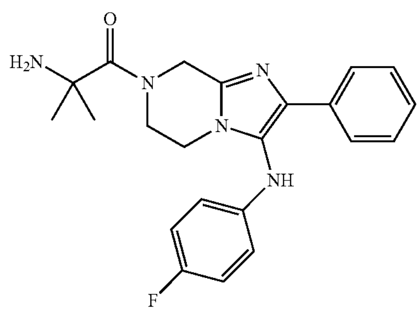 [SMILES: CC(C)(N)C(=O)N1CCn2c(nc(-c3ccccc3)c2Nc2ccc(F)cc2)C1] | 394.4 (M + 1) | 0.2 | 0.168 |
| 12 | 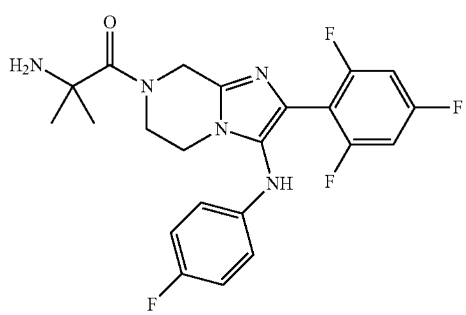 [SMILES: CC(C)(N)C(=O)N1CCn2c(nc(-c3c(F)cc(F)cc3F)c2Nc2ccc(F)cc2)C1] | 448.4 (M + 1) | 7.4 | 2.956 |
| 13 | 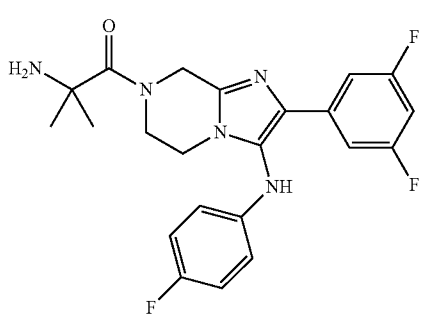 [SMILES: CC(C)(N)C(=O)N1CCn2c(nc(-c3cc(F)cc(F)c3)c2Nc2ccc(F)cc2)C1] | 430.4 (M + 1) | 0.26 | 0.137 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 14 | 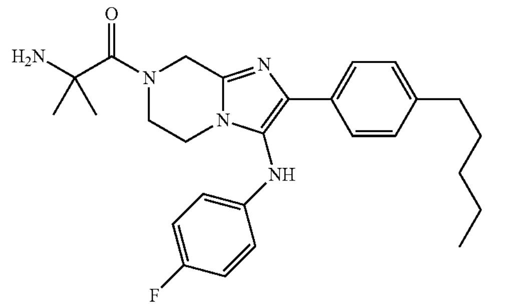 [SMILES: CCCCCc1ccc(-c2nc3n(c2Nc2ccc(F)cc2)CCN(C(=O)C(C)(C)N)C3)cc1] | 464.5 (M + 1) | 3.59 | 5.871 |
| 15 | 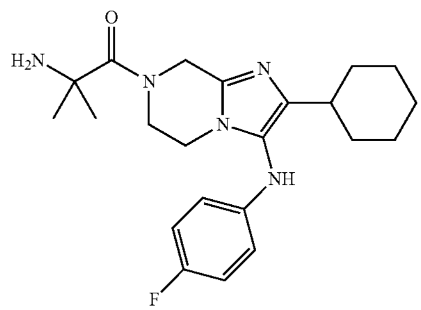 [SMILES: CC(C)(N)C(=O)N1CCn2c(nc(C3CCCCC3)c2Nc2ccc(F)cc2)C1] | 400.4 (M + 1) | 2.63 | 2.111 |
| 16 | 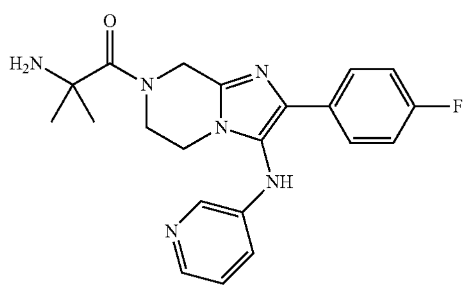 [SMILES: CC(C)(N)C(=O)N1CCn2c(nc(-c3ccc(F)cc3)c2Nc2cccnc2)C1] | 395.4 (M + 1) | 14.13 | 3.325 |
| 17 | 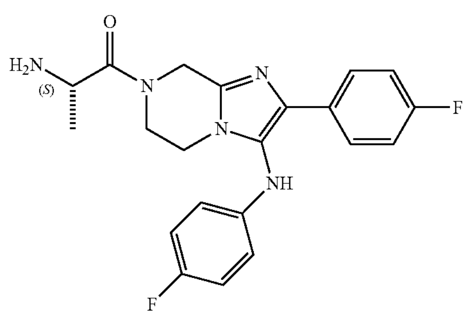 | 398.4 (M + 1) | 0.09 | 0.064 |
| 18 | 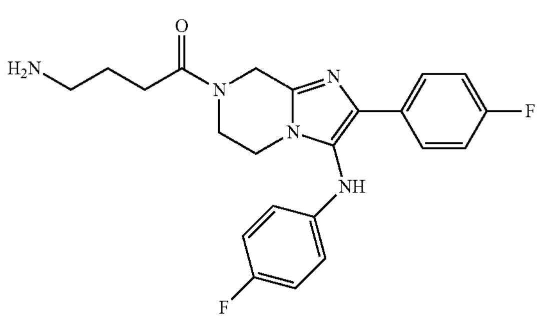 [SMILES: NCCCC(=O)N1CCn2c(nc(-c3ccc(F)cc3)c2Nc2ccc(F)cc2)C1] | 412.2 (M + 1) | 12.27 | 8.139 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 19 | 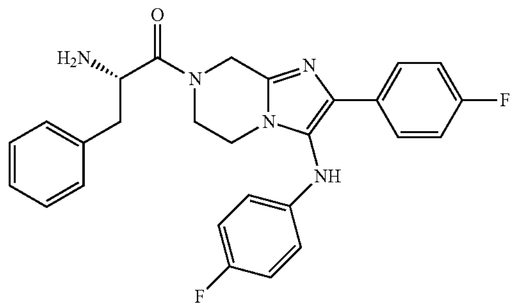 [SMILES: N[C@@H](Cc1ccccc1)C(=O)N1CCn2c(nc(-c3ccc(F)cc3)c2Nc2ccc(F)cc2)C1] | 474.2 (M + 1) | 0.07 | 0.059 |
| 20 | 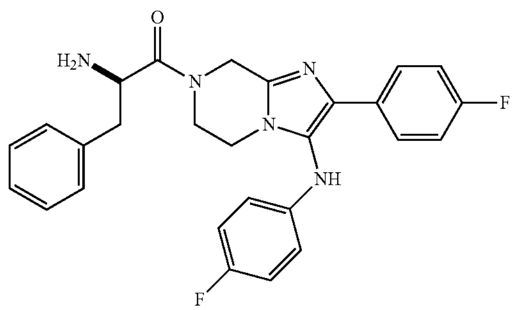 [SMILES: N[C@H](Cc1ccccc1)C(=O)N1CCn2c(nc(-c3ccc(F)cc3)c2Nc2ccc(F)cc2)C1] | 474.2 (M + 1) | 0.11 | 0.121 |
| 21 | 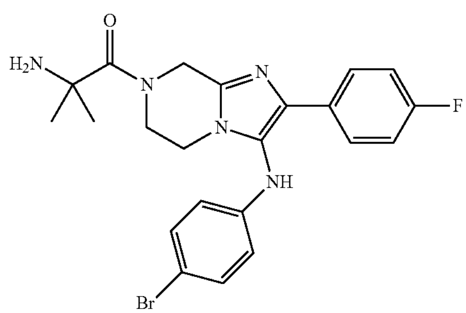 | 474.0 (M + 1) | 0.1 | 0.078 |
| 22 | 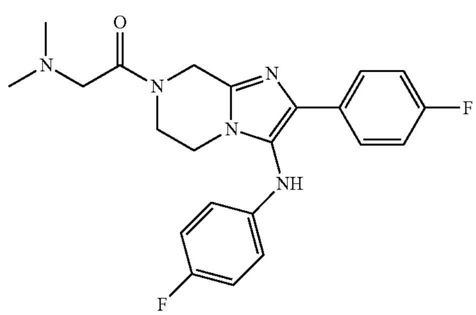 [SMILES: CN(C)CC(=O)N1CCn2c(nc(-c3ccc(F)cc3)c2Nc2ccc(F)cc2)C1] | 412.2 (M + 1) | 1.3 | 0.691 |
| 23 | 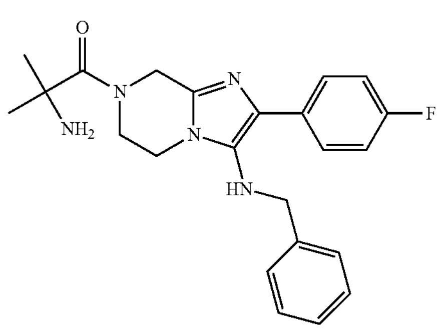 [SMILES: CC(C)(N)C(=O)N1CCn2c(nc(-c3ccc(F)cc3)c2NCc2ccccc2)C1] | 408.2 (M + 1) | >10.58 | 10.489 |

TABLE 2-continued

| Compound | Structure | Physical Data MS (m/z) and/or ¹H NMR | EC$_{50}$ 3D7 strain (μM) | EC$_{50}$ W2 strain (μM) |
| --- | --- | --- | --- | --- |
| 24 | 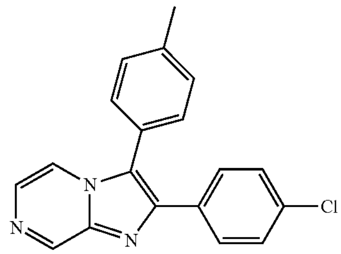 [SMILES: Cc1ccc(-c2c(-c3ccc(Cl)cc3)nc3cnccn23)cc1] | 320.3 (M + 1) | 8.92 | 2.862 |
| 25 | 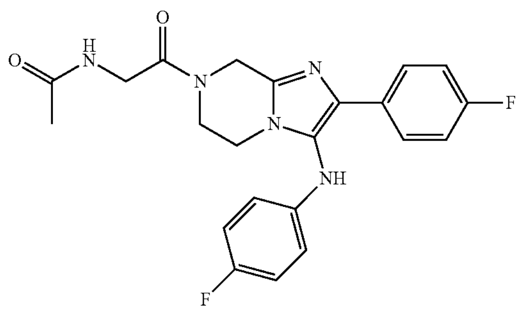 [SMILES: CC(=O)NCC(=O)N1CCn2c(nc(-c3ccc(F)cc3)c2Nc2ccc(F)cc2)C1] | 426.2 (M + 1) | >10.6 | 4.347 |
| 26 | 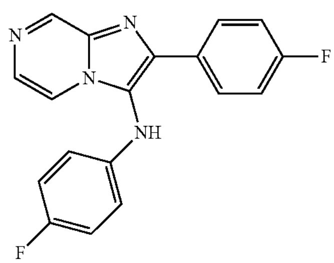 [SMILES: Fc1ccc(Nc2c(-c3ccc(F)cc3)nc3cnccn23)cc1] | 323.3 (M + 1) | >10 | 5.521 |
| 27 | 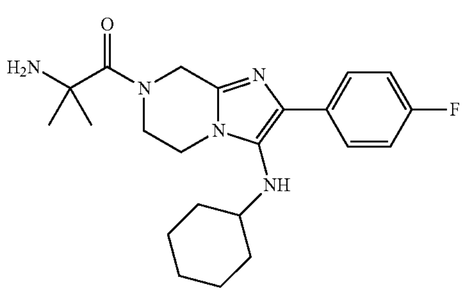 [SMILES: CC(C)(N)C(=O)N1CCn2c(nc(-c3ccc(F)cc3)c2NC2CCCCC2)C1] | 400.2 (M + 1) | 9.61 | 5.984 |
| 28 | 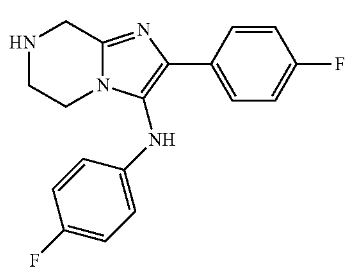 [SMILES: Fc1ccc(Nc2c(-c3ccc(F)cc3)nc3n2CCNC3)cc1] | 327.2 (M + 1)<br>¹H-NMR (300 MHz, DMSO-d$_6$): δ 7.81-7.72 (m, 2H), 7.11 (m, 2H), 6.97 (m, 2H), 6.56-6.52 (m, 2H), 3.86 (s, 2H), 3.55 (m, 2H), 3.02 (m, 2H) | 0.2 | 0.175 |

TABLE 2-continued

| Compound | Structure | Physical Data MS (m/z) and/or $^1$H NMR | EC$_{50}$ 3D7 strain (µM) | EC$_{50}$ W2 strain (µM) |
|---|---|---|---|---|
| 29 | 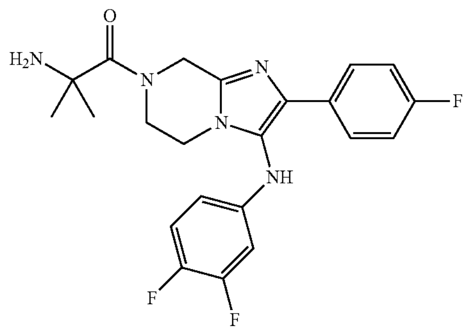 [SMILES: CC(C)(N)C(=O)N1CCn2c(nc(-c3ccc(F)cc3)c2Nc2ccc(F)c(F)c2)C1] | 430.2 (M + 1) $^1$H-NMR (400 MHz, MeOH-d$_4$) δ 7.64-7.70 (m, 1H); 6.95-6.91 (m, 3H); 6.33-6.39 (m, 1H); 6.27-6.22 (m, 1H); 4.97 (s, 2H); 4.17 (m, 2H); 3.73 (t, J = 2.8 Hz, 2H); 1.36 (s, 6H). Elemental Analysis: (compound + 2HCl + 0.40 H$_2$O): Elemental Analysis: % C, 51.85; % H, 4.91; % N, 13.74; (calculated). % C = 51.73, 51.85; % N = 13.5.13.51; % H = 4.87, 4.94 (experimental). | 0.03 | 0.036 |
| 30 | 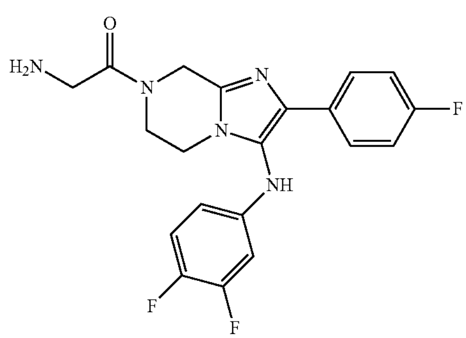 [SMILES: NCC(=O)N1CCn2c(nc(-c3ccc(F)cc3)c2Nc2ccc(F)c(F)c2)C1] | 402.1 (M + 1) $^1$H-NMR MeOH-d$_4$, (400 Hz) δ 7.64-7.59 (m, 2H); 6.96-6.89 (m, 2H); 6.38-6.34 (m, 1H); 6.27-6.23 (m, 1H); 4.74-4.63 (m, 2H); 3.94-3.41 (m, 6H). | 0.03 | 0.023 |
| 31 | 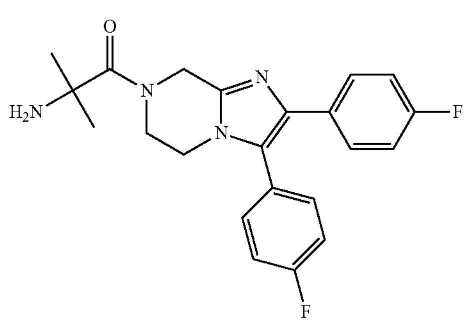 [SMILES: CC(C)(N)C(=O)N1CCn2c(nc(-c3ccc(F)cc3)c2-c2ccc(F)cc2)C1] | 397.2 (M + 1) | 13.08 | 6.893 |

TABLE 2-continued

| Compound | Structure | Physical Data MS (m/z) and/or ¹H NMR | EC$_{50}$ 3D7 strain (μM) | EC$_{50}$ W2 strain (μM) |
| --- | --- | --- | --- | --- |
| 32 | 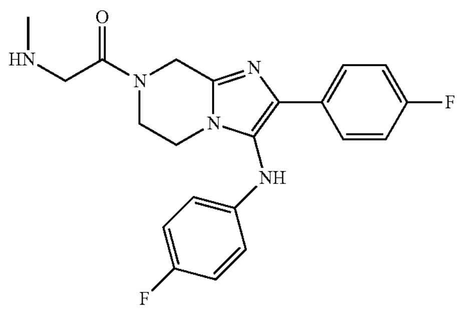 [SMILES: CNCC(=O)N1CCn2c(nc(-c3ccc(F)cc3)c2Nc2ccc(F)cc2)C1] | 398.2 (M + 1) | 0.21 | 0.219 |
| 33 | 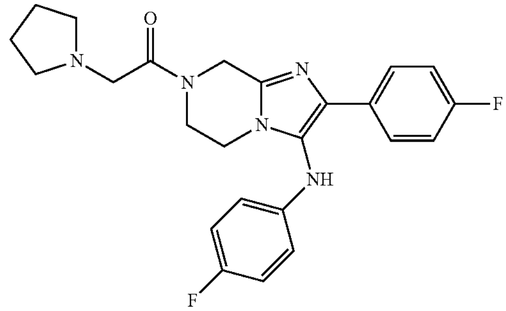 [SMILES: O=C(CN1CCCC1)N1CCn2c(nc(-c3ccc(F)cc3)c2Nc2ccc(F)cc2)C1] | 438.2 (M + 1) | 0.74 | 1.617 |
| 34 | 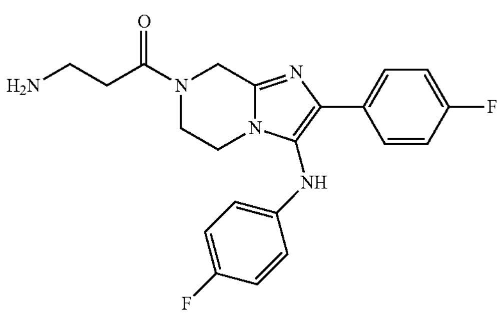 [SMILES: NCCC(=O)N1CCn2c(nc(-c3ccc(F)cc3)c2Nc2ccc(F)cc2)C1] | 398.4 (M + 1) <br> ¹H-NMR (400 MHz, MeOH-d$_4$) δ 7.64-7.60 (m, 2H); 6.93-6.87 (m, 2H); 6.80-6.75 (m, 2H); 6.49-6.45 (m, 2H); 4.71-4.70 (m, 2H); 3.85 (t, J = 5.2 Hz, 1H); 3.82 (t, J = 5.2 Hz, 1H) 3.72 (t, J = 5.2 Hz, 1H); 3.63 (t, J = 5.2 Hz, 1H); 2.83 (m, 2H); 2.54 (m, 2H). | 0.07 | 0.075 |
| 35 | 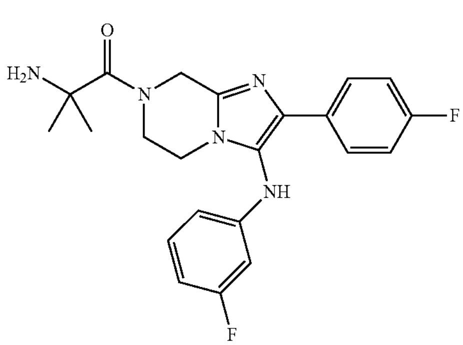 [SMILES: CC(C)(N)C(=O)N1CCn2c(nc(-c3ccc(F)cc3)c2Nc2cccc(F)c2)C1] | 412.2 (M + 1) | 0.12 | 0.105 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 36 | 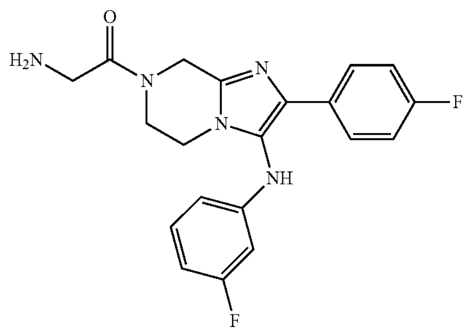 [SMILES: NCC(=O)N1CCn2c(nc(-c3ccc(F)cc3)c2Nc2cccc(F)c2)C1] | 384.4 (M + 1) | 0.05 | 0.034 |
| 37 | 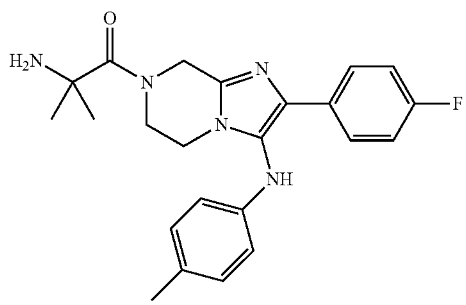 [SMILES: Cc1ccc(Nc2c(-c3ccc(F)cc3)nc3n2CCN(C(=O)C(C)(C)N)C3)cc1] | 408.2 (M + 1)<br>$^1$H-NMR: (MeOH-d$_4$, 400 Hz) δ 7.72 (m, 2H); 7.18 (t, J = 8.0 Hz, 2H); 7.02 (m, 2H), 6.7 (m, 2H); 5.19 (s, 2H); 4.07 (m, 2H), 2.21 (s, 6H); 1.77 (s, 6H) | 0.05 | 0.043 |
| 38 | 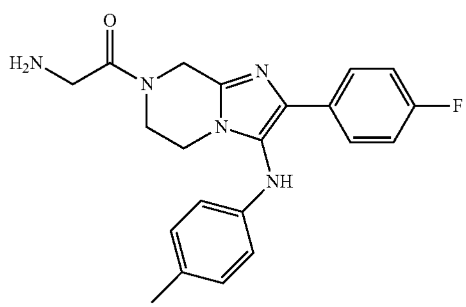 [SMILES: Cc1ccc(Nc2c(-c3ccc(F)cc3)nc3n2CCN(C(=O)CN)C3)cc1] | 380.4 (M + 1)<br>$^1$H-NMR (400 MHz, MeOH-d$_4$) δ 7.74-7.71 (m, 2H); 7.21-7.17 (m, 2H); 7.03 (t, J = 8.0 Hz, 2H); 6.67 (d, J = 8.4 Hz, 2H); 5.17-5.15 (m, 2H); 4.22-3.98 (m, 6H); 2.22 (s, 3H). | 0.01 | 0.013 |
| 39 | 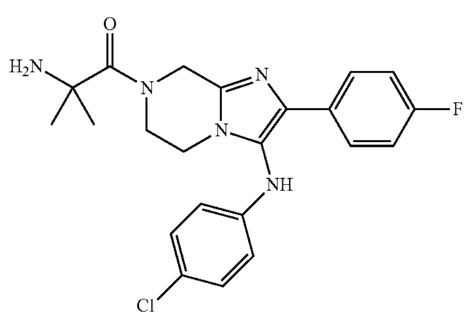 [SMILES: CC(C)(N)C(=O)N1CCn2c(nc(-c3ccc(F)cc3)c2Nc2ccc(Cl)cc2)C1] | 428.1 (M + 1)<br>$^1$H-NMR: (MeOH-d$_4$, 400 Hz) δ 7.70 (m, 2H); 7.21 (m, 4H); 6.8 (m, 2H), 4.26 (m, 2H); 4.0 (m, 2H), 1.77 (s, 6H) | 0.02 | 0.024 |
| 40 | 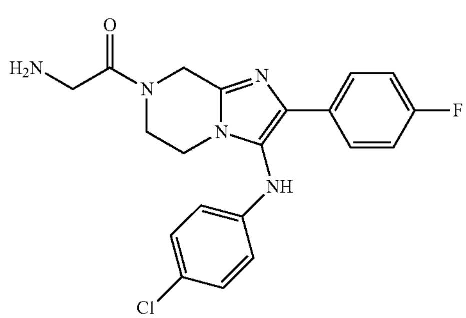 [SMILES: NCC(=O)N1CCn2c(nc(-c3ccc(F)cc3)c2Nc2ccc(Cl)cc2)C1] | 400.1 (M + 1)<br>$^1$H-NMR: (MeOH-d$_4$, 400 Hz) δ 7.59-7.56 (m, 2H); 7.15-7.09 (m, 4H); 6.68-6.65 (m, 2H), 5.05 (m, 2H); 4.04-3.87 (m, 6H). | 0.01 | 0.009 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 41 | 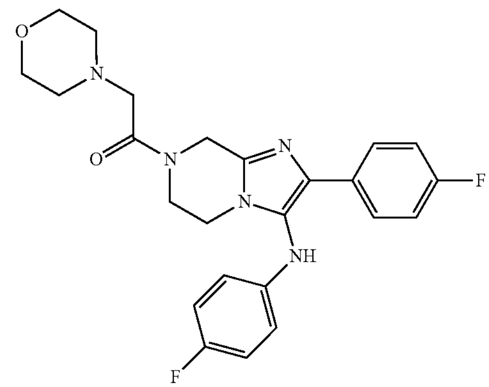 [SMILES: O=C(CN1CCOCC1)N1CCn2c(nc(-c3ccc(F)cc3)c2Nc2ccc(F)cc2)C1] | 454.2 (M + 1) | 2.65 | 1.79 |
| 42 | 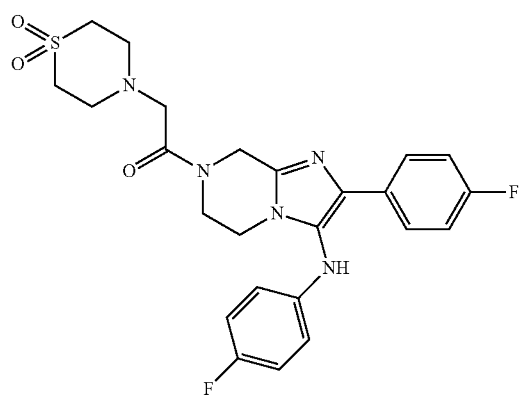 [SMILES: O=C(CN1CCS(=O)(=O)CC1)N1CCn2c(nc(-c3ccc(F)cc3)c2Nc2ccc(F)cc2)C1] | 502.3 (M + 1) | 6.1 | 4.611 |
| 43 | 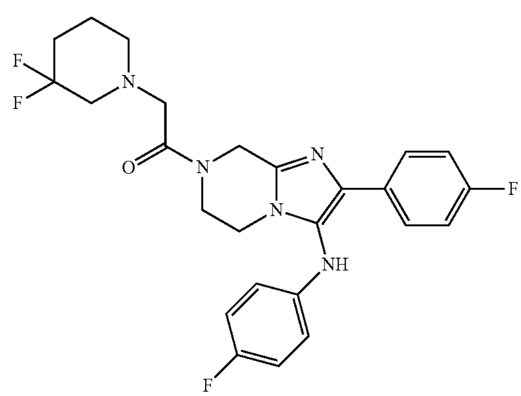 [SMILES: O=C(CN1CCCC(F)(F)C1)N1CCn2c(nc(-c3ccc(F)cc3)c2Nc2ccc(F)cc2)C1] | 488.2 (M + 1) | 0.18 | 0.149 |
| 44 | 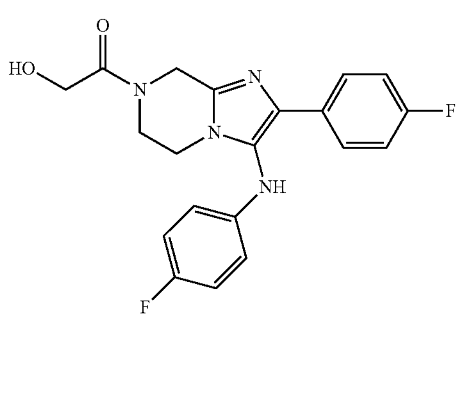 [SMILES: O=C(CO)N1CCn2c(nc(-c3ccc(F)cc3)c2Nc2ccc(F)cc2)C1] | 385.2 (M + 1) | 0.72 | 0.477 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 45 | 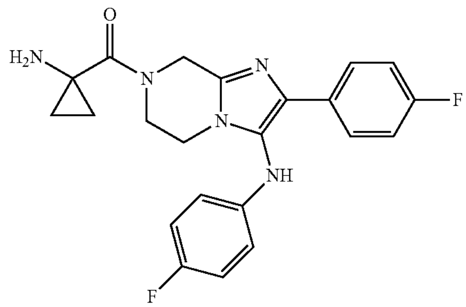 | 410.2 (M + 1) | 0.98 | 1.335 |
| 46 | 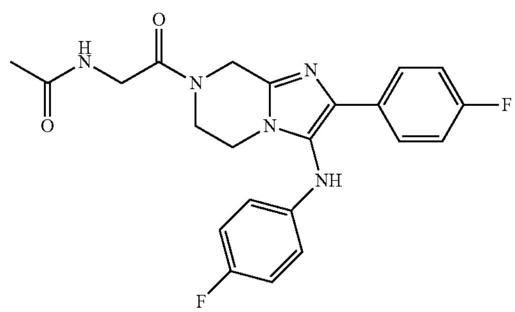 | 454.2 (M + 1) | 13.99 | 3.11 |
| 47 | 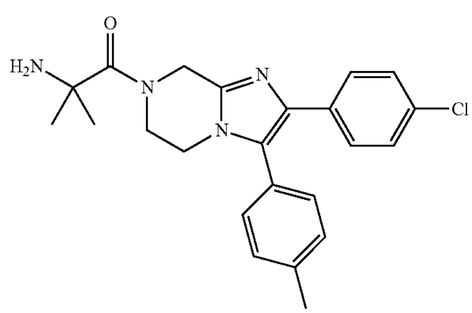 [SMILES: Cc1ccc(-c2c(-c3ccc(Cl)cc3)nc3n2CCN(C(=O)C(C)(C)N)C3)cc1] | 409.2 (M + 1) | 6.98 | 6.183 |
| 48 | 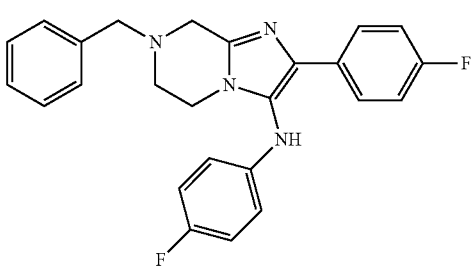 [SMILES: Fc1ccc(Nc2c(-c3ccc(F)cc3)nc3n2CCN(Cc2ccccc2)C3)cc1] | 417.2 (M + 1) | 1.84 | 1.752 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 49 | 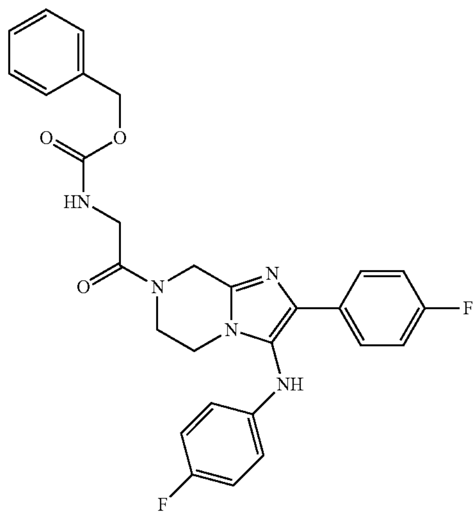 [SMILES: O=C(NCC(=O)N1CCn2c(nc(-c3ccc(F)cc3)c2Nc2ccc(F)cc2)C1)OCc1ccccc1] | 518.2 (M + 1) | 2.29 | 1.9 |
| 50 | 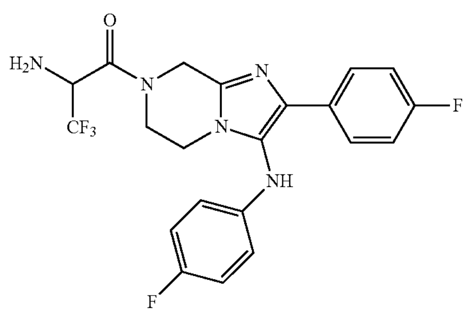 [SMILES: NC(C(=O)N1CCn2c(nc(-c3ccc(F)cc3)c2Nc2ccc(F)cc2)C1)C(F)(F)F] | 452.2 (M + 1) | 0.18 | 0.187 |
| 51 | 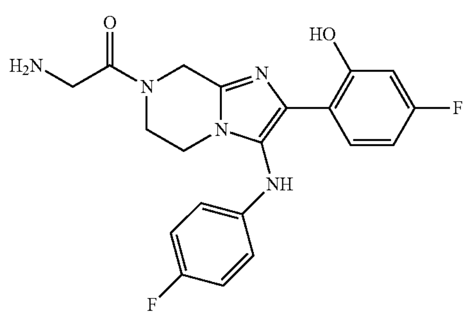 [SMILES: NCC(=O)N1CCn2c(nc(-c3ccc(F)cc3O)c2Nc2ccc(F)cc2)C1] | 400.2 (M + 1) | 0.07 | 0.062 |
| 52 | 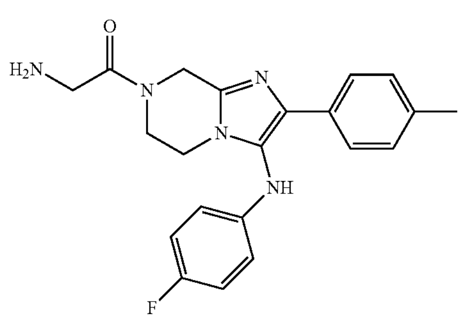 [SMILES: Cc1ccc(-c2nc3n(c2Nc2ccc(F)cc2)CCN(C(=O)CN)C3)cc1] | 380.2 (M + 1) | 3.14 | 3.36 |

TABLE 2-continued

| Compound | Structure | Physical Data MS (m/z) and/or ¹H NMR | EC$_{50}$ 3D7 strain (μM) | EC$_{50}$ W2 strain (μM) |
|---|---|---|---|---|
| 53 | 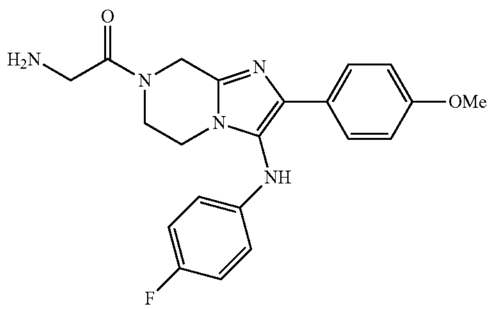 [SMILES: COc1ccc(-c2nc3n(c2Nc2ccc(F)cc2)CCN(C(=O)CN)C3)cc1] | 396.2 (M + 1) | 2.27 | 1.703 |
| 54 | 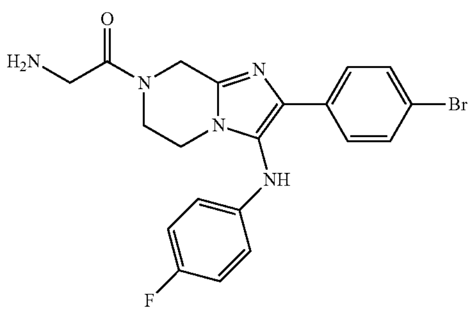 [SMILES: NCC(=O)N1CCn2c(nc(-c3ccc(Br)cc3)c2Nc2ccc(F)cc2)C1] | 445.3 (M + 1) | 1.29 | 0.764 |
| 55 | 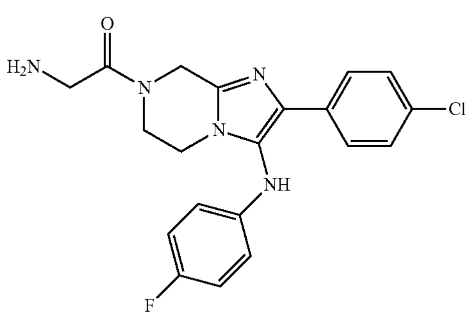 [SMILES: NCC(=O)N1CCn2c(nc(-c3ccc(Cl)cc3)c2Nc2ccc(F)cc2)C1] | 400.3 (M + 1) | 0.66 | 0.437 |
| 56 | 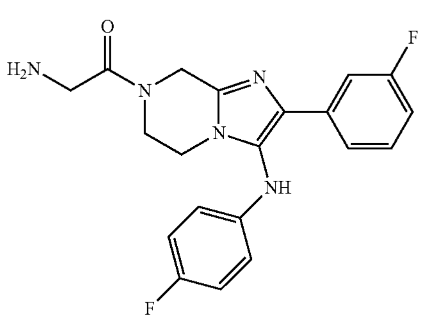 [SMILES: NCC(=O)N1CCn2c(nc(-c3cccc(F)c3)c2Nc2ccc(F)cc2)C1] | 384.2 (M + 1)<br>¹H-NMR: (MeOH-d$_4$, 400 Hz) δ 7.55-7.53 (m, 1H); 7.47-7.45 (m, 2H); 7.15 (m, 1H); 6.96-6.94 (m, 2H); 6.84-6.81 (m, 2H); 5.20 (m, 2H); 4.25-4.20 (m, 6H), 3.35 (s, NH). | 0.01 | 0.013 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 57 | 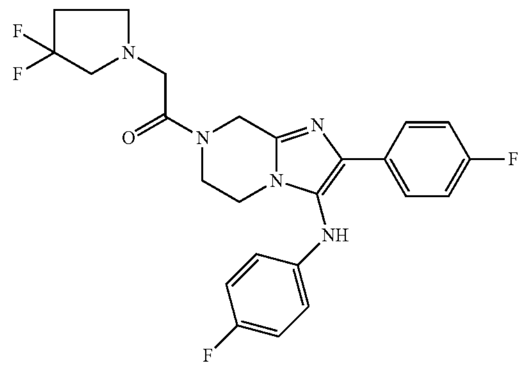 [SMILES: O=C(CN1CCC(F)(F)C1)N1CCn2c(nc(-c3ccc(F)cc3)c2Nc2ccc(F)cc2)C1] | 474.2 (M + 1) | 0.31 | 0.294 |
| 58 | 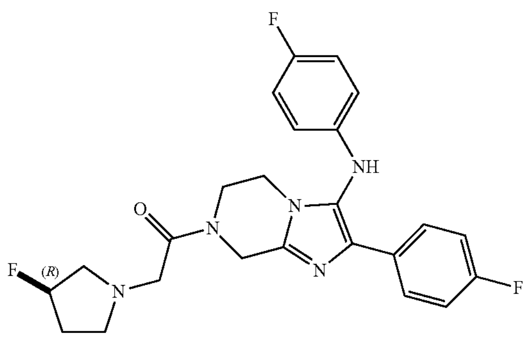 | 456.2 (M + 1) | 0.47 | 0.28 |
| 59 | 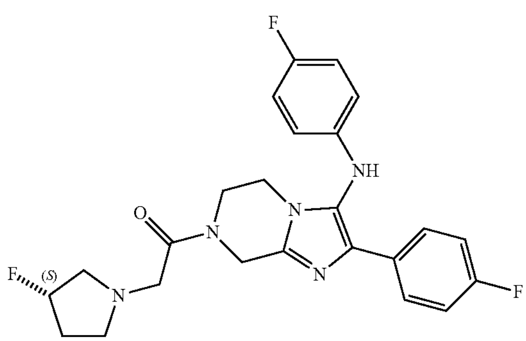 | 456.2 (M + 1) | 1.09 | 0.735 |
| 60 | 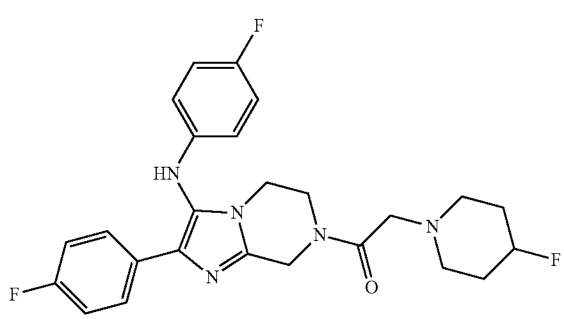 [SMILES: O=C(CN1CCC(F)CC1)N1CCn2c(nc(-c3ccc(F)cc3)c2Nc2ccc(F)cc2)C1] | 470.2 (M + 1) | 2.46 | 2.129 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 61 | 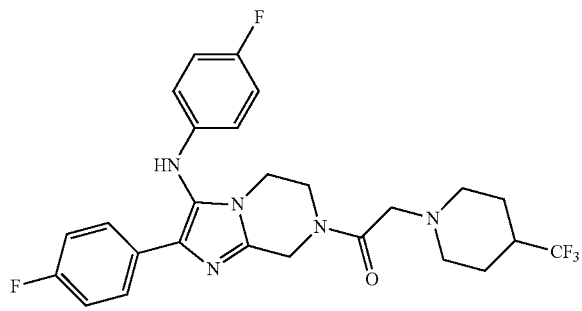 [SMILES: O=C(CN1CCC(C(F)(F)F)CC1)N1CCn2c(nc(-c3ccc(F)cc3)c2Nc2ccc(F)cc2)C1] | 520.2 (M + 1) | 9.24 | |
| 62 | 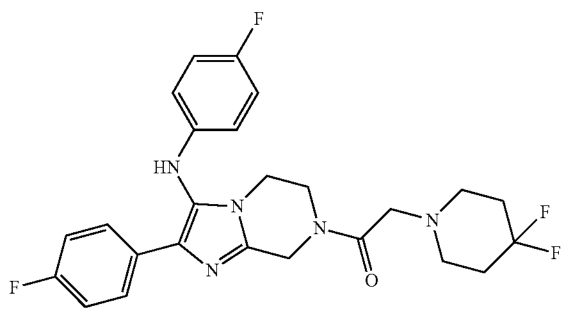 [SMILES: O=C(CN1CCC(F)(F)CC1)N1CCn2c(nc(-c3ccc(F)cc3)c2Nc2ccc(F)cc2)C1] | 488.2 (M + 1) | 4.74 | 4.738 |
| 63 | 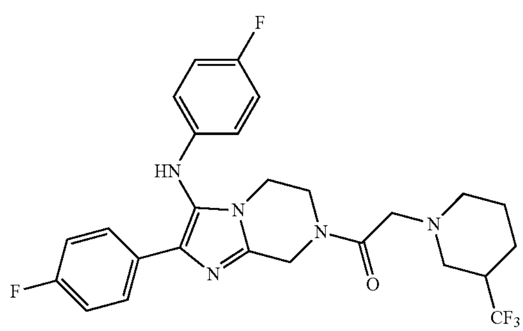 [SMILES: O=C(CN1CCCC(C(F)(F)F)C1)N1CCn2c(nc(-c3ccc(F)cc3)c2Nc2ccc(F)cc2)C1] | 520.2 (M + 1) | 1.95 | 1.606 |
| 64 | 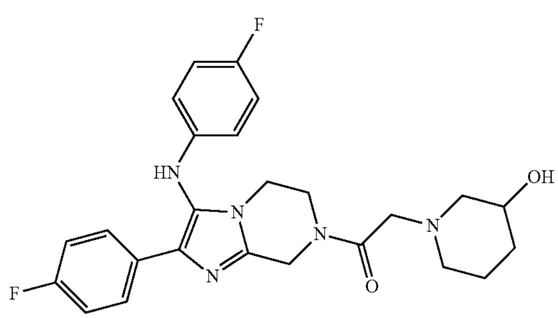 [SMILES: O=C(CN1CCCC(O)C1)N1CCn2c(nc(-c3ccc(F)cc3)c2Nc2ccc(F)cc2)C1] | 468.2 (M + 1) | 9.37 | 6.465 |

TABLE 2-continued

| Compound | Structure | Physical Data MS (m/z) and/or ¹H NMR | EC$_{50}$ 3D7 strain (μM) | EC$_{50}$ W2 strain (μM) |
| --- | --- | --- | --- | --- |
| 65 | 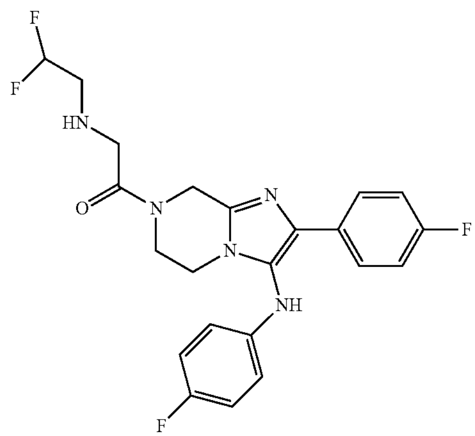 [SMILES: O=C(CNCC(F)F)N1CCn2c(nc(-c3ccc(F)cc3)c2Nc2ccc(F)cc2)C1] | 448.2 (M + 1) | 0.47 | 0.509 |
| 66 | 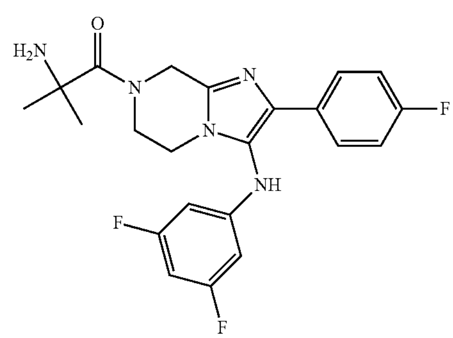 [SMILES: CC(C)(N)C(=O)N1CCn2c(nc(-c3ccc(F)cc3)c2Nc2cc(F)cc(F)c2)C1] | 430.2 (M + 1) | 0.22 | 0.244 |
| 67 | 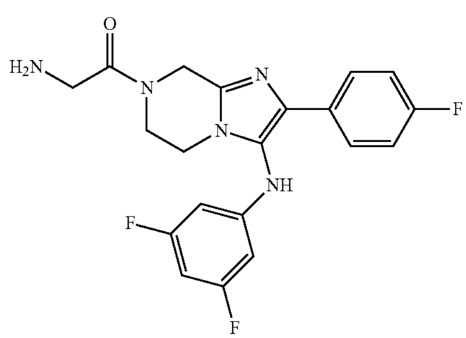 [SMILES: NCC(=O)N1CCn2c(nc(-c3ccc(F)cc3)c2Nc2cc(F)cc(F)c2)C1] | 402.2 (M + 1) | 0.19 | 0.197 |
| 68 | 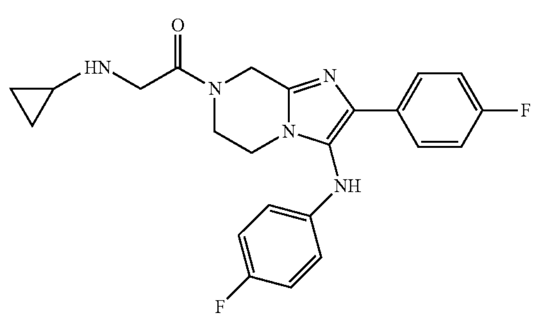 [SMILES: O=C(CNC1CC1)N1CCn2c(nc(-c3ccc(F)cc3)c2Nc2ccc(F)cc2)C1] | 424.2 (M + 1) ¹H-NMR: (MeOH-d$_4$, 400 Hz) δ 7.71-7.67 (m, 2H); 7.22 (t, J = 8.8 Hz, 2H); 6.97-6.95 (m, 2H), 6.8-6.77 (m, 2H); 5.15 (s, 2H); 4.19-3.99 (m, 4H), 3.74-3.58 (m, 2H); 2.9-2.82 (m, 1H); 0.98-0.97 (m, 4H). | 0.15 | 0.264 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 69 | 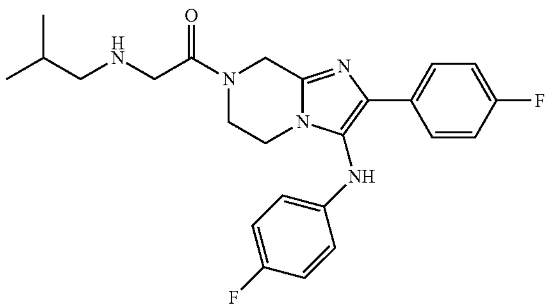 [SMILES: CC(C)CNCC(=O)N1CCn2c(nc(-c3ccc(F)cc3)c2Nc2ccc(F)cc2)C1] | 440.2 (M + 1) | 0.08 | 0.094 |
| 70 | 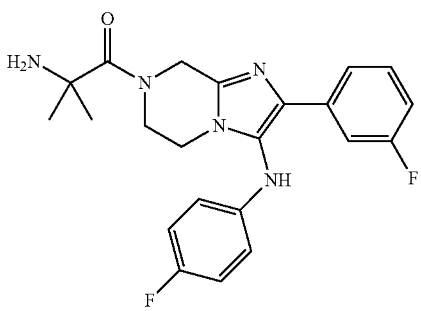 [SMILES: CC(C)(N)C(=O)N1CCn2c(nc(-c3cccc(F)c3)c2Nc2ccc(F)cc2)C1] | 412.2 (M + 1) $^1$H-NMR: (MeOH-d$_4$, 400 Hz) δ 7.50-7.48 (m, 2H); 7.44-7.40 (m, 2H); 7.18 (m, 1H); 6.98 (t, J = 8.8 Hz, 2H); 6.82-6.79 (m, 2H); 5.18 (m, 2H); 4.25 (t, J = 4.8 Hz, 2H); 4.07 (t, J = 4.8 Hz, 2H); 1.76 (s, 6H) | 0.05 | 0.079 |
| 71 | 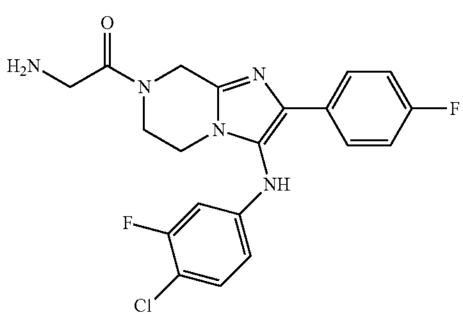 [SMILES: NCC(=O)N1CCn2c(nc(-c3ccc(F)cc3)c2Nc2ccc(Cl)c(F)c2)C1] | 418.1 (M + 1) $^1$H-NMR: (MeOH-d$_4$, 400 Hz) δ 7.7 (m, 2H); 7.28-7.22 (m, 2H); 6.71 (m, 1H); 6.64 (m, 1H); 5.16 (s, 2H); 4.18-4.01 (m, 6H) | 0.0 | 0.004 |
| 72 | 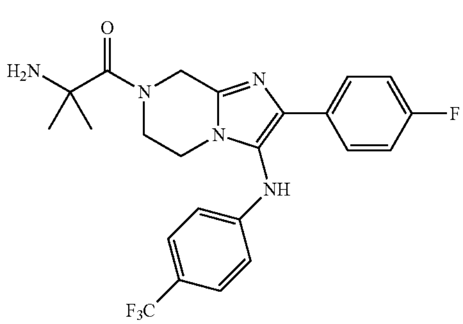 [SMILES: CC(C)(N)C(=O)N1CCn2c(nc(-c3ccc(F)cc3)c2Nc2ccc(C(F)(F)F)cc2)C1] | 462.2 (M + 1) | 0.95 | 0.589 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 73 | 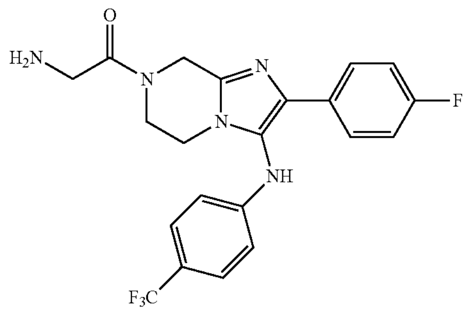 [SMILES: NCC(=O)N1CCn2c(nc(-c3ccc(F)cc3)c2Nc2ccc(C(F)(F)F)cc2)C1] | 434.2 (M + 1) | 0.08 | 0.059 |
| 74 | 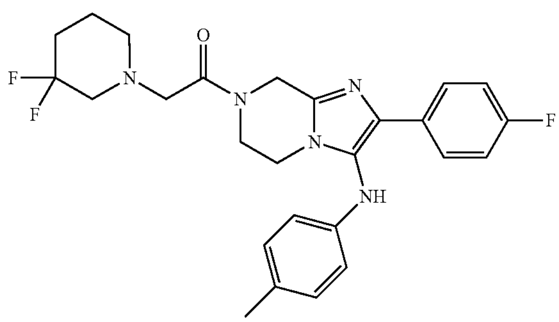 [SMILES: Cc1ccc(Nc2c(-c3ccc(F)cc3)nc3n2CCN(C(=O)CN2CCCC(F)(F)C2)C3)cc1] | 484.2 (M + 1) | 0.07 | 0.067 |
| 75 | 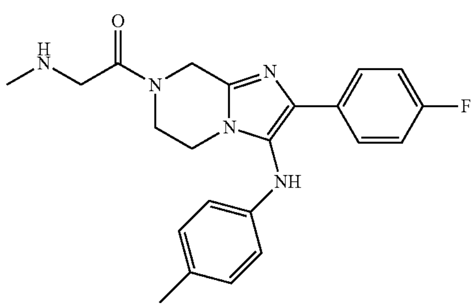 [SMILES: CNCC(=O)N1CCn2c(nc(-c3ccc(F)cc3)c2Nc2ccc(C)cc2)C1] | 394.2 (M + 1) | 0.25 | 0.19 |
| 76 | 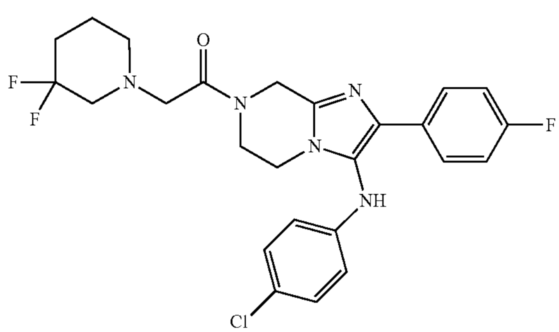 [SMILES: O=C(CN1CCCC(F)(F)C1)N1CCn2c(nc(-c3ccc(F)cc3)c2Nc2ccc(Cl)cc2)C1] | 504.2 (M + 1) | 0.06 | 0.061 |
| 77 | 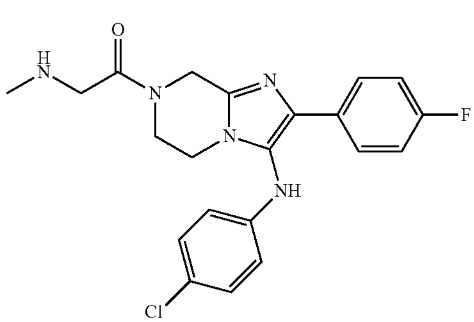 [SMILES: CNCC(=O)N1CCn2c(nc(-c3ccc(F)cc3)c2Nc2ccc(Cl)cc2)C1] | 414.2 (M + 1) | 0.06 | 0.039 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 78 | 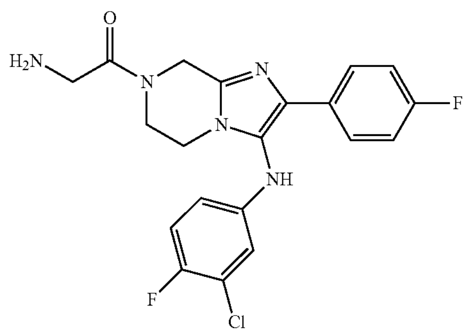 | 418.0 (M + 1) $^1$H-NMR (400 MHz, MeOH-d$_4$) δ 7.72-7.68 (m, 2H); 7.23 (t, J = 8.8 Hz, 2H); 7.08 (t, J = 8.8 Hz, 1H); 6.91 (dd, J = 3.2 Hz, J = 5.8 Hz, 1H); 5.16 (m, 2H); 4.22-4.05 (m, 6H) | 0.01 | |
| 79 | 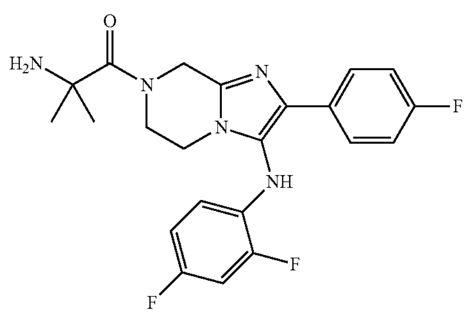 [SMILES: CC(C)(N)C(=O)N1CCn2c(nc(-c3ccc(F)cc3)c2Nc2ccc(F)cc2F)C1] | 430.2 (M + 1) | 0.11 | 0.09 |
| 80 | 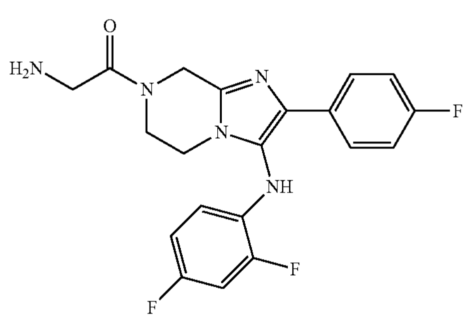 [SMILES: NCC(=O)N1CCn2c(nc(-c3ccc(F)cc3)c2Nc2ccc(F)cc2F)C1] | 402.2 (M + 1) | 0.06 | 0.063 |
| 81 | 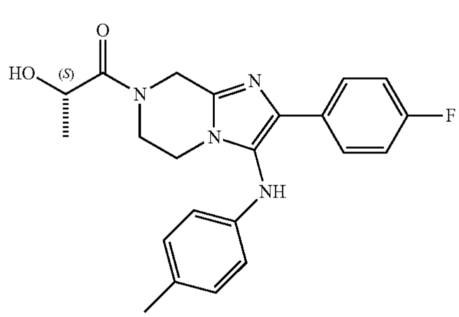 | 395.2 (M + 1) | 0.3 | 0.449 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 82 | 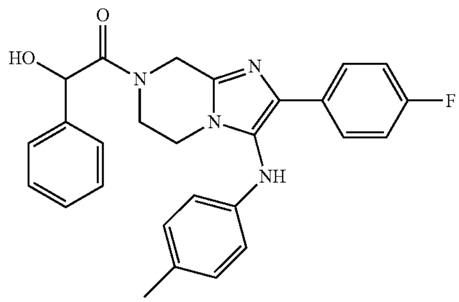 [SMILES: Cc1ccc(Nc2c(-c3ccc(F)cc3)nc3n2CCN(C(=O)C(O)c2ccccc2)C3)cc1] | 457.2 (M + 1) | 0.0 | 0.007 |
| 83 | 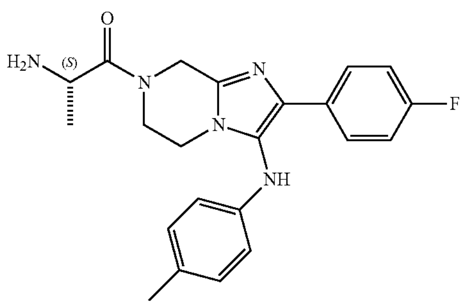 | 394.2 (M + 1) | 0.08 | 0.131 |
| 84 | 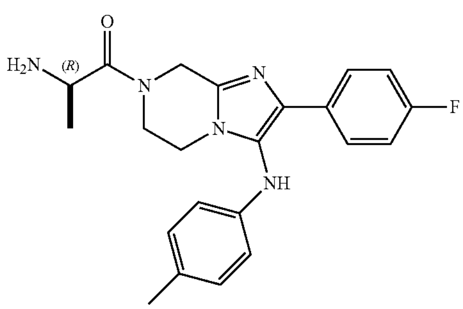 | 394.2 (M + 1) | 0.05 | 0.074 |
| 85 | 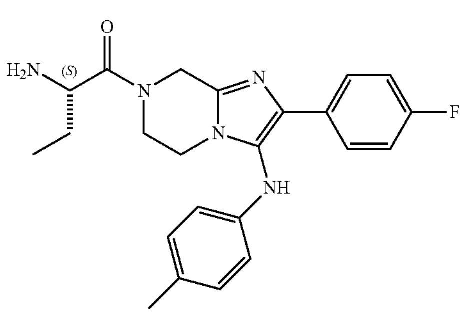 | 408.2 (M + 1) | 0.02 | 0.031 |

TABLE 2-continued

| Compound | Structure | Physical Data MS (m/z) and/or ¹H NMR | EC$_{50}$ 3D7 strain (μM) | EC$_{50}$ W2 strain (μM) |
|---|---|---|---|---|
| 86 | 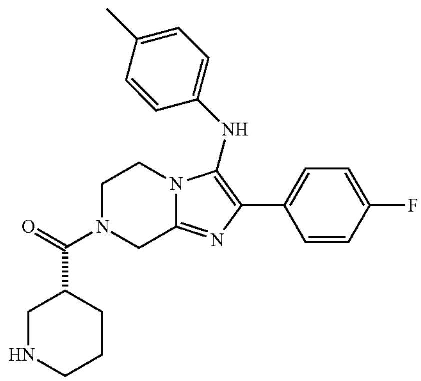 | 434.2 (M + 1) | 0.71 | 0.755 |
| 87 | 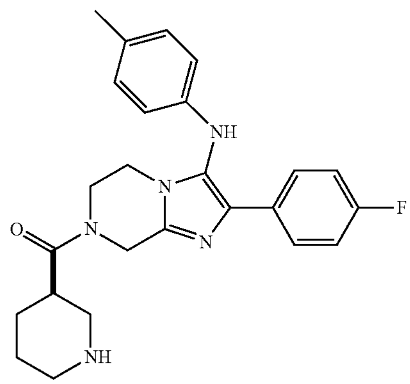 | 434.2 (M + 1) ¹H-NMR (400 MHz, MeOH-d$_4$) δ 7.71-7.68 (m, 2H); 7.21 (t, J = 8.8 Hz, 2H); 7.03 (d, J = 8.0 Hz, 2H) 6.67 (d, J = 8.4 Hz, 2H); 5.35-4.96 (m, 2H); 4.37-3.88 (m, 4H); 3.49-3.31 (m, 3H); 3.25-3.13 (m, 2H); 2.23 (s, 3H); 2.11-1.8 (m, 4H) | 0.02 | 0.012 |
| 88 | 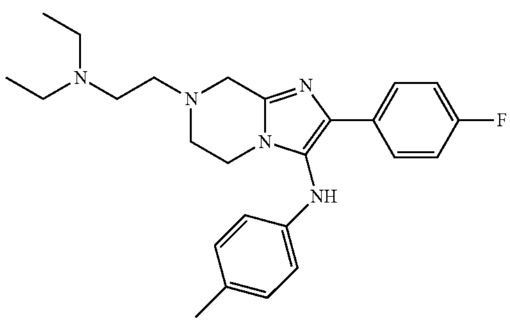 [SMILES: CCN(CC)CCN1CCn2c(nc(-c3ccc(F)cc3)c2Nc2ccc(C)cc2)C1] | 422.6 (M + 1) | 0.15 | 0.081 |
| 89 | 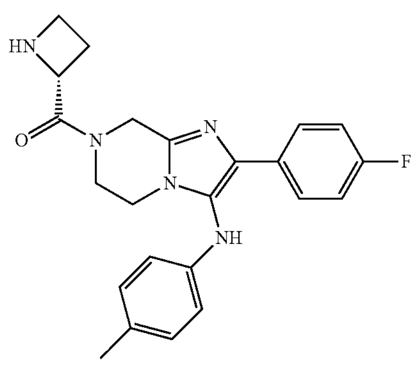 [SMILES: Cc1ccc(Nc2c(-c3ccc(F)cc3)nc3n2CCN(C(=O)[C@H]2CCN2)C3)cc1] | 406.2 (M + 1) | 0.05 | 0.073 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 90 | 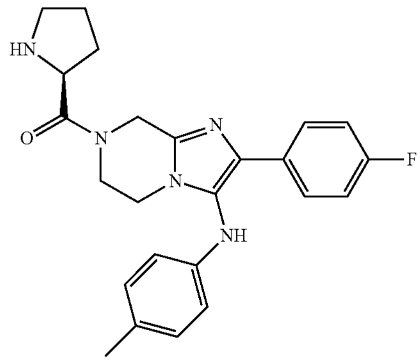 [SMILES: Cc1ccc(Nc2c(-c3ccc(F)cc3)nc3n2CCN(C(=O)[C@@H]2CCCN2)C3)cc1] | 420.2 (M + 1) | 0.65 | 0.6 |
| 91 | 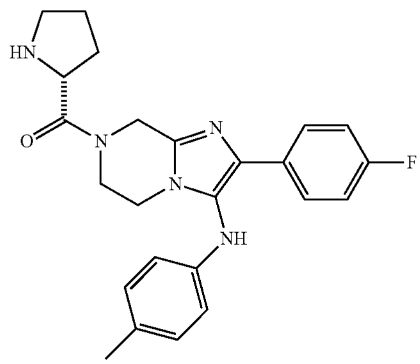 | 420.2 (M + 1) | 0.12 | 0.154 |
| 92 | 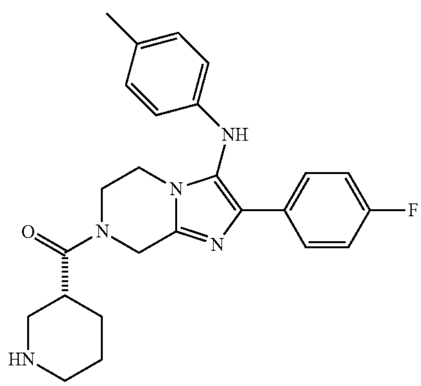 | 434.2 (M + 1) | 1.3 | 1.484 |
| 93 | 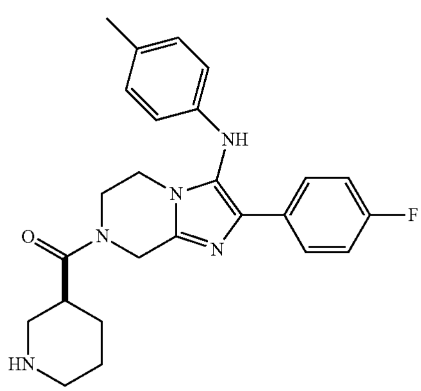 | 434.2 (M + 1) | 1.67 | 1.512 |

TABLE 2-continued

| Compound | Structure | Physical Data MS (m/z) and/or ¹H NMR | EC$_{50}$ 3D7 strain (μM) | EC$_{50}$ W2 strain (μM) |
|---|---|---|---|---|
| 94 | 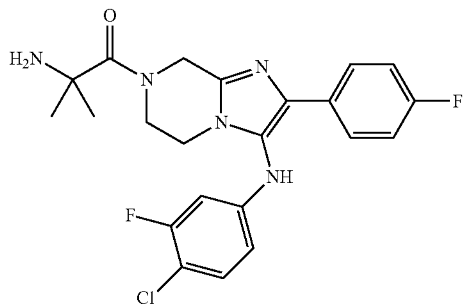 [SMILES: CC(C)(N)C(=O)N1CCn2c(nc(-c3ccc(F)cc3)c2Nc2ccc(Cl)c(F)c2)C1] | 446.2 (M + 1) ¹H-NMR: (MeOH-d$_4$, 400 Hz) δ 7.59-7.56 (m, 2H); 7.2-7.11 (m, 3H); 6.6-6.57 (m, 2H); 5.04 (s, 2H); 4.14 (m, 2H); 3.97 (m, 2H); 1.69 (s, 6H). | 0.04 | 0.052 |
| 95 | 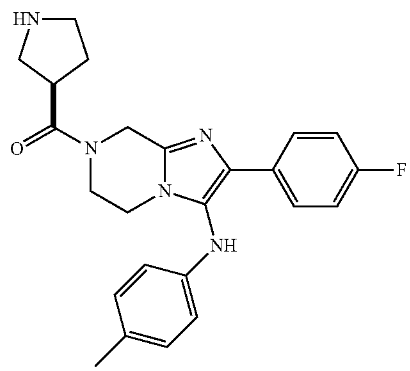 | 420.2 (M + 1) | 1.54 | 0.707 |
| 96 | 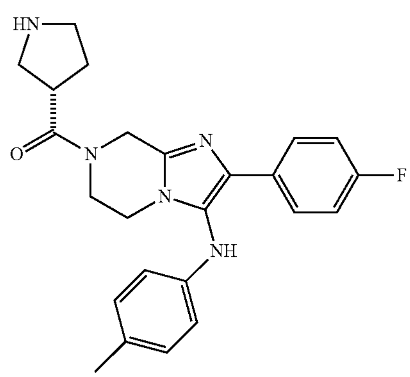 | 420.2 (M + 1) | 0.58 | 0.321 |
| 97 | 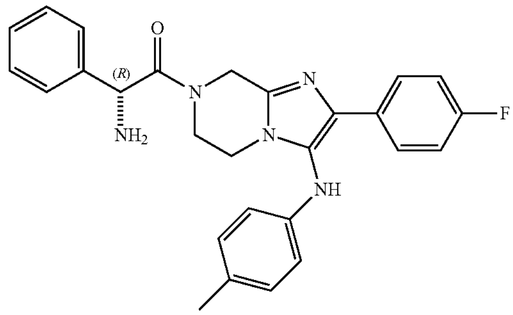 | 456.2 (M + 1) | 0.04 | 0.021 |

TABLE 2-continued
| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 98 | 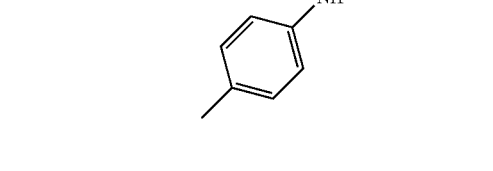 | 456.2 (M + 1) | 0.01 | 0.008 |
| 99 | 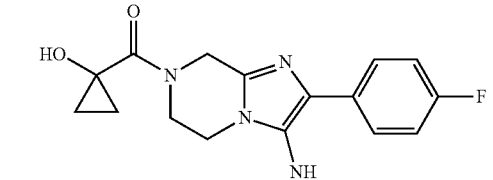 | 407.2 (M + 1) | 0.81 | 0.658 |
| 100 | 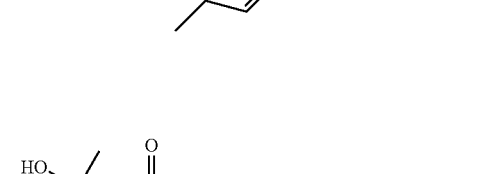 | 423.2 (M + 1) $^1$H-NMR (400 MHz, MeOH-d$_4$) δ 7.78-7.68 (m, 2H); 7.16 (t, J = 8.8 Hz, 2H); 7.02 (d, J = 8.0 Hz, 2H) 6.64-6.60 (m, 2H); 5.17-5.07 (m, 2H); 4.13-3.86 (m, 4H); 2.7 (s, 2H); 2.22 (2, 3H); 1.32 (s, 6H). | 0.15 | 0.143 |
| 101 | 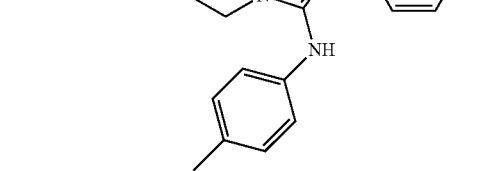 | 493.6 (M + 1) | 5.09 | 4.373 |

TABLE 2-continued
| Compound | Structure | Physical Data MS (m/z) and/or ¹H NMR | EC₅₀ 3D7 strain (μM) | EC₅₀ W2 strain (μM) |
|---|---|---|---|---|
| 102 | 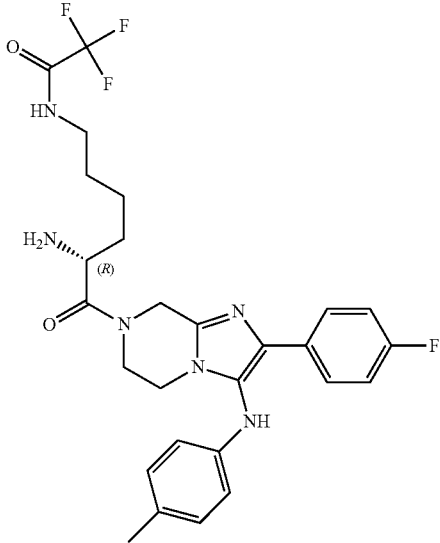 | 547.6 (M + 1) | 0.65 | 0.426 |
| 103 | 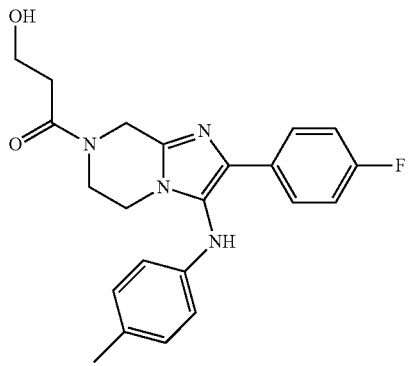 [SMILES: Cc1ccc(Nc2c(-c3ccc(F)cc3)nc3n2CCN(C(=O)CCO)C3)cc1] | 395.2 (M + 1) | 1.02 | |
| 104 | 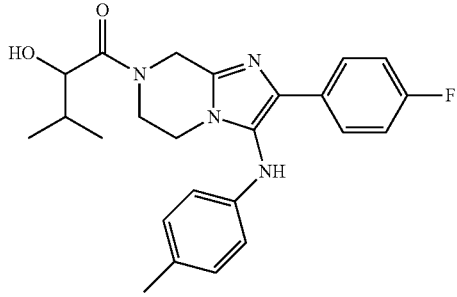 [SMILES: Cc1ccc(Nc2c(-c3ccc(F)cc3)nc3n2CCN(C(=O)C(O)C(C)C)C3)cc1] | 423.2 (M + 1) <br> ¹H-NMR: (MeOH-d₄, 400 Hz) δ 7.76-7.73 (m, 2H); 7.02-6.95 (m, 4H); 6.49 (m, 2H), 4.96-4.80 (m, 2H); 4.25-4.08 (m, 1H); 3.83-3.73 (m, 2H); 3.76-3.73 (m, 2H); 2.20 (s, 3H); 1.98 (m, 1H); 0.96 (t, J = 6.8 Hz, 6H). | 0.01 | 0.007 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 105 | 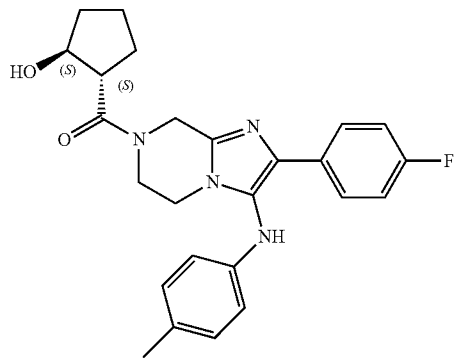 | 435.2 (M + 1) | 0.85 | |
| 106 | 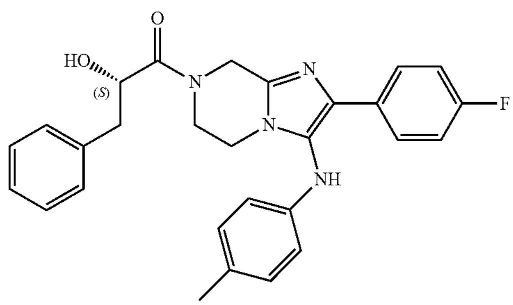 | 471.2 (M + 1)<br>$^1$H-NMR: (MeOH-d$_4$, 400 Hz) δ 7.64-7.59 (m, 2H); 7.13-6.85 (m, 9 H); 6.83 (t, J = 8.4 Hz, 2H); 4.73-4.35 (m, 3H); 3.94-3.49 (m, 4H); 4.03-3.87 (m, 2H); 2.93-2.88 (m, 2H); 2.11 (s, 3H). | 0.0 | 0.004 |
| 107 | 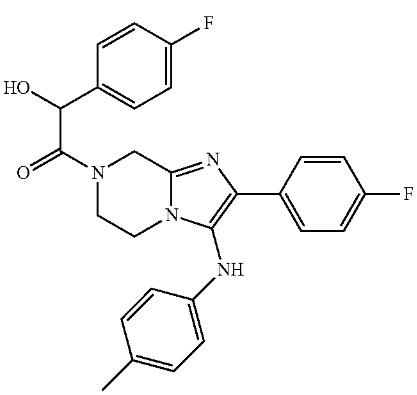 [SMILES: Cc1ccc(Nc2c(-c3ccc(F)cc3)nc3n2CCN(C(=O)C(O)c2ccc(F)cc2)C3)cc1] | 475.2 (M + 1) | 0.01 | 0.01 |
| 108 | 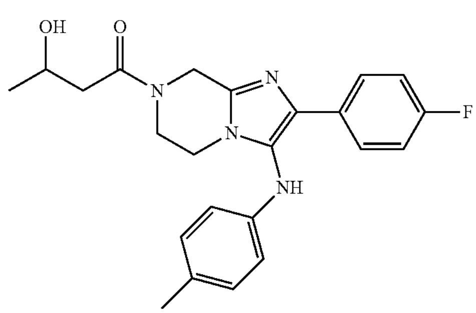 [SMILES: Cc1ccc(Nc2c(-c3ccc(F)cc3)nc3n2CCN(C(=O)CC(C)O)C3)cc1] | 409.2 (M + 1) | 0.96 | |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 109 | 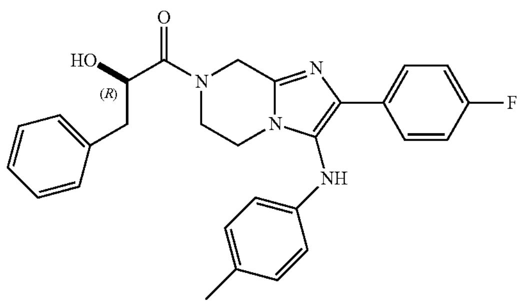 | 471.2 (M + 1) | 0.04 | |
| 110 | 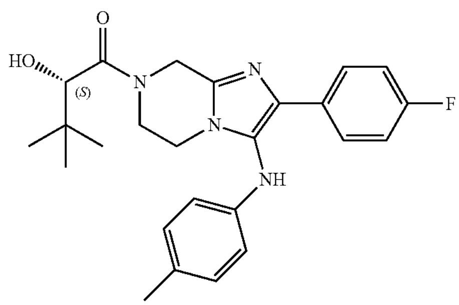 | 437.2 (M + 1) $^1$H-NMR: (MeOH-d$_4$, 400 Hz) δ 7.65-7.62 (m, 2H); 6.92-6.84 (m, 4 H); 6.49 (m, 2H), 6.39 (t, J = 8.8 Hz, 2H).4.95-4.62 (m, 2H); 4.18 (d, J = 8.4 Hz, 1H); 4.03-3.87 (m, 2H); 3.74-3.64 (m, 2H); 2.1 (s, 3H); 0.9 (d, J = 7.2 Hz, 9H). | 0.02 | 0.015 |
| 111 | 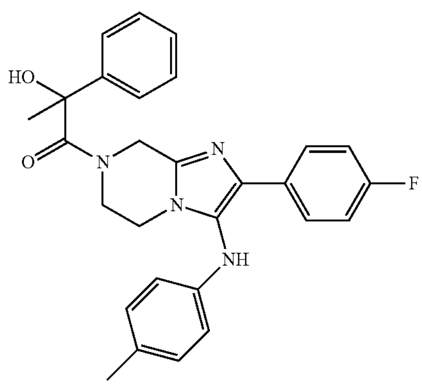 [SMILES: Cc1ccc(Nc2c(-c3ccc(F)cc3)nc3n2CCN(C(=O)C(C)(O)c2ccccc2)C3)cc1] | 471.2 (M + 1) | 0.02 | |
| 112 | 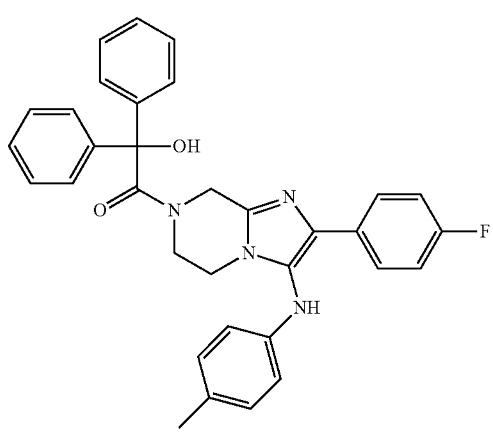 [SMILES: Cc1ccc(Nc2c(-c3ccc(F)cc3)nc3n2CCN(C(=O)C(O)(c2ccccc2)c2ccccc2)C3)cc1] | 533.6 (M + 1) | 1.43 | |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 113 | 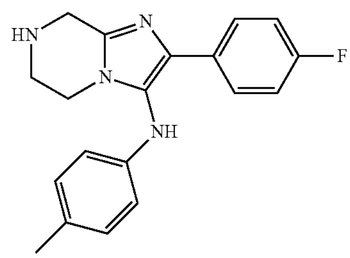 [SMILES: Cc1ccc(Nc2c(-c3ccc(F)cc3)nc3n2CCNC3)cc1] | 323.2 (M + 1)<br>$^1$H NMR (400 MHz, CD$_3$OD) 7.73 (d, J = 6.8 Hz, 2H), 7.00-6.99 (m, 4H), 6.49 (d, J = 8.0 Hz, 2H), 4.01 (s, 2H), 3.72 (s, 2H), 3.15 (s, 2H), 2.19 (s, 3H). | 0.15 | 0.146 |
| 114 | 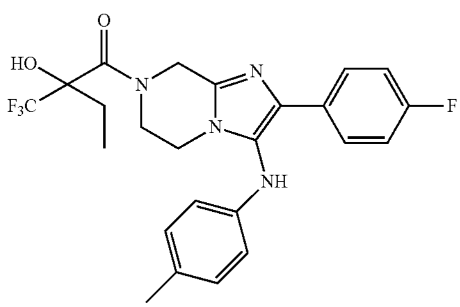 | 409.2 (M + 1) | 1.34 | 1.35 |
| 115 | 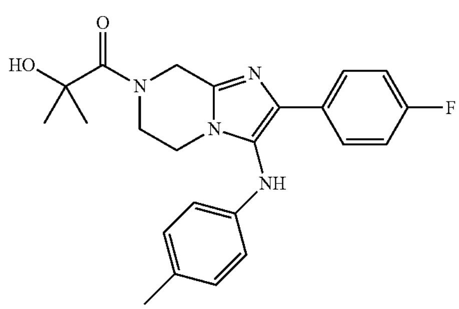 | 477.2 (M + 1) | 0.15 | 0.153 |
| 116 | 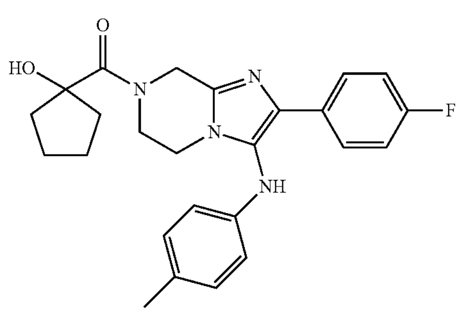 [SMILES: Cc1ccc(Nc2c(-c3ccc(F)cc3)nc3n2CCN(C(=O)C2(O)CCCC2)C3)cc1] | 435.2 (M + 1) | 1.64 | 1.509 |
| 117 | 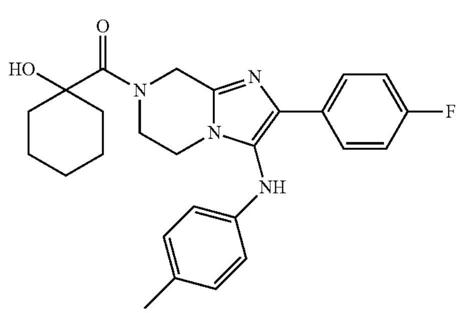 [SMILES: Cc1ccc(Nc2c(-c3ccc(F)cc3)nc3n2CCN(C(=O)C2(O)CCCCC2)C3)cc1] | 449.2 (M + 1) | 1.26 | 1.186 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 118 | 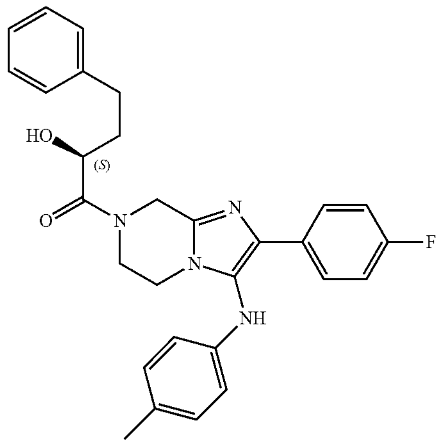 | 485.6 (M + 1) | 0.15 | 0.135 |
| 119 | 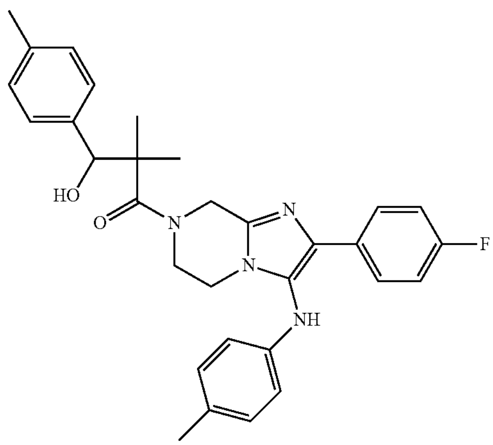 [SMILES: Cc1ccc(Nc2c(-c3ccc(F)cc3)nc3n2CCN(C(=O)C(C)(C)C(O)c2ccc(C)cc2)C3)cc1] | 513.4 (M + 1) | 4.74 | |
| 120 | 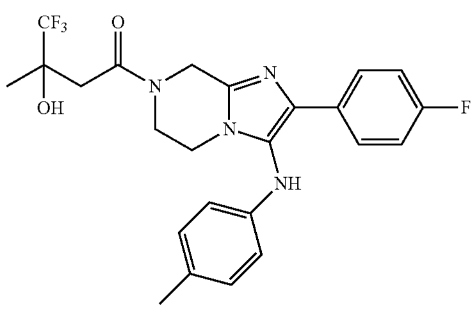 [SMILES: Cc1ccc(Nc2c(-c3ccc(F)cc3)nc3n2CCN(C(=O)CC(C)(O)C(F)(F)F)C3)cc1] | 477.2 (M + 1) | 0.11 | 0.123 |
| 121 | 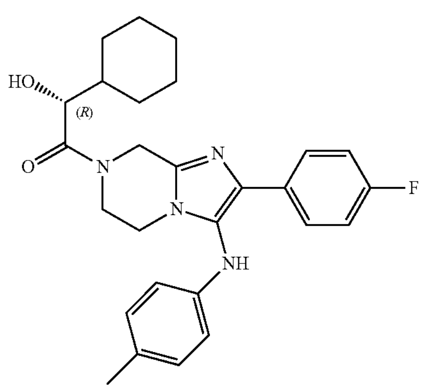 | 463.4 (M + 1) | 0.02 | 0.033 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 122 | (4-methoxyphenyl, hydroxy acetyl on tetrahydroimidazopyrazine; 2-(4-fluorophenyl); 3-(4-methylphenyl)amino) | 487.2 (M + 1) | 0.18 | 0.154 |
| 123 | (3,5-difluorophenyl, hydroxy acetyl; 2-(4-fluorophenyl); 3-(4-methylphenyl)amino) | 493.2 (M + 1) | 0.03 | |
| 124 | (3-trifluoromethylphenyl, hydroxy acetyl; 2-(4-fluorophenyl); 3-(4-methylphenyl)amino) | 525.2 (M + 1) | 0.04 | 0.028 |
| 125 | (phenyl, methoxy acetyl; 2-(4-fluorophenyl); 3-(4-methylphenyl)amino) | 471.3 (M + 1) | 0.05 | 0.044 |
| 126 | (4-bromophenyl, hydroxy acetyl; 2-(4-fluorophenyl); 3-(4-methylphenyl)amino) | 536.2 (M + 1) | 0.1 | 0.08 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 127 | 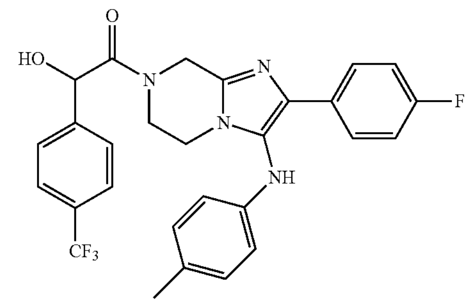 [SMILES: Cc1ccc(Nc2c(-c3ccc(F)cc3)nc3n2CCN(C(=O)C(O)c2ccc(C(F)(F)F)cc2)C3)cc1] | 525.4 (M + 1) | 0.06 | 0.051 |
| 128 | 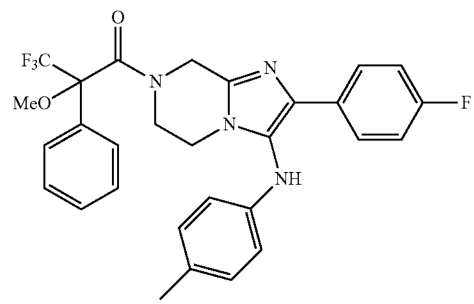 [SMILES: COC(C(=O)N1CCn2c(nc(-c3ccc(F)cc3)c2Nc2ccc(C)cc2)C1)(c1ccccc1)C(F)(F)F] | 539.2 (M + 1) | 1.18 | 0.743 |
| 129 | 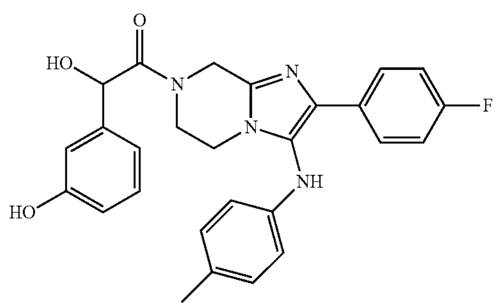 [SMILES: Cc1ccc(Nc2c(-c3ccc(F)cc3)nc3n2CCN(C(=O)C(O)c2cccc(O)c2)C3)cc1] | 473.2 (M + 1) | 0.01 | 0.006 |
| 130 | 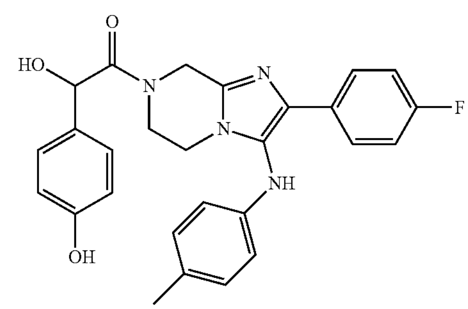 [SMILES: Cc1ccc(Nc2c(-c3ccc(F)cc3)nc3n2CCN(C(=O)C(O)c2ccc(O)cc2)C3)cc1] | 473.2 (M + 1) | 0.01 | |
| 131 | 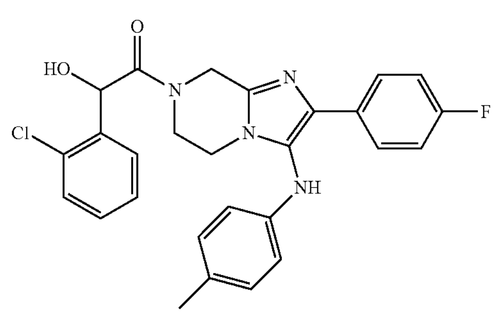 [SMILES: Cc1ccc(Nc2c(-c3ccc(F)cc3)nc3n2CCN(C(=O)C(O)c2ccccc2Cl)C3)cc1] | 492.0 (M + 1) | 0.04 | 0.03 |

TABLE 2-continued

| Compound | Structure | Physical Data MS (m/z) and/or ¹H NMR | EC$_{50}$ 3D7 strain (μM) | EC$_{50}$ W2 strain (μM) |
|---|---|---|---|---|
| 132 | 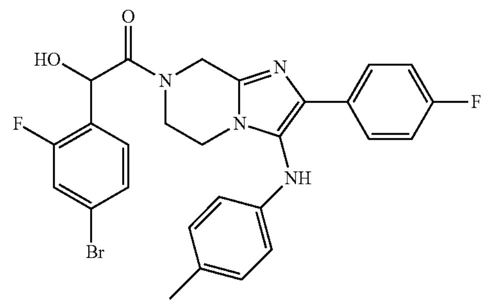 [SMILES: Cc1ccc(Nc2c(-c3ccc(F)cc3)nc3n2CCN(C(=O)C(O)c2ccc(Br)cc2F)C3)cc1] | 554.2 (M + 1) | 0.1 | 0.082 |
| 133 | 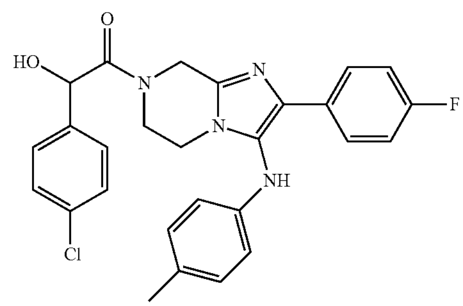 [SMILES: Cc1ccc(Nc2c(-c3ccc(F)cc3)nc3n2CCN(C(=O)C(O)c2ccc(Cl)cc2)C3)cc1] | 492.0 (M + 1) | 0.05 | 0.039 |
| 134 | 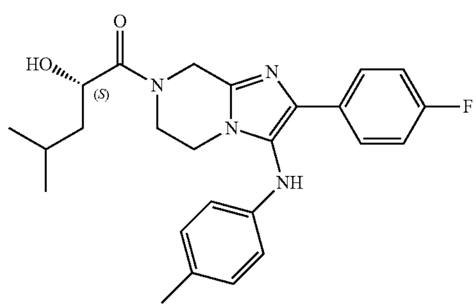 | 437.1 (M + 1) <br> ¹H-NMR: (MeOH-d$_4$, 400 Hz) δ 7.76-7.73 (m, 2H); 7.02-6.95 (m, 4 H); 6.50 (d, J = 7.2 Hz, 2H), 4.95-4.72 (m, 2H); 4.59-4.51 (m, 1H); 4.08-3.51 (m, 4H); 2.20 (s, 3H); 1.86 (m, 1H); 1.59 (m, 1H); 1.48 (m, 1H); 0.96 (d, J = 7.2 Hz, 6H), | 0.01 | 0.007 |
| 135 | 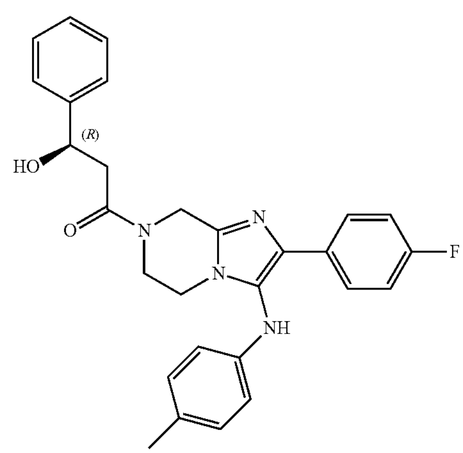 | 471.2 (M + 1) | 0.05 | 0.033 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 136 | 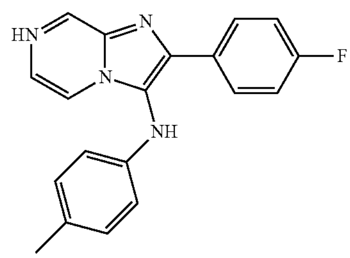 [SMILES: Cc1ccc(Nc2c(-c3ccc(F)cc3)nc3cnccn23)cc1] | 319.1 (M + 1) $^1$H NMR (400 MHz, CD$_3$OD) 9.04 (s, 1H); 8.03 (dd, J = 1.2 Hz, J = 4.8 Hz, 1H), 7.97 (m, 2H), 6.90 (d, J = 8.0 Hz, 2H), 6.41 (d, J = 8.4 Hz, 2H) 2.1 (s, 3H). | 2.02 | 2.693 |
| 137 | 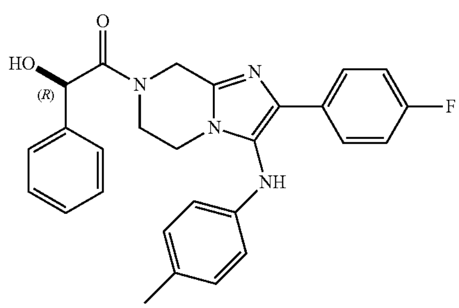 | 457.2 (M + 1) | 0.01 | 0.012 |
| 138 | 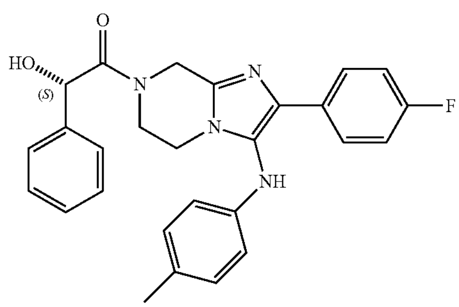 | 457.2 (M + 1) | 0.01 | 0.015 |
| 139 | 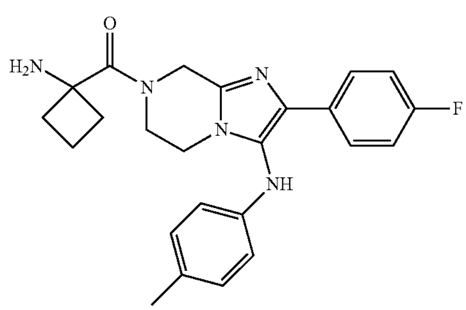 [SMILES: Cc1ccc(Nc2c(-c3ccc(F)cc3)nc3n2CCN(C(=O)C2(N)CCC2)C3)cc1] | 420.2 (M + 1) | 0.16 | 0.165 |
| 140 | 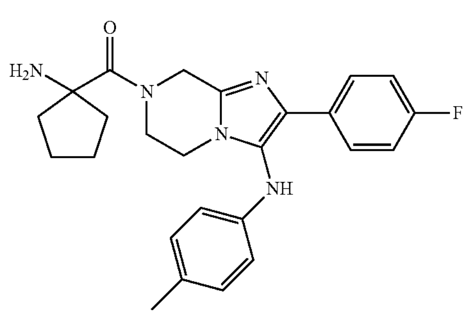 [SMILES: Cc1ccc(Nc2c(-c3ccc(F)cc3)nc3n2CCN(C(=O)C2(N)CCCC2)C3)cc1] | 434.2 (M + 1) | 0.09 | 0.128 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 141 | 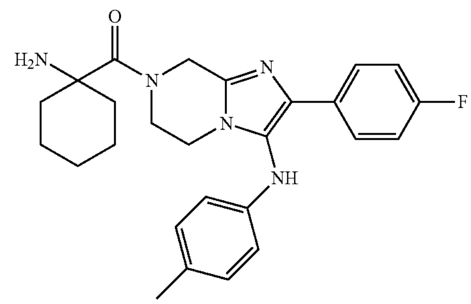 [SMILES: Cc1ccc(Nc2c(-c3ccc(F)cc3)nc3n2CCN(C(=O)C2(N)CCCCC2)C3)cc1] | 448.2 (M + 1) | 0.07 | 0.09 |
| 142 | 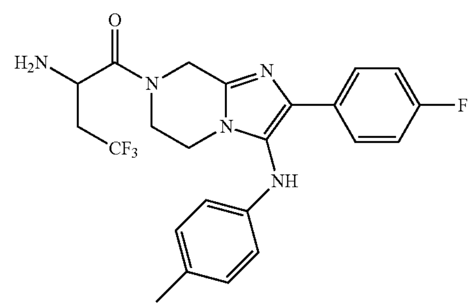 [SMILES: Cc1ccc(Nc2c(-c3ccc(F)cc3)nc3n2CCN(C(=O)C(N)CC(F)(F)F)C3)cc1] | 462.4 (M + 1) | 0.08 | 0.12 |
| 143 | 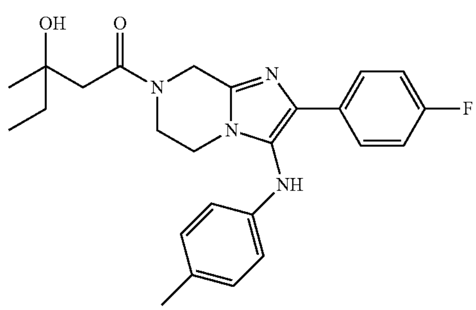 [SMILES: CCC(C)(O)CC(=O)N1CCn2c(nc(-c3ccc(F)cc3)c2Nc2ccc(C)cc2)C1] | 437.2 (M + 1) | 0.15 | 0.219 |
| 144 | 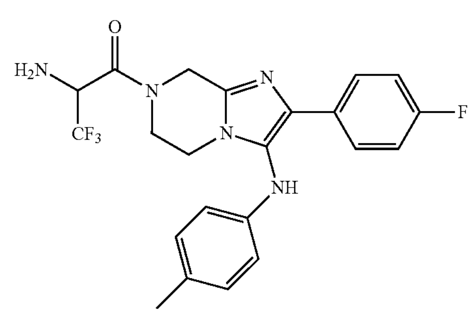 [SMILES: Cc1ccc(Nc2c(-c3ccc(F)cc3)nc3n2CCN(C(=O)C(N)C(F)(F)F)C3)cc1] | 448.2 (M + 1) | 0.05 | 0.073 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 145 | 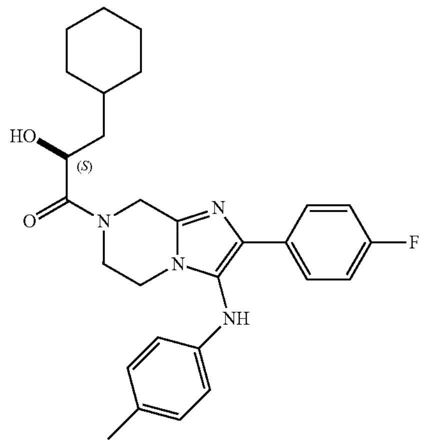 | 477.5 (M + 1) | 0.09 | 0.068 |
| 146 | 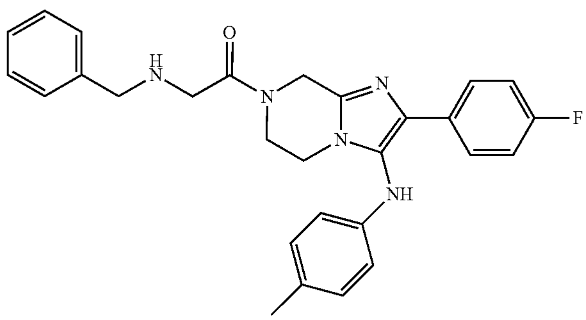 [SMILES: Cc1ccc(Nc2c(-c3ccc(F)cc3)nc3n2CCN(C(=O)CNCc2ccccc2)C3)cc1] | 470.5 (M + 1) | 0.02 | 0.014 |
| 147 | 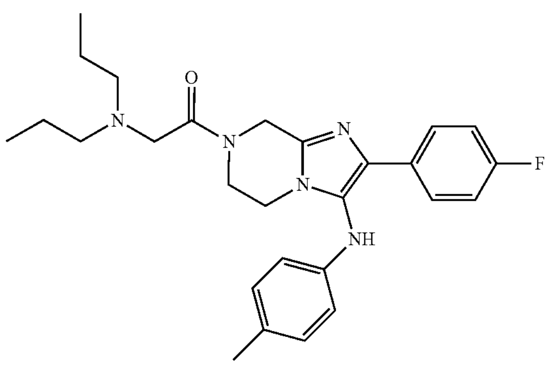 [SMILES: CCCN(CCC)CC(=O)N1CCn2c(nc(-c3ccc(F)cc3)c2Nc2ccc(C)cc2)C1] | 464.5 (M + 1) | 2.43 | 1.519 |
| 148 | 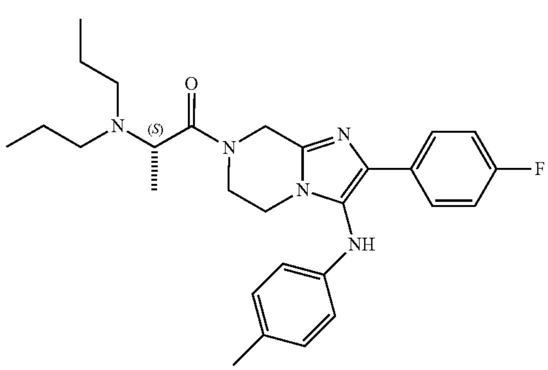 | 478.5 (M + 1) | 4.06 | 1.432 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 149 | 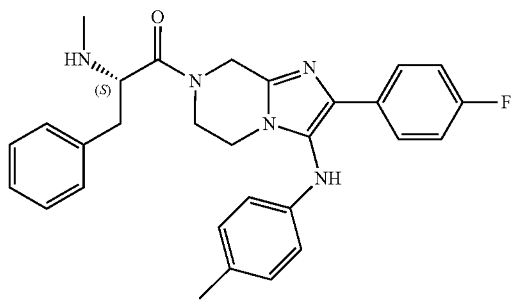 | 484.5 (M + 1) | 0.02 | 0.011 |
| 150 | 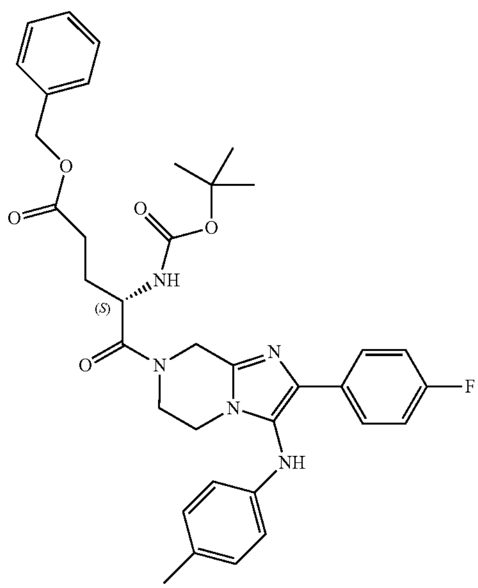 | 642.5 (M + 1) | 0.96 | 0.673 |
| 151 | 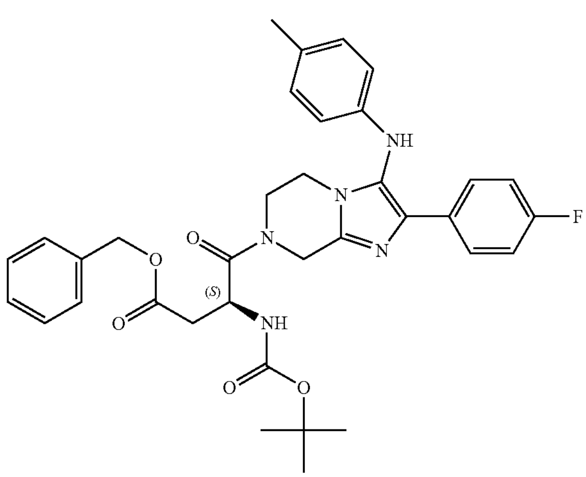 | 628.5 (M + 1) | 0.82 | 0.386 |

TABLE 2-continued
| Compound | Structure | Physical Data MS (m/z) and/or $^1$H NMR | EC$_{50}$ 3D7 strain (μM) | EC$_{50}$ W2 strain (μM) |
|---|---|---|---|---|
| 152 | 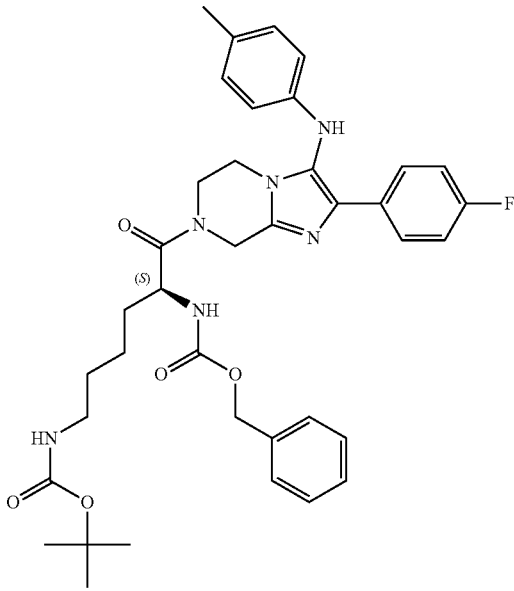 | 685.4 (M + 1) | 3.87 | 0.873 |
| 153 | 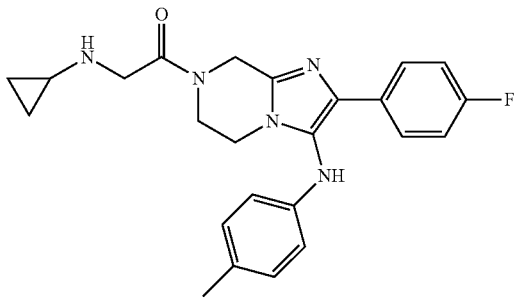 [SMILES: Cc1ccc(Nc2c(-c3ccc(F)cc3)nc3n2CCN(C(=O)CNC2CC2)C3)cc1] | 420.5 (M + 1) | 0.06 | 0.032 |
| 154 | 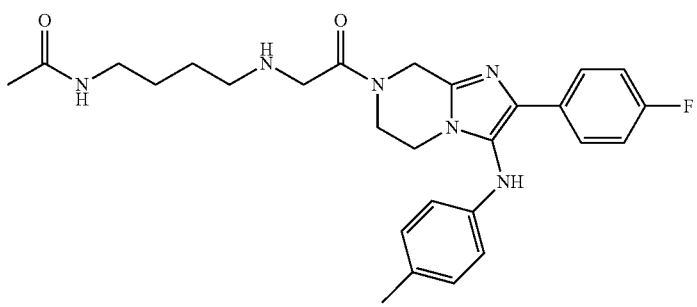 [SMILES: CC(=O)NCCCCNCC(=O)N1CCn2c(nc(-c3ccc(F)cc3)c2Nc2ccc(C)cc2)C1] | 493.5 M + 1) | 4.27 | 3.411 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 155 | 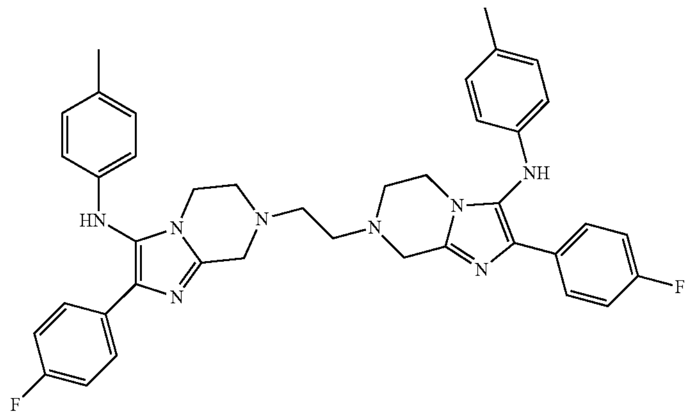 [SMILES: Cc1ccc(Nc2c(-c3ccc(F)cc3)nc3n2CCN(CCN2CCn4c(nc(-c5ccc(F)cc5)c4Nc4ccc(C)cc4)C2)C3)cc1] | 671.6 (M + 1) | 2.14 | 0.491 |
| 156 | 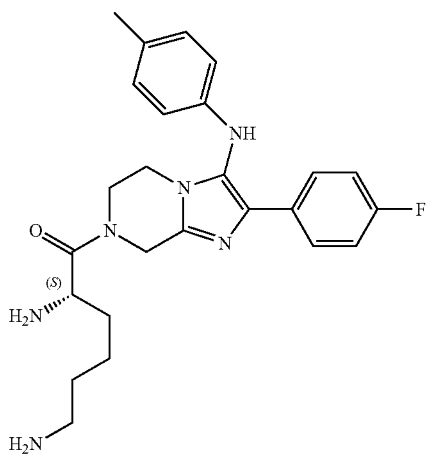 | 451.5 (M + 1) | 1.83 | 0.458 |
| 157 | 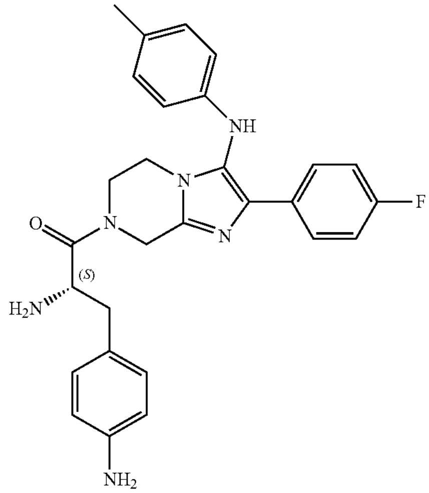 | 485.5 (M + 1) | 0.1 | 0.097 |

TABLE 2-continued
| Compound | Structure | Physical Data MS (m/z) and/or $^1$H NMR | EC$_{50}$ 3D7 strain (μM) | EC$_{50}$ W2 strain (μM) |
|---|---|---|---|---|
| 158 | 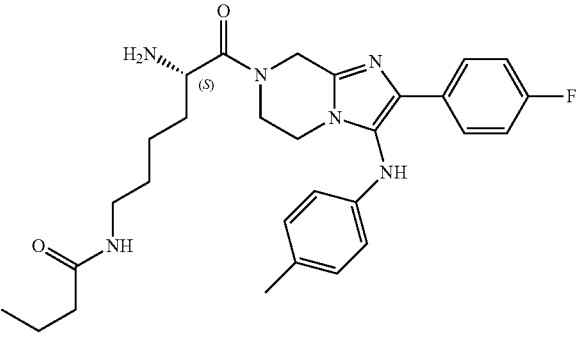 | 521.5 (M + 1) | 7.54 | 4.763 |
| 159 | 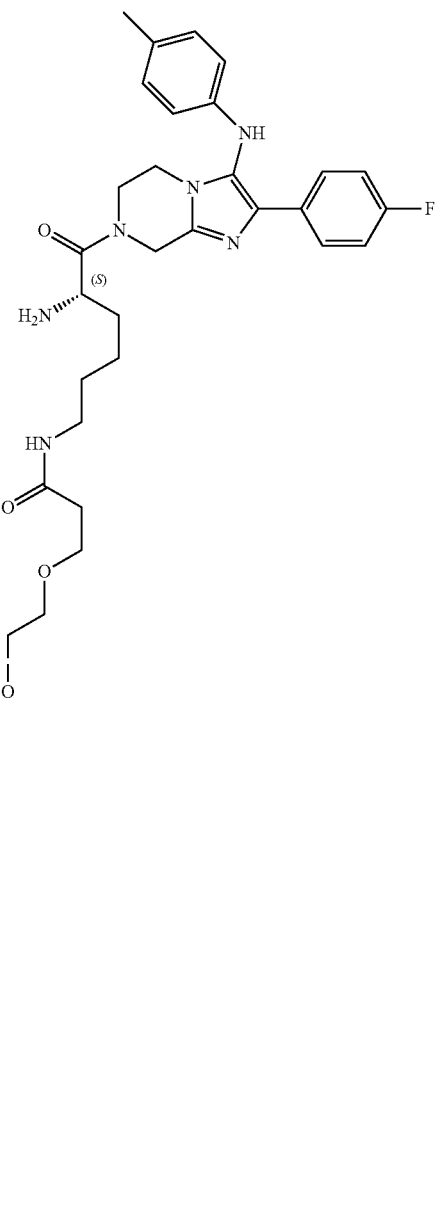 | 925.1 (M + 1) | 5.7 | 2.91 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 160 | 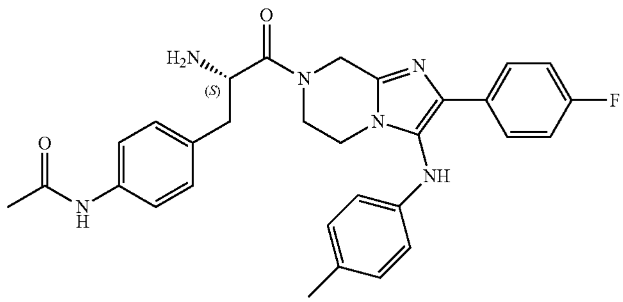 | 527.5 (M + 1) | 4.32 | 2.39 |
| 161 | 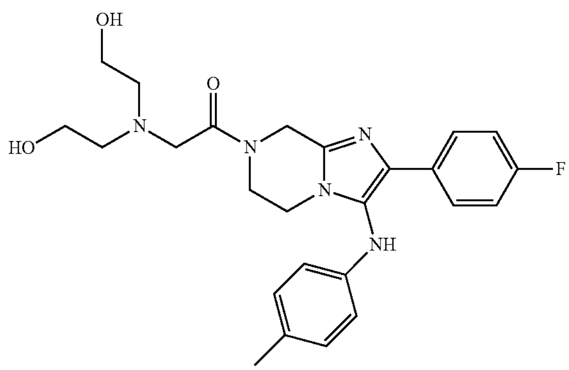 [SMILES: Cc1ccc(Nc2c(-c3ccc(F)cc3)nc3n2CCN(C(=O)CN(CCO)CCO)C3)cc1] | 468.2 (M + 1) | 0.54 | 0.51 |
| 162 | 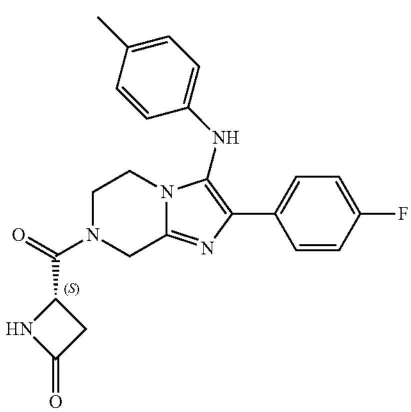 | 420.5 (M + 1) | 1.78 | 1.376 |
| 163 | 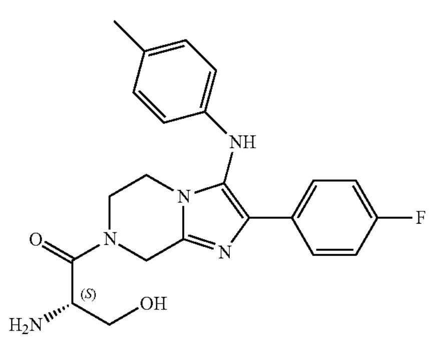 | 410.1 (M + 1) | 0.02 | 0.026 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 164 | 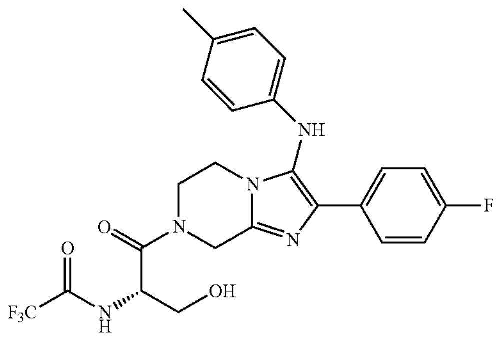 [SMILES: Cc1ccc(Nc2c(-c3ccc(F)cc3)nc3n2CCN(C(=O)[C@H](CO)NC(=O)C(F)(F)F)C3)cc1] | 506.2 (M + 1) | >9.81 | 3.757 |
| 165 | 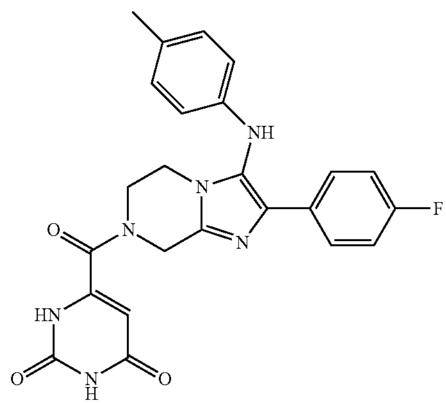 [SMILES: Cc1ccc(Nc2c(-c3ccc(F)cc3)nc3n2CCN(C(=O)c2cc(=O)[nH]c(=O)[nH]2)C3)cc1] | 461.2 (M + 1) | >10.23 | 4.642 |
| 166 | 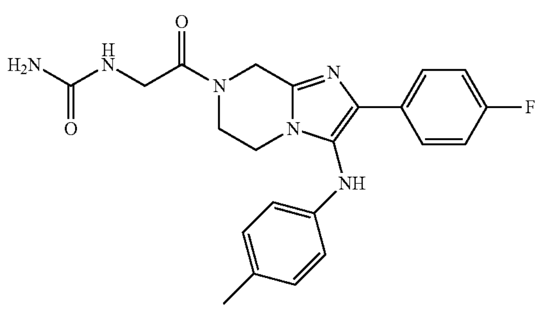 [SMILES: Cc1ccc(Nc2c(-c3ccc(F)cc3)nc3n2CCN(C(=O)CNC(N)=O)C3)cc1] | 423.2 (M + 1) | 2.87 | 2.229 |
| 167 | 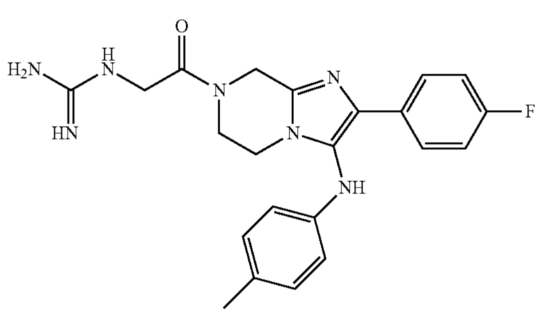 [SMILES: Cc1ccc(Nc2c(-c3ccc(F)cc3)nc3n2CCN(C(=O)CNC(=N)N)C3)cc1] | 422.2 (M + 1) | 0.18 | 0.145 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 168 | 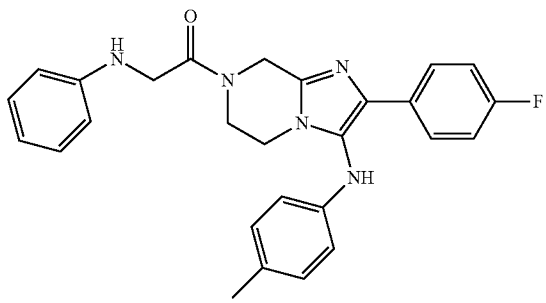 [SMILES: Cc1ccc(Nc2c(-c3ccc(F)cc3)nc3n2CCN(C(=O)CNc2ccccc2)C3)cc1] | 456.2 (M + 1) | 0.01 | 0.011 |
| 169 | 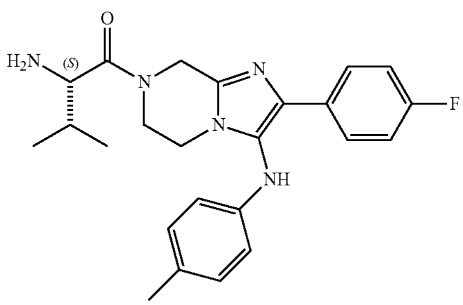 | 422.5 (M + 1) $^1$H-NMR: (MeOH-d$_4$, 400 Hz) δ 7.59-7.56 (m, 2H); 7.13-7.00 (m, 2H); 6.95-6.93 (m, 2H); 6.56-6.54 (m, 2H); 5.17-4.8 (m, 2H); 4.37-3.72 (m, 5H); 1.23-1.19 (m, 1H); 1.03 (d, J = 8.8 Hz, 3H); 1.03 (d, J = 8.8 Hz, 3H); 0.95 (d, J = 8.8 Hz, 3H). | 0.04 | |
| 170 | 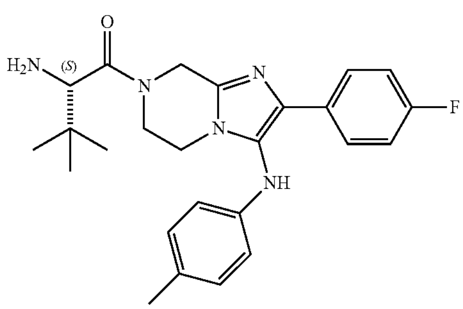 | 436.2 (M + 1) | 0.09 | 0.054 |
| 171 | 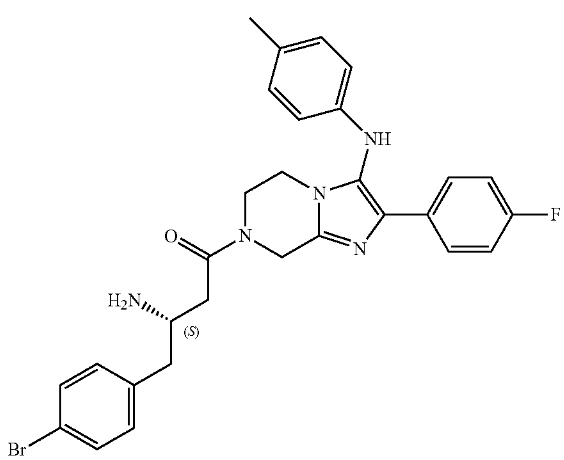 | 563.2 (M + 1) | 0.17 | 0.214 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 172 | 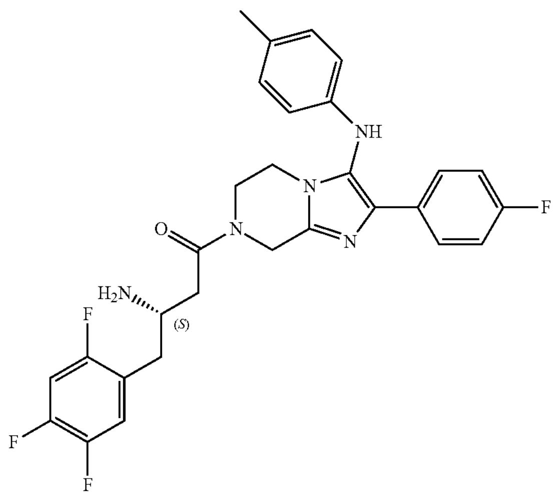 | 538.4 (M + 1) | 0.1 | 0.088 |
| 173 | 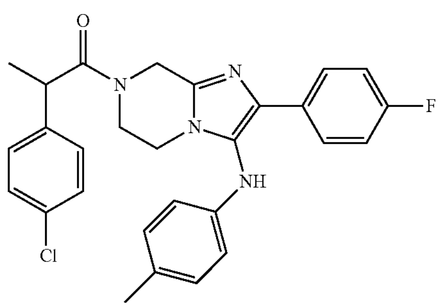 [SMILES: Cc1ccc(Nc2c(-c3ccc(F)cc3)nc3n2CCN(C(=O)C(C)c2ccc(Cl)cc2)C3)cc1] | 489.2 (M + 1) | 0.14 | 0.133 |
| 174 | 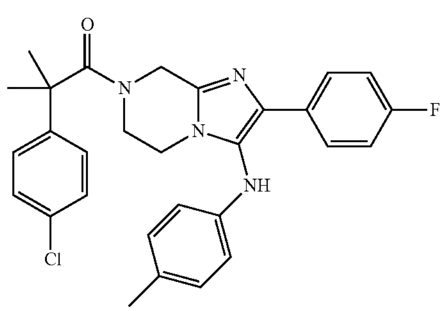 [SMILES: Cc1ccc(Nc2c(-c3ccc(F)cc3)nc3n2CCN(C(=O)C(C)(C)c2ccc(Cl)cc2)C3)cc1] | 503.5 (M + 1) | 6.06 | 1.475 |
| 175 | 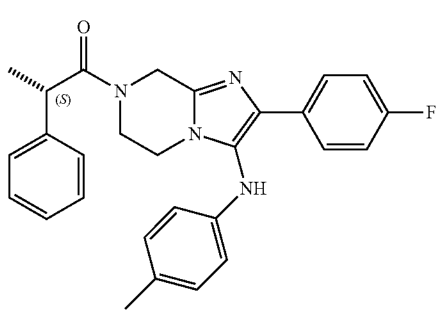 | 455.2 (M + 1) | 0.08 | 0.105 |

TABLE 2-continued

| Compound | Structure | Physical Data MS (m/z) and/or ¹H NMR | EC$_{50}$ 3D7 strain (μM) | EC$_{50}$ W2 strain (μM) |
| --- | --- | --- | --- | --- |
| 176 | 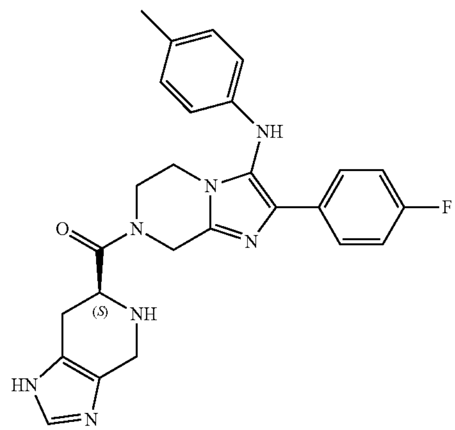 | 472.2 (M + 1) | 2.75 | 1.791 |
| 177 | 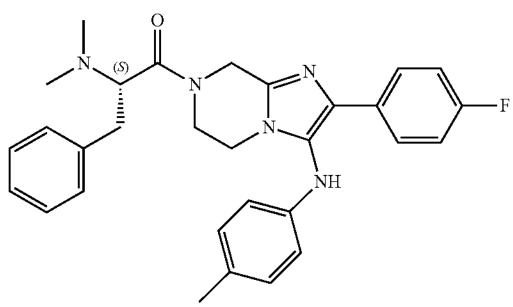 | 498.5 (M + 1) | 0.43 | 0.43 |
| 178 | 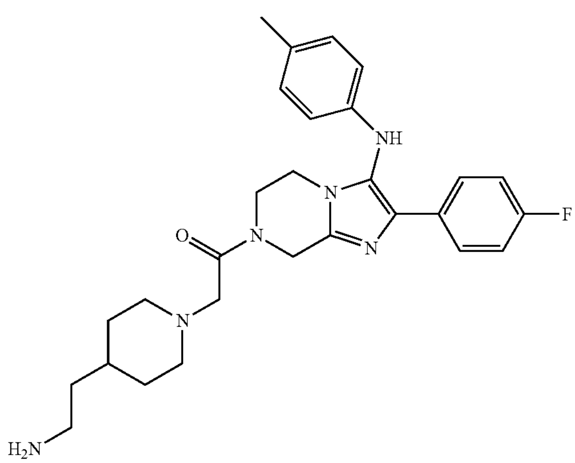 [SMILES: Cc1ccc(Nc2c(-c3ccc(F)cc3)nc3n2CCN(C(=O)CN2CCC(CCN)CC2)C3)cc1] | 491.5 (M + 1) | 3.05 | 3.321 |
| 179 | 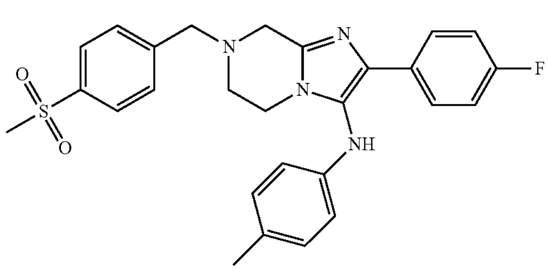 [SMILES: Cc1ccc(Nc2c(-c3ccc(F)cc3)nc3n2CCN(Cc2ccc(S(C)(=O)=O)cc2)C3)cc1] | 491.5 (M + 1) | 4.79 | 1.072 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 180 | 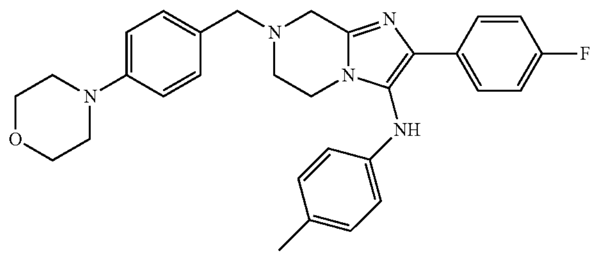 [SMILES: Cc1ccc(Nc2c(-c3ccc(F)cc3)nc3n2CCN(Cc2ccc(N4CCOCC4)cc2)C3)cc1] | 498.5 (M + 1) | 0.73 | 0.609 |
| 181 | 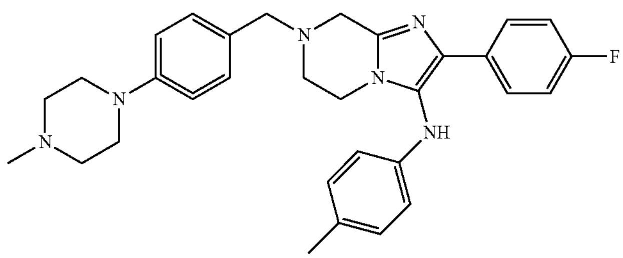 | 511.5 (M + 1) | 2.68 | 1.811 |
| 182 | 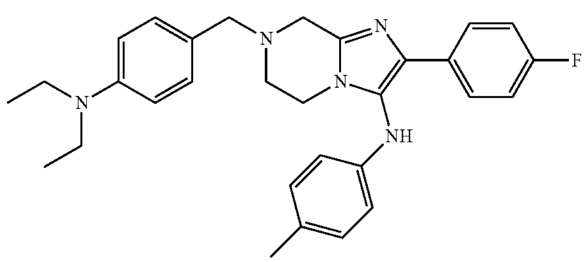 [SMILES: CCN(CC)c1ccc(CN2CCn3c(nc(-c4ccc(F)cc4)c3Nc3ccc(C)cc3)C2)cc1] | 484.5 (M + 1) | 1.37 | 1.076 |
| 183 | 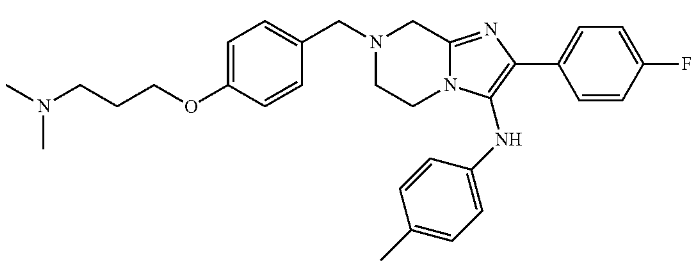 [SMILES: Cc1ccc(Nc2c(-c3ccc(F)cc3)nc3n2CCN(Cc2ccc(OCCCN(C)C)cc2)C3)cc1] | 514.5 (M + 1) | 1.9 | 1.342 |
| 184 | 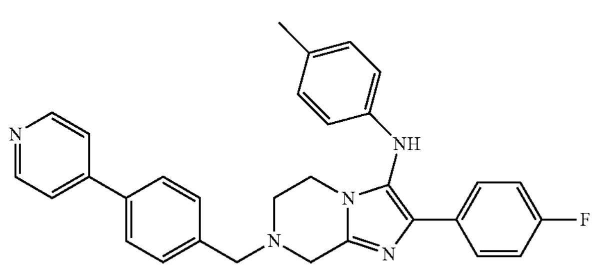 [SMILES: Cc1ccc(Nc2c(-c3ccc(F)cc3)nc3n2CCN(Cc2ccc(-c4ccncc4)cc2)C3)cc1] | 490.5 (M + 1) | 3.65 | 0.859 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 185 | 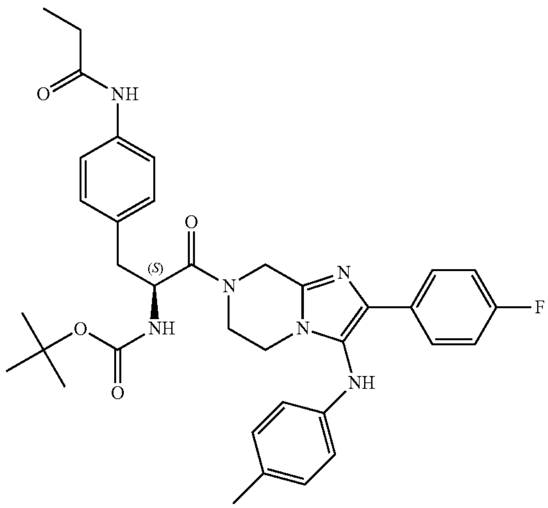 | 641.3 (M + 1) | 0.35 | 0.136 |
| 186 | 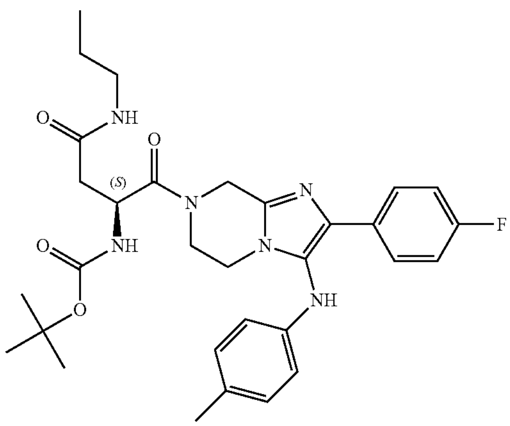 | 579.3 (M + 1) | 5.63 | 2.56 |
| 187 | 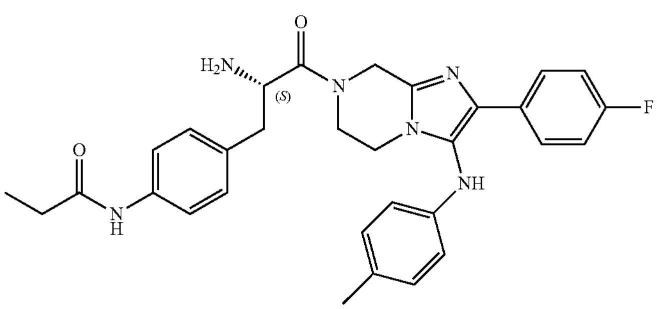 | 541.3 (M + 1) | 6.68 | 3.551 |
| 188 | 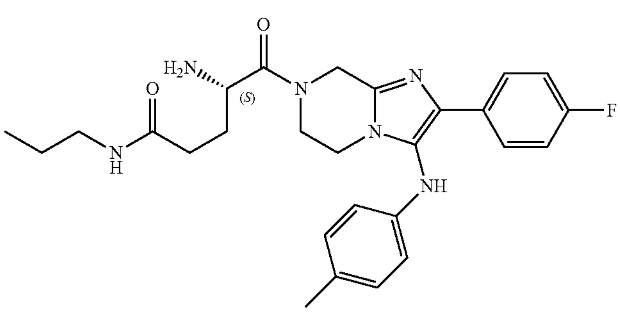 | 493.6 (M + 1) | 0.79 | 1.097 |

TABLE 2-continued

| Compound | Structure | Physical Data MS (m/z) and/or ¹H NMR | EC$_{50}$ 3D7 strain (μM) | EC$_{50}$ W2 strain (μM) |
|---|---|---|---|---|
| 189 | 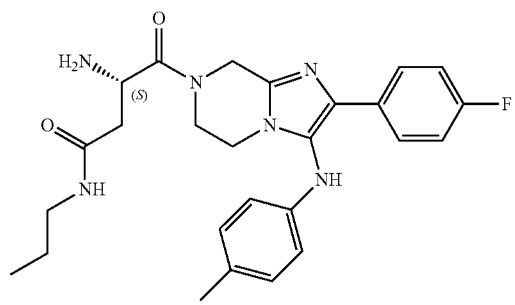 | 479.6 (M + 1) | 0.37 | 0.392 |
| 190 | 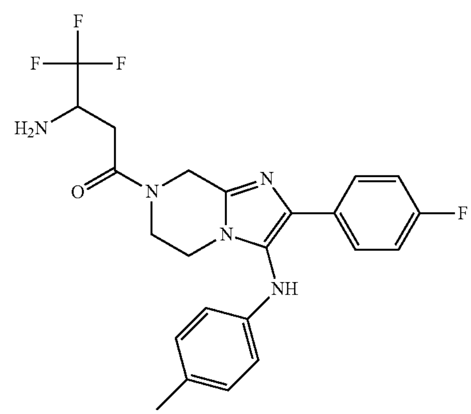 [SMILES: Cc1ccc(Nc2c(-c3ccc(F)cc3)nc3n2CCN(C(=O)CC(N)C(F)(F)F)C3)cc1] | 462.2 (M + 1) | 0.94 | 1.073 |
| 191 | 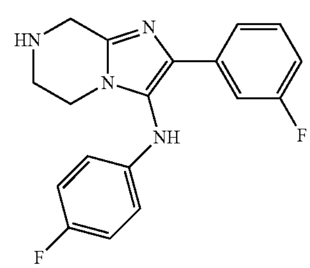 [SMILES: Fc1ccc(Nc2c(-c3cccc(F)c3)nc3n2CCNC3)cc1] | 327.2 (M + 1)<br>¹H-NMR: (300 MHz, DMSO-d$_6$): δ 2.50-2.52 (2H, t, J = 1.5 Hz), 3.54-3.58 (2H, t, J = 2.1 Hz), 3.87 (s, 2H), 6.53-6.58 (m, 2H), 6.91-7.02 (m, 3H), 7.27-7.36 (m, 1H), 7.50 (1H, d, J = 10.5 Hz), 7.62 (1H, d, J = 7.8 Hz), 7.79 (s, 1H) | 0.17 | 0.151 |
| 192 | 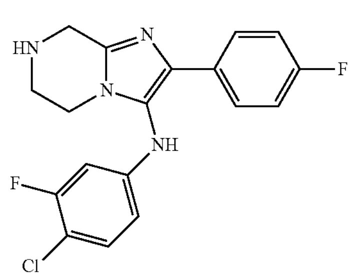 [SMILES: Fc1ccc(-c2nc3n(c2Nc2ccc(Cl)c(F)c2)CCNC3)cc1] | 361.1 (M + 1)<br>¹H NMR (400 MHz, CDCl$_3$) δ 7.75-7.70 (m, 2H) 7.25-7.19 (m, H), 7.05-7.02 (m, 2H), 6.48-6.41 (m, 2H), 4.16 (s, 2H), 3.70 (m, 2H), 3.24 (m, 2H). | 0.11 | 0.095 |

TABLE 2-continued

| Compound | Structure | Physical Data MS (m/z) and/or ¹H NMR | EC$_{50}$ 3D7 strain (μM) | EC$_{50}$ W2 strain (μM) |
|---|---|---|---|---|
| 193 | 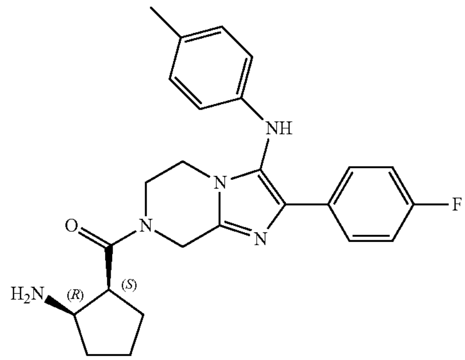 | 434.2 (M + 1) | 0.09 | 0.075 |
| 194 | 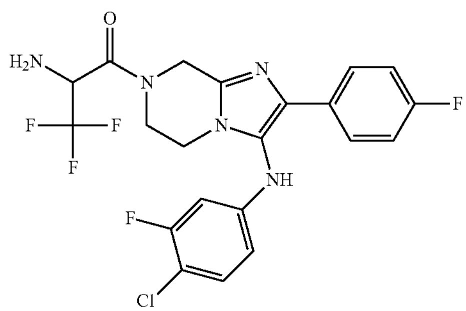 [SMILES: NC(C(=O)N1CCn2c(nc(-c3ccc(F)cc3)c2Nc2ccc(Cl)c(F)c2)C1)C(F)(F)F] | 486.2 (M + 1) | 0.05 | |
| 195 | 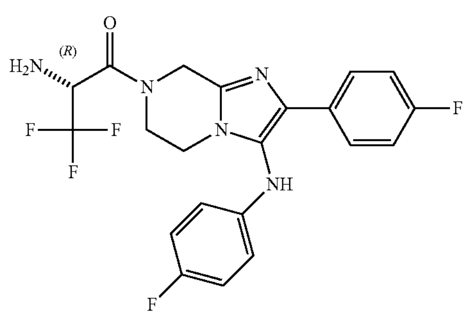 | 452.1 (M + 1) | 0.02 | 0.02 |
| 196 | 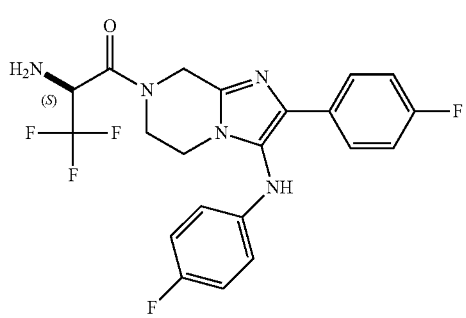 | 452.1 (M + 1) | 0.32 | 0.344 |

TABLE 2-continued

| Compound | Structure | Physical Data MS (m/z) and/or ¹H NMR | EC$_{50}$ 3D7 strain (μM) | EC$_{50}$ W2 strain (μM) |
| --- | --- | --- | --- | --- |
| 197 | 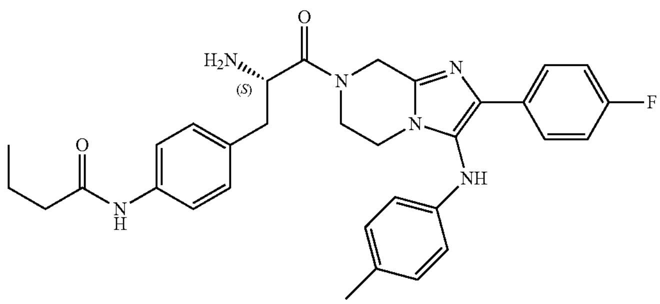 | 555.3 (M + 1) | 4.16 | 1.04 |
| 198 | 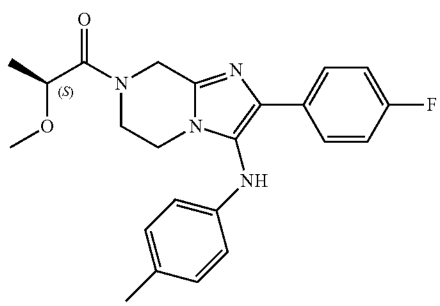 | 409.2 (M + 1) | 1.36 | |
| 199 | 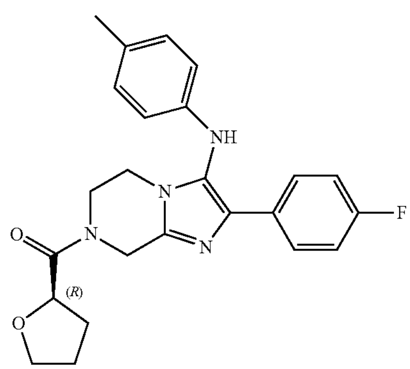 | 421.2 (M + 1) | 0.24 | 0.157 |
| 200 | 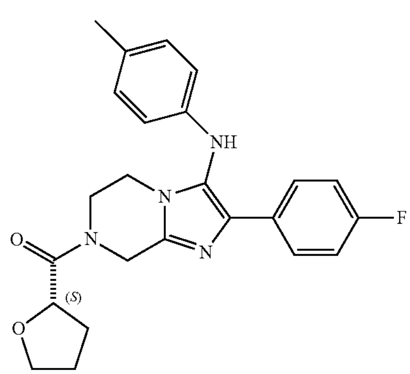 | 421.2 (M + 1) | 0.91 | |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 201 | 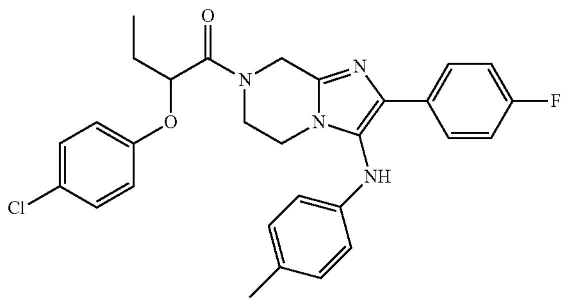 | 485.6 (M + 1) | 0.24 | 0.131 |
| 202 | 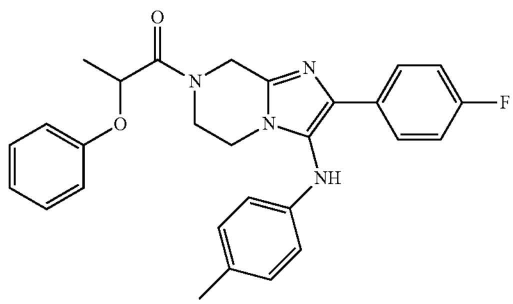 [SMILES: Cc1ccc(Nc2c(-c3ccc(F)cc3)nc3n2CCN(C(=O)C(C)Oc2ccccc2)C3)cc1] | 471.2 (M + 1) | 0.16 | 0.102 |
| 203 | 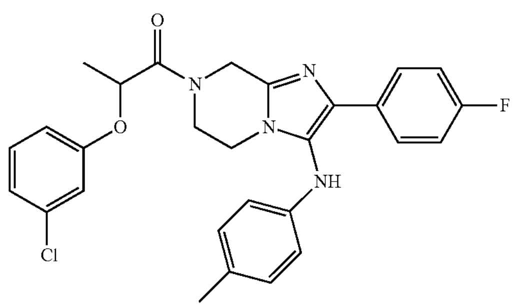 [SMILES: Cc1ccc(Nc2c(-c3ccc(F)cc3)nc3n2CCN(C(=O)C(C)Oc2cccc(Cl)c2)C3)cc1] | 505.1 (M + 1) | 0.97 | 0.369 |
| 204 | 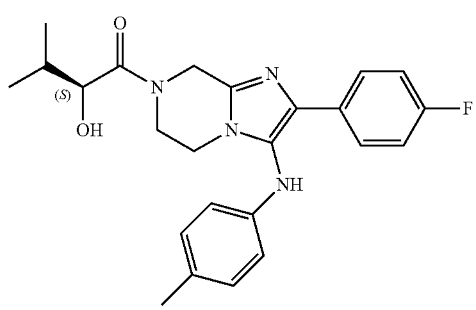 | 423.2 (M + 1) | 0.01 | 0.01 |
| 205 | 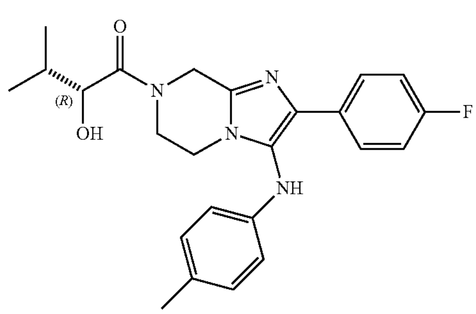 | 423.2 (M + 1) | 0.0 | 0.004 |

TABLE 2-continued

| Compound | Structure | Physical Data MS (m/z) and/or ¹H NMR | EC$_{50}$ 3D7 strain (μM) | EC$_{50}$ W2 strain (μM) |
| --- | --- | --- | --- | --- |
| 206 | 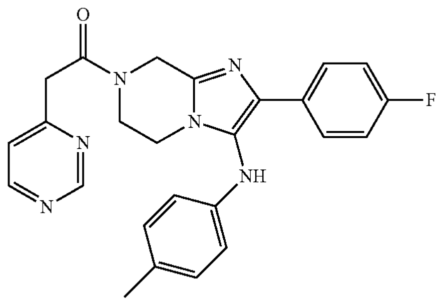 [SMILES: Cc1ccc(Nc2c(-c3ccc(F)cc3)nc3n2CCN(C(=O)Cc2ccncn2)C3)cc1] | 443.2 (M + 1) | 1.2 | 1.17 |
| 207 | 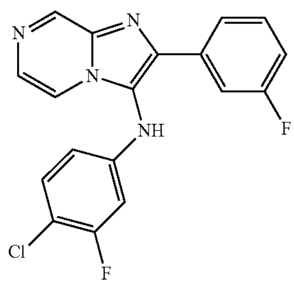 [SMILES: Fc1cccc(-c2nc3cnccn3c2Nc2ccc(Cl)c(F)c2)c1] | 357.1 (M + 1) | 9.31 | 2.421 |
| 208 | 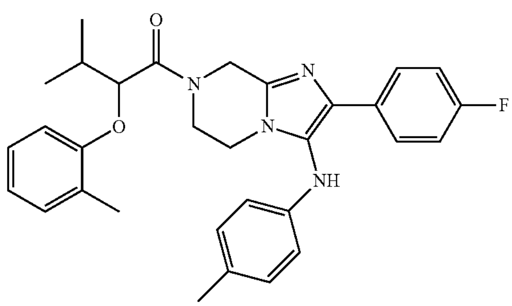 [SMILES: Cc1ccc(Nc2c(-c3ccc(F)cc3)nc3n2CCN(C(=O)C(Oc2ccccc2C)C(C)C)C3)cc1] | 513.2 (M + 1) | 5.87 | 1.057 |
| 209 | 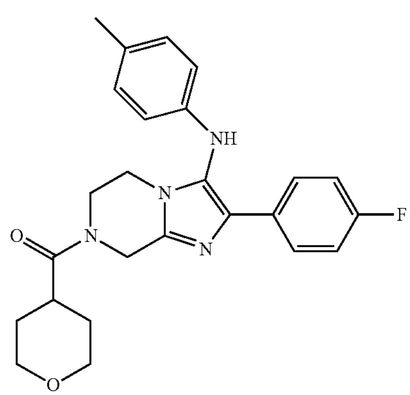 [SMILES: Cc1ccc(Nc2c(-c3ccc(F)cc3)nc3n2CCN(C(=O)C2CCOCC2)C3)cc1] | 435.2 (M + 1) | 11.62 | 4.362 |

TABLE 2-continued

| Compound | Structure | Physical Data MS (m/z) and/or ¹H NMR | EC$_{50}$ 3D7 strain (μM) | EC$_{50}$ W2 strain (μM) |
|---|---|---|---|---|
| 210 | 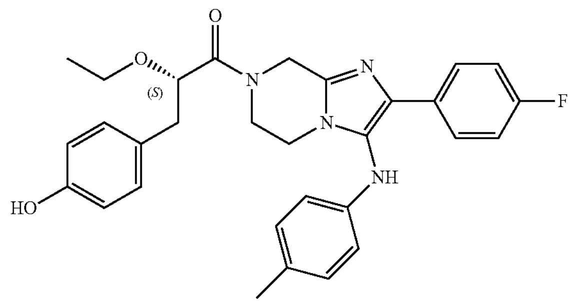 | 515.2 (M + 1) | 0.04 | 0.026 |
| 211 | 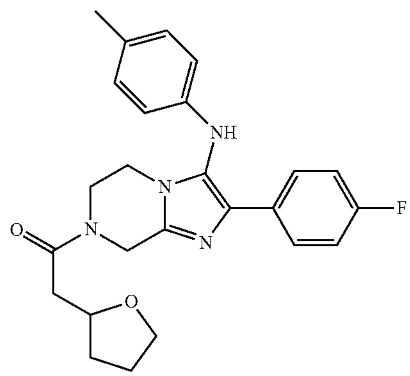 [SMILES: Cc1ccc(Nc2c(-c3ccc(F)cc3)nc3n2CCN(C(=O)CC2CCCO2)C3)cc1] | 435.2 (M + 1) | 0.3 | 0.283 |
| 212 | 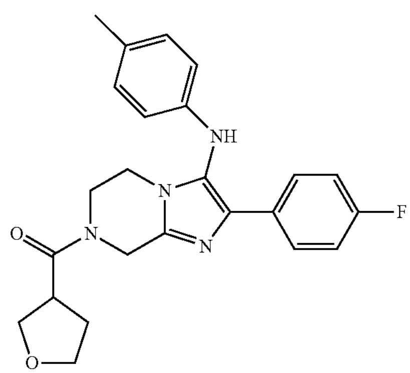 [SMILES: Cc1ccc(Nc2c(-c3ccc(F)cc3)nc3n2CCN(C(=O)C2CCOC2)C3)cc1] | 421.2 (M + 1) | 1.95 | 1.984 |
| 213 | 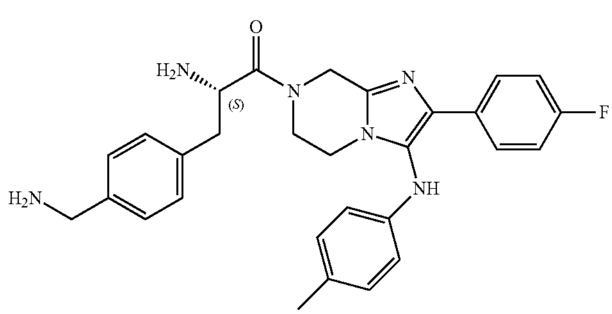 | 499.1 (M + 1) | 3.8 | 4.823 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 214 | 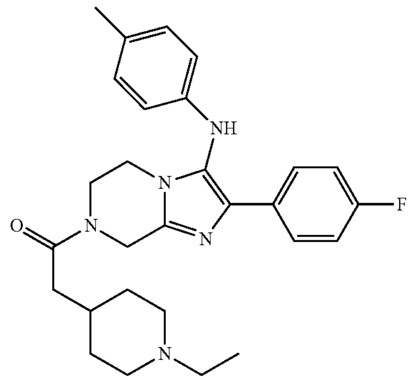 [SMILES: CCN1CCC(CC(=O)N2CCn3c(nc(-c4ccc(F)cc4)c3Nc3ccc(C)cc3)C2)CC1] | 476.3 (M + 1) | 2.85 | 2.008 |
| 215 | 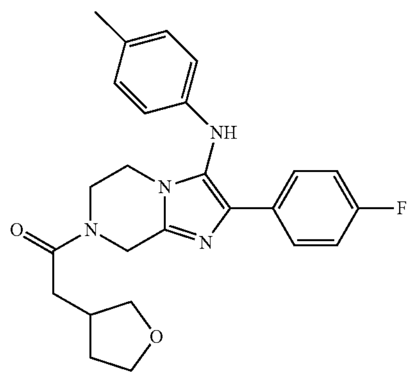 [SMILES: Cc1ccc(Nc2c(-c3ccc(F)cc3)nc3n2CCN(C(=O)CC2CCOC2)C3)cc1] | 435.2 (M + 1) | 0.83 | 0.65 |
| 216 | 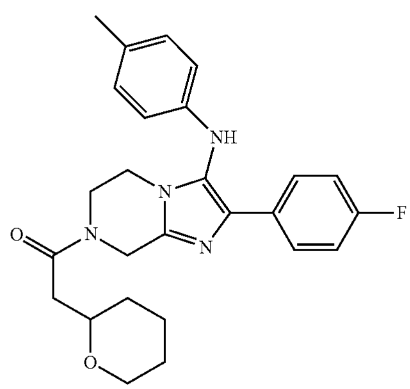 [SMILES: Cc1ccc(Nc2c(-c3ccc(F)cc3)nc3n2CCN(C(=O)CC2CCCCO2)C3)cc1] | 449.2 (M + 1) | 0.3 | 0.248 |
| 217 | 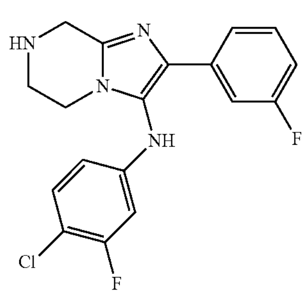 [SMILES: Fc1cccc(-c2nc3n(c2Nc2ccc(Cl)c(F)c2)CCNC3)c1] | 361.1 (M + 1)<br>$^1$H NMR (300 MHz, DMSO-d$_6$) δ 3.04 (2H, t, J = 5.1 Hz), 3.57 (s, 2H), 3.88 (s, 2H), 6.42-6.52 (m, 2H), 6.94-7.00 (m, 1H), 7.28-7.38 (m, 2H), 7.48 (1H, d, J = 7.2 Hz), 7.58 (1H, d, J = 7.8 Hz), 8.27 (s, 1H) | 0.13 | 0.106 |

TABLE 2-continued
| Compound | Structure | Physical Data MS (m/z) and/or $^1$H NMR | EC$_{50}$ 3D7 strain (μM) | EC$_{50}$ W2 strain (μM) |
|---|---|---|---|---|
| 218 | 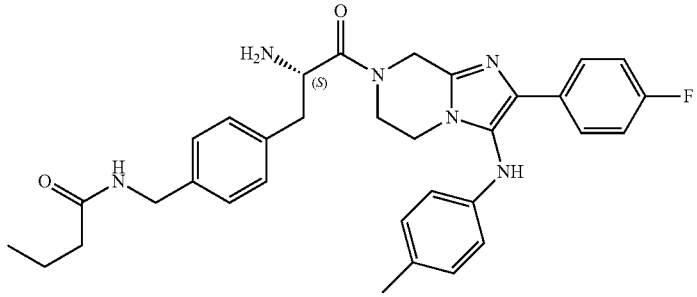 | 569.0 (M + 1) | 4.71 | 4.015 |
| 219 | 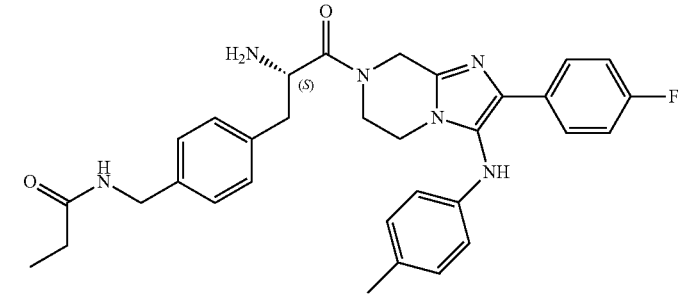 | 555.9 (M + 1) | 4.97 | 3.414 |
| 220 | 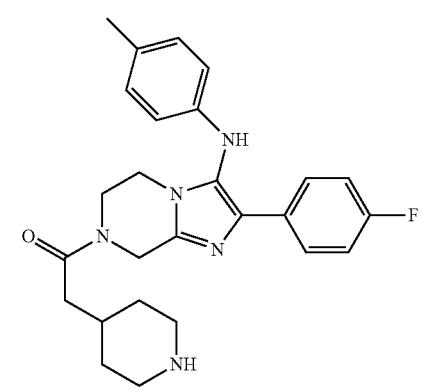 | 448.2 (M + 1) | 1.13 | 0.937 |
| 221 | 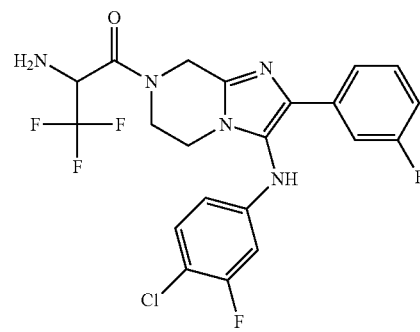 [SMILES: NC(C(=O)N1CCn2c(nc(-c3cccc(F)c3)c2Nc2ccc(Cl)c(F)c2)C1)C(F)(F)F] | 486.0 (M + 1) | 0.09 | 0.083 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 222 | 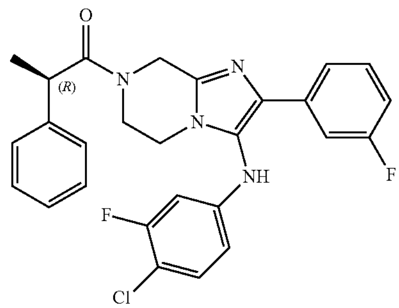 | 493.0 (M + 1) | 0.14 | 0.103 |
| 223 | 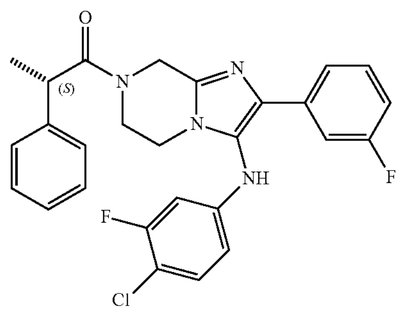 | 493.0 (M + 1) | 0.26 | 0.206 |
| 224 | 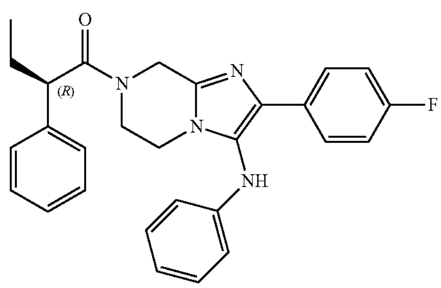 | 469.1 (M + 1) | 0.02 | 0.018 |
| 225 | 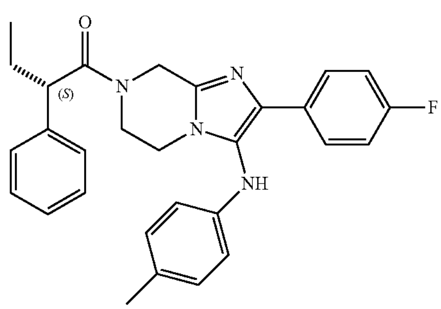 | 469.1 (M + 1) | 0.55 | 0.316 |
| 226 | 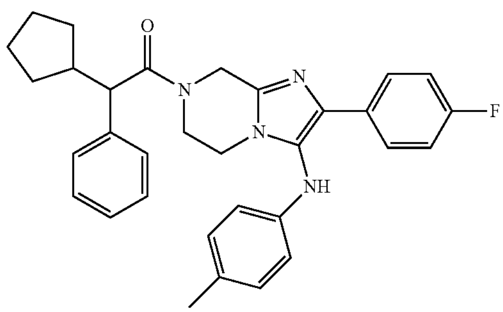 [SMILES: Cc1ccc(Nc2c(-c3ccc(F)cc3)nc3n2CCN(C(=O)C(c2ccccc2)C2CCCC2)C3)cc1] | 509.1 (M + 1) | 0.48 | 0.348 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 227 | 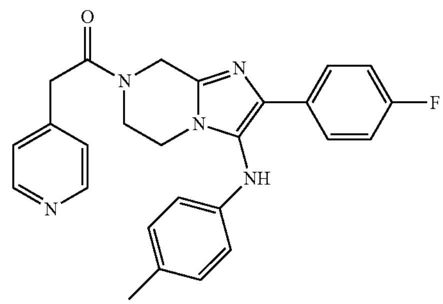 [SMILES: Cc1ccc(Nc2c(-c3ccc(F)cc3)nc3n2CCN(C(=O)Cc2ccncc2)C3)cc1] | 442.2 (M + 1) | 0.09 | 0.103 |
| 228 | 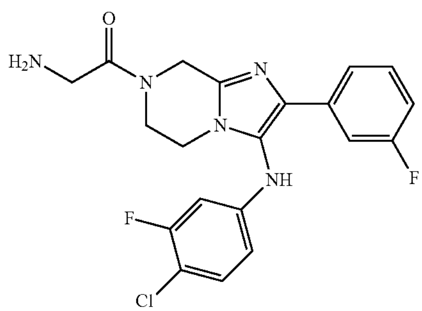 [SMILES: NCC(=O)N1CCn2c(nc(-c3cccc(F)c3)c2Nc2ccc(Cl)c(F)c2)C1] | 417.9 (M + 1) | 0.01 | 0.008 |
| 229 | 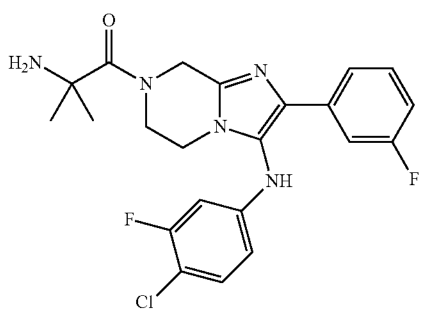 [SMILES: CC(C)(N)C(=O)N1CCn2c(nc(-c3cccc(F)c3)c2Nc2ccc(Cl)c(F)c2)C1] | 446.2 (M + 1) | 0.01 | 0.007 |
| 230 | 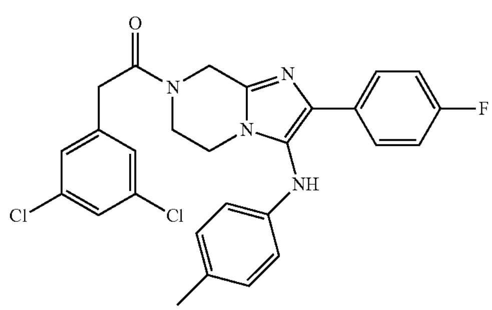 [SMILES: Cc1ccc(Nc2c(-c3ccc(F)cc3)nc3n2CCN(C(=O)Cc2cc(Cl)cc(Cl)c2)C3)cc1] | 510.2 (M + 1) | 0.32 | 0.255 |
| 231 | 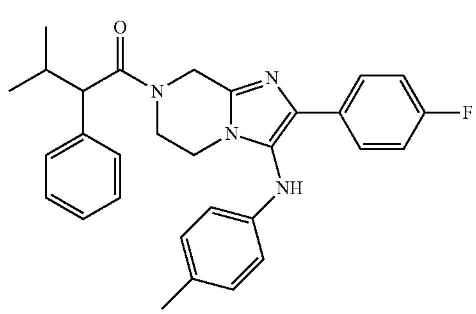 [SMILES: Cc1ccc(Nc2c(-c3ccc(F)cc3)nc3n2CCN(C(=O)C(c2ccccc2)C(C)C)C3)cc1] | 483.3 (M + 1) | 0.09 | 0.07 |

TABLE 2-continued
| Compound | Structure | Physical Data MS (m/z) and/or $^1$H NMR | EC$_{50}$ 3D7 strain (μM) | EC$_{50}$ W2 strain (μM) |
|---|---|---|---|---|
| 232 | 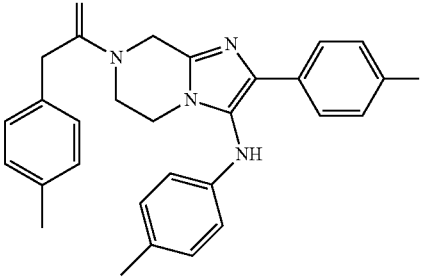 | 455.2 (M + 1) | 0.05 | 0.044 |
| 233 | 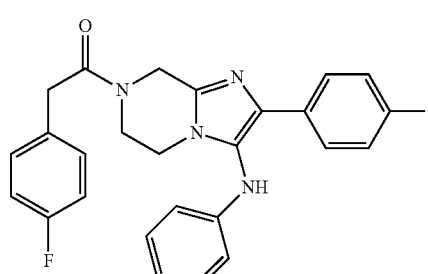 | 459.2 (M + 1) | 0.01 | 0.015 |
| 234 | 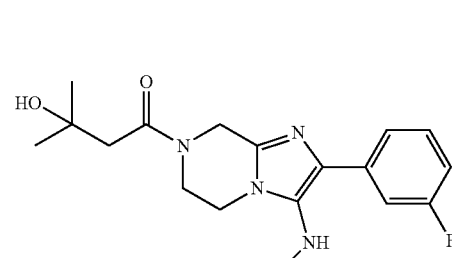 | 461.0 (M + 1) | 0.13 | 0.111 |
| 235 | 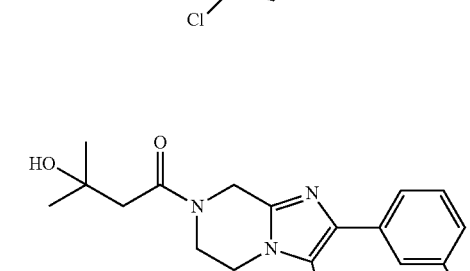 | 427.2 (M + 1) | 0.54 | 0.496 |

TABLE 2-continued

| Compound | Structure | Physical Data MS (m/z) and/or ¹H NMR | EC$_{50}$ 3D7 strain (µM) | EC$_{50}$ W2 strain (µM) |
| --- | --- | --- | --- | --- |
| 236 | 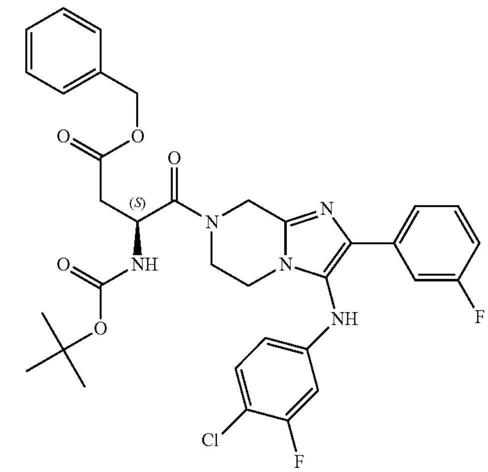 | 666.2 (M + 1) | 5.25 | 2.063 |
| 237 | 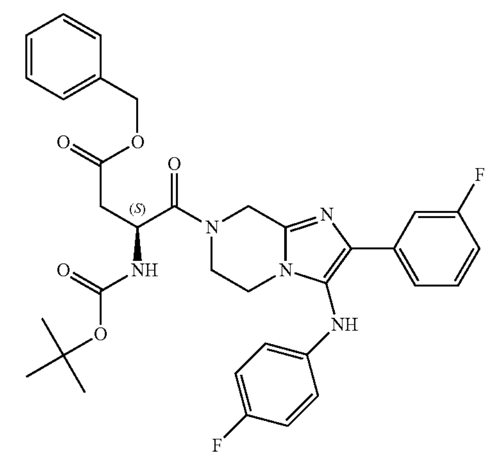 | 632.3 (M + 1) | 7.19 | 5.722 |
| 238 | 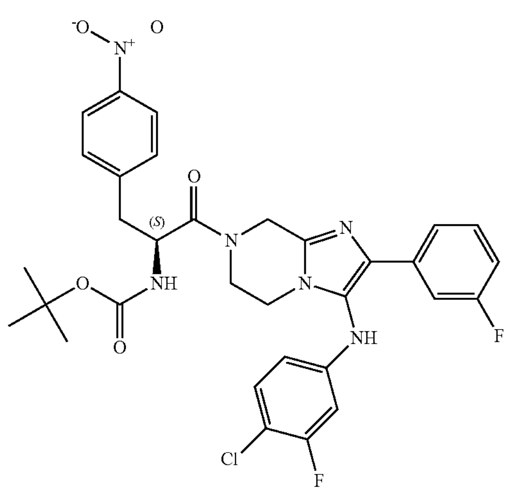 | 653.2 (M + 1) | 3.56 | 1.305 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 239 | 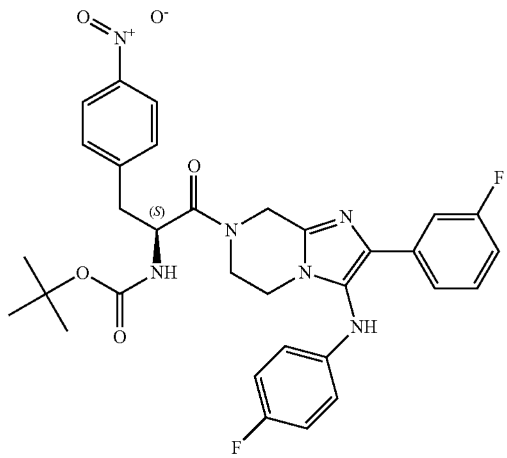 | 619.3 (M + 1) | 1.84 | 0.629 |
| 240 | 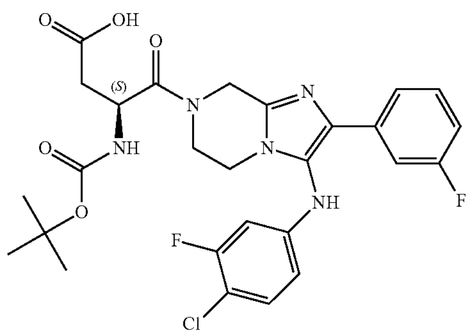 | 576.2 (M + 1) | 10.49 | 6.99 |
| 241 | 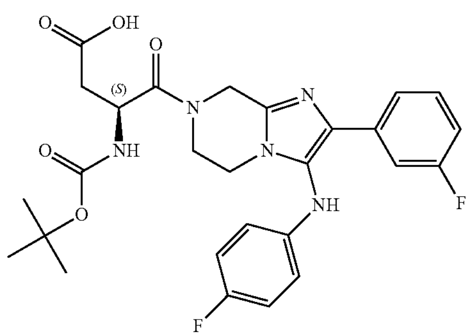 | 542.2 (M + 1) | 5.27 | 2.36 |
| 242 | 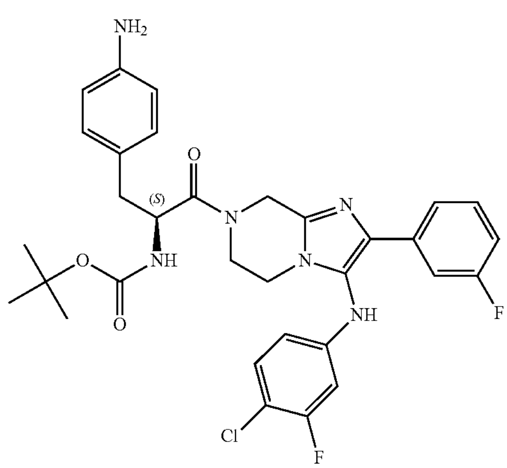 | 624.1 (M + 1) | 2.09 | 0.288 |

TABLE 2-continued
| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 243 | 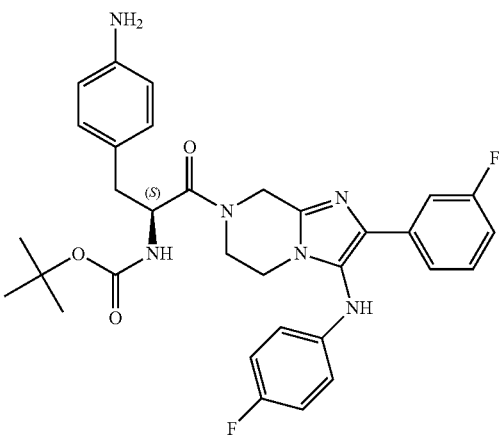 | 589.3 (M + 1) | 2.97 | 0.697 |
| 244 | 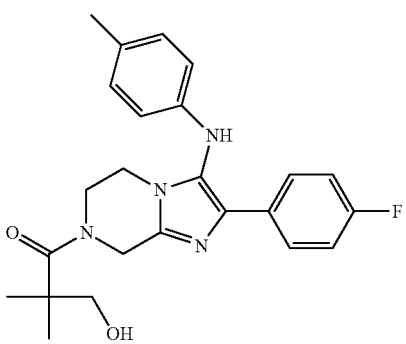 [SMILES: Cc1ccc(Nc2c(-c3ccc(F)cc3)nc3n2CCN(C(=O)C(C)(C)CO)C3)cc1] | 423.2 (M + 1) | 2.4 | 1.329 |
| 245 | 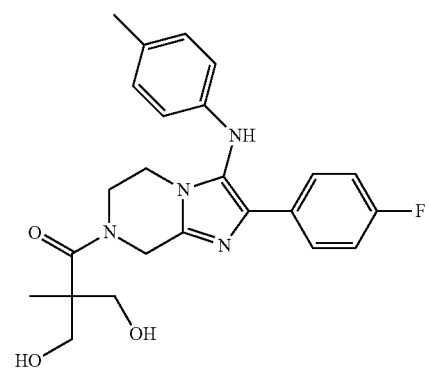 [SMILES: Cc1ccc(Nc2c(-c3ccc(F)cc3)nc3n2CCN(C(=O)C(C)(CO)CO)C3)cc1] | 439.2 (M + 1) | 2.53 | 1.804 |

TABLE 2-continued

| Compound | Structure | Physical Data MS (m/z) and/or ¹H NMR | EC$_{50}$ 3D7 strain (μM) | EC$_{50}$ W2 strain (μM) |
|---|---|---|---|---|
| 246 | 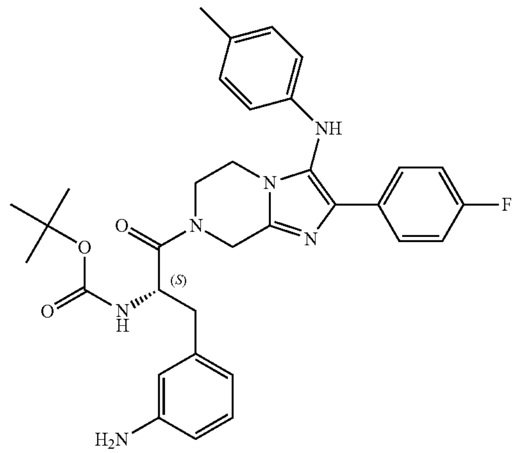 | 585.3 (M + 1) | 3.88 | 1.791 |
| 247 | 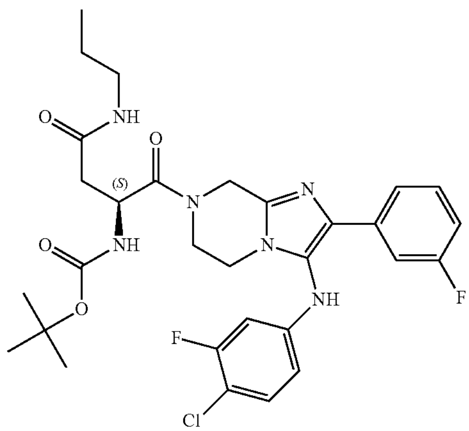 | 618.1 (M + 1) | 1.42 | 3.937 |
| 248 | 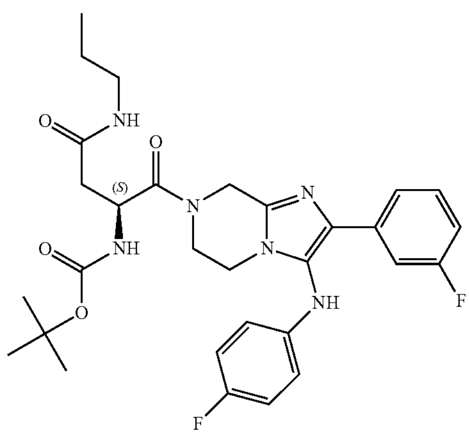 | 583.3 (M + 1) | 7.01 | 4.559 |
| 249 | 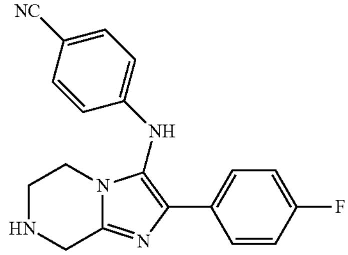 [SMILES: N#Cc1ccc(Nc2c(-c3ccc(F)cc3)nc3n2CCNC3)cc1] | 334.3 (M + 1) | 5.39 | 5.055 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 250 | 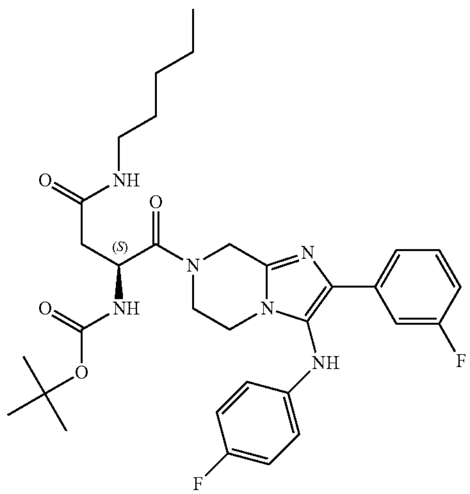 | 611.7 (M + 1) | 3.88 | 3.979 |
| 251 | 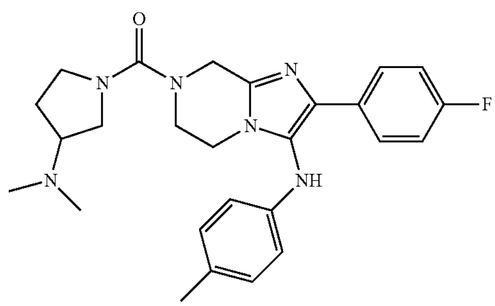 [SMILES: Cc1ccc(Nc2c(-c3ccc(F)cc3)nc3n2CCN(C(=O)N2CCC(N(C)C)C2)C3)cc1] | 463.3 (M + 1) | 3.68 | 2.548 |
| 252 | 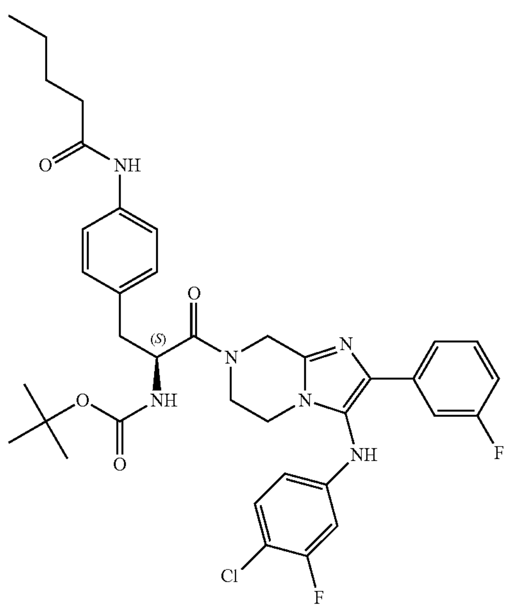 | 707.3 (M + 1) | 3.03 | 0.631 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 253 | 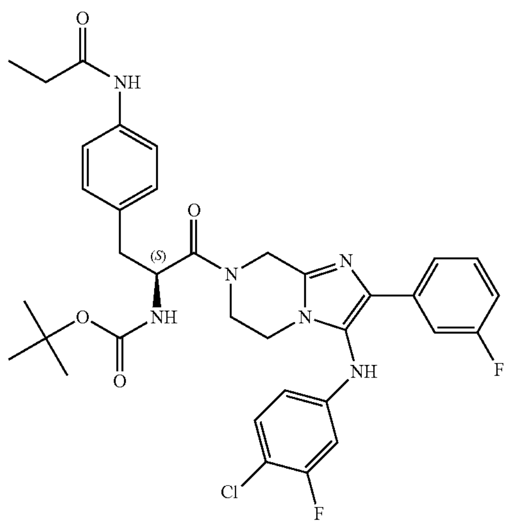 | 679.2 (M + 1) | 0.78 | 0.254 |
| 254 | 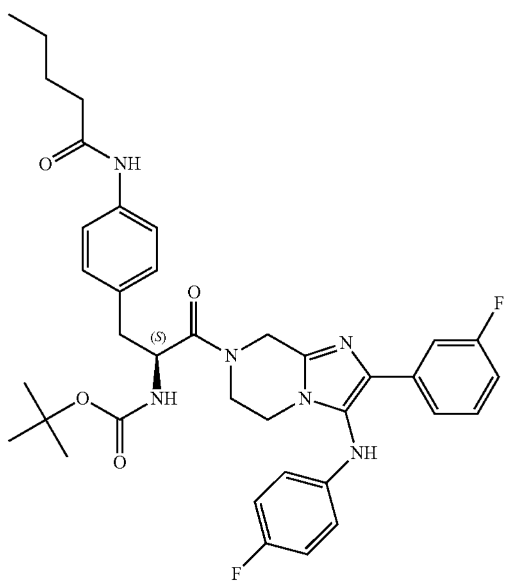 | 673.4 (M + 1) | 3.44 | 0.727 |
| 255 | 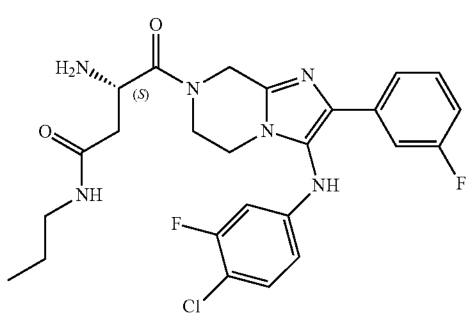 | 517.3 (M + 1) | 0.61 | 0.653 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 256 | 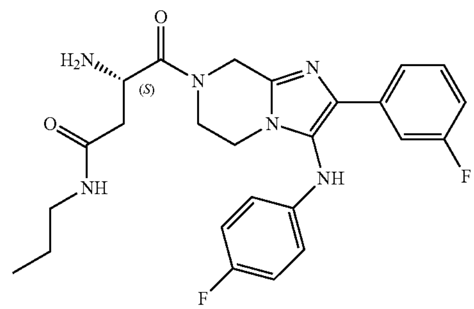 | 483.2 (M + 1) | 1.16 | 1.475 |
| 257 | 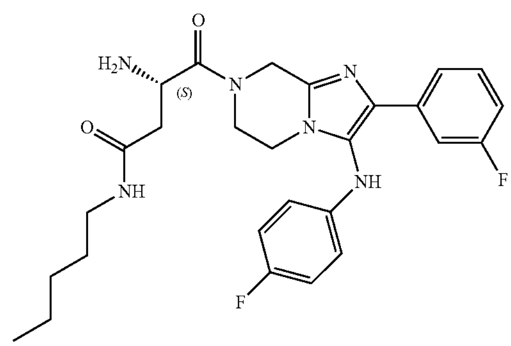 | 511.3 (M + 1) | 6.68 | 7.003 |
| 258 | 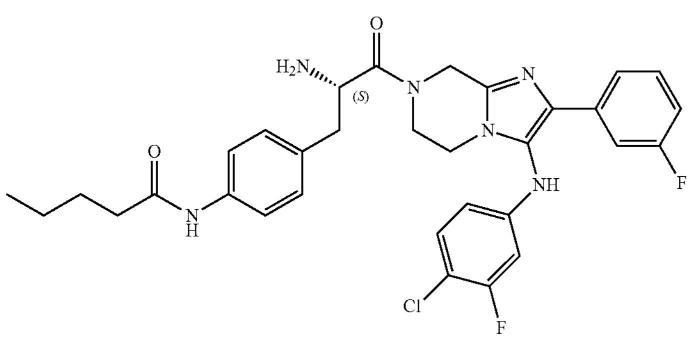 | 608.1 (M + 1) | 4.92 | 3.513 |
| 259 | 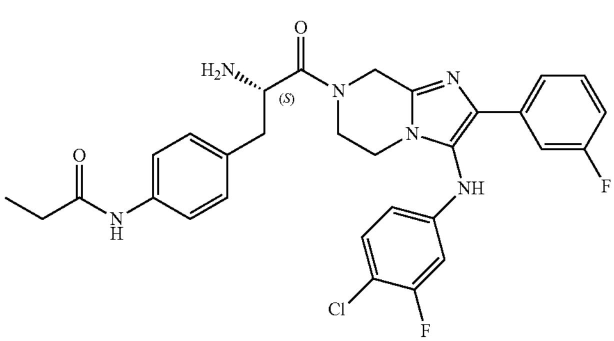 | 579.2 (M + 1) | 5.32 | 3.022 |

TABLE 2-continued

| Compound | Structure | Physical Data MS (m/z) and/or ¹H NMR | EC$_{50}$ 3D7 strain (μM) | EC$_{50}$ W2 strain (μM) |
| --- | --- | --- | --- | --- |
| 260 | 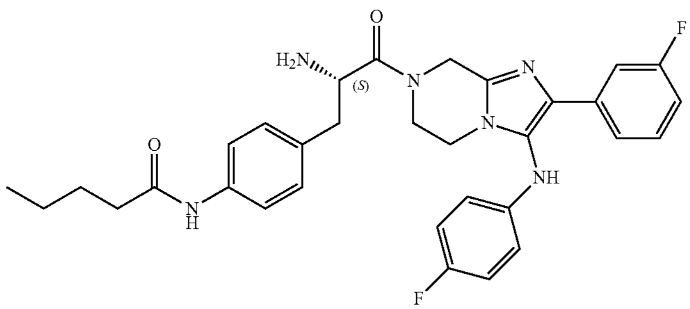 | 573.3 (M + 1) | 7.64 | 5.009 |
| 261 | 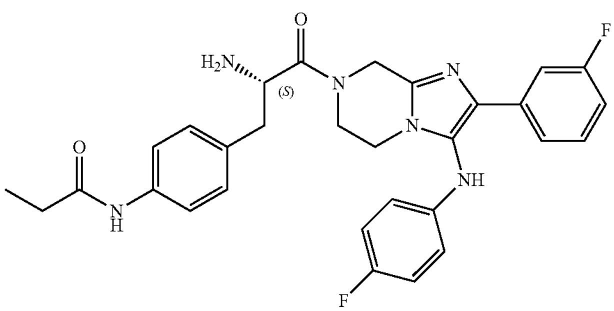 | 545.1 (M + 1) | 7.06 | 4.126 |
| 262 | 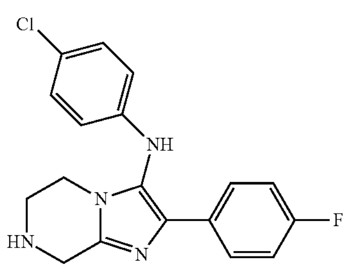 | 343.1 (M + 1) <br> ¹H NMR: (DMSO, ppm): δ 7.94 (s, 1H), 7.80-7.74 (m, 2H), 7.18-7.09 (m, 4H), 6.56 (d, J = 8.7 Hz, 2H), 3.87 (s, 2H), 3.55 (s, 2H), 3.02 (t, J = 5.4 Hz, 2H). | 0.24 | 0.267 |
| 263 | 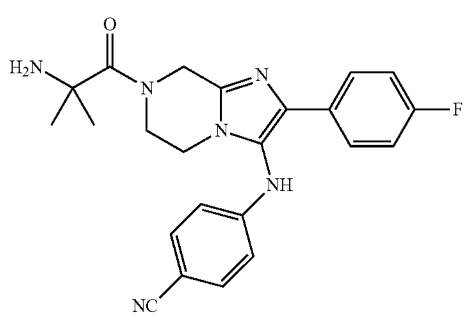 [SMILES: CC(C)(N)C(=O)N1CCn2c(nc(-c3ccc(F)cc3)c2Nc2ccc(C#N)cc2)C1] | 419.2 (M + 1) | 0.35 | 0.653 |
| 264 | 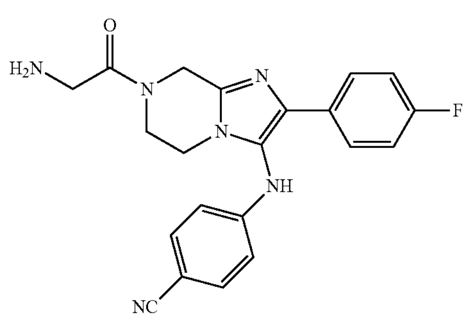 [SMILES: N#Cc1ccc(Nc2c(-c3ccc(F)cc3)nc3n2CCN(C(=O)CN)C3)cc1] | 391.2 (M + 1) | 0.11 | 0.154 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 265 | 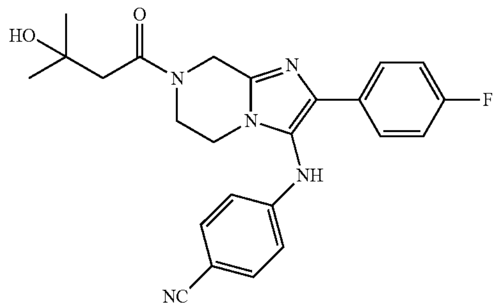 [SMILES: CC(C)(O)CC(=O)N1CCn2c(nc(-c3ccc(F)cc3)c2Nc2ccc(C#N)cc2)C1] | 434.2 (M + 1) | 1.35 | 1.585 |
| 266 | 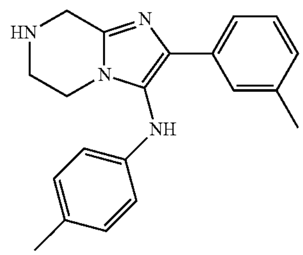 [SMILES: Cc1ccc(Nc2c(-c3cccc(C)c3)nc3n2CCNC3)cc1] | 319.2 (M + 1) $^1$H NMR: (300 MHz, CDCl$_3$) δ 7.70 (s, 1H), 7.56 (1H, d, J = 7.8 Hz), 7.21-7.15 (1H, t, J = 7.5 Hz), 7.04 (3H, d, J = 8.1 Hz), 5.21 (1H, s), 4.18 (s, 2H), 3.73-3.68 (t, 2H, J = 5.4 Hz), 3.23-3.18 (t, 2H, J = 5.4 Hz), 2.34 (s, 3H), 2.29 (s, 3H) | 1.17 | 1.313 |
| 267 | 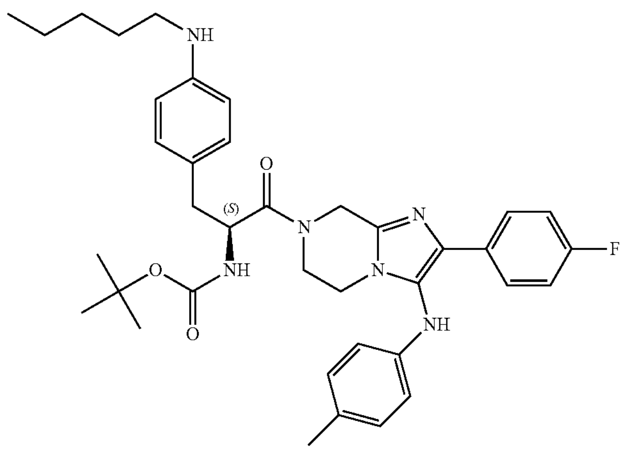 | 655.4 (M + 1) | 0.99 | 0.474 |
| 268 | 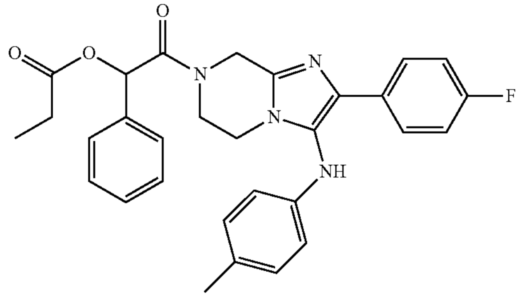 [SMILES: CCC(=O)OC(C(=O)N1CCn2c(nc(-c3ccc(F)cc3)c2Nc2ccc(C)cc2)C1)c1ccccc1] | 513.2 (M + 1) | 0.01 | 0.012 |

TABLE 2-continued
| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 269 | 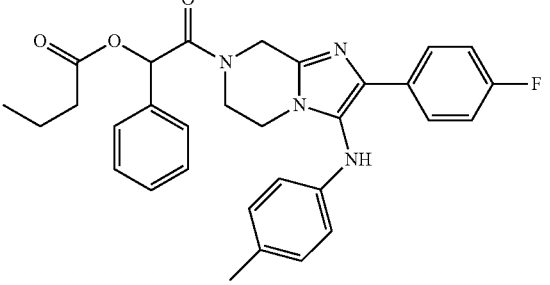 | 527.2 (M + 1) | 0.01 | 0.006 |
| 270 | 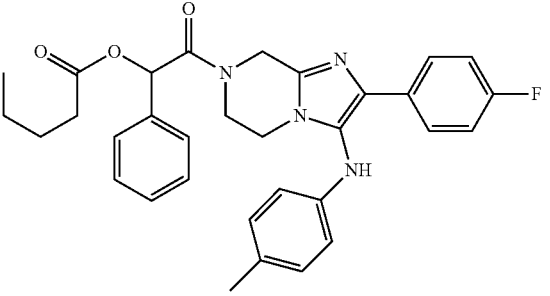 [SMILES: CCCCC(=O)OC(C(=O)N1CCn2c(nc(-c3ccc(F)cc3)c2Nc2ccc(C)cc2)C1)c1ccccc1] | 541.2 (M + 1) | 0.05 | |
| 271 | 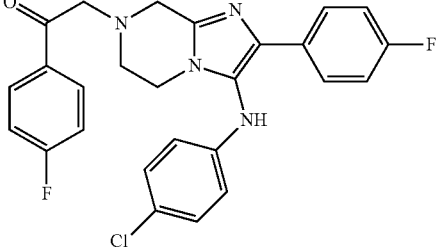 | 479.0 (M + 1) | 0.44 | 0.385 |
| 272 | 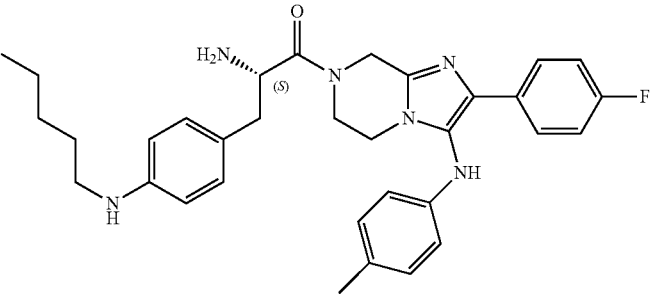 | 555.7 (M + 1) | 3.59 | 3.26 |
| 273 | 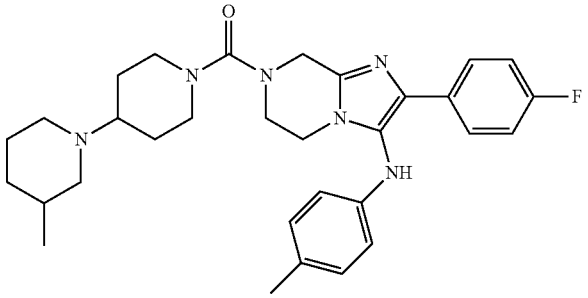 [SMILES: Cc1ccc(Nc2c(-c3ccc(F)cc3)nc3n2CCN(C(=O)N2CCC(N4CCCC(C)C4)CC2)C3)cc1] | 531.7 (M + 1) | 3.33 | 3.471 |

TABLE 2-continued
| Compound | Structure | Physical Data MS (m/z) and/or ¹H NMR | EC$_{50}$ 3D7 strain (μM) | EC$_{50}$ W2 strain (μM) |
|---|---|---|---|---|
| 274 | 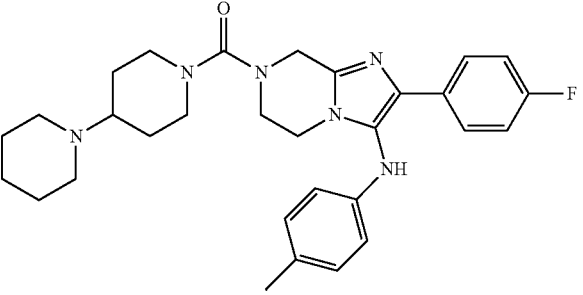 [SMILES: Cc1ccc(Nc2c(-c3ccc(F)cc3)nc3n2CCN(C(=O)N2CCC(N4CCCCC4)CC2)C3)cc1] | 517.7 (M + 1) | 5.14 | 5.673 |
| 275 | 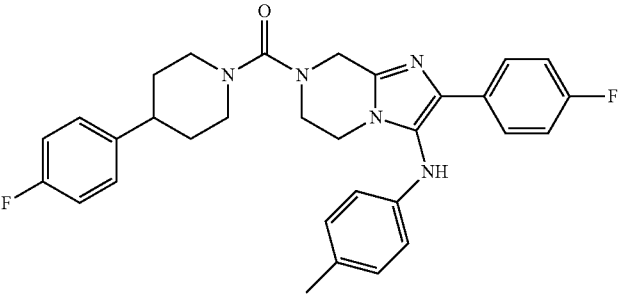 [SMILES: Cc1ccc(Nc2c(-c3ccc(F)cc3)nc3n2CCN(C(=O)N2CCC(c4ccc(F)cc4)CC2)C3)cc1] | 529.3 (M + 1) | 3.83 | 3.95 |
| 276 | 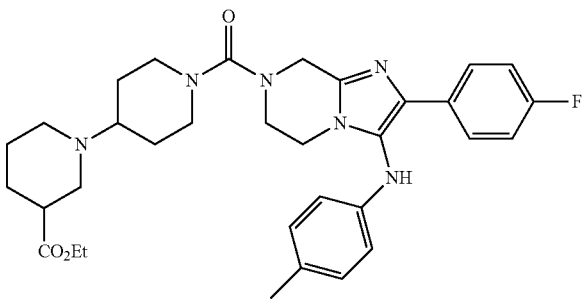 | 506.1 (M + 1) | | |
| 277 | 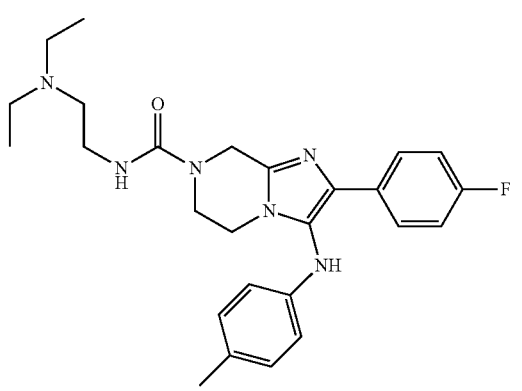 [SMILES: CCN(CC)CCNC(=O)N1CCn2c(nc(-c3ccc(F)cc3)c2Nc2ccc(C)cc2)C1] | 465.1 (M + 1) | | |

TABLE 2-continued

| Compound | Structure | Physical Data MS (m/z) and/or ¹H NMR | EC$_{50}$ 3D7 strain (μM) | EC$_{50}$ W2 strain (μM) |
|---|---|---|---|---|
| 278 | 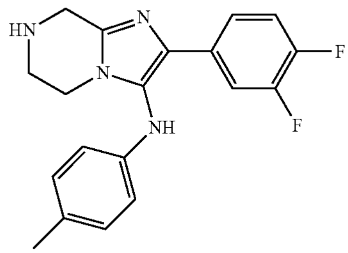 [SMILES: Cc1ccc(Nc2c(-c3ccc(F)c(F)c3)nc3n2CCNC3)cc1] | 341.2 (M + 1) ¹H NMR (400 MHz, CDCl$_3$) δ 7.70-7.53 (m, 2H), 7.12-7.04 (m, 3H), 6.58 (d, J = 8.4 Hz, 2H), 5.12 (s, 1H), 4.18 (s, 2H), 3.73 (m, 2H), 3.23 (m, 2H), 2.98 (s, 1H), 2.29 (s, 3H). | 0.21 | 0.269 |
| 279 | 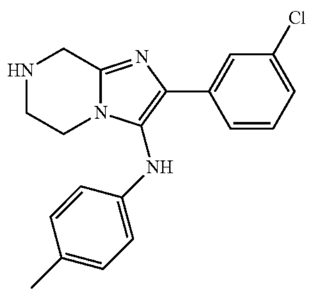 [SMILES: Cc1ccc(Nc2c(-c3cccc(Cl)c3)nc3n2CCNC3)cc1] | 339.1 (M + 1) ¹H NMR (300 MHz, CDCl$_3$) δ 7.70-7.62 (m, 1H), 7.24-7.15 (m, 2H), 7.05 (d, J = 8.1 Hz, 2H), 6.59 (d, J = 8.1 Hz, 2H), 5.15 (s, 1H), 4.18 (s, 2H), 3.72 (m, 2H), 3.22 (m, 2H), 2.29 (s, 3H) | 3.52 | 3.828 |
| 280 | 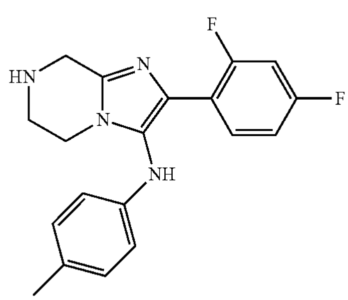 [SMILES: Cc1ccc(Nc2c(-c3ccc(F)cc3F)nc3n2CCNC3)cc1] | 341.2 (M + 1) ¹H NMR (300 MHz, CDCl$_3$) δ 7.70-7.62 (m, 1H), 7.01 (d, J = 8.1 Hz, 2H), 6.92-6.76 (m, 2H), 6.52 (d, J = 8.1 Hz, 2H), 5.33 (s, 1H), 4.23 (s, 2H), 3.77 (m, 2H), 3.26 (m, 2H), 2.25 (s, 3H). | 4.71 | 4.652 |
| 281 | 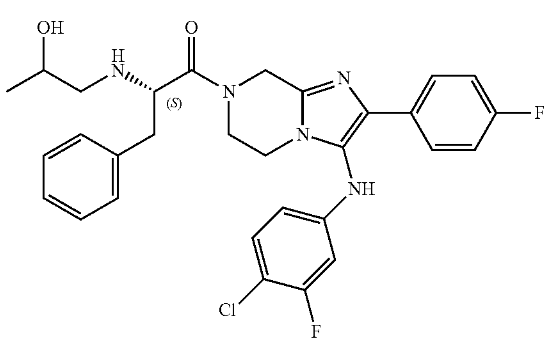 | 566.3 (M + 1) | 0.82 | 0.596 |

TABLE 2-continued

| Compound | Structure | Physical Data MS (m/z) and/or ¹H NMR | EC$_{50}$ 3D7 strain (μM) | EC$_{50}$ W2 strain (μM) |
|---|---|---|---|---|
| 282 | 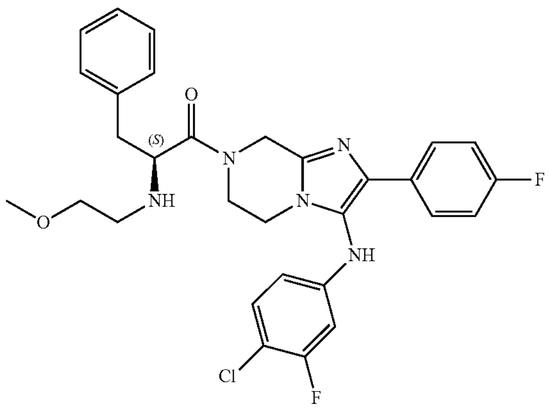 | 566.3 (M + 1) | 0.12 | 0.117 |
| 283 | 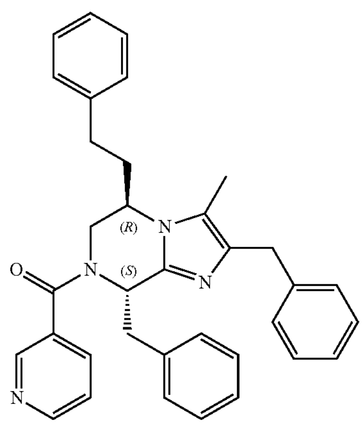 | 527.3 (M + 1) | 5.52 | 3.494 |
| 284 | 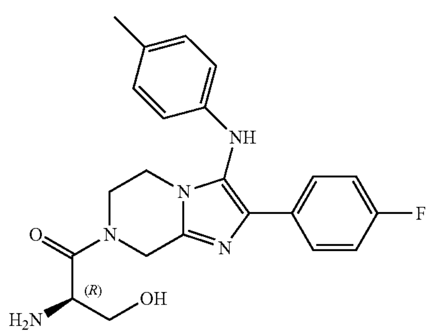 | 410.2 (M + 1) | 0.05 | 0.037 |
| 285 | 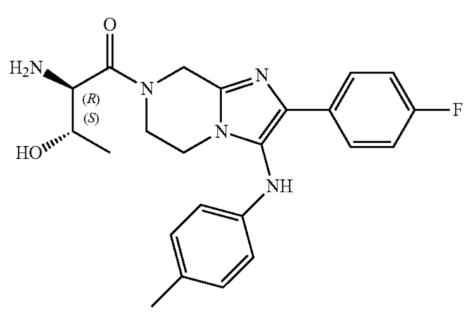 | 424.2 (M + 1) | 0.18 | 0.177 |

TABLE 2-continued
| Compound | Structure | Physical Data MS (m/z) and/or $^1$H NMR | EC$_{50}$ 3D7 strain (μM) | EC$_{50}$ W2 strain (μM) |
|---|---|---|---|---|
| 286 | 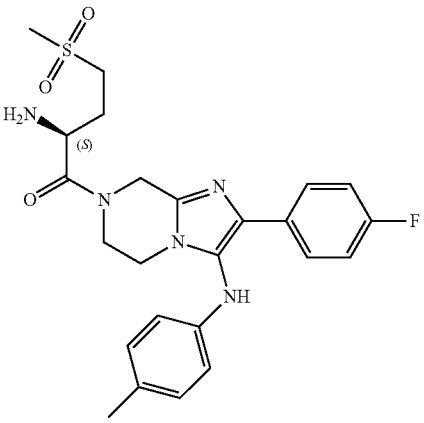 | 486.1 (M + 1) | 1.38 | 1.502 |
| 287 | 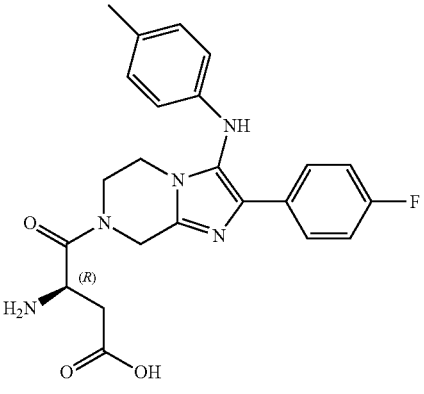 | 438.2 (M + 1) | 4.36 | 7.262 |
| 288 | 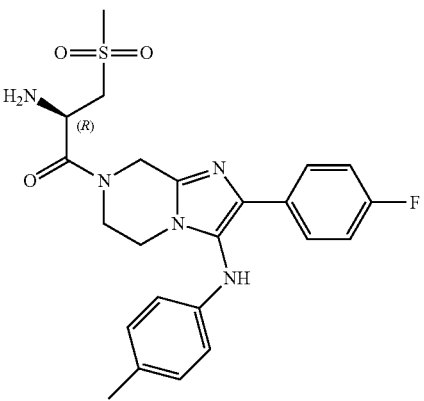 | 472.2 (M + 1) | 0.89 | 1.388 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 289 | 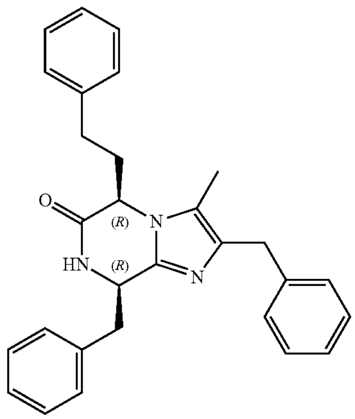 | 436.1 (M + 1) | 3.88 | 0.747 |
| 290 | 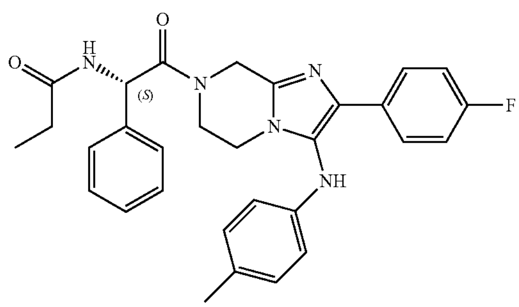 | 512.2 (M + 1) | 0.44 | 0.397 |
| 291 | 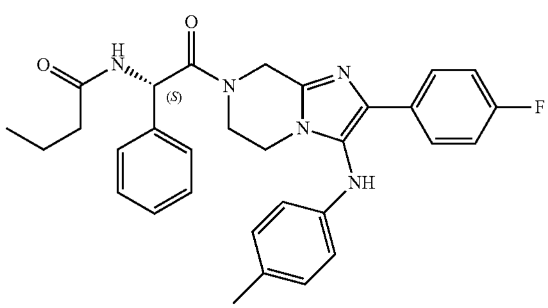 | 526.2 (M + 1) | 1.2 | 0.567 |
| 292 | 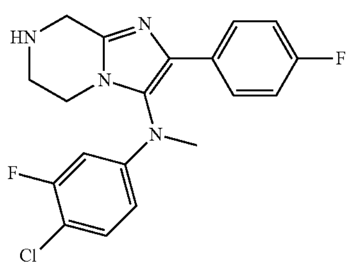 [SMILES: CN(c1ccc(Cl)c(F)c1)c1c(-c2ccc(F)cc2)nc2n1CCNC2] | 375.1 (M + 1) $^1$H NMR: (300 MHz, CDCl$_3$): δ 7.66-7.60 (m, 2H), 7.29-7.21 (m, 1H), 7.01-6.99 (m, 2H), 6.55-6.50 (m, 1H), 6.43-6.40 (m, 1H), 4.28 (s, 2H), 3.75-3.64 (m, 2H), 3.32-3.25 (m, 5H) | 0.15 | 0.156 |

TABLE 2-continued

| Compound | Structure | Physical Data MS (m/z) and/or ¹H NMR | EC$_{50}$ 3D7 strain (μM) | EC$_{50}$ W2 strain (μM) |
| --- | --- | --- | --- | --- |
| 293 | 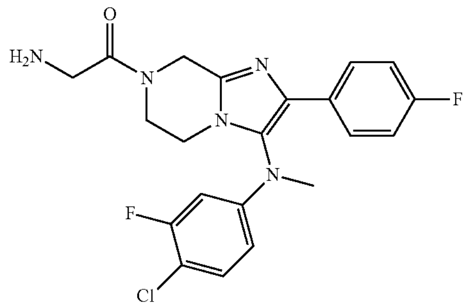 [SMILES: CN(c1ccc(Cl)c(F)c1)c1c(-c2ccc(F)cc2)nc2n1CCN(C(=O)CN)C2] | 432.0 (M + 1) ¹H-NMR: (MeOH-d$_4$, 400 Hz) δ 7.47-7.43 (m, 2H); 7.27-7.22 (m, 1 H); 7.14-7.07 (m, 2H); 6.7 (m, 1H); 6.53 (m, 1H); 4.99-4.80 (m, 2H); 4.04 (m, 2H); 3.85 (m, 4 H). | 0.02 | |
| 294 | 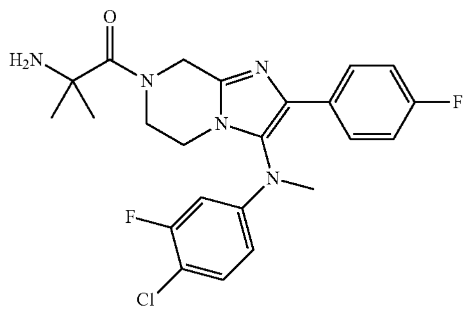 [SMILES: CN(c1ccc(Cl)c(F)c1)c1c(-c2ccc(F)cc2)nc2n1CCN(C(=O)C(C)(C)N)C2] | 460.2 (M + 1) | 0.11 | 0.113 |
| 295 | 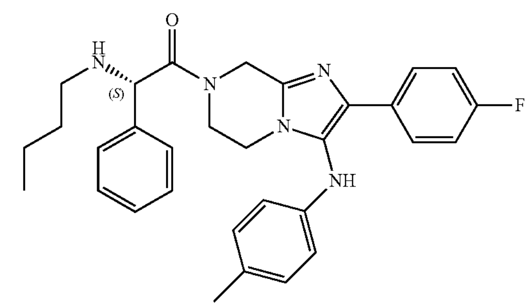 | 512.4 (M + 1) | 0.21 | 0.283 |
| 296 | 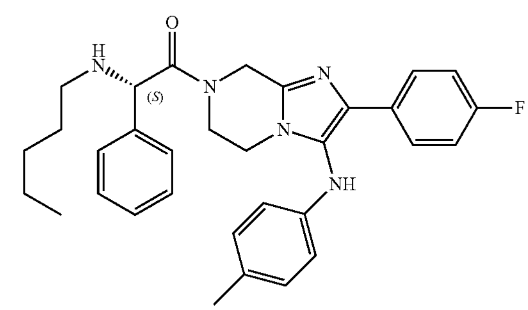 | 526.7 (M + 1) | 0.28 | 0.424 |
| 297 | 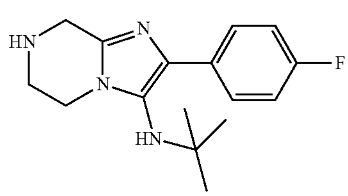 [SMILES: CC(C)(C)Nc1c(-c2ccc(F)cc2)nc2n1CCNC2] | 289.2 (M + 1) ¹H NMR: (300 MHz, CDCl$_3$): 7.72-7.75 (m, 2H), 7.03-7.10 (m, 2H), 4.16 (s, 2H), 3.86 (t, J = 5.4 Hz, 2H), 3.23 (t, J = 5.4 Hz, 2H), 1.04 (s, 9H). | 5.29 | 8.505 |

TABLE 2-continued

| Compound | Structure | Physical Data MS (m/z) and/or ¹H NMR | EC$_{50}$ 3D7 strain (μM) | EC$_{50}$ W2 strain (μM) |
| --- | --- | --- | --- | --- |
| 298 | 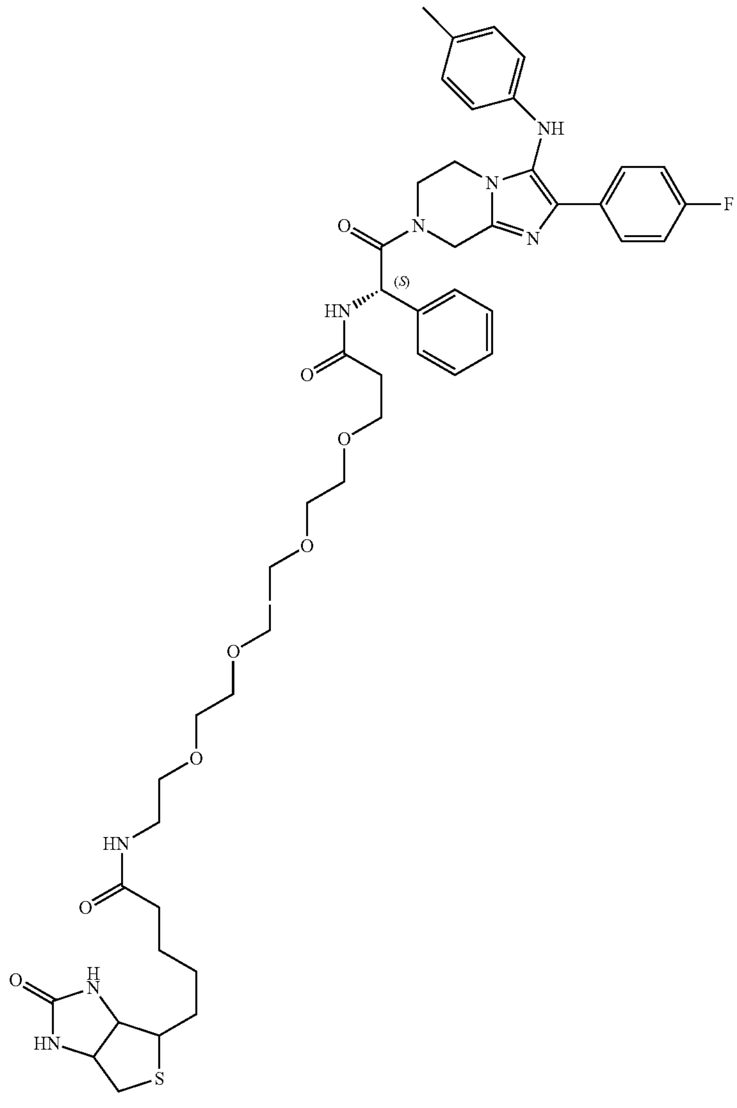 | 930.5 (M + 1) | 0.61 | 0.193 |
| 299 | 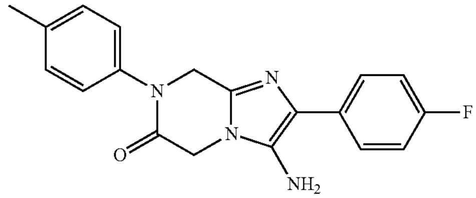 [SMILES: Cc1ccc(N2Cc3nc(-c4ccc(F)cc4)c(N)n3CC2=O)cc1] | 337.2 (M + 1) | >8.74 | 9.398 |
| 300 | 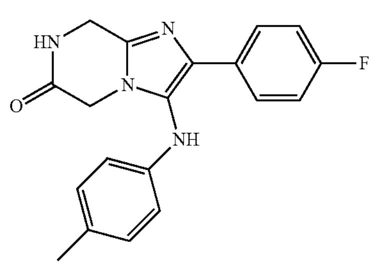 [SMILES: Cc1ccc(Nc2c(-c3ccc(F)cc3)nc3n2CC(=O)NC3)cc1] | 337.2 (M + 1) | 1.11 | 1.169 |

TABLE 2-continued
| Compound | Structure | Physical Data MS (m/z) and/or $^1$H NMR | EC$_{50}$ 3D7 strain (μM) | EC$_{50}$ W2 strain (μM) |
|---|---|---|---|---|
| 301 | 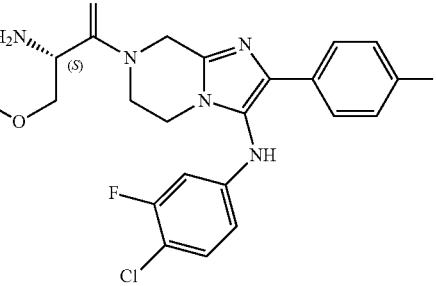 | 462.2 (M + 1) | 0.03 | 0.047 |
| 302 | 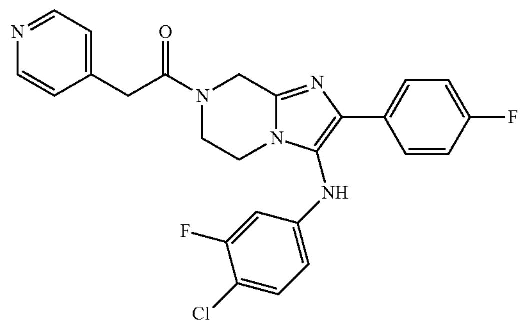 [SMILES: O=C(Cc1ccncc1)N1CCn2c(nc(-c3ccc(F)cc3)c2Nc2ccc(Cl)c(F)c2)C1] | 480.2 (M + 1) | 0.17 | 0.149 |
| 303 | 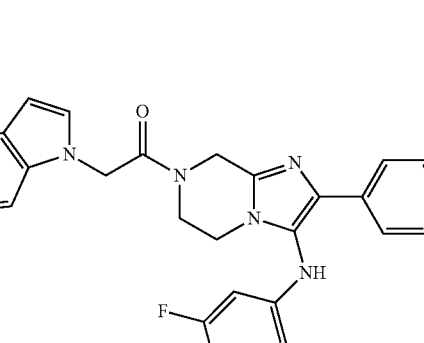 | 518.3 (M + 1) | 0.54 | 0.439 |
| 304 | 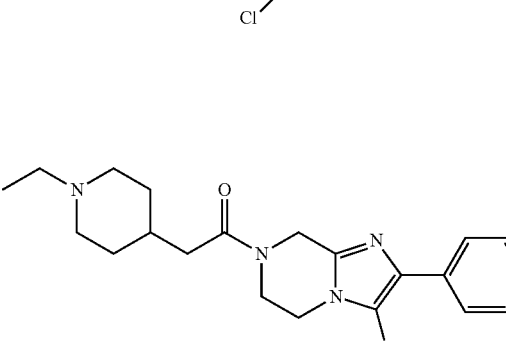 | 516.2 (M + 1) | 3.21 | 2.946 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 305 | 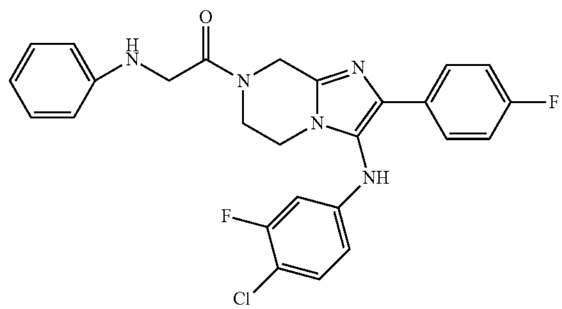 [SMILES: O=C(CNc1ccccc1)N1CCn2c(nc(-c3ccc(F)cc3)c2Nc2ccc(Cl)c(F)c2)C1] | 494.2 (M + 1) | 0.09 | 0.094 |
| 306 | 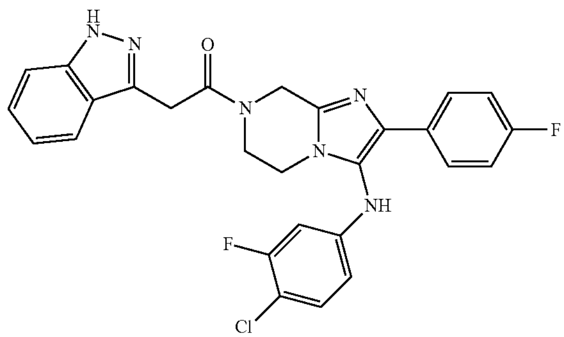 [SMILES: O=C(Cc1n[nH]c2ccccc12)N1CCn2c(nc(-c3ccc(F)cc3)c2Nc2ccc(Cl)c(F)c2)C1] | 519.2 (M + 1) | 0.42 | 0.334 |
| 307 | 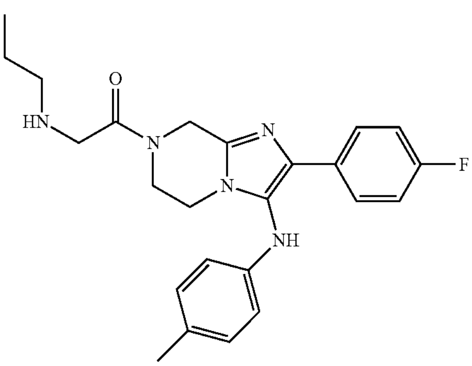 [SMILES: CCCNCC(=O)N1CCn2c(nc(-c3ccc(F)cc3)c2Nc2ccc(C)cc2)C1] | 422.2 (M + 1) | 0.03 | 0.022 |
| 308 | 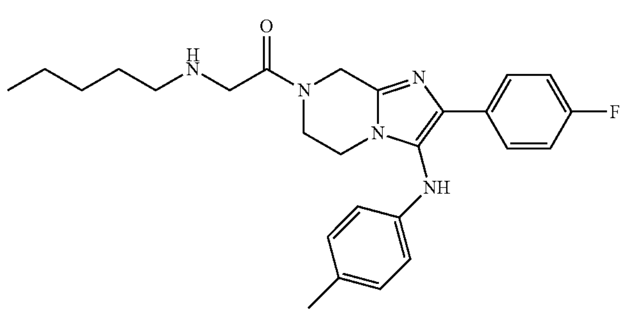 | 450.3 (M + 1) | 0.06 | 0.068 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 309 | 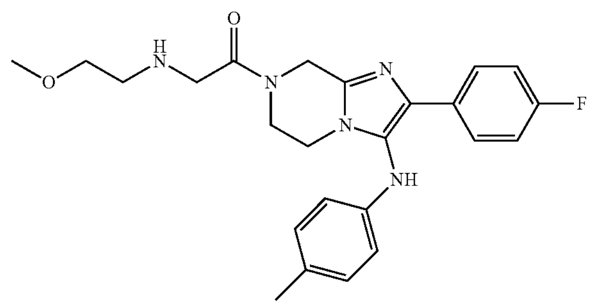 [SMILES: COCCNCC(=O)N1CCn2c(nc(-c3ccc(F)cc3)c2Nc2ccc(C)cc2)C1] | 438.2 (M + 1) | 0.08 | 0.068 |
| 310 | 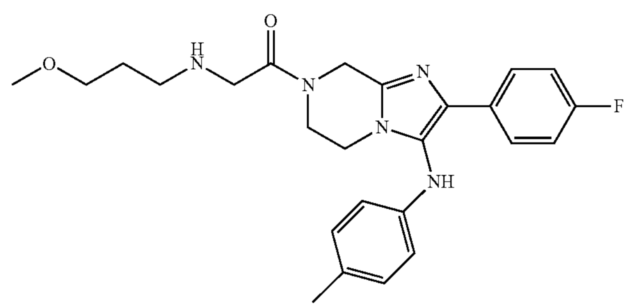 [SMILES: COCCCNCC(=O)N1CCn2c(nc(-c3ccc(F)cc3)c2Nc2ccc(C)cc2)C1] | 452.2 (M + 1) | 0.52 | 0.397 |
| 311 | 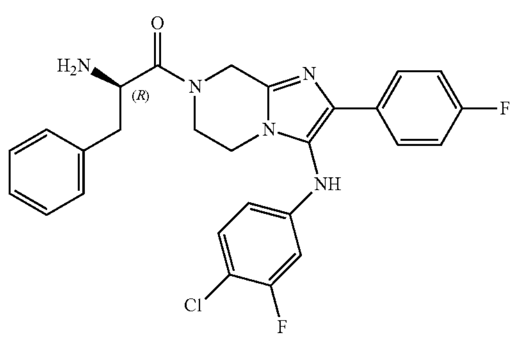 | 509.0 (M + 1) | 0.09 | 0.072 |
| 312 | 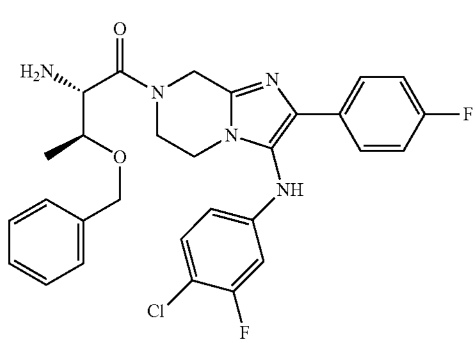 [SMILES: C[C@H](OCc1ccccc1)[C@H](N)C(=O)N1CCn2c(nc(-c3ccc(F)cc3)c2Nc2ccc(Cl)c(F)c2)C1] | 553.0 (M + 1) | 1.64 | 0.897 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 313 | 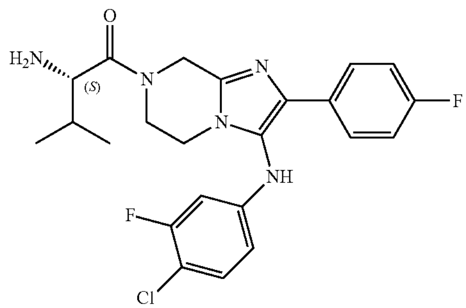 | 460.2 (M + 1) | 0.02 | 0.004 |
| 314 | 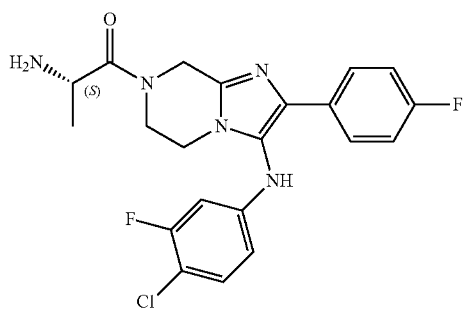 | 432.2 (M + 1) $^1$H-NMR: (MeOH-d$_4$, 400 Hz) δ 7.59-7.55 (m, 2H); 7.22-7.12 (m, 3H); 6.60-6.51 (m, 2H); 5.13-4.89 (m, 2H); 4.49 (m, 2H); 4.02-3.90 (m, 3H); 1.43 (d, J = 6.8 Hz, 3H). | 0.03 | 0.02 |
| 315 | 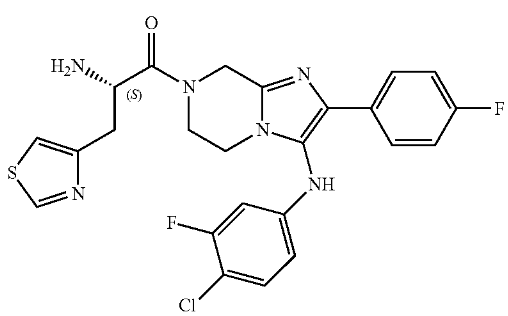 | 515.2 (M + 1) $^1$H-NMR: (MeOH-d$_4$, 400 Hz) δ 8.94-8.90 (m, 2H); 7.59-7.44 (m, 2H); 7.21-7.13 (m, 3H); 6.59-6.51 (m, 2H); 5.24-5.09 (m, 2H); 4.04-3.85 (m, 5H); 3.38-3.28 (m, 2H). | 0.02 | 0.008 |
| 316 | 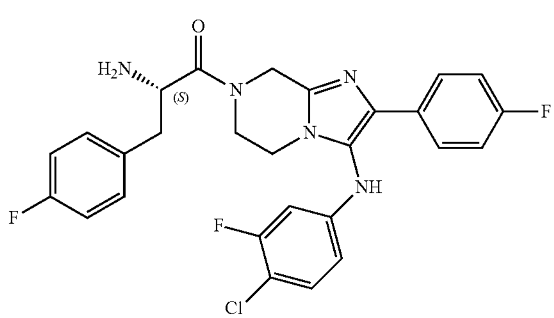 | 526.2 (M + 1) $^1$H-NMR: (MeOH-d$_4$, 400 Hz) δ 7.59-7.52 (m, 2H); 7.27-7.22 (m, 2H); 7.03-6.92 (m, 2H); 6.53-6.44 (m, 2H); 5.17 (m, 1H); 4.23 (m, 1H); 3.92-3.72 (m, 3H); 3.51-3.42 (m, 2H); 3.22 (m, 1H); 3.09-3.06 (m, 1H). | 0.02 | 0.014 |

TABLE 2-continued

| Compound | Structure | Physical Data MS (m/z) and/or ¹H NMR | EC$_{50}$ 3D7 strain (μM) | EC$_{50}$ W2 strain (μM) |
|---|---|---|---|---|
| 317 | 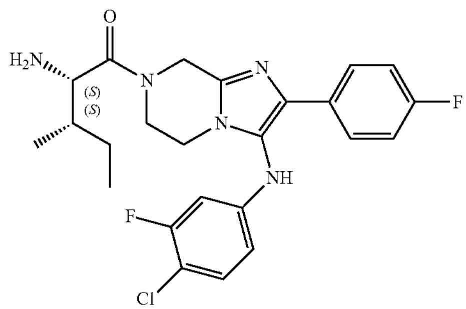 | 474.0 (M + 1) ¹H-NMR: (MeOH-d$_4$, 400 Hz) δ 7.59-7.56 (m, 2H); 7.22-7.11 (m, 3H); 6.58-6.49 (m, 2H); 5.2-4.88 (m, 2H); 4.5-3.62 (m, 5H); 1.91-1.88 (m, 1H); 1.5-1.46 (m, 1H); 1.27-0.87 (m, 7H). | 0.02 | |
| 318 | 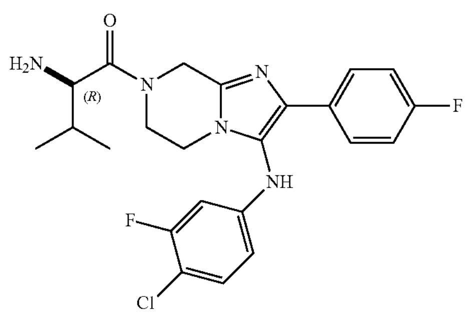 | 460.2 (M + 1) | 0.15 | 0.098 |
| 319 | 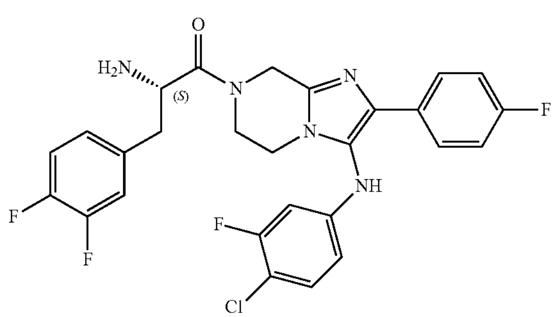 | 544.2 (M + 1) ¹H-NMR: (MeOH-d$_4$, 400 Hz) δ 7.58-7.53 (m, 2H); 7.22-7.12 (m, 6H); 6.59-6.49 (m, 2H); 5.3-5.25 (m, 1H); 4.93-4.73 (m, 2H); 4.05-3.65 (m, 4H); 3.15--3.1 (m, 1H); 3.07-2.97 (m, 1H). | 0.04 | 0.027 |
| 320 | 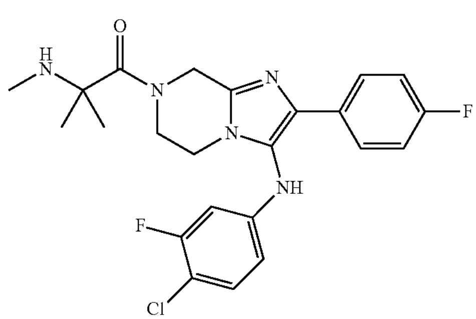 [SMILES: CNC(C)(C)C(=O)N1CCn2c(nc(-c3ccc(F)cc3)c2Nc2ccc(Cl)c(F)c2)C1] | 460.2 (M + 1) | 0.17 | 0.103 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 321 | 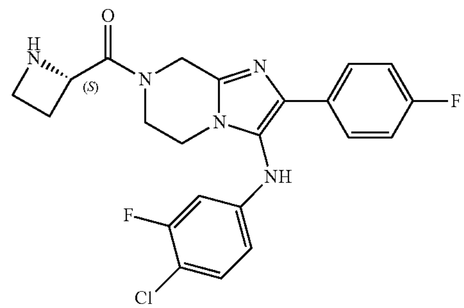 | 444.2 (M + 1) $^1$H-NMR: (MeOH-d$_4$, 400 Hz) δ 7.58-7.55 (m, 2H); 7.22-7.14 (m, 3H); 6.61-6.51 (m, 2H); 5034-5.20 (m, 2H); 4.53-4.39 (m, 2H); 4.15-4.1 (m, 2H); 4.02-3.95 (m, 3H); 1.18 (m, 1H); 1.06 (d, J = 7.2 Hz, 2H); 0.963 (d, J = 7.2 Hz, 2H). | 0.02 | 0.011 |
| 322 | 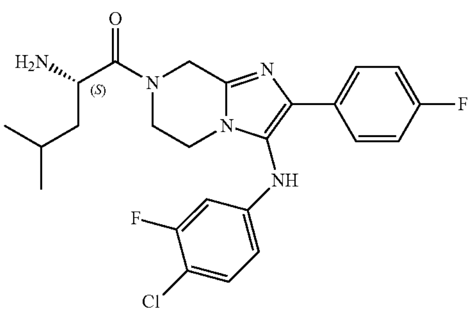 | 474.2 (M + 1) | 0.04 | |
| 323 | 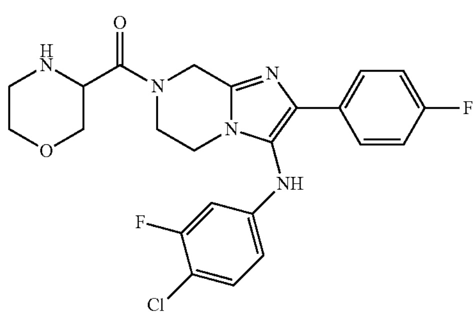 [SMILES: O=C(C1COCCN1)N1CCn2c(nc(-c3ccc(F)cc3)c2Nc2ccc(Cl)c(F)c2)C1] | 474.2 (M + 1) | 1.73 | 1.329 |
| 324 | 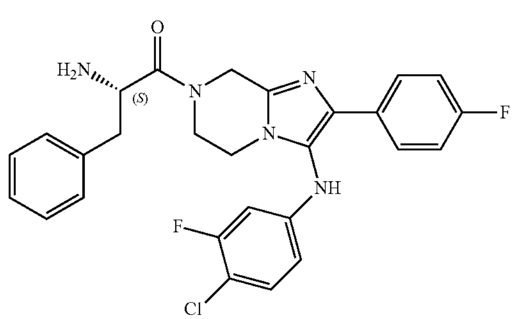 | 508.2 (M + 1) | 0.03 | 0.03 |

TABLE 2-continued
| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 325 | 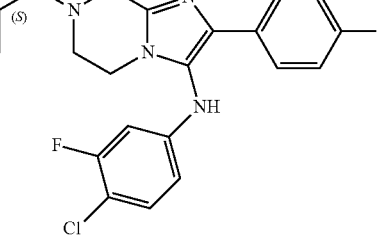 | 486.2 (M + 1) | 0.03 | 0.029 |
| 326 | 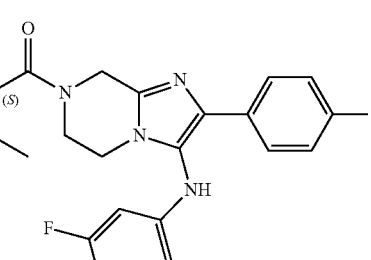 | 474.2 (M + 1) | 0.03 | 0.022 |
| 327 | 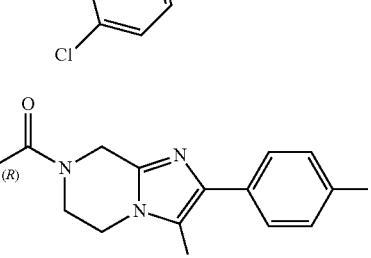 | 432.2 (M + 1) | 0.03 | 0.021 |
| 328 | 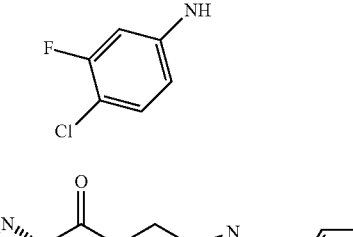 | 533.2 (M + 1) | 0.34 | 0.229 |
| 329 | 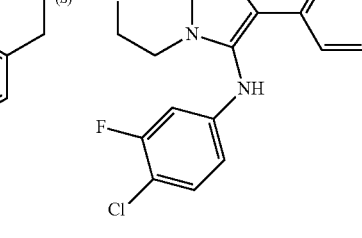 | 337.2 (M + 1) | 0.15 | 0.116 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 330 | 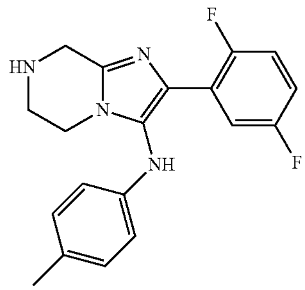 [SMILES: Cc1ccc(Nc2c(-c3cc(F)ccc3F)nc3n2CCNC3)cc1] | 341.2 (M + 1) $^1$H NMR: (300 Hz, DMSO-d$_6$) δ 7.47 (s, 1H), 7.32 (1H, d, J = 4.5 Hz), 7.17 (1H, d, J = 3.6 Hz), 7.05 (s, 1H), 3.91 (2H, d, J = 7.5 Hz), 6.44 (2H, d, J = 7.8 Hz), 3.87 (s, 2H), 3.55 (s, 2H), 3.02 (s, 2H), 2.15 (s, 3H) | 4.47 | |
| 331 | 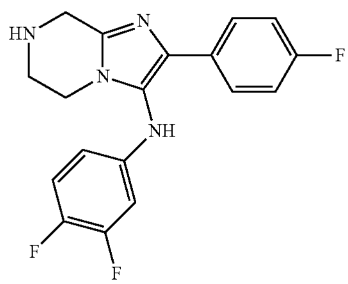 [SMILES: Fc1ccc(-c2nc3n(c2Nc2ccc(F)c(F)c2)CCNC3)cc1] | 345.1 (M + 1) $^1$H NMR (300 MHz, CDCl$_3$) δ 7.76-7.72 (m, 2H) 7.08-6.99 (m, 3H) 6.50-6.43 (m, H) 6.38-6.35 (m, 1H) 5.26 (s, H) 4.17 (s, 2H) 3.73-3.69 (m, 2H) 3.27-3.23 (m, 2H) 2.05 (s, 2H). | 0.14 | |
| 332 | 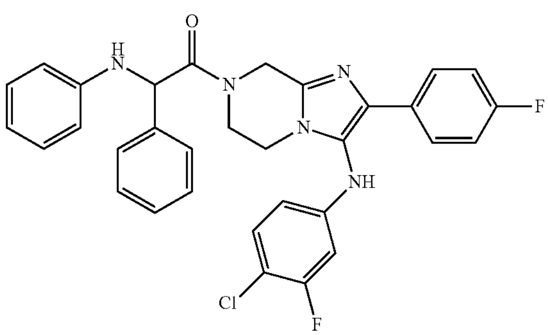 [SMILES: O=C(C(Nc1ccccc1)c1ccccc1)N1CCn2c(nc(-c3ccc(F)cc3)c2Nc2ccc(Cl)c(F)c2)C1] | 570.3 (M + 1) | 1.04 | |
| 333 | 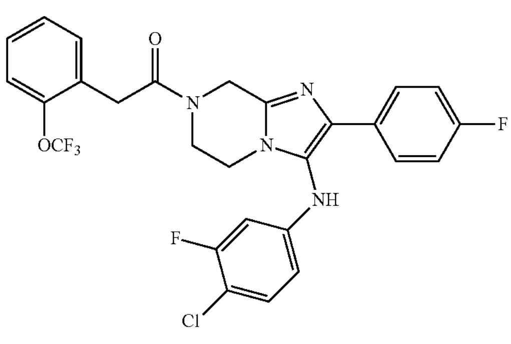 [SMILES: O=C(Cc1ccccc1OC(F)(F)F)N1CCn2c(nc(-c3ccc(F)cc3)c2Nc2ccc(Cl)c(F)c2)C1] | 563.2 (M + 1) | 1.11 | |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 334 | 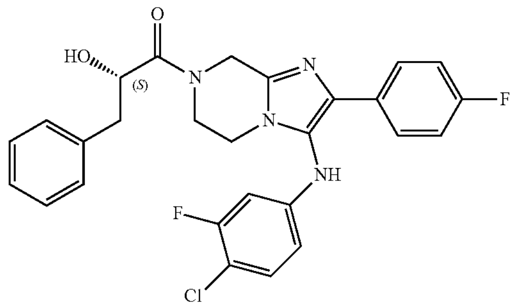 | 509.2 (M + 1) | 0.05 | |
| 335 | 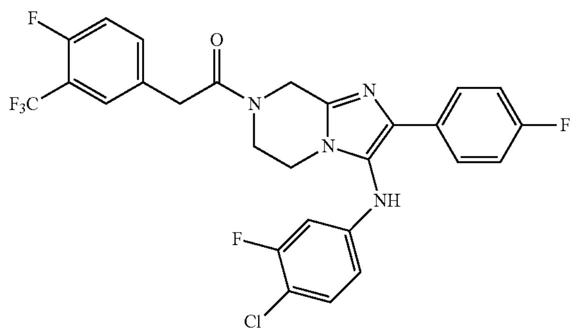 [SMILES: O=C(Cc1ccc(F)c(C(F)(F)F)c1)N1CCn2c(nc(-c3ccc(F)cc3)c2Nc2ccc(Cl)c(F)c2)C1] | 565.2 (M + 1) | 2.3 | |
| 336 | 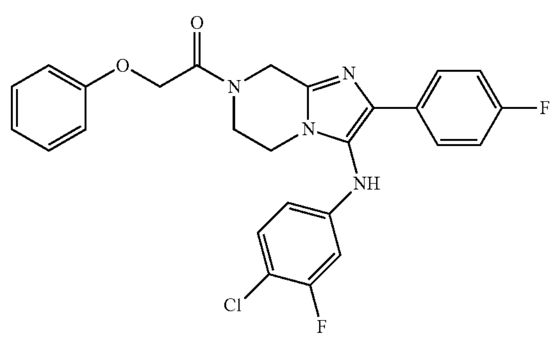 [SMILES: O=C(COc1ccccc1)N1CCn2c(nc(-c3ccc(F)cc3)c2Nc2ccc(Cl)c(F)c2)C1] | 495.2 (M + 1) | 0.04 | |
| 337 | 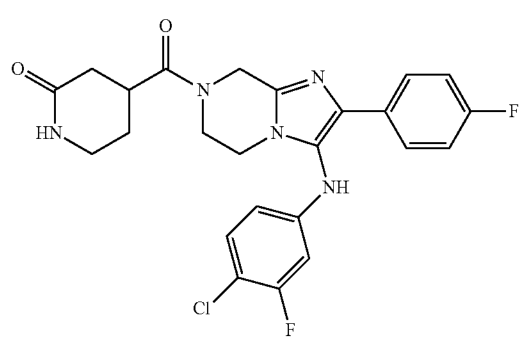 [SMILES: O=C1CC(C(=O)N2CCn3c(nc(-c4ccc(F)cc4)c3Nc3ccc(Cl)c(F)c3)C2)CCN1] | 486.2 (M + 1) | >10 | |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 338 | 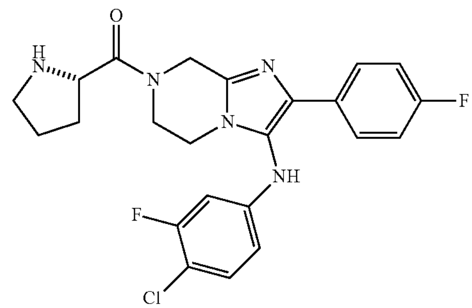 [SMILES: O=C([C@@H]1CCCN1)N1CCn2c(nc(-c3ccc(F)cc3)c2Nc2ccc(Cl)c(F)c2)C1] | 458.2 (M + 1) | 0.19 | |
| 339 | 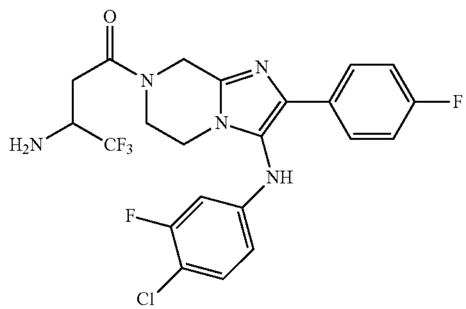 [SMILES: NC(CC(=O)N1CCn2c(nc(-c3ccc(F)cc3)c2Nc2ccc(Cl)c(F)c2)C1)C(F)(F)F] | 500.2 (M + 1) | 0.52 | |
| 340 | 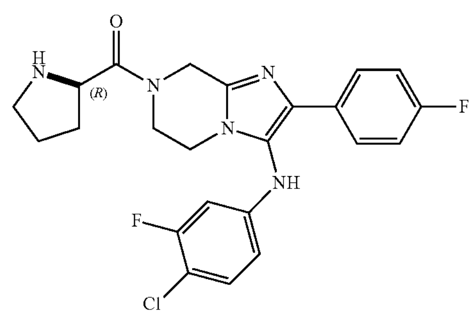 | 458.2 (M + 1) | 0.2 | |
| 341 | 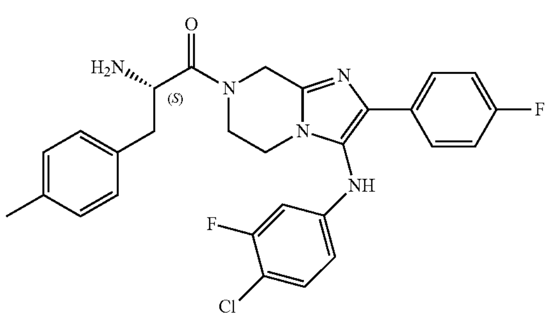 | 522.3 (M + 1) | 0.01 | |
| 342 | 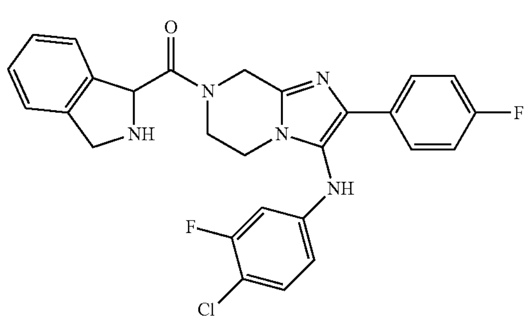 [SMILES: O=C(C1NCc2ccccc21)N1CCn2c(nc(-c3ccc(F)cc3)c2Nc2ccc(Cl)c(F)c2)C1] | 506.2 (M + 1) | 5.24 | |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 343 | 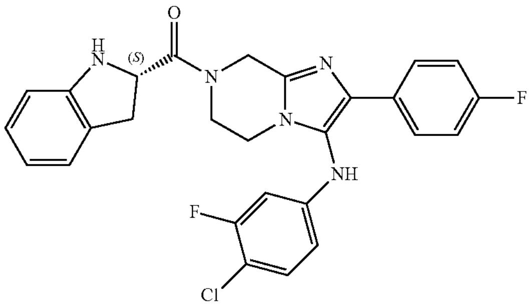 | 506.2 (M + 1) | 7.5 | |
| 344 | 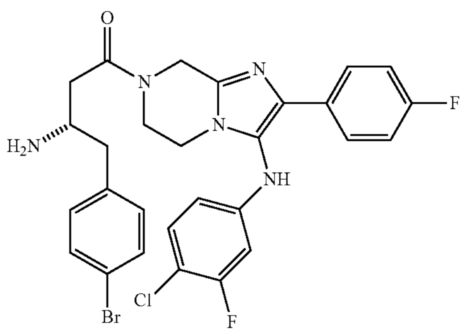 [SMILES: N[C@H](CC(=O)N1CCn2c(nc(-c3ccc(F)cc3)c2Nc2ccc(Cl)c(F)c2)C1)Cc1ccc(Br)cc1] | 601.2 (M + 1) | 0.21 | |
| 345 | 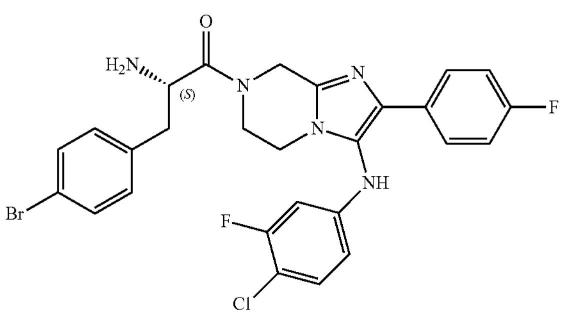 | 587.2 (M + 1) | | |
| 346 | 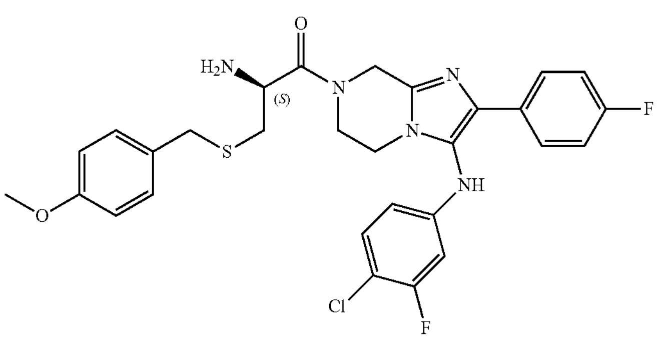 | 585.1 (M + 1) | >8.8 | |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 347 | 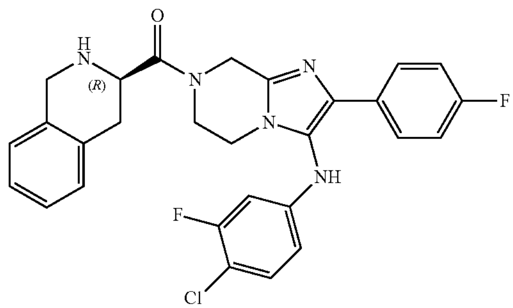 | 520.3 (M + 1) | 5.92 | |
| 348 | 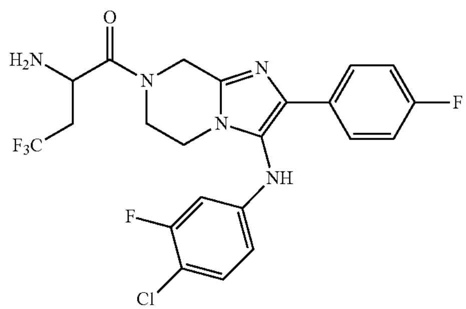 [SMILES: NC(CC(F)(F)F)C(=O)N1CCn2c(nc(-c3ccc(F)cc3)c2Nc2ccc(Cl)c(F)c2)C1] | 499.9 (M + 1) | 0.05 | |
| 349 | 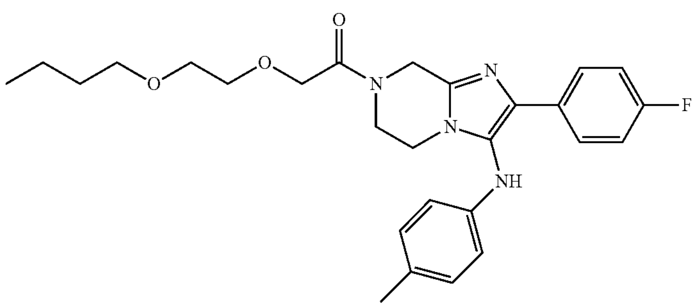 [SMILES: CCCCOCCOCC(=O)N1CCn2c(nc(-c3ccc(F)cc3)c2Nc2ccc(C)cc2)C1] | 481.6 (M + 1) | 7.48 | |
| 350 | 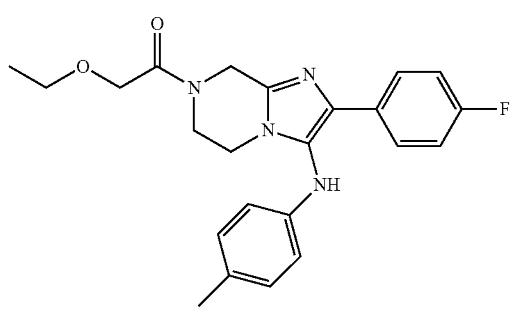 [SMILES: CCOCC(=O)N1CCn2c(nc(-c3ccc(F)cc3)c2Nc2ccc(C)cc2)C1] | 409.2 (M + 1) | 0.66 | |
| 351 | 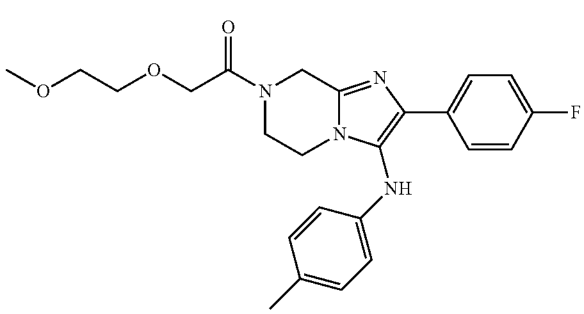 | 439.2 (M + 1) | 1.24 | |

TABLE 2-continued

| Compound | Structure | Physical Data MS (m/z) and/or ¹H NMR | EC$_{50}$ 3D7 strain (μM) | EC$_{50}$ W2 strain (μM) |
|---|---|---|---|---|
| 352 | 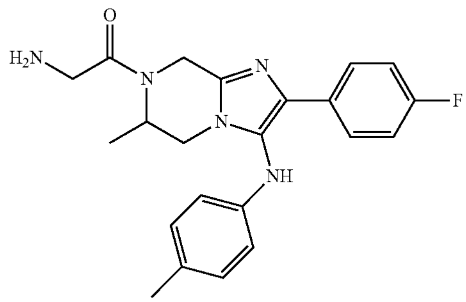 [SMILES: Cc1ccc(Nc2c(-c3ccc(F)cc3)nc3n2CC(C)N(C(=O)CN)C3)cc1] | 394.2 (M + 1) | 0.01 | |
| 353 | 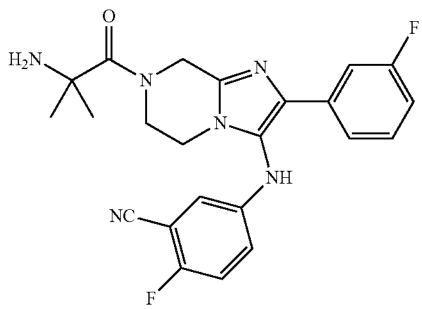 [SMILES: CC(C)(N)C(=O)N1CCn2c(nc(-c3cccc(F)c3)c2Nc2ccc(F)c(C#N)c2)C1] | 437.2 (M + 1) | 0.21 | |
| 354 | 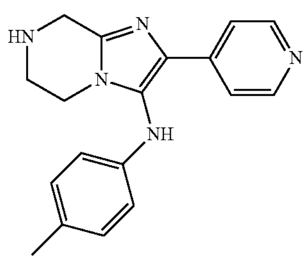 [SMILES: Cc1ccc(Nc2c(-c3ccncc3)nc3n2CCNC3)cc1] | 306.2 (M + 1) H-NMR (300 MHz, CDCl$_3$): 2.29 (s, 3H), 3.03 (m, 2H), 3.43 (s, 1H), 3.81 (m, 2H), 3.90 (s, 2H), 5.57 (s, 1H), 6.60-6.63 (2H, d, J = 8.4 Hz), 7.06-7.09 (2H, d, J = 8.1 Hz), 7.79 (m, 2H), 8.44-8.46 (m, 2H) | 6.32 | 0.564 |
| 355 | 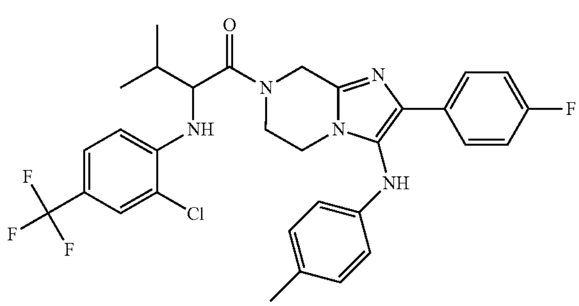 [SMILES: Cc1ccc(Nc2c(-c3ccc(F)cc3)nc3n2CCN(C(=O)C(Nc2ccc(C(F)(F)F)cc2Cl)C(C)C)C3)cc1] | 600 (M + 1) | 2.81 | 2.266 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 356 | 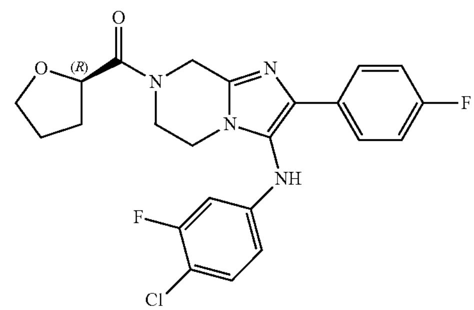 | 459.2 (M + 1) | 1.26 | 0.872 |
| 357 | 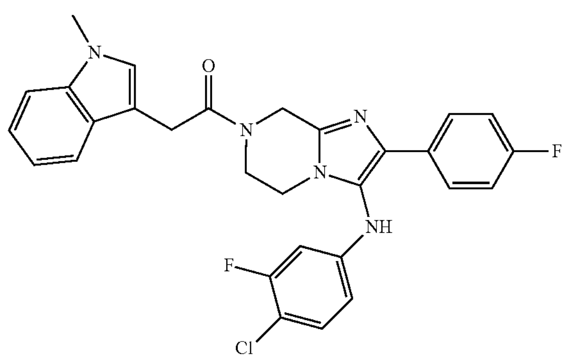 [SMILES: Cn1cc(CC(=O)N2CCn3c(nc(-c4ccc(F)cc4)c3Nc3ccc(Cl)c(F)c3)C2)c2ccccc21] | 532.3 (M + 1) | 7.49 | 4.712 |
| 358 | 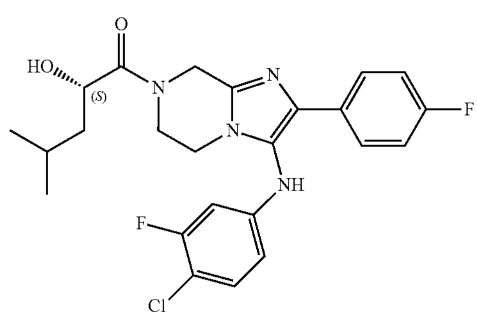 | 475.2 (M + 1) | 0.13 | 0.049 |
| 359 | 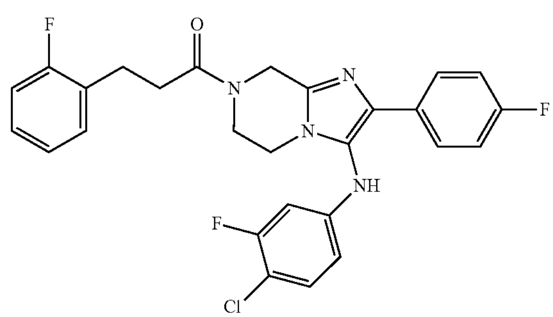 [SMILES: O=C(CCc1ccccc1F)N1CCn2c(nc(-c3ccc(F)cc3)c2Nc2ccc(Cl)c(F)c2)C1] | 511.2 (M + 1) | 0.14 | 0.108 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 360 | 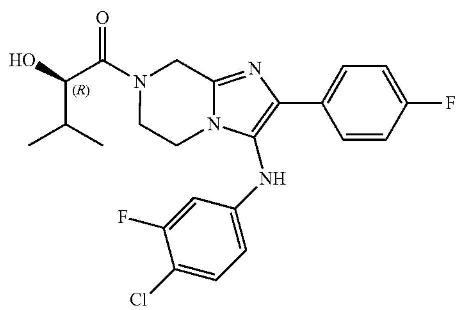 | 461.2 (M + 1) | 0.03 | 0.015 |
| 361 | 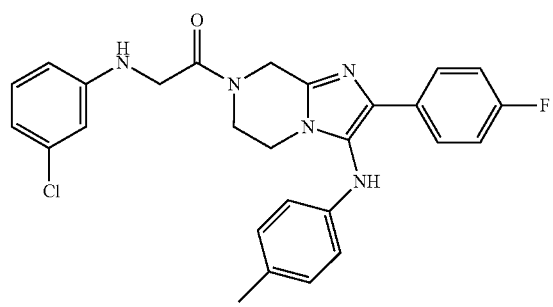 [SMILES: Cc1ccc(Nc2c(-c3ccc(F)cc3)nc3n2CCN(C(=O)CNc2cccc(Cl)c2)C3)cc1] | 490.3 (M + 1) | 2.35 | 1.141 |
| 362 | 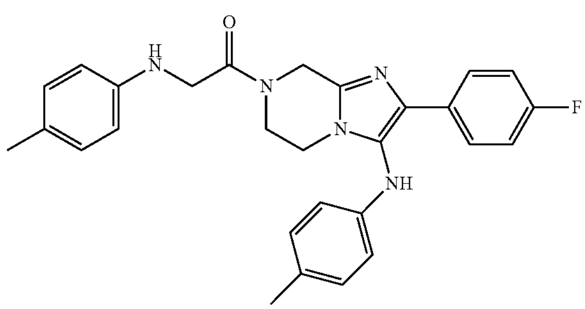 [SMILES: Cc1ccc(NCC(=O)N2CCn3c(nc(-c4ccc(F)cc4)c3Nc3ccc(C)cc3)C2)cc1] | 470.6 (M + 1) | 0.81 | 0.203 |
| 363 | 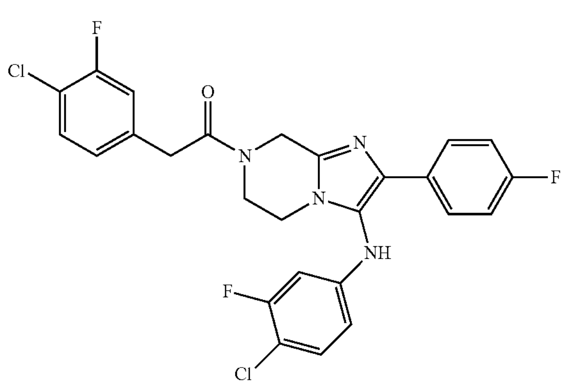 [SMILES: O=C(Cc1ccc(Cl)c(F)c1)N1CCn2c(nc(-c3ccc(F)cc3)c2Nc2ccc(Cl)c(F)c2)C1] | 532.2 (M + 1) | 1.75 | 1.133 |

TABLE 2-continued
| Compound | Structure | Physical Data MS (m/z) and/or ¹H NMR | EC$_{50}$ 3D7 strain (μM) | EC$_{50}$ W2 strain (μM) |
|---|---|---|---|---|
| 364 | 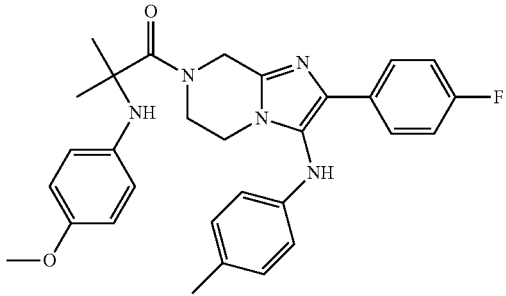 [SMILES: COc1ccc(NC(C)(C)C(=O)N2CCn3c(nc(-c4ccc(F)cc4)c3Nc3ccc(C)cc3)C2)cc1] | 514.6 (M + 1) | 4.95 | 3.742 |
| 365 | 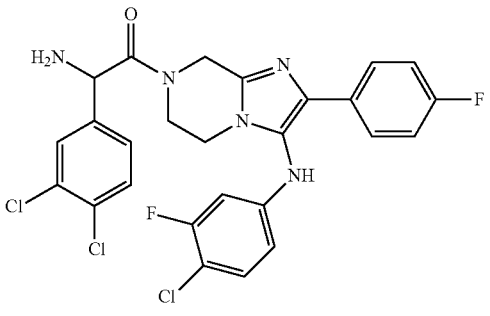 [SMILES: NC(C(=O)N1CCn2c(nc(-c3ccc(F)cc3)c2Nc2ccc(Cl)c(F)c2)C1)c1ccc(Cl)c(Cl)c1] | 562.1 (M + 1) | 0.61 | 0.26 |
| 366 | 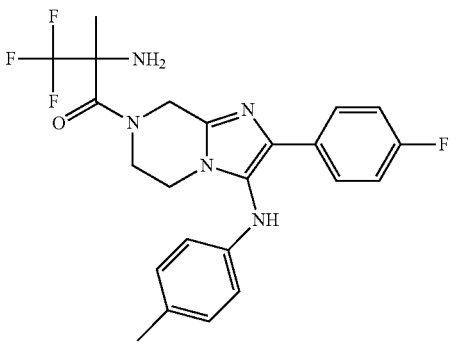 [SMILES: Cc1ccc(Nc2c(-c3ccc(F)cc3)nc3n2CCN(C(=O)C(C)(N)C(F)(F)F)C3)cc1] | 462.2 (M + 1) | 3.47 | 1.824 |
| 367 | 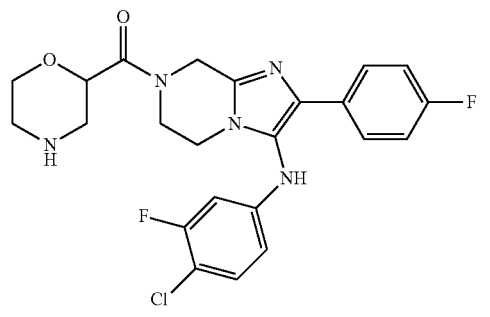 | 474.2 (M + 1) | 0.19 | 0.148 |

TABLE 2-continued

| Compound | Structure | Physical Data MS (m/z) and/or ¹H NMR | EC$_{50}$ 3D7 strain (μM) | EC$_{50}$ W2 strain (μM) |
|---|---|---|---|---|
| 368 | 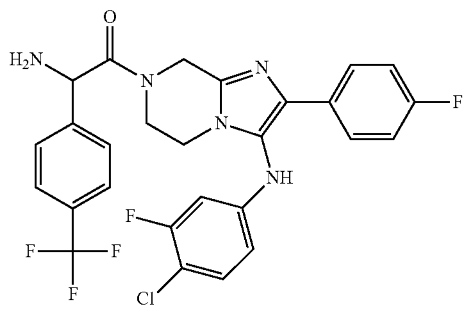 [SMILES: NC(C(=O)N1CCn2c(nc(-c3ccc(F)cc3)c2Nc2ccc(Cl)c(F)c2)C1)c1ccc(C(F)(F)F)cc1] | 562.2 (M + 1) | 0.52 | 0.286 |
| 369 | 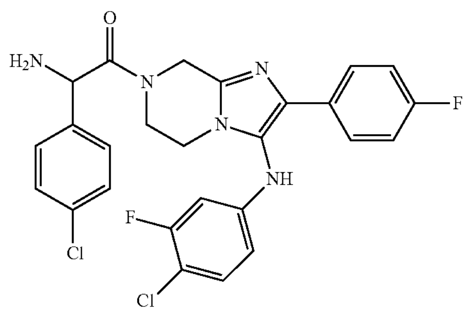 [SMILES: NC(C(=O)N1CCn2c(nc(-c3ccc(F)cc3)c2Nc2ccc(Cl)c(F)c2)C1)c1ccc(Cl)cc1] | 529.2 (M + 1) | 0.11 | 0.084 |
| 370 | 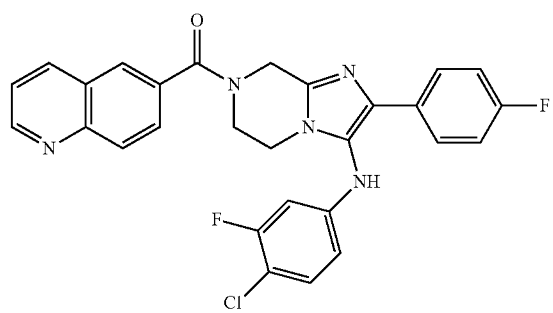 [SMILES: O=C(c1ccc2ncccc2c1)N1CCn2c(nc(-c3ccc(F)cc3)c2Nc2ccc(Cl)c(F)c2)C1] | 516.1 (M + 1) | 4.35 | 8.345 |
| 371 | 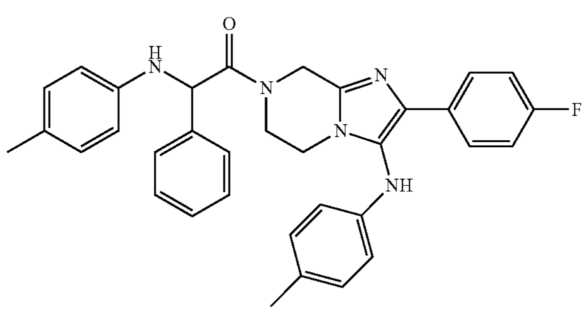 [SMILES: Cc1ccc(Nc2c(-c3ccc(F)cc3)nc3n2CCN(C(=O)C(Nc2ccc(C)cc2)c2ccccc2)C3)cc1] | 546.6 (M + 1) | 1.52 | 1.283 |
| 372 | 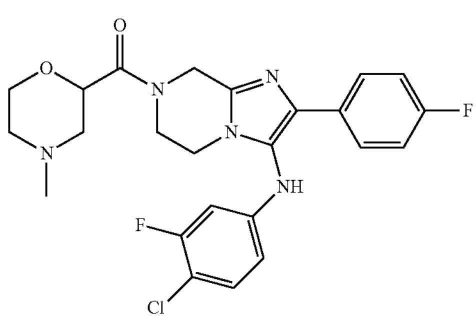 [SMILES: CN1CCOC(C(=O)N2CCn3c(nc(-c4ccc(F)cc4)c3Nc3ccc(Cl)c(F)c3)C2)C1] | 488.2 (M + 1) | 0.69 | 0.554 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 373 | 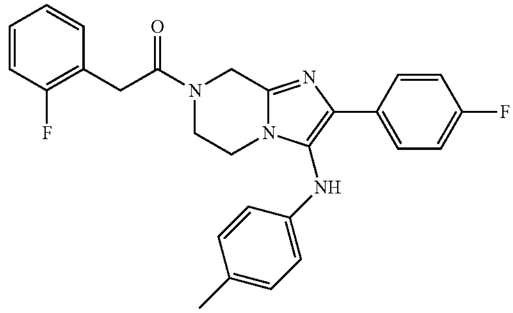 | 474.3 (M + 1) | 0.43 | 0.32 |
| 374 | 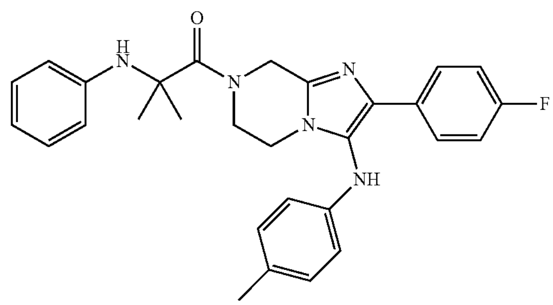 [SMILES: Cc1ccc(Nc2c(-c3ccc(F)cc3)nc3n2CCN(C(=O)C(C)(C)Nc2ccccc2)C3)cc1] | 484.3 (M + 1) | 0.59 | 0.248 |
| 375 | 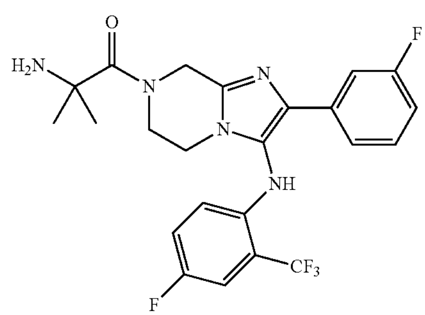 [SMILES: CC(C)(N)C(=O)N1CCn2c(nc(-c3cccc(F)c3)c2Nc2ccc(F)cc2C(F)(F)F)C1] | 480.2 (M + 1) | 1.13 | 0.679 |
| 376 | 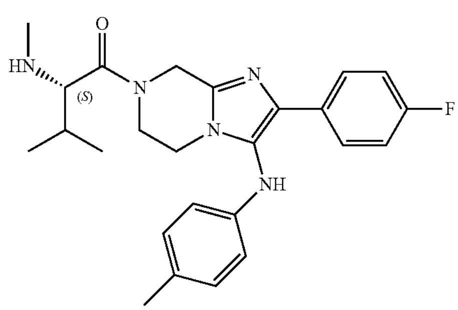 | 436.2 (M + 1) | 0.06 | 0.079 |
| 377 | 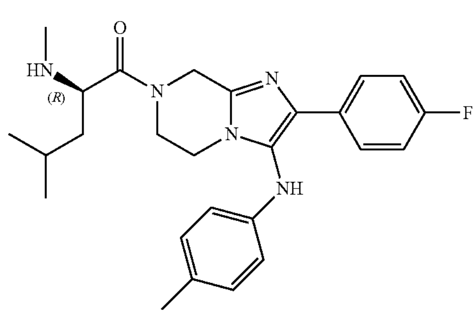 | 450.3 (M + 1) | | 0.574 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 378 | 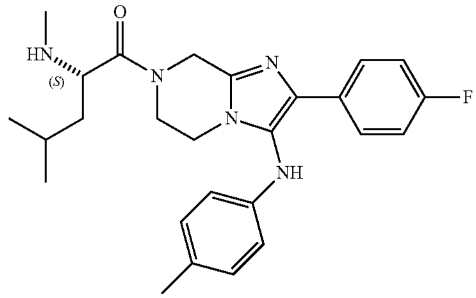 | 450.3 (M + 1) | 0.06 | 0.063 |
| 379 | 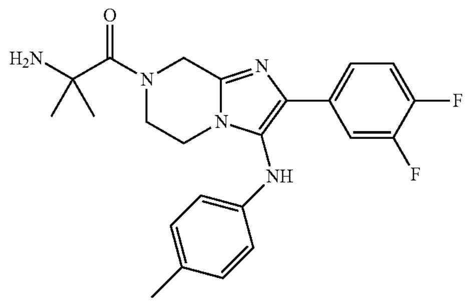 [SMILES: Cc1ccc(Nc2c(-c3ccc(F)c(F)c3)nc3n2CCN(C(=O)C(C)(C)N)C3)cc1] | 426.2 (M + 1) | 0.06 | 0.05 |
| 380 | 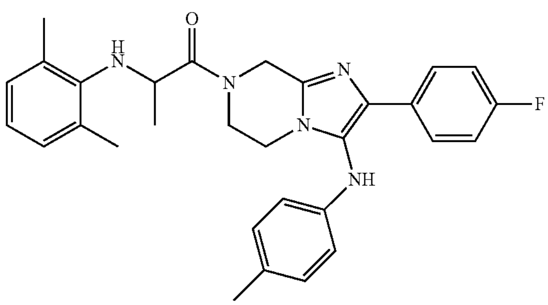 [SMILES: Cc1ccc(Nc2c(-c3ccc(F)cc3)nc3n2CCN(C(=O)C(C)Nc2c(C)cccc2C)C3)cc1] | 498.3 (M + 1) | 1.13 | 1.789 |
| 381 | 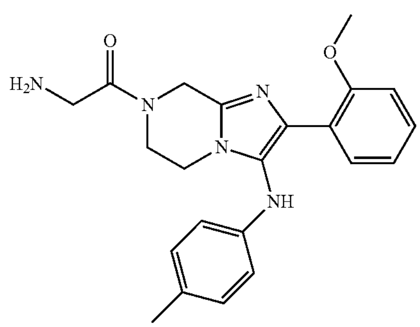 [SMILES: COc1ccccc1-c1nc2n(c1Nc1ccc(C)cc1)CCN(C(=O)CN)C2] | 392.2 (M + 1) | 1.97 | 1.798 |
| 382 | 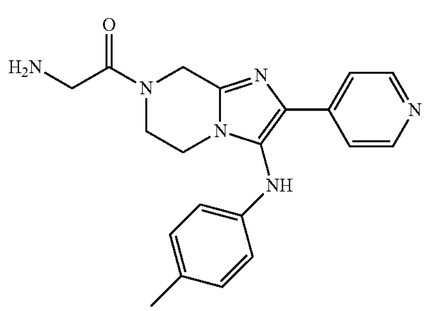 [SMILES: Cc1ccc(Nc2c(-c3ccncc3)nc3n2CCN(C(=O)CN)C3)cc1] | 363.2 (M + 1) | 1.05 | 1.039 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 383 | 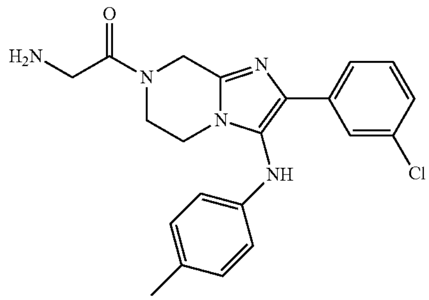 [SMILES: Cc1ccc(Nc2c(-c3cccc(Cl)c3)nc3n2CCN(C(=O)CN)C3)cc1] | 396.2 (M + 1) $^1$H-NMR (400 MHz, MeOH-d$_4$) δ 7.62-7.59 (m, 2H); 7.14-7.04 (m, 2H); 6.85 (d, J = 2.4 Hz, 1H); 6.65-6.5 (dd, J = 2.7 Hz, J = 8.4 Hz, 1H); 4.0-3.98 (m, 4H); 2.16 (s, 3H); 2.00 (s, 6H); 1.64 (s, 6H). | 0.05 | 0.032 |
| 384 | 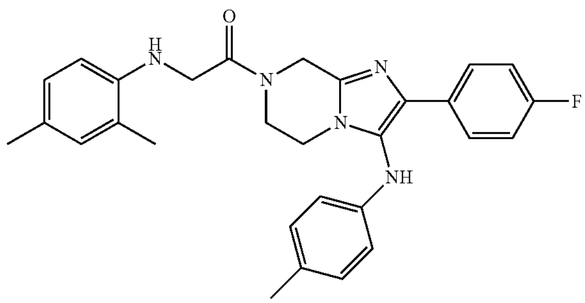 [SMILES: Cc1ccc(Nc2c(-c3ccc(F)cc3)nc3n2CCN(C(=O)CNc2ccc(C)cc2C)C3)cc1] | 484.3 (M + 1) | 0.47 | 0.889 |
| 385 | 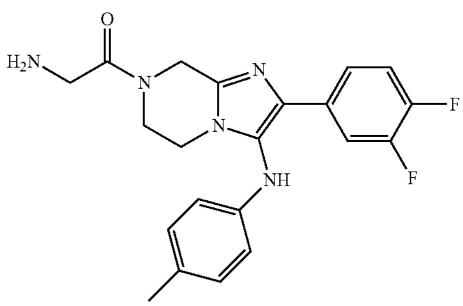 | 398.2 (M + 1) | 0.02 | 0.02 |
| 386 | 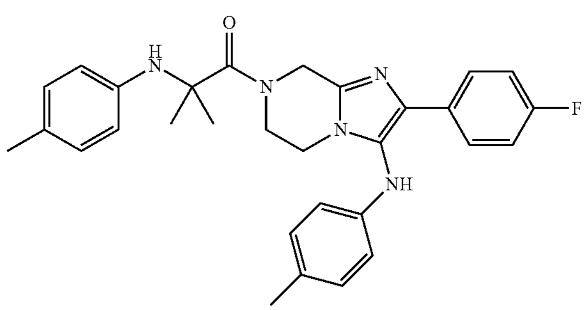 [SMILES: Cc1ccc(Nc2c(-c3ccc(F)cc3)nc3n2CCN(C(=O)C(C)(C)Nc2ccc(C)cc2)C3)cc1] | 498.3 (M + 1) | 2.62 | 3.028 |
| 387 | 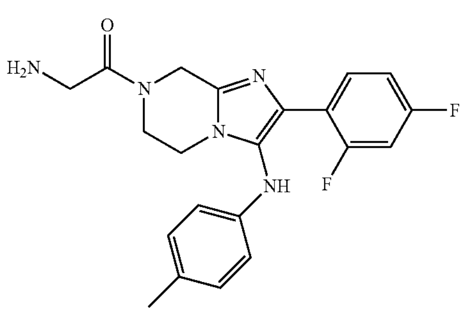 [SMILES: Cc1ccc(Nc2c(-c3ccc(F)cc3F)nc3n2CCN(C(=O)CN)C3)cc1] | 398.2 (M + 1) | 0.11 | 0.08 |

TABLE 2-continued

| Compound | Structure | Physical Data MS (m/z) and/or ¹H NMR | EC$_{50}$ 3D7 strain (μM) | EC$_{50}$ W2 strain (μM) |
|---|---|---|---|---|
| 388 | 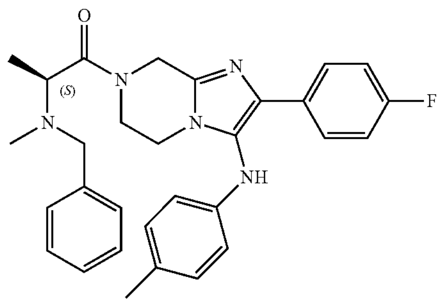 | 498.3 (M + 1) | 3.22 | 1.772 |
| 389 | 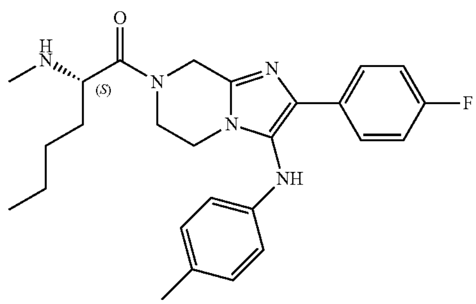 | 450.3 (M + 1) | 0.06 | 0.051 |
| 390 | 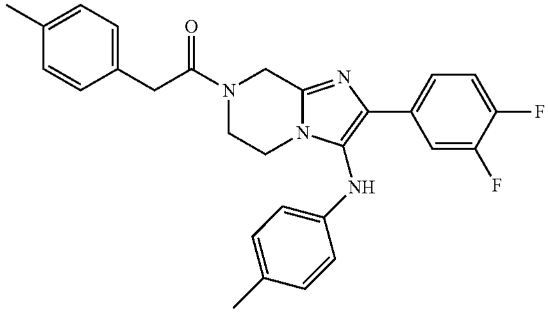 [SMILES: Cc1ccc(CC(=O)N2CCn3c(nc(-c4ccc(F)c(F)c4)c3Nc3ccc(C)cc3)C2)cc1] | 473.3 (M + 1) | 0.03 | 0.028 |
| 391 | 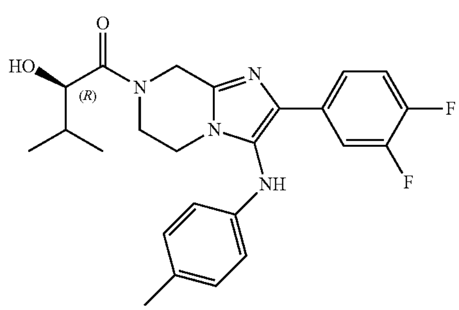 | 441.2 (M + 1) | 0.01 | 0.007 |
| 392 | 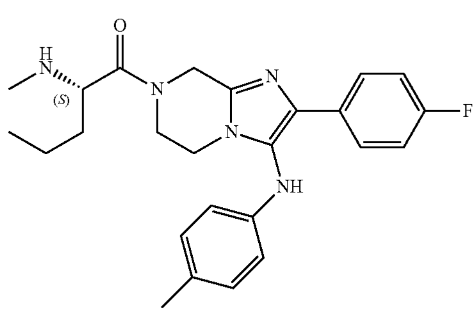 | 436.3 (M + 1) | 0.03 | 0.039 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 393 | 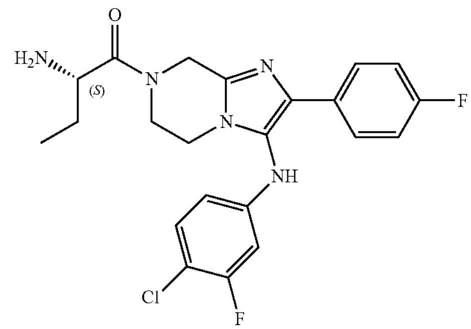 | 446.2 (M + 1) | 0.02 | |
| 394 | 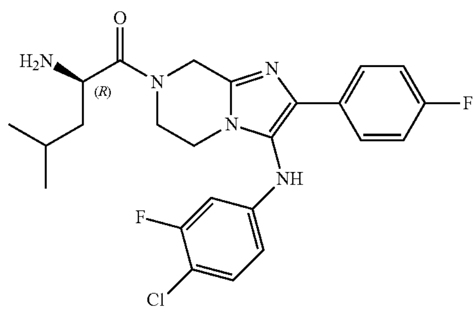 | 474.0 (M + 1) | 0.05 | 0.043 |
| 395 | 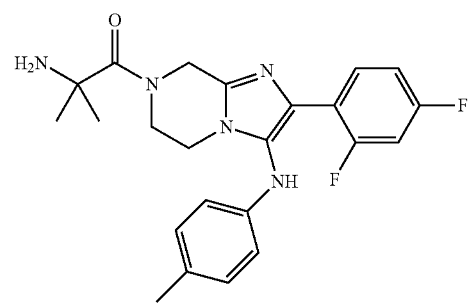 [SMILES: Cc1ccc(Nc2c(-c3ccc(F)cc3F)nc3n2CCN(C(=O)C(C)(C)N)C3)cc1] | 426.2 (M + 1) | 0.44 | 0.246 |
| 396 | 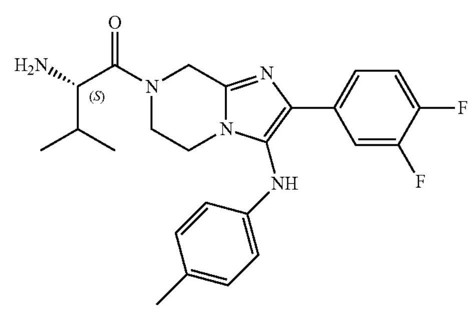 | 440.2 (M + 1) | 0.03 | 0.022 |
| 397 | 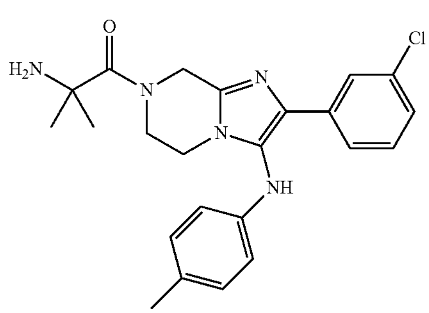 [SMILES: Cc1ccc(Nc2c(-c3cccc(Cl)c3)nc3n2CCN(C(=O)C(C)(C)N)C3)cc1] | 424.2 (M + 1) | 2.45 | 1.673 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 398 | 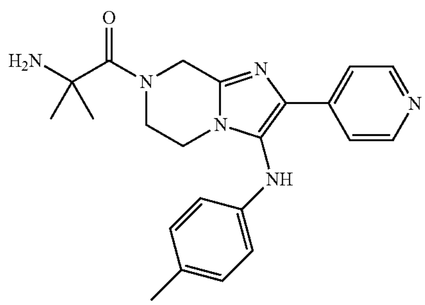 [SMILES: Cc1ccc(Nc2c(-c3ccncc3)nc3n2CCN(C(=O)C(C)(C)N)C3)cc1] | 391.2 (M + 1) | 2.73 | 2.685 |
| 399 | 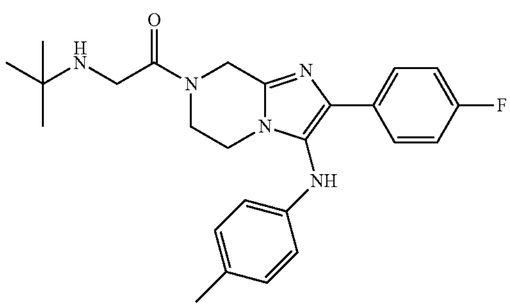 [SMILES: Cc1ccc(Nc2c(-c3ccc(F)cc3)nc3n2CCN(C(=O)CNC(C)(C)C)C3)cc1] | 436.2 (M + 1) | 0.22 | 0.196 |
| 400 | 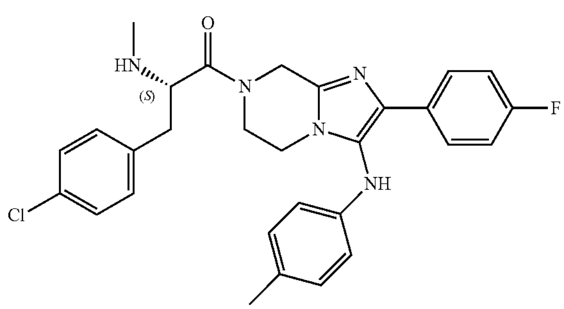 | 518.2 (M + 1) | 0.18 | 0.105 |
| 401 | 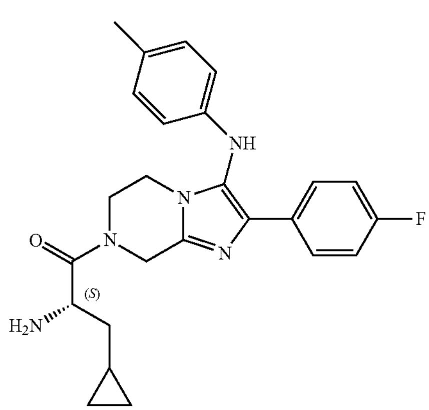 | 434.2 (M + 1) | 0.02 | 0.012 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 402 | 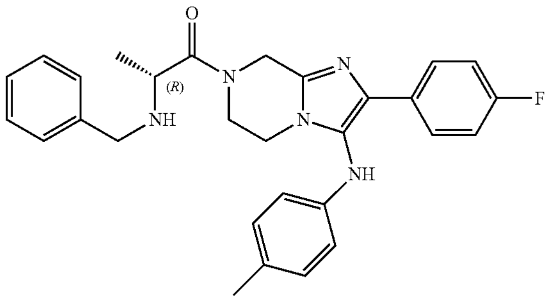 | 484.3 (M + 1) | 0.12 | 0.122 |
| 403 | 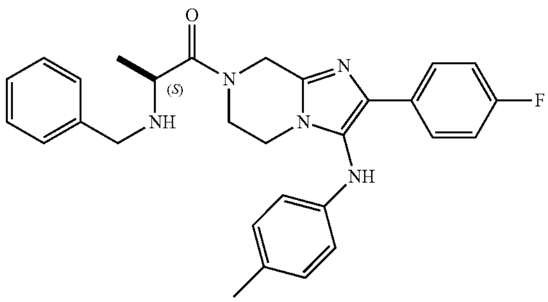 | 484.3 (M + 1) | 0.51 | 0.543 |
| 404 | 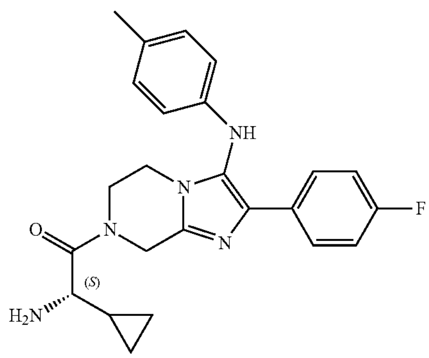 | 420.2 (M + 1) | 0.02 | 0.012 |
| 405 | 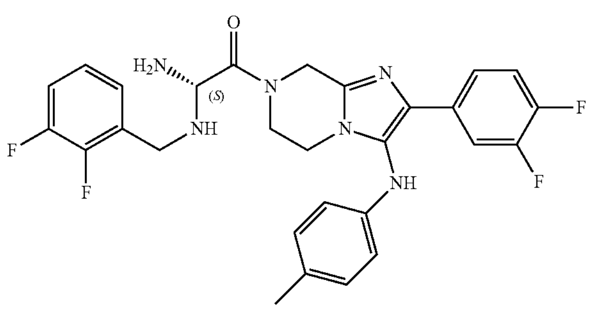 | 524.2 (M + 1) | 0.02 | 0.012 |
| 406 | 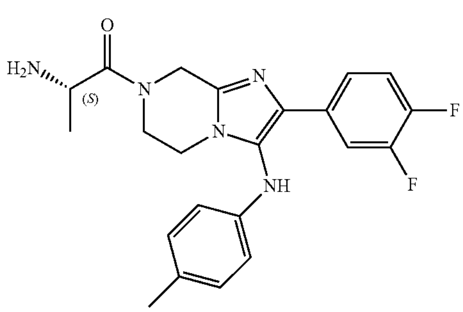 | 412.2 (M + 1) | 0.06 | 0.04 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 407 | 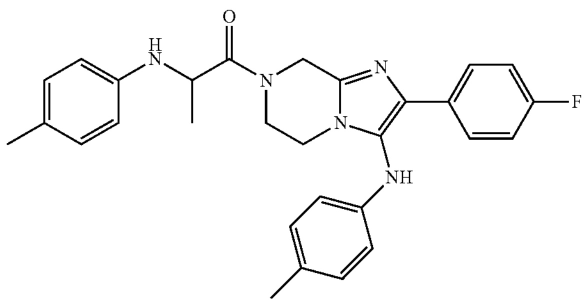 [SMILES: Cc1ccc(Nc2c(-c3ccc(F)cc3)nc3n2CCN(C(=O)C(C)Nc2ccc(C)cc2)C3)cc1] | 484.3 (M + 1) | 0.71 | 0.523 |
| 408 | 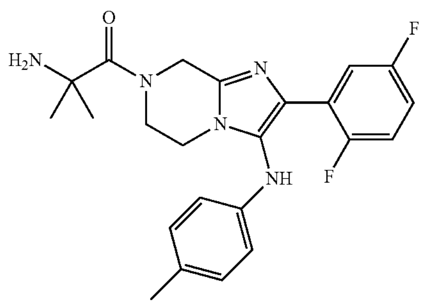 [SMILES: Cc1ccc(Nc2c(-c3cc(F)ccc3F)nc3n2CCN(C(=O)C(C)(C)N)C3)cc1] | 426.2 (M + 1) | 0.93 | 0.908 |
| 409 | 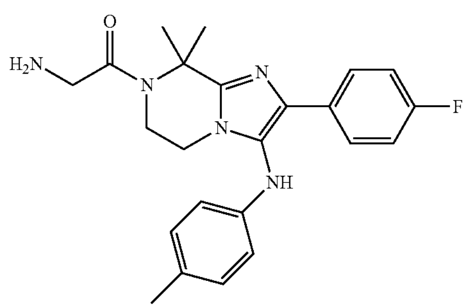 [SMILES: Cc1ccc(Nc2c(-c3ccc(F)cc3)nc3n2CCN(C(=O)CN)C3(C)C)cc1] | 408.1 (M + 1) $^1$H-NMR: (MeOH-d$_4$, 400 Hz) δ 7.79-7.69 (m, 2H), 7.21 (t, J = 8.4 Hz, 2H), 7.04 (d, J = 8.0 Hz, 2H), 6.76 (d, J = 8.2 Hz, 2H), 4.11 (s, 2H), 3.88 (m, 4H), 2.22 (s, 3H), 2.12 (s, 6H). | 0.01 | 0.006 |
| 410 | 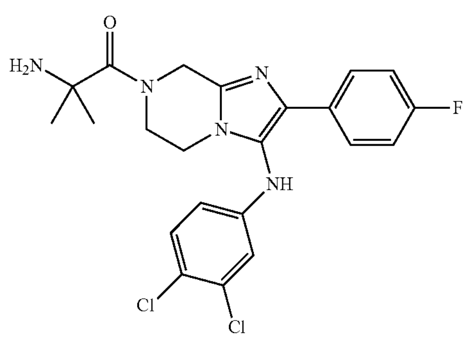 [SMILES: CC(C)(N)C(=O)N1CCn2c(nc(-c3ccc(F)cc3)c2Nc2ccc(Cl)c(Cl)c2)C1] | 463.3 (M + 1) | 0.06 | 0.037 |
| 411 | 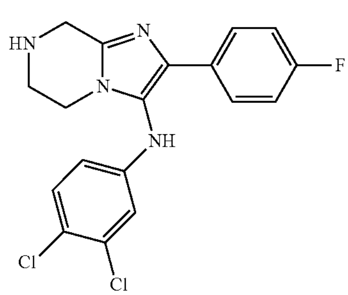 [SMILES: Fc1ccc(-c2nc3n(c2Nc2ccc(Cl)c(Cl)c2)CCNC3)cc1] | 378.2 (M + 1) | 0.14 | 0.106 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 412 | 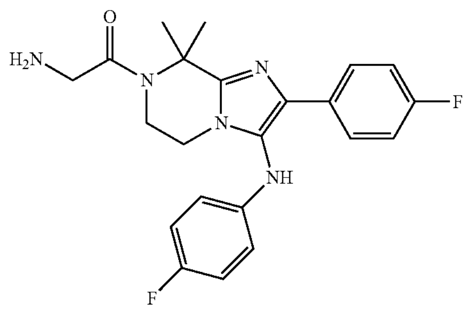 [SMILES: CC1(C)c2nc(-c3ccc(F)cc3)c(Nc3ccc(F)cc3)n2CCN1C(=O)CN] | 412.1 (M + 1) $^1$H-NMR: (MeOH-d$_4$, 400 Hz) δ 7.61-7.57 (m, 2H), 6.94 (2H, J = 8.8 Hz, t), 6.81 (2H, J = 8.8 Hz, t), 6.47 (m, 2H), 3.72 (m, 2H), 3.58 (m, 2H), 3.42 (m, 2H), 1.85 (s, 6H). Elemental Analysis: (compound + 0.65 H$_2$O): C, 62.44; N, 16.55; H, 5.79, (calculated). C = 62.54/62.44; N = 16.35/16.29; H = 5.52/5.61 (experimental) | 0.01 | 0.006 |
| 413 | 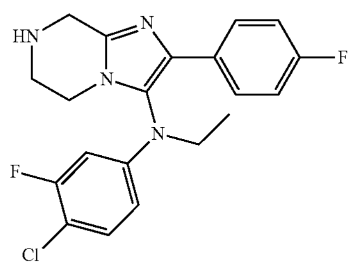 [SMILES: CCN(c1ccc(Cl)c(F)c1)c1c(-c2ccc(F)cc2)nc2n1CCNC2] | 389.1 (M + 1) $^1$H NMR: (300 Hz, DMSO-d$_6$) δ 7.59 (m, 2H), 7.35 (t, J = 6.6 Hz, 1H), 7.12 (t, J = 6.6, 2H), 6.68 (d, J = 8.7 Hz, 1H), 6.42 (d, J = 6.9 Hz, 1H), 3.88 (d, J = 1.5 Hz, 2H), 3.68-3.61 (m, 2H), 3.57-3.50 (m, 2H), 3.02 (t, J = 4.2 Hz, 2H), 1.04 (t, J = 5.4 Hz, 3H) | 0.18 | 0.131 |
| 414 | 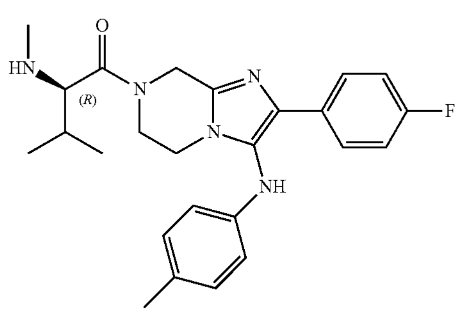 | 436.2 (M + 1) | 0.16 | 0.156 |
| 415 | 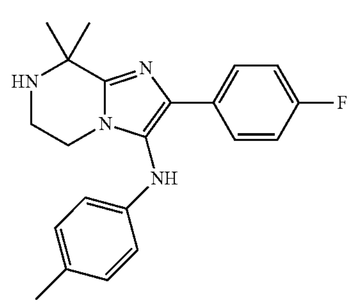 [SMILES: Cc1ccc(Nc2c(-c3ccc(F)cc3)nc3n2CCNC3(C)C)cc1] | 351.2 (M + 1) | 0.01 | 0.013 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 416 | 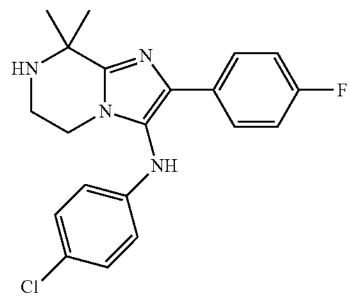 | 371.2 (M + 1) $^1$H-NMR: (MeOH-d$_4$, 400 Hz) δ 7.77-7.73 (m, 2H); 7.25-7.18 (m, 4H); 6.84-6.82 (m, 2H); 4.38 (m, 2H); 3.95 (m, 2H); 2.11 (s, 6H). | 0.01 | 0.016 |
| 417 | 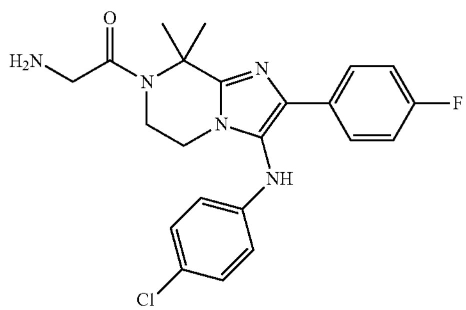 [SMILES: CC1(C)c2nc(-c3ccc(F)cc3)c(Nc3ccc(Cl)cc3)n2CCN1C(=O)CN] | 428.1 (M + 1) $^1$H-NMR: (MeOH-d$_4$, 400 Hz) δ 7.75-7.71 (m, 2H), 7.13-7.1 (m, 2H), 6.59 (t J = 8.8 Hz, 2H), 6.58 (d, J = 8.8 Hz, 2H), 3.80 (m, 2H), 3.65 (m, 2H), 3.31 (m, 2H), 1.95 (s, 6H). Elemental Analysis: (compound + 0.33 H$_2$O): Elemental Analysis: C, 60.11; N, 15.93; H, 5.57; (calculated). % C, 60.93/60.79; % N, 15.99/16.08; % H, 5.54/5.40 (experimental) | 0.01 | 0.006 |
| 418 | 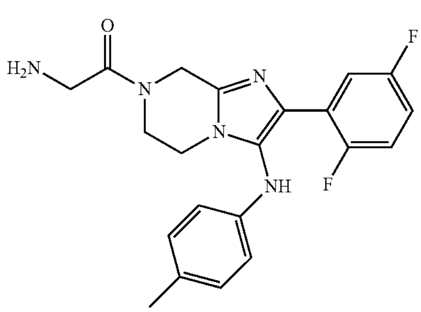 [SMILES: Cc1ccc(Nc2c(-c3cc(F)ccc3F)nc3n2CCN(C(=O)CN)C3)cc1] | 398.2 (M + 1) | 0.09 | 0.146 |
| 419 | 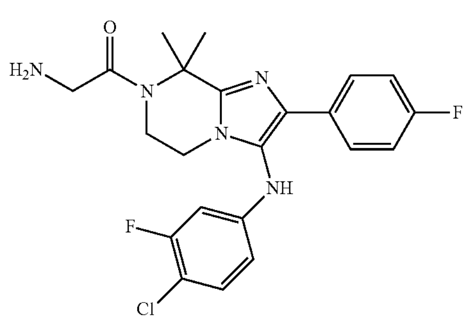 [SMILES: CC1(C)c2nc(-c3ccc(F)cc3)c(Nc3ccc(Cl)c(F)c3)n2CCN1C(=O)CN] | 446.2 (M + 1) $^1$H-NMR: (MeOH-d$_4$, 400 Hz) δ 7.59-7.55 (m, 2H); 7.20-7.13 (m, 3H); 6.60 (dd, J = 10.8 Hz, J = 11.2 Hz, 1H); 6.53 (dd, J = 0.8 Hz, J = 2.4 Hz, 1H); 4.0 (m, 4H); 3.78 (m, 2H); 2.00 (s, 6H). | 0.03 | 0.024 |

TABLE 2-continued

| Compound | Structure | Physical Data MS (m/z) and/or ¹H NMR | EC$_{50}$ 3D7 strain (μM) | EC$_{50}$ W2 strain (μM) |
| --- | --- | --- | --- | --- |
| 420 | 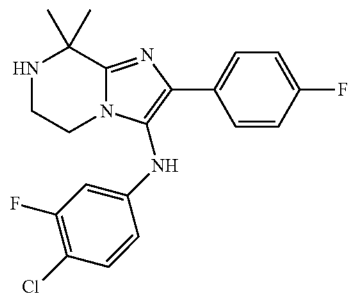 [SMILES: CC1(C)NCCn2c1nc(-c1ccc(F)cc1)c2Nc1ccc(Cl)c(F)c1] | 389.8 (M + 1) | 0.02 | 0.028 |
| 421 | 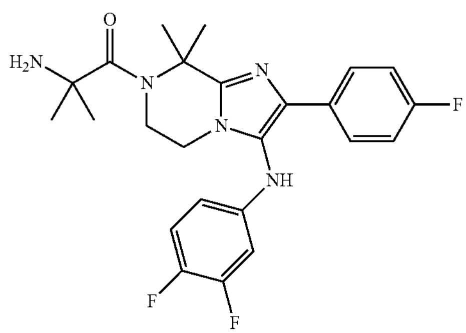 | 430.2 (M + 1)<br>¹H-NMR: (MeOH-d$_4$, 400 Hz) δ 7.73-7.69 (m, 2H); 7.07-6.99 (m, 3H); 6.46-6.40 (m, 1H); 6.34-6.32 (m, 1H); 3.78 (m, 2H), 3.62 (m, 2H), 3.5 (m, 2H); 1.98 (s, 6H); 1.48 (s, 6H). | 0.003 | 0.005 |
| 422 | 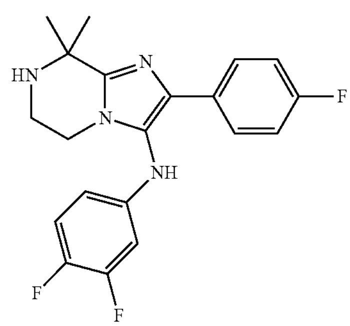 [SMILES: CC1(C)NCCn2c1nc(-c1ccc(F)cc1)c2Nc1ccc(F)c(F)c1] | 373.2 (M + 1) | 0.01 | 0.021 |
| 423 | 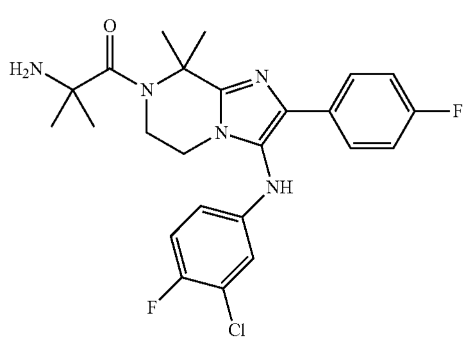 | 446.2 (M + 1)<br>¹H-NMR: (MeOH-d$_4$, 400 Hz) δ 7.70-7.66 (m, 2H); 7.18-7.14 (m, 3H); 7.07 (t, J = 9.2 Hz, 1H); 6.8-6.78 (m, 1H); 6.64-6.60 (M, 1H); 2.04 (s, 6H). | 0.01 | 0.009 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 424 | 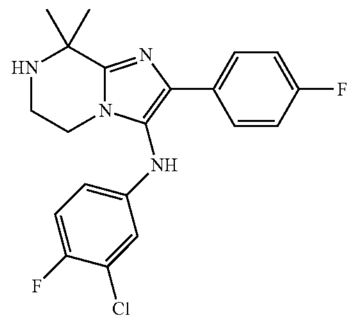 | 389.1 (M + 1) | 0.02 | 0.03 |
| 425 | 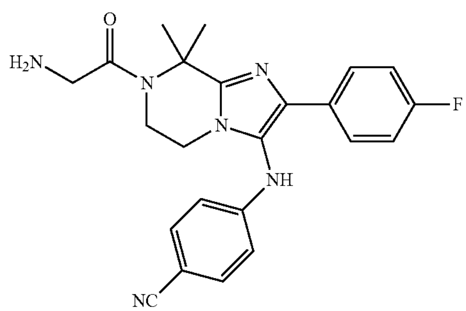 | 419.1 (M + 1)<br>$^1$H-NMR: (MeOH-d$_4$, 400 Hz) δ 7.68-7.65 (m, 2H); 7.54 (d, J = 8.8 Hz, 2H); 7.17 (t, J = 8.8 Hz, 2H); 6.83 (d, J = 8.4 Hz, 2H); 4.07 (s, 2H); 4.03 (s, 2h); 3.82 (m, 2H); 2.06 (s, 6H). | 0.01 | 0.012 |
| 426 | 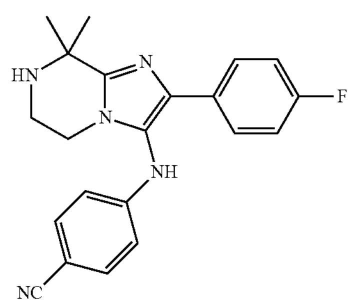 [SMILES: CC1(C)NCCn2c1nc(-c1ccc(F)cc1)c2Nc1ccc(C#N)cc1] | 362.1 (M + 1)<br>$^1$H-NMR: (MeOH-d$_4$, 400 Hz) 7.69 (m, 2H); 7.51 (d, J = 8.4 Hz, 2H);. 7.07 (t, J = 8.8 Hz, 2H); 6.73 (d, J = 8.8 Hz, 2H); 4.01 (m, 2H); 3.78 (m, 2H); 1.86 (s, 6H). | 0.18 | 0.271 |
| 427 | 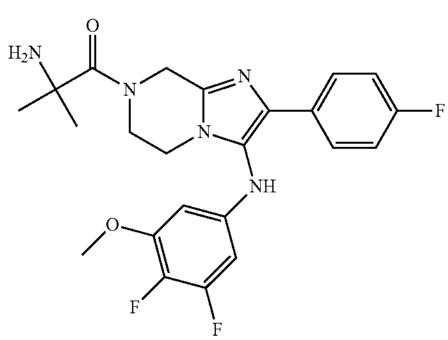 [SMILES: COc1cc(Nc2c(-c3ccc(F)cc3)nc3n2CCN(C(=O)C(C)(C)N)C3)cc(F)c1F] | 460.2 (M + 1) | 0.21 | 0.436 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 428 | 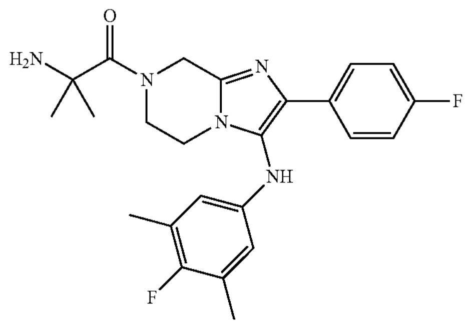 [SMILES: Cc1cc(Nc2c(-c3ccc(F)cc3)nc3n2CCN(C(=O)C(C)(C)N)C3)cc(C)c1F] | 440.2 (M + 1) | 0.17 | 0.242 |
| 429 | 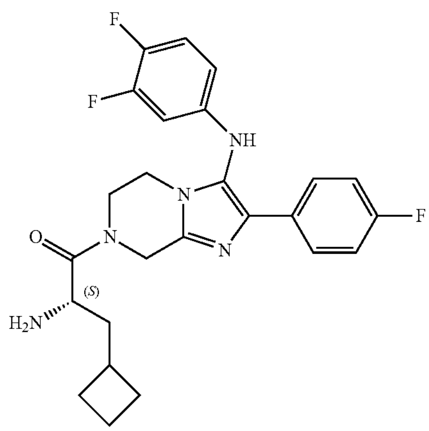 | 470.2 (M + 1) | 0.02 | 0.036 |
| 430 | 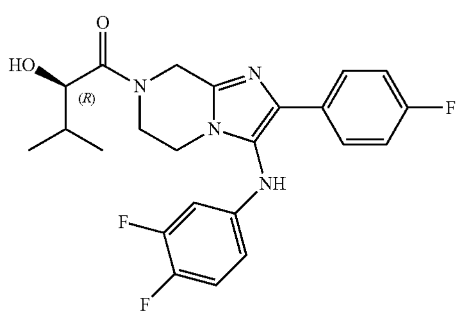 | 445.2 (M + 1) | 0.01 | 0.019 |
| 431 | 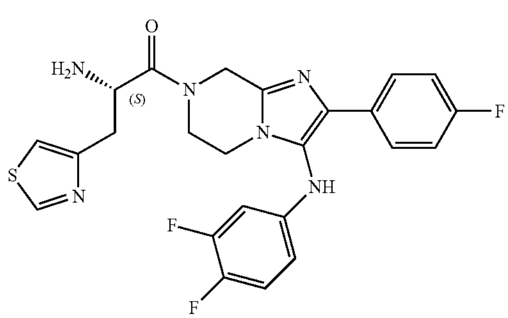 | 499.2 (M + 1) | 0.07 | 0.08 |

TABLE 2-continued
| Compound | Structure | Physical Data MS (m/z) and/or $^1$H NMR | EC$_{50}$ 3D7 strain (μM) | EC$_{50}$ W2 strain (μM) |
|---|---|---|---|---|
| 432 | 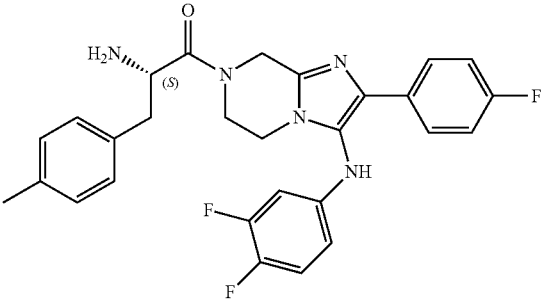 | 506.2 (M + 1) | 0.06 | 0.067 |
| 433 | 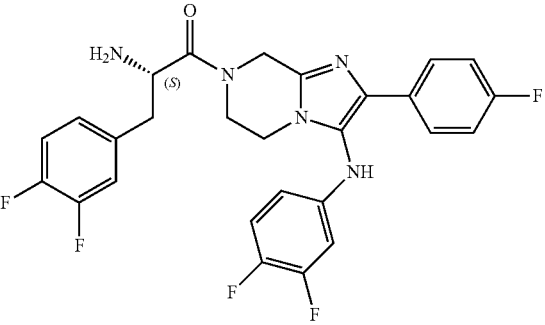 | 528.2 (M + 1) | 0.04 | 0.049 |
| 434 | 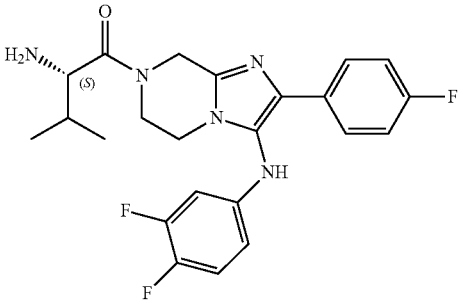 | 444.2 (M + 1) | 0.02 | 0.019 |
| 435 | 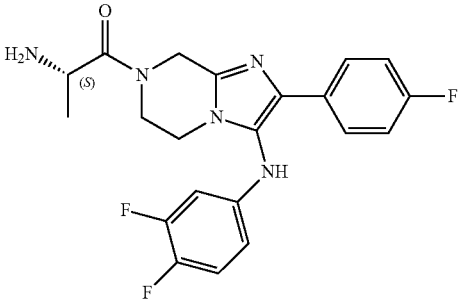 | 416.2 (M + 1) | 0.05 | 0.098 |
| 436 | 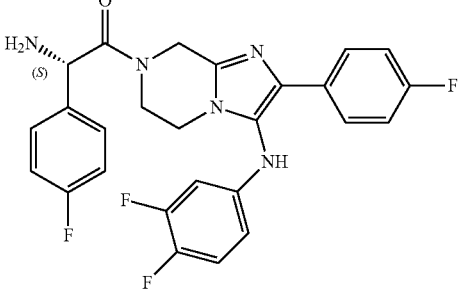 | 496.3 (M + 1) | 0.03 | 0.052 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 437 | 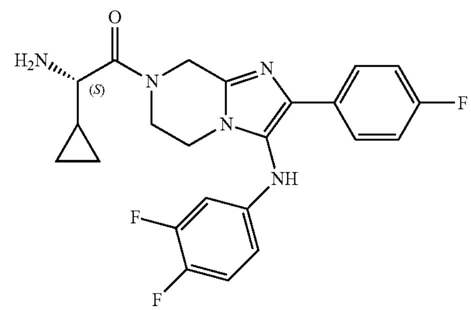 | 442.2 (M + 1) | 0.02 | 0.028 |
| 438 | 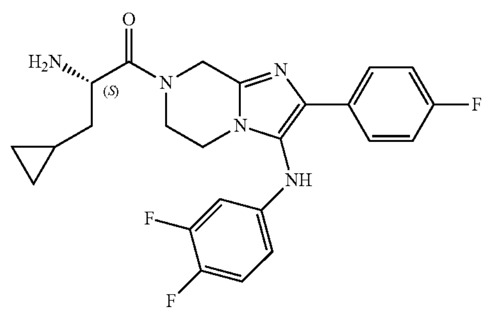 | 456.3 (M + 1) | 0.02 | 0.023 |
| 439 | 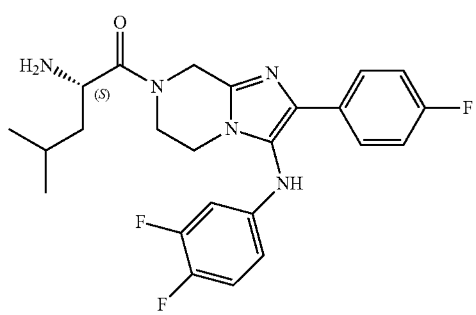 | 458.3 (M + 1) | 0.03 | 0.04 |
| 440 | 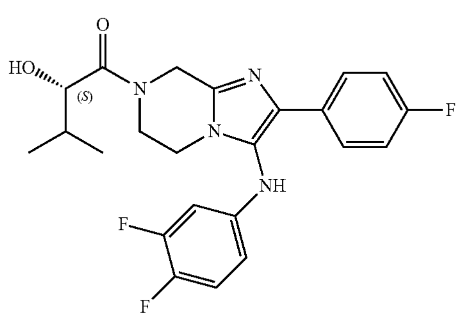 | 445.2 (M + 1) | 0.02 | 0.028 |
| 441 | 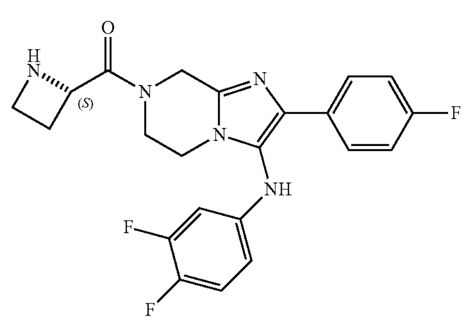 | 428.2 (M + 1) | 0.06 | 0.081 |

TABLE 2-continued

| Compound | Structure | Physical Data MS (m/z) and/or ¹H NMR | EC$_{50}$ 3D7 strain (μM) | EC$_{50}$ W2 strain (μM) |
| --- | --- | --- | --- | --- |
| 442 | 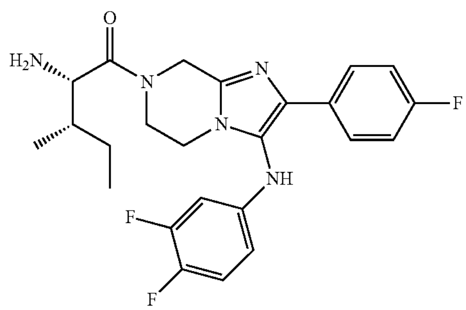 [SMILES: CC[C@H](C)[C@H](N)C(=O)N1CCn2c(nc(-c3ccc(F)cc3)c2Nc2ccc(F)c(F)c2)C1] | 458.2 (M + 1) | 0.02 | 0.033 |
| 443 | 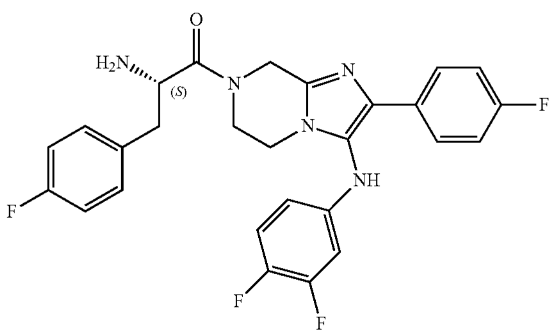 | 510.2 (M + 1) | 0.05 | 0.055 |
| 444 | 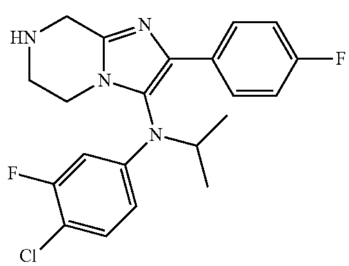 [SMILES: CC(C)N(c1ccc(Cl)c(F)c1)c1c(-c2ccc(F)cc2)nc2n1CCNC2] | 403.2 (M + 1) <br> ¹H NMR: (300 MHz, CDCl$_3$) δ 7.60-7.55 (m, 2H), 7.28-7.21 (m, 1H), 7.03-6.97 (m, 2H), 6.58-6.53 (m, 1H), 6.44-6.39 (m, 1H), 4.29 (s, 2H), 4.19-4.10 (m, 1H), 3.79 (br, 1H), 3.55 (br, 1H), 3.30-3.26 (br, 2H), 1.18-1.16 (br, 3H), 1.01-0.99 (br, 3H). | 7.22 | 5.965 |
| 445 | 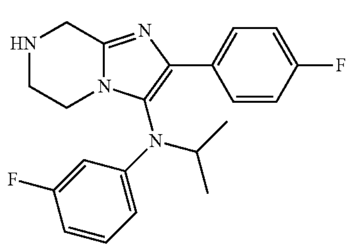 [SMILES: CC(C)N(c1cccc(F)c1)c1c(-c2ccc(F)cc2)nc2n1CCNC2] | 369.2 (M + 1) | 2.6 | 3.272 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 446 | 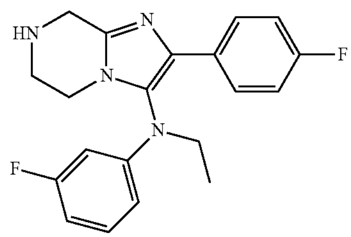 [SMILES: CCN(c1cccc(F)c1)c1c(-c2ccc(F)cc2)nc2n1CCNC2] | 355.2 (M + 1) H-NMR: (DMSO, 300 Hz): δ 7.67-7.63 (m, 2H), 7.23-7.16 (m, 1H), 7.03-6.97 (m, 2H), 6.57-6.41 (m, 3H), 4.22 (s, 1H), 3.69-3.55 (m, 4H), 3.24 (t, J = 4.8 Hz, 2H), 2.61 (s, 2H), 1.17 (t, J = 7.2 Hz, 3H) | 0.31 | 0.243 |
| 447 | 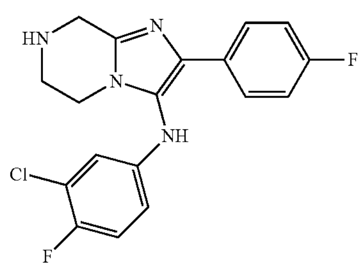 [SMILES: Fc1ccc(-c2nc3n(c2Nc2ccc(F)c(Cl)c2)CCNC3)cc1] | 361.0 (M + 1) 1H NMR: (300 MHz, CDCl3) δ 7.76-7.71 (m, 2H), 7.25-7.19 (m, 1H), 7.05-6.99 (m, 2H), 6.48-6.41 (m, 2H), 5.44 (s, H), 4.17 (s, 2H), 3.73-3.70 (m, 2H), 3.27-3.23 (m, 2H) | 0.23 | |
| 448 | 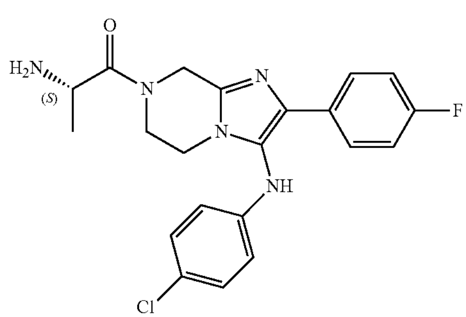 | 414.2 (M + 1) | 0.02 | 0.022 |
| 449 | 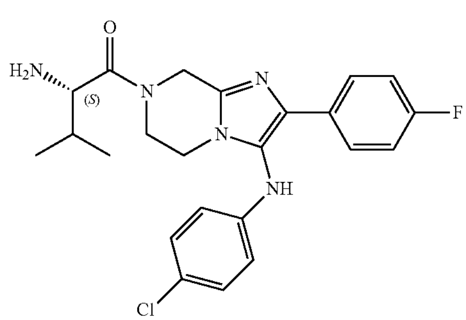 | 442.2 (M + 1) | 0.03 | 0.026 |

TABLE 2-continued
| Compound | Structure | Physical Data MS (m/z) and/or $^1$H NMR | EC$_{50}$ 3D7 strain (μM) | EC$_{50}$ W2 strain (μM) |
|---|---|---|---|---|
| 450 | 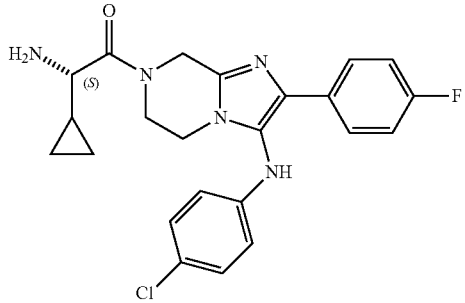 | 440.2 (M + 1) | 0.02 | 0.015 |
| 451 | 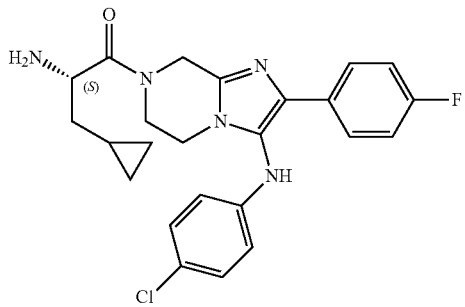 | 454.2 (M + 1) | 0.03 | 0.019 |
| 452 | 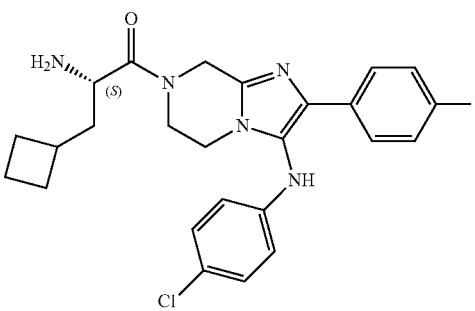 | 469.0 (M + 1) | 0.02 | 0.019 |
| 453 | 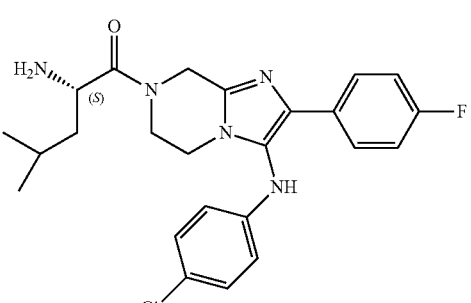 | 456.2 (M + 1) | 0.02 | 0.021 |
| 454 | 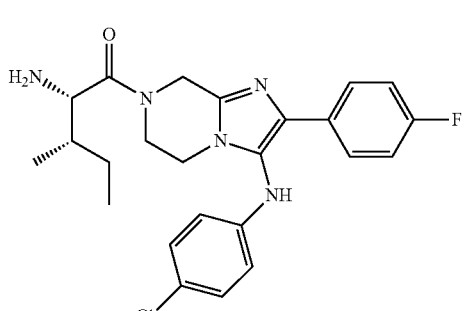 | 456.2 (M + 1) | 0.02 | 0.008 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 455 | 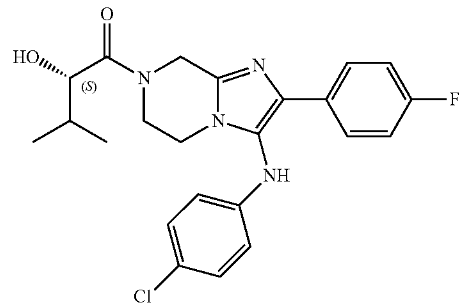 | 443.0 (M + 1) | 0.01 | 0.008 |
| 456 | 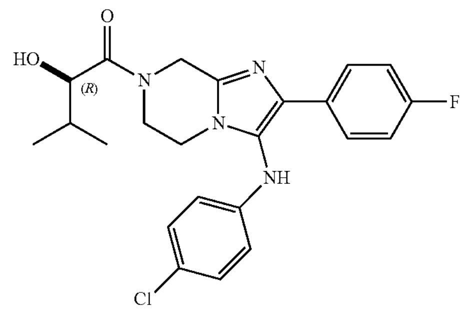 | 443.0 (M + 1) | 0.02 | 0.015 |
| 457 | 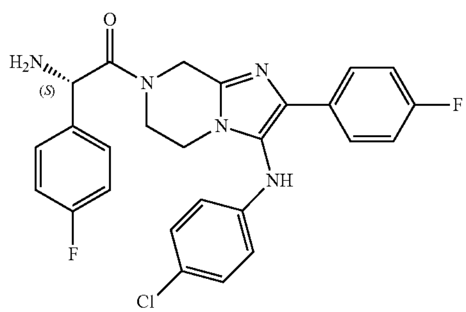 | 494.2 (M + 1) | 0.02 | 0.011 |
| 458 | 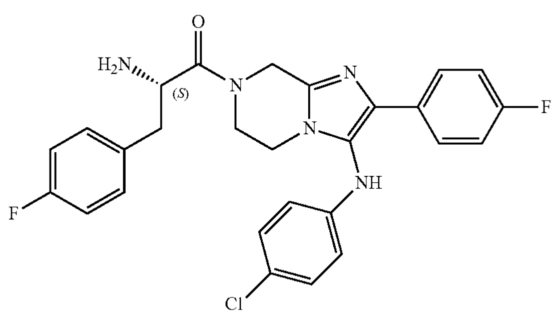 | 508.2 (M + 1) | 0.02 | 0.017 |
| 459 | 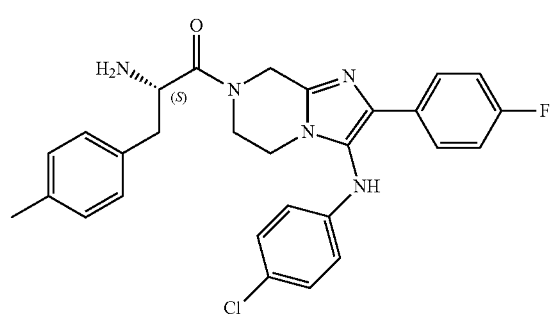 | 504.2 (M + 1) | 0.04 | 0.024 |

TABLE 2-continued

| Compound | Structure | Physical Data MS (m/z) and/or ¹H NMR | EC$_{50}$ 3D7 strain (μM) | EC$_{50}$ W2 strain (μM) |
|---|---|---|---|---|
| 460 | 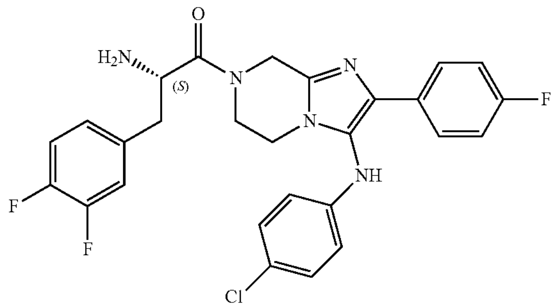 | 526.2 (M + 1) | 0.04 | 0.033 |
| 461 | 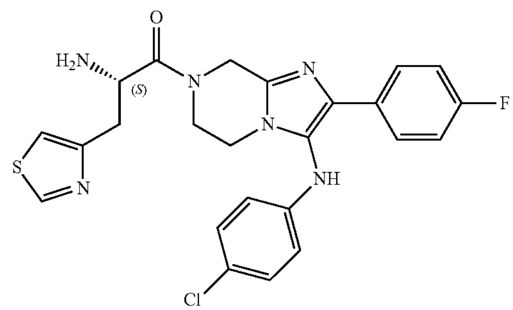 | 497.2 (M + 1) | 0.03 | 0.022 |
| 462 | 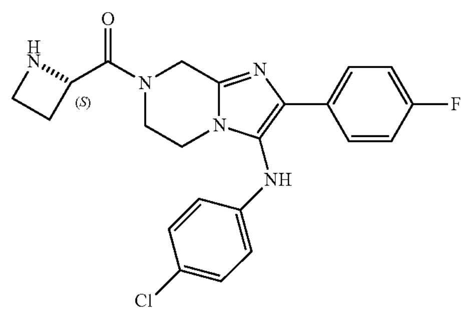 | 426.2 (M + 1) | 0.05 | 0.037 |
| 463 | 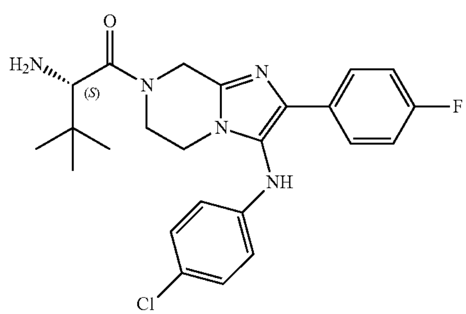 | 456.2 (M + 1) | 0.04 | 0.024 |
| 464 | 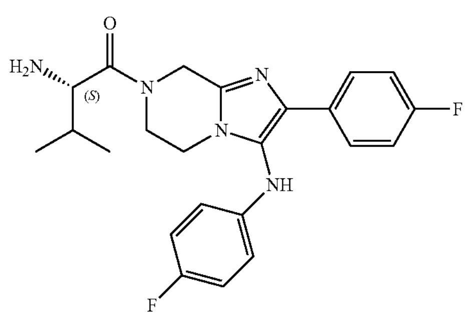 | 426.2 (M + 1) | 0.03 | 0.024 |

TABLE 2-continued
| Compound | Structure | Physical Data MS (m/z) and/or ¹H NMR | EC$_{50}$ 3D7 strain (μM) | EC$_{50}$ W2 strain (μM) |
|---|---|---|---|---|
| 465 | 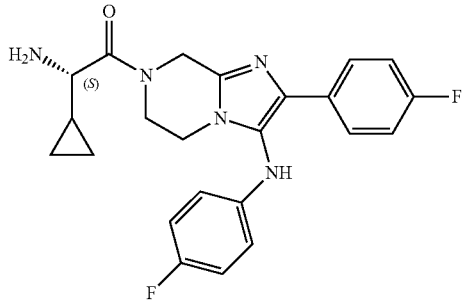 | 424.2 (M + 1) | 0.0019 | 0.002 |
| 466 | 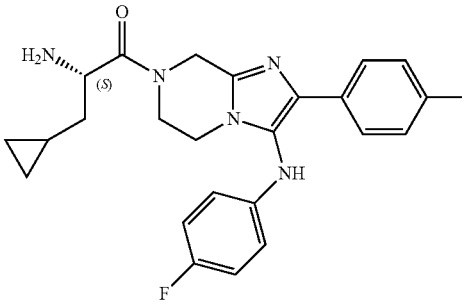 | 438.2 (M + 1) | 0.03 | |
| 467 | 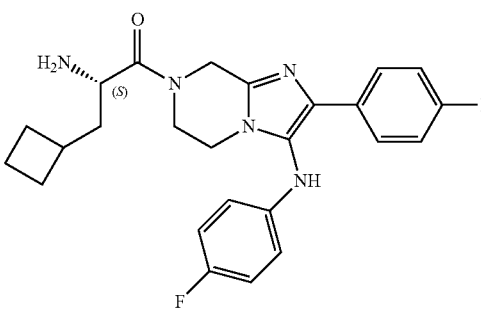 | 452.2 (M + 1) | 0.02 | 0.016 |
| 468 | 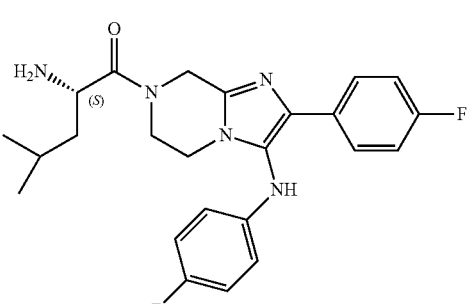 | 440.2 (M + 1) | 0.03 | 0.02 |
| 469 | 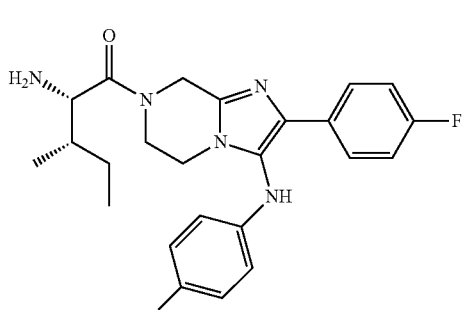 | 440.2 (M + 1) | 0.02 | 0.016 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 470 | 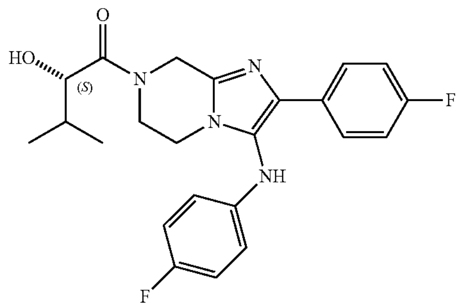 | 427.1 (M + 1) | 0.01 | 0.012 |
| 471 | 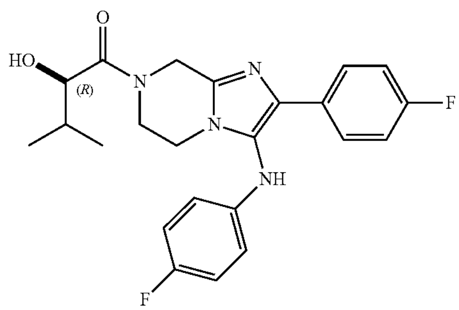 | 427.1 (M + 1) | 0.03 | 0.03 |
| 472 | 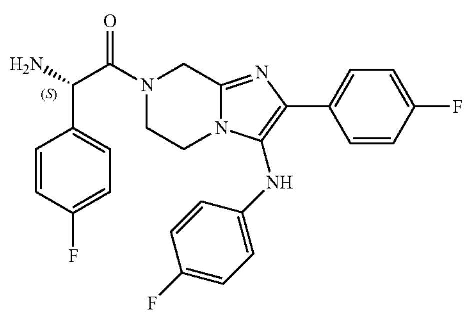 | 478.2 (M + 1) | 0.05 | 0.037 |
| 473 | 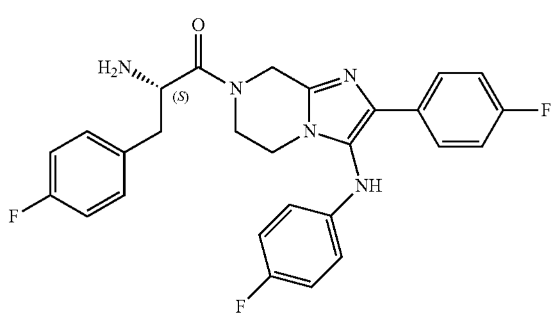 | 492.2 (M + 1) | 0.03 | 0.021 |
| 474 | 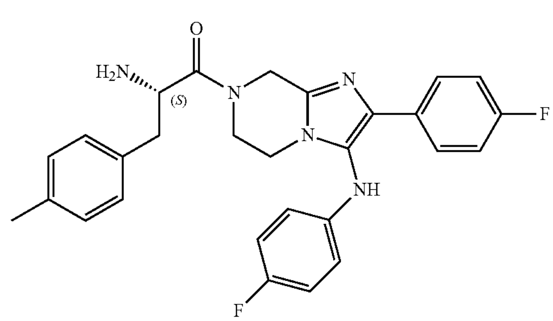 | 488.2 (M + 1) | 0.13 | 0.088 |

TABLE 2-continued

| Compound | Structure | Physical Data MS (m/z) and/or ¹H NMR | EC$_{50}$ 3D7 strain (μM) | EC$_{50}$ W2 strain (μM) |
|---|---|---|---|---|
| 475 | 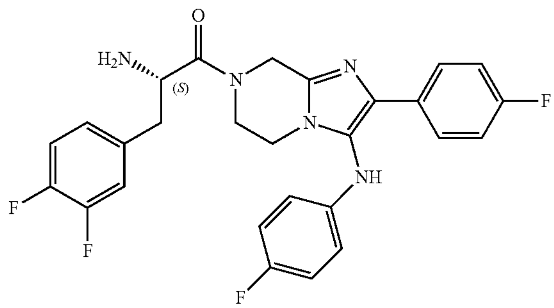 | 510.0 (M + 1) | 0.04 | 0.03 |
| 476 | 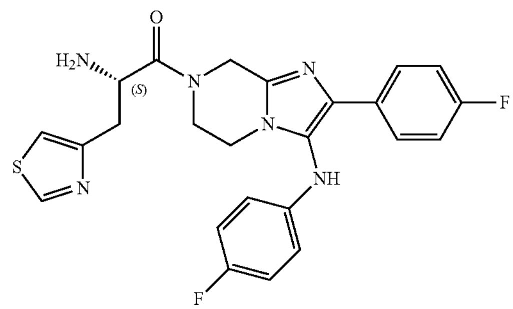 | 480.9 (M + 1) | 0.04 | 0.027 |
| 477 | 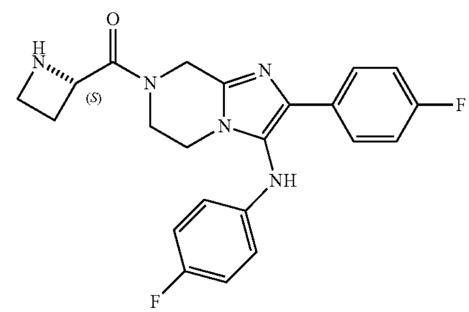 | 410.0 (M + 1) | 0.07 | 0.055 |
| 478 | 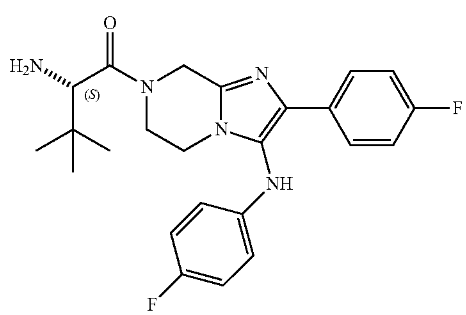 | 440.0 (M + 1) | 0.06 | 0.039 |
| 479 | 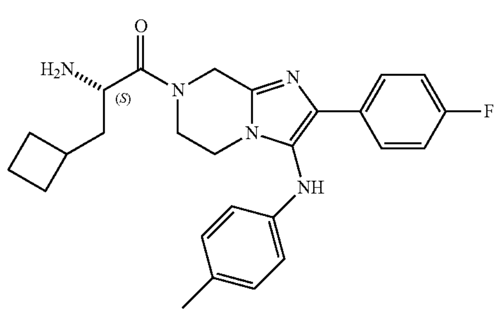 | 448.2 (M + 1) | 0.02 | 0.012 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 480 | 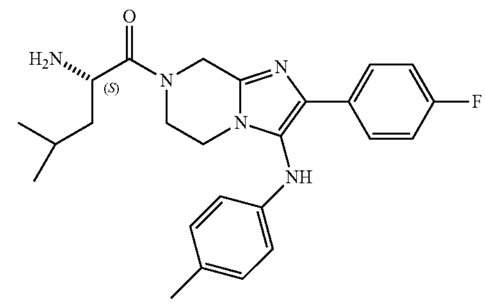 | 436.2 (M + 1) | 0.03 | 0.022 |
| 481 | 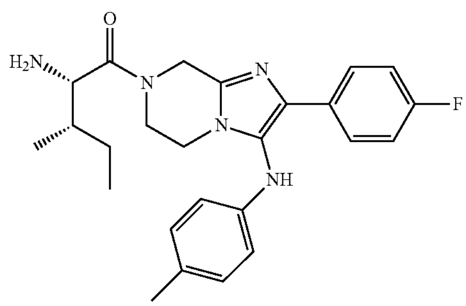 [SMILES: CC[C@H](C)[C@H](N)C(=O)N1CCn2c(nc(-c3ccc(F)cc3)c2Nc2ccc(C)cc2)C1] | 436.2 (M + 1) | 0.02 | 0.014 |
| 482 | 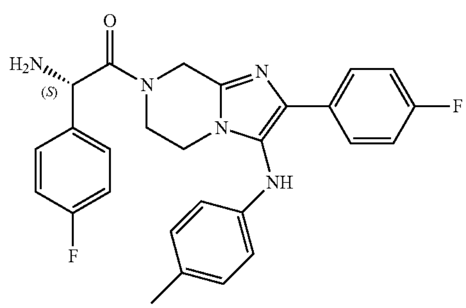 | 474.2 (M + 1) | 0.02 | 0.009 |
| 483 | 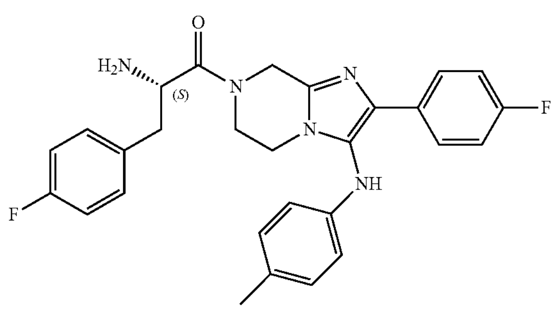 | 488.2 (M + 1) | 0.05 | 0.025 |
| 484 | 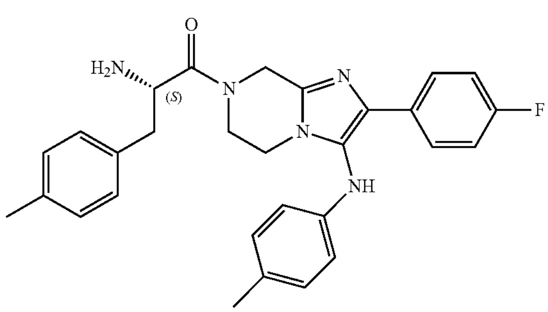 | 484.3 (M + 1) | 0.04 | 0.023 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 485 | 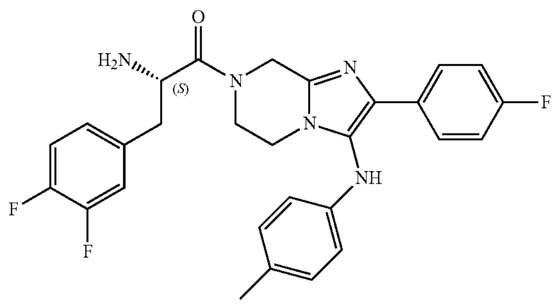 | 506.2 (M + 1) | 0.03 | 0.023 |
| 486 | 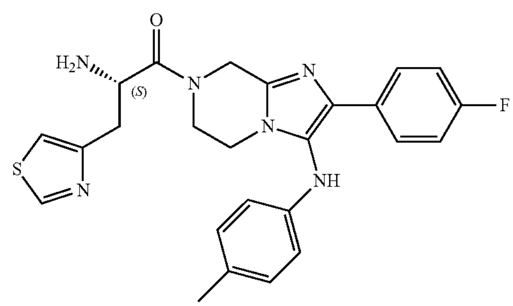 | 477.0 (M + 1) | 0.03 | 0.016 |
| 487 | 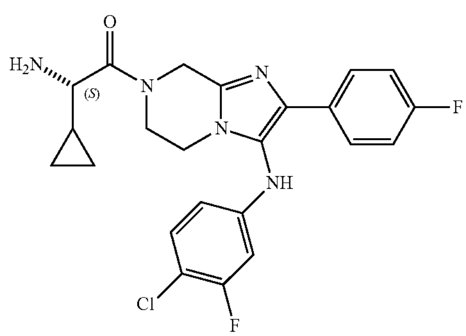 | 458 (M + 1) | 0.04 | 0.031 |
| 488 | 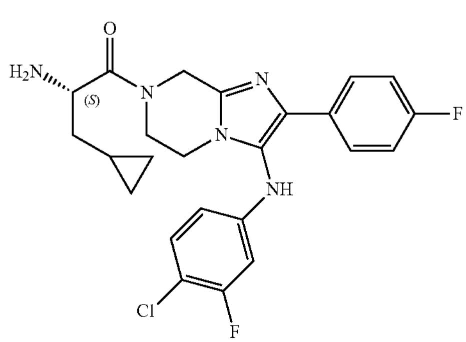 | 472.2 (M + 1) | 0.02 | 0.013 |

TABLE 2-continued
| Compound | Structure | Physical Data MS (m/z) and/or $^1$H NMR | EC$_{50}$ 3D7 strain (μM) | EC$_{50}$ W2 strain (μM) |
|---|---|---|---|---|
| 489 | 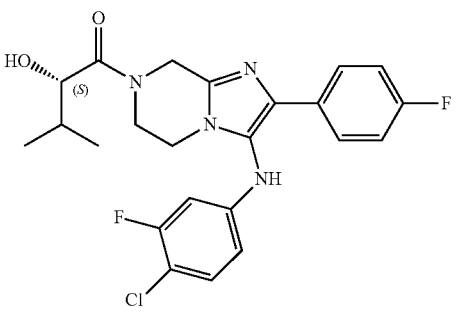 | 461.2 (M + 1) | 0.01 | 0.009 |
| 490 | 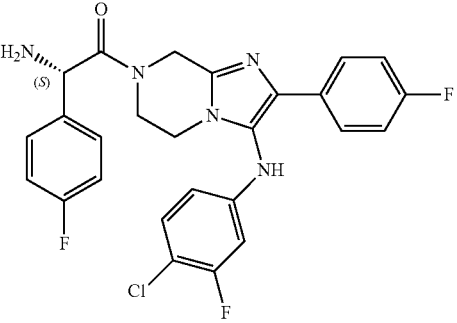 | 512.2 (M + 1) | 0.05 | 0.033 |
| 491 | 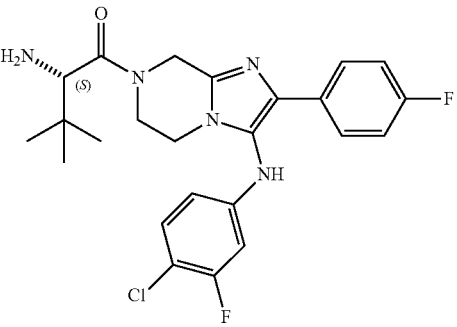 | 458 (M + 1) | 0.08 | 0.055 |
| 492 | 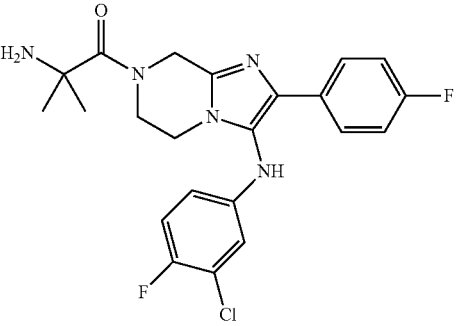 | 446.2 (M + 1) | 0.05 | |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 493 | 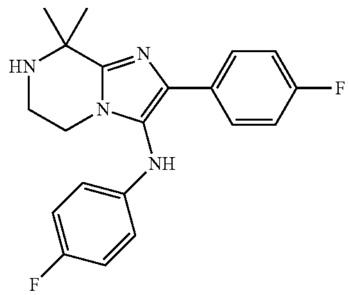 | 355.1 (M + 1) $^1$H-NMR: (MeOH-d$_4$, 400 Hz) δ 7.62-7.58 (m, 2H); 7.12-7.08 (m, 2H); 6.68-6.63 (m, 2H); 6.67 (m, 2H); 4.16 (m, 2H); 3.78 (m, 2H); 1.92 (s, 6H). | 0.004 | 0.005 |
| 494 | 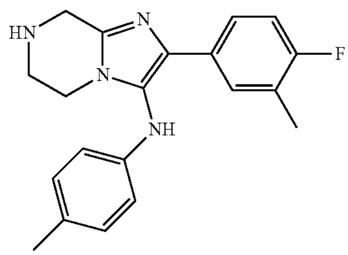 [SMILES: Cc1ccc(Nc2c(-c3ccc(F)c(C)c3)nc3n2CCNC3)cc1] | 337.2 (M + 1) | 2.82 | 2.141 |
| 495 | 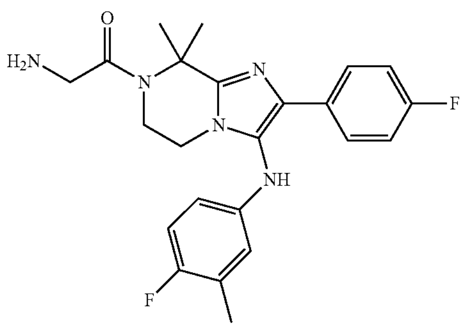 | 426.0 (M + 1) | 0.09 | 0.039 |
| 496 | 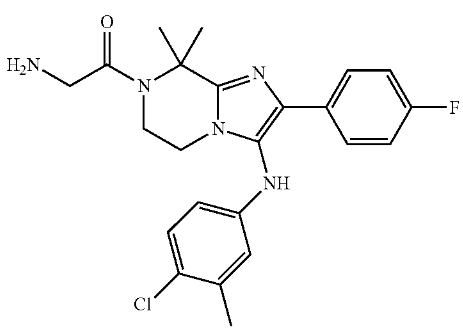 [SMILES: Cc1cc(Nc2c(-c3ccc(F)cc3)nc3n2CCN(C(=O)CN)C3(C)C)ccc1Cl] | 442.2 (M + 1) | 0.03 | 0.008 |
| 497 | 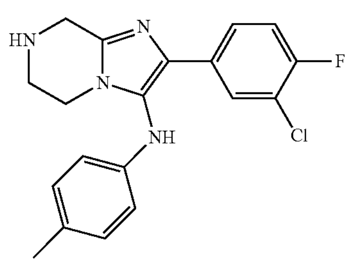 | 357.1 (M + 1) | 8.0 | 5.825 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 498 | 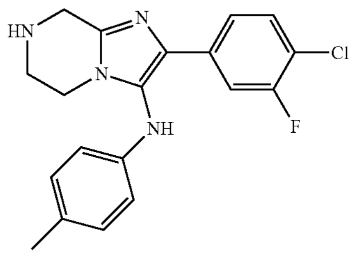 [SMILES: Cc1ccc(Nc2c(-c3ccc(Cl)c(F)c3)nc3n2CCNC3)cc1] | 357.1 (M + 1) | 6.34 | 6.738 |
| 499 | 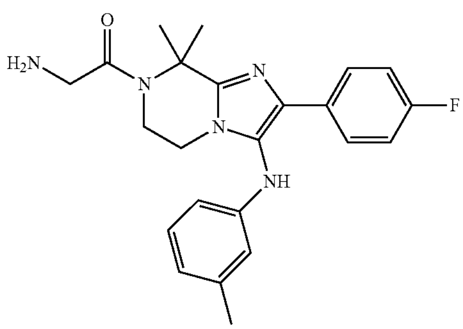 [SMILES: Cc1cccc(Nc2c(-c3ccc(F)cc3)nc3n2CCN(C(=O)CN)C3(C)C)c1] | 408.2 (M + 1) | 0.01 | 0.006 |
| 500 | 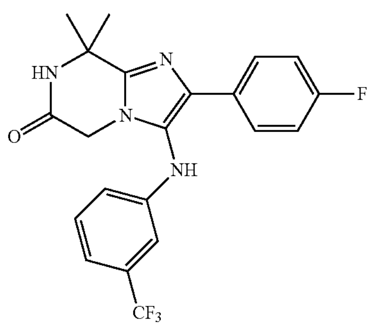 [SMILES: CC1(C)NC(=O)Cn2c1nc(-c1ccc(F)cc1)c2Nc1cccc(C(F)(F)F)c1] | 419.0 (M + 1) | 1.56 | 1.1 |
| 501 | 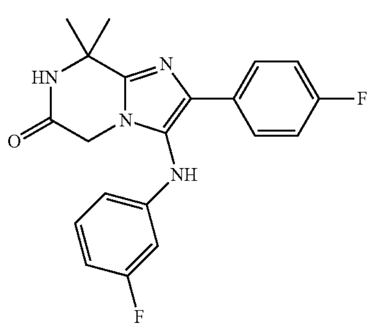 [SMILES: CC1(C)NC(=O)Cn2c1nc(-c1ccc(F)cc1)c2Nc1cccc(F)c1] | 369.2 (M + 1) | 0.4 | 0.305 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 502 | 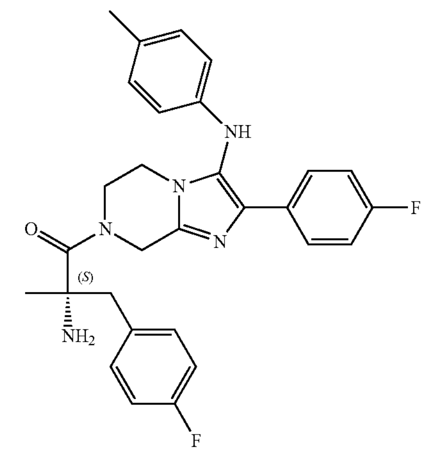 | 502.3 (M + 1) | 1.39 | 1.373 |
| 503 | 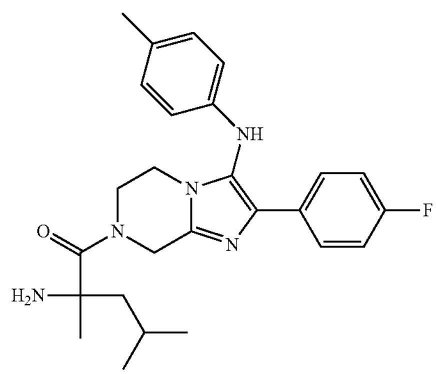 [SMILES: Cc1ccc(Nc2c(-c3ccc(F)cc3)nc3n2CCN(C(=O)C(C)(N)CC(C)C)C3)cc1] | 450.3 (M + 1) | 0.12 | 0.095 |
| 504 | 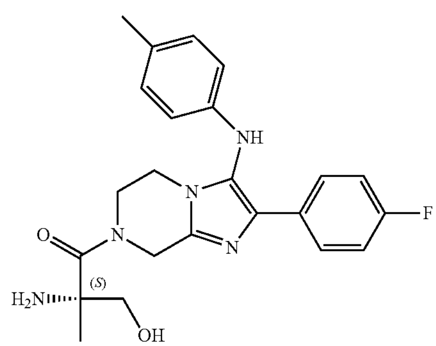 | 424.0 (M + 1) | 0.09 | 0.093 |
| 505 | 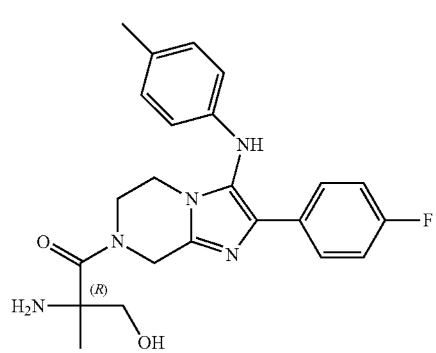 | 424.2 (M + 1) | 0.14 | 0.116 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 506 | 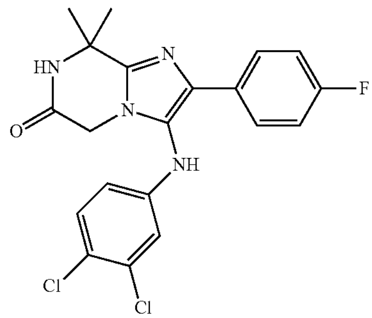 [SMILES: CC1(C)NC(=O)Cn2c1nc(-c1ccc(F)cc1)c2Nc1ccc(Cl)c(Cl)c1] | 420.3 (M + 1) | 0.19 | 0.198 |
| 507 | 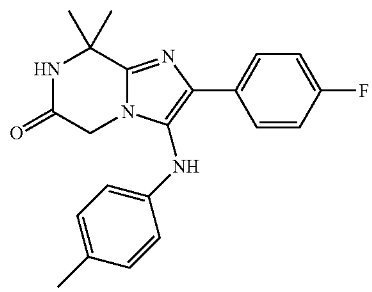 [SMILES: Cc1ccc(Nc2c(-c3ccc(F)cc3)nc3n2CC(=O)NC3(C)C)cc1] | 365.2 (M + 1) | 0.14 | 0.136 |
| 508 | 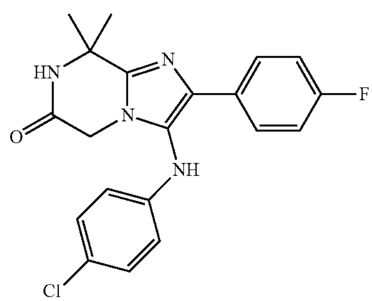 [SMILES: CC1(C)NC(=O)Cn2c1nc(-c1ccc(F)cc1)c2Nc1ccc(Cl)cc1] | 385.0 (M + 1) | 0.13 | 0.126 |
| 509 | 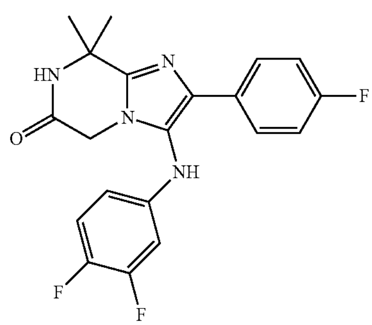 | 387.2 (M + 1) | 0.13 | 0.134 |
| 510 | 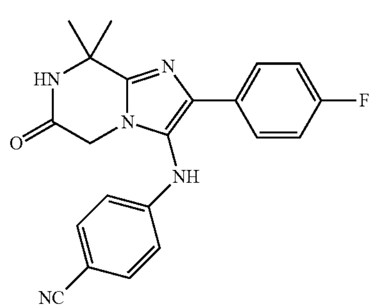 | 387.2 (M + 1) | 2.05 | 1.564 |

TABLE 2-continued

| Compound | Structure | Physical Data MS (m/z) and/or ¹H NMR | EC$_{50}$ 3D7 strain (μM) | EC$_{50}$ W2 strain (μM) |
|---|---|---|---|---|
| 511 | 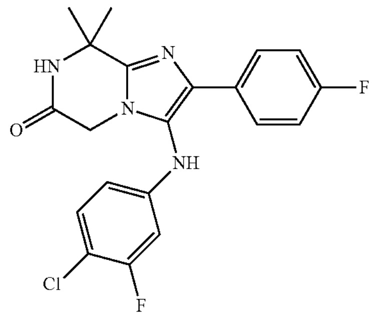 | 403.1 (M + 1) ¹H-NMR: (MeOH-d$_4$, 400 Hz) δ 7.74-7.70 (m, 2H); 7.21 (t, J = 8.4 Hz, 1H), 7.08 (m, 2H); 6.49-6.40 (m, 2H); 4.43 (s, 2H); 1.72 (s, 6H). | 0.04 | 0.065 |
| 512 | 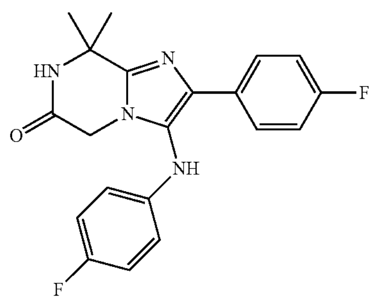 [SMILES: CC1(C)NC(=O)Cn2c1nc(-c1ccc(F)cc1)c2Nc1ccc(F)cc1] | 369.2 (M + 1) | 0.19 | 0.165 |
| 513 | 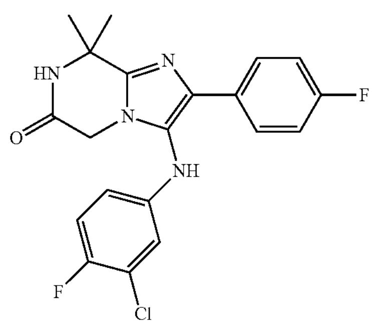 [SMILES: CC1(C)NC(=O)Cn2c1nc(-c1ccc(F)cc1)c2Nc1ccc(F)c(Cl)c1] | 403.0 (M + 1) | 0.17 | 0.195 |
| 514 | 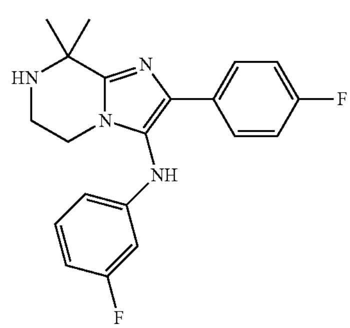 [SMILES: CC1(C)NCCn2c1nc(-c1ccc(F)cc1)c2Nc1cccc(F)c1] | 355.1 (M + 1) | 0.03 | 0.024 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 515 | 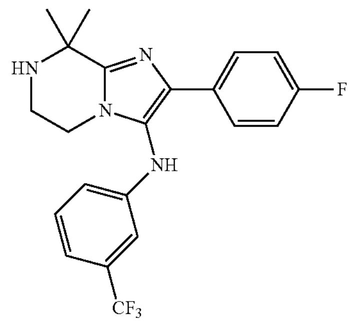 [SMILES: CC1(C)NCCn2c1nc(-c1ccc(F)cc1)c2Nc1cccc(C(F)(F)F)c1] | 405.1 (M + 1) | 0.04 | 0.034 |
| 516 | 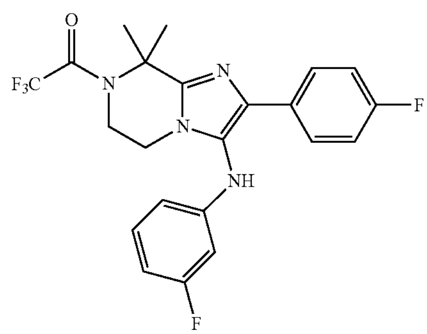 [SMILES: CC1(C)c2nc(-c3ccc(F)cc3)c(Nc3cccc(F)c3)n2CCN1C(=O)C(F)(F)F] | 451.2 (M + 1) | 0.03 | 0.026 |
| 517 | 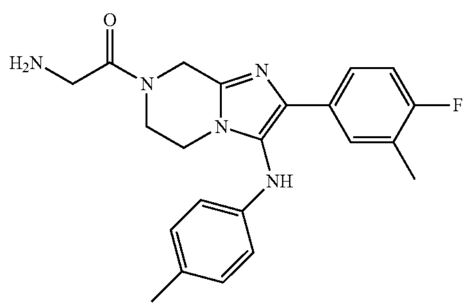 [SMILES: Cc1ccc(Nc2c(-c3ccc(F)c(C)c3)nc3n2CCN(C(=O)CN)C3)cc1] | 394.1 (M + 1) | 0.05 | 0.051 |
| 518 | 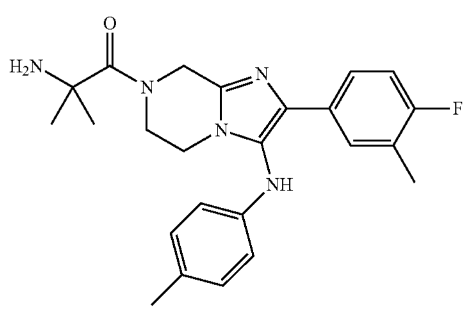 | 422.2 (M + 1) | 4.98 | 2.888 |
| 519 | 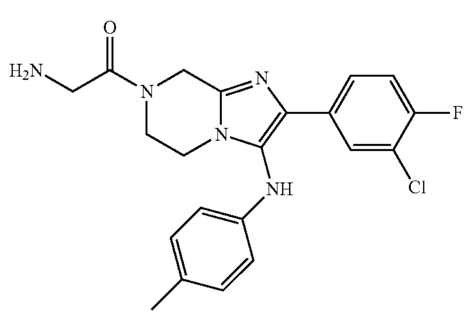 | 414.2 (M + 1) | 0.84 | 0.59 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 520 | 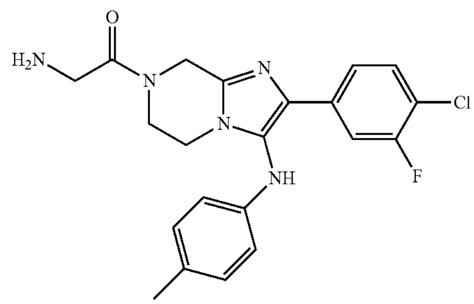 [SMILES: Cc1ccc(Nc2c(-c3ccc(Cl)c(F)c3)nc3n2CCN(C(=O)CN)C3)cc1] | 414.2 (M + 1) | 0.16 | 0.158 |
| 521 | 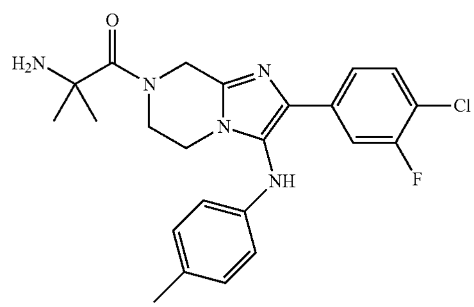 [SMILES: Cc1ccc(Nc2c(-c3ccc(Cl)c(F)c3)nc3n2CCN(C(=O)C(C)(C)N)C3)cc1] | 442.2 (M + 1) | 5.0 | 3.026 |
| 522 | 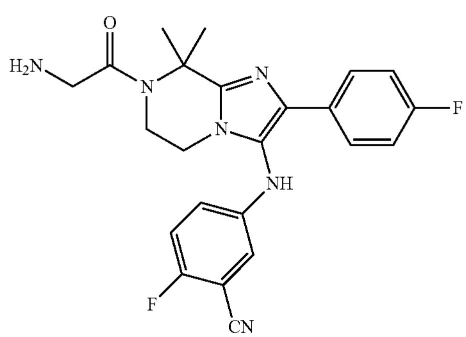 [SMILES: CC1(C)c2nc(-c3ccc(F)cc3)c(Nc3ccc(F)c(C#N)c3)n2CCN1C(=O)CN] | 437.0 (M + 1) $^1$H-NMR: (MeOH-d$_4$, 400 Hz) δ 7.61-7.57 (m, 2H); 7.15-7.07 (m, 4H); 7.02-7.01 (m, 1H); 4.0 (m, 4H); 3.81 (m, 2H); 2.01 (s, 6H). | 0.0017 | 0.002 |
| 523 | 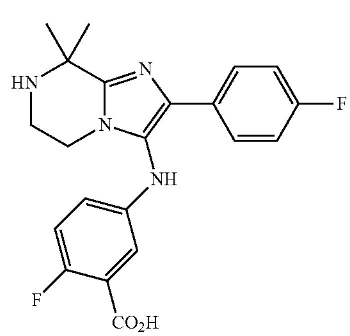 | 399.0 (M + 1) | 13.11 | 11.649 |

TABLE 2-continued

| Compound | Structure | Physical Data MS (m/z) and/or ¹H NMR | EC$_{50}$ 3D7 strain (μM) | EC$_{50}$ W2 strain (μM) |
|---|---|---|---|---|
| 524 | 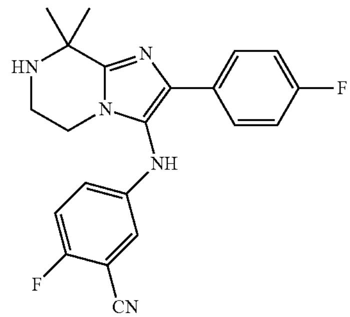 | 380.2 (M + 1) | 0.04 | 0.057 |
| 525 | 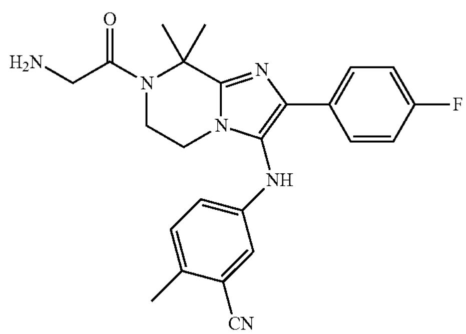 [SMILES: Cc1ccc(Nc2c(-c3ccc(F)cc3)nc3n2CCN(C(=O)CN)C3(C)C)cc1C#N] | 433.5 (M + 1) | 0.01 | 0.013 |
| 526 | 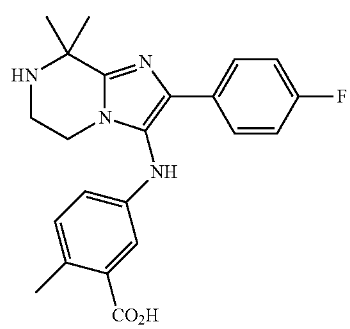 [SMILES: Cc1ccc(Nc2c(-c3ccc(F)cc3)nc3n2CCNC3(C)C)cc1C(=O)O] | 395.0 (M + 1) | 1.12 | 0.974 |
| 527 | 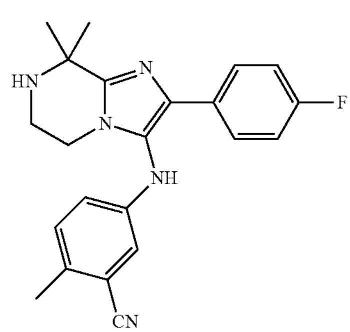 [SMILES: Cc1ccc(Nc2c(-c3ccc(F)cc3)nc3n2CCNC3(C)C)cc1C#N] | 376.1 (M + 1) <br> ¹H-NMR: (MeOH-d$_4$, 400 Hz) δ 7.61-7.57 (m, 2H); 7.15-7.07 (m, 4H); 7.02-7.01 (m, 1H); 4.0 (m, 4H); 3.81 (m, 2H); 2.01 (s, 6H). | 0.004 | 0.006 |

TABLE 2-continued

| Compound | Structure | Physical Data MS (m/z) and/or ¹H NMR | EC$_{50}$ 3D7 strain (μM) | EC$_{50}$ W2 strain (μM) |
|---|---|---|---|---|
| 528 | 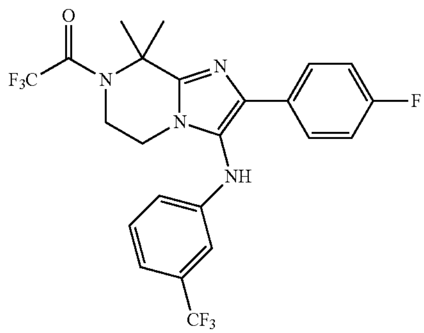 [SMILES: CC1(C)c2nc(-c3ccc(F)cc3)c(Nc3cccc(C(F)(F)F)c3)n2CCN1C(=O)C(F)(F)F] | 501.2 (M + 1) | 0.15 | 0.121 |
| 529 | 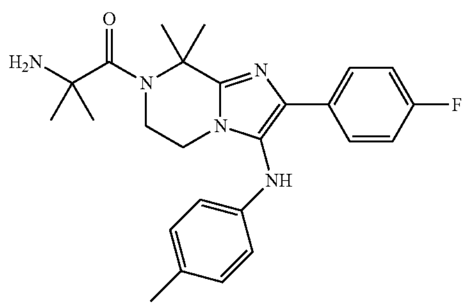 [SMILES: Cc1ccc(Nc2c(-c3ccc(F)cc3)nc3n2CCN(C(=O)C(C)(C)N)C3(C)C)cc1] | 436.2 (M + 1)<br>¹H-NMR: (MeOH-d$_4$, 400 Hz) δ 7.78-7.75 (m, 2H); 7.06-6.97 (m, 4H); 6.56 (d, J = 8.4 Hz, 2H), 5.16 (s, NH); 4.33 (t, J = 4.8 Hz, 2H), 3.74 (t, J = 4.8 Hz, 2H), 4.16 (m, 2H); 2.29 (s, 3H); 1.95 (s, 6H); 1.45 (s, 6H). | 0.002 | 0.004 |
| 530 | 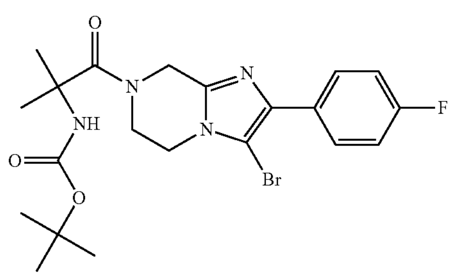 [SMILES: CC(C)(C)OC(=O)NC(C)(C)C(=O)N1CCn2c(nc(-c3ccc(F)cc3)c2Br)C1] | 482.2 (M + 1) | 1.23 | 6.422 |
| 531 | 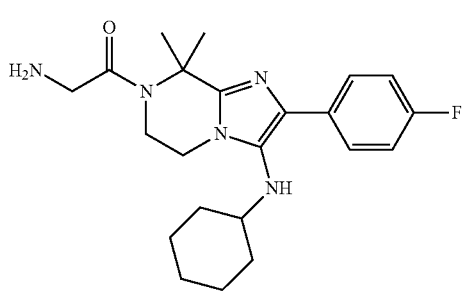 [SMILES: CC1(C)c2nc(-c3ccc(F)cc3)c(NC3CCCCC3)n2CCN1C(=O)CN] | 400.1 (M + 1)<br>¹H-NMR: (MeOH-d$_4$, 400 Hz) δ 7.67-7.63 (m, 2H); 7.21-7.17 (t, J = 8.8 Hz, 2H), 4.15 (m, 2H); 3.79 (m, 2H); 2.72 (m, 1H); 1.95 (s, 6H); 1.72 (m, 2H); 1.58 (m, 2H); 1.46 (m, 1H); 1.1-1.05 (m, 5H). | 0.04 | 0.057 |

TABLE 2-continued
| Compound | Structure | Physical Data MS (m/z) and/or ¹H NMR | EC$_{50}$ 3D7 strain (μM) | EC$_{50}$ W2 strain (μM) |
|---|---|---|---|---|
| 532 | 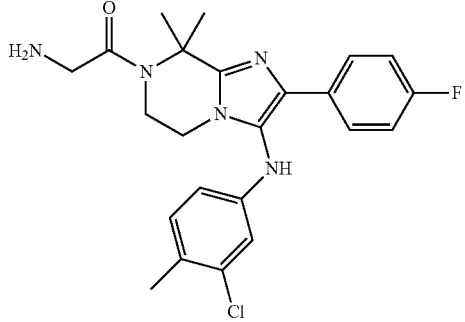 [SMILES: Cc1ccc(Nc2c(-c3ccc(F)cc3)nc3n2CCN(C(=O)CN)C3(C)C)cc1Cl] | 442.2 (M + 1) | 0.02 | 0.009 |
| 533 | 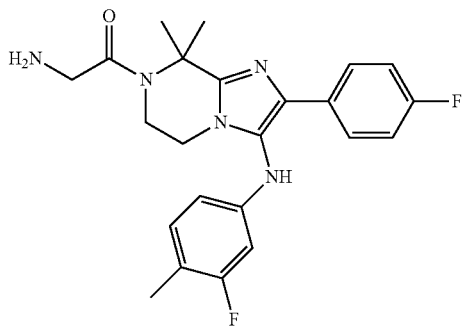 [SMILES: Cc1ccc(Nc2c(-c3ccc(F)cc3)nc3n2CCN(C(=O)CN)C3(C)C)cc1F] | 426.2 (M + 1) | 0.03 | 0.022 |
| 534 | 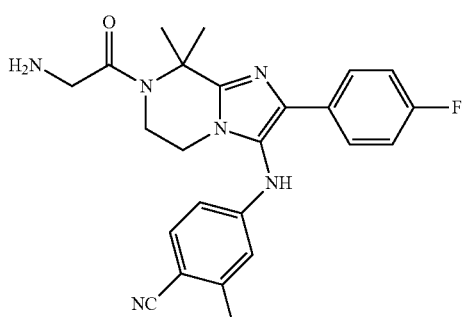 | 453.2 (M + 1) | 0.04 | 0.019 |
| 535 | 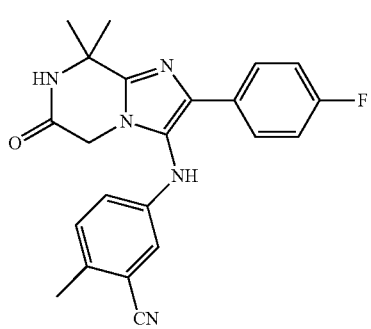 [SMILES: Cc1ccc(Nc2c(-c3ccc(F)cc3)nc3n2CC(=O)NC3(C)C)cc1C#N] | 390.2 (M + 1) | 2.72 | 2.351 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 536 | 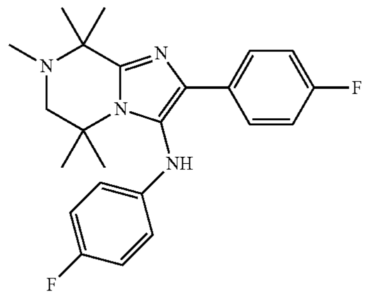 [SMILES: CN1CC(C)(C)n2c(nc(-c3ccc(F)cc3)c2Nc2ccc(F)cc2)C1(C)C] | 397.2 (M + 1) | 6.4 | 5.93 |
| 537 | 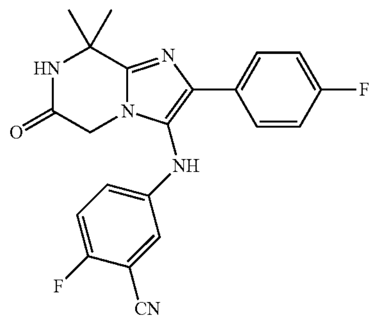 [SMILES: CC1(C)NC(=O)Cn2c1nc(-c1ccc(F)cc1)c2Nc1ccc(F)c(C#N)c1] | 394.2 (M + 1) | 11.91 | 8.342 |
| 538 | 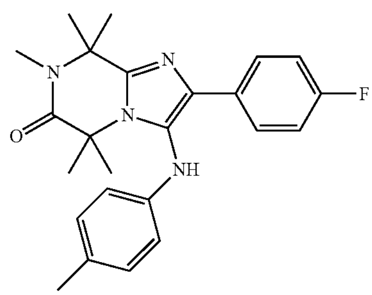 [SMILES: Cc1ccc(Nc2c(-c3ccc(F)cc3)nc3n2C(C)(C)C(=O)N(C)C3(C)C)cc1] | 407.2 (M + 1) | 7.67 | 8.065 |
| 539 | 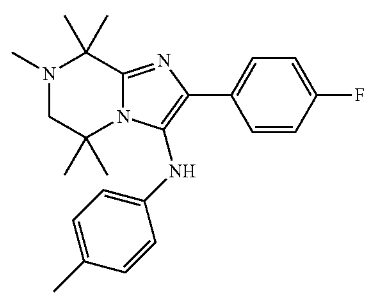 [SMILES: Cc1ccc(Nc2c(-c3ccc(F)cc3)nc3n2C(C)(C)CN(C)C3(C)C)cc1] | 393.2 (M + 1) | 3.06 | 3.123 |
| 540 | 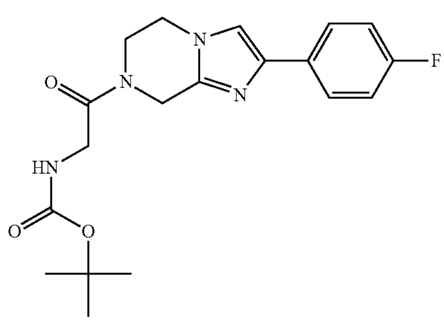 [SMILES: CC(C)(C)OC(=O)NCC(=O)N1CCn2cc(-c3ccc(F)cc3)nc2C1] | 375.2 (M + 1) $^1$H-NMR: (300 Hz, CD$_3$OD) δ 7.74-7.69 (m, 2H), 7.42 (s, 1H), 7.13-7.07 (m, 2H), 4.84 (s, 2H), 4.19-3.97 (6H, m), 1.47 (9H, s) | 8.42 | 9.807 |

TABLE 2-continued

| Compound | Structure | Physical Data MS (m/z) and/or ¹H NMR | EC$_{50}$ 3D7 strain (μM) | EC$_{50}$ W2 strain (μM) |
|---|---|---|---|---|
| 541 | 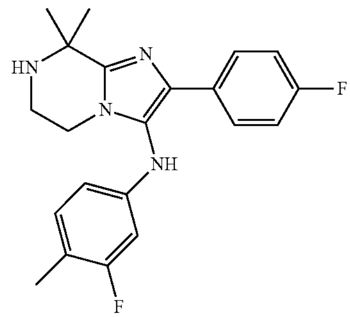 [SMILES: Cc1ccc(Nc2c(-c3ccc(F)cc3)nc3n2CCNC3(C)C)cc1F] | 369.2 (M + 1) | 0.01 | 0.01 |
| 542 | 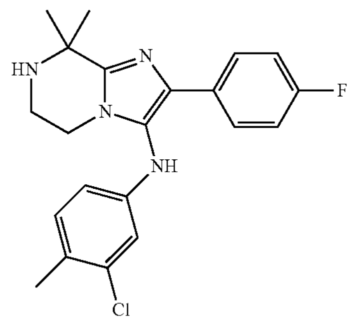 | 369.2 (M + 1) | 0.002 | 0.003 |
| 543 | 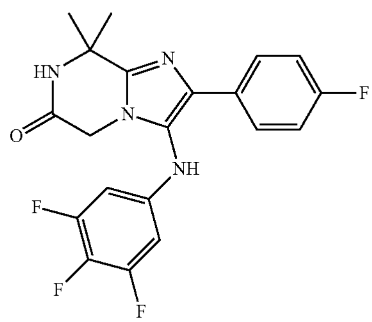 [SMILES: CC1(C)NC(=O)Cn2c1nc(-c1ccc(F)cc1)c2Nc1cc(F)c(F)c(F)c1] | 405.2 (M + 1) | 0.17 | 0.305 |
| 544 | 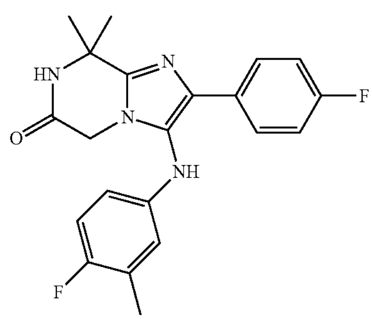 [SMILES: Cc1cc(Nc2c(-c3ccc(F)cc3)nc3n2CC(=O)NC3(C)C)ccc1F] | 383.2 (M + 1) ¹H-NMR: (MeOH-d$_4$, 400 Hz) δ 7.65-7.62 (m, 2H); 6.95-6.91 (m, 1H); 6.72 (t, J = 9.2 Hz, 1H), 6.28-6.25 (m, 1H); 4.30 (s, 2H) 2.04 (s, 3H); 1.81 (s, 6H). | 0.02 | 0.037 |
| 545 | 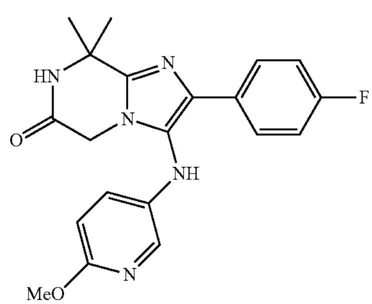 [SMILES: COc1ccc(Nc2c(-c3ccc(F)cc3)nc3n2CC(=O)NC3(C)C)cn1] | 382.2 (M + 1) | 3.38 | 5.618 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 546 | 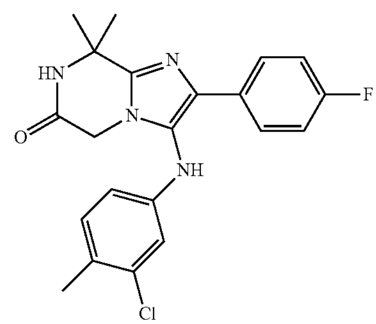 [SMILES: Cc1ccc(Nc2c(-c3ccc(F)cc3)nc3n2CC(=O)NC3(C)C)cc1Cl] | 399.1 (M + 1) $^1$H-NMR: (MeOH-d$_4$, 400 Hz) δ 7.60-7.56 (m, 2H); 7.09-7.05 (m, 2H); 6.99 (d, J = 8.0 Hz, 1H), 6.67 (d, J = 2.4 Hz, 2H); 6.46 (dd, J = 2.4 Hz, J = 8.0 Hz, 1H); 4.44 (s, 2H) 2.13 (s, 3H); 1.71 (s, 6H). | 0.03 | 0.052 |
| 547 | 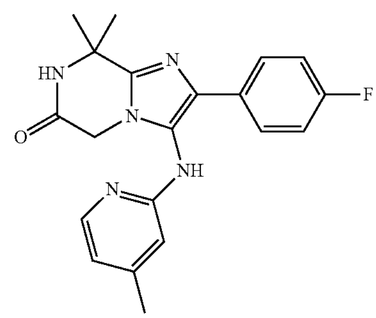 [SMILES: Cc1ccnc(Nc2c(-c3ccc(F)cc3)nc3n2CC(=O)NC3(C)C)c1] | 366.2 (M + 1) | 1.82 | 4.662 |
| 548 | 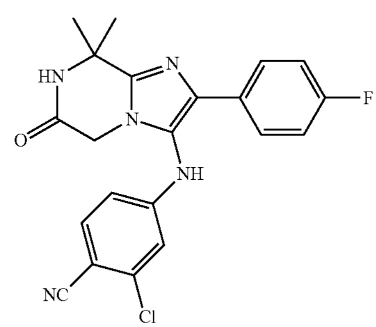 [SMILES: CC1(C)NC(=O)Cn2c1nc(-c1ccc(F)cc1)c2Nc1ccc(C#N)c(Cl)c1] | 410.0 (M + 1) | 2.63 | 5.549 |
| 549 | 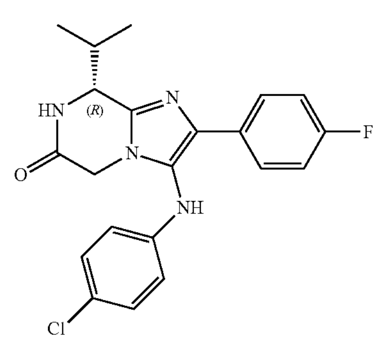 | 399.1 (M + 1) | 1.7 | 3.261 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 550 | 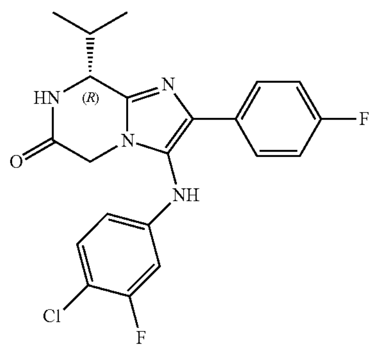 | 417.1 (M + 1) | 2.56 | 3.6 |
| 551 | 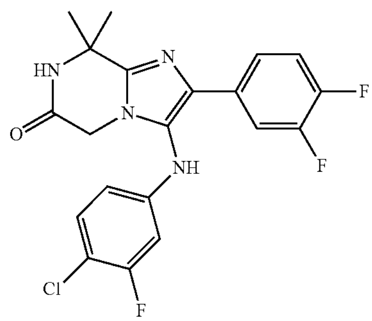 [SMILES: CC1(C)NC(=O)Cn2c1nc(-c1ccc(F)c(F)c1)c2Nc1ccc(Cl)c(F)c1] | 421.0 (M + 1) | 0.04 | 0.098 |
| 552 | 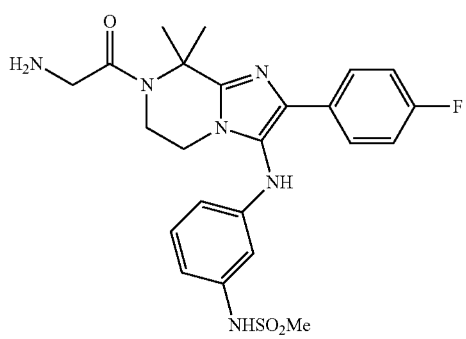 | 487.2 (M + 1) $^1$H-NMR: (MeOH-d$_4$, 400 Hz) δ 7.72-7.67 (m, 4H); 7.2 (t, J = 8.8 Hz, 2H); 6.8 (d, J = 8.4 Hz, 2H), 4.01 (m, 4H), 3.86 (t, J = 4.4 Hz, 2H); 2.88 (s, 3H); 2.1 (s, 6H). | 2.52 | 4.482 |
| 553 | 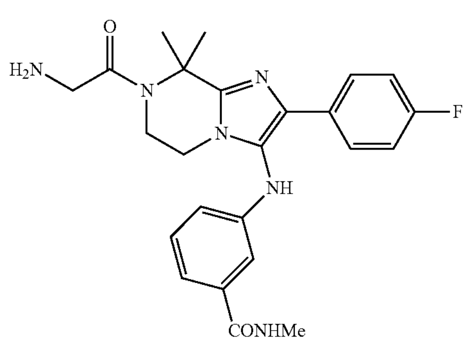 | 451.2 (M + 1) | 2.37 | 4.658 |

TABLE 2-continued

| Compound | Structure | Physical Data MS (m/z) and/or ¹H NMR | EC$_{50}$ 3D7 strain (μM) | EC$_{50}$ W2 strain (μM) |
| --- | --- | --- | --- | --- |
| 554 | 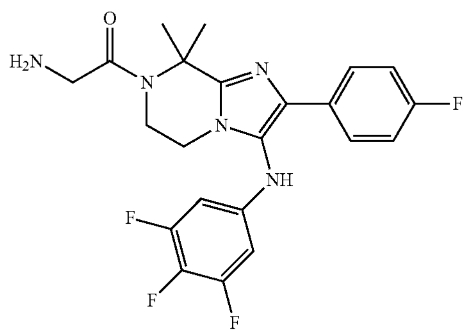 [SMILES: CC1(C)c2nc(-c3ccc(F)cc3)c(Nc3cc(F)c(F)c(F)c3)n2CCN1C(=O)CN] | 448.0 (M + 1) | 0.0 | 0.007 |
| 555 | 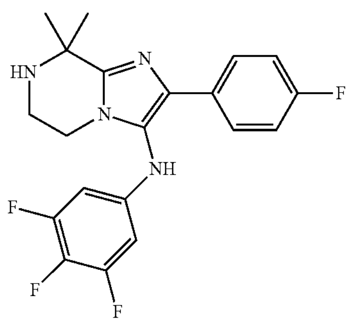 [SMILES: CC1(C)NCCn2c1nc(-c1ccc(F)cc1)c2Nc1cc(F)c(F)c(F)c1] | 391.2 (M + 1) | 0.01 | 0.016 |
| 556 | 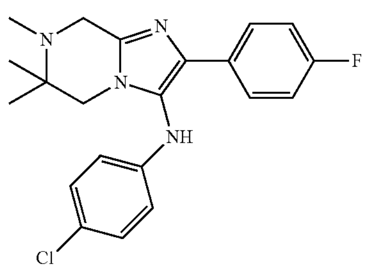 [SMILES: CN1Cc2nc(-c3ccc(F)cc3)c(Nc3ccc(Cl)cc3)n2CC1(C)C] | 385.2 (M + 1)<br>¹H-NMR: (MeOH-d$_4$, 400 Hz) δ 7.72-7.69 (m, 2H); 7.19-7.15 (4H, m); 6.67 (2H, J = 9.2 Hz, d); 4.64 (s, 2H); 4.64 (s, 2H); 3.99 (s, 2H), 2.91 (s, 2H), 1.43 (s, 6H). | 0.06 | 0.075 |
| 557 | 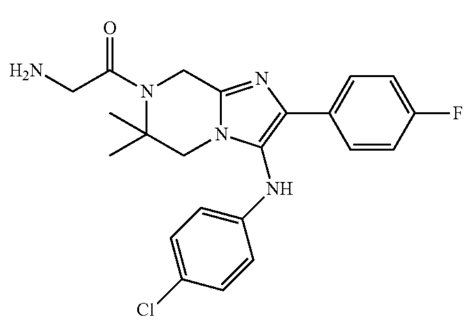 [SMILES: CC1(C)Cn2c(nc(-c3ccc(F)cc3)c2Nc2ccc(Cl)cc2)CN1C(=O)CN] | 428.2 (M + 1)<br>¹H-NMR: (MeOH-d$_4$, 400 Hz) δ 7.74 (m, 2H); 7.19-7.15 (m, 2H); 6.69 (d, J = 8.8 Hz, 2H); 4.88 (s, 2H); 4.08 (s, 2H); 3.99 (s, 2H), 2.91 (s, 2H), 1.54 (s, 6H). | 0.02 | 0.02 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 558 | 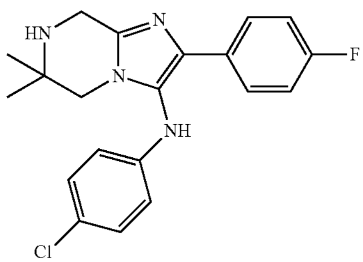 [SMILES: CC1(C)Cn2c(nc(-c3ccc(F)cc3)c2Nc2ccc(Cl)cc2)CN1] | 371.1 (M + 1) $^1$H-NMR: (CDCl$_3$, 400 Hz) δ 7.75-7.71 (m, 2H); 7.18 (d, J = 9.2 Hz, 2H); 6.99 (t, J = 8.8 Hz, 2H); 6.56 (d, J = 8.8 Hz, 2H); 5.37 (s, NH); 4.15 (s, 2H); 3.49 (s, NH); 3.42 (s, 2H); 1.22 (s, 6H). | 0.06 | 0.089 |
| 559 | 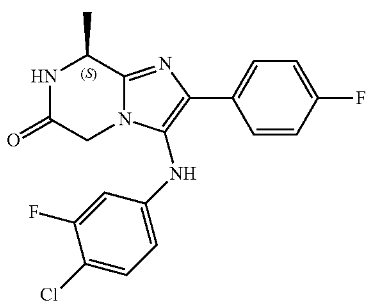 | 389.0 (M + 1) | 0.53 | 0.642 |
| 560 | 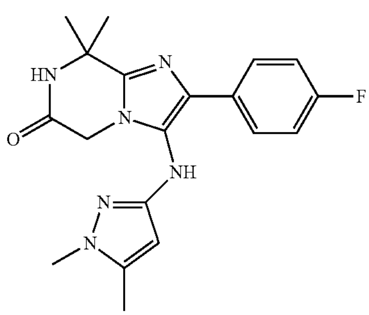 [SMILES: Cc1cc(Nc2c(-c3ccc(F)cc3)nc3n2CC(=O)NC3(C)C)nn1C] | 369.2 (M + 1) | 3.61 | 5.219 |
| 561 | 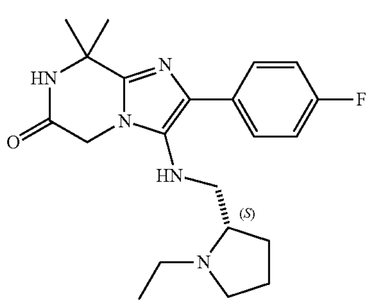 | 386.2 (M + 1) | 7.17 | 4.403 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 562 | 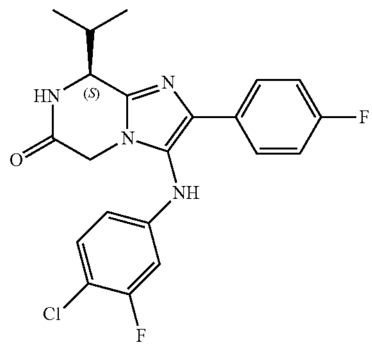 | 417.2 (M + 1) | 4.82 | 6.293 |
| 563 | 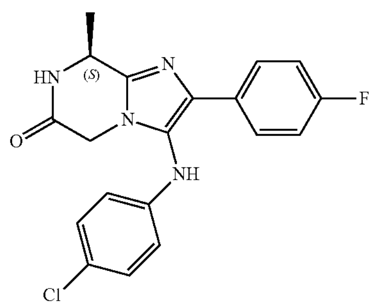 | 371.0 (M + 1) | 0.31 | 0.445 |
| 564 | 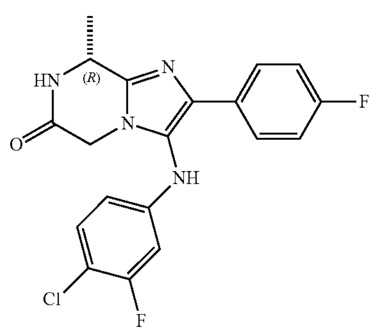 | 389.0 (M + 1) | 0.25 | 0.359 |
| 565 | 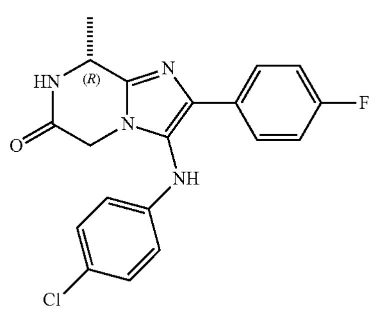 | 371.0 (M + 1) | 0.07 | 0.105 |

TABLE 2-continued

| Compound | Structure | Physical Data MS (m/z) and/or ¹H NMR | EC$_{50}$ 3D7 strain (μM) | EC$_{50}$ W2 strain (μM) |
|---|---|---|---|---|
| 566 | 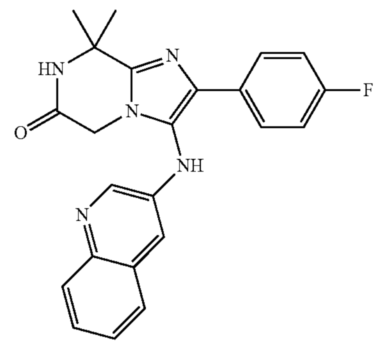 [SMILES: CC1(C)NC(=O)Cn2c1nc(-c1ccc(F)cc1)c2Nc1cnc2ccccc2c1] | 402.2 (M + 1) | 5.48 | 4.463 |
| 567 | 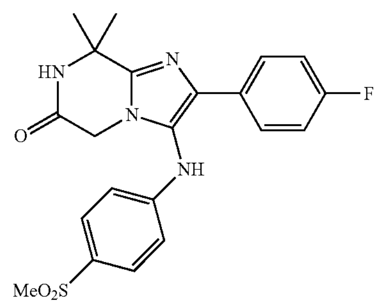 [SMILES: CC1(C)NC(=O)Cn2c1nc(-c1ccc(F)cc1)c2Nc1ccc(S(C)(=O)=O)cc1] | 429.2 (M + 1) | 6.46 | 8.458 |
| 568 | 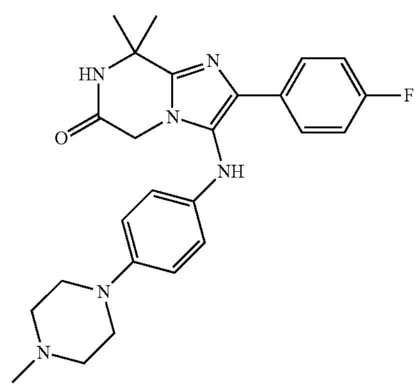 [SMILES: CN1CCN(c2ccc(Nc3c(-c4ccc(F)cc4)nc4n3CC(=O)NC4(C)C)cc2)CC1] | 449.0 (M + 1) | >8.04 | >11.3 |
| 569 | 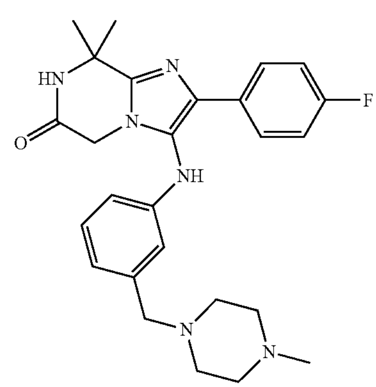 [SMILES: CN1CCN(Cc2cccc(Nc3c(-c4ccc(F)cc4)nc4n3CC(=O)NC4(C)C)c2)CC1] | 463.3 (M + 1) | 9.27 | 7.916 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 570 | 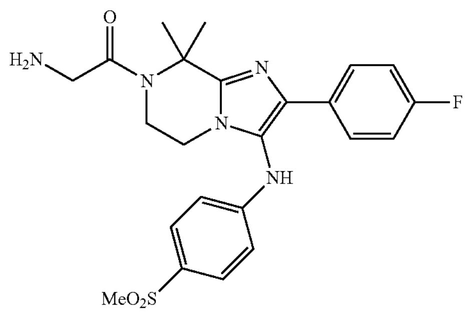 [SMILES: CC1(C)c2nc(-c3ccc(F)cc3)c(Nc3ccc(S(C)(=O)=O)cc3)n2CCN1C(=O)CN] | 472.2 (M + 1) | 5.68 | 5.562 |
| 571 | 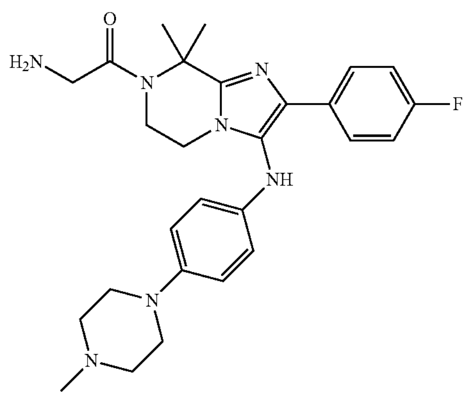 [SMILES: CN1CCN(c2ccc(Nc3c(-c4ccc(F)cc4)nc4n3CCN(C(=O)CN)C4(C)C)cc2)CC1] | 492.1 (M + 1) | 6.2 | 7.48 |
| 572 | 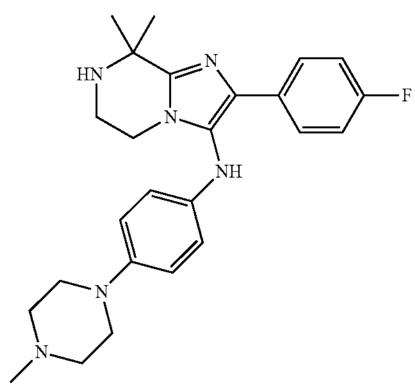 [SMILES: CN1CCN(c2ccc(Nc3c(-c4ccc(F)cc4)nc4n3CCNC4(C)C)cc2)CC1] | 435.1 (M + 1) | 11.18 | 8.73 |
| 573 | 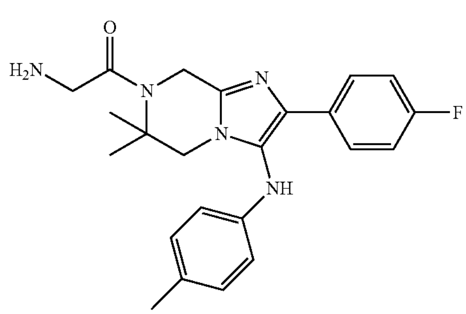 [SMILES: Cc1ccc(Nc2c(-c3ccc(F)cc3)nc3n2CC(C)(C)N(C(=O)CN)C3)cc1] | 408.2 (M + 1) | 0.04 | 0.055 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 574 | 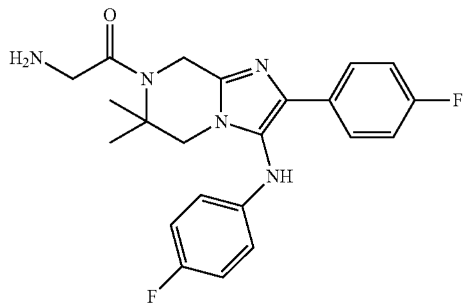 | 412.1 (M + 1) | 0.08 | 0.111 |
| 575 | 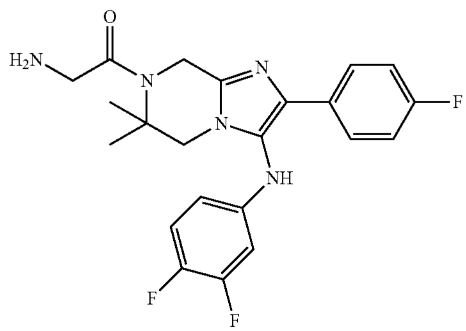 [SMILES: CC1(C)Cn2c(nc(-c3ccc(F)cc3)c2Nc2ccc(F)c(F)c2)CN1C(=O)CN] | 430.2 (M + 1) | 0.08 | 0.081 |
| 576 | 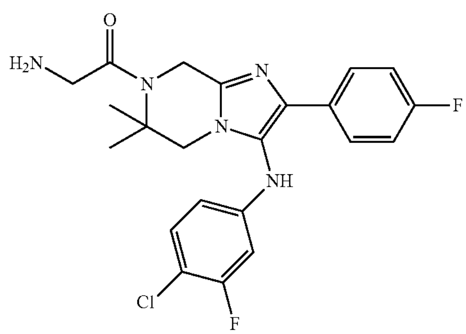 [SMILES: CC1(C)Cn2c(nc(-c3ccc(F)cc3)c2Nc2ccc(Cl)c(F)c2)CN1C(=O)CN] | 446.2 (M + 1) | 0.2 | 0.234 |
| 577 | 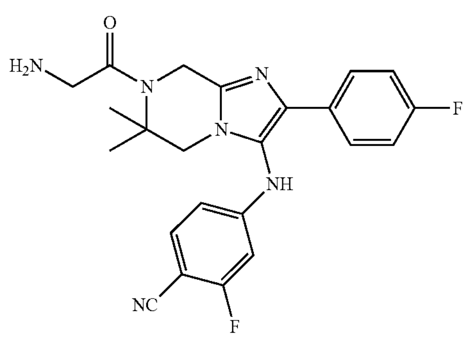 [SMILES: CC1(C)Cn2c(nc(-c3ccc(F)cc3)c2Nc2ccc(C#N)c(F)c2)CN1C(=O)CN] | 437.1 (M + 1) | 0.63 | 0.611 |
| 578 | 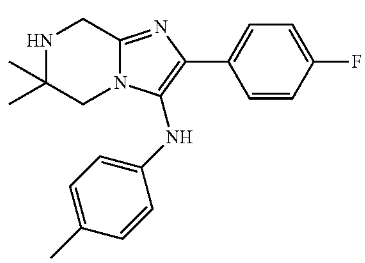 [SMILES: Cc1ccc(Nc2c(-c3ccc(F)cc3)nc3n2CC(C)(C)NC3)cc1] | 351.2 (M + 1) | 0.25 | 0.339 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 579 | 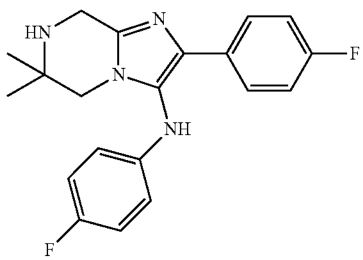 [SMILES: CC1(C)Cn2c(nc(-c3ccc(F)cc3)c2Nc2ccc(F)cc2)CN1] | 355.2 (M + 1) | 0.18 | 0.146 |
| 580 | 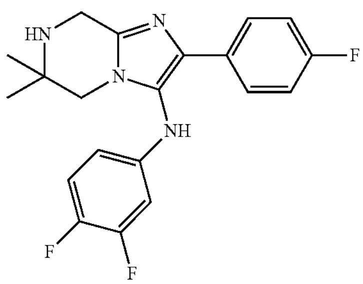 [SMILES: CC1(C)Cn2c(nc(-c3ccc(F)cc3)c2Nc2ccc(F)c(F)c2)CN1] | 373.2 (M + 1) | 0.15 | 0.169 |
| 581 | 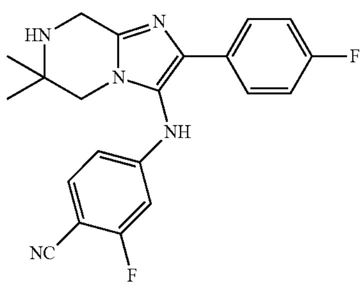 [SMILES: CC1(C)Cn2c(nc(-c3ccc(F)cc3)c2Nc2ccc(C#N)c(F)c2)CN1] | 380.2 (M + 1) | 0.65 | 0.668 |
| 582 | 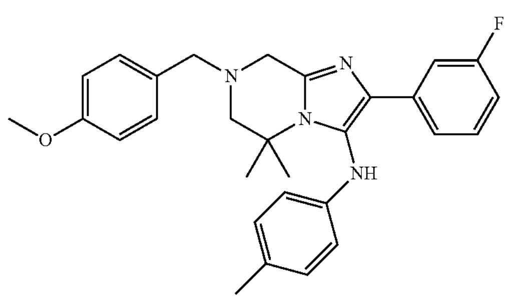 [SMILES: COc1ccc(CN2Cc3nc(-c4cccc(F)c4)c(Nc4ccc(C)cc4)n3C(C)(C)C2)cc1] | 471.1 (M + 1) | 5.56 | 5.919 |
| 583 | 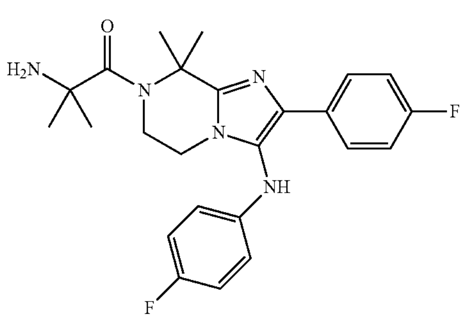 [SMILES: CC(C)(N)C(=O)N1CCn2c(nc(-c3ccc(F)cc3)c2Nc2ccc(F)cc2)C1(C)C] | 440.0 (M + 1) $^1$H-NMR (400 MHz, MeOH-d$_4$) δ 7.66 (dd, J = 5.2 Hz, J = 9.2 Hz, 2H): 7.11 (t, J = 8.8 Hz, 2H); 6.81 (t, J = 8.8 Hz, 2H); 6.72-6.68 (m, 2H); 4.04-3.99 (m, 4H); 2.01 (s, 6H); 1.66 (s, 6H). | 0.01 | 0.009 |

TABLE 2-continued

| Compound | Structure | Physical Data MS (m/z) and/or ¹H NMR | EC$_{50}$ 3D7 strain (μM) | EC$_{50}$ W2 strain (μM) |
|---|---|---|---|---|
| 584 | 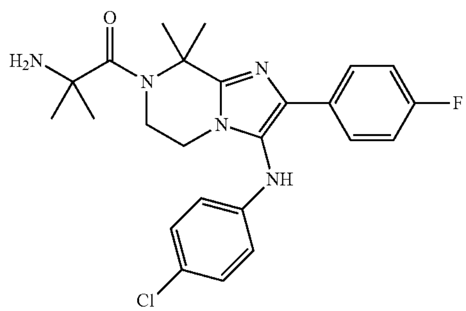 [SMILES: CC(C)(N)C(=O)N1CCn2c(nc(-c3ccc(F)cc3)c2Nc2ccc(Cl)cc2)C1(C)C] | 456.2 (M + 1) ¹H-NMR (400 MHz, MeOH-d$_4$) δ 7.60-7.59 (m, 2H); 7.16-7.09 (m, 4H); 6.7 (d, J = 8.4 Hz, 2H); 4.01 (m, 4H); 2.01 (s, 6H); 1.65 (s, 6H). | 0.02 | 0.021 |
| 585 | 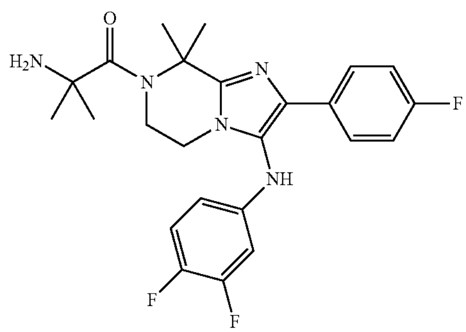 [SMILES: CC(C)(N)C(=O)N1CCn2c(nc(-c3ccc(F)cc3)c2Nc2ccc(F)c(F)c2)C1(C)C] | 458.1 (M + 1) ¹H-NMR (400 MHz, MeOH-d$_4$) δ 7.63-7.60 (m, 2H); 7.14 (t, J = 8.4 Hz, 2H); 7.01 (dd, J = 8.8 Hz, J = 18.8 Hz, 1H); 6.68-6.63 (m, 1H); 6.5 (m, 1H); 4.03 (m, 2H); 4.01 (m, 2H); 2.01 (s, 6H); 1.66 (s, 6H). | 0.01 | 0.007 |
| 586 | 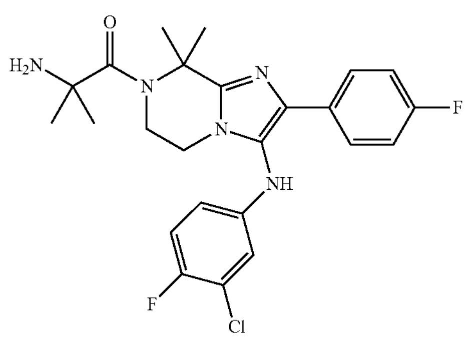 | 474.2 (M + 1) ¹H-NMR (400 MHz, MeOH-d$_4$) δ 7.63-7.59 (m, 2H); 7.13 (t, J = 8.8 Hz, 2H); 6.97 (t, J = 9.2 Hz, 1H); 6.84 (t, J = 3.6 Hz, 1H); 4.03 (m, 2H); 4.01 (m, 2H); 2.01 (s, 6H); 1.66 (s, 6H). | 0.01 | 0.007 |
| 587 | 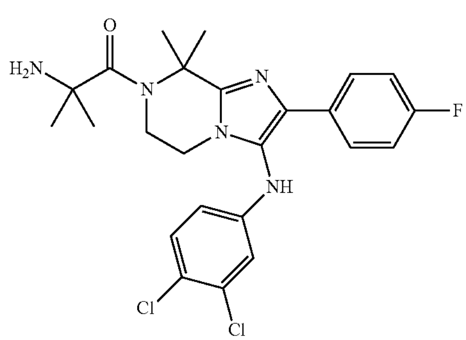 [SMILES: CC(C)(N)C(=O)N1CCn2c(nc(-c3ccc(F)cc3)c2Nc2ccc(Cl)c(Cl)c2)C1(C)C] | 491.2 (M + 1) | 0.01 | 0.012 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 588 | 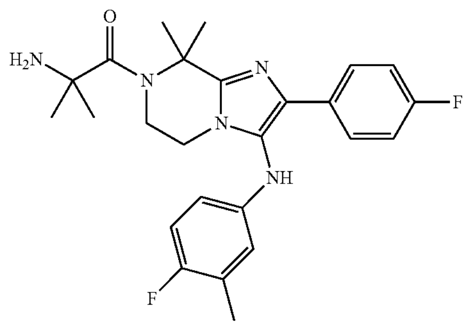 [SMILES: Cc1cc(Nc2c(-c3ccc(F)cc3)nc3n2CCN(C(=O)C(C)(C)N)C3(C)C)ccc1F] | 454.2 (M + 1) $^1$H-NMR (400 MHz, MeOH-d$_4$) δ 7.73-7.70 (m, 2H); 7.21 (t, J = 8.8 Hz, 2H); 6.87 (t, J = 8.8 Hz, 1H); 6.68 (m, 1H); 4.12 (m, 4H); 2.17 (s, 3H); 2.15 (s, 6H); 1.76 (s, 6H). | 0.01 | 0.004 |
| 589 | 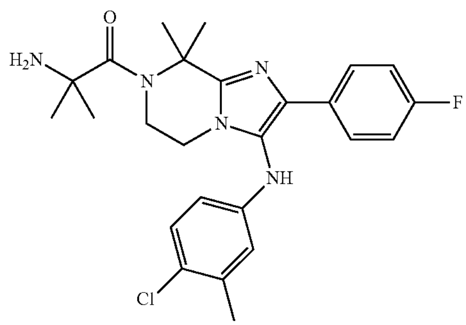 [SMILES: Cc1cc(Nc2c(-c3ccc(F)cc3)nc3n2CCN(C(=O)C(C)(C)N)C3(C)C)ccc1Cl] | 470.2 (M + 1) $^1$H-NMR (400 MHz, MeOH-d$_4$) δ 7.62-7.59 (m, 2H); 7.16-7.06 (m, 3H); 6.66 (d, J = 2.4 Hz, 1H); 6.50 (dd, J = 2.8 Hz, J = 8.4 Hz, 1H); 3.99 (m, 4H); 2.17 (s, 3H); 2.01 (s, 6H); 1.65 (s, 6H). | 0.01 | 0.006 |
| 590 | 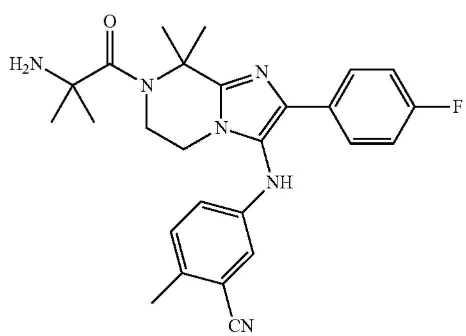 [SMILES: Cc1ccc(Nc2c(-c3ccc(F)cc3)nc3n2CCN(C(=O)C(C)(C)N)C3(C)C)cc1C#N] | 461.2 (M + 1) $^1$H-NMR (400 MHz, MeOH-d$_4$) δ 7.32-7.59 (m, 2H); 7.14 (m, 3H); 6.97 (m, 2H); 4.01 (m, 4H); 2.29 (s, 3H); 2.02 (s, 6H); 1.81 (s, 6H). | 0.03 | 0.018 |
| 591 | 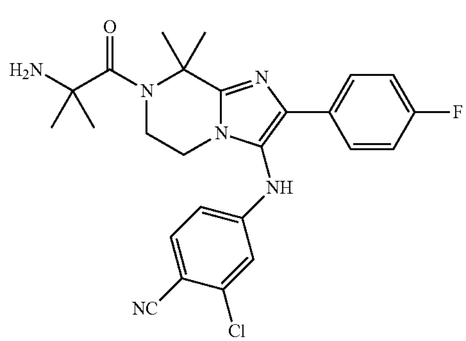 [SMILES: CC(C)(N)C(=O)N1CCn2c(nc(-c3ccc(F)cc3)c2Nc2ccc(C#N)c(Cl)c2)C1(C)C] | 481.0 (M + 1) | 0.06 | 0.046 |

TABLE 2-continued
| Compound | Structure | Physical Data MS (m/z) and/or ¹H NMR | EC$_{50}$ 3D7 strain (μM) | EC$_{50}$ W2 strain (μM) |
|---|---|---|---|---|
| 592' | 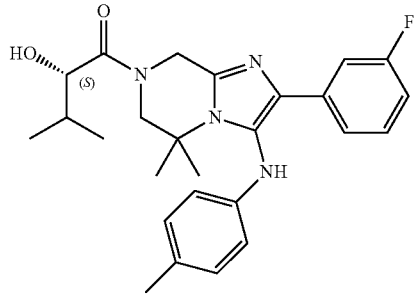 | 451.2 (M + 1) | 6.01 | 5.256 |
| 593 | 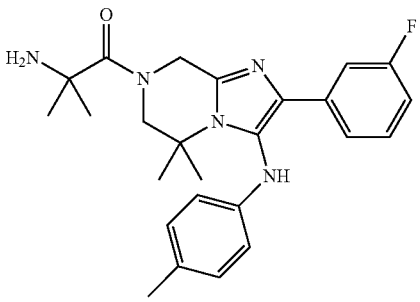 [SMILES: Cc1ccc(Nc2c(-c3cccc(F)c3)nc3n2C(C)(C)CN(C(=O)C(C)(C)N)C3)cc1] | 436.2 (M + 1) | 5.06 | 3.937 |
| 594 | 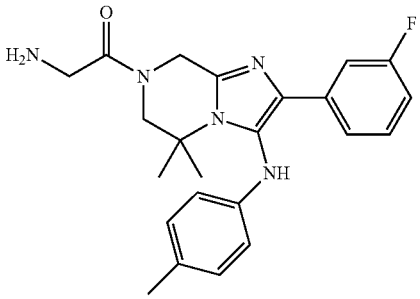 [SMILES: Cc1ccc(Nc2c(-c3cccc(F)c3)nc3n2C(C)(C)CN(C(=O)CN)C3)cc1] | 408.2 (M + 1)<br>¹H-NMR: (MeOH-d$_4$, 400 Hz) δ 7.58-7.40 (m, 3H); 7.13 (t, J = 8.4 Hz, 1H); 6.99 (m, 2H); 6.61 (d, J = 8.0 Hz, 2H); 5.17-5.14 (m, 2H); 4.28-3.92 (m, 4H); 2.20 (s, 3H), 1.70 (s, 3H), 1.65 (s, 3H). | 0.02 | 0.032 |
| 595 | 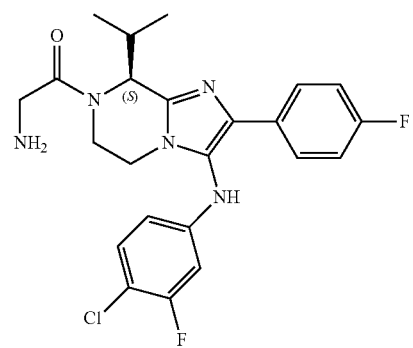 | 460.2 (M + 1) | 0.34 | 0.485 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 596 | 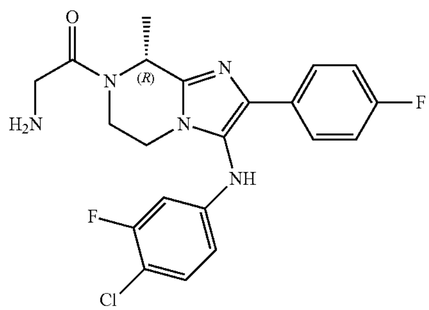 | 432.2 (M + 1) | 0.03 | 0.029 |
| 597 | 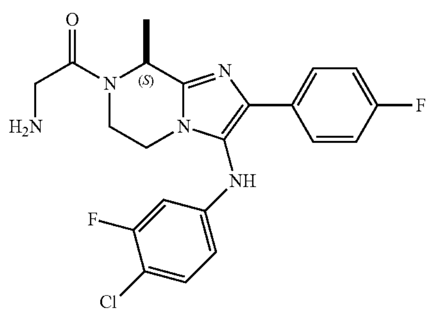 | 432.2 (M + 1) | 0.03 | 0.024 |
| 598 | 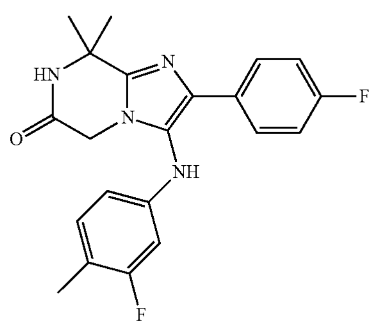 [SMILES: Cc1ccc(Nc2c(-c3ccc(F)cc3)nc3n2CC(=O)NC3(C)C)cc1F] | 383.2 (M + 1) | 0.04 | 0.074 |
| 599 | 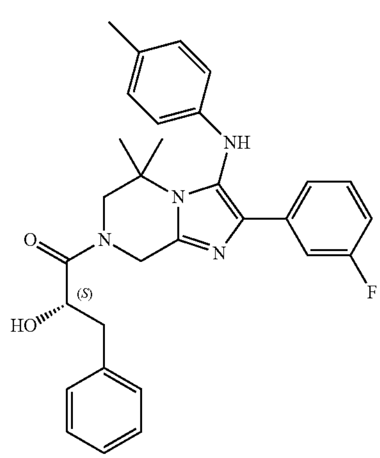 | 499.3 (M + 1) | 0.12 | 0.134 |

TABLE 2-continued

| Compound | Structure | Physical Data MS (m/z) and/or ¹H NMR | EC$_{50}$ 3D7 strain (μM) | EC$_{50}$ W2 strain (μM) |
|---|---|---|---|---|
| 600 | 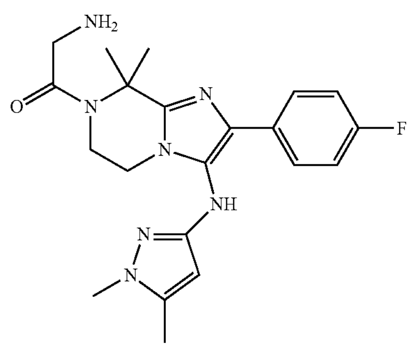 [SMILES: Cc1cc(Nc2c(-c3ccc(F)cc3)nc3n2CCN(C(=O)CN)C3(C)C)nn1C] | 412.2 (M + 1) ¹H-NMR (400 MHz, MeOH-d$_4$) δ 7.76 (dd, J = 5.2 Hz, J = 8.8 Hz, 2H); 7.29 (t, J = 8.4 Hz, 2H); 4.26 (s, 2H); 4.16 (s, 2H); 4.00 (s, 2H); 3.76 (s, 3H); 1.92 (s, 6H); 2.14 (s, 6H). | 0.07 | 0.05 |
| 601 | 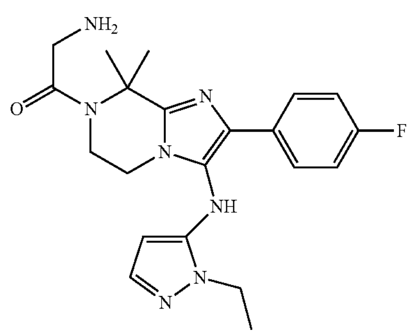 [SMILES: CCn1nccc1Nc1c(-c2ccc(F)cc2)nc2n1CCN(C(=O)CN)C2(C)C] | 412.2 (M + 1) | 3.96 | 4.117 |
| 602 | 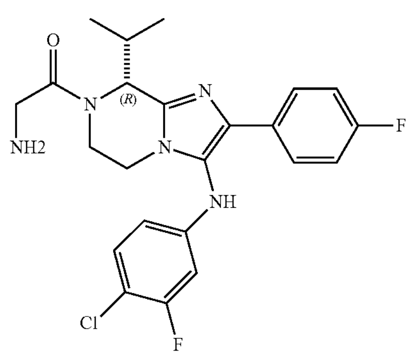 | 460.2 (M + 1) | 0.17 | 0.204 |
| 603 | 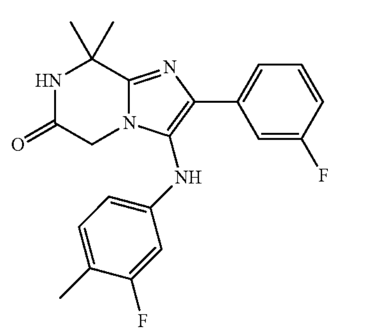 [SMILES: Cc1ccc(Nc2c(-c3cccc(F)c3)nc3n2CC(=O)NC3(C)C)cc1F] | 383.2 (M + 1) | 0.05 | 0.073 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 604 | 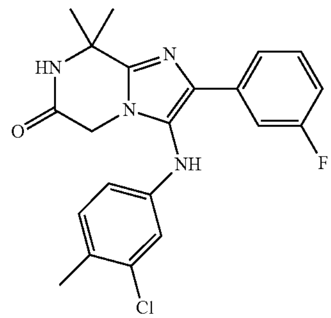 [SMILES: Cc1ccc(Nc2c(-c3cccc(F)c3)nc3n2CC(=O)NC3(C)C)cc1Cl] | 399.2 (M + 1) | 0.04 | 0.049 |
| 605 | 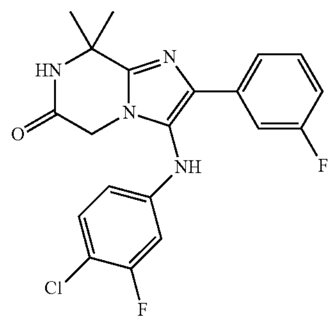 | 403.0 (M + 1) $^1$H-NMR: (MeOH-d$_4$, 400 Hz) δ 7.43 (td, J = 8.0 Hz, J = 1.0 Hz 1H); 7.38-7.34 (m, 1H); 7.24-7.18 (m, 1H); 7.11 (t, J = 8.40 Hz, 1H); 6.87-6.8 (m, 1H); 6.37 (dd, J = 11.2 Hz, J = 2.40 Hz 1H); 6.33-6.30 (m, 1H); 4.33 (s, 2H), 1.62 (s, 6H). | 0.04 | 0.057 |
| 606 | 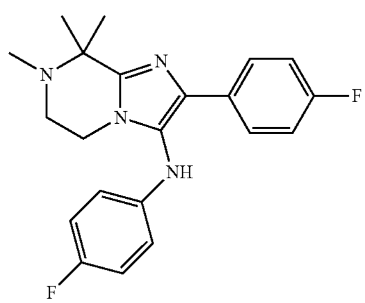 [SMILES: CN1CCn2c(nc(-c3ccc(F)cc3)c2Nc2ccc(F)cc2)C1(C)C] | 369.1 (M + 1) $^1$H-NMR: (MeOH-d$_4$, 400 Hz) δ 7.63-7.59 (m, 2H); 7.11 (t, J = 8.40 Hz, 2H); 6.85 (t, J = 8.40 Hz, 2H); 6.7-6.68 (m, 2H); 4.3 (m, 2H); 3.87 (m, 2H); 3.01 (s, 3H); 1.97 (s, 6H). | 0.02 | 0.028 |
| 607 | 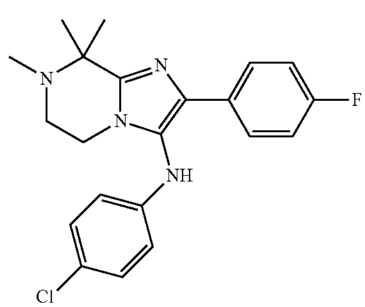 [SMILES: CN1CCn2c(nc(-c3ccc(F)cc3)c2Nc2ccc(Cl)cc2)C1(C)C] | 385.2 (M + 1) | 0.03 | 0.048 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 608 | 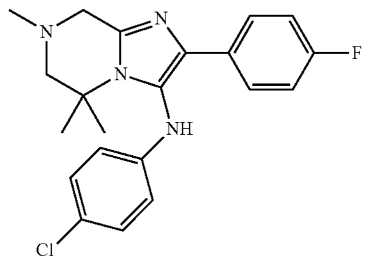 [SMILES: CN1Cc2nc(-c3ccc(F)cc3)c(Nc3ccc(Cl)cc3)n2C(C)(C)C1] | 385.1 (M + 1) | 6.91 | 5.562 |
| 609 | 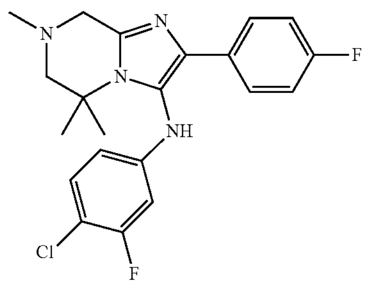 [SMILES: CN1Cc2nc(-c3ccc(F)cc3)c(Nc3ccc(Cl)c(F)c3)n2C(C)(C)C1] | 403.2 (M + 1) | 7.02 | 4.929 |
| 610 | 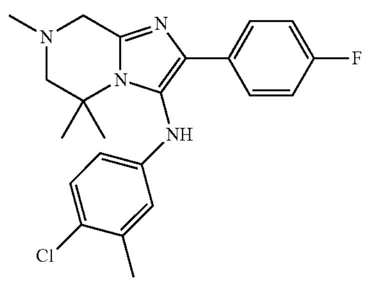 [SMILES: Cc1cc(Nc2c(-c3ccc(F)cc3)nc3n2C(C)(C)CN(C)C3)ccc1Cl] | 399.1 (M + 1) | 6.25 | 4.903 |
| 611 | 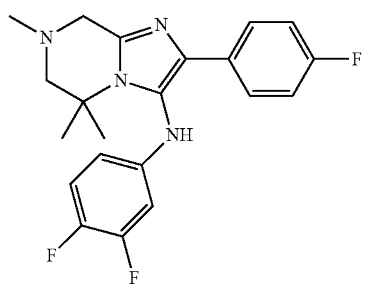 [SMILES: CN1Cc2nc(-c3ccc(F)cc3)c(Nc3ccc(F)c(F)c3)n2C(C)(C)C1] | 387.1 (M + 1) | 7.67 | 5.762 |
| 612 | 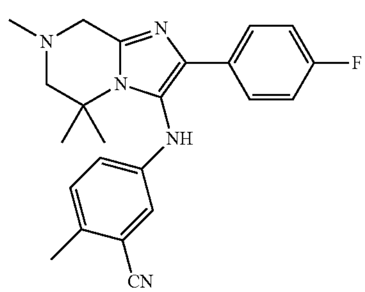 [SMILES: Cc1ccc(Nc2c(-c3ccc(F)cc3)nc3n2C(C)(C)CN(C)C3)cc1C#N] | 390.2 (M + 1) | 6.9 | 6.082 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 613 | 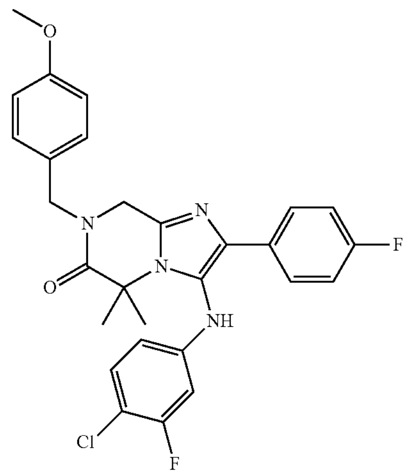 [SMILES: COc1ccc(CN2Cc3nc(-c4ccc(F)cc4)c(Nc4ccc(Cl)c(F)c4)n3C(C)(C)C2=O)cc1] | 523.2 (M + 1) | 6.27 | 5.711 |
| 614 | 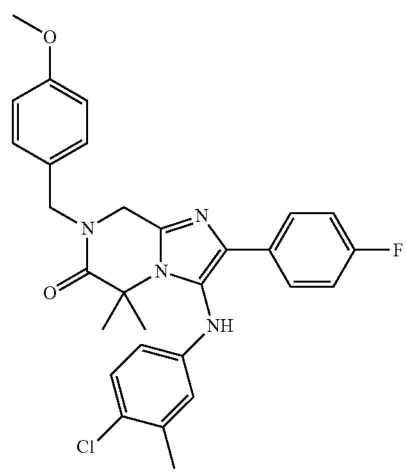 [SMILES: COc1ccc(CN2Cc3nc(-c4ccc(F)cc4)c(Nc4ccc(Cl)c(C)c4)n3C(C)(C)C2=O)cc1] | 519.2 (M + 1) | 5.02 | 4.524 |
| 615 | 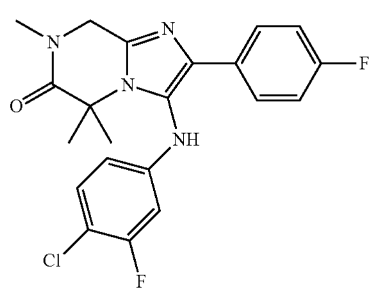 [SMILES: CN1Cc2nc(-c3ccc(F)cc3)c(Nc3ccc(Cl)c(F)c3)n2C(C)(C)C1=O] | 417.0 (M + 1) | 6.41 | 5.609 |
| 616 | 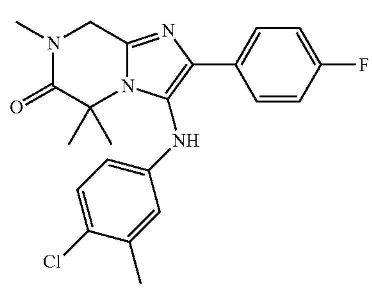 | 413.2 (M + 1) | 5.72 | 4.562 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 617 | 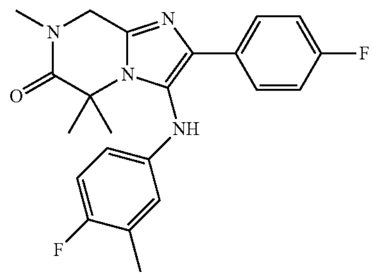 [SMILES: Cc1cc(Nc2c(-c3ccc(F)cc3)nc3n2C(C)(C)C(=O)N(C)C3)ccc1F] | 397.2 (M + 1) | 6.33 | 6.878 |
| 618 | 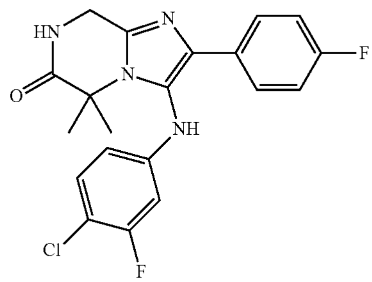 [SMILES: CC1(C)C(=O)NCc2nc(-c3ccc(F)cc3)c(Nc3ccc(Cl)c(F)c3)n21] | 403.8 (M + 1) | 2.13 | 2.887 |
| 619 | 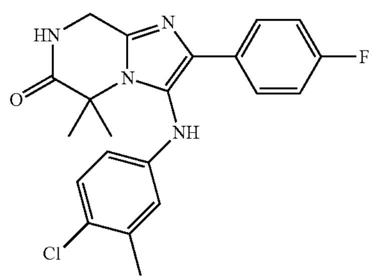 [SMILES: Cc1cc(Nc2c(-c3ccc(F)cc3)nc3n2C(C)(C)C(=O)NC3)ccc1Cl] | 399.2 (M + 1) | 0.57 | 0.713 |
| 620 | 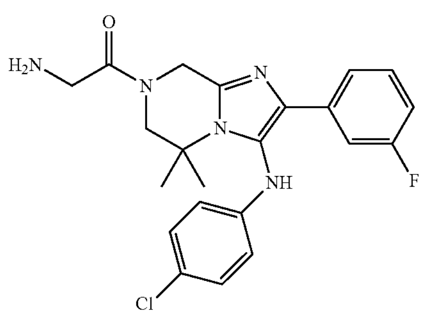 | 428.0 (M + 1) $^1$H-NMR: (MeOH-d$_4$, 400 Hz) δ 7.48-7.41 (m, 3H); 7.16-7.14 (m, 3H); 6.71 (d, J = 8.4 Hz, 2H); 5.17-5.14 (m, 2H); 4.28-3.92 (m, 4H); 1.71 (s, 3H), 1.66 (s, 3H). | 0.04 | 0.041 |
| 621 | 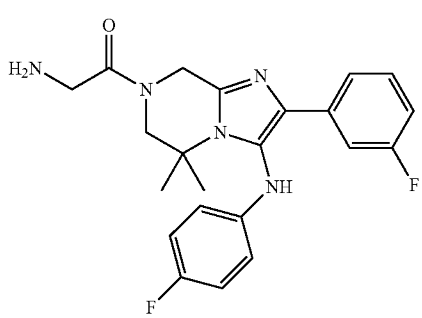 | 412.2 (M + 1) | 0.04 | 0.045 |

TABLE 2-continued
| Compound | Structure | Physical Data MS (m/z) and/or ¹H NMR | EC$_{50}$ 3D7 strain (μM) | EC$_{50}$ W2 strain (μM) |
|---|---|---|---|---|
| 622 | 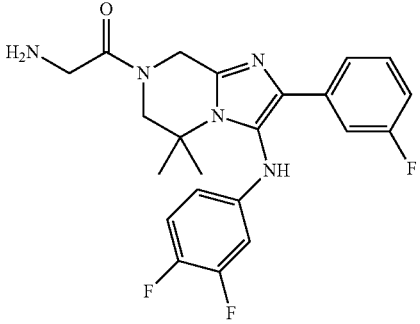 | 430.2 (M + 1) | 0.1 | 0.121 |
| 623 | 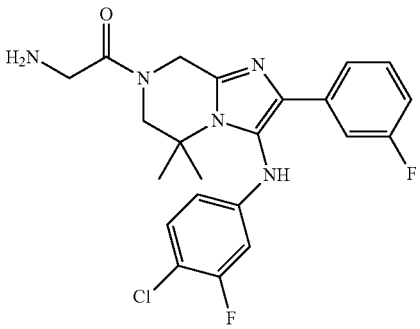 | 446.2 (M + 1) | 0.03 | 0.032 |
| 624 | 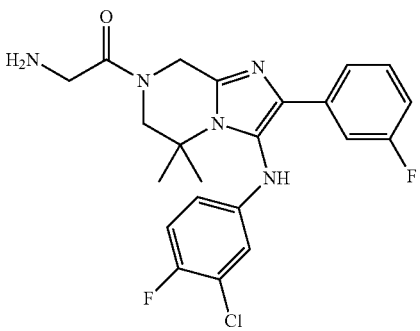 [SMILES: CC1(C)CN(C(=O)CN)Cc2nc(-c3cccc(F)c3)c(Nc3ccc(F)c(Cl)c3)n21] | 446.2 (M + 1) | 0.1 | 0.167 |
| 625 | 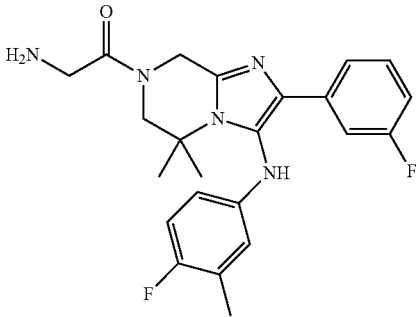 [SMILES: Cc1cc(Nc2c(-c3cccc(F)c3)nc3n2C(C)(C)CN(C(=O)CN)C3)ccc1F] | 426.2 (M + 1) | 0.17 | 0.194 |

TABLE 2-continued

| Compound | Structure | Physical Data MS (m/z) and/or ¹H NMR | EC$_{50}$ 3D7 strain (μM) | EC$_{50}$ W2 strain (μM) |
|---|---|---|---|---|
| 626 | 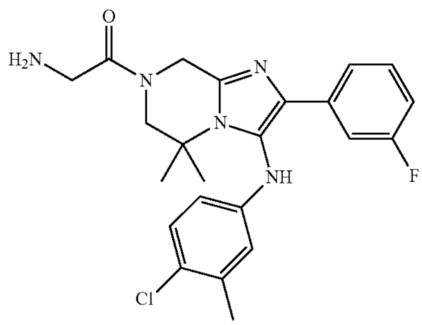 [SMILES: Cc1cc(Nc2c(-c3cccc(F)c3)nc3n2C(C)(C)CN(C(=O)CN)C3)ccc1Cl] | 442.0 (M + 1) ¹H-NMR: (MeOH-d$_4$, 400 Hz) δ 7.47-7.39 (m, 2H); 7.19-7.11 (m, 2H); 6.67 (s, 1H); 6.52 (d, J = 8.0 Hz, 1H); 5.15 (s, 2H); 4.27-3.91 (m, 2H); 2.24 (s, 3H), 1.71 (s, 3H), 1.65 (s, 3H). | 0.02 | 0.017 |
| 627 | 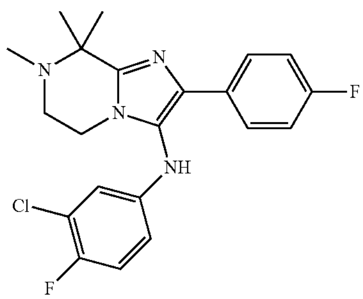 [SMILES: CN1CCn2c(nc(-c3ccc(F)cc3)c2Nc2ccc(F)c(Cl)c2)C1(C)C] | 403.2 (M + 1) | 0.17 | 0.194 |
| 628 | 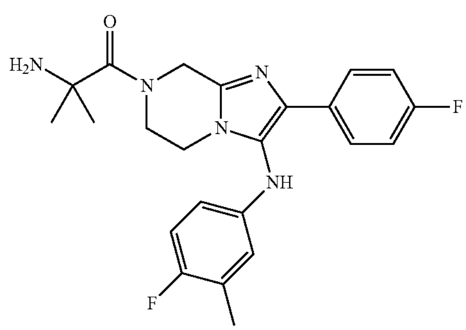 [SMILES: Cc1cc(Nc2c(-c3ccc(F)cc3)nc3n2CCN(C(=O)C(C)(C)N)C3)ccc1F] | 426.2 (M + 1) ¹H NMR (400 MHz, CD$_3$OD): δ 7.69-7.73 (m, 2H), 7.18 (t, J = 8.8 Hz, 2H), 6.87 (t, J = 8.8 Hz, 2H), 6.62-6.63 (m, 1H), 6.51-6.55 (m, 1H), 5.12 (s, 2H), 4.21 (t, J = 4.8 Hz, 2H), 4.02 (t, J = 4.8 Hz, 2H), 2.17 (s, 3H), 1.75 (s, 6H) | 0.033 | 0.04 |
| 629 | 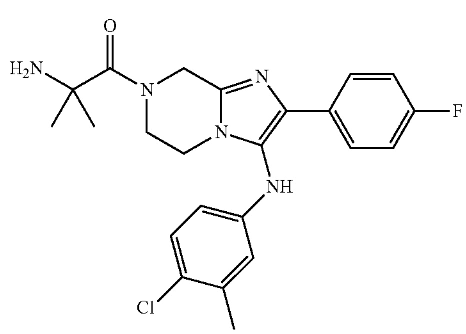 [SMILES: Cc1cc(Nc2c(-c3ccc(F)cc3)nc3n2CCN(C(=O)C(C)(C)N)C3)ccc1Cl] | 442.1 (M + 1) ¹H NMR (400 MHz, CD$_3$OD): δ 7.70-7.73 (m, 2H), 7.22 (t, J = 8.0 Hz, 2H), 7.17 (d, J = 7.2 Hz, 1H), 6.77 (s, 1H), 6.62 (d, J = 6.0 Hz, 1H), 5.20 (s, 2H), 4.27 (s, 2H), 4.08 (s, 2H), 2.27 (s, 3H), 1.78 (s, 6H) | 0.017 | 0.023 |

TABLE 2-continued

| Compound | Structure | Physical Data MS (m/z) and/or ¹H NMR | EC$_{50}$ 3D7 strain (μM) | EC$_{50}$ W2 strain (μM) |
|---|---|---|---|---|
| 630 | 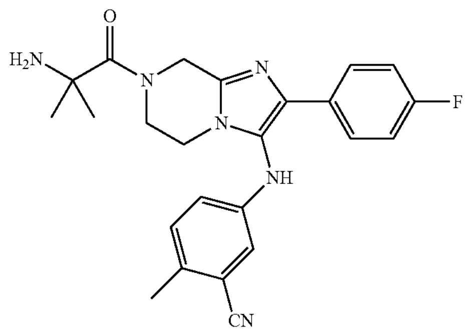 | 433.3 (M + 1) | 0.035 | 0.085 |
| 631 | 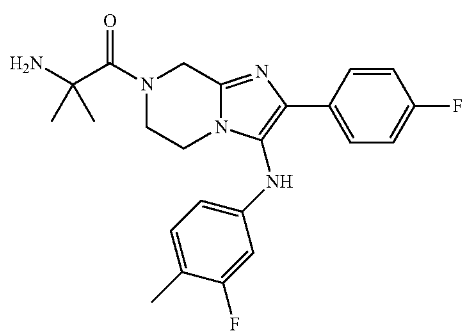 [SMILES: Cc1ccc(Nc2c(-c3ccc(F)cc3)nc3n2CCN(C(=O)C(C)(C)N)C3)cc1F] | 426.3 (M + 1)<br>¹H NMR (400 MHz, CD$_3$OD): δ 7.72-7.76 (m, 2H), 7.22 (t, J = 8.8 Hz, 2H), 7.06 (t, J = 8.8 Hz, 1H), 8.56 (s, 1H), 6.53-6.54 (m, 1H), 5.20 (s, 2H), 4.27 (t, J = 4.8 Hz, 2H), 4.09 (t, J = 4.8 Hz, 2H), 2.13 (s, 3H), 1.79 (s, 6H) | 0.049 | 0.062 |
| 632 | 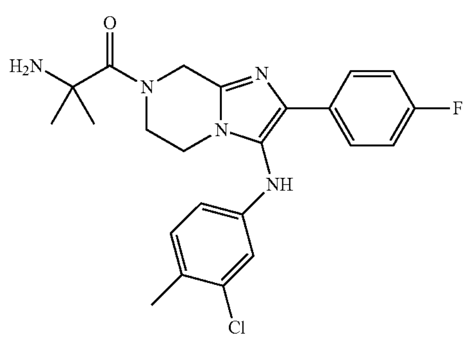 [SMILES: Cc1ccc(Nc2c(-c3ccc(F)cc3)nc3n2CCN(C(=O)C(C)(C)N)C3)cc1Cl] | 442.2 (M + 1)<br>¹H NMR (400 MHz, CD$_3$OD): δ 7.71-7.74 (m, 2H), 7.22 (t, J = 8.8 Hz, 2H), 7.11 (d, J = 8.4 Hz, 1H), 6.85 (d, J = 2.4 Hz, 1H), 6.67 (dd, J = 2.4, 8.4 Hz, 1H), 5.20 (s, 2H), 4.27 (t, J = 4.2 Hz, 2H), 4.09 (t, J = 4.2 Hz, 2H), 2.24 (s, 3H), 1.78 (s, 6H) | 0.015 | 0.016 |
| 633 | 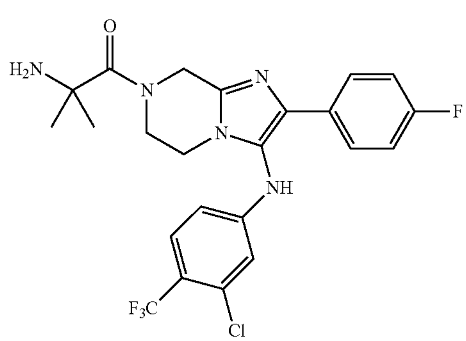 | 496.1 (M + 1) | 0.528 | 0.331 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 634 | 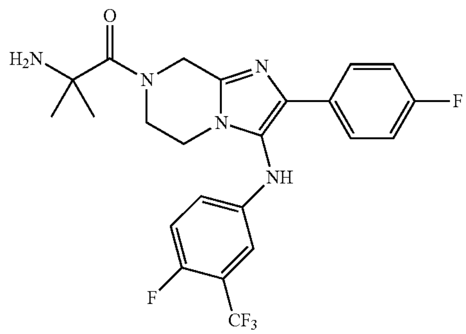 [SMILES: CC(C)(N)C(=O)N1CCn2c(nc(-c3ccc(F)cc3)c2Nc2ccc(F)c(C(F)(F)F)c2)C1] | 480.1 (M + 1) | 0.467 | 0.447 |
| 635 | 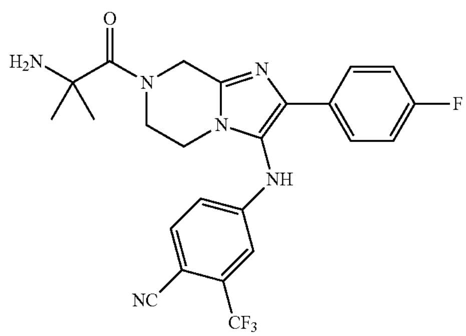 [SMILES: CC(C)(N)C(=O)N1CCn2c(nc(-c3ccc(F)cc3)c2Nc2ccc(C#N)c(C(F)(F)F)c2)C1] | 487.1 (M + 1) | 0.94 | 1.758 |
| 636 | 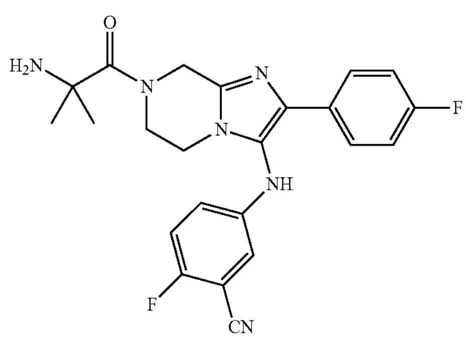 [SMILES: CC(C)(N)C(=O)N1CCn2c(nc(-c3ccc(F)cc3)c2Nc2ccc(F)c(C#N)c2)C1] | 437.2 (M + 1) | 0.21 | 0.183 |
| 637 | 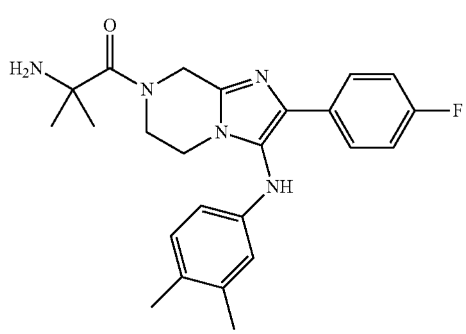 [SMILES: Cc1ccc(Nc2c(-c3ccc(F)cc3)nc3n2CCN(C(=O)C(C)(C)N)C3)cc1C] | 422.3 (M + 1) | 0.027 | 0.026 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 638 | 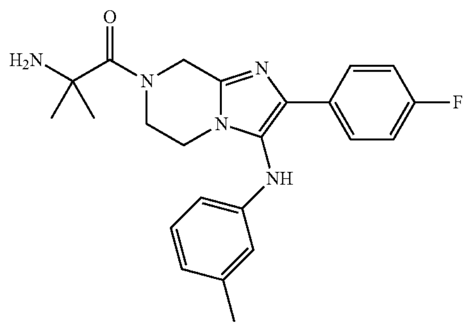 [SMILES: Cc1cccc(Nc2c(-c3ccc(F)cc3)nc3n2CCN(C(=O)C(C)(C)N)C3)c1] | 408.3 (M + 1) | 0.065 | 0.068 |
| 639 | 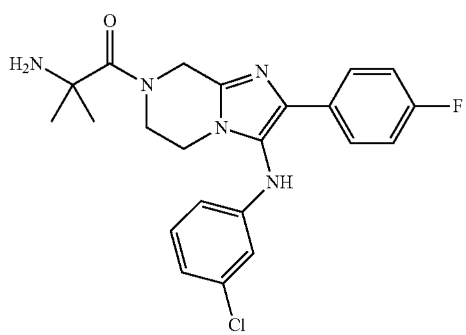 [SMILES: CC(C)(N)C(=O)N1CCn2c(nc(-c3ccc(F)cc3)c2Nc2cccc(Cl)c2)C1] | 428.2 (M + 1) | 0.082 | 0.093 |
| 640 | 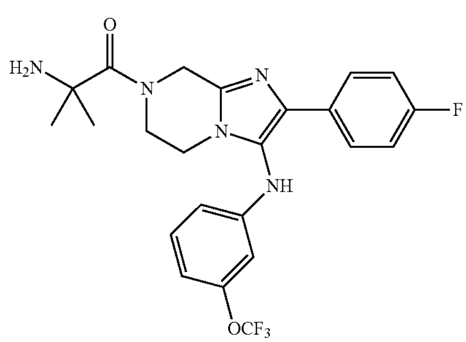 [SMILES: CC(C)(N)C(=O)N1CCn2c(nc(-c3ccc(F)cc3)c2Nc2cccc(OC(F)(F)F)c2)C1] | 478.2 (M + 1) | 3.95 | 4.51 |
| 641 | 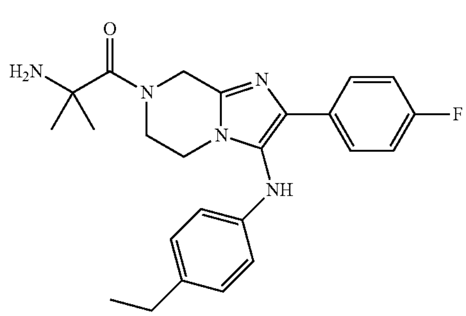 [SMILES: CCc1ccc(Nc2c(-c3ccc(F)cc3)nc3n2CCN(C(=O)C(C)(C)N)C3)cc1] | 422.2 (M + 1) | 0.799 | 1.285 |

TABLE 2-continued

| Compound | Structure | Physical Data MS (m/z) and/or ¹H NMR | EC$_{50}$ 3D7 strain (μM) | EC$_{50}$ W2 strain (μM) |
| --- | --- | --- | --- | --- |
| 642 | 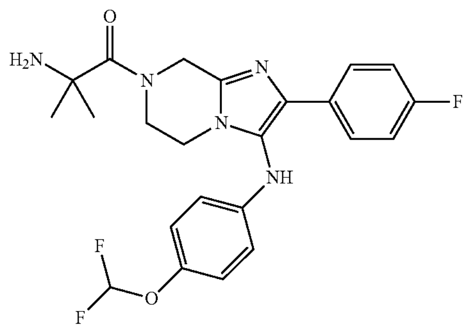 [SMILES: CC(C)(N)C(=O)N1CCn2c(nc(-c3ccc(F)cc3)c2Nc2ccc(OC(F)F)cc2)C1] | 460.2 (M + 1) | 2.01 | 2.497 |
| 643 | 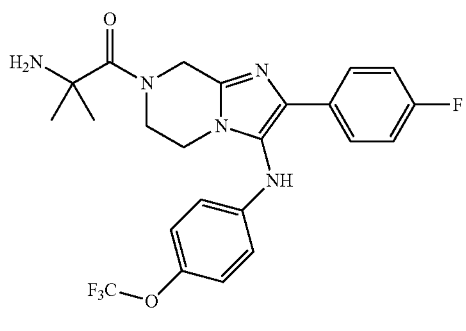 [SMILES: CC(C)(N)C(=O)N1CCn2c(nc(-c3ccc(F)cc3)c2Nc2ccc(OC(F)(F)F)cc2)C1] | 478.2 (M + 1) | 2.798 | 2.171 |
| 644 | 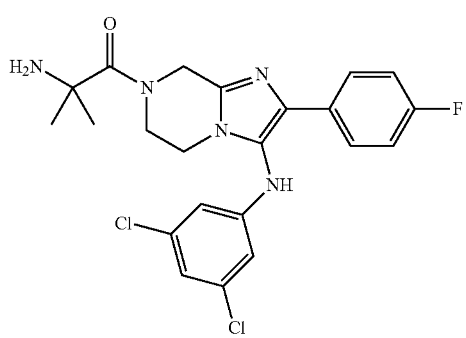 [SMILES: CC(C)(N)C(=O)N1CCn2c(nc(-c3ccc(F)cc3)c2Nc2cc(Cl)cc(Cl)c2)C1] | 462.1 (M + 1) | 0.31 | 0.49 |
| 645 | 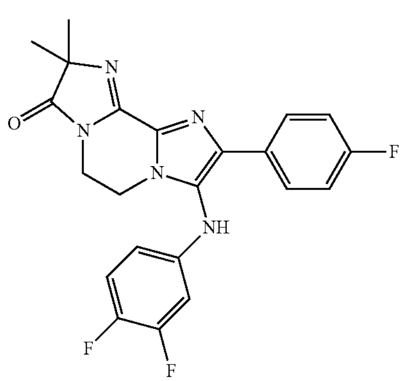 [SMILES: CC1(C)N=C2c3nc(-c4ccc(F)cc4)c(Nc4ccc(F)c(F)c4)n3CCN2C1=O] | 426.1 (M + 1)<br>¹H NMR (400 MHz, CD$_3$OD): δ 7.75-7.78 (m, 2H), 6.95-7.01 (m, 3H), 6.44-6.50 (m, 1H), 6.32-6.36 (m, 1H), 4.19 (dd, J = 1.6, 6.8 Hz, 2H), 4.00 (dd, J = 1.6, 6.8 Hz, 2H), 1.47 (s, 6H) | 5.13 | 7.6 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 646 | 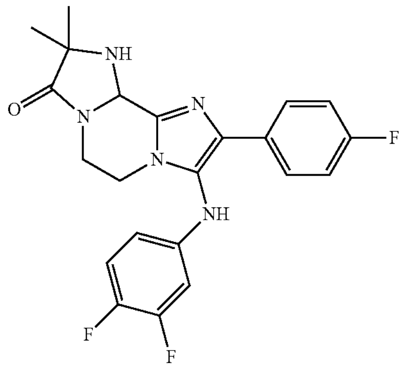 [SMILES: CC1(C)NC2c3nc(-c4ccc(F)cc4)c(Nc4ccc(F)c(F)c4)n3CCN2C1=O] | 428.1 (M + 1) $^1$H NMR (400 MHz, CD$_3$OD): δ 7.59-7.63 (m, 2H), 7.09 (t, J = 6.4 Hz, 2H), 6.95-7.02 (m, 1H), 6.46-6.52 (m, 1H), 6.34-6.38 (m, 1H), 5.92 (s, 1H), 4.33 (dd, J = 4.4, 14 Hz, 1H), 3.96 (dd, J = 4.8, 13.2 Hz, 1H), 3.70-3.78 (m, 1H), 3.46-3.54 (m, 1H), 1.73 (s, 3H), 1.36 (s, 3H) | 5.68 | 6.13 |
| 647 | 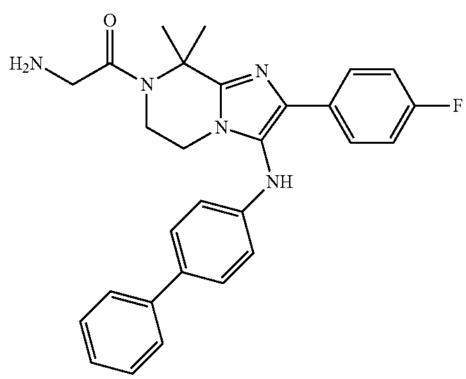 [SMILES: CC1(C)c2nc(-c3ccc(F)cc3)c(Nc3ccc(-c4ccccc4)cc3)n2CCN1C(=O)CN] | 470.2 (M + 1) $^1$H NMR (400 MHz, CD$_3$OD): δ 7.72-7.76 (m, 2H), 7.50-7.54 (m, 4H), 7.39 (t, J = 8.0 Hz, 2H), 7.27 (t, J = 7.2 Hz, 1H), 7.20 (t, J = 8.8 Hz, 2H), 6.82 (d, J = 8.4 Hz, 2H), 4.07-4.10 (m, 4H), 3.84 (t, J = 4.8 Hz, 2H), 2.09 (s, 6H) | 0.279 | 0.25 |
| 648 | 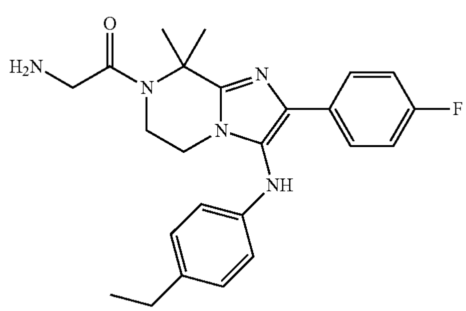 [SMILES: CCc1ccc(Nc2c(-c3ccc(F)cc3)nc3n2CCN(C(=O)CN)C3(C)C)cc1] | 422.2 (M + 1) $^1$H NMR (400 MHz, CD$_3$OD): δ 7.76-7.71 (m, 2H), 7.21 (t, J = 8.8 Hz, 2H), 7.07 (d, J = 8.4 Hz, 2H), 6.67 (d, J = 8.4 Hz, 2H), 4.05-4.08 (m, 4H), 3.83-3.85 (m, 2H), 2.55 (q, J = 7.6 Hz, 2H), 2.09 (s, 6H), 1.18 (t, J = 7.6 Hz, 3H) | 0.009 | 0.008 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 649 | 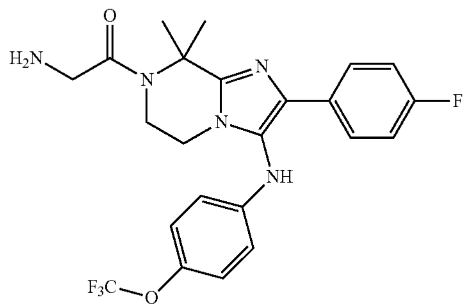 [SMILES: CC1(C)c2nc(-c3ccc(F)cc3)c(Nc3ccc(OC(F)(F)F)cc3)n2CCN1C(=O)CN] | 478.1 (M + 1) | 0.024 | 0.018 |
| 650 | 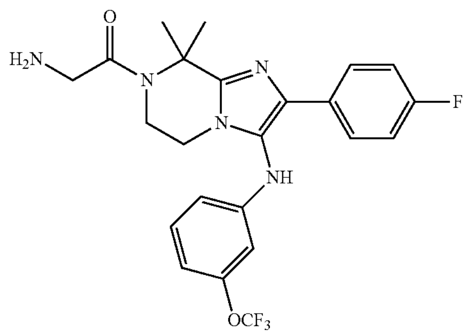 [SMILES: CC1(C)c2nc(-c3ccc(F)cc3)c(Nc3cccc(OC(F)(F)F)c3)n2CCN1C(=O)CN] | 478.1 (M + 1) | 0.012 | 0.009 |
| 651 | 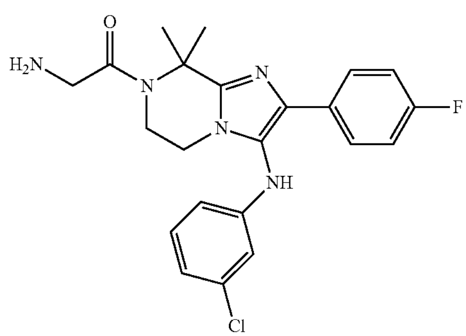 [SMILES: CC1(C)c2nc(-c3ccc(F)cc3)c(Nc3cccc(Cl)c3)n2CCN1C(=O)CN] | 428.1 (M + 1) | 0.008 | 0.005 |
| 652 | 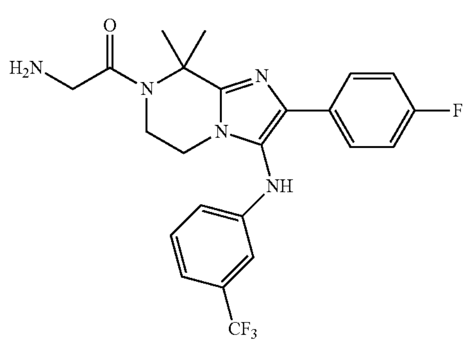 [SMILES: CC1(C)c2nc(-c3ccc(F)cc3)c(Nc3cccc(C(F)(F)F)c3)n2CCN1C(=O)CN] | 462.1 (M + 1) | 0.019 | 0.012 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 653 | 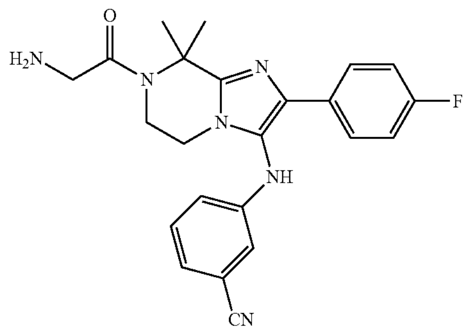 | 419.1 (M + 1) | 0.006 | 0.009 |
| 654 | 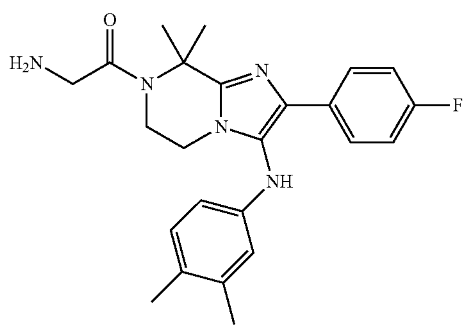 [SMILES: Cc1ccc(Nc2c(-c3ccc(F)cc3)nc3n2CCN(C(=O)CN)C3(C)C)cc1C] | 422.2 (M + 1) | 0.005 | 0.006 |
| 655 | 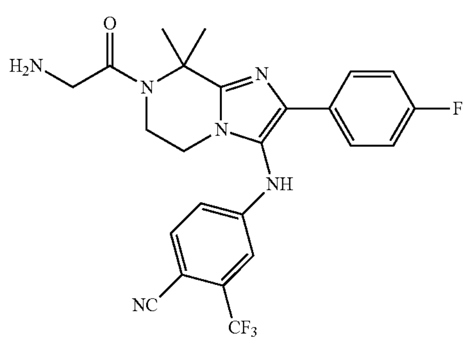 [SMILES: CC1(C)c2nc(-c3ccc(F)cc3)c(Nc3ccc(C#N)c(C(F)(F)F)c3)n2CCN1C(=O)CN] | 487.1 (M + 1) | 0.017 | 0.02 |
| 656 | 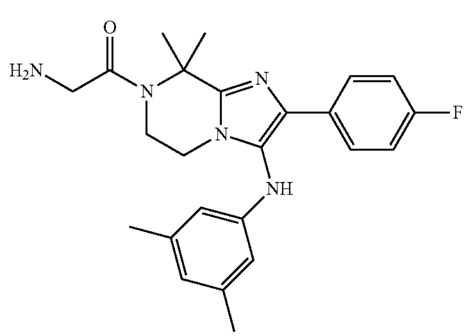 [SMILES: Cc1cc(C)cc(Nc2c(-c3ccc(F)cc3)nc3n2CCN(C(=O)CN)C3(C)C)c1] | 422.1 (M + 1) | 0.006 | 0.007 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 657 | 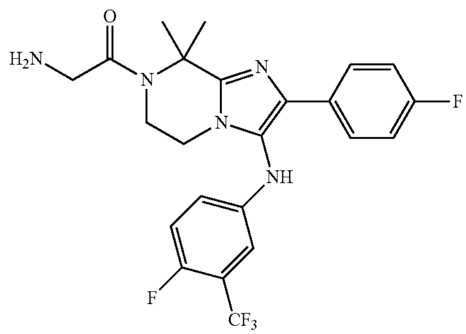 [SMILES: CC1(C)c2nc(-c3ccc(F)cc3)c(Nc3ccc(F)c(C(F)(F)F)c3)n2CCN1C(=O)CN] | 480.1 (M + 1) | 0.618 | 1.086 |
| 658 | 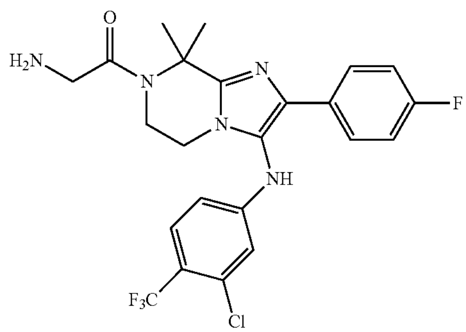 [SMILES: CC1(C)c2nc(-c3ccc(F)cc3)c(Nc3ccc(C(F)(F)F)c(Cl)c3)n2CCN1C(=O)CN] | 496.0 (M + 1) | 0.005 | 0.006 |
| 659 | 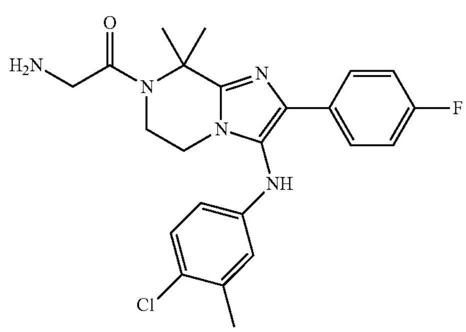 | 442.6 (M + 1) | 4.39 | 5.28 |
| 660 | 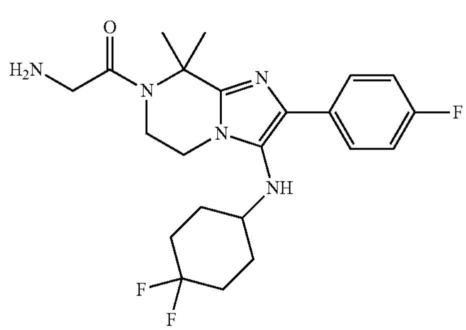 [SMILES: CC1(C)c2nc(-c3ccc(F)cc3)c(NC3CCC(F)(F)CC3)n2CCN1C(=O)CN] | 436.1 (M + 1) | 0.003 | 0.006 |

TABLE 2-continued

| Compound | Structure | Physical Data MS (m/z) and/or ¹H NMR | EC$_{50}$ 3D7 strain (μM) | EC$_{50}$ W2 strain (μM) |
|---|---|---|---|---|
| 661 | 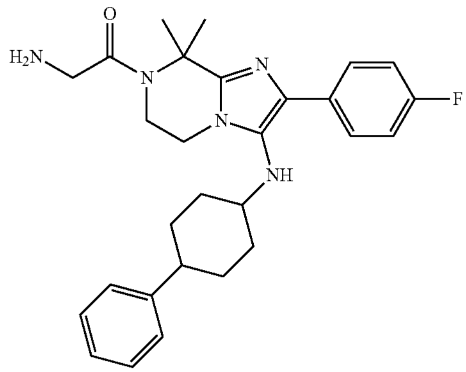 [SMILES: CC1(C)c2nc(-c3ccc(F)cc3)c(NC3CCC(c4ccccc4)CC3)n2CCN1C(=O)CN] | 476.2 (M + 1) | 0.339 | 0.52 |
| 662 | 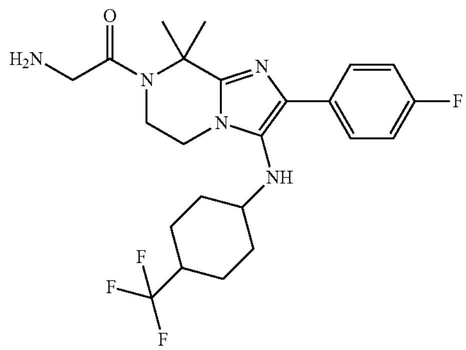 [SMILES: CC1(C)c2nc(-c3ccc(F)cc3)c(NC3CCC(C(F)(F)F)CC3)n2CCN1C(=O)CN] | 468.1 (M + 1) | 0.038 | 0.033 |
| 663 | 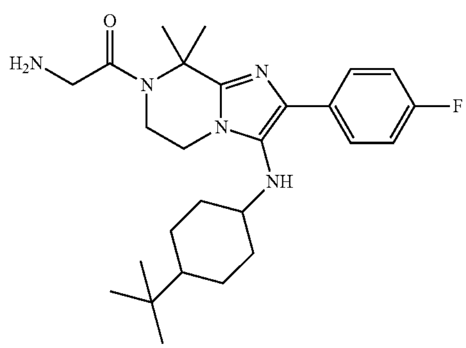 [SMILES: CC(C)(C)C1CCC(Nc2c(-c3ccc(F)cc3)nc3n2CCN(C(=O)CN)C3(C)C)CC1] | 456.2 (M + 1) | 1.062 | 1.658 |
| 664 | 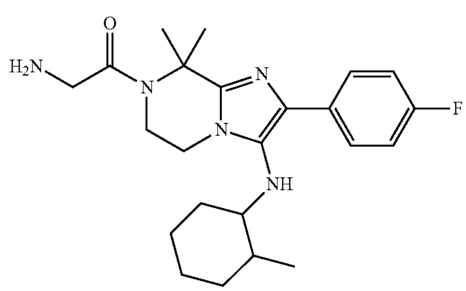 [SMILES: CC1CCCCC1Nc1c(-c2ccc(F)cc2)nc2n1CCN(C(=O)CN)C2(C)C] | 414.2 (M + 1) | 3.69 | 4.08 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 665 | 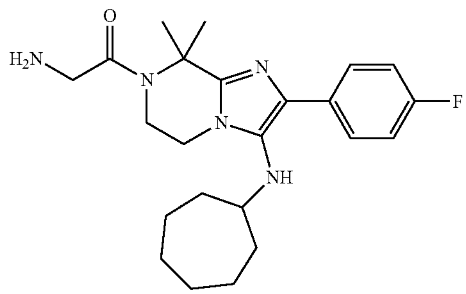 [SMILES: CC1(C)c2nc(-c3ccc(F)cc3)c(NC3CCCCCC3)n2CCN1C(=O)CN] | 414.2 (M + 1) $^1$H NMR (400 MHz, CD$_3$OD): δ 7.71-7.74 (m, 2H), 7.29 (t, J = 8.8 Hz, 2H), 4.20 (t, J = 4.8 Hz, 2H), 4.12 (s, 2H), 3.86 (t, J = 4.8 Hz, 2H), 3.02-3.09 (m, 1H), 2.02 (s, 6H), 1.79-1.86 (m, 2H), 1.57-1.63 (m, 2H), 1.48-1.52 (m, 4H), 1.39-1.46 (m, 2H), 1.21-1.30 (m, 2H) | 0.102 | 0.069 |
| 666 | 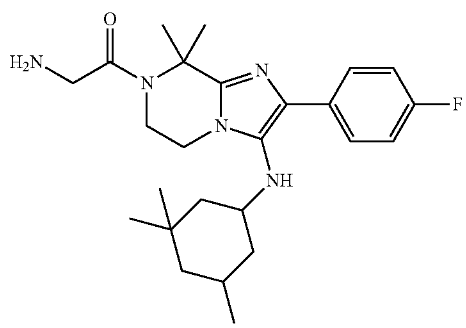 [SMILES: CC1CC(Nc2c(-c3ccc(F)cc3)nc3n2CCN(C(=O)CN)C3(C)C)CC(C)(C)C1] | 442.2 (M + 1) | >10 | 4.97 |
| 667 | 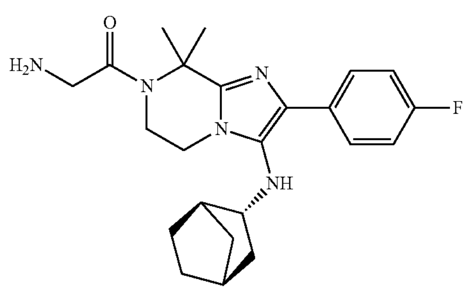 [SMILES: CC1(C)c2nc(-c3ccc(F)cc3)c(N[C@@H]3C[C@H]4CC[C@@H]3C4)n2CCN1C(=O)CN] | 412.2 (M + 1) | 0.104 | 0.082 |
| 668 | 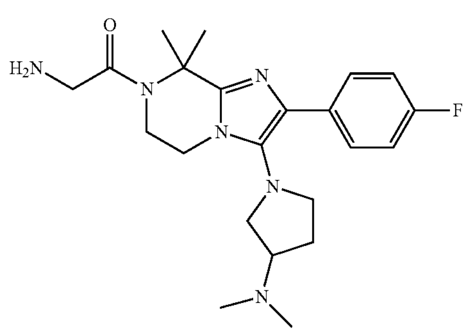 [SMILES: CN(C)C1CCN(c2c(-c3ccc(F)cc3)nc3n2CCN(C(=O)CN)C3(C)C)C1] | 415.7 (M + 1) $^1$H NMR (400 MHz, CD$_3$OD): δ 7.59-7.63 (m, 2H), 7.32 (t, J = 8.8 Hz, 2H), 4.25 (d, J = 4.8 Hz, 2H), 4.13 (s, 2H), 3.97-4.04 (m, 1H), 3.88 (d, J = 4.8 Hz, 2H), 3.49-3.54 (m, 1H), 3.41-3.47 (m, 2H), 3.25-3.30 (m, 1H), 2.92 (s, 6H), 2.45-2.53 (m, 1H), 2.23-2.28 (m, 1H), 2.01 (s, 6H) | 3.43 | >10 |

TABLE 2-continued

| Compound | Structure | Physical Data MS (m/z) and/or ¹H NMR | EC$_{50}$ 3D7 strain (μM) | EC$_{50}$ W2 strain (μM) |
| --- | --- | --- | --- | --- |
| 669 | 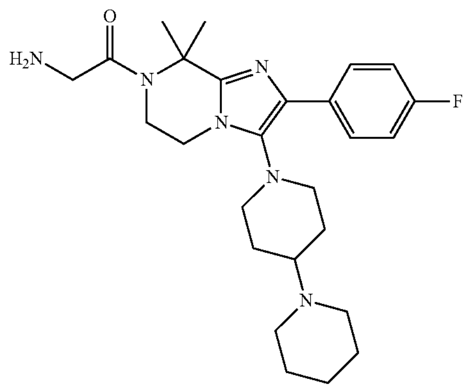 [SMILES: CC1(C)c2nc(-c3ccc(F)cc3)c(N3CCC(N4CCCCC4)CC3)n2CCN1C(=O)CN] | 469.7 (M + 1) <br> ¹H NMR (400 MHz, CD$_3$OD): δ 7.47-7.51 (m, 2H), 7.22 (t, J = 8.8 Hz, 2H), 4.13 (t, J = 4.4 Hz, 2H), 4.03 (s, 2H), 3.42 (d, J = 11.6 Hz, 2H), 3.15 (d, J = 12.4 Hz, 2H), 2.90 (dd, J = 10.8, 22.4 Hz, 4H), 2.00-2.03 (m, 2H), 1.90 (s, 6H), 1.68-1.87 (m, 6H), 1.37-1.47 (m, 1H | 3.98 | >10 |
| 670 | 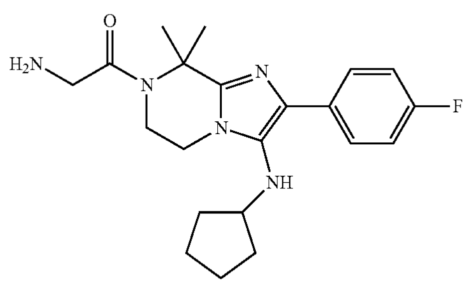 [SMILES: CC1(C)c2nc(-c3ccc(F)cc3)c(NC3CCCC3)n2CCN1C(=O)CN] | 386.6 (M + 1) | 0.402 | 0.711 |
| 671 | 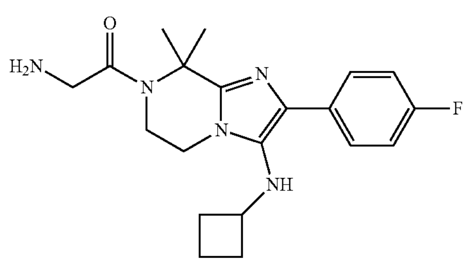 [SMILES: CC1(C)c2nc(-c3ccc(F)cc3)c(NC3CCC3)n2CCN1C(=O)CN] | 372.3 (M + 1) | 1.286 | 1.087 |
| 672 | 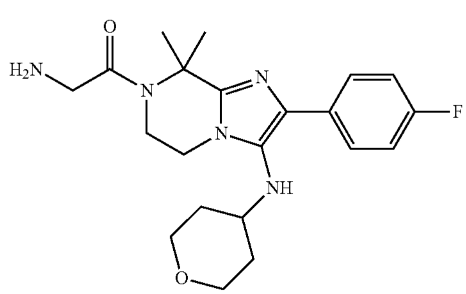 [SMILES: CC1(C)c2nc(-c3ccc(F)cc3)c(NC3CCOCC3)n2CCN1C(=O)CN] | 402.3 (M + 1) | 9.84 | 7.14 |

TABLE 2-continued

| Compound | Structure | Physical Data MS (m/z) and/or ¹H NMR | EC$_{50}$ 3D7 strain (μM) | EC$_{50}$ W2 strain (μM) |
|---|---|---|---|---|
| 673 | 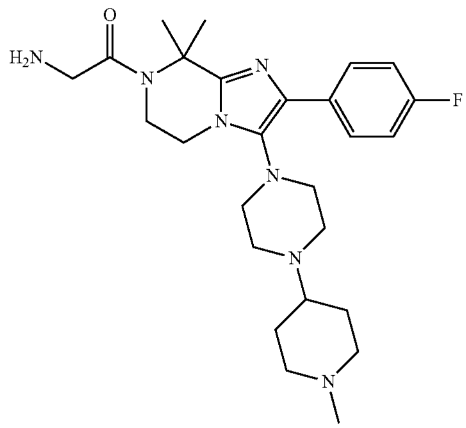 [SMILES: CN1CCC(N2CCN(c3c(-c4ccc(F)cc4)nc4n3CCN(C(=O)CN)C4(C)C)CC2)CC1] | | 8.87 | >8.72 |
| 674 | 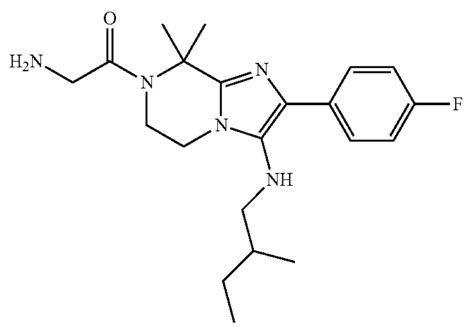 [SMILES: CCC(C)CNc1c(-c2ccc(F)cc2)nc2n1CCN(C(=O)CN)C2(C)C] | | 6.28 | 6.31 |
| 675 | 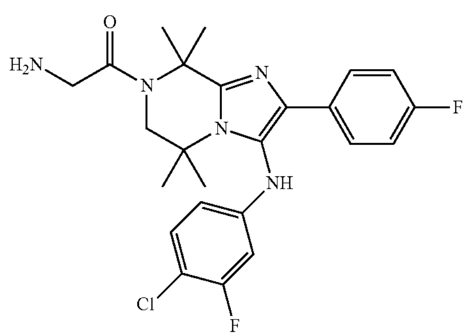 | 446.5 (M + 1) | 0.014 | 0.021 |
| 676 | 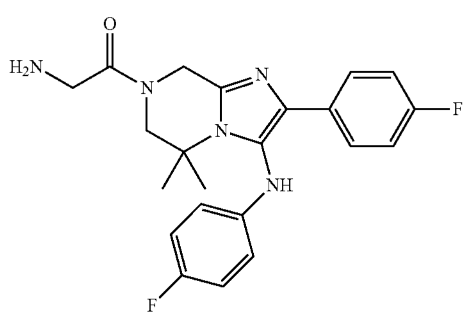 | 415.7 (M + 1) ¹H NMR (400 MHz, CD$_3$OD): δ 7.59-7.63 (m, 2H), 7.32 (t, J = 8.8 Hz, 2H), 4.25 (d, J = 4.8 Hz, 2H), 4.13 (s, 2H), 3.97-4.04 (m, 1H), 3.88 (d, J = 4.8 Hz, 2H), 3.49-3.54 (m, 1H), 3.41-3.47 (m, 2H), 3.25-3.30 (m, 1H), 2.92 (s, 6H), 2.45-2.53 (m, 1H), 2.23-2.28 (m, 1H), 2.01 (s, 6H) | 0.032 | 0.031 |

TABLE 2-continued

| Compound | Structure | Physical Data MS (m/z) and/or ¹H NMR | EC$_{50}$ 3D7 strain (μM) | EC$_{50}$ W2 strain (μM) |
|---|---|---|---|---|
| 677 | 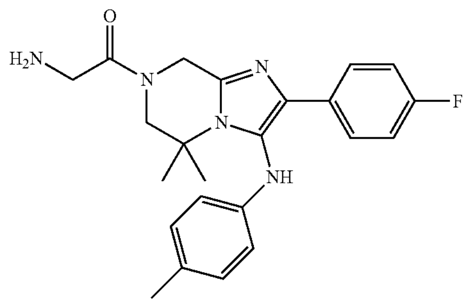 | 469.7 (M + 1) ¹H NMR (400 MHz, CD$_3$OD): δ 7.47-7.51 (m, 2H), 7.22 (t, J = 8.8 Hz, 2H), 4.13 (t, J = 4.4 Hz, 2H), 4.03 (s, 2H), 3.42 (d, J = 11.6 Hz, 2H), 3.15 (d, J = 12.4 Hz, 2H), 2.90 (dd, J = 10.8, 22.4 Hz, 4H), 2.00-2.03 (m, 2H), 1.90 (s, 6H), 1.68-1.87 (m, 6H), 1.37-1.47 (m, 1H | 0.08 | 0.076 |
| 678 | 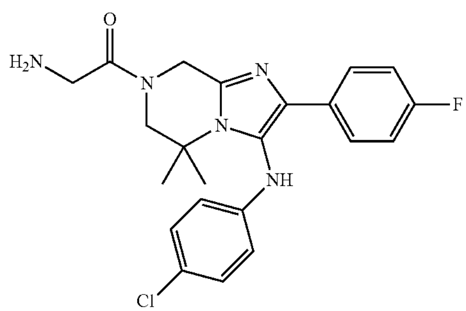 | 415.7 (M + 1) ¹H NMR (400 MHz, CD$_3$OD): δ 7.59-7.63 (m, 2H), 7.32 (t, J = 8.8 Hz, 2H), 4.25 (d, J = 4.8 Hz, 2H), 4.13 (s, 2H), 3.97-4.04 (m, 1H), 3.88 (d, J = 4.8 Hz, 2H), 3.49-3.54 (m, 1H), 3.41-3.47 (m, 2H), 3.25-3.30 (m, 1H), 2.92 (s, 6H), 2.45-2.53 (m, 1H), 2.23-2.28 (m, 1H), 2.01 (s, 6H) | 0.053 | 0.047 |
| 679 | 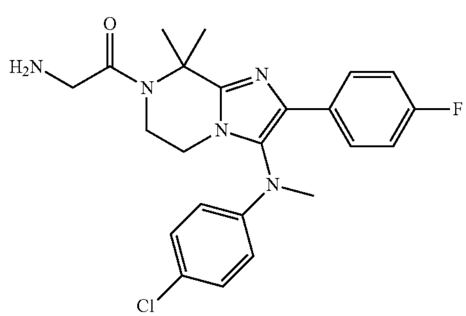 | 469.7 (M + 1) ¹H NMR (400 MHz, CD$_3$OD): δ 7.47-7.51 (m, 2H), 7.22 (t, J = 8.8 Hz, 2H), 4.13 (t, J = 4.4 Hz, 2H), 4.03 (s, 2H), 3.42 (d, J = 11.6 Hz, 2H), 3.15 (d, J = 12.4 Hz, 2H), 2.90 (dd, J = 10.8, 22.4 Hz, 4H), 2.00-2.03 (m, 2H), 1.90 (s, 6H), 1.68-1.87 (m, 6H), 1.37-1.47 (m, 1H | 0.173 | 0.153 |

TABLE 2-continued

| Compound | Structure | Physical Data MS (m/z) and/or ¹H NMR | EC$_{50}$ 3D7 strain (μM) | EC$_{50}$ W2 strain (μM) |
|---|---|---|---|---|
| 680 | 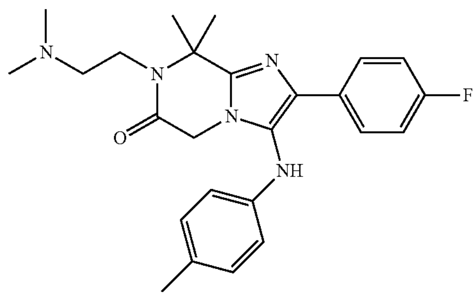 | 415.7 (M + 1)<br>¹H NMR (400 MHz, CD$_3$OD): δ 7.59-7.63 (m, 2H), 7.32 (t, J = 8.8 Hz, 2H), 4.25 (d, J = 4.8 Hz, 2H), 4.13 (s, 2H), 3.97-4.04 (m, 1H), 3.88 (d, J = 4.8 Hz, 2H), 3.49-3.54 (m, 1H), 3.41-3.47 (m, 2H), 3.25-3.30 (m, 1H), 2.92 (s, 6H), 2.45-2.53 (m, 1H), 2.23-2.28 (m, 1H), 2.01 (s, 6H) | 0.085 | 0.173 |
| 681 | 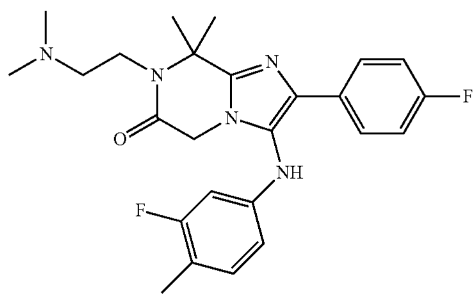 [SMILES: Cc1ccc(Nc2c(-c3ccc(F)cc3)nc3n2CC(=O)N(CCN(C)C)C3(C)C)cc1F] | 454.1 (M + 1) | 0.272 | 0.196 |
| 682 | 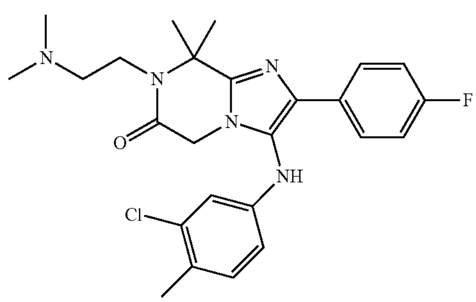 [SMILES: Cc1ccc(Nc2c(-c3ccc(F)cc3)nc3n2CC(=O)N(CCN(C)C)C3(C)C)cc1Cl] | 470.1 (M + 1) | 0.124 | 0.111 |
| 683 | 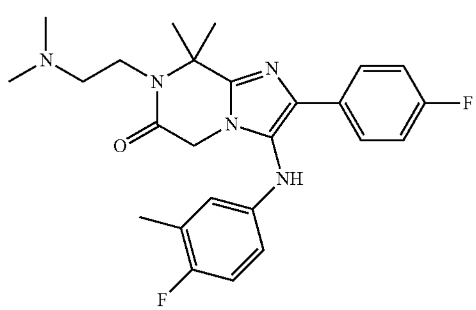 [SMILES: Cc1cc(Nc2c(-c3ccc(F)cc3)nc3n2CC(=O)N(CCN(C)C)C3(C)C)ccc1F] | 454.1 (M + 1) | 0.125 | 0.112 |

US 9,469,645 B2

TABLE 2-continued

| Compound | Structure | Physical Data MS (m/z) and/or ¹H NMR | EC$_{50}$ 3D7 strain (μM) | EC$_{50}$ W2 strain (μM) |
| --- | --- | --- | --- | --- |
| 684 | 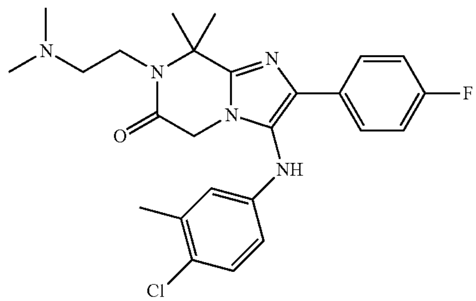 [SMILES: Cc1cc(Nc2c(-c3ccc(F)cc3)nc3n2CC(=O)N(CCN(C)C)C3(C)C)ccc1Cl] | 470.1 (M + 1) | 0.03 | 0.017 |
| 685 | 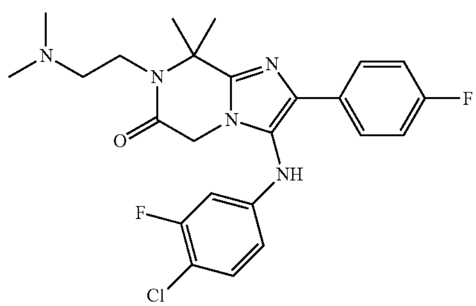 [SMILES: CN(C)CCN1C(=O)Cn2c(nc(-c3ccc(F)cc3)c2Nc2ccc(Cl)c(F)c2)C1(C)C] | 474.1 (M + 1) | 0.173 | 0.131 |
| 686 | 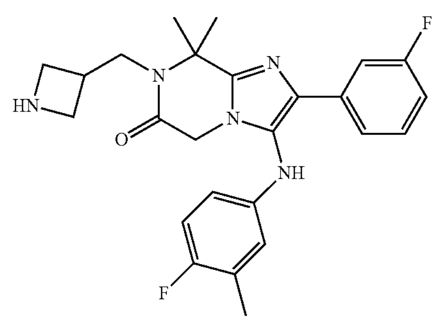 [SMILES: Cc1cc(Nc2c(-c3cccc(F)c3)nc3n2CC(=O)N(CC2CNC2)C3(C)C)ccc1F] | 452.2 (M + 1) | 0.628 | 0.524 |
| 687 | 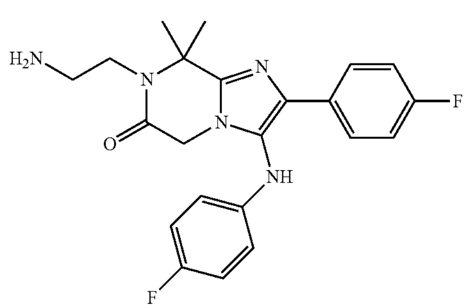 [SMILES: CC1(C)c2nc(-c3ccc(F)cc3)c(Nc3ccc(F)cc3)n2CC(=O)N1CCN] | 412.2 (M + 1)<br>¹H NMR (400 MHz, CD$_3$OD): δ 7.70-7.74 (m, 2H), 7.21 (t, J = 8.4 Hz, 2H), 6.96 (d, J = 7.6 Hz, 2H), 6.62 (s, 1H), 6.50 (d, J = 7.6 Hz, 1H), 5.19 (s, 2H), 4.25 (s, 2H), 4.07 (s, 2H), 1.77 (s, 6H) | 3.42 (NF54) | 3.35 |

TABLE 2-continued

| Compound | Structure | Physical Data MS (m/z) and/or ¹H NMR | EC$_{50}$ 3D7 strain (μM) | EC$_{50}$ W2 strain (μM) |
|---|---|---|---|---|
| 688 | 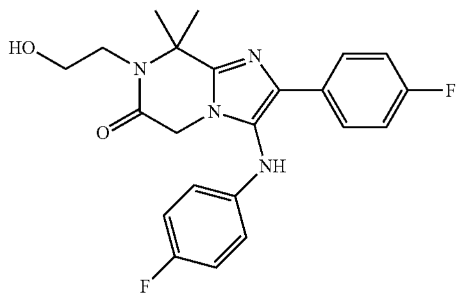 [SMILES: CC1(C)c2nc(-c3ccc(F)cc3)c(Nc3ccc(F)cc3)n2CC(=O)N1CCO] | 413.2 (M + 1)<br>¹H NMR (400 MHz, CD$_3$OD): δ 7.67-7.71 (m, 2H), 7.15-7.21 (m, 2H), 6.92-6.97 (m, 2H), 6.71-6.76 (m, 2H), 4.57-4.63 (dm, 1H), 3.76-3.79 (m, 1H), 3.68-3.70 (m, 1H), 1.91 (s, 3H), 1.84 (s, 3H) | 0.106 (NF54) | 0.134 |
| 689 | 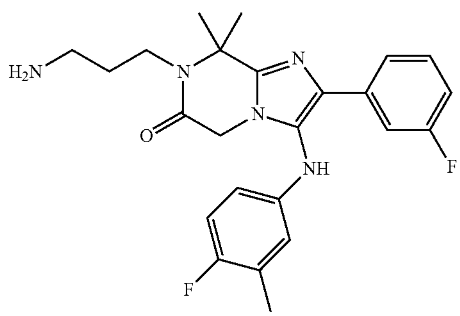 [SMILES: Cc1cc(Nc2c(-c3cccc(F)c3)nc3n2CC(=O)N(CCCN)C3(C)C)ccc1F] | 440.2 (M + 1)<br>¹H NMR (400 MHz, CD$_3$OD): δ 7.33-7.42 (m, 3H), 7.06-7.08 (m, 1H), 6.70 (t, J = 9.2 Hz, 2H), 6.69-6.71 (m, 1H), 6.58-6.62 (m, 1H), 4.38 (s, 2H), 3.66 (t, J = 8.0 Hz, 2H), 2.89 (t, J = 8.0 Hz, 2H), 2.25 (d, J = 1.6 Hz, 3H), 1.88-1.95 (m, 2H), 1.77 (s, 6H) | 0.512 | 0.295 |
| 690 | 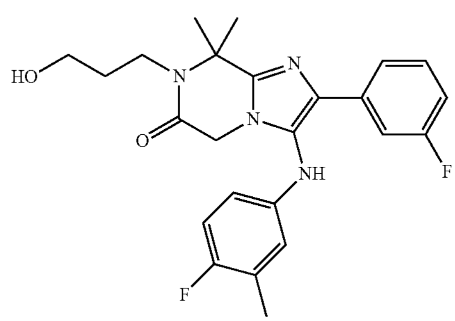 [SMILES: Cc1cc(Nc2c(-c3cccc(F)c3)nc3n2CC(=O)N(CCCO)C3(C)C)ccc1F] | 441.2 (M + 1)<br>¹H NMR (400 MHz, CD$_3$OD): δ 7.51-7.54 (m, 1H), 7.44-7.48 (m, 1H), 7.37-7.42 (m, 1H), 7.05-7.12 (m, 1H), 6.86 (dt, J = 1.6, 9.2 Hz, 1H), 6.57-6.61 (m, 1H), 6.47-6.53 (m, 1H), 4.58 (d, J = 2.0 Hz, 2H), 3.91 (t, J = 6.0 Hz, 1H), 3.64-3.72 (m, 3H), 3.36 (s, 3H), 2.17 (d, J = 1.2 Hz, 2H), 1.91 (s, 3H), 1.89 (s, 3H) | 0.866 | 0.76 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 691 | 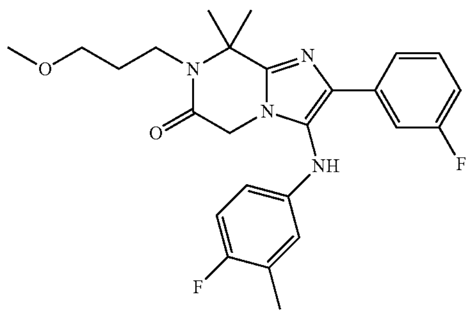 [SMILES: COCCCN1C(=O)Cn2c(nc(-c3cccc(F)c3)c2Nc2ccc(F)c(C)c2)C1(C)C] | 455.2 (M + 1) $^1$H NMR (400 MHz, CD$_3$OD): δ 7.37-7.43 (m, 2H), 7.31-7.34 (m, 1H), 7.06-7.11 (m, 1H), 6.97 (t, J = 8.8 Hz, 1H), 6.71-6.73 (m, 1H), 6.58-6.62 (m, 1H), 4.39 (s, 2H), 3.62-3.65 (m, 2H), 3.36 (br, 5H), 3.34 (s, 1H), 3.26 (s, 3H), 2.24 (d, J = 2.0 Hz, 3H), 1.79 (s, 6H) | 0.068 | 0.06 |
| 692 | 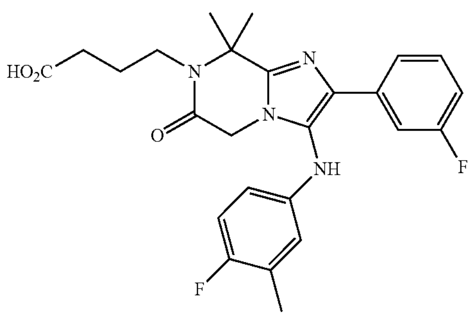 [SMILES: Cc1cc(Nc2c(-c3cccc(F)c3)nc3n2CC(=O)N(CCCC(=O)O)C3(C)C)ccc1F] | 469.2 (M + 1) | 6.45 | 5.34 |
| 693 | 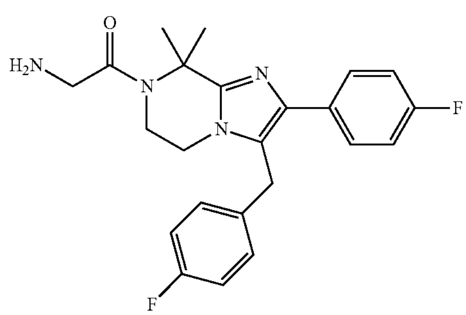 [SMILES: CC1(C)c2nc(-c3ccc(F)cc3)c(Cc3ccc(F)cc3)n2CCN1C(=O)CN] | 411.2 (M + 1) $^1$H NMR (400 MHz, CD$_3$OD): δ 7.58-7.62 (m, 2H), 7.30 (d, J = 8.8 Hz, 2H), 7.21 (dd, J = 5.6, 8.8 Hz, 2H), 7.08 (d, J = 8.8 Hz, 2H), 4.23 (s, 2H), 4.06-4.09 (m, 4H), 3.83 (d, J = 5.6 Hz, 2H), 2.05 (s, 6H) | 0.008 | 0.008 |
| 694 | 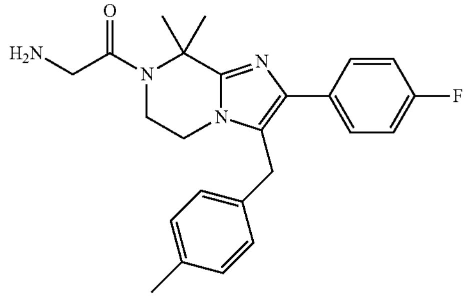 [SMILES: Cc1ccc(Cc2c(-c3ccc(F)cc3)nc3n2CCN(C(=O)CN)C3(C)C)cc1] | 407.3 (M + 1) $^1$H NMR (400 MHz, CD$_3$OD): δ 7.59-7.62 (m, 2H), 7.29 (t, J = 8.4 Hz, 2H), 7.16 (d, J = 8.0 Hz, 2H), 7.06 (d, J = 8.0 Hz, 2H), 4.19 (s, 2H), 4.04-4.08 (m, 4H), 3.80 (t, J = 4.8 Hz, 2H), 2.31 (s, 3H), 2.04 (s, 6H) | 0.011 | 0.007 |

TABLE 2-continued

| Compound | Structure | Physical Data MS (m/z) and/or ¹H NMR | EC$_{50}$ 3D7 strain (μM) | EC$_{50}$ W2 strain (μM) |
|---|---|---|---|---|
| 695 | 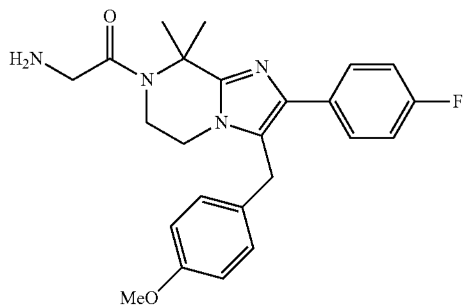 [SMILES: COc1ccc(Cc2c(-c3ccc(F)cc3)nc3n2CCN(C(=O)CN)C3(C)C)cc1] | 423.1 (M + 1) | 0.017 | 0.019 |
| 696 | 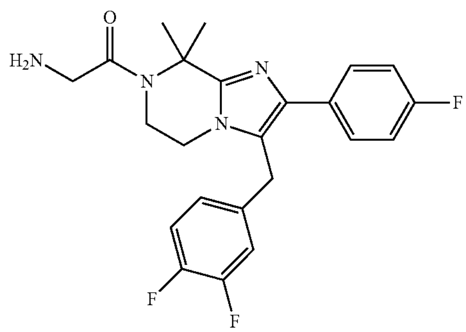 [SMILES: CC1(C)c2nc(-c3ccc(F)cc3)c(Cc3ccc(F)c(F)c3)n2CCN1C(=O)CN] | 429.2 (M + 1) | 0.02 | 0.022 |
| 697 | 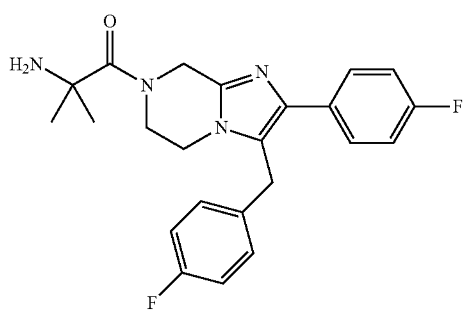 [SMILES: CC(C)(N)C(=O)N1CCn2c(nc(-c3ccc(F)cc3)c2Cc2ccc(F)cc2)C1] | 411.1 (M + 1) | 0.362 | 0.256 |
| 698 | 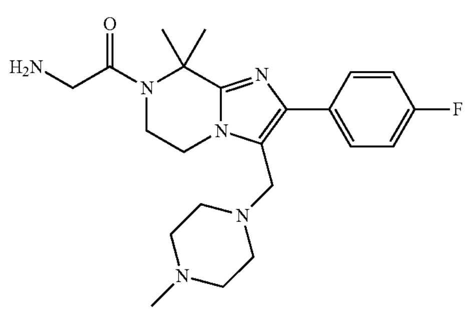 [SMILES: CN1CCN(Cc2c(-c3ccc(F)cc3)nc3n2CCN(C(=O)CN)C3(C)C)CC1] | 415.3 (M + 1) | 8.81 | 9.02 |
| 699 | 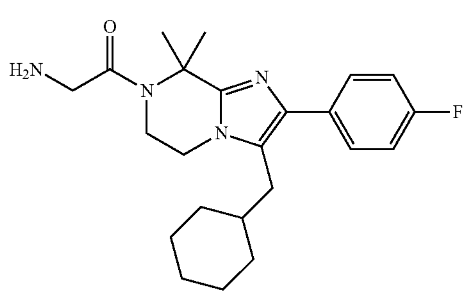 [SMILES: CC1(C)c2nc(-c3ccc(F)cc3)c(CC3CCCCC3)n2CCN1C(=O)CN] | 399.3 (M + 1) | 0.678 (NF54) | ND |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 700 | 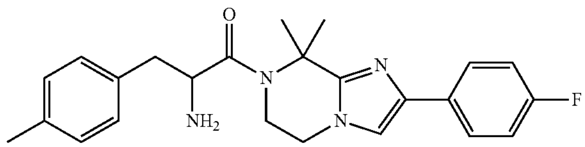 [SMILES: Cc1ccc(CC(N)C(=O)N2CCn3cc(-c4ccc(F)cc4)nc3C2(C)C)cc1] | 407.2 (M + 1) $^1$H NMR (400 MHz, CD$_3$OD): δ 7.73-7.77 (m, 3H), 7.21-7.30 (m, 6H), 4.82-4.86 (m, 1H), 4.13-4.18 (m, 2H), 4.61 (s, 1H), 3.71-3.77 (m, 1H), 3.53-3.58 (m, 1H), 3.09-3.21 (m, 1H), 2.34 (s, 3H), 2.01 (s, 3H), 1.99 (s, 3H) | >9.51 | 7.0 |
| 701 | 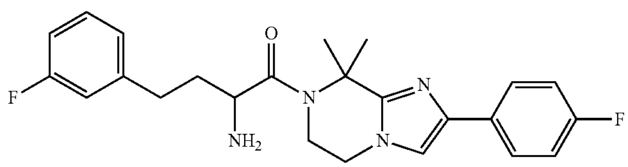 [SMILES: CC1(C)c2nc(-c3ccc(F)cc3)cn2CCN1C(=O)C(N)CCc1cccc(F)c1] | 425.2 (M + 1) $^1$H NMR (400 MHz, CD$_3$OD): δ 7.76-7.79 (m, 3H), 7.32-7.38 (m, 1H), 7.28 (t, J = 8.8 Hz, 2H), 7.11 (d, J = 4.0 Hz, 1H), 7.06 (dt, J = 10, 2.4 Hz, 1H), 6.99 (dt, J = 2.8, 8.4 Hz, 1H), 4.62 (t, J = 6.4 Hz, 1H), 4.35 (t, J = 4.8 Hz, 2H), 3.84-3.98 (m, 2H), 2.79-2.87 (m, 2H), 2.14-2.20 (m, 2H), 2.04 (s, 3H), 2.03 (s, 3H) | 8.27 | 7.35 |
| 702 | 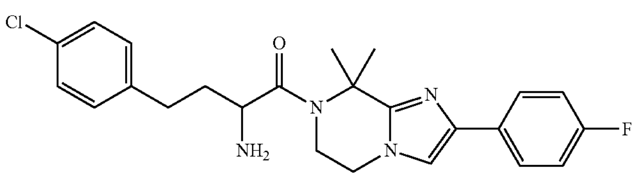 [SMILES: CC1(C)c2nc(-c3ccc(F)cc3)cn2CCN1C(=O)C(N)CCc1ccc(Cl)cc1] | 441.2 (M + 1) | 6.03 | 5.85 |
| 703 | 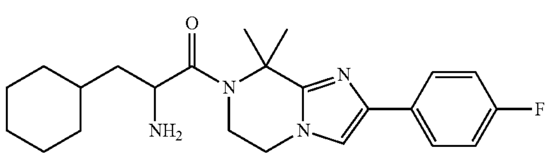 [SMILES: CC1(C)c2nc(-c3ccc(F)cc3)cn2CCN1C(=O)C(N)CC1CCCCC1] | 399.3 (M + 1) $^1$H NMR (400 MHz, CD$_3$OD): δ 7.81 (s, 1H), 7.76-7.80 (m, 2H), 7.29 (t, J = 8.8 Hz, 2H), 4.60-4.64 (m, 2H), 4.40-4.43 (m, 2H), 3.92-3.95 (m, 2H), 2.05 (s, 3H), 2.04 (s, 3H), 1.70-1.83 (m, 6H), 1.49-1.53 (m, 1H), 1.20-1.42 (m, 4H), 0.99-1.35 (m, 2H) | 8.57 | 8.29 |

TABLE 2-continued

| Compound | Structure | Physical Data MS (m/z) and/or ¹H NMR | EC$_{50}$ 3D7 strain (μM) | EC$_{50}$ W2 strain (μM) |
|---|---|---|---|---|
| 704 | 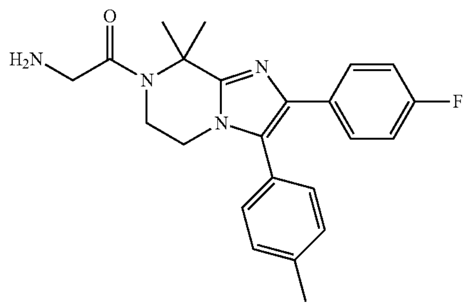 [SMILES: Cc1ccc(-c2c(-c3ccc(F)cc3)nc3n2CCN(C(=O)CN)C3(C)C)cc1] | 393.3 (M + 1) ¹H NMR (400 MHz, CD$_3$OD): δ 7.42-7.46 (m, 2H), 7.31-7.39 (m, 4H), 7.13 (t, J = 8.8 Hz, 2H), 4.09-4.12 (m, 4H), 3.82 (t, J = 4.8 Hz, 2H), 2.42 (s, 3H), 2.08 (s, 6H) | 0.236 | 0.232 |
| 705 | 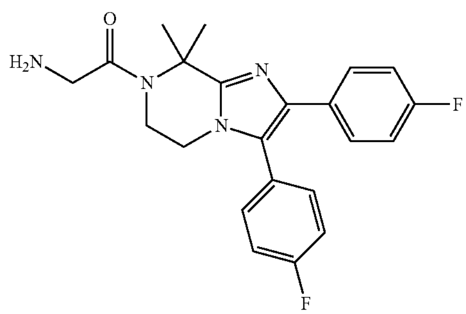 [SMILES: CC1(C)c2nc(-c3ccc(F)cc3)c(-c3ccc(F)cc3)n2CCN1C(=O)CN] | 397.3 (M + 1) | 1.241 | 0.76 |
| 706 | 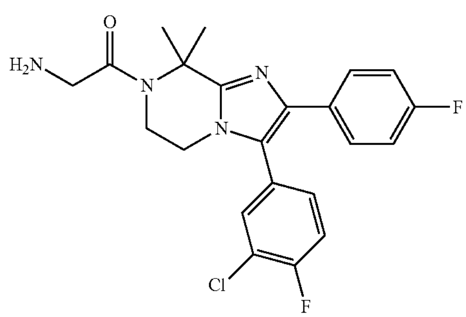 [SMILES: CC1(C)c2nc(-c3ccc(F)cc3)c(-c3ccc(F)c(Cl)c3)n2CCN1C(=O)CN] | 431.2 (M + 1) | 0.252 | 0.237 |
| 707 | 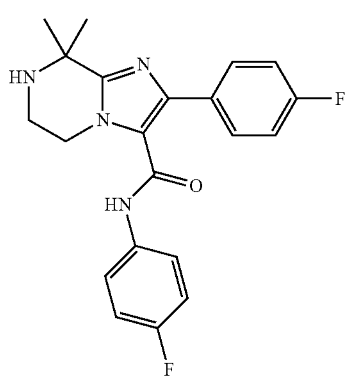 [SMILES: CC1(C)NCCn2c1nc(-c1ccc(F)cc1)c2C(=O)Nc1ccc(F)cc1] | 383.1 (M + 1) | 6.54 | >10 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 708 | 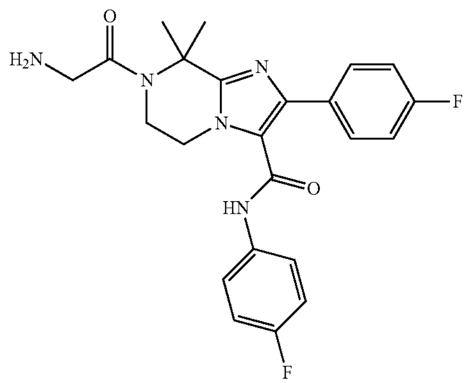 [SMILES: CC1(C)c2nc(-c3ccc(F)cc3)c(C(=O)Nc3ccc(F)cc3)n2CCN1C(=O)CN] | 440.1 (M + 1) | 0.809 | 1.134 |
| 709 | 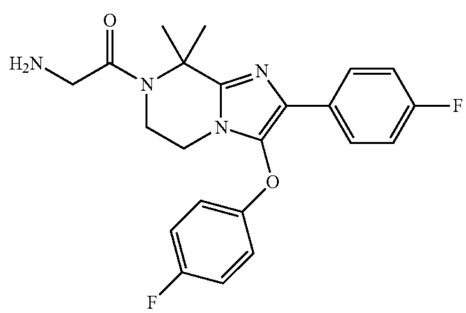 | 413.1 (M + 1) $^1$H NMR (400 MHz, CD$_3$OD): δ 7.67-7.71 (m, 2H), 7.09-7.17 (m, 6H), 4.06 (s, 2H), 4.02 (t, J = 4.8 Hz, 2H), 3.80 (t, J = 4.8 Hz, 2H), 2.04 (s, 6H) | 0.003 | 0.008 |
| 710 | 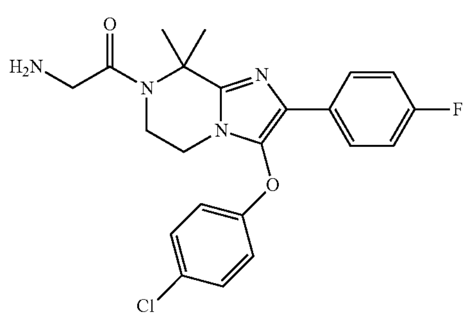 | 429.1 (M + 1) | 0.028 (NF54) | ND |
| 711 | 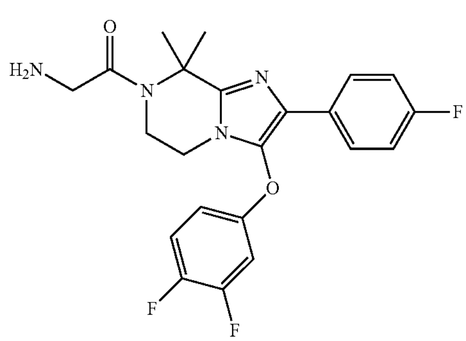 [SMILES: CC1(C)c2nc(-c3ccc(F)cc3)c(Oc3ccc(F)c(F)c3)n2CCN1C(=O)CN] | 431.1 (M + 1) | 0.034 (NF54) | ND |

TABLE 2-continued

| Compound | Structure | Physical Data MS (m/z) and/or ¹H NMR | EC$_{50}$ 3D7 strain (μM) | EC$_{50}$ W2 strain (μM) |
| --- | --- | --- | --- | --- |
| 712 | 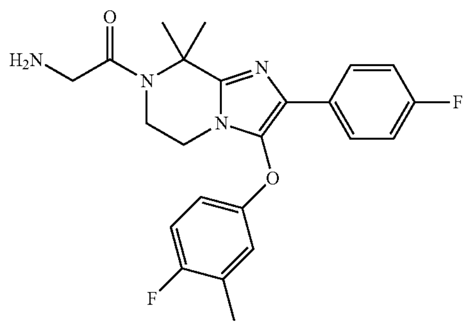 [SMILES: Cc1cc(Oc2c(-c3ccc(F)cc3)nc3n2CCN(C(=O)CN)C3(C)C)ccc1F] | 427.2 (M + 1) | 0.019 (NF54) | ND |
| 713 | 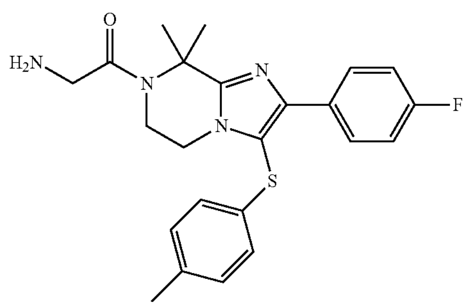 | 425.2 (M + 1) ¹H NMR (400 MHz, CD$_3$OD): δ 7.83-7.87 (m, 2H), 7.22 (t, J = 8.8 Hz, 2H), 7.16 (d, J = 8.4 Hz, 2H), 7.04 (d, J = 8.87 Hz, 2H), 4.11 (t, J = 4.4 Hz, 2H), 3.98 (s, 2H), 3.83 (t, J = 4.4 Hz, 2H), 2.29 (s, 3H), 1.98 (s, 6H) | 0.008 | ND |
| 714 | 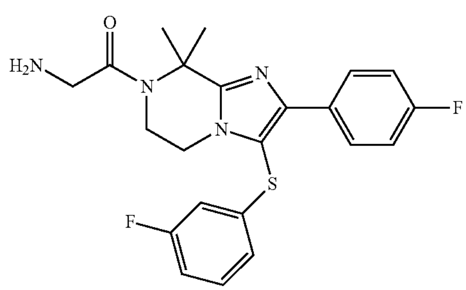 [SMILES: CC1(C)c2nc(-c3ccc(F)cc3)c(Sc3cccc(F)c3)n2CCN1C(=O)CN] | 429.2 (M + 1) | 0.007 | 0.004 |
| 715 | 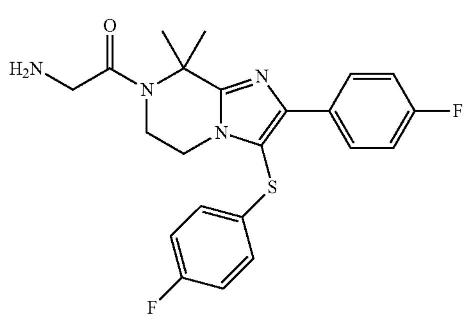 | 429.1 (M + 1) | 0.006 | 0.006 |

TABLE 2-continued

| Compound | Structure | Physical Data MS (m/z) and/or ¹H NMR | EC$_{50}$ 3D7 strain (μM) | EC$_{50}$ W2 strain (μM) |
| --- | --- | --- | --- | --- |
| 716 | (structure) | 445.1 (M + 1) | 0.002 | 0.001 |
| 717 | (structure) | 439.2 (M + 1) | 0.026 | 0.016 |
| 718 | (structure) | 447.1 (M + 1) | 0.008 | 0.006 |
| 719 | (structure) | 445.1 (M + 1) <br> ¹H NMR (400 MHz, CD$_3$OD): δ 7.58-7.62 (m, 2H), 7.23 (d, J = 8.4 Hz, 2H), 7.14 (t, J = 8.4 Hz, 2H), 6.89 (s, 1H), 6.67 (d, J = 7.6 Hz, 1H), 5.09 (s, 2H), 4.17 (s, 2H), 3.99 (s, 2H), 1.67 (s, 6H) | 0.481 | 0.361 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 720 | 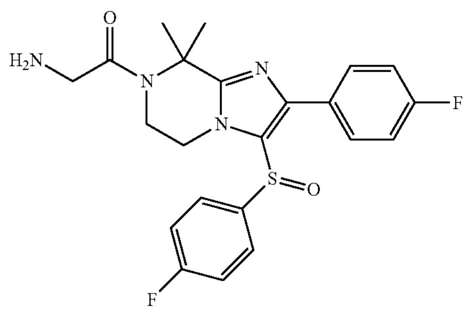 [SMILES: CC1(C)c2nc(-c3ccc(F)cc3)c(S(=O)c3ccc(F)cc3)n2CCN1C(=O)CN] | 445.1 (M + 1) $^1$H NMR (400 MHz, CD$_3$OD): δ 7.60-7.63 (m, 2H), 7.11 (t, J = 8.4 Hz, 2H), 6.75-6.80 (m, 1H), 6.59 (d, J = 4.8 Hz, 1H), 6.50 (br, 1H), 5.09 (s, 2H), 4.16 (s, 2H), 3.97 (s, 2H), 2.07 (s, 3H), 1.67 (s, 6H) | 0.07 | 0.069 |
| 721 | 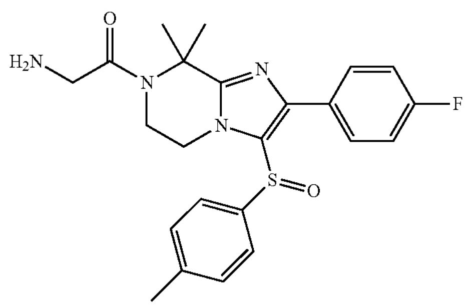 [SMILES: Cc1ccc(S(=O)c2c(-c3ccc(F)cc3)nc3n2CCN(C(=O)CN)C3(C)C)cc1] | 441.0 (M + 1) $^1$H NMR (400 MHz, CD$_3$OD): δ 7.78-7.82 (m, 2H), 7.60 (d, J = 8.4 Hz, 2H), 7.44 (d, J = 8.0 Hz, 2H), 7.35 (t, J = 8.8 Hz, 2H), 4.61-4.65 (m, 1H), 4.08 (s, 2H), 3.77-3.92 (m, 3H), 2.43 (s, 3H), 2.07 (s, 3H), 2.05 (s, 3H) | 0.042 | ND |
| 722 | 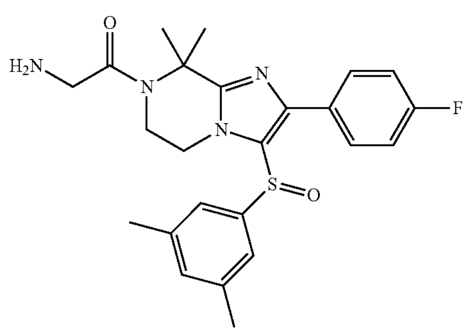 [SMILES: Cc1cc(C)cc(S(=O)c2c(-c3ccc(F)cc3)nc3n2CCN(C(=O)CN)C3(C)C)c1] | 455.1 (M + 1) | 0.381 | 0.281 |
| 723 | 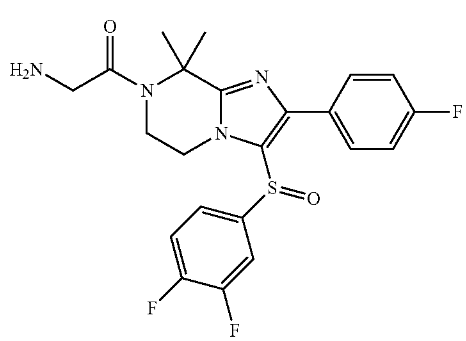 [SMILES: CC1(C)c2nc(-c3ccc(F)cc3)c(S(=O)c3ccc(F)c(F)c3)n2CCN1C(=O)CN] | 463.1 (M + 1) | 0.089 | 0.068 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 724 | 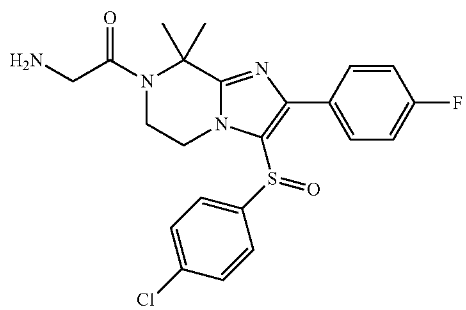 | 461.1 (M + 1) $^1$H NMR (400 MHz, CD$_3$OD): δ 7.70-7.74 (m, 2H), 7.21 (t, J = 8.4 Hz, 2H), 6.96 (d, J = 7.6 Hz, 2H), 6.62 (s, 1H), 6.50 (d, J = 7.6 Hz, 1H), 5.19 (s, 2H), 4.25 (s, 2H), 4.07 (s, 2H), 1.77 (s, 6H) | 0.509 | 0.287 |
| 725 | 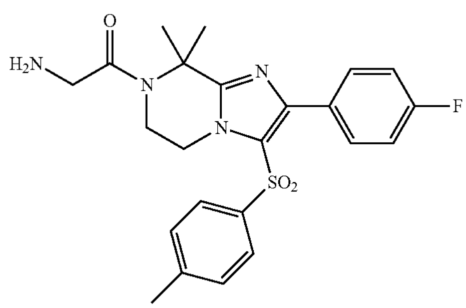 [SMILES: Cc1ccc(S(=O)(=O)c2c(-c3ccc(F)cc3)nc3n2CCN(C(=O)CN)C3(C)C)cc1] | 457.1 | 5.21 (NF54) | ND |
| 726 | 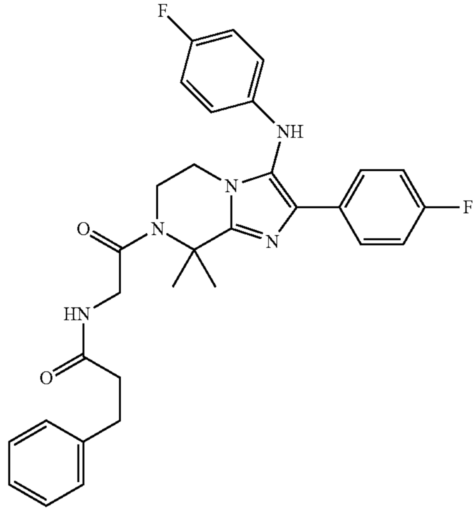 [SMILES: CC1(C)c2nc(-c3ccc(F)cc3)c(Nc3ccc(F)cc3)n2CCN1C(=O)CNC(=O)CCc1ccccc1] | 544.3 (M + 1) | 1.925 | 1.48 |

TABLE 2-continued
| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 727 | 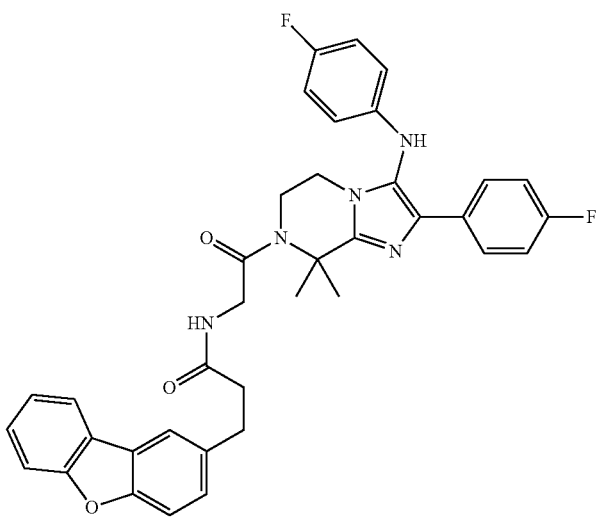 [SMILES: CC1(C)c2nc(-c3ccc(F)cc3)c(Nc3ccc(F)cc3)n2CCN1C(=O)CNC(=O)CCc1ccc2oc3ccccc3c2c1] | 634.3 (M + 1) | 6.56 | 2.969 |
| 728 | 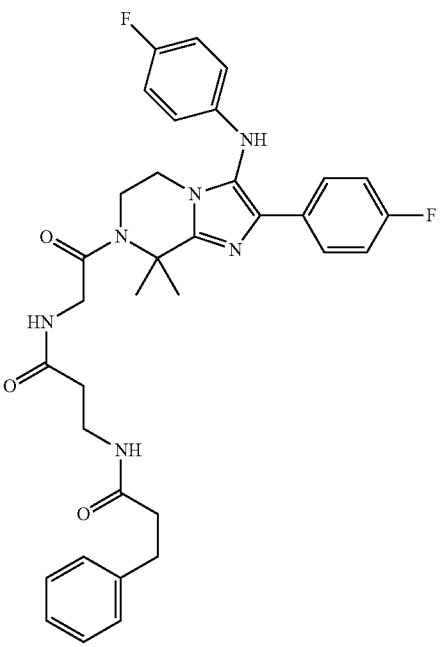 [SMILES: CC1(C)c2nc(-c3ccc(F)cc3)c(Nc3ccc(F)cc3)n2CCN1C(=O)CNC(=O)CCNC(=O)CCc1ccccc1] | 615.3 (M + 1) | 5.4 | 1.485 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 729 | 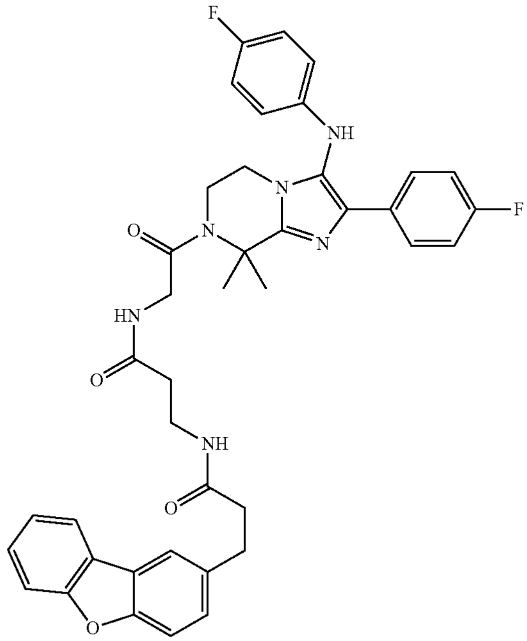 [SMILES: CC1(C)c2nc(-c3ccc(F)cc3)c(Nc3ccc(F)cc3)n2CCN1C(=O)CNC(=O)CCNC(=O)CCc1ccc2oc3ccccc3c2c1] | 705.3 (M + 1) | >10 | 6.29 |
| 730 | 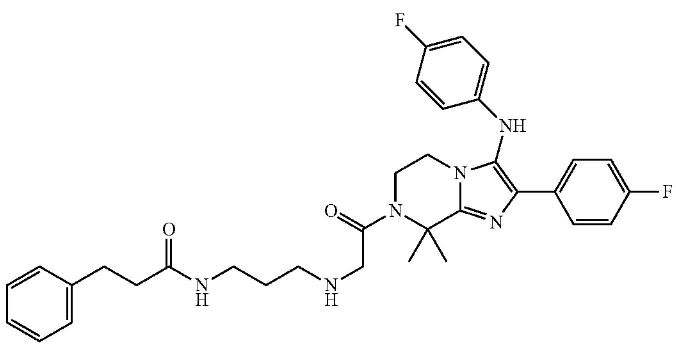 [SMILES: CC1(C)c2nc(-c3ccc(F)cc3)c(Nc3ccc(F)cc3)n2CCN1C(=O)CNCCCNC(=O)CCc1ccccc1] | 601.2 (M + 1) | 1.365 | 0.474 |
| 731 | 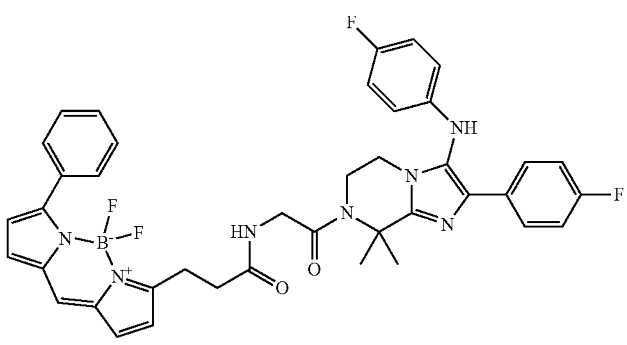 [SMILES: CC1(C)c2nc(-c3ccc(F)cc3)c(Nc3ccc(F)cc3)n2CCN1C(=O)CNC(=O)CCC1=[N+]2C(=Cc3ccc(-c4ccccc4)n3[B-]2(F)F)C=C1] | 734.2 (M + 1) | 2.27 (NF54) | 5.61 |
| 732 | 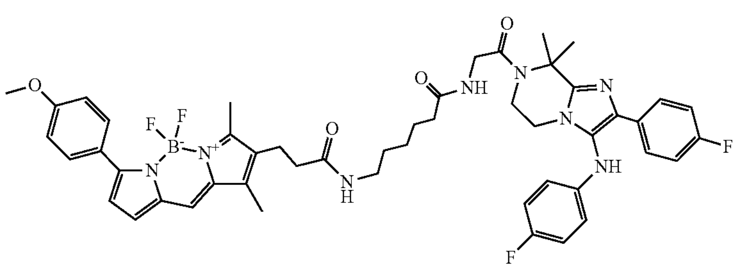 [SMILES: COc1ccc(-c2ccc3n2[B-](F)(F)[N+]2=C(C)C(CCC(=O)NCCCCCC(=O)NCC(=O)N4CCn5c(nc(-c6ccc(F)cc6)c5Nc5ccc(F)cc5)C4(C)C)=C(C)C2=C3)cc1] | 905.4 (M + 1) | 1.223 (NF54) | 1.438 |

TABLE 2-continued
| Compound | Structure | Physical Data MS (m/z) and/or $^1$H NMR | EC$_{50}$ 3D7 strain (μM) | EC$_{50}$ W2 strain (μM) |
|---|---|---|---|---|
| 737 | 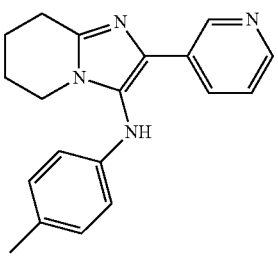 [SMILES: Cc1ccc(Nc2c(-c3cccnc3)nc3n2CCCC3)cc1] | 305.2 (M + 1) $^1$H NMR (400 MHz, CDCl$_3$): δ 9.27 (s, 1H), 8.76 (d, J = 8.0 Hz, 1H), 8.55 (d, J = 3.2 Hz, 1H), 7.79 (t, J = 3.2 Hz, 1H), 7.33 (br, 1H), 6.99 (d, J = 8.4 Hz, 2H), 6.56 (d, J = 8.4 Hz, 2H), 3.87 (s, 2H), 3.14 (s, 2H), 2.22 (s, 3H), 2.02 (s, 4H) | 7.85 | 4.09 |
| 738 | 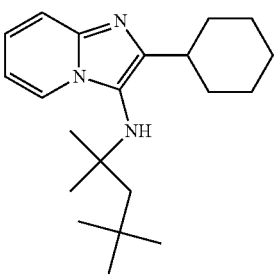 [SMILES: CC(C)(C)CC(C)(C)Nc1c(C2CCCCC2)nc2ccccn12] | 328.5 (M + 1) | 3.24 | 1.555 |
| 739 | 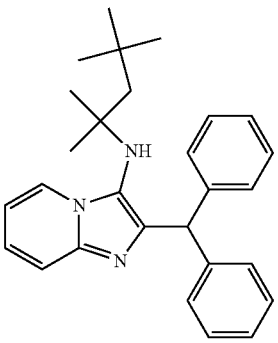 [SMILES: CC(C)(C)CC(C)(C)Nc1c(C(c2ccccc2)c2ccccc2)nc2ccccn12] | 412.6 (M + 1) | 0.768 | 0.881 |
| 740 | 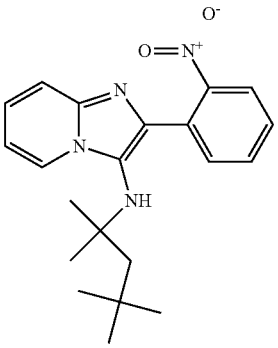 | 367.2 (M + 1) | 9.33 | 8.73 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 741 | 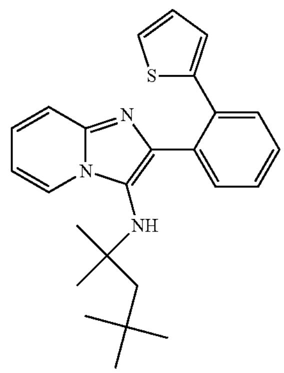 [SMILES: CC(C)(C)CC(C)(C)Nc1c(-c2ccccc2-c2cccs2)nc2ccccn12] | 404.6 (M + 1) | 5.25 | 4.83 |
| 742 | 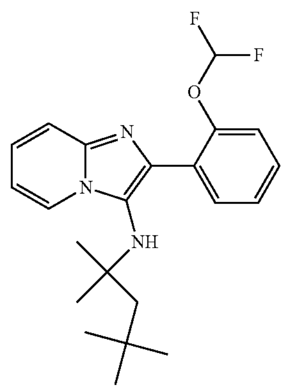 [SMILES: CC(C)(C)CC(C)(C)Nc1c(-c2ccccc2OC(F)F)nc2ccccn12] | 388.2 (M + 1) | 6.43 | 11.6 |
| 743 | 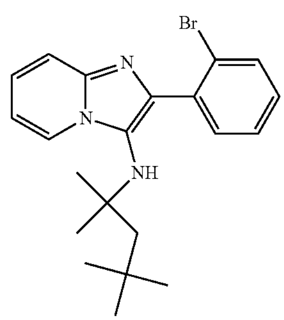 [SMILES: CC(C)(C)CC(C)(C)Nc1c(-c2ccccc2Br)nc2ccccn12] | 401.2 (M + 1) | 2.675 | 3.003 |
| 744 | 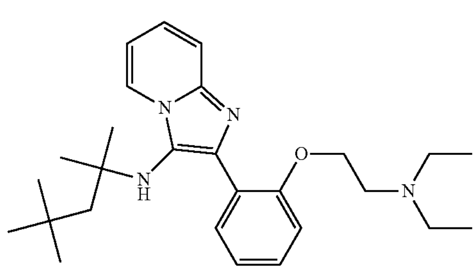 [SMILES: CCN(CC)CCOc1ccccc1-c1nc2ccccn2c1NC(C)(C)CC(C)(C)C] | 437.6 (M + 1) | 5.24 | 2.813 |

TABLE 2-continued

| Compound | Structure | Physical Data MS (m/z) and/or $^1$H NMR | EC$_{50}$ 3D7 strain (μM) | EC$_{50}$ W2 strain (μM) |
| --- | --- | --- | --- | --- |
| 745 | 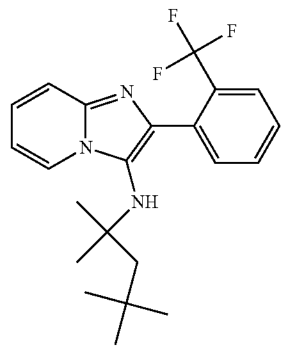 [SMILES: CC(C)(C)CC(C)(C)Nc1c(-c2ccccc2C(F)(F)F)nc2ccccn12] | 390.2 (M + 1) | 3.57 | 4.23 |
| 746 | 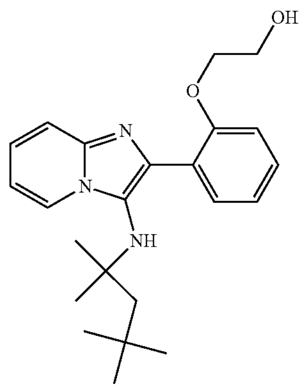 [SMILES: CC(C)(C)CC(C)(C)Nc1c(-c2ccccc2OCCO)nc2ccccn12] | 382.2 (M + 1) | >10 | 6.94 |
| 747 | 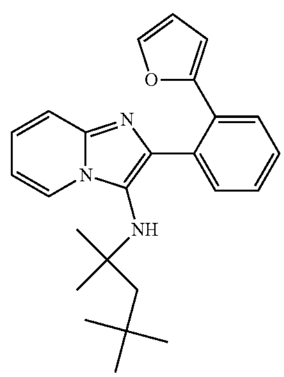 [SMILES: CC(C)(C)CC(C)(C)Nc1c(-c2ccccc2-c2ccco2)nc2ccccn12] | 388.2 (M + 1) | 2.234 | 4.48 |
| 748 | 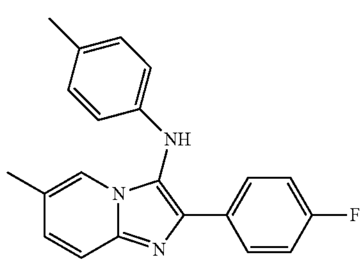 [SMILES: Cc1ccc(Nc2c(-c3ccc(F)cc3)nc3ccc(C)cn23)cc1] | 332.2 (M + 1)<br>$^1$H NMR (400 MHz, CD$_3$OD): δ 8.09 (s, 1H), 7.75-7.79 (m, 4H), 7.17 (t, J = 8.8 Hz, 2H), 6.93 (d, J = 8.0 Hz, 1H), 6.49 (d, J = 8.4 Hz, 2H), 2.35 (s, 3H), 2.14 (s, 3H) | 3.44 | 4.15 |

TABLE 2-continued

| Compound | Structure | Physical Data MS (m/z) and/or ¹H NMR | EC$_{50}$ 3D7 strain (μM) | EC$_{50}$ W2 strain (μM) |
| --- | --- | --- | --- | --- |
| 749 | 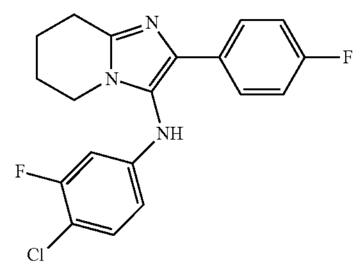 [SMILES: Fc1ccc(-c2nc3n(c2Nc2ccc(Cl)c(F)c2)CCCC3)cc1] | 360.8 (M + 1) ¹H NMR (400 MHz, CD$_3$OD): δ 7.64-7.67 (m, 2H), 7.20-7.29 (m, 3H), 6.64 (dd, J = 2.8, 11.2 Hz, 1H), 6.55-6.58 (m, 1H), 3.90 (t, J = 5.6 Hz, 2H), 3.11 (t, J = 5.6 Hz, 2H), 2.05-2.12 (m, 4H) | 1.053 | 0.814 |
| 750 | 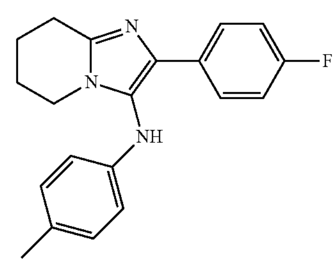 [SMILES: Cc1ccc(Nc2c(-c3ccc(F)cc3)nc3n2CCCC3)cc1] | 322.2 (M + 1) | 4.77 | 4.96 |
| 751 | 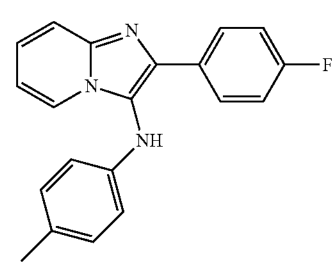 [SMILES: Cc1ccc(Nc2c(-c3ccc(F)cc3)nc3ccccn23)cc1] | 318.2 (M + 1) ¹H NMR (400 MHz, CD$_3$OD): δ 8.39 (d, J = 6.8 Hz, 1H), 7.89-8.02 (m, 4H), 7.47 (dt, J = 1.2, 6.8 Hz, 1H), 7.29 (d, J = 8.8 Hz, 2H), 7.04 (d, J = 8.0 Hz, 2H), 6.61 (d, J = 8.4 Hz, 2H), 2.24 (s, 3H) | 1.792 | 4.55 |
| 752 | 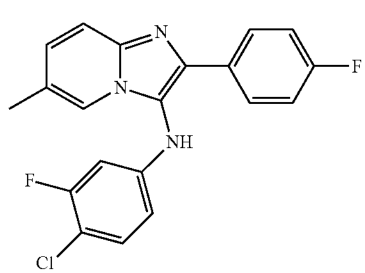 [SMILES: Cc1ccc2nc(-c3ccc(F)cc3)c(Nc3ccc(Cl)c(F)c3)n2c1] | 370.8 (M + 1) | 1.619 | 2.381 |

TABLE 2-continued

| Compound | Structure | Physical Data MS (m/z) and/or $^1$H NMR | EC$_{50}$ 3D7 strain (μM) | EC$_{50}$ W2 strain (μM) |
|---|---|---|---|---|
| 753 | (structure) | 336.2 (M + 1) $^1$H NMR (400 MHz, CD$_3$OD): δ 7.65-7.68 (m, 2H), 7.19 (t, J = 8.8 Hz, 2H), 7.03 (d, J = 8.4 Hz, 2H), 6.62 (dd, J = 2.0, 6.4 Hz, 1H), 4.00-4.05 (m, 1H), 3.35-3.38 (m, 1H), 3.17-3.24 (m, 1H), 3.05-3.14 (m, 1H), 2.24 (s, 3H), 2.12-2.21 (m, 2H), 1.67-1.77 (m, 1H), 1.12 (d, J = 6.4 Hz, 3H) | 0.376 | 0.592 |
| 754 | (structure) | 374.8 (M + 1) | 0.104 | 0.19 |

Assays

Compounds of the invention can be assayed to measure their capacity to inhibit proliferation of parasitemia in infected red blood cells. The proliferation is quantified by the addition of SYBR Green I (INVITROGEN)® dye which has a high affinity for double stranded DNA.

The following assay illustrates the invention without in any way limiting the scope of the invention. This parasite proliferation assay measures the increase in parasite DNA content using a DNA intercalating dye, SYBR Green®.

3D7 *P. falciparum* strain is grown in complete culturing media until parasitemia reaches 3% to 8% with O+ human erythrocytes. 20 μl of screening media is dispensed into 384 well assay plates. 50 nl of compounds of the invention (in DMSO), including antimalarial controls (mefloquine, pyrimethamine and artemisinin), are then transferred into the assay plates, as well as DMSO alone to serve as a negative control for inhibition. Then 30 μl of a suspension of a 3D7 *P. falciparum* infected erythrocytes in screening media is dispensed into the assay plates such that the final hematocrit is 2.5% with a final parasitemia of 0.3%. The plates are placed in a 37° C. incubator for 72 hours in a low oxygen environment containing 93% N$_2$, 4% CO$_2$, and 3% O$_2$ gas mixture. 10 μl of lysis buffer (saponin, triton-X, EDTA) containing a 10× solution of SYBR Green I® in RPMI media is dispensed into the plates. The plates are lidded and kept at room temperature overnight for the lysis of the infected red blood cells. The fluorescence intensity is measured (excitation 425 nm, emission 530 nm) using the Envision™ system (Perkin Elmer). The percentage inhibition of 50%, EC$_{50}$, is calculated for each compound.

Compounds of the invention have an EC$_{50}$ of 10 μM or less, preferably less than 1 μM, 750 nM, 500 nM 400 nM, 300 nM, 200 nM, 100 nM and 50 nM. Compounds of the invention can significantly delay the increase in parasitemia.

Compounds of the invention can be assayed to measure their capacity to inhibit proliferation of kinetoplastid parasite *Trypanosoma brucei*. The proliferation is quantified by the addition of Cell Titer Glo (Promega®) a luminescent cell viability assay that measures the number of viable cells in culture based on the quantification of cellular ATP amount, which is an indicator of metabolically active cells.

The following assay illustrates the invention without in any way limiting the scope of the invention. This parasite proliferation assay measures the increase in parasite growth using an assay that measures ATP activity, Cell Titer Glo®.

*Trypanosoma brucei* Lister 427 strain is grown in HMI-9 Trypanosome media for *T. brucei* bloodstream form. 30 μl of HMI-9 media is dispensed into 384 well assay plates. 200 nl of compounds of the invention (in DMSO), including anti-trypanosome controls (Pentamidine and suramin), are then transferred into the assay plates, as well as DMSO alone to serve as a negative control for inhibition. Then 25 μl of a suspension of *T. brucei* culture in HMI-9 media is dispensed into the assay plates. The final concentration of parasites in culture corresponds to 1.7% of 0.5 uM ATP activity with Cell Titer Glo® in HMI-9 media. The plates are placed in a 37° C. incubator for 48 hours in an atmospheric environment containing 5% $CO_2$. 40 μl of Cell Titer Glo® is dispensed into the plates. The plates are then read for luminescence. The percentage inhibition of 50%, $EC_{50}$, is calculated for each compound.

Compounds of the invention have an $EC_{50}$ of 10 μM or less, preferably less than 1 μM, 750 nM, 500 nM 400 nM, 300 nM, 200 nM, 100 nM and 50 nM. Compounds of the invention can significantly delay the proliferation of *T. brucei*. For example, 2-amino-1-(2-(4-fluorophenyl)-3-(4-fluorophenylamino)-8,8-dimethyl-5,6-dihydroimidazo[1,2-a]pyrazin-7(8H)-yl)ethanone (example 412) and 2-amino-1-(3-(3,4-difluorophenylamino)-2-(4-fluorophenyl)-5,6-dihydroimidazo[1,2-a]pyrazin-7(8H)-yl)-2-methylpropan-1-one (Example 29) have an $EC_{50}$ of 10 μM and 7 μM, respectively.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:

1. A method for prevention or treatment of malaria, comprising administering to a subject in need thereof a therapeutically effective amount of a compound and optionally in combination with one or more therapeutic agents, wherein the compound is of Formula 1a:

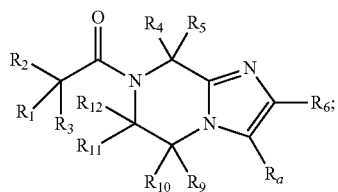

Ia or a pharmaceutically acceptable salt thereof; in which:

$R_a$ is selected from $-X_3NR_7R_8$, $-X_3OR_8$, $-X_3S(O)_{0-2}R_8$, $-X_3C(O)NR_7R_8$, and benzyl optionally substituted with 1 to 3 radicals independently selected from halo, $C_{1-4}$alkyl, halo-substituted-$C_{1-4}$alkyl, $C_{1-4}$alkoxy and halo-substituted-$C_{1-4}$alkoxy; wherein $X_3$ is selected from a bond and $C_{1-4}$alkylene;

$R_1$ is selected from $-OR_B$, $-C(O)OR_{13}$, $-NR_{13}R_{14}$, $C_{6-10}$aryl and a saturated, unsaturated or partially unsaturated 4-9 member heterocyclic ring containing up to three nitrogens; wherein $R_{13}$ is selected from hydrogen, $C_{1-6}$alkyl, halo-substituted-$C_{1-6}$alkyl, hydroxy-substituted-$C_{1-6}$alkyl, $C_{6-10}$aryl-$C_{0-4}$alkyl, $C_{3-8}$cycloalkyl-$C_{0-4}$alkyl, $-X_1NHC(O)R_{15}$, $-X_1C(NH)NHR_{15}$, $-X_1C(O)NHR_{15}$, $-X_1NHR_{15}$, $-X_1OR_{15}$, $-C(O)R_{15}$ and $-C(O)OR_{15}$; wherein $X_1$ is selected from a bond and $C_{1-4}$alkylene; $R_{15}$ is selected from hydrogen, $C_{1-6}$alkyl, halo-substituted-$C_{1-6}$alkyl, and benzyl; and $R_{14}$ is selected from hydrogen, $C_{1-6}$alkyl and hydroxy-substituted-$C_{1-6}$alkyl;

any aryl or heterocyclic of $R_1$ is optionally substituted with 1-3 radicals independently selected from halo, $C_{1-6}$alkyl, halo-substituted-$C_{1-6}$alkyl, $C_{1-6}$alkoxy and halo-substituted-$C_{1-6}$alkoxy;

or $R_{13}$ and $R_{14}$ together with the nitrogen to which $R_{13}$ and $R_{14}$ are attached form a saturated, unsaturated or partially unsaturated 5-9 member heterocyclic ring containing up to three heteroatoms selected from N, $NR_{30}$, $S(O)_{0-2}$ and O; wherein $R_{30}$ is selected from hydrogen and $C_{1-6}$alkyl; wherein said heterocyclic form the combination of $R_{13}$ and $R_{14}$ is optionally substituted with 1 to 3 radicals independently selected from halo, hydroxy, $C_{1-6}$alkyl, amino-substituted-$C_{1-6}$alkyl and halo-substituted-$C_{1-6}$alkyl;

$R_2$ is selected from hydrogen, $C_{1-6}$alkyl, amino, $C_{3-8}$cycloalkyl-$C_{0-4}$alkyl, $C_{6-10}$aryl-$C_{0-4}$alkyl, halo-substituted-$C_{1-6}$alkyl, hydroxy-substituted-$C_{1-6}$alkyl and heterocyclyl-$C_{0-4}$alkyl; wherein said heterocyclyl is a saturated, unsaturated or partially unsaturated 5-9 member heterocyclic ring containing up to three heteroatoms selected from N, $NR_{30}$, $S(O)_{0-2}$ and O; wherein $R_{30}$ is selected from hydrogen and $C_{1-6}$alkyl;

said $C_{6-10}$aryl or heterocyclic of $R_2$ is optionally substituted with 1 to 3 radicals independently selected from halo, hydroxy, cyano, nitro, $-NHR_{17}$, $-(CH_2)_{0-2}NHC(O)R_{17}$, $C_{1-6}$alkyl, halo-substituted-$C_{1-6}$alkyl, amino-substituted-$C_{1-6}$alkyl and $C_{1-6}$alkoxy; wherein $R_{17}$ is selected from hydrogen and $C_{1-6}$alkyl;

$R_3$ is selected from hydrogen, $C_{1-6}$alkyl, $C_{6-10}$aryl-$C_{0-4}$alkyl, $-X_2C(O)OR_{16}$, $-X_2S(O)_{0-2}R_{16}$, $-X_2OR_{16}$, $-X_2C(O)NHR_{16}$ and $-X_2NHC(O)R_{16}$; wherein $X_2$ is selected from a bond and $C_{1-4}$alkylene; and $R_{16}$ is selected from hydrogen, $C_{1-6}$alkyl and $C_{6-10}$aryl-$C_{0-4}$alkyl; wherein said aryl of $R_{16}$ is optionally substituted with 1 to 3 radicals independently selected from halo, $C_{1-6}$alkyl, halo-substituted-$C_{1-6}$alkyl, $C_{1-6}$alkoxy and halo-substituted-$C_{1-6}$alkoxy;

or $R_2$ and $R_3$ together with the carbon atom to which $R_2$ and $R_3$ are attached forms $C_{3-8}$cycloalkyl;

or $R_2$ and $R_{13}$ together with the atoms to which $R_2$ and $R_{13}$ are attached form a ring selected from $C_{3-8}$cycloalkyl and a saturated, unsaturated or partially unsaturated 5-9 member mono or fused heterocyclic ring containing up to three heteroatoms or groups selected from N, C(O), $NR_{30}$, $S(O)_{0-2}$ and O; wherein $R_{30}$ is selected from hydrogen and $C_{1-6}$alkyl; wherein said heterocyclic form the combination of $R_2$ and $R_{13}$ is optionally substituted with 1 to 3 radicals independently selected from halo, hydroxy, $C_{1-6}$alkyl and halo-substituted-$C_{1-6}$alkyl;

$R_4$ is selected from hydrogen and $C_{1-6}$alkyl;

$R_5$ is selected from hydrogen and $C_{1-6}$alkyl; or $R_4$ and $R_5$ together with the carbon atom to which $R_4$ and $R_5$ are attached forms $C_{3-8}$cycloalkyl;

$R_6$ is selected from $C_{6-10}$aryl, $C_{3-8}$cycloalkyl and a saturated, unsaturated or partially unsaturated 5-9 member mono or fused heterocyclic ring containing up to three heteroatoms or groups selected from N, C(O), $NR_{30}$, $S(O)_{0-2}$ and O; wherein $R_{30}$ is selected from hydrogen and $C_{1-6}$alkyl; wherein said aryl or heterocyclic of $R_6$ is optionally substituted by 1 to 3 radicals independently selected from halo, hydroxy, $C_{1-6}$alkyl and $C_{1-6}$alkoxy;

$R_7$ is selected from hydrogen, methyl, ethyl and isopropyl; and $R_8$ is selected from phenyl, benzyl, benzo[d][1,3]dioxol-5-yl, cyclobutyl, cyclopentyl, cycloheptyl, cyclohexyl, bicyclo[2.2.1]heptyl, tetrahydro-2H-pyranyl, pyridinyl, piperidinyl, piperazinyl, quinolinyl, pyrrolidinyl and pyrazolyl; wherein said phenyl, benzyl, benzo[d][1,3]dioxol-5-yl, cyclobutyl, cyclopentyl, cycloheptyl, cyclohexyl, bicyclo[2.2.1]heptyl, tetrahydro-2H-pyranyl, pyridinyl, piperidinyl, piperazinyl, quinolinyl, pyrrolidinyl or pyrazolyl of $R_8$ is optionally substituted by 1 to 3 radicals independently selected from halo, cyano, methyl, ethyl, t-butyl, trifluoromethyl, trifluoromethoxy, dimethyl-amino, difluoromethoxy, carboxy, methoxy-carbonyl, methyl-sulfonyl-amino, methyl-sulfonyl, methyl-amino-carbonyl, phenyl, piperidinyl, piperidinyl-methyl, piperazinyl and piperazinyl-methyl;

$R_9$ is selected from hydrogen and $C_{1-6}$alkyl;
$R_{10}$ is selected from hydrogen and $C_{1-6}$alkyl;
$R_{11}$ is selected from hydrogen and $C_{1-6}$alkyl;
$R_{12}$ is selected from hydrogen and $C_{1-6}$alkyl;
or $R_{11}$ and $R_{12}$ combine to form C(O).

2. The method of claim 1, wherein the one or more therapeutic agents are selected from a kinase inhibitor, an anti-malarial drug and an anti-inflammatory agent.

3. The method of claim 2 wherein the anti-malarial drug is selected from proguanil, chlorproguanil, trimethoprim, chloroquine, mefloquine, lumefantrine, atovaquone, pyrimethamine-sulfadoxine, pyrimethamine-dapsone, halofantrine, quinine, quinidine, amodiaquine, amopyroquine, sulphonamides, artemisinin, arteflene, artemether, artesunate, primaquine, and pyronaridine.

4. The method of claim 3, wherein the compound of claim 1 is administered prior to, simultaneously with, or after the one or more therapeutic agents.

5. The method of claim 1, wherein said subject is a human.

6. The method of claim 1, wherein the compound in which $R_1$ is selected from $-OR_{13}$, $-C(O)OR_{13}$, $-NR_{13}R_{14}$, phenyl, pyridinyl, indolyl, azetidinyl, 1H-indazolyl, piperidinyl and pyrimidinyl; wherein $R_{13}$ is selected from hydrogen, methyl, ethyl, propyl, butyl, pentyl, cyclopropyl, phenyl, benzyl, amino-butyl, hydroxy-ethyl, methoxy-ethyl, butoxy-ethyl, methoxy-propyl, $-C(O)R_{15}$, $-C(O)OR_{15}$, $-X_1OR_{15}$, $-X_1C(NH)NHR_{15}$, $-X_1NHC(O)R_{15}$ and $X_1C(O)NHR_{15}$; wherein $X_1$ is selected from a bond and $C_{1-4}$alkylene; and $R_{15}$ is selected from hydrogen, methyl, ethyl, propyl, butyl, t-butyl, and trifluoromethyl and trifluoromethyl-carbonyl;

$R_{14}$ is selected from hydrogen, methyl, ethyl, propyl, butyl, pentyl, isobutyl, hydroxy-ethyl, and isobutyl;

any phenyl, benzyl or heterocyclic of $R_1$ is optionally substituted with 1-3 radicals independently selected from halo, methyl, ethyl, trifluoromethoxy and trifluoromethyl;

or $R_{13}$ and $R_{14}$ together with the nitrogen to which $R_{13}$ and $R_{14}$ are attached form pyrrolidinyl, morpholino, thiomorpholino and piperidinyl; wherein said heterocyclic form the combination of $R_{13}$ and $R_{14}$ is optionally substituted with 1 to 3 radicals independently selected from halo, trifluoromethyl, hydroxy and amino-ethyl;

$R_2$ is selected from hydrogen, methyl, ethyl, isopropyl, propyl, isobutyl, butyl, t-butyl, trifluoromethyl, trifluoro-ethyl, phenyl, benzyl, phenethyl, cyclobutyl-methyl, cyclopentyl, cyclohexyl, cyclohexyl-methyl, hydroxy-methyl and 1-hydroxy-ethyl; wherein said phenyl, benzyl or phenethyl of $R_2$ is optionally substituted with 1 to 3 radicals independently selected from halo, methoxy, trifluoromethyl, hydroxy, amino, nitro, cyano, amino-methyl, methyl-carbonyl-amino, $-NHR_{17}$, $-CH_2NHC(O)R_{17}$ and $-NHC(O)R_{17}$; wherein $R_{17}$ is selected from hydrogen, ethyl, propyl, butyl and pentyl;

$R_3$ is selected from hydrogen, methyl, methyl-carbonyl-amino-butyl, propyl-amino-carbonyl-methyl, carboxy-methyl, propyl-amino-carbonyl-methyl, butyl-amino-carbonyl-methyl, pentyl-amino-carbonyl-methyl, propyl-amino-carbonyl-ethyl, phenyl, benzyl-sulfanyl-methyl, benzoxy-carbonyl-methyl, methyl-sulfonyl-methyl, 1-(benzyloxy)ethyl, and benzoxy-carbonyl-ethyl;

or $R_2$ and $R_3$ together with the carbon atom to which $R_2$ and $R_3$ are attached form cyclopropyl, cyclobutyl, cyclopentyl or cyclohexyl;

or $R_2$ and $R_{13}$ together with the atoms to which $R_2$ and $R_{13}$ are attached form piperidinyl, cyclobutyl, pyrrolidinyl, morpholino, piperidinyl, tetrahydrofuranyl, tetrahydro-2H-pyran-4-yl, indolyl, 2,6-dioxo-1,2,3,6-tetrahydro-pyrimidin-4-yl, oxopiperidin-3-yl, or 4,5,6,7-tetrahydro-3H-imidazo[4,5-c]pyridin-6-yl.

7. The method of claim 6, wherein the compound in which $R_4$, $R_5$, $R_9$ and $R_{10}$ are independently selected from hydrogen and methyl; and $R_{11}$ and $R_{12}$ are both hydrogen; or $R_{11}$ and $R_{12}$ combine to form C(O).

8. The method of claim 7, wherein the compound in which $R_6$ is selected from phenyl, cyclohexyl and pyridinyl; wherein said phenyl or pyridinyl of $R_6$ is optionally substituted by 1 to 3 radicals independently selected from halo, pentyl, hydroxy, methyl and methoxy.

9. The method of claim 1, wherein the compound is of Formula Id:

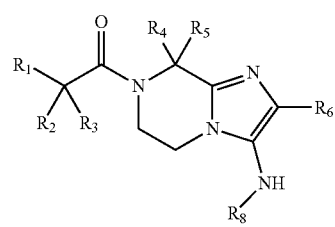

or a pharmaceutically acceptable salt thereof; in which:
$R_1$ is $-NH_2$; $R_2$ and $R_3$ are independently selected from hydrogen and methyl;
$R_4$ and $R_5$ are independently selected from hydrogen and methyl;
$R_6$ is phenyl substituted with a fluoro; and
$R_8$ is a phenyl substituted with 1 to 2 radicals independently selected from chloro and fluoro.

10. The method of claim 1, wherein the compound is selected from:

2-amino-1-(3-(benzo[d][1,3]dioxol-5-ylamino)-2-phenyl-5,6-dihydroimidazo[1,2-a]pyrazin-7(8H)-yl)ethanone;
2-amino-1-{3-[(3,5-dimethylphenyl)amino]-2-phenyl-5H,6H,7H,8H-imidazo[1,2-a]pyrazin-7-yl}ethan-1-one;
2-amino-1-[2-(4-fluorophenyl)-3-[(4-fluorophenyl)amino]-5H,6H,7H,8H-imidazo[1,2-a]pyrazin-7-yl]-2-methylpropan-1-one;
2-amino-1-[2-(4-fluorophenyl)-3-[(4-fluorophenyl)amino]-5H,6H,7H,8H-imidazo[1,2-a]pyrazin-7-yl]ethan-1-one;
2-amino-1-[3-(2H-1,3-benzodioxol-5-ylamino)-2-(4-fluorophenyl)-5H,6H,7H,8H-imidazo[1,2-a]pyrazin-7-yl]-2-methylpropan-1-one;
2-amino-1-[3-(cyclopentylamino)-2-(4-fluorophenyl)-5H,6H,7H,8H-imidazo[1,2-a]pyrazin-7-yl]ethan-1-one;
2-amino-1-[3-(cyclopentylamino)-2-phenyl-5H,6H,7H,8H-imidazo[1,2-a]pyrazin-7-yl]ethan-1-one;
2-amino-2-methyl-1-[2-phenyl-3-(phenylamino)-5H,6H,7H,8H-imidazo[1,2-a]pyrazin-7-yl]propan-1-one;
methyl 4-{[7-(2-amino-2-methylpropanoyl)-2-phenyl-5H,6H,7H,8H-imidazo[1,2-a]pyrazin-3-yl]amino}benzoate;
2-amino-1-[2-(2-fluorophenyl)-3-[(4-fluorophenyl)amino]-5H,6H,7H,8H-imidazo[1,2-a]pyrazin-7-yl]-2-methylpropan-1-one;
2-amino-1-{3-[(4-fluorophenyl)amino]-2-phenyl-5H,6H,7H,8H-imidazo[1,2-a]pyrazin-7-yl}-2-methylpropan-1-one;
2-amino-1-{3-[(4-fluorophenyl)amino]-2-(2,4,6-trifluorophenyl)-5H,6H,7H,8H-imidazo[1,2-a]pyrazin-7-yl}-2-methylpropan-1-one;
2-amino-1-[2-(3,5-difluorophenyl)-3-[(4-fluorophenyl)amino]-5H,6H,7H,8H-imidazo[1,2-a]pyrazin-7-yl]-2-methylpropan-1-one;
2-amino-1-{3-[(4-fluorophenyl)amino]-2-(4-pentylphenyl)-5H,6H,7H,8H-imidazo[1,2-a]pyrazin-7-yl}-2-methylpropan-1-one;
2-amino-1-{2-cyclohexyl-3-[(4-fluorophenyl)amino]-5H,6H,7H,8H-imidazo[1,2-a]pyrazin-7-yl}-2-methylpropan-1-one;
2-amino-1-[2-(4-fluorophenyl)-3-(pyridin-3-ylamino)-5H,6H,7H,8H-imidazo[1,2-a]pyrazin-7-yl]-2-methylpropan-1-one;
(2S)-2-amino-1-[2-(4-fluorophenyl)-3-[(4-fluorophenyl)amino]-5H,6H,7H,8H-imidazo[1,2-a]pyrazin-7-yl]propan-1-one;
(2S)-2-amino-1-[2-(4-fluorophenyl)-3-[(4-fluorophenyl)amino]-5H,6H,7H,8H-imidazo[1,2-a]pyrazin-7-yl]-3-phenylpropan-1-one;
(2R)-2-amino-1-[2-(4-fluorophenyl)-3-[(4-fluorophenyl)amino]-5H,6H,7H,8H-imidazo[1,2-a]pyrazin-7-yl]-3-phenylpropan-1-one;
2-amino-1-{3-[(4-bromophenyl)amino]-2-(4-fluorophenyl)-5H,6H,7H,8H-imidazo[1,2-a]pyrazin-7-yl}-2-methylpropan-1-one;
2-(dimethylamino)-1-[2-(4-fluorophenyl)-3-[(4-fluorophenyl)amino]-5H,6H,7H,8H-imidazo[1,2-a]pyrazin-7-yl]ethan-1-one;
2-amino-1-[3-(benzylamino)-2-(4-fluorophenyl)-5H,6H,7H,8H-imidazo[1,2-a]pyrazin-7-yl]-2-methylpropan-1-one;
N-{2-[2-(4-fluorophenyl)-3-[(4-fluorophenyl)amino]-5H,6H,7H,8H-imidazo[1,2-a]pyrazin-7-yl]-2-oxoethyl}acetamide;
2-amino-1-[3-(cyclohexylamino)-2-(4-fluorophenyl)-5H,6H,7H,8H-imidazo[1,2-a]pyrazin-7-yl]-2-methylpropan-1-one;
2-amino-1-{3-[(3,4-difluorophenyl)amino]-2-(4-fluorophenyl)-5H,6H,7H,8H-imidazo[1,2-a]pyrazin-7-yl}-2-methylpropan-1-one;
2-amino-1-{3-[(3,4-difluorophenyl)amino]-2-(4-fluorophenyl)-5H,6H,7H,8H-imidazo[1,2-a]pyrazin-7-yl}ethan-1-one;
2-amino-1-[2,3-bis(4-fluorophenyl)-5H,6H,7H,8H-imidazo[1,2-a]pyrazin-7-yl]-2-methylpropan-1-one;
1-[2-(4-fluorophenyl)-3-[(4-fluorophenyl)amino]-5H,6H,7H,8H-imidazo[1,2-a]pyrazin-7-yl]-2-(methylamino)ethan-1-one;
1-[2-(4-fluorophenyl)-3-[(4-fluorophenyl)amino]-5H,6H,7H,8H-imidazo[1,2-a]pyrazin-7-yl]-2-(pyrrolidin-1-yl)ethan-1-one;
3-amino-1-[2-(4-fluorophenyl)-3-[(4-fluorophenyl)amino]-5H,6H,7H,8H-imidazo[1,2-a]pyrazin-7-yl]propan-1-one;
2-amino-1-[2-(4-fluorophenyl)-3-[(3-fluorophenyl)amino]-5H,6H,7H,8H-imidazo[1,2-a]pyrazin-7-yl]-2-methylpropan-1-one;
2-amino-1-[2-(4-fluorophenyl)-3-[(3-fluorophenyl)amino]-5H,6H,7H,8H-imidazo[1,2-a]pyrazin-7-yl]ethan-1-one;
2-amino-1-[2-(4-fluorophenyl)-3-[(4-methylphenyl)amino]-5H,6H,7H,8H-imidazo[1,2-a]pyrazin-7-yl]-2-methylpropan-1-one;
2-amino-1-[2-(4-fluorophenyl)-3-[(4-methylphenyl)amino]-5H,6H,7H,8H-imidazo[1,2-a]pyrazin-7-yl]ethan-1-one;
2-amino-1-{3-[(4-chlorophenyl)amino]-2-(4-fluorophenyl)-5H,6H,7H,8H-imidazo[1,2-a]pyrazin-7-yl}-2-methylpropan-1-one;
2-amino-1-{3-[(4-chlorophenyl)amino]-2-(4-fluorophenyl)-5H,6H,7H,8H-imidazo[1,2-a]pyrazin-7-yl}ethan-1-one;
1-[2-(4-fluorophenyl)-3-[(4-fluorophenyl)amino]-5H,6H,7H,8H-imidazo[1,2-a]pyrazin-7-yl]-2-(morpholin-4-yl)ethan-1-one;
4-{2-[2-(4-fluorophenyl)-3-[(4-fluorophenyl)amino]-5H,6H,7H,8H-imidazo[1,2-a]pyrazin-7-yl]-2-oxoethyl}thiomorpholine-1,1-dione;
2-(3,3-difluoropiperidin-1-yl)-1-[2-(4-fluorophenyl)-3-[(4-fluorophenyl)amino]-5H,6H,7H,8H-imidazo[1,2-a]pyrazin-7-yl]ethan-1-one;
1-[2-(4-fluorophenyl)-3-[(4-fluorophenyl)amino]-5H,6H,7H,8H-imidazo[1,2-a]pyrazin-7-yl]-2-hydroxyethan-1-one;
7-[(1-aminocyclopropyl)carbonyl]-N,2-bis(4-fluorophenyl)-5H,6H,7H,8H-imidazo[1,2-a]pyrazin-3-amine;
N-{1-[2-(4-fluorophenyl)-3-[(4-fluorophenyl)amino]-5H,6H,7H,8H-imidazo[1,2-a]pyrazin-7-yl]-2-methyl-1-oxopropan-2-yl}acetamide;
2-amino-1-[2-(4-chlorophenyl)-3-(4-methylphenyl)-5H,6H,7H,8H-imidazo[1,2-a]pyrazin-7-yl]-2-methylpropan-1-one;
benzyl N-{2-[2-(4-fluorophenyl)-3-[(4-fluorophenyl)amino]-5H,6H,7H,8H-imidazo[1,2-a]pyrazin-7-yl]-2-oxoethyl}carbamate;
2-amino-3,3,3-trifluoro-1-[2-(4-fluorophenyl)-3-[(4-fluorophenyl)amino]-5H,6H,7H,8H-imidazo[1,2-a]pyrazin-7-yl]propan-1-one;

2-amino-1-[2-(4-fluoro-2-hydroxyphenyl)-3-[(4-fluorophenyl)amino]-5H,6H,7H,8H-imidazo[1,2-a]pyrazin-7-yl]ethan-1-one;
2-amino-1-{3-[(4-fluorophenyl)amino]-2-(4-methylphenyl)-5H,6H,7H,8H-imidazo[1,2-a]pyrazin-7-yl}ethan-1-one;
2-amino-1-{3-[(4-fluorophenyl)amino]-2-(4-methoxyphenyl)-5H,6H,7H,8H-imidazo[1,2-a]pyrazin-7-yl}ethan-1-one;
2-amino-1-[2-(4-bromophenyl)-3-[(4-fluorophenyl)amino]-5H,6H,7H,8H-imidazo[1,2-a]pyrazin-7-yl]ethan-1-one;
2-amino-1-[2-(4-chlorophenyl)-3-[(4-fluorophenyl)amino]-5H,6H,7H,8H-imidazo[1,2-a]pyrazin-7-yl]ethan-1-one;
2-amino-1-[2-(3-fluorophenyl)-3-[(4-fluorophenyl)amino]-5H,6H,7H,8H-imidazo[1,2-a]pyrazin-7-yl]ethan-1-one;
2-(3,3-difluoropyrrolidin-1-yl)-1-[2-(4-fluorophenyl)-3-[(4-fluorophenyl)amino]-5H,6H,7H,8H-imidazo[1,2-a]pyrazin-7-yl]ethan-1-one;
1-[2-(4-fluorophenyl)-3-[(4-fluorophenyl)amino]-5H,6H,7H,8H-imidazo[1,2-a]pyrazin-7-yl]-2-[(3R)-3-fluoropyrrolidin-1-yl]ethan-1-one;
1-[2-(4-fluorophenyl)-3-[(4-fluorophenyl)amino]-5H,6H,7H,8H-imidazo[1,2-a]pyrazin-7-yl]-2-[(3S)-3-fluoropyrrolidin-1-yl]ethan-1-one;
1-[2-(4-fluorophenyl)-3-[(4-fluorophenyl)amino]-5H,6H,7H,8H-imidazo[1,2-a]pyrazin-7-yl]-2-(4-fluoropiperidin-1-yl)ethan-1-one;
1-[2-(4-fluorophenyl)-3-[(4-fluorophenyl)amino]-5H,6H,7H,8H-imidazo[1,2-a]pyrazin-7-yl]-2-[4-(trifluoromethyl)piperidin-1-yl]ethan-1-one;
2-(4,4-difluoropiperidin-1-yl)-1-[2-(4-fluorophenyl)-3-[(4-fluorophenyl)amino]-5H,6H,7H,8H-imidazo[1,2-a]pyrazin-7-yl]ethan-1-one;
1-[2-(4-fluorophenyl)-3-[(4-fluorophenyl)amino]-5H,6H,7H,8H-imidazo[1,2-a]pyrazin-7-yl]-2-[3-(trifluoromethyl)piperidin-1-yl]ethan-1-one;
1-[2-(4-fluorophenyl)-3-[(4-fluorophenyl)amino]-5H,6H,7H,8H-imidazo[1,2-a]pyrazin-7-yl]-2-(3-hydroxypiperidin-1-yl)ethan-1-one;
2-[(2,2-difluoroethyl)amino]-1-[2-(4-fluorophenyl)-3-[(4-fluorophenyl)amino]-5H,6H,7H,8H-imidazo[1,2-a]pyrazin-7-yl]ethan-1-one;
2-amino-1-{3-[(3,5-difluorophenyl)amino]-2-(4-fluorophenyl)-5H,6H,7H,8H-imidazo[1,2-a]pyrazin-7-yl}-2-methylpropan-1-one;
2-amino-1-{3-[(3,5-difluorophenyl)amino]-2-(4-fluorophenyl)-5H,6H,7H,8H-imidazo[1,2-a]pyrazin-7-yl}ethan-1-one;
2-(cyclopropylamino)-1-[2-(4-fluorophenyl)-3-[(4-fluorophenyl)amino]-5H,6H,7H,8H-imidazo[1,2-a]pyrazin-7-yl]ethan-1-one;
1-[2-(4-fluorophenyl)-3-[(4-fluorophenyl)amino]-5H,6H,7H,8H-imidazo[1,2-a]pyrazin-7-yl]-2-[(2-methylpropyl)amino]ethan-1-one;
2-amino-1-[2-(3-fluorophenyl)-3-[(4-fluorophenyl)amino]-5H,6H,7H,8H-imidazo[1,2-a]pyrazin-7-yl]-2-methylpropan-1-one;
2-amino-1-{3-[(4-chloro-3-fluorophenyl)amino]-2-(4-fluorophenyl)-5H,6H,7H,8H-imidazo[1,2-a]pyrazin-7-yl}ethan-1-one;
2-amino-1-[2-(4-fluorophenyl)-3-{[4-(trifluoromethyl)phenyl]amino}-5H,6H,7H,8H-imidazo[1,2-a]pyrazin-7-yl]-2-methylpropan-1-one;
2-amino-1-[2-(4-fluorophenyl)-3-{[4-(trifluoromethyl)phenyl]amino}-5H,6H,7H,8H-imidazo[1,2-a]pyrazin-7-yl]ethan-1-one;
2-(3,3-difluoropiperidin-1-yl)-1-[2-(4-fluorophenyl)-3-[(4-methylphenyl)amino]-5H,6H,7H,8H-imidazo[1,2-a]pyrazin-7-yl]ethan-1-one;
1-[2-(4-fluorophenyl)-3-[(4-methylphenyl)amino]-5H,6H,7H,8H-imidazo[1,2-a]pyrazin-7-yl]-2-(methylamino)ethan-1-one;
1-{3-[(4-chlorophenyl)amino]-2-(4-fluorophenyl)-5H,6H,7H,8H-imidazo[1,2-a]pyrazin-7-yl}-2-(3,3-difluoropiperidin-1-yl)ethan-1-one;
1-{3-[(4-chlorophenyl)amino]-2-(4-fluorophenyl)-5H,6H,7H,8H-imidazo[1,2-a]pyrazin-7-yl}-2-(methylamino)ethan-1-one;
2-amino-1-{3-[(3-chloro-4-fluorophenyl)amino]-2-(4-fluorophenyl)-5H,6H,7H,8H-imidazo[1,2-a]pyrazin-7-yl}ethan-1-one;
2-amino-1-{3-[(2,4-difluorophenyl)amino]-2-(4-fluorophenyl)-5H,6H,7H,8H-imidazo[1,2-a]pyrazin-7-yl}-2-methylpropan-1-one;
2-amino-1-{3-[(2,4-difluorophenyl)amino]-2-(4-fluorophenyl)-5H,6H,7H,8H-imidazo[1,2-a]pyrazin-7-yl}ethan-1-one;
(2S)-1-[2-(4-fluorophenyl)-3-[(4-methylphenyl)amino]-5H,6H,7H,8H-imidazo[1,2-a]pyrazin-7-yl]-2-hydroxypropan-1-one;
1-[2-(4-fluorophenyl)-3-[(4-methylphenyl)amino]-5H,6H,7H,8H-imidazo[1,2-a]pyrazin-7-yl]-2-hydroxy-2-phenylethan-1-one;
(2S)-2-amino-1-[2-(4-fluorophenyl)-3-[(4-methylphenyl)amino]-5H,6H,7H,8H-imidazo[1,2-a]pyrazin-7-yl]propan-1-one;
(2R)-2-amino-1-[2-(4-fluorophenyl)-3-[(4-methylphenyl)amino]-5H,6H,7H,8H-imidazo[1,2-a]pyrazin-7-yl]propan-1-one;
(2S)-2-amino-1-[2-(4-fluorophenyl)-3-[(4-methylphenyl)amino]-5H,6H,7H,8H-imidazo[1,2-a]pyrazin-7-yl]butan-1-one;
2-(4-fluorophenyl)-N-(4-methylphenyl)-7-{[(3R)-piperidin-3-yl]carbonyl}-5H,6H,7H,8H-imidazo[1,2-a]pyrazin-3-amine;
2-(4-fluorophenyl)-N-(4-methylphenyl)-7-{[(3S)-piperidin-3-yl]carbonyl}-5H,6H,7H,8H-imidazo[1,2-a]pyrazin-3-amine;
2-(4-fluorophenyl)-N-(4-methylphenyl)-7-{[(2R)-pyrrolidin-2-yl]carbonyl}-5H,6H,7H,8H-imidazo[1,2-a]pyrazin-3-amine;
2-(4-fluorophenyl)-N-(4-methylphenyl)-7-{[(2S)-pyrrolidin-2-yl]carbonyl}-5H,6H,7H,8H-imidazo[1,2-a]pyrazin-3-amine;
2-(4-fluorophenyl)-N-(4-methylphenyl)-7-{[(2S)-piperidin-2-yl]carbonyl}-5H,6H,7H,8H-imidazo[1,2-a]pyrazin-3-amine;
2-(4-fluorophenyl)-N-(4-methylphenyl)-7-{[(2R)-piperidin-2-yl]carbonyl}-5H,6H,7H,8H-imidazo[1,2-a]pyrazin-3-amine;
2-amino-1-{3-[(4-chloro-3-fluorophenyl)amino]-2-(4-fluorophenyl)-5H,6H,7H,8H-imidazo[1,2-a]pyrazin-7-yl}-2-methylpropan-1-one;
2-(4-fluorophenyl)-N-(4-methylphenyl)-7-{[(3R)-pyrrolidin-3-yl]carbonyl}-5H,6H,7H,8H-imidazo[1,2-a]pyrazin-3-amine;
2-(4-fluorophenyl)-N-(4-methylphenyl)-7-{[(3S)-pyrrolidin-3-yl]carbonyl}-5H,6H,7H,8H-imidazo[1,2-a]pyrazin-3-amine;

(2R)-2-amino-1-[2-(4-fluorophenyl)-3-[(4-methylphenyl)amino]-5H,6H,7H,8H-imidazo[1,2-a]pyrazin-7-yl]-2-phenylethan-1-one;

(2S)-2-amino-1-[2-(4-fluorophenyl)-3-[(4-methylphenyl)amino]-5H,6H,7H,8H-imidazo[1,2-a]pyrazin-7-yl]-2-phenylethan-1-one;

1-{[2-(4-fluorophenyl)-3-[(4-methylphenyl)amino]-5H,6H,7H,8H-imidazo[1,2-a]pyrazin-7-yl]carbonyl}cyclopropan-1-ol;

1-[2-(4-fluorophenyl)-3-[(4-methylphenyl)amino]-5H,6H,7H,8H-imidazo[1,2-a]pyrazin-7-yl]-3-hydroxy-3-methylbutan-1-one;

N-[(5S)-5-amino-6-[2-(4-fluorophenyl)-3-[(4-methylphenyl)amino]-5H,6H,7H,8H-imidazo[1,2-a]pyrazin-7-yl]-6-oxohexyl]acetamide;

N-[(5S)-5-amino-6-[2-(4-fluorophenyl)-3-[(4-methylphenyl)amino]-5H,6H,7H,8H-imidazo[1,2-a]pyrazin-7-yl]-6-oxohexyl]-2,2,2-trifluoroacetamide;

1-[2-(4-fluorophenyl)-3-[(4-methylphenyl)amino]-5H,6H,7H,8H-imidazo[1,2-a]pyrazin-7-yl]-3-hydroxypropan-1-one;

1-[2-(4-fluorophenyl)-3-[(4-methylphenyl)amino]-5H,6H,7H,8H-imidazo[1,2-a]pyrazin-7-yl]-2-hydroxy-3-methylbutan-1-one;

(2S)-1-[2-(4-fluorophenyl)-3-[(4-methylphenyl)amino]-5H,6H,7H,8H-imidazo[1,2-a]pyrazin-7-yl]-2-hydroxy-3-phenylpropan-1-one;

2-(4-fluorophenyl)-1-[2-(4-fluorophenyl)-3-[(4-methylphenyl)amino]-5H,6H,7H,8H-imidazo[1,2-a]pyrazin-7-yl]-2-hydroxyethan-1-one;

(2R)-1-[2-(4-fluorophenyl)-3-[(4-methylphenyl)amino]-5H,6H,7H,8H-imidazo[1,2-a]pyrazin-7-yl]-2-hydroxy-3-phenylpropan-1-one;

(2S)-1-[2-(4-fluorophenyl)-3-[(4-methylphenyl)amino]-5H,6H,7H,8H-imidazo[1,2-a]pyrazin-7-yl]-2-hydroxy-3,3-dimethylbutan-1-one;

1-[2-(4-fluorophenyl)-3-[(4-methylphenyl)amino]-5H,6H,7H,8H-imidazo[1,2-a]pyrazin-7-yl]-2-hydroxy-2-phenylpropan-1-one;

1-[2-(4-fluorophenyl)-3-[(4-methylphenyl)amino]-5H,6H,7H,8H-imidazo[1,2-a]pyrazin-7-yl]-2-hydroxy-2,2-diphenylethan-1-one;

1-[2-(4-fluorophenyl)-3-[(4-methylphenyl)amino]-5H,6H,7H,8H-imidazo[1,2-a]pyrazin-7-yl]-2-hydroxy-2-(trifluoromethyl)butan-1-one;

1-[2-(4-fluorophenyl)-3-[(4-methylphenyl)amino]-5H,6H,7H,8H-imidazo[1,2-a]pyrazin-7-yl]-2-hydroxy-2-methylpropan-1-one;

1-{[2-(4-fluorophenyl)-3-[(4-methylphenyl)amino]-5H,6H,7H,8H-imidazo[1,2-a]pyrazin-7-yl]carbonyl}cyclopentan-1-ol;

1-{[2-(4-fluorophenyl)-3-[(4-methylphenyl)amino]-5H,6H,7H,8H-imidazo[1,2-a]pyrazin-7-yl]carbonyl}cyclohexan-1-ol;

(2R)-1-[2-(4-fluorophenyl)-3-[(4-methylphenyl)amino]-5H,6H,7H,8H-imidazo[1,2-a]pyrazin-7-yl]-2-hydroxy-4-phenylbutan-1-one;

(2S)-2-cyclohexyl-1-[2-(4-fluorophenyl)-3-[(4-methylphenyl)amino]-5H,6H,7H,8H-imidazo[1,2-a]pyrazin-7-yl]-2-hydroxyethan-1-one;

1-[2-(4-fluorophenyl)-3-[(4-methylphenyl)amino]-5H,6H,7H,8H-imidazo[1,2-a]pyrazin-7-yl]-2-hydroxy-2-(4-methoxyphenyl)ethan-1-one;

2-(3,5-difluorophenyl)-1-[2-(4-fluorophenyl)-3-[(4-methylphenyl)amino]-5H,6H,7H,8H-imidazo[1,2-a]pyrazin-7-yl]-2-hydroxyethan-1-one;

1-[2-(4-fluorophenyl)-3-[(4-methylphenyl)amino]-5H,6H,7H,8H-imidazo[1,2-a]pyrazin-7-yl]-2-hydroxy-2-[3-(trifluoromethyl)phenyl]ethan-1-one;

1-[2-(4-fluorophenyl)-3-[(4-methylphenyl)amino]-5H,6H,7H,8H-imidazo[1,2-a]pyrazin-7-yl]-2-methoxy-2-phenylethan-1-one;

2-(4-bromophenyl)-1-[2-(4-fluorophenyl)-3-[(4-methylphenyl)amino]-5H,6H,7H,8H-imidazo[1,2-a]pyrazin-7-yl]-2-hydroxyethan-1-one;

1-[2-(4-fluorophenyl)-3-[(4-methylphenyl)amino]-5H,6H,7H,8H-imidazo[1,2-a]pyrazin-7-yl]-2-hydroxy-2-[4-(trifluoromethyl)phenyl]ethan-1-one;

3,3,3-trifluoro-1-[2-(4-fluorophenyl)-3-[(4-methylphenyl)amino]-5H,6H,7H,8H-imidazo[1,2-a]pyrazin-7-yl]-2-methoxy-2-phenylpropan-1-one;

1-[2-(4-fluorophenyl)-3-[(4-methylphenyl)amino]-5H,6H,7H,8H-imidazo[1,2-a]pyrazin-7-yl]-2-hydroxy-2-(3-hydroxyphenyl)ethan-1-one;

1-[2-(4-fluorophenyl)-3-[(4-methylphenyl)amino]-5H,6H,7H,8H-imidazo[1,2-a]pyrazin-7-yl]-2-hydroxy-2-(4-hydroxyphenyl)ethan-1-one;

2-(2-chlorophenyl)-1-[2-(4-fluorophenyl)-3-[(4-methylphenyl)amino]-5H,6H,7H,8H-imidazo[1,2-a]pyrazin-7-yl]-2-hydroxyethan-1-one;

2-(4-bromo-2-fluorophenyl)-1-[2-(4-fluorophenyl)-3-[(4-methylphenyl)amino]-5H,6H,7H,8H-imidazo[1,2-a]pyrazin-7-yl]-2-hydroxyethan-1-one;

2-(4-chlorophenyl)-1-[2-(4-fluorophenyl)-3-[(4-methylphenyl)amino]-5H,6H,7H,8H-imidazo[1,2-a]pyrazin-7-yl]-2-hydroxyethan-1-one;

(2S)-1-[2-(4-fluorophenyl)-3-[(4-methylphenyl)amino]-5H,6H,7H,8H-imidazo[1,2-a]pyrazin-7-yl]-2-hydroxy-4-methylpentan-1-one;

(2R)-1-[2-(4-fluorophenyl)-3-[(4-methylphenyl)amino]-5H,6H,7H,8H-imidazo[1,2-a]pyrazin-7-yl]-2-hydroxy-2-phenylethan-1-one;

(2S)-1-[2-(4-fluorophenyl)-3-[(4-methylphenyl)amino]-5H,6H,7H,8H-imidazo[1,2-a]pyrazin-7-yl]-2-hydroxy-2-phenylethan-1-one;

7-[(1-aminocyclobutyl)carbonyl]-2-(4-fluorophenyl)-N-(4-methylphenyl)-5H,6H,7H,8H-imidazo[1,2-a]pyrazin-3-amine;

7-[(1-aminocyclopentyl)carbonyl]-2-(4-fluorophenyl)-N-(4-methylphenyl)-5H,6H,7H,8H-imidazo[1,2-a]pyrazin-3-amine;

7-[(1-aminocyclohexyl)carbonyl]-2-(4-fluorophenyl)-N-(4-methylphenyl)-5H,6H,7H,8H-imidazo[1,2-a]pyrazin-3-amine;

2-amino-4,4,4-trifluoro-1-[2-(4-fluorophenyl)-3-[(4-methylphenyl)amino]-5H,6H,7H,8H-imidazo[1,2-a]pyrazin-7-yl]butan-1-one;

2-amino-3,3,3-trifluoro-1-[2-(4-fluorophenyl)-3-[(4-methylphenyl)amino]-5H,6H,7H,8H-imidazo[1,2-a]pyrazin-7-yl]propan-1-one;

(2S)-3-cyclohexyl-1-[2-(4-fluorophenyl)-3-[(4-methylphenyl)amino]-5H,6H,7H,8H-imidazo[1,2-a]pyrazin-7-yl]-2-hydroxypropan-1-one;

2-(benzylamino)-1-[2-(4-fluorophenyl)-3-[(4-methylphenyl)amino]-5H,6H,7H,8H-imidazo[1,2-a]pyrazin-7-yl]ethan-1-one;

2-(dipropylamino)-1-[2-(4-fluorophenyl)-3-[(4-methylphenyl)amino]-5H,6H,7H,8H-imidazo[1,2-a]pyrazin-7-yl]ethan-1-one;

(2S)-2-(dipropylamino)-1-[2-(4-fluorophenyl)-3-[(4-methylphenyl)amino]-5H,6H,7H,8H-imidazo[1,2-a]pyrazin-7-yl]propan-1-one;

(2S)-1-[2-(4-fluorophenyl)-3-[(4-methylphenyl)amino]-5H,6H,7H,8H-imidazo[1,2-a]pyrazin-7-yl]-2-(methylamino)-3-phenylpropan-1-one;

benzyl(4S)-4-{[(tert-butoxy)carbonyl]amino}-5-[2-(4-fluorophenyl)-3-[(4-methylphenyl)amino]-5H,6H,7H,8H-imidazo[1,2-a]pyrazin-7-yl]-5-oxopentanoate;

benzyl (3 S)-3-{[(tert-butoxy)carbonyl]amino}-4-[2-(4-fluorophenyl)-3-[(4-methylphenyl)amino]-5H,6H,7H,8H-imidazo[1,2-a]pyrazin-7-yl]-4-oxobutanoate;

2-(cyclopropylamino)-1-[2-(4-fluorophenyl)-3-[(4-methylphenyl)amino]-5H,6H,7H,8H-imidazo[1,2-a]pyrazin-7-yl]ethan-1-one;

N-[4-({2-[2-(4-fluorophenyl)-3-[(4-methylphenyl)amino]-5H,6H,7H,8H-imidazo[1,2-a]pyrazin-7-yl]-2-oxoethyl}amino)butyl]acetamide;

(2S)-2,6-diamino-1-[2-(4-fluorophenyl)-3-[(4-methylphenyl)amino]-5H,6H,7H,8H-imidazo[1,2-a]pyrazin-7-yl]hexan-1-one;

(2S)-2-amino-3-(4-aminophenyl)-1-[2-(4-fluorophenyl)-3-[(4-methylphenyl)amino]-5H,6H,7H,8H-imidazo[1,2-a]pyrazin-7-yl]propan-1-one;

N-[(5S)-5-amino-6-[2-(4-fluorophenyl)-3-[(4-methylphenyl)amino]-5H,6H,7H,8H-imidazo[1,2-a]pyrazin-7-yl]-6-oxohexyl]butanamide;

N-{4-[(2S)-2-amino-3-[2-(4-fluorophenyl)-3-[(4-methylphenyl)amino]-5H,6H,7H,8H-imidazo[1,2-a]pyrazin-7-yl]-3-oxopropyl]phenyl}acetamide;

2-[bis(2-hydroxyethyl)amino]-1-[2-(4-fluorophenyl)-3-[(4-methylphenyl)amino]-5H,6H,7H,8H-imidazo[1,2-a]pyrazin-7-yl]ethan-1-one;

(2S)-2-amino-1-[2-(4-fluorophenyl)-3-[(4-methylphenyl)amino]-5H,6H,7H,8H-imidazo[1,2-a]pyrazin-7-yl]-3-hydroxypropan-1-one;

2,2,2-trifluoro-N-[(2S)-1-[2-(4-fluorophenyl)-3-[(4-methylphenyl)amino]-5H,6H,7H,8H-imidazo[1,2-a]pyrazin-7-yl]-3-hydroxy-1-oxopropan-2-yl]acetamide;

1-{2-[2-(4-fluorophenyl)-3-[(4-methylphenyl)amino]-5H,6H,7H,8H-imidazo[1,2-a]pyrazin-7-yl]-2-oxoethyl}guanidine;

1-[2-(4-fluorophenyl)-3-[(4-methylphenyl)amino]-5H,6H,7H,8H-imidazo[1,2-a]pyrazin-7-yl]-2-(phenylamino)ethan-1-one;

(2S)-2-amino-1-[2-(4-fluorophenyl)-3-[(4-methylphenyl)amino]-5H,6H,7H,8H-imidazo[1,2-a]pyrazin-7-yl]-3-methylbutan-1-one;

(2S)-2-amino-1-[2-(4-fluorophenyl)-3-[(4-methylphenyl)amino]-5H,6H,7H,8H-imidazo[1,2-a]pyrazin-7-yl]-3,3-dimethylbutan-1-one;

2-(4-chlorophenyl)-1-[2-(4-fluorophenyl)-3-[(4-methylphenyl)amino]-5H,6H,7H,8H-imidazo[1,2-a]pyrazin-7-yl]propan-1-one;

2-(4-chlorophenyl)-1-[2-(4-fluorophenyl)-3-[(4-methylphenyl)amino]-5H,6H,7H,8H-imidazo[1,2-a]pyrazin-7-yl]-2-methylpropan-1-one;

(2S)-1-[2-(4-fluorophenyl)-3-[(4-methylphenyl)amino]-5H,6H,7H,8H-imidazo[1,2-a]pyrazin-7-yl]-2-phenylpropan-1-one;

2-(4-fluorophenyl)-7-{[(6S)-1H,4H,5H,6H,7H-imidazo[4,5-c]pyridin-6-yl]carbonyl}-N-(4-methylphenyl)-5H,6H,7H,8H-imidazo[1,2-a]pyrazin-3-amine;

(2S)-2-(dimethylamino)-1-[2-(4-fluorophenyl)-3-[(4-methylphenyl)amino]-5H,6H,7H,8H-imidazo[1,2-a]pyrazin-7-yl]-3-phenylpropan-1-one;

2-[4-(2-aminoethyl)piperidin-1-yl]-1-[2-(4-fluorophenyl)-3-[(4-methylphenyl)amino]-5H,6H,7H,8H-imidazo[1,2-a]pyrazin-7-yl]ethan-1-one;

tert-butyl N-[(2S)-1-[2-(4-fluorophenyl)-3-[(4-methylphenyl)amino]-5H,6H,7H,8H-imidazo[1,2-a]pyrazin-7-yl]-1-oxo-3-(4-propanamidophenyl)propan-2-yl]carbamate;

tert-butyl N-[(2S)-1-[2-(4-fluorophenyl)-3-[(4-methylphenyl)amino]-5H,6H,7H,8H-imidazo[1,2-a]pyrazin-7-yl]-1-oxo-3-(propylcarbamoyl)propan-2-yl]carbamate;

N-{4-[(2S)-2-amino-3-[2-(4-fluorophenyl)-3-[(4-methylphenyl)amino]-5H,6H,7H,8H-imidazo[1,2-a]pyrazin-7-yl]-3-oxopropyl]phenyl}propanamide;

(4S)-4-amino-5-[2-(4-fluorophenyl)-3-[(4-methylphenyl)amino]-5H,6H,7H,8H-imidazo[1,2-a]pyrazin-7-yl]-5-oxo-N-propylpentanamide;

(3S)-3-amino-4-[2-(4-fluorophenyl)-3-[(4-methylphenyl)amino]-5H,6H,7H,8H-imidazo[1,2-a]pyrazin-7-yl]-4-oxo-N-propylbutanamide;

2-amino-1-{3-[(4-chloro-3-fluorophenyl)amino]-2-(4-fluorophenyl)-5H,6H,7H,8H-imidazo[1,2-a]pyrazin-7-yl}-3,3,3-trifluoropropan-1-one;

(2R)-2-amino-3,3,3-trifluoro-1-[2-(4-fluorophenyl)-3-[(4-fluorophenyl)amino]-5H,6H,7H,8H-imidazo[1,2-a]pyrazin-7-yl]propan-1-one;

(2S)-2-amino-3,3,3-trifluoro-1-[2-(4-fluorophenyl)-3-[(4-fluorophenyl)amino]-5H,6H,7H,8H-imidazo[1,2-a]pyrazin-7-yl]propan-1-one;

N-{4-[(2S)-2-amino-3-[2-(4-fluorophenyl)-3-[(4-methylphenyl)amino]-5H,6H,7H,8H-imidazo[1,2-a]pyrazin-7-yl]-3-oxopropyl]phenyl}butanamide;

(2S)-1-[2-(4-fluorophenyl)-3-[(4-methylphenyl)amino]-5H,6H,7H,8H-imidazo[1,2-a]pyrazin-7-yl]-2-methoxypropan-1-one;

2-(4-fluorophenyl)-N-(4-methylphenyl)-7-{[(2R)-oxolan-2-yl]carbonyl}-5H,6H,7H,8H-imidazo[1,2-a]pyrazin-3-amine;

2-(4-fluorophenyl)-N-(4-methylphenyl)-7-{[(2S)-oxolan-2-yl]carbonyl}-5H,6H,7H,8H-imidazo[1,2-a]pyrazin-3-amine;

1-[2-(4-fluorophenyl)-3-[(4-methylphenyl)amino]-5H,6H,7H,8H-imidazo[1,2-a]pyrazin-7-yl]-2-phenoxybutan-1-one;

1-[2-(4-fluorophenyl)-3-[(4-methylphenyl)amino]-5H,6H,7H,8H-imidazo[1,2-a]pyrazin-7-yl]-2-phenoxypropan-1-one;

2-(3-chlorophenoxy)-1-[2-(4-fluorophenyl)-3-[(4-methylphenyl)amino]-5H,6H,7H,8H-imidazo[1,2-a]pyrazin-7-yl]propan-1-one;

(2S)-1-[2-(4-fluorophenyl)-3-[(4-methylphenyl)amino]-5H,6H,7H,8H-imidazo[1,2-a]pyrazin-7-yl]-2-hydroxy-3-methylbutan-1-one;

(2R)-1-[2-(4-fluorophenyl)-3-[(4-methylphenyl)amino]-5H,6H,7H,8H-imidazo[1,2-a]pyrazin-7-yl]-2-hydroxy-3-methylbutan-1-one;

1-[2-(4-fluorophenyl)-3-[(4-methylphenyl)amino]-5H,6H,7H,8H-imidazo[1,2-a]pyrazin-7-yl]-2-(pyrimidin-4-yl)ethan-1-one;

1-[2-(4-fluorophenyl)-3-[(4-methylphenyl)amino]-5H,6H,7H,8H-imidazo[1,2-a]pyrazin-7-yl]-3-methyl-2-(2-methylphenoxy)butan-1-one;

2-(4-fluorophenyl)-N-(4-methylphenyl)-7-[(oxan-4-yl)carbonyl]-5H,6H,7H,8H-imidazo[1,2-a]pyrazin-3-amine;

(2S)-2-ethoxy-1-[2-(4-fluorophenyl)-3-[(4-methylphenyl)amino]-5H,6H,7H,8H-imidazo[1,2-a]pyrazin-7-yl]-3-(4-hydroxyphenyl)propan-1-one;

1-[2-(4-fluorophenyl)-3-[(4-methylphenyl)amino]-5H, 6H,7H,8H-imidazo[1,2-a]pyrazin-7-yl]-2-(oxolan-2-yl)ethan-1-one;

2-(4-fluorophenyl)-N-(4-methylphenyl)-7-[(oxolan-3-yl)carbonyl]-5H,6H,7H,8H-imidazo[1,2-a]pyrazin-3-amine;

2-(1-ethylpiperidin-4-yl)-1-[2-(4-fluorophenyl)-3-[(4-methylphenyl)amino]-5H,6H,7H,8H-imidazo[1,2-a]pyrazin-7-yl]ethan-1-one;

N-({4-[(2S)-2-amino-3-[2-(4-fluorophenyl)-3-[(4-methylphenyl)amino]-5H,6H,7H,8H-imidazo[1,2-a]pyrazin-7-yl]-3-oxopropyl]phenyl}methyl)butanamide;

N-({4-[(2S)-2-amino-3-[2-(4-fluorophenyl)-3-[(4-methylphenyl)amino]-5H,6H,7H,8H-imidazo[1,2-a]pyrazin-7-yl]-3-oxopropyl]phenyl}methyl)propanamide;

1-[2-(4-fluorophenyl)-3-[(4-methylphenyl)amino]-5H, 6H,7H,8H-imidazo[1,2-a]pyrazin-7-yl]-2-(piperidin-4-yl)ethan-1-one;

2-amino-1-{3-[(4-chloro-3-fluorophenyl)amino]-2-(3-fluorophenyl)-5H,6H,7H,8H-imidazo[1,2-a]pyrazin-7-yl}-3,3,3-trifluoropropan-1-one;

(2R)-1-{3-[(4-chloro-3-fluorophenyl)amino]-2-(3-fluorophenyl)-5H,6H,7H,8H-imidazo[1,2-a]pyrazin-7-yl}-2-phenylpropan-1-one;

(2S)-1-{3-[(4-chloro-3-fluorophenyl)amino]-2-(3-fluorophenyl)-5H,6H,7H,8H-imidazo[1,2-a]pyrazin-7-yl}-2-phenylpropan-1-one;

(2R)-1-[2-(4-fluorophenyl)-3-[(4-methylphenyl)amino]-5H,6H,7H,8H-imidazo[1,2-a]pyrazin-7-yl]-2-phenylbutan-1-one;

(2S)-1-[2-(4-fluorophenyl)-3-[(4-methylphenyl)amino]-5H,6H,7H,8H-imidazo[1,2-a]pyrazin-7-yl]-2-phenylbutan-1-one;

2-cyclopentyl-1-[2-(4-fluorophenyl)-3-[(4-methylphenyl)amino]-5H,6H,7H,8H-imidazo[1,2-a]pyrazin-7-yl]-2-phenylethan-1-one;

1-[2-(4-fluorophenyl)-3-[(4-methylphenyl)amino]-5H, 6H,7H,8H-imidazo[1,2-a]pyrazin-7-yl]-2-(pyridin-4-yl)ethan-1-one;

2-amino-1-{3-[(4-chloro-3-fluorophenyl)amino]-2-(3-fluorophenyl)-5H,6H,7H,8H-imidazo[1,2-a]pyrazin-7-yl}ethan-1-one;

2-amino-1-{3-[(4-chloro-3-fluorophenyl)amino]-2-(3-fluorophenyl)-5H,6H,7H,8H-imidazo[1,2-a]pyrazin-7-yl}-2-methylpropan-1-one;

2-(3,5-dichlorophenyl)-1-[2-(4-fluorophenyl)-3-[(4-methylphenyl)amino]-5H,6H,7H,8H-imidazo[1,2-a]pyrazin-7-yl]ethan-1-one;

1-[2-(4-fluorophenyl)-3-[(4-methylphenyl)amino]-5H, 6H,7H,8H-imidazo[1,2-a]pyrazin-7-yl]-3-methyl-2-phenylbutan-1-one;

1-[2-(4-fluorophenyl)-3-[(4-methylphenyl)amino]-5H, 6H,7H,8H-imidazo[1,2-a]pyrazin-7-yl]-2-(4-methylphenyl)ethan-1-one;

2-(4-fluorophenyl)-1-[2-(4-fluorophenyl)-3-[(4-methylphenyl)amino]-5H,6H,7H,8H-imidazo[1,2-a]pyrazin-7-yl]ethan-1-one;

1-[2-(3-fluorophenyl)-3-[(4-fluorophenyl)amino]-5H,6H, 7H,8H-imidazo[1,2-a]pyrazin-7-yl]-3-hydroxy-3-methylbutan-1-one;

benzyl(3S)-3-{[(tert-butoxy)carbonyl]amino}-4-{3-[(4-chloro-3-fluorophenyl)amino]-2-(3-fluorophenyl)-5H, 6H,7H,8H-imidazo[1,2-a]pyrazin-7-yl}-4-oxobutanoate;

benzyl (3 S)-3-{[(tert-butoxy)carbonyl]amino}-4-[2-(3-fluorophenyl)-3-[(4-fluorophenyl)amino]-5H,6H,7H, 8H-imidazo[1,2-a]pyrazin-7-yl]-4-oxobutanoate;

tert-butyl N-[(2S)-1-{3-[(4-chloro-3-fluorophenyl)amino]-2-(3-fluorophenyl)-5H,6H,7H,8H-imidazo[1, 2-a]pyrazin-7-yl}-3-(4-nitrophenyl)-1-oxopropan-2-yl]carbamate;

tert-butyl N-[(2S)-1-[2-(3-fluorophenyl)-3-[(4-fluorophenyl)amino]-5H,6H,7H,8H-imidazo[1,2-a]pyrazin-7-yl]-3-(4-nitrophenyl)-1-oxopropan-2-yl]carbamate;

(3 S)-3-{[(tert-butoxy)carbonyl]amino}-4-{3-[(4-chloro-3-fluorophenyl)amino]-2-(3-fluorophenyl)-5H,6H,7H, 8H-imidazo[1,2-a]pyrazin-7-yl}-4-oxobutanoic acid;

(3 S)-3-{[(tert-butoxy)carbonyl]amino}-4-[2-(3-fluorophenyl)-3-[(4-fluorophenyl)amino]-5H,6H,7H,8H-imidazo[1,2-a]pyrazin-7-yl]-4-oxobutanoic acid;

tert-butyl N-[(2S)-3-(4-aminophenyl)-1-{3-[(4-chloro-3-fluorophenyl)amino]-2-(3-fluorophenyl)-5H,6H,7H, 8H-imidazo[1,2-a]pyrazin-7-yl}-1-oxopropan-2-yl]carbamate;

tert-butyl N-[(2S)-3-(4-aminophenyl)-1-[2-(3-fluorophenyl)-3-[(4-fluorophenyl)amino]-5H,6H,7H,8H-imidazo[1,2-a]pyrazin-7-yl]-1-oxopropan-2-yl]carbamate;

1-[2-(4-fluorophenyl)-3-[(4-methylphenyl)amino]-5H, 6H,7H,8H-imidazo[1,2-a]pyrazin-7-yl]-3-hydroxy-2, 2-dimethylpropan-1-one;

1-[2-(4-fluorophenyl)-3-[(4-methylphenyl)amino]-5H, 6H,7H,8H-imidazo[1,2-a]pyrazin-7-yl]-3-hydroxy-2-(hydroxymethyl)-2-methylpropan-1-one;

tert-butyl N-[(2S)-3-(3-aminophenyl)-1-[2-(4-fluorophenyl)-3-[(4-methylphenyl)amino]-5H,6H,7H,8H-imidazo[1,2-a]pyrazin-7-yl]-1-oxopropan-2-yl]carbamate;

tert-butyl N-[(2S)-1-{3-[(4-chloro-3-fluorophenyl)amino]-2-(3-fluorophenyl)-5H,6H,7H,8H-imidazo[1, 2-a]pyrazin-7-yl}-1-oxo-3-(propylcarbamoyl)propan-2-yl]carbamate;

tert-butyl N-[(2S)-1-[2-(3-fluorophenyl)-3-[(4-fluorophenyl)amino]-5H,6H,7H,8H-imidazo[1,2-a]pyrazin-7-yl]-1-oxo-3-(propylcarbamoyl)propan-2-yl]carbamate;

tert-butyl N-[(2S)-1-[2-(3-fluorophenyl)-3-[(4-fluorophenyl)amino]-5H,6H,7H,8H-imidazo[1,2-a]pyrazin-7-yl]-1-oxo-3-(pentylcarbamoyl)propan-2-yl]carbamate;

tert-butyl N-[(2S)-1-{3-[(4-chloro-3-fluorophenyl)amino]-2-(3-fluorophenyl)-5H,6H,7H,8H-imidazo[1, 2-a]pyrazin-7-yl}-1-oxo-3-(4-pentanamidophenyl)propan-2-yl]carbamate;

tert-butyl N-[(2S)-1-{3-[(4-chloro-3-fluorophenyl)amino]-2-(3-fluorophenyl)-5H,6H,7H,8H-imidazo[1, 2-a]pyrazin-7-yl}-1-oxo-3-(4-propanamidophenyl)propan-2-yl]carbamate;

tert-butyl N-[(2S)-1-[2-(3-fluorophenyl)-3-[(4-fluorophenyl)amino]-5H,6H,7H,8H-imidazo[1,2-a]pyrazin-7-yl]-1-oxo-3-(4-pentanamidophenyl)propan-2-yl]carbamate;

(3S)-3-amino-4-{3-[(4-chloro-3-fluorophenyl)amino]-2-(3-fluorophenyl)-5H,6H,7H,8H-imidazo[1,2-a]pyrazin-7-yl}-4-oxo-N-propylbutanamide;

(3S)-3-amino-4-[2-(3-fluorophenyl)-3-[(4-fluorophenyl)amino]-5H,6H,7H,8H-imidazo[1,2-a]pyrazin-7-yl]-4-oxo-N-propylbutanamide;

(3S)-3-amino-4-[2-(3-fluorophenyl)-3-[(4-fluorophenyl)amino]-5H,6H,7H,8H-imidazo[1,2-a]pyrazin-7-yl]-4-oxo-N-pentylbutanamide;

N-{4-[(2S)-2-amino-3-{3-[(4-chloro-3-fluorophenyl)amino]-2-(3-fluorophenyl)-5H,6H,7H,8H-imidazo[1, 2-a]pyrazin-7-yl}-3-oxopropyl]phenyl}pentanamide;

N-{4-[(2S)-2-amino-3-{3-[(4-chloro-3-fluorophenyl)amino]-2-(3-fluorophenyl)-5H,6H,7H,8H-imidazo[1,2-a]pyrazin-7-yl}-3-oxopropyl]phenyl}propanamide;

N-{4-[(2S)-2-amino-3-[2-(3-fluorophenyl)-3-[(4-fluorophenyl)amino]-5H,6H,7H,8H-imidazo[1,2-a]pyrazin-7-yl]-3-oxopropyl]phenyl}pentanamide;

N-{4-[(2S)-2-amino-3-[2-(3-fluorophenyl)-3-[(4-fluorophenyl)amino]-5H,6H,7H,8H-imidazo[1,2-a]pyrazin-7-yl]-3-oxopropyl]phenyl}propanamide;

4-{[7-(2-amino-2-methylpropanoyl)-2-(4-fluorophenyl)-5H,6H,7H,8H-imidazo[1,2-a]pyrazin-3-yl]amino}benzonitrile;

4-{[7-(2-aminoacetyl)-2-(4-fluorophenyl)-5H,6H,7H,8H-imidazo[1,2-a]pyrazin-3-yl]amino}benzonitrile;

tert-butyl N-[(2S)-1-[2-(4-fluorophenyl)-3-[(4-methylphenyl)amino]-5H,6H,7H,8H-imidazo[1,2-a]pyrazin-7-yl]-1-oxo-3-[4-(pentylamino)phenyl]propan-2-yl]carbamate;

2-[2-(4-fluorophenyl)-3-[(4-methylphenyl)amino]-5H,6H,7H,8H-imidazo[1,2-a]pyrazin-7-yl]-2-oxo-1-phenylethyl propanoate;

2-[2-(4-fluorophenyl)-3-[(4-methylphenyl)amino]-5H,6H,7H,8H-imidazo[1,2-a]pyrazin-7-yl]-2-oxo-1-phenylethyl butanoate;

2-[2-(4-fluorophenyl)-3-[(4-methylphenyl)amino]-5H,6H,7H,8H-imidazo[1,2-a]pyrazin-7-yl]-2-oxo-1-phenylethyl pentanoate;

(2S)-2-amino-1-[2-(4-fluorophenyl)-3-[(4-methylphenyl)amino]-5H,6H,7H,8H-imidazo[1,2-a]pyrazin-7-yl]-3-[4-(pentylamino)phenyl]propan-1-one;

(2S)-1-{3-[(4-chloro-3-fluorophenyl)amino]-2-(4-fluorophenyl)-5H,6H,7H,8H-imidazo[1,2-a]pyrazin-7-yl}-2-[(2-hydroxypropyl)amino]-3-phenylpropan-1-one;

(2S)-1-{3-[(4-chloro-3-fluorophenyl)amino]-2-(4-fluorophenyl)-5H,6H,7H,8H-imidazo[1,2-a]pyrazin-7-yl}-2-[(2-methoxyethyl)amino]-3-phenylpropan-1-one;

(2R)-2-amino-1-[2-(4-fluorophenyl)-3-[(4-methylphenyl)amino]-5H,6H,7H,8H-imidazo[1,2-a]pyrazin-7-yl]-3-hydroxypropan-1-one;

(2R,3S)-2-amino-1-[2-(4-fluorophenyl)-3-[(4-methylphenyl)amino]-5H,6H,7H,8H-imidazo[1,2-a]pyrazin-7-yl]-3-hydroxybutan-1-one;

(2S)-2-amino-1-[2-(4-fluorophenyl)-3-[(4-methylphenyl)amino]-5H,6H,7H,8H-imidazo[1,2-a]pyrazin-7-yl]-4-methanesulfonylbutan-1-one;

(3R)-3-amino-4-[2-(4-fluorophenyl)-3-[(4-methylphenyl)amino]-5H,6H,7H,8H-imidazo[1,2-a]pyrazin-7-yl]-4-oxobutanoic acid;

(2R)-2-amino-1-[2-(4-fluorophenyl)-3-[(4-methylphenyl)amino]-5H,6H,7H,8H-imidazo[1,2-a]pyrazin-7-yl]-3-methanesulfonylpropan-1-one;

N-[(1S)-2-[2-(4-fluorophenyl)-3-[(4-methylphenyl)amino]-5H,6H,7H,8H-imidazo[1,2-a]pyrazin-7-yl]-2-oxo-1-phenylethyl]propanamide;

N-[(1S)-2-[2-(4-fluorophenyl)-3-[(4-methylphenyl)amino]-5H,6H,7H,8H-imidazo[1,2-a]pyrazin-7-yl]-2-oxo-1-phenylethyl]butanamide;

2-amino-1-{3-[(4-chloro-3-fluorophenyl)(methyl)amino]-2-(4-fluorophenyl)-5H,6H,7H,8H-imidazo[1,2-a]pyrazin-7-yl}ethan-1-one;

2-amino-1-{3-[(4-chloro-3-fluorophenyl)(methyl)amino]-2-(4-fluorophenyl)-5H,6H,7H,8H-imidazo[1,2-a]pyrazin-7-yl}-2-methylpropan-1-one;

(2S)-2-(butylamino)-1-[2-(4-fluorophenyl)-3-[(4-methylphenyl)amino]-5H,6H,7H,8H-imidazo[1,2-a]pyrazin-7-yl]-2-phenylethan-1-one;

(2S)-1-[2-(4-fluorophenyl)-3-[(4-methylphenyl)amino]-5H,6H,7H,8H-imidazo[1,2-a]pyrazin-7-yl]-2-(pentylamino)-2-phenylethan-1-one;

(2S)-2-amino-1-{3-[(4-chloro-3-fluorophenyl)amino]-2-(4-fluorophenyl)-5H,6H,7H,8H-imidazo[1,2-a]pyrazin-7-yl}-3-methoxypropan-1-one;

1-{3-[(4-chloro-3-fluorophenyl)amino]-2-(4-fluorophenyl)-5H,6H,7H,8H-imidazo[1,2-a]pyrazin-7-yl}-2-(pyridin-4-yl)ethan-1-one;

1-{3-[(4-chloro-3-fluorophenyl)amino]-2-(4-fluorophenyl)-5H,6H,7H,8H-imidazo[1,2-a]pyrazin-7-yl}-2-(1H-indol-1-yl)ethan-1-one;

1-{3-[(4-chloro-3-fluorophenyl)amino]-2-(4-fluorophenyl)-5H,6H,7H,8H-imidazo[1,2-a]pyrazin-7-yl}-2-(1-ethylpiperidin-4-yl)ethan-1-one;

1-{3-[(4-chloro-3-fluorophenyl)amino]-2-(4-fluorophenyl)-5H,6H,7H,8H-imidazo[1,2-a]pyrazin-7-yl}-2-(phenylamino)ethan-1-one;

1-{3-[(4-chloro-3-fluorophenyl)amino]-2-(4-fluorophenyl)-5H,6H,7H,8H-imidazo[1,2-a]pyrazin-7-yl}-2-(1H-indazol-3-yl)ethan-1-one;

1-[2-(4-fluorophenyl)-3-[(4-methylphenyl)amino]-5H,6H,7H,8H-imidazo[1,2-a]pyrazin-7-yl]-2-(propylamino)ethan-1-one;

1-[2-(4-fluorophenyl)-3-[(4-methylphenyl)amino]-5H,6H,7H,8H-imidazo[1,2-a]pyrazin-7-yl]-2-(pentylamino)ethan-1-one;

1-[2-(4-fluorophenyl)-3-[(4-methylphenyl)amino]-5H,6H,7H,8H-imidazo[1,2-a]pyrazin-7-yl]-2-[(2-methoxyethyl)amino]ethan-1-one;

1-[2-(4-fluorophenyl)-3-[(4-methylphenyl)amino]-5H,6H,7H,8H-imidazo[1,2-a]pyrazin-7-yl]-2-[(3-methoxypropyl)amino]ethan-1-one;

(2R)-2-amino-1-{3-[(4-chloro-3-fluorophenyl)amino]-2-(4-fluorophenyl)-5H,6H,7H,8H-imidazo[1,2-a]pyrazin-7-yl}-3-phenylpropan-1-one;

(2S,3S)-2-amino-3-(benzyloxy)-1-{3-[(4-chloro-3-fluorophenyl)amino]-2-(4-fluorophenyl)-5H,6H,7H,8H-imidazo[1,2-a]pyrazin-7-yl}butan-1-one;

(2S)-2-amino-1-{3-[(4-chloro-3-fluorophenyl)amino]-2-(4-fluorophenyl)-5H,6H,7H,8H-imidazo[1,2-a]pyrazin-7-yl}-3-methylbutan-1-one;

(2S)-2-amino-1-{3-[(4-chloro-3-fluorophenyl)amino]-2-(4-fluorophenyl)-5H,6H,7H,8H-imidazo[1,2-a]pyrazin-7-yl}propan-1-one;

(2S)-2-amino-1-{3-[(4-chloro-3-fluorophenyl)amino]-2-(4-fluorophenyl)-5H,6H,7H,8H-imidazo[1,2-a]pyrazin-7-yl}-3-(1,3-thiazol-4-yl)propan-1-one;

(2S)-2-amino-1-{3-[(4-chloro-3-fluorophenyl)amino]-2-(4-fluorophenyl)-5H,6H,7H,8H-imidazo[1,2-a]pyrazin-7-yl}-3-(4-fluorophenyl)propan-1-one;

(2S,3S)-2-amino-1-{3-[(4-chloro-3-fluorophenyl)amino]-2-(4-fluorophenyl)-5H,6H,7H,8H-imidazo[1,2-a]pyrazin-7-yl}-3-methylpentan-1-one;

(2R)-2-amino-1-{3-[(4-chloro-3-fluorophenyl)amino]-2-(4-fluorophenyl)-5H,6H,7H,8H-imidazo[1,2-a]pyrazin-7-yl}-3-methylbutan-1-one;

(2S)-2-amino-1-{3-[(4-chloro-3-fluorophenyl)amino]-2-(4-fluorophenyl)-5H,6H,7H,8H-imidazo[1,2-a]pyrazin-7-yl}-3-(3,4-difluorophenyl)propan-1-one;

1-{3-[(4-chloro-3-fluorophenyl)amino]-2-(4-fluorophenyl)-5H,6H,7H,8H-imidazo[1,2-a]pyrazin-7-yl}-2-methyl-2-(methylamino)propan-1-one;

(2S)-2-amino-1-{3-[(4-chloro-3-fluorophenyl)amino]-2-(4-fluorophenyl)-5H,6H,7H,8H-imidazo[1,2-a]pyrazin-7-yl}-4-methylpentan-1-one;

N-(4-chloro-3-fluorophenyl)-2-(4-fluorophenyl)-7-[(morpholin-3-yl)carbonyl]-5H,6H,7H,8H-imidazo[1,2-a]pyrazin-3-amine;

(2S)-2-amino-1-{3-[(4-chloro-3-fluorophenyl)amino]-2-(4-fluorophenyl)-5H,6H,7H,8H-imidazo[1,2-a]pyrazin-7-yl}-3-phenylpropan-1-one;

(2S)-2-amino-1-{3-[(4-chloro-3-fluorophenyl)amino]-2-(4-fluorophenyl)-5H,6H,7H,8H-imidazo[1,2-a]pyrazin-7-yl}-3-cyclobutylpropan-1-one;

(2S)-2-amino-1-{3-[(4-chloro-3-fluorophenyl)amino]-2-(4-fluorophenyl)-5H,6H,7H,8H-imidazo[1,2-a]pyrazin-7-yl}-3,3-dimethylbutan-1-one;

(2R)-2-amino-1-{3-[(4-chloro-3-fluorophenyl)amino]-2-(4-fluorophenyl)-5H,6H,7H,8H-imidazo[1,2-a]pyrazin-7-yl}propan-1-one;

4-[(2S)-2-amino-3-{3-[(4-chloro-3-fluorophenyl)amino]-2-(4-fluorophenyl)-5H,6H,7H,8H-imidazo[1,2-a]pyrazin-7-yl}-3-oxopropyl]benzonitrile;

1-{3-[(4-chloro-3-fluorophenyl)amino]-2-(4-fluorophenyl)-5H,6H,7H,8H-imidazo[1,2-a]pyrazin-7-yl}-2-phenyl-2-(phenylamino)ethan-1-one;

1-{3-[(4-chloro-3-fluorophenyl)amino]-2-(4-fluorophenyl)-5H,6H,7H,8H-imidazo[1,2-a]pyrazin-7-yl}-2-[2-(trifluoromethoxy)phenyl]ethan-1-one;

(2S)-1-{3-[(4-chloro-3-fluorophenyl)amino]-2-(4-fluorophenyl)-5H,6H,7H,8H-imidazo[1,2-a]pyrazin-7-yl}-2-hydroxy-3-phenylpropan-1-one;

1-{3-[(4-chloro-3-fluorophenyl)amino]-2-(4-fluorophenyl)-5H,6H,7H,8H-imidazo[1,2-a]pyrazin-7-yl}-2-[4-fluoro-3-(trifluoromethyl)phenyl]ethan-1-one;

1-{3-[(4-chloro-3-fluorophenyl)amino]-2-(4-fluorophenyl)-5H,6H,7H,8H-imidazo[1,2-a]pyrazin-7-yl}-2-phenoxyethan-1-one;

5-({3-[(4-chloro-3-fluorophenyl)amino]-2-(4-fluorophenyl)-5H,6H,7H,8H-imidazo[1,2-a]pyrazin-7-yl}carbonyl)piperidin-2-one;

N-(4-chloro-3-fluorophenyl)-2-(4-fluorophenyl)-7-{[(2S)-pyrrolidin-2-yl]carbonyl}-5H,6H,7H,8H-imidazo[1,2-a]pyrazin-3-amine;

3-amino-1-{3-[(4-chloro-3-fluorophenyl)amino]-2-(4-fluorophenyl)-5H,6H,7H,8H-imidazo[1,2-a]pyrazin-7-yl}-4,4,4-trifluorobutan-1-one;

N-(4-chloro-3-fluorophenyl)-2-(4-fluorophenyl)-7-{[(3S)-pyrrolidin-3-yl]carbonyl}-5H,6H,7H,8H-imidazo[1,2-a]pyrazin-3-amine;

(2S)-2-amino-1-{3-[(4-chloro-3-fluorophenyl)amino]-2-(4-fluorophenyl)-5H,6H,7H,8H-imidazo[1,2-a]pyrazin-7-yl}-3-(4-methylphenyl)propan-1-one;

N-(4-chloro-3-fluorophenyl)-7-[(2,3-dihydro-1H-isoindol-1-yl)carbonyl]-2-(4-fluorophenyl)-5H,6H,7H,8H-imidazo[1,2-a]pyrazin-3-amine;

N-(4-chloro-3-fluorophenyl)-7-{[(2S)-2,3-dihydro-1H-indol-2-yl]carbonyl}-2-(4-fluorophenyl)-5H,6H,7H,8H-imidazo[1,2-a]pyrazin-3-amine;

(2R)-2-amino-3-(4-bromophenyl)-1-{3-[(4-chloro-3-fluorophenyl)amino]-2-(4-fluorophenyl)-5H,6H,7H,8H-imidazo[1,2-a]pyrazin-7-yl}propan-1-one;

(2S)-2-amino-1-{3-[(4-chloro-3-fluorophenyl)amino]-2-(4-fluorophenyl)-5H,6H,7H,8H-imidazo[1,2-a]pyrazin-7-yl}-3-{[(4-methoxyphenyl)methyl]sulfanyl}propan-1-one;

2-amino-1-{3-[(4-chloro-3-fluorophenyl)amino]-2-(4-fluorophenyl)-5H,6H,7H,8H-imidazo[1,2-a]pyrazin-7-yl}-4,4,4-trifluorobutan-1-one;

2-(2-butoxyethoxy)-1-[2-(4-fluorophenyl)-3-[(4-methylphenyl)amino]-5H,6H,7H,8H-imidazo[1,2-a]pyrazin-7-yl]ethan-1-one;

2-ethoxy-1-[2-(4-fluorophenyl)-3-[(4-methylphenyl)amino]-5H,6H,7H,8H-imidazo[1,2-a]pyrazin-7-yl]ethan-1-one;

1-[2-(4-fluorophenyl)-3-[(4-methylphenyl)amino]-5H,6H,7H,8H-imidazo[1,2-a]pyrazin-7-yl]-2-(2-methoxyethoxy)ethan-1-one;

2-amino-1-[2-(4-fluorophenyl)-6-methyl-3-[(4-methylphenyl)amino]-5H,6H,7H,8H-imidazo[1,2-a]pyrazin-7-yl]ethan-1-one;

5-{[7-(2-amino-2-methylpropanoyl)-2-(3-fluorophenyl)-5H,6H,7H,8H-imidazo[1,2-a]pyrazin-3-yl]amino}-2-fluorobenzonitrile;

2-{[2-chloro-4-(trifluoromethyl)phenyl]amino}-1-[2-(4-fluorophenyl)-3-[(4-methylphenyl)amino]-5H,6H,7H,8H-imidazo[1,2-a]pyrazin-7-yl]-3-methylbutan-1-one;

N-(4-chloro-3-fluorophenyl)-2-(4-fluorophenyl)-7-{[(2R)-oxolan-2-yl]carbonyl}-5H,6H,7H,8H-imidazo[1,2-a]pyrazin-3-amine;

1-{3-[(4-chloro-3-fluorophenyl)amino]-2-(4-fluorophenyl)-5H,6H,7H,8H-imidazo[1,2-a]pyrazin-7-yl}-2-(1-methyl-1H-indol-3-yl)ethan-1-one;

(2S)-1-{3-[(4-chloro-3-fluorophenyl)amino]-2-(4-fluorophenyl)-5H,6H,7H,8H-imidazo[1,2-a]pyrazin-7-yl}-2-hydroxy-4-methylpentan-1-one;

(2R)-1-{3-[(4-chloro-3-fluorophenyl)amino]-2-(4-fluorophenyl)-5H,6H,7H,8H-imidazo[1,2-a]pyrazin-7-yl}-2-hydroxy-3-methylbutan-1-one;

2-[(3-chlorophenyl)amino]-1-[2-(4-fluorophenyl)-3-[(4-methylphenyl)amino]-5H,6H,7H,8H-imidazo[1,2-a]pyrazin-7-yl]ethan-1-one;

1-[2-(4-fluorophenyl)-3-[(4-methylphenyl)amino]-5H,6H,7H,8H-imidazo[1,2-a]pyrazin-7-yl]-2-[(4-methylphenyl)amino]ethan-1-one;

2-(4-chloro-3-fluorophenyl)-1-{3-[(4-chloro-3-fluorophenyl)amino]-2-(4-fluorophenyl)-5H,6H,7H,8H-imidazo[1,2-a]pyrazin-7-yl}ethan-1-one;

1-[2-(4-fluorophenyl)-3-[(4-methylphenyl)amino]-5H,6H,7H,8H-imidazo[1,2-a]pyrazin-7-yl]-2-[(4-methoxyphenyl)amino]-2-methylpropan-1-one;

2-amino-1-{3-[(4-chloro-3-fluorophenyl)amino]-2-(4-fluorophenyl)-5H,6H,7H,8H-imidazo[1,2-a]pyrazin-7-yl}-2-(3,4-dichlorophenyl)ethan-1-one;

2-amino-3,3,3-trifluoro-1-[2-(4-fluorophenyl)-3-[(4-methylphenyl)amino]-5H,6H,7H,8H-imidazo[1,2-a]pyrazin-7-yl]-2-methylpropan-1-one;

N-(4-chloro-3-fluorophenyl)-2-(4-fluorophenyl)-7-[(morpholin-2-yl)carbonyl]-5H,6H,7H,8H-imidazo[1,2-a]pyrazin-3-amine;

2-amino-1-{3-[(4-chloro-3-fluorophenyl)amino]-2-(4-fluorophenyl)-5H,6H,7H,8H-imidazo[1,2-a]pyrazin-7-yl}-2-[4-(trifluoromethyl)phenyl]ethan-1-one;

2-amino-1-{3-[(4-chloro-3-fluorophenyl)amino]-2-(4-fluorophenyl)-5H,6H,7H,8H-imidazo[1,2-a]pyrazin-7-yl}-2-(4-chlorophenyl)ethan-1-one;

1-[2-(4-fluorophenyl)-3-[(4-methylphenyl)amino]-5H,6H,7H,8H-imidazo[1,2-a]pyrazin-7-yl]-2-[(4-methylphenyl)amino]-2-phenylethan-1-one;

N-(4-chloro-3-fluorophenyl)-2-(4-fluorophenyl)-7-[(4-methylmorpholin-2-yl)carbonyl]-5H,6H,7H,8H-imidazo[1,2-a]pyrazin-3-amine;

1-[2-(4-fluorophenyl)-3-[(4-methylphenyl)amino]-5H,6H,7H,8H-imidazo[1,2-a]pyrazin-7-yl]-2-[(2-fluorophenyl)amino]ethan-1-one;

1-[2-(4-fluorophenyl)-3-[(4-methylphenyl)amino]-5H,6H,7H,8H-imidazo[1,2-a]pyrazin-7-yl]-2-methyl-2-(phenylamino)propan-1-one;

2-amino-1-(3-{[4-fluoro-2-(trifluoromethyl)phenyl]amino}-2-(3-fluorophenyl)-5H,6H,7H,8H-imidazo[1,2-a]pyrazin-7-yl)-2-methylpropan-1-one;

(2S)-1-[2-(4-fluorophenyl)-3-[(4-methylphenyl)amino]-5H,6H,7H,8H-imidazo[1,2-a]pyrazin-7-yl]-3-methyl-2-(methylamino)butan-1-one;

(2R)-1-[2-(4-fluorophenyl)-3-[(4-methylphenyl)amino]-5H,6H,7H,8H-imidazo[1,2-a]pyrazin-7-yl]-4-methyl-2-(methylamino)pentan-1-one;

(2S)-1-[2-(4-fluorophenyl)-3-[(4-methylphenyl)amino]-5H,6H,7H,8H-imidazo[1,2-a]pyrazin-7-yl]-4-methyl-2-(methylamino)pentan-1-one;

2-amino-1-[2-(3,4-difluorophenyl)-3-[(4-methylphenyl)amino]-5H,6H,7H,8H-imidazo[1,2-a]pyrazin-7-yl]-2-methylpropan-1-one;

2-[(2,6-dimethylphenyl)amino]-1-[2-(4-fluorophenyl)-3-[(4-methylphenyl)amino]-5H,6H,7H,8H-imidazo[1,2-a]pyrazin-7-yl]propan-1-one;

2-amino-1-[2-(2-methoxyphenyl)-3-[(4-methylphenyl)amino]-5H,6H,7H,8H-imidazo[1,2-a]pyrazin-7-yl]ethan-1-one;

2-amino-1-{3-[(4-methylphenyl)amino]-2-(pyridin-4-yl)-5H,6H,7H,8H-imidazo[1,2-a]pyrazin-7-yl}ethan-1-one;

2-amino-1-[2-(3-chlorophenyl)-3-[(4-methylphenyl)amino]-5H,6H,7H,8H-imidazo[1,2-a]pyrazin-7-yl]ethan-1-one;

2-[(2,4-dimethylphenyl)amino]-1-[2-(4-fluorophenyl)-3-[(4-methylphenyl)amino]-5H,6H,7H,8H-imidazo[1,2-a]pyrazin-7-yl]ethan-1-one;

2-amino-1-[2-(3,4-difluorophenyl)-3-[(4-methylphenyl)amino]-5H,6H,7H,8H-imidazo[1,2-a]pyrazin-7-yl]ethan-1-one;

1-[2-(4-fluorophenyl)-3-[(4-methylphenyl)amino]-5H,6H,7H,8H-imidazo[1,2-a]pyrazin-7-yl]-2-methyl-2-[(4-methylphenyl)amino]propan-1-one;

2-amino-1-[2-(2,4-difluorophenyl)-3-[(4-methylphenyl)amino]-5H,6H,7H,8H-imidazo[1,2-a]pyrazin-7-yl]ethan-1-one;

(2S)-2-[benzyl(methyl)amino]-1-[2-(4-fluorophenyl)-3-[(4-methylphenyl)amino]-5H,6H,7H,8H-imidazo[1,2-a]pyrazin-7-yl]propan-1-one;

(2S)-1-[2-(4-fluorophenyl)-3-[(4-methylphenyl)amino]-5H,6H,7H,8H-imidazo[1,2-a]pyrazin-7-yl]-2-(methylamino)hexan-1-one;

1-[2-(3,4-difluorophenyl)-3-[(4-methylphenyl)amino]-5H,6H,7H,8H-imidazo[1,2-a]pyrazin-7-yl]-2-(4-methylphenyl)ethan-1-one;

(2R)-1-[2-(3,4-difluorophenyl)-3-[(4-methylphenyl)amino]-5H,6H,7H,8H-imidazo[1,2-a]pyrazin-7-yl]-2-hydroxy-3-methylbutan-1-one;

(2S)-1-[2-(4-fluorophenyl)-3-[(4-methylphenyl)amino]-5H,6H,7H,8H-imidazo[1,2-a]pyrazin-7-yl]-2-(methylamino)pentan-1-one;

(2S)-2-amino-1-{3-[(4-chloro-3-fluorophenyl)amino]-2-(4-fluorophenyl)-5H,6H,7H,8H-imidazo[1,2-a]pyrazin-7-yl}butan-1-one;

(2R)-2-amino-1-{3-[(4-chloro-3-fluorophenyl)amino]-2-(4-fluorophenyl)-5H,6H,7H,8H-imidazo[1,2-a]pyrazin-7-yl}-4-methylpentan-1-one;

2-amino-1-[2-(2,4-difluorophenyl)-3-[(4-methylphenyl)amino]-5H,6H,7H,8H-imidazo[1,2-a]pyrazin-7-yl]-2-methylpropan-1-one;

(2S)-2-amino-1-[2-(3,4-difluorophenyl)-3-[(4-methylphenyl)amino]-5H,6H,7H,8H-imidazo[1,2-a]pyrazin-7-yl]-3-methylbutan-1-one;

2-amino-1-[2-(3-chlorophenyl)-3-[(4-methylphenyl)amino]-5H,6H,7H,8H-imidazo[1,2-a]pyrazin-7-yl]-2-methylpropan-1-one;

2-amino-2-methyl-1-{3-[(4-methylphenyl)amino]-2-(pyridin-4-yl)-5H,6H,7H,8H-imidazo[1,2-a]pyrazin-7-yl}propan-1-one;

2-(tert-butylamino)-1-[2-(4-fluorophenyl)-3-[(4-methylphenyl)amino]-5H,6H,7H,8H-imidazo[1,2-a]pyrazin-7-yl]ethan-1-one;

(2S)-3-(4-chlorophenyl)-1-[2-(4-fluorophenyl)-3-[(4-methylphenyl)amino]-5H,6H,7H,8H-imidazo[1,2-a]pyrazin-7-yl]-2-(methylamino)propan-1-one;

(2S)-2-amino-3-cyclopropyl-1-[2-(4-fluorophenyl)-3-[(4-methylphenyl)amino]-5H,6H,7H,8H-imidazo[1,2-a]pyrazin-7-yl]propan-1-one;

(2R)-2-(benzylamino)-1-[2-(4-fluorophenyl)-3-[(4-methylphenyl)amino]-5H,6H,7H,8H-imidazo[1,2-a]pyrazin-7-yl]propan-1-one;

(2S)-2-(benzylamino)-1-[2-(4-fluorophenyl)-3-[(4-methylphenyl)amino]-5H,6H,7H,8H-imidazo[1,2-a]pyrazin-7-yl]propan-1-one;

(2S)-2-amino-2-cyclopropyl-1-[2-(4-fluorophenyl)-3-[(4-methylphenyl)amino]-5H,6H,7H,8H-imidazo[1,2-a]pyrazin-7-yl]ethan-1-one;

(2S)-2-amino-3-(3,4-difluorophenyl)-1-[2-(3,4-difluorophenyl)-3-[(4-methylphenyl)amino]-5H,6H,7H,8H-imidazo[1,2-a]pyrazin-7-yl]propan-1-one;

(2S)-2-amino-1-[2-(3,4-difluorophenyl)-3-[(4-methylphenyl)amino]-5H,6H,7H,8H-imidazo[1,2-a]pyrazin-7-yl]propan-1-one;

1-[2-(4-fluorophenyl)-3-[(4-methylphenyl)amino]-5H,6H,7H,8H-imidazo[1,2-a]pyrazin-7-yl]-2-[(4-methylphenyl)amino]propan-1-one;

2-amino-1-[2-(2,5-difluorophenyl)-3-[(4-methylphenyl)amino]-5H,6H,7H,8H-imidazo[1,2-a]pyrazin-7-yl]-2-methylpropan-1-one;

2-amino-1-[2-(4-fluorophenyl)-8,8-dimethyl-3-[(4-methylphenyl)amino]-5H,6H,7H,8H-imidazo[1,2-a]pyrazin-7-yl]ethan-1-one;

2-amino-1-{3-[(3,4-dichlorophenyl)amino]-2-(4-fluorophenyl)-5H,6H,7H,8H-imidazo[1,2-a]pyrazin-7-yl}-2-methylpropan-1-one;

2-amino-1-[2-(4-fluorophenyl)-3-[(4-fluorophenyl)amino]-8,8-dimethyl-5H,6H,7H,8H-imidazo[1,2-a]pyrazin-7-yl]ethan-1-one;

(2R)-1-[2-(4-fluorophenyl)-3-[(4-methylphenyl)amino]-5H,6H,7H,8H-imidazo[1,2-a]pyrazin-7-yl]-3-methyl-2-(methylamino)butan-1-one;

2-amino-1-{3-[(4-chlorophenyl)amino]-2-(4-fluorophenyl)-8,8-dimethyl-5H,6H,7H,8H-imidazo[1,2-a]pyrazin-7-yl}ethan-1-one;

2-amino-1-[2-(2,5-difluorophenyl)-3-[(4-methylphenyl)amino]-5H,6H,7H,8H-imidazo[1,2-a]pyrazin-7-yl]ethan-1-one;

2-amino-1-{3-[(4-chloro-3-fluorophenyl)amino]-2-(4-fluorophenyl)-8,8-dimethyl-5H,6H,7H,8H-imidazo[1,2-a]pyrazin-7-yl}ethan-1-one;

4-{[7-(2-aminoacetyl)-2-(4-fluorophenyl)-8,8-dimethyl-5H,6H,7H,8H-imidazo[1,2-a]pyrazin-3-yl]amino}benzonitrile;

2-amino-1-{3-[(3,4-difluoro-5-methoxyphenyl)amino]-2-(4-fluorophenyl)-5H,6H,7H,8H-imidazo[1,2-a]pyrazin-7-yl}-2-methylpropan-1-one;

2-amino-1-{3-[(4-fluoro-3,5-dimethylphenyl)amino]-2-(4-fluorophenyl)-5H,6H,7H,8H-imidazo[1,2-a]pyrazin-7-yl}-2-methylpropan-1-one;

(2S)-2-amino-3-cyclobutyl-1-{3-[(3,4-difluorophenyl)amino]-2-(4-fluorophenyl)-5H,6H,7H,8H-imidazo[1,2-a]pyrazin-7-yl}propan-1-one;

(2R)-1-{3-[(3,4-difluorophenyl)amino]-2-(4-fluorophenyl)-5H,6H,7H,8H-imidazo[1,2-a]pyrazin-7-yl}-2-hydroxy-3-methylbutan-1-one;

(2S)-2-amino-1-{3-[(3,4-difluorophenyl)amino]-2-(4-fluorophenyl)-5H,6H,7H,8H-imidazo[1,2-a]pyrazin-7-yl}-3-(1,3-thiazol-4-yl)propan-1-one;

(2S)-2-amino-1-{3-[(3,4-difluorophenyl)amino]-2-(4-fluorophenyl)-5H,6H,7H,8H-imidazo[1,2-a]pyrazin-7-yl}-3-(4-methylphenyl)propan-1-one;

(2S)-2-amino-3-(3,4-difluorophenyl)-1-{3-[(3,4-difluorophenyl)amino]-2-(4-fluorophenyl)-5H,6H,7H,8H-imidazo[1,2-a]pyrazin-7-yl}propan-1-one;

(2S)-2-amino-1-{3-[(3,4-difluorophenyl)amino]-2-(4-fluorophenyl)-5H,6H,7H,8H-imidazo[1,2-a]pyrazin-7-yl}-3-methylbutan-1-one;

(2S)-2-amino-1-{3-[(3,4-difluorophenyl)amino]-2-(4-fluorophenyl)-5H,6H,7H,8H-imidazo[1,2-a]pyrazin-7-yl}propan-1-one;

(2S)-2-amino-1-{3-[(3,4-difluorophenyl)amino]-2-(4-fluorophenyl)-5H,6H,7H,8H-imidazo[1,2-a]pyrazin-7-yl}-2-(4-fluorophenyl)ethan-1-one;

(2S)-2-amino-2-cyclopropyl-1-{3-[(3,4-difluorophenyl)amino]-2-(4-fluorophenyl)-5H,6H,7H,8H-imidazo[1,2-a]pyrazin-7-yl}ethan-1-one;

(2S)-2-amino-3-cyclopropyl-1-{3-[(3,4-difluorophenyl)amino]-2-(4-fluorophenyl)-5H,6H,7H,8H-imidazo[1,2-a]pyrazin-7-yl}propan-1-one;

(2S)-2-amino-1-{3-[(3,4-difluorophenyl)amino]-2-(4-fluorophenyl)-5H,6H,7H,8H-imidazo[1,2-a]pyrazin-7-yl}-4-methylpentan-1-one;

(2S)-1-{3-[(3,4-difluorophenyl)amino]-2-(4-fluorophenyl)-5H,6H,7H,8H-imidazo[1,2-a]pyrazin-7-yl}-2-hydroxy-3-methylbutan-1-one;

(2S,3S)-2-amino-1-{3-[(3,4-difluorophenyl)amino]-2-(4-fluorophenyl)-5H,6H,7H,8H-imidazo[1,2-a]pyrazin-7-yl}-3-methylpentan-1-one;

(2S)-2-amino-1-{3-[(3,4-difluorophenyl)amino]-2-(4-fluorophenyl)-5H,6H,7H,8H-imidazo[1,2-a]pyrazin-7-yl}-3-(4-fluorophenyl)propan-1-one;

(2S)-2-amino-1-{3-[(4-chlorophenyl)amino]-2-(4-fluorophenyl)-5H,6H,7H,8H-imidazo[1,2-a]pyrazin-7-yl}propan-1-one;

(2S)-2-amino-1-{3-[(4-chlorophenyl)amino]-2-(4-fluorophenyl)-5H,6H,7H,8H-imidazo[1,2-a]pyrazin-7-yl}-3-methylbutan-1-one;

(2S)-2-amino-1-{3-[(4-chlorophenyl)amino]-2-(4-fluorophenyl)-5H,6H,7H,8H-imidazo[1,2-a]pyrazin-7-yl}-2-cyclopropylethan-1-one;

(2S)-2-amino-1-{3-[(4-chlorophenyl)amino]-2-(4-fluorophenyl)-5H,6H,7H,8H-imidazo[1,2-a]pyrazin-7-yl}-3-cyclopropylpropan-1-one;

(2S)-2-amino-1-{3-[(4-chlorophenyl)amino]-2-(4-fluorophenyl)-5H,6H,7H,8H-imidazo[1,2-a]pyrazin-7-yl}-3-cyclobutylpropan-1-one;

(2S)-2-amino-1-{3-[(4-chlorophenyl)amino]-2-(4-fluorophenyl)-5H,6H,7H,8H-imidazo[1,2-a]pyrazin-7-yl}-4-methylpentan-1-one;

(2S,3S)-2-amino-1-{3-[(4-chlorophenyl)amino]-2-(4-fluorophenyl)-5H,6H,7H,8H-imidazo[1,2-a]pyrazin-7-yl}-3-methylpentan-1-one;

(2S)-1-{3-[(4-chlorophenyl)amino]-2-(4-fluorophenyl)-5H,6H,7H,8H-imidazo[1,2-a]pyrazin-7-yl}-2-hydroxy-3-methylbutan-1-one;

(2R)-1-{3-[(4-chlorophenyl)amino]-2-(4-fluorophenyl)-5H,6H,7H,8H-imidazo[1,2-a]pyrazin-7-yl}-2-hydroxy-3-methylbutan-1-one;

(2S)-2-amino-1-{3-[(4-chlorophenyl)amino]-2-(4-fluorophenyl)-5H,6H,7H,8H-imidazo[1,2-a]pyrazin-7-yl}-2-(4-fluorophenyl)ethan-1-one;

(2S)-2-amino-1-{3-[(4-chlorophenyl)amino]-2-(4-fluorophenyl)-5H,6H,7H,8H-imidazo[1,2-a]pyrazin-7-yl}-3-(4-fluorophenyl)propan-1-one;

(2S)-2-amino-1-{3-[(4-chlorophenyl)amino]-2-(4-fluorophenyl)-5H,6H,7H,8H-imidazo[1,2-a]pyrazin-7-yl}-3-(4-methylphenyl)propan-1-one;

(2S)-2-amino-1-{3-[(4-chlorophenyl)amino]-2-(4-fluorophenyl)-5H,6H,7H,8H-imidazo[1,2-a]pyrazin-7-yl}-3-(3,4-difluorophenyl)propan-1-one;

(2S)-2-amino-1-{3-[(4-chlorophenyl)amino]-2-(4-fluorophenyl)-5H,6H,7H,8H-imidazo[1,2-a]pyrazin-7-yl}-3-(1,3-thiazol-4-yl)propan-1-one;

(2S)-2-amino-1-{3-[(4-chlorophenyl)amino]-2-(4-fluorophenyl)-5H,6H,7H,8H-imidazo[1,2-a]pyrazin-7-yl}-3,3-dimethylbutan-1-one;

(2S)-2-amino-1-[2-(4-fluorophenyl)-3-[(4-fluorophenyl)amino]-5H,6H,7H,8H-imidazo[1,2-a]pyrazin-7-yl]-3-methylbutan-1-one;

(2S)-2-amino-2-cyclopropyl-1-[2-(4-fluorophenyl)-3-[(4-fluorophenyl)amino]-5H,6H,7H,8H-imidazo[1,2-a]pyrazin-7-yl]ethan-1-one;

(2S)-2-amino-3-cyclopropyl-1-[2-(4-fluorophenyl)-3-[(4-fluorophenyl)amino]-5H,6H,7H,8H-imidazo[1,2-a]pyrazin-7-yl]propan-1-one;

(2S)-2-amino-3-cyclobutyl-1-[2-(4-fluorophenyl)-3-[(4-fluorophenyl)amino]-5H,6H,7H,8H-imidazo[1,2-a]pyrazin-7-yl]propan-1-one;

(2S)-2-amino-1-[2-(4-fluorophenyl)-3-[(4-fluorophenyl)amino]-5H,6H,7H,8H-imidazo[1,2-a]pyrazin-7-yl]-4-methylpentan-1-one;

(2S,3S)-2-amino-1-[2-(4-fluorophenyl)-3-[(4-fluorophenyl)amino]-5H,6H,7H,8H-imidazo[1,2-a]pyrazin-7-yl]-3-methylpentan-1-one;

(2S)-1-[2-(4-fluorophenyl)-3-[(4-fluorophenyl)amino]-5H,6H,7H,8H-imidazo[1,2-a]pyrazin-7-yl]-2-hydroxy-3-methylbutan-1-one;

(2R)-1-[2-(4-fluorophenyl)-3-[(4-fluorophenyl)amino]-5H,6H,7H,8H-imidazo[1,2-a]pyrazin-7-yl]-2-hydroxy-3-methylbutan-1-one;

(2S)-2-amino-2-(4-fluorophenyl)-1-[2-(4-fluorophenyl)-3-[(4-fluorophenyl)amino]-5H,6H,7H,8H-imidazo[1,2-a]pyrazin-7-yl]ethan-1-one;

(2S)-2-amino-3-(4-fluorophenyl)-1-[2-(4-fluorophenyl)-3-[(4-fluorophenyl)amino]-5H,6H,7H,8H-imidazo[1,2-a]pyrazin-7-yl]propan-1-one;

(2S)-2-amino-1-[2-(4-fluorophenyl)-3-[(4-fluorophenyl)amino]-5H,6H,7H,8H-imidazo[1,2-a]pyrazin-7-yl]-3-(4-methylphenyl)propan-1-one;

(2S)-2-amino-3-(3,4-difluorophenyl)-1-[2-(4-fluorophenyl)-3-[(4-fluorophenyl)amino]-5H,6H,7H,8H-imidazo[1,2-a]pyrazin-7-yl]propan-1-one;

(2S)-2-amino-1-[2-(4-fluorophenyl)-3-[(4-fluorophenyl)amino]-5H,6H,7H,8H-imidazo[1,2-a]pyrazin-7-yl]-3-(1,3-thiazol-4-yl)propan-1-one;

(2S)-2-amino-1-[2-(4-fluorophenyl)-3-[(4-fluorophenyl)amino]-5H,6H,7H,8H-imidazo[1,2-a]pyrazin-7-yl]-3,3-dimethylbutan-1-one;

(2S)-2-amino-3-cyclobutyl-1-[2-(4-fluorophenyl)-3-[(4-methylphenyl)amino]-5H,6H,7H,8H-imidazo[1,2-a]pyrazin-7-yl]propan-1-one;

(2S)-2-amino-1-[2-(4-fluorophenyl)-3-[(4-methylphenyl)amino]-5H,6H,7H,8H-imidazo[1,2-a]pyrazin-7-yl]-4-methylpentan-1-one;

(2S,3S)-2-amino-1-[2-(4-fluorophenyl)-3-[(4-methylphenyl)amino]-5H,6H,7H,8H-imidazo[1,2-a]pyrazin-7-yl]-3-methylpentan-1-one;

(2S)-2-amino-2-(4-fluorophenyl)-1-[2-(4-fluorophenyl)-3-[(4-methylphenyl)amino]-5H,6H,7H,8H-imidazo[1,2-a]pyrazin-7-yl]ethan-1-one;

(2S)-2-amino-1-[2-(4-fluorophenyl)-3-[(4-methylphenyl)amino]-5H,6H,7H,8H-imidazo[1,2-a]pyrazin-7-yl]-3-(4-methylphenyl)propan-1-one;

(2S)-2-amino-3-(4-fluorophenyl)-1-[2-(4-fluorophenyl)-3-[(4-methylphenyl)amino]-5H,6H,7H,8H-imidazo[1,2-a]pyrazin-7-yl]propan-1-one;

(2S)-2-amino-3-(3,4-difluorophenyl)-1-[2-(4-fluorophenyl)-3-[(4-methylphenyl)amino]-5H,6H,7H,8H-imidazo[1,2-a]pyrazin-7-yl]propan-1-one;

(2S)-2-amino-1-[2-(4-fluorophenyl)-3-[(4-methylphenyl)amino]-5H,6H,7H,8H-imidazo[1,2-a]pyrazin-7-yl]-3-(1,3-thiazol-4-yl)propan-1-one;

(2S)-2-amino-1-{3-[(4-chloro-3-fluorophenyl)amino]-2-(4-fluorophenyl)-5H,6H,7H,8H-imidazo[1,2-a]pyrazin-7-yl}-2-cyclopropylethan-1-one;

(2S)-2-amino-1-{3-[(4-chloro-3-fluorophenyl)amino]-2-(4-fluorophenyl)-5H,6H,7H,8H-imidazo[1,2-a]pyrazin-7-yl}-3-cyclopropylpropan-1-one;

(2S)-1-{3-[(4-chloro-3-fluorophenyl)amino]-2-(4-fluorophenyl)-5H,6H,7H,8H-imidazo[1,2-a]pyrazin-7-yl}-2-hydroxy-3-methylbutan-1-one;

(2S)-2-amino-1-{3-[(4-chloro-3-fluorophenyl)amino]-2-(4-fluorophenyl)-5H,6H,7H,8H-imidazo[1,2-a]pyrazin-7-yl}-2-(4-fluorophenyl)ethan-1-one;

(2S)-2-amino-1-{3-[(3,4-difluorophenyl)amino]-2-(4-fluorophenyl)-5H,6H,7H,8H-imidazo[1,2-a]pyrazin-7-yl}-3,3-dimethylbutan-1-one;

2-amino-1-{3-[(3-chloro-4-fluorophenyl)amino]-2-(4-fluorophenyl)-5H,6H,7H,8H-imidazo[1,2-a]pyrazin-7-yl}-2-methylpropan-1-one;

2-amino-1-{3-[(4-fluoro-3-methylphenyl)amino]-2-(4-fluorophenyl)-8,8-dimethyl-5H,6H,7H,8H-imidazo[1,2-a]pyrazin-7-yl}ethan-1-one;

2-amino-1-{3-[(4-chloro-3-methylphenyl)amino]-2-(4-fluorophenyl)-8,8-dimethyl-5H,6H,7H,8H-imidazo[1,2-a]pyrazin-7-yl}ethan-1-one;

2-amino-1-[2-(4-fluorophenyl)-8,8-dimethyl-3-[(3-methylphenyl)amino]-5H,6H,7H,8H-imidazo[1,2-a]pyrazin-7-yl]ethan-1-one;

(2S)-2-amino-3-(4-fluorophenyl)-1-[2-(4-fluorophenyl)-3-[(4-methylphenyl)amino]-5H,6H,7H,8H-imidazo[1,2-a]pyrazin-7-yl]-2-methylpropan-1-one;

2-amino-1-[2-(4-fluorophenyl)-3-[(4-methylphenyl)amino]-5H,6H,7H,8H-imidazo[1,2-a]pyrazin-7-yl]-2,4-dimethylpentan-1-one;

(2S)-2-amino-1-[2-(4-fluorophenyl)-3-[(4-methylphenyl)amino]-5H,6H,7H,8H-imidazo[1,2-a]pyrazin-7-yl]-3-hydroxy-2-methylpropan-1-one;

(2R)-2-amino-1-[2-(4-fluorophenyl)-3-[(4-methylphenyl)amino]-5H,6H,7H,8H-imidazo[1,2-a]pyrazin-7-yl]-3-hydroxy-2-methylpropan-1-one;

2-amino-1-[2-(4-fluoro-3-methylphenyl)-3-[(4-methylphenyl)amino]-5H,6H,7H,8H-imidazo[1,2-a]pyrazin-7-yl]ethan-1-one;

2-amino-1-[2-(4-fluoro-3-methylphenyl)-3-[(4-methylphenyl)amino]-5H,6H,7H,8H-imidazo[1,2-a]pyrazin-7-yl]-2-methylpropan-1-one;

2-amino-1-[2-(3-chloro-4-fluorophenyl)-3-[(4-methylphenyl)amino]-5H,6H,7H,8H-imidazo[1,2-a]pyrazin-7-yl]ethan-1-one;

2-amino-1-[2-(4-chloro-3-fluorophenyl)-3-[(4-methylphenyl)amino]-5H,6H,7H,8H-imidazo[1,2-a]pyrazin-7-yl]ethan-1-one;

2-amino-1-[2-(4-chloro-3-fluorophenyl)-3-[(4-methylphenyl)amino]-5H,6H,7H,8H-imidazo[1,2-a]pyrazin-7-yl]-2-methylpropan-1-one;

5-{[7-(2-aminoacetyl)-2-(4-fluorophenyl)-8,8-dimethyl-5H,6H,7H,8H-imidazo[1,2-a]pyrazin-3-yl]amino}-2-fluorobenzonitrile;

5-{[7-(2-aminoacetyl)-2-(4-fluorophenyl)-8,8-dimethyl-5H,6H,7H,8H-imidazo[1,2-a]pyrazin-3-yl]amino}-2-methylbenzonitrile;

2-amino-1-[2-(4-fluorophenyl)-8,8-dimethyl-3-[(4-methylphenyl)amino]-5H,6H,7H,8H-imidazo[1,2-a]pyrazin-7-yl]-2-methylpropan-1-one;

2-amino-1-[3-(cyclohexylamino)-2-(4-fluorophenyl)-8,8-dimethyl-5H,6H,7H,8H-imidazo[1,2-a]pyrazin-7-yl]ethan-1-one;

2-amino-1-{3-[(3-chloro-4-methylphenyl)amino]-2-(4-fluorophenyl)-8,8-dimethyl-5H,6H,7H,8H-imidazo[1,2-a]pyrazin-7-yl}ethan-1-one;

2-amino-1-{3-[(3-fluoro-4-methylphenyl)amino]-2-(4-fluorophenyl)-8,8-dimethyl-5H,6H,7H,8H-imidazo[1,2-a]pyrazin-7-yl}ethan-1-one;

4-{[7-(2-aminoacetyl)-2-(4-fluorophenyl)-8,8-dimethyl-5H,6H,7H,8H-imidazo[1,2-a]pyrazin-3-yl]amino}-2-chlorobenzonitrile;

N-(3-{[7-(2-aminoacetyl)-2-(4-fluorophenyl)-8,8-dimethyl-5H,6H,7H,8H-imidazo[1,2-a]pyrazin-3-yl]amino}phenyl)methanesulfonamide;

3-{[7-(2-aminoacetyl)-2-(4-fluorophenyl)-8,8-dimethyl-5H,6H,7H,8H-imidazo[1,2-a]pyrazin-3-yl]amino}-N-methylbenzamide;

2-amino-1-[2-(4-fluorophenyl)-8,8-dimethyl-3-[(3,4,5-trifluorophenyl)amino]-5H,6H,7H,8H-imidazo[1,2-a]pyrazin-7-yl]ethan-1-one;

2-amino-1-{3-[(4-chlorophenyl)amino]-2-(4-fluorophenyl)-6,6-dimethyl-5H,6H,7H,8H-imidazo[1,2-a]pyrazin-7-yl}ethan-1-one;

2-amino-1-[2-(4-fluorophenyl)-3-[(4-methanesulfonylphenyl)amino]-8,8-dimethyl-5H,6H,7H,8H-imidazo[1,2-a]pyrazin-7-yl]ethan-1-one;

2-amino-1-[2-(4-fluorophenyl)-8,8-dimethyl-3-{[4-(4-methylpiperazin-1-yl)phenyl]amino}-5H,6H,7H,8H-imidazo[1,2-a]pyrazin-7-yl]ethan-1-one;

2-amino-1-[2-(4-fluorophenyl)-6,6-dimethyl-3-[(4-methylphenyl)amino]-5H,6H,7H,8H-imidazo[1,2-a]pyrazin-7-yl]ethan-1-one;

2-amino-1-[2-(4-fluorophenyl)-3-[(4-fluorophenyl)amino]-6,6-dimethyl-5H,6H,7H,8H-imidazo[1,2-a]pyrazin-7-yl]ethan-1-one;

2-amino-1-{3-[(3,4-difluorophenyl)amino]-2-(4-fluorophenyl)-6,6-dimethyl-5H,6H,7H,8H-imidazo[1,2-a]pyrazin-7-yl}ethan-1-one;

2-amino-1-{3-[(3-chloro-4-fluorophenyl)amino]-2-(4-fluorophenyl)-6,6-dimethyl-5H,6H,7H,8H-imidazo[1,2-a]pyrazin-7-yl}ethan-1-one;

5-{[7-(2-aminoacetyl)-2-(4-fluorophenyl)-6,6-dimethyl-5H,6H,7H,8H-imidazo[1,2-a]pyrazin-3-yl]amino}-2-fluorobenzonitrile;

2-amino-1-[2-(4-fluorophenyl)-3-[(4-fluorophenyl)amino]-8,8-dimethyl-5H,6H,7H,8H-imidazo[1,2-a]pyrazin-7-yl]-2-methylpropan-1-one;

2-amino-1-{3-[(4-chlorophenyl)amino]-2-(4-fluorophenyl)-8,8-dimethyl-5H,6H,7H,8H-imidazo[1,2-a]pyrazin-7-yl}-2-methylpropan-1-one;
2-amino-1-{3-[(3,4-difluorophenyl)amino]-2-(4-fluorophenyl)-8,8-dimethyl-5H,6H,7H,8H-imidazo[1,2-a]pyrazin-7-yl}-2-methylpropan-1-one;
2-amino-1-{3-[(3-chloro-4-fluorophenyl)amino]-2-(4-fluorophenyl)-8,8-dimethyl-5H,6H,7H,8H-imidazo[1,2-a]pyrazin-7-yl}-2-methylpropan-1-one;
2-amino-1-{3-[(3,4-dichlorophenyl)amino]-2-(4-fluorophenyl)-8,8-dimethyl-5H,6H,7H,8H-imidazo[1,2-a]pyrazin-7-yl}-2-methylpropan-1-one;
2-amino-1-{3-[(4-fluoro-3-methylphenyl)amino]-2-(4-fluorophenyl)-8,8-dimethyl-5H,6H,7H,8H-imidazo[1,2-a]pyrazin-7-yl}-2-methylpropan-1-one;
2-amino-1-{3-[(4-chloro-3-methylphenyl)amino]-2-(4-fluorophenyl)-8,8-dimethyl-5H,6H,7H,8H-imidazo[1,2-a]pyrazin-7-yl}-2-methylpropan-1-one;
5-{[7-(2-amino-2-methylpropanoyl)-2-(4-fluorophenyl)-8,8-dimethyl-5H,6H,7H,8H-imidazo[1,2-a]pyrazin-3-yl]amino}-2-methylbenzonitrile;
4-{[7-(2-amino-2-methylpropanoyl)-2-(4-fluorophenyl)-8,8-dimethyl-5H,6H,7H,8H-imidazo[1,2-a]pyrazin-3-yl]amino}-2-chlorobenzonitrile;
(2S)-1-[2-(3-fluorophenyl)-5,5-dimethyl-3-[(4-methylphenyl)amino]-5H,6H,7H,8H-imidazo[1,2-a]pyrazin-7-yl]-2-hydroxy-3-methylbutan-1-one;
2-amino-1-[2-(3-fluorophenyl)-5,5-dimethyl-3-[(4-methylphenyl)amino]-5H,6H,7H,8H-imidazo[1,2-a]pyrazin-7-yl]-2-methylpropan-1-one;
2-amino-1-[2-(3-fluorophenyl)-5,5-dimethyl-3-[(4-methylphenyl)amino]-5H,6H,7H,8H-imidazo[1,2-a]pyrazin-7-yl]ethan-1-one;
2-amino-1-[(8S)-3-[(4-chloro-3-fluorophenyl)amino]-2-(4-fluorophenyl)-8-(propan-2-yl)-5H,6H,7H,8H-imidazo[1,2-a]pyrazin-7-yl]ethan-1-one;
2-amino-1-[(8R)-3-[(4-chloro-3-fluorophenyl)amino]-2-(4-fluorophenyl)-8-methyl-5H,6H,7H,8H-imidazo[1,2-a]pyrazin-7-yl]ethan-1-one;
2-amino-1-[(8S)-3-[(4-chloro-3-fluorophenyl)amino]-2-(4-fluorophenyl)-8-methyl-5H,6H,7H,8H-imidazo[1,2-a]pyrazin-7-yl]ethan-1-one;
(2S)-1-[2-(3-fluorophenyl)-5,5-dimethyl-3-[(4-methylphenyl)amino]-5H,6H,7H,8H-imidazo[1,2-a]pyrazin-7-yl]-2-hydroxy-3-phenylpropan-1-one;
2-amino-1-{3-[(1,5-dimethyl-1H-pyrazol-3-yl)amino]-2-(4-fluorophenyl)-8,8-dimethyl-5H,6H,7H,8H-imidazo[1,2-a]pyrazin-7-yl}ethan-1-one;
2-amino-1-{3-[(1-ethyl-1H-pyrazol-5-yl)amino]-2-(4-fluorophenyl)-8,8-dimethyl-5H,6H,7H,8H-imidazo[1,2-a]pyrazin-7-yl}ethan-1-one;
2-amino-1-[(8R)-3-[(4-chloro-3-fluorophenyl)amino]-2-(4-fluorophenyl)-8-(propan-2-yl)-5H,6H,7H,8H-imidazo[1,2-a]pyrazin-7-yl]ethan-1-one;
2-amino-1-{3-[(4-chlorophenyl)amino]-2-(3-fluorophenyl)-5,5-dimethyl-5H,6H,7H,8H-imidazo[1,2-a]pyrazin-7-yl}ethan-1-one;
2-amino-1-[2-(3-fluorophenyl)-3-[(4-fluorophenyl)amino]-5,5-dimethyl-5H,6H,7H,8H-imidazo[1,2-a]pyrazin-7-yl]ethan-1-one;
2-amino-1-{3-[(3,4-difluorophenyl)amino]-2-(3-fluorophenyl)-5,5-dimethyl-5H,6H,7H,8H-imidazo[1,2-a]pyrazin-7-yl}ethan-1-one;
2-amino-1-{3-[(4-chloro-3-fluorophenyl)amino]-2-(3-fluorophenyl)-5,5-dimethyl-5H,6H,7H,8H-imidazo[1,2-a]pyrazin-7-yl}ethan-1-one;
2-amino-1-{3-[(3-chloro-4-fluorophenyl)amino]-2-(3-fluorophenyl)-5,5-dimethyl-5H,6H,7H,8H-imidazo[1,2-a]pyrazin-7-yl}ethan-1-one;
2-amino-1-{3-[(4-fluoro-3-methylphenyl)amino]-2-(3-fluorophenyl)-5,5-dimethyl-5H,6H,7H,8H-imidazo[1,2-a]pyrazin-7-yl}ethan-1-one;
2-amino-1-{3-[(4-chloro-3-methylphenyl)amino]-2-(3-fluorophenyl)-5,5-dimethyl-5H,6H,7H,8H-imidazo[1,2-a]pyrazin-7-yl}ethan-1-one;
2-amino-1-{3-[(4-fluoro-3-methylphenyl)amino]-2-(4-fluorophenyl)-5H,6H,7H,8H-imidazo[1,2-a]pyrazin-7-yl}-2-methylpropan-1-one;
2-amino-1-{3-[(4-chloro-3-methylphenyl)amino]-2-(4-fluorophenyl)-5H,6H,7H,8H-imidazo[1,2-a]pyrazin-7-yl}-2-methylpropan-1-one;
5-{[7-(2-amino-2-methylpropanoyl)-2-(4-fluorophenyl)-5H,6H,7H,8H-imidazo[1,2-a]pyrazin-3-yl]amino}-2-methylbenzonitrile;
2-amino-1-{3-[(3-fluoro-4-methylphenyl)amino]-2-(4-fluorophenyl)-5H,6H,7H,8H-imidazo[1,2-a]pyrazin-7-yl}-2-methylpropan-1-one;
2-amino-1-{3-[(3-chloro-4-methylphenyl)amino]-2-(4-fluorophenyl)-5H,6H,7H,8H-imidazo[1,2-a]pyrazin-7-yl}-2-methylpropan-1-one;
2-amino-1-(3-{[3-chloro-4-(trifluoromethyl)phenyl]amino}-2-(4-fluorophenyl)-5H,6H,7H,8H-imidazo[1,2-a]pyrazin-7-yl)-2-methylpropan-1-one;
2-amino-1-(3-{[4-fluoro-3-(trifluoromethyl)phenyl]amino}-2-(4-fluorophenyl)-5H,6H,7H,8H-imidazo[1,2-a]pyrazin-7-yl)-2-methylpropan-1-one;
4-{[7-(2-amino-2-methylpropanoyl)-2-(4-fluorophenyl)-5H,6H,7H,8H-imidazo[1,2-a]pyrazin-3-yl]amino}-2-(trifluoromethyl)benzonitrile;
5-{[7-(2-amino-2-methylpropanoyl)-2-(4-fluorophenyl)-5H,6H,7H,8H-imidazo[1,2-a]pyrazin-3-yl]amino}-2-fluorobenzonitrile;
2-amino-1-{3-[(3,4-dimethylphenyl)amino]-2-(4-fluorophenyl)-5H,6H,7H,8H-imidazo[1,2-a]pyrazin-7-yl}-2-methylpropan-1-one;
2-amino-1-[2-(4-fluorophenyl)-3-[(3-methylphenyl)amino]-5H,6H,7H,8H-imidazo[1,2-a]pyrazin-7-yl]-2-methylpropan-1-one;
2-amino-1-{3-[(3-chlorophenyl)amino]-2-(4-fluorophenyl)-5H,6H,7H,8H-imidazo[1,2-a]pyrazin-7-yl}-2-methylpropan-1-one;
2-amino-1-[2-(4-fluorophenyl)-3-{[3-(trifluoromethoxy)phenyl]amino}-5H,6H,7H,8H-imidazo[1,2-a]pyrazin-7-yl]-2-methylpropan-1-one;
2-amino-1-{3-[(4-ethylphenyl)amino]-2-(4-fluorophenyl)-5H,6H,7H,8H-imidazo[1,2-a]pyrazin-7-yl}-2-methylpropan-1-one;
2-amino-1-(3-{[4-(difluoromethoxy)phenyl]amino}-2-(4-fluorophenyl)-5H,6H,7H,8H-imidazo[1,2-a]pyrazin-7-yl)-2-methylpropan-1-one;
2-amino-1-[2-(4-fluorophenyl)-3-{[4-(trifluoromethoxy)phenyl]amino}-5H,6H,7H,8H-imidazo[1,2-a]pyrazin-7-yl]-2-methylpropan-1-one;
2-amino-1-{3-[(3,5-dichlorophenyl)amino]-2-(4-fluorophenyl)-5H,6H,7H,8H-imidazo[1,2-a]pyrazin-7-yl}-2-methylpropan-1-one;
2-amino-1-[2-(4-fluorophenyl)-8,8-dimethyl-3-[(4-phenylphenyl)amino]-5H,6H,7H,8H-imidazo[1,2-a]pyrazin-7-yl]ethan-1-one;
2-amino-1-{3-[(4-ethylphenyl)amino]-2-(4-fluorophenyl)-8,8-dimethyl-5H,6H,7H,8H-imidazo[1,2-a]pyrazin-7-yl}ethan-1-one;

2-amino-1-[2-(4-fluorophenyl)-8,8-dimethyl-3-{[4-(trifluoromethoxy)phenyl]amino}-5H,6H,7H,8H-imidazo[1,2-a]pyrazin-7-yl]ethan-1-one;
2-amino-1-[2-(4-fluorophenyl)-8,8-dimethyl-3-{[3-(trifluoromethoxy)phenyl]amino}-5H,6H,7H,8H-imidazo[1,2-a]pyrazin-7-yl]ethan-1-one;
2-amino-1-{3-[(3-chlorophenyl)amino]-2-(4-fluorophenyl)-8,8-dimethyl-5H,6H,7H,8H-imidazo[1,2-a]pyrazin-7-yl}ethan-1-one;
2-amino-1-[2-(4-fluorophenyl)-8,8-dimethyl-3-{[3-(trifluoromethyl)phenyl]amino}-5H,6H,7H,8H-imidazo[1,2-a]pyrazin-7-yl]ethan-1-one;
3-{[7-(2-aminoacetyl)-2-(4-fluorophenyl)-8,8-dimethyl-5H,6H,7H,8H-imidazo[1,2-a]pyrazin-3-yl]amino}benzonitrile;
2-amino-1-{3-[(3,4-dimethylphenyl)amino]-2-(4-fluorophenyl)-8,8-dimethyl-5H,6H,7H,8H-imidazo[1,2-a]pyrazin-7-yl}ethan-1-one;
4-{[7-(2-aminoacetyl)-2-(4-fluorophenyl)-8,8-dimethyl-5H,6H,7H,8H-imidazo[1,2-a]pyrazin-3-yl]amino}-2-(trifluoromethyl)benzonitrile;
2-amino-1-{3-[(3,5-dimethylphenyl)amino]-2-(4-fluorophenyl)-8,8-dimethyl-5H,6H,7H,8H-imidazo[1,2-a]pyrazin-7-yl}ethan-1-one;
2-amino-1-(3-{[4-fluoro-3-(trifluoromethyl)phenyl]amino}-2-(4-fluorophenyl)-8,8-dimethyl-5H,6H,7H,8H-imidazo[1,2-a]pyrazin-7-yl)ethan-1-one;
2-amino-1-(3-{[3-chloro-4-(trifluoromethyl)phenyl]amino}-2-(4-fluorophenyl)-8,8-dimethyl-5H,6H,7H,8H-imidazo[1,2-a]pyrazin-7-yl)ethan-1-one;
2-amino-1-{3-[(4-chloro-3-methylphenyl)amino]-2-(4-fluorophenyl)-5,5-dimethyl-5H,6H,7H,8H-imidazo[1,2-a]pyrazin-7-yl}ethan-1-one;
2-amino-1-{3-[(4,4-difluorocyclohexyl)amino]-2-(4-fluorophenyl)-8,8-dimethyl-5H,6H,7H,8H-imidazo[1,2-a]pyrazin-7-yl}ethan-1-one;
2-amino-1-[2-(4-fluorophenyl)-8,8-dimethyl-3-[(4-phenylcyclohexyl)amino]-5H,6H,7H,8H-imidazo[1,2-a]pyrazin-7-yl]ethan-1-one;
2-amino-1-[2-(4-fluorophenyl)-8,8-dimethyl-3-{[4-(trifluoromethyl)cyclohexyl]amino}-5H,6H,7H,8H-imidazo[1,2-a]pyrazin-7-yl]ethan-1-one;
2-amino-1-{3-[(4-tert-butylcyclohexyl)amino]-2-(4-fluorophenyl)-8,8-dimethyl-5H,6H,7H,8H-imidazo[1,2-a]pyrazin-7-yl}ethan-1-one;
2-amino-1-[2-(4-fluorophenyl)-8,8-dimethyl-3-[(2-methylcyclohexyl)amino]-5H,6H,7H,8H-imidazo[1,2-a]pyrazin-7-yl]ethan-1-one;
2-amino-1-[3-(cycloheptylamino)-2-(4-fluorophenyl)-8,8-dimethyl-5H,6H,7H,8H-imidazo[1,2-a]pyrazin-7-yl]ethan-1-one;
2-amino-1-[2-(4-fluorophenyl)-8,8-dimethyl-3-[(3,3,5-trimethylcyclohexyl)amino]-5H,6H,7H,8H-imidazo[1,2-a]pyrazin-7-yl]ethan-1-one;
2-amino-1-{3-[(1R,2R,4S)-bicyclo[2.2.1]heptan-2-ylamino]-2-(4-fluorophenyl)-8,8-dimethyl-5H,6H,7H,8H-imidazo[1,2-a]pyrazin-7-yl}ethan-1-one;
2-amino-1-[3-(cyclopentylamino)-2-(4-fluorophenyl)-8,8-dimethyl-5H,6H,7H,8H-imidazo[1,2-a]pyrazin-7-yl]ethan-1-one;
2-amino-1-[3-(cyclobutylamino)-2-(4-fluorophenyl)-8,8-dimethyl-5H,6H,7H,8H-imidazo[1,2-a]pyrazin-7-yl]ethan-1-one;
2-amino-1-[2-(4-fluorophenyl)-8,8-dimethyl-3-(oxan-4-ylamino)-5H,6H,7H,8H-imidazo[1,2-a]pyrazin-7-yl]ethan-1-one;
2-amino-1-{3-[(4-chloro-3-fluorophenyl)amino]-2-(4-fluorophenyl)-5,5-dimethyl-5H,6H,7H,8H-imidazo[1,2-a]pyrazin-7-yl}ethan-1-one;
2-amino-1-[2-(4-fluorophenyl)-3-[(4-fluorophenyl)amino]-5,5-dimethyl-5H,6H,7H,8H-imidazo[1,2-a]pyrazin-7-yl]ethan-1-one;
2-amino-1-[2-(4-fluorophenyl)-5,5-dimethyl-3-[(4-methylphenyl)amino]-5H,6H,7H,8H-imidazo[1,2-a]pyrazin-7-yl]ethan-1-one;
2-amino-1-{3-[(4-chlorophenyl)amino]-2-(4-fluorophenyl)-5,5-dimethyl-5H,6H,7H,8H-imidazo[1,2-a]pyrazin-7-yl}ethan-1-one;
2-amino-1-{3-[(4-chlorophenyl)(methyl)amino]-2-(4-fluorophenyl)-8,8-dimethyl-5H,6H,7H,8H-imidazo[1,2-a]pyrazin-7-yl}ethan-1-one;
2-amino-1-[2-(4-fluorophenyl)-3-[(4-fluorophenyl)methyl]-8,8-dimethyl-5H,6H,7H,8H-imidazo[1,2-a]pyrazin-7-yl]ethan-1-one;
2-amino-1-[2-(4-fluorophenyl)-8,8-dimethyl-3-[(4-methylphenyl)methyl]-5H,6H,7H,8H-imidazo[1,2-a]pyrazin-7-yl]ethan-1-one;
2-amino-1-[2-(4-fluorophenyl)-3-[(4-methoxyphenyl)methyl]-8,8-dimethyl-5H,6H,7H,8H-imidazo[1,2-a]pyrazin-7-yl]ethan-1-one;
2-amino-1-{3-[(3,4-difluorophenyl)methyl]-2-(4-fluorophenyl)-8,8-dimethyl-5H,6H,7H,8H-imidazo[1,2-a]pyrazin-7-yl}ethan-1-one;
2-amino-1-[2-(4-fluorophenyl)-3-[(4-fluorophenyl)methyl]-5H,6H,7H,8H-imidazo[1,2-a]pyrazin-7-yl]-2-methylpropan-1-one;
7-(2-aminoacetyl)-N,2-bis(4-fluorophenyl)-8,8-dimethyl-5H,6H,7H,8H-imidazo[1,2-a]pyrazine-3-carboxamide;
2-amino-1-[3-(4-fluorophenoxy)-2-(4-fluorophenyl)-8,8-dimethyl-5H,6H,7H,8H-imidazo[1,2-a]pyrazin-7-yl]ethan-1-one;
2-amino-1-[3-(4-chlorophenoxy)-2-(4-fluorophenyl)-8,8-dimethyl-5H,6H,7H,8H-imidazo[1,2-a]pyrazin-7-yl]ethan-1-one;
2-amino-1-[3-(3,4-difluorophenoxy)-2-(4-fluorophenyl)-8,8-dimethyl-5H,6H,7H,8H-imidazo[1,2-a]pyrazin-7-yl]ethan-1-one;
2-amino-1-[3-(4-fluoro-3-methylphenoxy)-2-(4-fluorophenyl)-8,8-dimethyl-5H,6H,7H,8H-imidazo[1,2-a]pyrazin-7-yl]ethan-1-one;
2-amino-1-[2-(4-fluorophenyl)-8,8-dimethyl-3-[(4-methylphenyl)sulfanyl]-5H,6H,7H,8H-imidazo[1,2-a]pyrazin-7-yl]ethan-1-one;
2-amino-1-[2-(4-fluorophenyl)-3-[(3-fluorophenyl)sulfanyl]-8,8-dimethyl-5H,6H,7H,8H-imidazo[1,2-a]pyrazin-7-yl]ethan-1-one;
2-amino-1-[2-(4-fluorophenyl)-3-[(4-fluorophenyl)sulfanyl]-8,8-dimethyl-5H,6H,7H,8H-imidazo[1,2-a]pyrazin-7-yl]ethan-1-one;
2-amino-1-{3-[(4-chlorophenyl)sulfanyl]-2-(4-fluorophenyl)-8,8-dimethyl-5H,6H,7H,8H-imidazo[1,2-a]pyrazin-7-yl}ethan-1-one;
2-amino-1-{3-[(3,5-dimethylphenyl)sulfanyl]-2-(4-fluorophenyl)-8,8-dimethyl-5H,6H,7H,8H-imidazo[1,2-a]pyrazin-7-yl}ethan-1-one;
2-amino-1-{3-[(3,4-difluorophenyl)sulfanyl]-2-(4-fluorophenyl)-8,8-dimethyl-5H,6H,7H,8H-imidazo[1,2-a]pyrazin-7-yl}ethan-1-one;
2-amino-1-{3-[(3-fluorobenzene)sulfinyl]-2-(4-fluorophenyl)-8,8-dimethyl-5H,6H,7H,8H-imidazo[1,2-a]pyrazin-7-yl}ethan-1-one;

2-amino-1-{3-[(4-fluorobenzene)sulfinyl]-2-(4-fluorophenyl)-8,8-dimethyl-5H,6H,7H,8H-imidazo[1,2-a]pyrazin-7-yl}ethan-1-one;

2-amino-1-[2-(4-fluorophenyl)-8,8-dimethyl-3-[(4-methylbenzene)sulfinyl]-5H,6H,7H,8H-imidazo[1,2-a]pyrazin-7-yl]ethan-1-one;

2-amino-1-{3-[(3,5-dimethylbenzene)sulfinyl]-2-(4-fluorophenyl)-8,8-dimethyl-5H,6H,7H,8H-imidazo[1,2-a]pyrazin-7-yl}ethan-1-one;

2-amino-1-{3-[(3,4-difluorobenzene)sulfinyl]-2-(4-fluorophenyl)-8,8-dimethyl-5H,6H,7H,8H-imidazo[1,2-a]pyrazin-7-yl}ethan-1-one;

2-amino-1-{3-[(4-chlorobenzene)sulfinyl]-2-(4-fluorophenyl)-8,8-dimethyl-5H,6H,7H,8H-imidazo[1,2-a]pyrazin-7-yl}ethan-1-one; and 2-amino-1-[2-(4-fluorophenyl)-8,8-dimethyl-3-[(4-methylbenzene)sulfonyl]-5H,6H,7H,8H-imidazo[1,2-a]pyrazin-7-yl]ethan-1-one.

11. The method of claim 1, wherein the compound is 2-amino-1-(2-(4-fluorophenyl)-3-(4-fluorophenylamino)-8,8-dimethyl-5,6-dihydroimidazo[1,2-a]pyrazin-7(8H)-yl)ethanone having the formula:

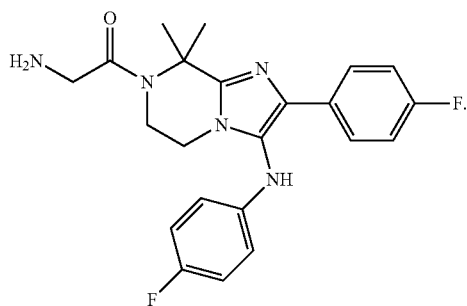 [SMILES: CC1(C)c2nc(-c3ccc(F)cc3)c(Nc3ccc(F)cc3)n2CCN1C(=O)CN]

12. The method of claim 1, wherein the compound is 2-amino-1-(3-(3,4-difluorophenylamino)-2-(4-fluorophenyl)-5,6-dihydroimidazo[1,2-a]pyrazin-7(8H)-yl)-2-methylpropan-1-one of the formula:

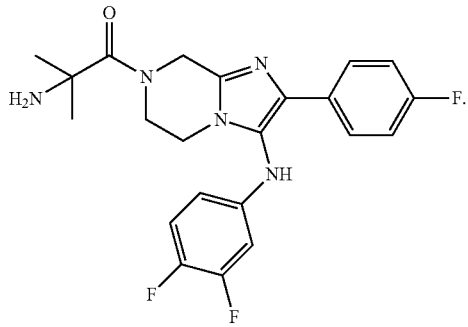 [SMILES: CC(C)(N)C(=O)N1CCn2c(nc(-c3ccc(F)cc3)c2Nc2ccc(F)c(F)c2)C1]

13. The method of claim 1, wherein the compound is 2-amino-1-(3-(4-chlorophenylamino)-2-(4-fluorophenyl)-8,8-dimethyl-5,6-dihydroimidazo[1,2-a]pyrazin-7(8H)-yl)ethanone having the formula:

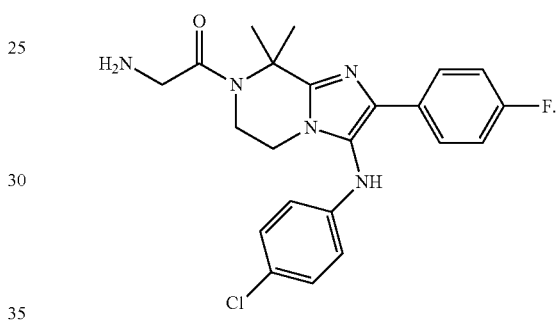

* * * * *